US012545689B2

(12) United States Patent
Blom et al.

(10) Patent No.: US 12,545,689 B2
(45) Date of Patent: Feb. 10, 2026

(54) MACROCYCLIC LRRK2 KINASE INHIBITORS

(71) Applicant: ONCODESIGN PRECISION MEDICINE, Dijon (FR)

(72) Inventors: Petra Marcella Blom, Destelbergen (BE); Christopher Gaétan Housseman, Massy (FR); Alain Daugan, Vaugrigneuse (FR); Audrey Dumoulin, Antony (FR); Maxime Laugeois, Paris (FR); Alexis Denis, Paris (FR); Nicolas Faucher, Suresnes (FR); Iuliana Botez, Rueil Malmaison (FR); Arnaud Le Tiran, Croissy sur Seine (FR); Kenneth Christensen, Copenhagen (DK); Yann Lamotte, Antony (FR)

(73) Assignee: ONCODESIGN PRECISION MEDICINE, Dijon (FR)

( * ) Notice: Subject to any disclaimer, the term of this patent is extended or adjusted under 35 U.S.C. 154(b) by 565 days.

(21) Appl. No.: 17/923,002

(22) PCT Filed: May 5, 2021

(86) PCT No.: PCT/EP2021/061827
§ 371 (c)(1),
(2) Date: Nov. 3, 2022

(87) PCT Pub. No.: WO2021/224320
PCT Pub. Date: Nov. 11, 2021

(65) Prior Publication Data

US 2023/0357269 A1 Nov. 9, 2023

(30) Foreign Application Priority Data

May 6, 2020 (EP) .................................... 20315236
Jan. 28, 2021 (EP) .................................... 21305112

(51) Int. Cl.
*C07D 498/18* (2006.01)
*A61P 25/16* (2006.01)
*C07D 498/08* (2006.01)
*C07D 513/18* (2006.01)

(52) U.S. Cl.
CPC ............ *C07D 498/18* (2013.01); *A61P 25/16* (2018.01); *C07D 498/08* (2013.01); *C07D 513/18* (2013.01)

(58) Field of Classification Search
CPC .. C07D 498/18; C07D 498/08; C07D 513/18; C07D 498/16
See application file for complete search history.

(56) References Cited

U.S. PATENT DOCUMENTS

2015/0290198 A1 10/2015 Hoflack

FOREIGN PATENT DOCUMENTS

WO WO2015026683 2/2015
WO WO2039241540 12/2019

OTHER PUBLICATIONS

International Search Report for PCT/EP2021/063827 dated May 25, 2021.

*Primary Examiner* — Susanna Moore
(74) *Attorney, Agent, or Firm* — KDW Firm PLLC

(57) ABSTRACT

Compounds of Formula (I):

(I)

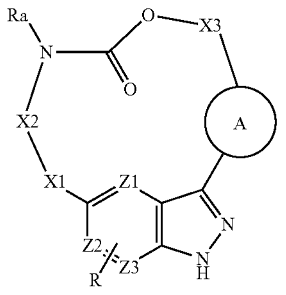

wherein R, X1, X2, X3, Z1, Z2, Z3, A and Ra are as defined in the description.

46 Claims, No Drawings

MACROCYCLIC LRRK2 KINASE INHIBITORS

FIELD OF THE INVENTION

The present invention relates to novel macrocyclic compounds and compositions containing said compounds acting as kinase inhibitors, in particular as inhibitors of LRRK2 (Leucine-Rich Repeat Kinase 2). Moreover, the present invention provides processes for the preparation of the disclosed compounds, pharmaceutical compositions containing them, as well as methods of using them, for instance as a medicine or diagnostic agent, in particular for the treatment and/or diagnosis of diseases impacted or modulated by LRRK2 kinase activity such as neurological disorders including Parkinson's disease and Alzheimer's disease, but also cardiac diseases or inflammatory disorders such as Crohn's disease.

BACKGROUND OF THE INVENTION

Parkinson's disease is the most common movement disorder and the second most common neurodegenerative disease after Alzheimer's disease. Parkinson's disease affects approximately 1% of the population above 65 years and is characterized by the four classical core motor complications: resting tremor, bradykinesia, postural instability and muscular rigidity. Patients with Parkinson's disease are also impacted by a host of non-motor symptoms such as constipation, hyposmia, orthostatic hypotension, sleep disturbances including REM sleep behavior disorder, dementia, visual disturbances, depression, anxiety, hallucinations and mood swings.

Standard of care in Parkinson's disease is symptomatic relief of motor complications using dopamine replacement therapy such as the dopamine precursor L-dopa, dopamine agonists or compounds that impact the half-life of dopamine such as MAO-B inhibitors. As of today, there is no approved therapy to prevent, cure or delay the progression of Parkinson's disease.

The pathological hallmarks of Parkinson's disease are the loss of dopaminergic neurons in the substantia nigra pars compacta as well as postmortem evidence of protein inclusions, also known as Lewy bodies and Lewy neurites. In postmortem tissue from Parkinson's disease patients Lewy bodies and neurites are seen throughout the central nervous system and in peripheral tissues as well. A major component of the inclusions is the aggregated and misfolded α-synuclein protein phosphorylated at a serine at amino acid position 129 (*Nature* 388, 839-840, 1997; *Nat Cell Biol* 4, 160-64, 2002). Lewy bodies and neurites also contain proteins implicated in other neurodegenerative diseases such as the hyperphosphorylated tau protein which is a pathological hallmark of tauopathies such as Alzheimer's disease (AD), frontotemporal dementia (FTD), progressive supranuclear palsy (PSP) and corticobasal degeneration (CBD) (*Biochem Soc Trans* 26(3), 463-71, 1998; *Am J Hum Genet* 64(2), 414-21, 1999; *J Neuropathol Exp Neurol* 62(4), 389-97, 2003). The pathological process in Parkinson's disease is not restricted to the loss of dopaminergic neurons in the basal ganglia system. Distinct neuronal populations in other brain regions such as the neocortex, sleep nuclei or the raphe nucleus as well as peripheral organs and tissues such as the heart and the gastro-intestinal system are also impacted by degenerative processes in Parkinson's disease patients.

Leucine-rich repeat kinase 2 (LRRK2) is a 2527 amino acid protein with a molecular weight of 286 kDa that is encoded by the LRRK2 gene. It consists of the following functional and structural proteins domains: armadillo (ARM), ankyrin (ANK), leucine rich repeat (LRR), Ras of complex domain (Roc), c-terminal of Roc (COR), map kinase (MAPK) and tryptophan-aspartate repeat domain (WD40). LRRK2 exists primarily as a dimeric protein either associated with membrane structures or cytoplasmic localized. The armadillo, ankyrin, LRR and WD40 protein-protein interaction domains enables LRRK2 to interact with a host of different protein partners to impact its own as well as its partner proteins subcellular localization. The central enzymatic core of the LRRK2 protein containing the Roc-COR and the MAPK domain have distinct GTPase and ATPase enzymatic activities enabling LRRK2 to phosphorylate and control the function of intracellular substrates. LRRK2 impacts, via its enzymatic activity and substrate interactions, various subcellular processes and biological mechanisms important for trafficking of intracellular vesicular structures and organelles such as lysosomes, endosomes, autophagosomes, the Golgi and mitochondria. Structural work as well as modelling highlights how naturally occurring missense variation in functional and structural domains of LRRK2 impacts enzymatic activity (*bioRxiv* 2020.01.06.895367). In the inactive (open) LRRK2 conformation there are major interactions between the enzymatic GTPase (Roc-COR) and ATPase (MAPK) domains. In addition, the ultimate C-terminal proceeding the WD40 domain binds along the entire kinase (MAPK) domain. In the active (closed) LRRK2 conformation the LRR domain positions the autophosphorylation site Ser1292 in proximity to the kinase active site. Phosphorylation of LRRK2 at a cluster of serines immediately preceding the LRR domain enables the LRR domain of LRRK2 to bind to 14-3-3 proteins. Among those phosphorylation sites are serines (Ser) at the following amino acid positions: Ser910, Ser935, Ser955 and Ser973. Pathogenic LRRK2 mutations originating in the GTPase domain has diminished phosphorylation at these sites and therefore reduced 14-3-3 binding leading to increased microtubule network recruitment. All ATP-competitive LRRK2 inhibitors induce dephosphorylation at the Ser910, Ser935, Ser955 and Ser973 sites making these sites useful as surrogate target engagement markers (*Biochem J* 430(3), 405-13, 2010; *J Neurochem* 120(1), 37-45, 2012). The bona fide LRRK2 substrates consists of a subset of small Rab GTPases including Rab10 and Rab29. The Golgi-resident protein Rab29 also known as Rab7L1 is a Parkinson's disease susceptibility gene located at the PARK16 locus (*Nat Genet* 41(12), 1308-12, 2009).

Rare protein-encoding variants in the LRRK2 gene cause Parkinson's disease. The most common pathogenic variant causing autosomal dominant familial Parkinson's disease is the p.G2019S substitution which changes a glycine to a serine in the activation loop of the LRRK2 kinase domain rendering the p.G2019S variant more active than the wild type LRRK2 protein (*Lancet* 365(9457), 412-5, 2005). This results in increased autophosphorylation at the serine at amino acid position 1292 (*Sci Transl Med,* 4(164), 164ra161, 2012). The estimated worldwide prevalence of the p.G2019S mutation in patients with PD is 1-2%; whereas, in Ashkenazi Jewish and North African Arab-Berber populations the p.G2019S prevalence in PD patients is up to 30% and 40%, respectively (*Lancet Neurol* 7, 583-90, 2008; *N Engl J Med* 354(4), 424-5, 2006; *Lancet Neurol* 7, 591-4, 2008). The clinical manifestation of Parkinson's disease in patients carrying the p.G2019S mutation is indistinguishable from patients with the sporadic form of Parkinson's disease (*Ann Neurol* 57(5), 762-5, 2005).

Besides p.G2019S seven additional rare LRRK2 exonic variants having non-synonymous amino acid substitutions in the central enzymatic core (p.N1437H; p.R1441C/G/H; p.Y1699C; p.S1761R; p.I2020T) also cause autosomal dominant Parkinson's disease (*Parkinsonism Relat Disord* 15(6), 466-7, 2009; *Mov Disord* 25(14), 2340-5, 2010; *Neuron* 44(4), 601-7, 2004; *Parkinsonism Relat Disord* 18(4), 332-8, 2012; *Ann Neurol* 57(6), 918-21, 2005; *Mov Disord* 27(1), 146-51, 2012). As with p.G2019S the clinical representations are indistinguishable from idiopathic PD (*Neurology* 70, 1456-60, 2008). LRRK2 missense variants exhibit increased Ser1292 phosphorylation, increased trans-Golgi recruitment by Rab29 and increased phosphorylation of Rab10 at amino acid position 73 (Rab10-Thr73) that can be reversed by LRRK2 inhibition (*Sci Transl Med* 4(164), 164ra161, 2012; *EMBO J* 37(1), 1-18, 2018; *Proc Natl Acad Sci USA* 111, 2626-31, 2014). Common protein-coding variants in the LRRK2 gene are also associated with risk of Parkinson's disease. Variants such as p.A419V, p.M1646T, p.R1628P and p.G2385R increase the risk of Parkinson's disease and have increased kinase activity (*bioRxiv* 447946, 2018) (*Proc Natl Acad Sci USA* 116(5), 1579-1584, 2019) whereas the p.N551K variant is associated with reduced risk of Parkinson's disease (*Lancet Neurol* 10(10), 898-908, 2011) and have reduced kinase activity (*bioRxiv* 447946, 2018). Evidence that LRRK2 also plays a role in sporadic Parkinson's disease comes from both genetic studies as well as postmortem analyses of PD brains. A single nucleotide polymorphism (SNP) at the LRRK2 genetic locus is genome-wide associated with risk of Parkinson's disease (*Nat Genet* 46(9), 989-93, 2014). This particular SNP variant is associated with increased LRRK2 expression (*Sci Transl Med* 9 (421), 2017) which is in agreement with the increased LRRK2 kinase activity observed in surviving dopamine neurons from postmortem brains of sporadic PD patients (*Sci Transl Med* 10 (451), 2018).

Thus, inhibitors of LRRK2 kinase activity can be used as therapies for both sporadic PD patients as well as for PD patients with LRRK2 mutations or Rab29/Rab7L1 polymorphisms.

Parkinson's disease risk loci containing several genes encoding proteins involved in endosomal-lysosomal processes such as GBA, SCARB2, GALC, VPS35, LAMP1, VPS13C, VPS35, TMEM175, ATP6V0A1 and CTSB have been identified by Genome Wide Association Study (GWAS) and linkage studies. LRRK2 also plays a key role in the endosomal-lysosomal system and in the processes linked to endosomal function such as autophagy and mitophagy. LRRK2 interacts with the vacuolar H+-ATPase α subunit to regulate lysosomal pH and endosomal-lysosomal dysfunction induced by rotenone, a toxin known to be associated with increased risk of Parkinson's disease, can be alleviated by LRRK2 inhibition (*Neurobiol Dis* 134, 104626, 2020). Disease-causing LRRK2 mutations induce lysosomal stress by enlarging lysosomes (*Hum Mol Genet* 24(21), 6013-28, 2015). Likewise, an aspartate to asparagine missense mutation in the retromer complex protein VPS35 at amino acid position 620 (VPS35-D620N) causes late onset autosomal dominant familial Parkinson's disease. In the disease state the VPS35-D620N missense mutation disrupts trafficking of cathepsin D, the protease responsible for degradation of α-synuclein (*Traffic* 15(2), 230-44, 2014) and activates LRRK2 which leads to increased autophosphorylation at the LRRK2-Ser1292 site and increased Rab10-Thr73 phosphorylation (*Biochem J* 475(11), 1861-1883, 2018). In the lysosomes LRRK2 interacts with GBA that is causally linked with the lysosomal storage disorder Gaucher's disease and a risk gene for Parkinson's disease. LRRK2 missense mutations reduce GBA activity that can be counteracted by LRRK2 inhibition (*Nat Commun* 10(1), 5570, 2019). Reversely, GBA disease-relevant deficits in lysosomal biology processes in astrocytes can also be alleviated by LRRK2 inhibition (*Mov Disord Feb.* 8, 2020, doi: 10.1002 mds.27994). Missense mutations in the mitochondrial kinase PINK1 and the E3 ligase PARKIN both cause autosomal recessive early onset Parkinson's disease that is associated with mitochondrial dysfunction (*Science* 304 (5674), 1158-60, 2004; *Nature* 392(6676), 605-8, 1998). LRRK2-dependent phoshorylation of Rab8a on threonine at amino acid position 72 is modulated by PINK1 phosphorylation of serine on amino acid position 111 on Rab8a (*Biochem J. Mar.* 30, 2020, doi: 10.1042 BCJ20190664). Besides this LRRK2 activity impairs mitophagy that under normal conditions is regulated by the PINK1/PARKIN pathway. This can be reversed by LRRK2 inhibition (*Hum Mol Genet* 28(10), 1645-1660, 2019). LRRK2 missense mutations cause mitochondrial DNA damage that can be reversed by gene corrections (*Neurobiol Dis* 62, 381-6, 2014) as well as with inhibitors of LRRK2 (*Hum Mol Genet.* 26(22), 4340-4351, 2017). This suggests that LRRK2 inhibitors are useful for treating lysosomal storage disorders such as Gaucher's disease, Krabbe's disease, Niemann-Pick's disease and Fabry's disease, disorders with mitochondrial deficits including early onset Parkinson's disease associated with PINK1 and PARKIN missense mutations as well as Parkinson's disease in patients with polymorphisms in genes encoding proteins involved in the endosomal-lysosomal system such as GBA, GALC, VPS35, VPS13C, ATP6V0A1, LAMP1, SCARB2, TMEM175 and CTSB. Postmortem analysis of brains from Parkinson's disease patient carrying LRRK2 mutations show presence of α-synuclein pathology (*JAMA Neurol.* 72(1), 100-5, 2015). In preclinical Parkinson's disease (PD) models, p.G2019S aggravates PD-related pathology that can be reversed by LRRK2 inhibition. LRRK2 has been identified in Lewy bodies in nigral and brain stem regions (*Neuropathol Appl Neurobiol* 34(3), 272-83, 2008) and has also been shown to phosphorylate α-synuclein on Ser129 (*Biochem Biophys Res Commun* 387(1), 149-52, 2009). LRRK2 exonic variation is associated with risk of multiple system atrophy (*Neurology* 83(24), 2256-61, 2014) and LRRK2 missense mutations have also been reported in patients with multiple system atrophy (*J Parkinsons Dis;* 8(1), 93-100, 2018). Single nucleotide polymorphisms in the MAPT (tau) locus is associated with increased risk of Parkinson's disease and multiple system atrophy (*Hum Genet* 124(6), 593-605, 2009; *Parkinsonism Relat Disord* 30, 40-5, 2016). Tau pathology is also a prominent feature seen in Parkinson's disease patients with LRRK2 missense mutations (*Acta Neuropathol Commun* 7(1), 183, 2019). Overexpression of pathogenic LRRK2 in animal models increase tau pathology (*Neurobiol Dis* 40(3), 503-17, 2010). LRRK2 missense mutations have been reported in patients suffering from tauopathies such as progressive supranuclear palsy and corticobasal degeneration (*Mov Disord.* 32(1), 115-123, 2017). Common variation at the LRRK2 locus is associated with survival in the primary tauopathy progressive supranuclear palsy (*bioRxiv* 2020.02.04.932335) and GWAS studies have identified risk for frontotemporal dementia at the LRRK2 locus (*PLoS Med* 15(1), e1002487, 2018).

This suggests that LRRK2 inhibitors are useful for treating synucleinopathies and tauopathies including frontotemporal dementia, progressive supranuclear palsy, corticobasal degeneration and Alzheimer's disease. LRRK2 mRNA and protein are broadly expressed but particular enriched in brain tissue as well as in peripheral organs more specifically kidney, lung, intestine and spleen. Besides this LRRK2 expression is highly enriched in immune cells in the brain and in neutrophils, B-cells, macrophages and monocytes in the periphery. LRRK2 mRNA and protein expression is induced after pro-inflammatory stimuli or pathogens thereby increasing LRRK2 kinase activity. In human peripheral blood mononuclear cells, the LRRK2 substrates Rab10 and Rab12 are phosphorylated after stimulation with reagents mimicking viral infections (*Sci Rep* 7(1), 10300, 2017). Consistent with LRRK2 biology playing a role in response to inflammatory stimuli LRRK2 missense mutations are associated with risk of the inflammatory bowel disorder Crohn's disease and GWAS studies has identified single nucleotide polymorphisms in the LRRK2 locus associated with genome wide significant risk of Crohn's disease (*Inflamm Bowel Dis* 17(12), 2407-15, 2011). In Ashkenazi Jewish populations there is a two- to four-fold increased prevalence of Crohn's disease and in the same population LRRK2 variants are associated with increased risk of Crohn's disease (*PLoS Genet* 14(5), e1007329, 2018). LRRK2 exonic variants such as p.N2081D and p.M2397T increase the risk of Crohn's disease and as observed for Parkinson's disease the protective haplotype variant p.N551K/p.R1348H lowers the risk of Crohn's disease. In cell-based studies the p.N2081D variant has increased kinase activity which leads to augmented Rab10 phosphorylation (*bioRxiv* 447946, 2018; Sci Transl Med 10(423), 2018). The biological link between Parkinson's disease and autoimmune disorders are further supported by studies finding that common genetic pathways which also includes LRRK2 are shared between Parkinson's disease and autoimmune disorders such as rheumatoid arthritis, ulcerative colitis and Crohn's disease (*JAMA Neurol* 74(7), 780-92, 2017). Consistent with this LRRK2 is also associated with risk of lupus (*Oncotarget* 8, 13754-61, 2017; *J Transl Med* 17(1), 37, 2019) and leprosy (*N Engl J Med* 361(27), 2609-18, 2009; *PLoS One* 8(8), e73103, 2013; *PLoS Negl Trop Dis* 10(2), e0004412, 2016).

Thus, LRRK2 inhibitors can be used for treatment of Crohn's disease and other autoimmune disorder such as but not restricted to rheumatoid arthritis, ulcerative colitis, lupus and leprosy. LRRK2 plays a role in tumor growth in renal and thyroid cancers by impacting MET signaling, and lowering of LRRK2 expression induces growth arrest (*Proc Natl Acad Sci USA* 108(4), 1439-44, 2011). LRRK2-PD patients have increased risks of leukemia as well as skin and colon cancers (*Mov Disord* 34(9), 1392-8, 2019). Carriers of p.G2019S also have an overall increased risk of non-skin cancer; in particular breast cancer and hormone-related cancers in females (*JAMA Neurol* 72(1), 58-65, 2015). Studies have shown that LRRK2 silencing promotes T-cell growth inhibition and facilitates apoptosis and cell cycle arrest (*Int J Oncol* 55(1), 21-34, 2019). LRRK2 is also differentially expressed in lung adeno- and lung squamous cell carcinomas as well as non-small-cell lung cancer (*J Cell Physiol* 234(7), 10918-25, 2019; *J Cell Physiol* 234(12), 22742-52, 2019).

Thus, LRRK2 inhibitors have anti-carcinogenic effects and can be used for treatment of skin cancer and non-skin cancers such as renal cancer, colon cancer, adeno- and squamous lung cancers, non-small-cell lung cancer, hormone-related cancer, thyroid cancer, leukemia and breast cancer.

Extended prior art is known in the field of LRRK2 inhibitors. The most recent patent applications filed in the field cover oligomeric derivatives such as compounds disclosed in WO2020/006267, non-macrocyclic or polycyclic structures such as compounds disclosed in WO2019/222173, WO2019/112269, WO2019/074809, WO2018/217946, WO2018/163066, WO2018/155916, WO2018/137618, WO2018/06931, and also macrocyclic derivatives such as compounds disclosed in WO2019/012093, WO2016/042089. Notwithstanding the huge amounts of structures elaborated over the last years, there is a continuing need to design new scaffolds having a better potency and selectivity to meet the unmet medical needs.

DETAILED DESCRIPTION OF THE INVENTION

The present invention will be described below. In the following passages, different aspects of the invention are defined in more details. Each aspect so defined may be combined with any other aspect or aspects unless clearly indicated to the contrary. In particular, any feature indicated as being preferred or advantageous may be combined with any other feature or features indicated as being preferred or advantageous.

In a first aspect the present invention provides a compound of Formula (I)

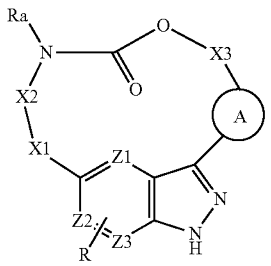

(I)

wherein:

- R represents a hydrogen atom, a halogen atom or an alkyl group,
- Z1, Z2, Z3, independently each represents a carbon or a nitrogen atom, it being understood that the 6-membered cycle containing Z1, Z2 and Z3 can have 0, 1 or 2 nitrogen atoms,
- —X1- is absent or represents —O—, —S—, or —N(R'a)-, wherein R'a represents a hydrogen atom or an alkyl group,
- —X2- represents an alkanediyl group optionally substituted with one or more substituents, identical or different, selected from halogen atoms, polyhalogenoalkyl group, alkoxy group, hydroxy group, amino group, alkylamino group, dialkylamino group and cyano group,
  it being understood that the carbon atom in the alpha position of —N(Ra), and the carbon atom in alpha position of —X1- when —X1- represents —O—, —S—, or —N(R'a)-, cannot be substituted with an oxygen or a nitrogen heteroatom,
- —X3- represents an alkanediyl group optionally substituted with one or more substituents, identical or different, selected from halogen atoms, polyhalogenoalkyl group, alkoxy group, hydroxy group, amino group, alkylamino group, dialkylamino group, cyano group, cycloalkyl group and heterocycloalkyl group, it being understood that the carbon atom in alpha position of —O—, and the carbon atom in alpha position of A1 when A1 represents a nitrogen atom, cannot be substituted with an oxygen or a nitrogen heteroatom, Ra represents a hydrogen atom or an alkyl group, it being understood that when Ra represents an alkyl group, one carbon atom of Ra can be linked to a carbon atom of —X2-, or to a carbon atom of —X3- to form a cyclic moiety containing 5 or 6 ring-members, A represents an aromatic or partially hydrogenated cyclic group of the formula (a):

(a)

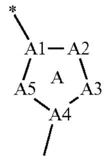

wherein

A1, A4 each independently represents a carbon atom or a nitrogen atom,

A2, A3, A5 each independently represents a carbon atom, an oxygen atom, a sulfur atom or a nitrogen atom, it being understood that A1, A2, A3, A4 and A5 cannot simultaneously represent a heteroatom, or an aromatic or partially hydrogenated cyclic group of the formula (b):

(b)

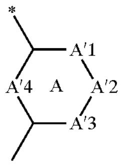

wherein A'1, A'2, A'3, A'4 each independently represents a carbon atom or a nitrogen atom, it being understood that * means that the bond is linked to X3, the aromatic or partially hydrogenated cyclic group A such defined being optionally substituted with one or more substituents, identical or different, selected from halogen atoms, alkyl group, alkoxy group, hydroxy group, oxo group, alkoxyalkyl group, alkoxyalkoxy group, polyhalogenoalkyl group, polyhalogenoalkoxy group, heterocycloalkyl group, heterocycloalkylalkyl group, (alkoxyalkyl)(alkyl)amino group, amino group, alkylamino group, dialkylamino group, cycloalkyl group, (heterocycloalkyl)(alkyl)amino group, dialkylaminoalkyl group, heterocycloalkylalkoxy group, cyano group and cyanoalkyl group, wherein the heterocycloalkyl and cycloalkyl group such defined can be optionally substituted by one or more substituents chosen from alkyl group, halogen atoms, polyhalogenoalkyl group, polyhalogenoalkoxy group, alkoxy group, alkoxyalkyl group, hydroxy group, cyano group and oxo group, their enantiomers, diastereoisomers, tautomers, racemic, hydrates, solvates, N-oxide, isotopes, deuterated derivatives and addition salts thereof with a pharmaceutically acceptable acid or base.

When describing the compounds of the invention, the terms used are to be construed in accordance with the following definitions, unless a context dictates otherwise:

The term "alkyl" by itself or as part of another substituent refers to fully saturated monovalent hydrocarbon radical, including corresponding deuterated derivatives. Alkyl groups of this invention comprise from 1 to 6 carbon atoms. Alkyl groups may be linear or branched, may include spiranic structure, and may be optionally substituted as indicated herein. Examples of alkyl groups are methyl, ethyl, n-propyl, i-propyl, butyl and its isomers (e.g. n-butyl, i-butyl and t-butyl), pentyl and its isomers, hexyl and its isomers.

The term "alkanediyl" means a fully saturated divalent hydrocarbon radical having two single bonds for attachment to two other groups, and can be represented as "-(alkyl)-" group wherein alkyl is as defined above. Alkanediyl groups of this invention comprise from 1 to 6 carbon atoms, may be linear or branched, may include spiranic structure, and may be substituted as indicated herein. Non-limiting examples of alkanediyl groups includes: $—CH_2—$, $—CH_2—CH_2—$, $—CD_2-$, $-CD_2-CD_2-$, $—CH(CH_3)—$, $—CH(CH_2—CH_3)—$, $—CH(i\text{-}Pr)—$, $—C(CH_3)(CH_3)—$, $—CH_2—C(CH_3)(CH_3)—$, $—CH_2—CH_2—C(CH_3)(CH_3)—$,

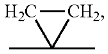 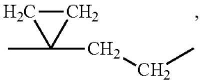 , 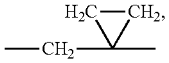

$—CH_2—CH(i\text{-}Pr)—$, $—CH(i\text{-}Pr)—CH_2—$, $—CH_2—CH(i\text{-}Bu)-$, $—CH(i\text{-}Bu)-CH_2—$, $—CH(CH_3)—CH_2—$, $—CH_2—CH(CH_3)—$, $—CH_2—CH_2—CH_2—$, $—CD_2-CD_2-CD_2-$, $—CH(CH_3)—CH_2—CH_2—$, $—CH_2—CH_2—CH(CH_3)—$, $—CH_2—CH(CH_3)—CH_2—$, $—CH(CH_3)—CH_2—CH(CH_3)—$, $—CH_2—CH_2—CH(CH_2—CH_3)—$, $—CH(CH_2—CH_3)—CH_2—CH_2—$, $—CH(CH_2—CH_3)—CH_2—CH(CH_3)—$, $—CH(CH_3)—CH_2—CH(CH_2—CH_3)—$, it being possible for those groups, when indicated, to be further substituted. For example, an alkanediyl group substituted by an alkoxy group will include, but will not be limited to, $—CH(OCH_3)—$, $—CH(OCH_3)—CH(CH_3)—$, $—CH_2—CH_2—CH(OCH_3)—$, $—CH(OCH_3)—CH_2—CH_2—$, $—CH_2—CH_2—CH(CH_2—OCH_3)—$, $—CH(CH_2—OCH_3)—CH_2—CH_2—$, $—CH(O—CH_2—CH_3)—CH_2—$, $—CH_2—CH(O—CH_2—CH_3)—$. As nonlimited other example, an alkanediyl group substituted by a cycloalkyl group will include $—CH_2—CH(Cy\text{-}Pr)—$, $—CH(Cy\text{-}Pr)—CH_2—$, wherein Cy-Pr means cyclopropyl. An alkanediyl group substituted by one or more halogen atoms includes for example, but will not be limited to $—CHF—$, $—CHF—CH_2—$, $—CF_2—$, $—CF_2—CH_2—$, $—CH_2—CF_2—$. An alkanediyl group substituted by a heterocycloalkyl group will include for example but will not be limited to $—CH_2—CH$(tetrahydropyranyl)-, —CH(tetrahydropyranyl)-$CH_2—$, $—CH_2—CH$(oxolanyl)-, —CH(oxolanyl)-$CH_2—$.

The term "cycloalkyl" by itself or as part of another substituent is a monovalent, saturated, or unsaturated hydrocarbon group having one or two cyclic structures. Cycloalkyl includes all saturated, partially saturated or aromatic hydrocarbon groups having one or two cyclic structures.

Cycloalkyl groups comprise 3 or more carbon atoms and generally, according to this invention comprise from 3 to 10 carbon atoms.

Examples of cycloalkyl groups having one cyclic structure include but are not limited to phenyl, cyclopropyl, cyclobutyl, cyclopentyl, cyclohexyl.

When a bi-cyclic ring structure is envisaged, the two rings can be:

- fused, meaning they share a common bond; exemplary cycloalkyl bi-cyclic fused systems include but is not limited to naphthalenyl, bicyclo[1.1.0]butanyl, octahydropentalenyl, decahydronaphthalenyl, octahydro-1H-indenyl;
- linked via a bond between the two cyclic structures; exemplary cycloalkyl bi-cyclic linked systems include but is not limited to bi-phenyl, bi-cyclopropanyl, bi-cyclopentenyl, bi-cyclohexanyl, cyclopropylcyclohexanyl, cyclopropylcyclopentanyl;
- bridged meaning that the two rings share three or more atoms, separating the two bridgehead atoms by a bridge containing at least one atom; exemplary cycloalkyl bi-cyclic bridged systems include but is not limited to bicyclo[2.2.1]heptanyl, bicyclo[2.2.2]octanyl;
- or represent a spiro bi-cyclic ring system wherein the two rings are connected through a single atom; exemplary cycloalkyl spiro bi-cyclic systems include but is not limited to spiro[2.2]pentanyl, spiro[2.4]heptanyl, spiro[4.4]nonanyl, spiro[5.5]undecanyl.

The "cycloalkyl group" such defined can be optionally substituted by 1 to 3 substituents chosen from alkyl group, halogen atoms, polyhalogenoalkyl group, polyhalogenoalkoxy group, alkoxy group, alkoxyalkyl group, hydroxy group, cyano group and oxo group. When the cycloalkyl group is substituted by 2 or 3 substituents, substituents can be beared by the same atom or different atoms, provided the valency of each atom is respected.

The term "alkoxy" by itself or as part of another substituent refers to an "(alkyl)-O—" group wherein "alkyl" is as defined above. Non-limiting examples of alkoxy groups includes methoxy, ethyloxy, n-propyloxy, i-propyloxy, butyloxy (and its isomers), pentyloxy (and its isomers), hexyloxy (and its isomers).

The term "alkoxyalkyl" refers to an "(alkyl)-O-(alkyl)-" group wherein "alkyl" is as defined above. Non-limiting examples include $CH_3$—O—$CH_2$—, $CH_3$—O—$CH_2$—$CH_2$—.

The term "alkoxyalkoxy" refers to an "(alkyl)-O-(alkyl)-O—" group wherein "alkyl" is as defined above. Non-limiting examples include $CH_3$—O—$CH_2$—O—, $CH_3$—O—$CH_2$—$CH_2$—O—.

The term "alkylamino" refers to an "—NH-(alkyl)" group wherein "alkyl" is as defined above. Non-limiting examples include —NH—$CH_3$, —NH—$CH_2$—$CH_3$, —NH—CH($CH_3$)($CH_3$).

The term "dialkylamino" refers to an "—N(alkyl)(alkyl)" group wherein "alkyl" is as defined above. Non-limiting examples include —N($CH_3$)$_2$, —N($CH_3$)($CH_2$—$CH_3$).

The term "polyhalogenoalkyl" refers to an alkyl group as defined above wherein one or more hydrogen atom, carried by the same or different carbon atoms, is replaced by one or more halogen atoms. Non-limiting examples includes fluoromethyl, difluoromethyl, trifluoromethyl, 2-chloroethyl.

The term "polyhalogenoalkoxy" refers to a "(polyhalogenoalkyl)-O—" group wherein "polyhalogenoalkyl" is as defined above. Non-limiting examples includes fluoromethoxy, difluoromethoxy, trifluoromethoxy, 2-chloroethoxy.

The term "heterocycloalkyl" means a monovalent mono- or bi-cyclic aromatic or non-aromatic carbocyclic group containing from 3 to 10 ring members and containing from 1 to 3 heteroatoms selected from oxygen atom, sulfur atom and nitrogen atom. The heterocycloalkyl group can be linked by a carbon or a nitrogen atom when possible. The heterocycloalkyl group such defined can be a monocyclic ring system or a bi-cyclic ring system. Heterocycloalkyl monocyclic ring system include but is not limited to pyridinyl, piperazinyl, piperidinyl, tetrahydropyridinyl, tetrahydropyranyl, pyrrolidinyl, dihydropyrrolyl, oxolanyl, dihydrofuranyl, morpholinyl, pyrazolyl, azetidinyl, oxetanyl. When a bi-cyclic ring system is envisaged, the two rings can be:

- fused, meaning they share a common bond; exemplary heterocycloalkyl bi-cyclic fused systems include but is not limited to indolyl, indolinyl, benzopyranyl, benzofuranyl, naphthyridinyl, quinolinyl, pyridopyrazinyl, pyridopyridazinyl, pyridopyrimidinyl, dihydroquinolinyl, tetrahydroquinolinyl, dihydrobenzofuranyl, benzopyranyl, dihydrobenzopyranyl;
- linked via a bond between the two cyclic structures; exemplary heterocycloalkyl bi-cyclic linked systems include but is not limited to phenylpyridinyl, bipyridinyl, oxetanylpyridinyl, oxetanylpiperidinyl oxetanyltetrahydropyridinyl, pyrrolidinylpiperidinyl, morpholinopiperidinyl, pyrrolidinyltetrahydropyridinyl, pyrrolidinylpyridinyl, oxetanylpiperazinyl, pyrrolidinylpiperazinyl;
- bridged meaning that the two rings share three or more atoms, separating the two bridgehead atoms by a bridge containing at least one atom; exemplary heterocycloalkyl bi-cyclic bridged systems include but is not limited to azabicyclo[2.2.1]heptanyl, oxaazabicyclo[2.2.1]heptanyl;
- or represent a spiro bi-cyclic ring system wherein the two rings are connected through a single atom; exemplary heterocycloalkyl spiro bi-cyclic systems include but is not limited to oxaspirooctane, azaspirooctane, diazaspirooctane, oxaazaspirooctane, oxaspirononane, azaspirononane, diazaspirononane, oxaazaspirononane.

The "heterocycloalkyl group" such defined can be optionally substituted by 1 to 3 substituents chosen from alkyl group, halogen atoms, polyhalogenoalkyl group, polyhalogenoalkoxy group, alkoxy group, alkoxyalkyl group, hydroxy group, cyano group and oxo group. When the heterocycloalkyl group is substituted by 2 or 3 substituents, substituents can be beared by the same atom or different atoms, provided the valency of each atom is respected.

The term "heterocycloalkylalkyl" refers to a "(heterocycloalkyl)-(alkyl)-" group wherein the heterocycloalkyl and the alkyl moieties are as defined above. Non-limiting examples include morpholinylmethyl, pyrrolidinylmethyl, piperazinylmethyl, piperidinylmethyl.

The term "halogen atoms" means a fluorine, chlorine, bromine or iodine atom.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Specific embodiments of compounds of formula (I) of the invention are described below. Characteristics of those specific embodiments can be taken alone or combined to generate new specific embodiments.

In a specific embodiment, the invention more preferably refers to compounds of formula (I) wherein R represents a hydrogen atom.

In another embodiment, R represents advantageously a halogen atom, and most preferably a fluorine or a chlorine atom.

When R is an alkyl group, it is preferably a methyl group.

R is preferably linked to Z2 when Z2 represents a carbon atom.

In another specific preferred embodiment of the invention, Z1, Z2 and Z3 represent simultaneously a carbon atom.

In an advantageous alternative embodiment, one of Z1, Z2 and Z3 is a nitrogen atom while the two others represent a carbon atom. More particularly when one of Z1, Z2 and Z3 represents a nitrogen atom, it is preferentially Z1 or Z2.

Another specific embodiment of the invention relates to compounds of formula (I) wherein —X1- represents —O— or —NH—. More preferably, —X1- represents —O—.

In another specific embodiment of the invention, —X2- represents an alkanediyl group linear or branched having 2, 3, 4 or 5 carbon atoms, and more preferably 3, 4 or 5 carbon atoms. —X2- is preferably not substituted. When —X2- is substituted, fluor or methoxy group is preferred.

Advantageously —X2- represents $—(CH_2)_2—$, $—(CH_2)_3—$, $—CH(CH_3)—(CH_2)_2—$, $—(CH_2)_2—CH(CH_3)—$, $—CH_2—CH(CH_3)—CH_2—$,

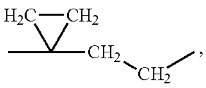

$—CH_2—CHF—CH_2—$, $—CH_2—CF_2—CH_2—$, $—(CH_2)_2—CH(CH_2—CH_3)—$ or $—CH(CH_2—CH_3)—(CH_2)_2—$. Even more preferably, —X2- represents $—(CH_2)_3—$, $—CH(CH_3)—(CH_2)_2—$, $—(CH_2)_2—CH(CH_3)—$, $—CH_2—CF_2—CH_2—$ or $—CH_2—CHF—CH_2—$.

The preferred value for Ra in compounds of formula (I) is hydrogen atom.

In another specific embodiment of the invention, —X3- represents an alkanediyl group linear or branched having 1, 2, 3, 4 or 5 carbon atoms, and more preferably 1 or 2 carbon atoms. —X3- is preferably not substituted. Advantageously —X3- represents $—CH_2—$, $—CH(CH_3)—$, $—(CH_2)_2—$, $—(CH_2)_3—$, $—CH(CH_2—CH_3)—$, $—CH(CH_3)—CH_2—$, $—CH_2—CH(CH_3)—$, $—CH_2—CH(i\text{-}Pr)—$, $—CH(i\text{-}Pr)—CH_2—$, $—CH_2—CH(Cy\text{-}Pr)—$, $—CH(Cy\text{-}Pr)—CH_2—$. Even more preferably, —X3- represents $—(CH_2)_2—$, $—CH_2—$ or $—CH(CH_3)—$.

Another specific embodiment of the present invention is represented by compounds of formula (I) for which A represents a group of formula (b):

(b)

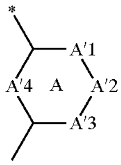

Preferred values for (A'1, A'2, A'3, A'4) are:

four carbon atoms, or three carbon atoms and one nitrogen atom, more preferably the nitrogen atom being in A'4, or two carbon atoms and two nitrogen atoms.

A'3 is advantageously a carbon atom.

As a particular embodiment of the invention, A represents the following preferred scaffolds, being represented herein without any substitution:

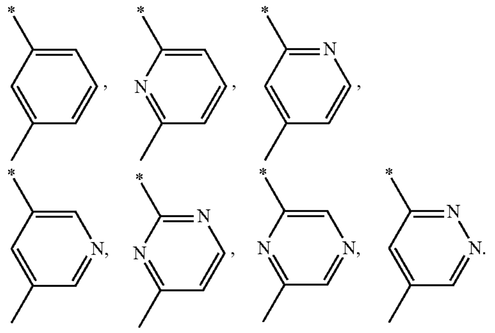

Most preferred embodiment for A of formula (b) is phenyl or pyridinyl group. An advantageous alternative for A is pyrazinyl group.

An advantageous alternative for A is represented by a group of formula (a):

(a)

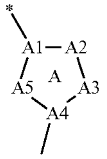

Most preferred scaffold of formula (a) contains one, two, or three heteroatoms, one of them being a nitrogen atom. Representative preferred scaffolds of formula (a) are as follows, being represented herein without any substitution:

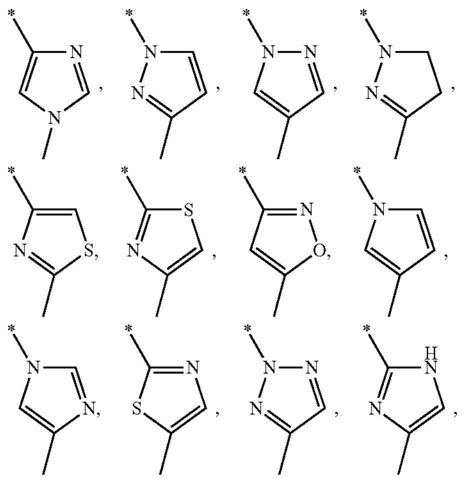

-continued

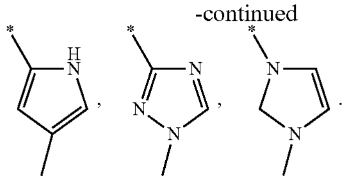

Most preferred embodiment for A of formula (a) is triazolyl or pyrazolyl group.

Preferentially the group A of the compounds of formula (I) is not substituted.

When the group A of the compounds of formula (I) is substituted, the substitution can occur on any carbon or nitrogen atom of the A scaffolds having at least one free valence. Most preferred substitutions include halogen atoms, cyano group, cyanoalkyl group, oxo group, alkoxy group, alkyl group, cycloalkyl group and heterocycloalkyl group. Particularly, preferred substitutions include fluor, bromine, or chlorine atoms, methyl, ethyl, cyclopropyl, methoxy, isopropyloxy, cyano, cyanomethyl and oxo groups.

Most preferred heterocycloalkyl group include pyrrolidinyl group, piperazinyl group, morpholinyl group, azetidinyl group, piperidinyl, tetrahydropyridinyl, tetrahydrofuranyl, dihydrofuranyl, oxetanyl, pyrazolidinyl.

Most preferred substitutions of the group A are fluorine or bromine atom, methoxy group, methyl group, ethyl group, pyrrolidinyl group unsubstituted or substituted, piperazinyl group unsubstituted or substituted.

Another specific embodiment of the invention is represented by compounds of formula (I-a):

(I-a)

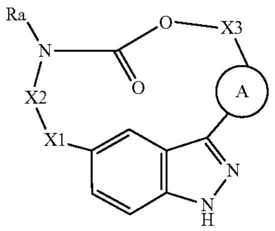

wherein X1, X2, X3, Ra and A are as defined for formula (I).

In another preferred embodiment the invention concerns compounds of formula (I-b):

(I-b)

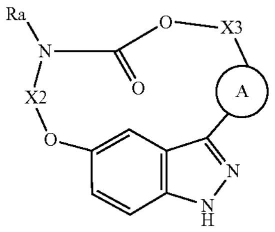

wherein X2, X3, Ra and A are as defined for formula (I). Most preferred compounds of formula (I-b) are those for which —X2- represents —$(CH_2)_3$—, —$CH(CH_3)$—$(CH_2)_2$—, —$CH_2$—CHF—$CH_2$—, —$CH_2$—$CF_2$—$CH_2$— or —$(CH_2)_2$—$CH(CH_3)$—. Another most preferred compounds of formula (I-b) are those for which —$X_3$— represents —$CH_2$— or —(CH)($CH_3$)—.

Another specific embodiment of the invention concerns compounds of formula (I) for which the —X1-X2-N(Ra)—C(O)O—X3- chain represents preferentially —O—$(CH_2)_3$—NH—C(O)O—$CH_2$—, —O—$CH(CH_3)$—$(CH_2)_2$—NH—C(O)O—$CH_2$—, —O—$CH_2$—CHF—$CH_2$—NHC(O)O—$CH_2$—, —O—$CH_2$—$CF_2$—$CH_2$—NHC(O)O—$CH_2$—, —O—$CH(CH_3)$—$(CH_2)_2$—NHC(O)O—$(CH_2)_2$— or —O—$CH(CH_3)$—$(CH_2)_2$—NH—C(O)O—$CH(CH_3)$—.

Preferentially, compounds of the invention are compounds of formula (I-c) or (I-c'):

(I-c)

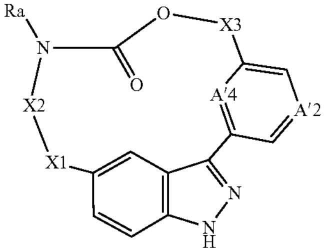

(I-c')

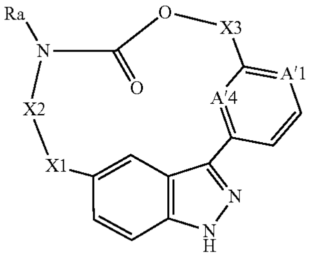

wherein X1, X2, X3, Ra, A'1, A'2 and A'4 are as defined for formula (I).

Another specific embodiment is related to compounds of formula (I-d) or (I-d'):

(I-d)

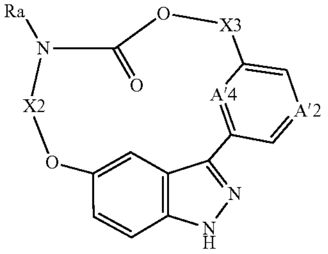

(I-d')

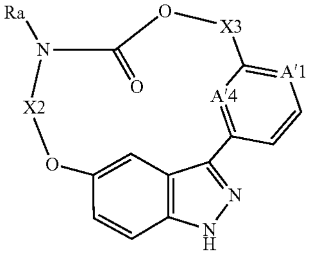

wherein X2, X3, Ra, A'1, A'2 and A'4 are as defined for formula (I). Most preferred compounds of formula (I-d) or (I-d') are those for which —X2- represents —$(CH_2)_3$—, —CH(CH$_3$)—(CH$_2$)$_2$—, —CH$_2$—CHF—CH$_2$—, —CH$_2$—CF$_2$—CH$_2$— or —(CH$_2$)$_2$—CH(CH$_3$)—. Another most preferred compounds of formula (I-d) or (I-d') are those for which —X3- represents —CH$_2$— or —(CH$_2$)$_2$—.

Another preferred compounds of the invention are compounds of formula (I-e):

(I-e)

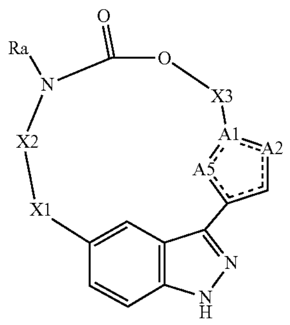

wherein X1, X2, X3, Ra, A1, A2 and A5 are as defined for formula (I).

Another preferred compounds of the invention are compounds of formula (I-f):

(I-f)

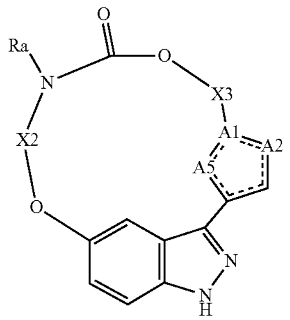

wherein X2, X3, Ra, A1, A2 and A5 are as defined for formula (I). Most preferred compounds of formula (I-f) are those for which —X2- represents —(CH$_2$)$_3$—, —CH(CH$_3$)—(CH$_2$)$_2$—, —CH$_2$—CHF—CH$_2$—, —CH$_2$—CF$_2$—CH$_2$— or —(CH$_2$)$_2$—CH(CH$_3$)—. Another most preferred compounds of formula (I-f) are those for which —X3- represents —CH$_2$— or —(CH$_2$)$_2$—.

In another specific embodiment, preferred compounds of the invention are:

8,14-dioxa-4,10,19,20-tetraazatetracyclo[13.5.2.1$^{2,6}$.0$^{18,21}$]$^{tricosa-}$1(20),2,4,6(23),15,17,21-heptaen-9-one;

10-methyl-8,14-dioxa-4,10,19,20-tetraazatetracyclo[13.5.2.1$^{2,6}$.0$^{18,21}$]tricosa-1(20),2,4, 6(23),15,17,21-heptaen-9-one;

4-fluoro-8,14-dioxa-10,19,20-triazatetracyclo[13.5.2.1$^{2,6}$.0$^{18,21}$]tricosa-1(20),2,4,6(23), 15,17,21-heptaen-9-one;

8,14-dioxa-10,19,20,23-tetraazatetracyclo[13.5.2.1$^{2,6}$.0$^{18,21}$]tricosa-1(20),2,4,6(23), 15,17,21-heptaen-9-one;

8,14-dioxa-10,19,20-triazatetracyclo[13.5.2.1$^{2,6}$.0$^{18,21}$]tricosa-1(20),2,4,6(23),15,17,21-heptaen-9-one;

10-(propan-2-yl)-8,14-dioxa-4,10,19,20-tetraazatetracyclo[13.5.2.1$^{2,6}$.0$^{18,21}$]tricosa-1(20),2,4,6(23),15,17,21-heptaen-9-one;

8,14-dioxa-5,10,19,20-tetraazatetracyclo[13.5.2.1$^{2,6}$.0$^{18,21}$]tricosa-1(20),2,4,6(23), 15,17,21-heptaen-9-one;

4-methoxy-8,14-dioxa-10,19,20-triazatetracyclo[13.5.2.1$^{2,6}$.0$^{18,21}$]tricosa-1(20),2,4, 6(23),15,17,21-heptaen-9-one;

4-bromo-8,14-dioxa-10,19,20-triazatetracyclo[13.5.2.1$^{2,6}$.0$^{18,21}$]tricosa-1(20),2,4,6(23), 15,17,21-heptaen-9-one;

5-fluoro-8,14-dioxa-10,19,20-triazatetracyclo[13.5.2.1$^{2,6}$.0$^{18,21}$]tricosa-1(20),2,4,6(23), 15,17,21-heptaen-9-one;

5-methyl-8,14-dioxa-10,19,20-triazatetracyclo[13.5.2.1$^{2,6}$.0$^{18,21}$]tricosa-1(20),2,4,6(23), 15,17,21-heptaen-9-one;

4-(pyrrolidin-1-yl)-8,14-dioxa-10,19,20-triazatetracyclo[13.5.2.1$^{2,6}$.0$^{18,21}$]tricosa-1(20), 2,4,6(23),15,17,21-heptaen-9-one;

4-[4-(propan-2-yl)piperazin-1-yl]-8,14-dioxa-10,19,20-triazatetracyclo[13.5.2.1$^{2,6}$.0$^{18,21}$]tricosa-1(20),2,4,6(23), 15,17,21-heptaen-9-one;

4-{2-oxa-6-azaspiro[3.4]octan-6-yl}-8,14-dioxa-10,19,20-triazatetracyclo[13.5.2.1$^{2,6}$.0$^{18,21}$]tricosa-1(20),2,4,6(23), 15,17,21-heptaen-9-one;

4-[4-(oxetan-3-yl)piperazin-1-yl]-8,14-dioxa-10,19,20-triazatetracyclo[13.5.2.1$^{2,6}$.0$^{18,21}$]tricosa-1(20),2,4,6(23), 15,17,21-heptaen-9-one;

4-(morpholin-4-yl)-8,14-dioxa-10,19,20-triazatetracyclo[13.5.2.1$^{2,6}$.0$^{18,21}$]tricosa-1(20), 2,4,6(23),15,17,21-heptaen-9-one;

4-[(2R,6S)-2,6-dimethylmorpholin-4-yl]-8,14-dioxa-10,19,20-triazatetracyclo[13.5.2.1$^{2,6}$.0$^{18,21}$]tricosa-1(20),2,4,6(23),15,17,21-heptaen-9-one;

4-methyl-8,14-dioxa-10,19,20-triazatetracyclo[13.5.2.1$^{2,6}$.0$^{18,21}$]tricosa-1(20),2,4,6(23), 15,17,21-heptaen-9-one;

5-methoxy-8,14-dioxa-10,19,20-triazatetracyclo[13.5.2.1$^{2,6}$.0$^{18,21}$]tricosa-1(20),2,4, 6(23),15,17,21-heptaen-9-one;

4-(4,4-difluoropiperidin-1-yl)-8,14-dioxa-10,19,20-triazatetracyclo[13.5.2.1$^{2,6}$.0$^{18,21}$]tricosa-1(20),2,4,6(23),15, 17,21-heptaen-9-one;

4-(3,3-difluoropyrrolidin-1-yl)-8,14-dioxa-10,19,20-triazatetracyclo[13.5.2.1$^{2,6}$.0$^{18,21}$]tricosa-1(20),2,4,6(23),15, 17,21-heptaen-9-one;

7-methyl-8,14-dioxa-10,19,20-triazatetracyclo[13.5.2.1$^{2,6}$.0$^{18,21}$]tricosa-1(20),2,4,6(23), 15,17,21-heptaen-9-one;

4-[4-(2-methoxyethyl)piperidin-1-yl]-8,14-dioxa-10,19,20-triazatetracyclo[13.5.2.1$^{2,6}$.0$^{18,21}$]tricosa-1(20),2,4,6(23), 15,17,21-heptaen-9-one;

9,14-dioxa-11,19,20-triazatetracyclo[13.5.2.1$^{2,6}$.0$^{18,21}$]tricosa-1(20),2,4,6(23),15,17,21-heptaen-10-one;

4-[(3R)-3-hydroxypyrrolidin-1-yl]-8,14-dioxa-10,19,20-triazatetracyclo[13.5.2.1$^{2,6}$.0$^{18,21}$]tricosa-1(20),2,4,6(23), 15,17,21-heptaen-9-one;

4-[(2-methoxyethyl)(methyl)amino]-8,14-dioxa-10,19,20-triazatetracyclo[13.5.2.1$^{2,6}$.0$^{18,21}$]tricosa-1(20),2,4,6(23), 15,17,21-heptaen-9-one;

4-chloro-8,14-dioxa-10,19,20-triazatetracyclo[13.5.2.1$^{2,6}$.0$^{18,21}$]tricosa-1(20),2,4,6(23), 15,17,21-heptaen-9-one;

4-fluoro-5-methyl-8,14-dioxa-10,19,20-triazatetracyclo[13.5.2.1$^{2,6}$.0$^{18,21}$]tricosa-1(20),2,4,6(23),15,17,21-heptaen-9-one;

4,5-difluoro-8,14-dioxa-10,19,20-triazatetracyclo[13.5.2.1$^{2,6}$.0$^{18,21}$]tricosa-1(20),2,4, 6(23),15,17,21-heptaen-9-one;

5-bromo-8,14-dioxa-10,19,20-triazatetracyclo[13.5.2.1$^{2,6}$.0$^{18,21}$]tricosa-1(20),2,4,6(23), 15,17,21-heptaen-9-one;

4-(4-methylpiperazin-1-yl)-8,14-dioxa-10,19,20-triazatetracyclo[13.5.2.1$^{2,6}$.0$^{18,21}$]tricosa-1(20),2,4,6(23),15,17,21-heptaen-9-one;

4-(3-methoxyazetidin-1-yl)-8,14-dioxa-10,19,20-triazatetracyclo[13.5.2.1$^{2,6}$.0$^{18,21}$]tricosa-1(20),2,4,6(23),15,17, 21-heptaen-9-one;

1-{9-oxo-8,14-dioxa-10,19,20-triazatetracyclo[13.5.2.1$^{2,6}$.0$^{18,21}$]tricosa-1(20),2,4,6(23), 15,17,21-heptaen-4-yl}piperidine-4-carbonitrile;

4-[4-(pyrrolidin-1-yl)piperidin-1-yl]-8,14-dioxa-10,19,20-triazatetracyclo[13.5.2.1$^{2,6}$.0$^{18,21}$]tricosa-1(20),2,4,6(23),15,17,21-heptaen-9-one;

4-(azetidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one;

4-(piperidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one;

4-(2,5-dihydrofuran-3-yl)-8,14-dioxa-10,19,20-triazatetracyclo[13.5.2.1$^{2,6}$.0$^{18,21}$]tricosa-1(20),2,4,6(23),15,17,21-heptaen-9-one;

4-[4-(morpholin-4-yl)piperidin-1-yl]-8,14-dioxa-10,19,20-triazatetracyclo[13.5.2.1$^{2,6}$.0$^{18,21}$]tricosa-1(20),2,4,6(23),15,17,21-heptaen-9-one;

4-(1-methyl-1,2,3,6-tetrahydropyridin-4-yl)-8,14-dioxa-10,19,20-triazatetracyclo[13.5.2.1$^{2,6}$.0$^{18,21}$]tricosa-1(20),2,4,6(23),15,17,21-heptaen-9-one;

4-[(2S,5S)-2,5-dimethylmorpholin-4-yl]-8,14-dioxa-10,19,20-triazatetracyclo[13.5.2.1$^{2,6}$.0$^{18,21}$]tricosa-1(20),2,4,6(23),15,17,21-heptaen-9-one;

4-[(morpholin-4-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one;

4-[(pyrrolidin-1-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one;

4-[(pyrrolidin-1-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one;

4-[(4-methylpiperazin-1-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one;

5-(morpholin-4-yl)-8,14-dioxa-10,19,20-triazatetracyclo[13.5.2.1$^{2,6}$.0$^{18,21}$]tricosa-1(20),2,4,6(23),15,17,21-heptaen-9-one;

4-[4-(2-methoxyethyl)piperazin-1-yl]-8,14-dioxa-10,19,20-triazatetracyclo[13.5.2.1$^{2,6}$.0$^{18,21}$]tricosa-1(20),2,4,6(23),15,17,21-heptaen-9-one;

4-(diethylamino)-8,14-dioxa-10,19,20-triazatetracyclo[13.5.2.1$^{2,6}$.0$^{18,21}$]tricosa-1(20),2,4,6(23),15,17,21-heptaen-9-one;

4-cyclopropyl-8,14-dioxa-10,19,20-triazatetracyclo[13.5.2.1$^{2,6}$.0$^{18,21}$]tricosa-1(20),2,4,6(23),15,17,21-heptaen-9-one;

5-(4-methylpiperazin-1-yl)-8,14-dioxa-10,19,20-triazatetracyclo[13.5.2.1$^{2,6}$.0$^{18,21}$]tricosa-1(20),2,4,6(23),15,17,21-heptaen-9-one;

13-methyl-8,14-dioxa-10,19,20-triazatetracyclo[13.5.2.1$^{2,6}$.0$^{18,21}$]tricosa-1(20),2,4,6(23), 15,17,21-heptaen-9-one;

8,14-dioxa-4,5,10,19,20-pentaazatetracyclo[13.5.2.1$^{2,5}$.0$^{18,21}$]tricosa-1(20),2(23),3, 15(22),16,18(21)-hexaen-9-one;

4-[methyl(oxetan-3-yl)amino]-8,14-dioxa-10,19,20-triazatetracyclo[13.5.2.1$^{2,6}$.0$^{18,21}$]tricosa-1(20),2,4,6(23),15,17,21-heptaen-9-one;

4-[(dimethylamino)methyl]-8,14-dioxa-10,19,20-triazatetracyclo[13.5.2.1$^{2,6}$.0$^{18,21}$]tricosa-1(20),2,4,6(23),15,17,21-heptaen-9-one;

4,10-dimethyl-8,14-dioxa-10,19,20-triazatetracyclo[13.5.2.1$^{2,6}$.0$^{18,21}$]tricosa-1(20),2,4, 6(23),15,17,21-heptaen-9-one;

4-(propan-2-yloxy)-8,14-dioxa-10,19,20-triazatetracyclo[13.5.2.1$^{2,6}$.0$^{18,21}$]tricosa-1(20),2,4,6(23),15,17,21-heptaen-9-one;

4-fluoro-7-methyl-8,14-dioxa-10,19,20-triazatetracyclo[13.5.2.1$^{2,6}$.0$^{18,21}$]tricosa-1(20),2,4,6(23),15,17,21-heptaen-9-one;

4-[1-(oxetan-3-yl)-1,2,3,6-tetrahydropyridin-4-yl]-8,14-dioxa-10,19,20-triazatetracyclo[13.5.2.1$^{2,6}$.0$^{18,21}$]tricosa-1(20),2,4,6(23),15,17,21-heptaen-9-one;

4-(3-methylpiperidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one;

4-[(3S)-3-hydroxypyrrolidin-1-yl]-8,14-dioxa-10,19,20-triazatetracyclo[13.5.2.1$^{2,6}$.0$^{18,21}$]tricosa-1(20),2,4,6(23),15,17,21-heptaen-9-one;

4-fluoro-8,14-dioxa-10,19,20-triazapentacyclo[13.5.2.1$^{2,6}$.1$^{7,10}$.0$^{18,21}$]tetracosa-1(20), 2(24),3,5,15(22),16,18(21)-heptaen-9-one;

4-(oxolan-3-yl)-8,14-dioxa-10,19,20-triazatetracyclo[13.5.2.1$^{2,6}$.0$^{18,21}$]tricosa-1(20), 2,4,6(23),15,17,21-heptaen-9-one;

(13S)-13-methyl-8,14-dioxa-10,19,20-triazatetracyclo[13.5.2.1$^{2,6}$.0$^{18,21}$]tricosa-1(20), 2(23),3,5,15(22),16,18(21)-heptaen-9-one;

(13R)-13-methyl-8,14-dioxa-10,19,20-triazatetracyclo[13.5.2.1$^{2,6}$.0$^{18,21}$]tricosa-1(20), 2(23),3,5,15(22),16,18(21)-heptaen-9-one;

4-(1-methyl-1H-pyrazol-3-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one;

(7S)-7-methyl-8,14-dioxa-10,19,20-triazatetracyclo[13.5.2.1$^{2,6}$.0$^{18,21}$]tricosa-1(20), 2(23),3,5,15(22),16,18(21)-heptaen-9-one;

4-[2-(morpholin-4-yl)ethoxy]-8,14-dioxa-10,19,20-triazatetracyclo[13.5.2.1$^{2,6}$.0$^{18,21}$]tricosa-1(20),2(23),3,5,15(22),16,18(21)-heptaen-9-one;

4-(2-methoxyethyl)-8,14-dioxa-10,19,20-triazatetracyclo[13.5.2.1$^{2,6}$.0$^{18,21}$]tricosa-1(20), 2(23), 3,5,15(22),16,18(21)-heptaen-9-one;

(7R)-7-methyl-8,14-dioxa-10,19,20-triazatetracyclo[13.5.2.1$^{2,6}$.0$^{18,21}$]tricosa-1(20), 2(23),3,5,15(22),16,18(21)-heptaen-9-one;

5-cyclopropyl-8,14-dioxa-10,19,20-triazatetracyclo[13.5.2.1$^{2,6}$.0$^{18,21}$]tricosa-1(20),2,4,6(23),15,17,21-heptaen-9-one;

4-(2-methoxyethoxy)-8,14-dioxa-10,19,20-triazatetracyclo[13.5.2.1$^{2,6}$.0$^{18,21}$]tricosa-1(20),2,4,6(23),15,17,21-heptaen-9-one;

4-fluoro-13-methyl-8,14-dioxa-10,19,20-triazatetracyclo[13.5.2.1$^{2,6}$.0$^{18,21}$]tricosa-1(20), 2,4,6(23),15,17,21-heptaen-9-one;

11-methyl-8,14-dioxa-10,19,20-triazatetracyclo[13.5.2.1$^{2,6}$.0$^{18,21}$]tricosa-1(20),2,4,6(23), 15,17,21-heptaen-9-one;

4-(3-oxomorpholin-4-yl)-8,14-dioxa-10,19,20-triazatetracyclo[13.5.2.1$^{2,6}$.0$^{18,21}$]tricosa-1(20), 2(23),3,5,15(22),16,18(21)-heptaen-9-one;

4-(2-oxopyrrolidin-1-yl)-8,14-dioxa-10,19,20-triazatetracyclo[13.5.2.1$^{2,6}$.0$^{18,21}$]tricosa-1(20),2(23), 3,5,15(22),16,18(21)-heptaen-9-one;

5-(2-oxopyrrolidin-1-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one;

4-(2-methylpyrrolidin-1-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one;

2-{9-oxo-8,14-dioxa-10,19,20-triazatetracyclo[13.5.2.1$^{2,6}$.0$^{18,21}$]tricosa-1(20),2(23), 3,5,15(22),16,18(21)-heptaen-4-yl}acetonitrile;

(11R)-11-methyl-8,14-dioxa-10,19,20-triazatetracyclo[13.5.2.1$^{2,6}$.0$^{18,21}$]tricosa-1(20), 2(23),3,5,15(22),16,18(21)-heptaen-9-one;

(11S)-11-methyl-8,14-dioxa-10,19,20-triazatetracyclo[13.5.2.$1^{2,6}$.$0^{18,21}$]tricosa-1(20), 2(23),3,5,15(22),16,18(21)-heptaen-9-one;

4-ethynyl-8,14-dioxa-10,19,20-triazatetracyclo[13.5.2.$1^{2,6}$.$0^{18,21}$]tricosa-1(20),2(23),3,5, 15(22),16,18(21)-heptaen-9-one;

4-(piperazin-1-yl)-8,14-dioxa-10,19,20-triazatetracyclo[13.5.2.$1^{2,6}$.$0^{18,21}$]tricosa-1(20), 2(23),3,5,15(22),16,18(21)-heptaen-9-one;

4-(1,2,3,6-tetrahydropyridin-4-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one;

11-(methoxymethyl)-8,14-dioxa-10,19,20-triazatetracyclo[13.5.2.$1^{2,6}$.$0^{18,21}$]tricosa-1(20),2(23),3,5,15(22),16,18(21)-heptaen-9-one;

8,14-dioxa-5,10,19,20,23-pentaazatetracyclo[13.5.2.$1^{2,5}$.$0^{18,21}$]tricosa-1(20),2(23),3, 15(22),16,18(21)-hexaen-9-one;

11-methyl-8,14-dioxa-4,5,10,19,20-pentaazatetracyclo[13.5.2.$1^{2,5}$.$0^{18,21}$]tricosa-1(20), 2(23),3,15(22),16,18(21)-hexaen-9-one;

12-methyl-8,14-dioxa-10,19,20-triazatetracyclo[13.5.2.$1^{2,6}$.$0^{18,21}$]tricosa-1(20),2(23),3,5, 15(22),16,18(21)-heptaen-9-one;

11-ethyl-8,14-dioxa-10,19,20-triazatetracyclo[13.5.2.$1^{2,6}$.$0^{18,21}$]tricosa-1(20),2(23),3,5, 15(22),16,18(21)-heptaen-9-one;

4-fluoro-5,7-dimethyl-8,14-dioxa-10,19,20-triazatetracyclo[13.5.2.$1^{2,6}$.$0^{18,21}$]tricosa-1(20),2(23), 3,5,15(22),16,18(21)-heptaen-9-one;

4-fluoro-5-methoxy-7-methyl-8,14-dioxa-10,19,20-triazatetracyclo[13.5.2.$1^{2,6}$.$0^{18,21}$]tricosa-1(20),2(23),3,5,15(22),16,18(21)-heptaen-9-one;

5-fluoro-4,7-dimethyl-8,14-dioxa-10,19,20-triazatetracyclo[13.5.2.$1^{2,6}$.$0^{18,21}$]tricosa-1(20),2(23),3,5,15(22),16,18(21)-heptaen-9-one;

8,14-dioxa-10,19,20-triazapentacyclo[13.5.2.$1^{2,6}$.$1^{7,10}$.$0^{18,21}$]tetracosa-1(20),2(24),3,5, 15(22),16,18(21)-heptaen-9-one;

13-methyl-8,14-dioxa-10,19,20,23-tetraazatetracyclo[13.5.2.$1^{2,6}$.$0^{18,21}$]tricosa-1(20), 2(23),3,5,15(22),16,18(21)-heptaen-9-one;

12-methyl-8,14-dioxa-4,5,10,19,20-pentaazatetracyclo[13.5.2.$1^{2,5}$.$0^{18,21}$]tricosa-1(20), 2(23),3,15(22),16,18(21)-hexaen-9-one;

7-methyl-8,14-dioxa-4,5,10,19,20-pentaazatetracyclo[13.5.2.$1^{2,5}$.$0^{18,21}$]tricosa-1(20), 2(23),3,15(22),16,18(21)-hexaen-9-one;

5-fluoro-4-methoxy-7-methyl-8,14-dioxa-10,19,20-triazatetracyclo[13.5.2.$1^{2,6}$.$0^{18,21}$]tricosa-1(20),2(23),3,5,15(22),16,18(21)-heptaen-9-one;

(7R,13R)-7,13-dimethyl-8,14-dioxa-10,19,20-triazatetracyclo[13.5.2.$1^{2,6}$.$0^{18,21}$]tricosa-1(20),2(23),3,5,15(22),16,18(21)-heptaen-9-one;

(13R)-13-methyl-8,14-dioxa-4,5,10,19,20-pentaazatetracyclo[13.5.2.$1^{2,5}$.$0^{18,21}$]tricosa-1(20),2(23),3,15,17,21-hexaen-9-one;

8,15-dioxa-4,10,20,21-tetraazapentacyclo[14.5.2.$1^{2,6}$.$1^{10,13}$.$0^{19,22}$]pentacosa-1(21),2(25), 3,5,16(23),17,19(22)-heptaen-9-one;

8,14-dioxa-5,10,19,20-tetraazatetracyclo[13.5.2.$1^{2,5}$.$0^{18,21}$]tricosa-1(20),2(23),3,15(22), 16,18(21)-hexaen-9-one;

(13S)-4-fluoro-13-methyl-8,14-dioxa-10,19,20-triazatetracyclo[13.5.2.$1^{2,6}$.$0^{18,21}$]tricosa-1(20),2(23),3,5,15(22),16,18(21)-heptaen-9-one;

(13R)-4-fluoro-13-methyl-8,14-dioxa-10,19,20-triazatetracyclo[13.5.2.$1^{2,6}$.$0^{18,21}$]tricosa-1(20),2(23),3,5,15(22),16,18(21)-heptaen-9-one;

(13R)-13-methyl-8,14-dioxa-4,10,19,20-tetraazatetracyclo[13.5.2.$1^{2,6}$.$0^{18,21}$]tricosa-1(20),2(23), 3,5,15(22),16,18(21)-heptaen-9-one;

6-cyclopropyl-8,14-dioxa-4,5,10,19,20-pentaazatetracyclo[13.5.2.$1^{2,5}$.$0^{18,21}$]tricosa-1(20), 2(23),3,15(22),16,18(21)-hexaen-9-one;

7-ethyl-8,14-dioxa-10,19,20-triazatetracyclo[13.5.2.$1^{2,6}$.$0^{18,21}$]tricosa-1(20),2,4,6(23), 15,17,21-heptaen-9-one;

(13R)-13-ethyl-8,14-dioxa-5,10,19,20,23-pentaazatetracyclo[13.5.2.$1^{2,6}$.$0^{18,21}$]tricosa-1(20),2,4,6(23), 15,17,21-heptaen-9-one;

(7R,13R)-4-fluoro-7,13-dimethyl-8,14-dioxa-10,19,20-triazatetracyclo[13.5.2.$1^{2,6}$.$0^{18,21}$]tricosa-1(20),2,4,6(23),15,17,21-heptaen-9-one;

7-methyl-8,14-dioxa-4,10,19,20-tetraazatetracyclo[13.5.2.$1^{2,6}$.$0^{18,21}$]tricosa-1(20),2,4, 6(23),15,17,21-heptaen-9-one;

(7R)-4-fluoro-7-methyl-8,14-dioxa-10,19,20-triazatetracyclo[13.5.2.$1^{2,6}$.$0^{18,21}$]tricosa-1(20),2,4,6(23),15,17,21-heptaen-9-one;

(7S)-4-fluoro-7-methyl-8,14-dioxa-10,19,20-triazatetracyclo[13.5.2.$1^{2,6}$.$0^{18,21}$]tricosa-1(20),2,4,6(23),15,17,21-heptaen-9-one;

6-methyl-8,14-dioxa-4,5,10,19,20-pentaazatetracyclo[13.5.2.$1^{2,5}$.$0^{18,21}$]tricosa-1(20), 2(23),3,15,17,21-hexaen-9-one;

7-methyl-8,14-dioxa-10,19,20,23-tetraazatetracyclo[13.5.2.$1^{2,6}$.$0^{18,21}$]tricosa-1(20),2,4, 6(23),15,17,21-heptaen-9-one;

6-(propan-2-yl)-8,14-dioxa-4,5,10,19,20-pentaazatetracyclo[13.5.2.$1^{2,5}$.$0^{18,21}$]tricosa-1(20),2(23),3,15(22),16,18(21)-hexaen-9-one;

(13R)-7,13-dimethyl-8,14-dioxa-4,5,10,19,20-pentaazatetracyclo[13.5.2.$1^{2,5}$.$0^{18,21}$]tricosa-1(20),2(23),3,15(22),16,18(21)-hexaen-9-one;

(13R)-13-methyl-8,14-dioxa-10,19,20,23-tetraazatetracyclo[13.5.2.$1^{2,6}$.$0^{18,21}$]tricosa-1(20),2,4,6(23),15,17,21-heptaen-9-one;

(7R)-7-ethyl-8,14-dioxa-10,19,20-triazatetracyclo[13.5.2.$1^{2,6}$.$0^{18,21}$]tricosa-1(20),2,4, 6(23),15,17,21-heptaen-9-one;

(7S)-7-ethyl-8,14-dioxa-10,19,20-triazatetracyclo[13.5.2.$1^{2,6}$.$0^{18,21}$]tricosa-1(20),2,4, 6(23),15,17,21-heptaen-9-one;

(13R)-13-methyl-8,14-dioxa-5,10,19,20-tetraazatetracyclo[13.5.2.$1^{2,6}$.$0^{18,21}$]tricosa-1(20),2,4,6(23),15,17,21-heptaen-9-one;

6-(oxan-4-yl)-8,14-dioxa-4,5,10,19,20-pentaazatetracyclo[13.5.2.$1^{2,5}$.$0^{18,21}$]tricosa-1(20),2(23),3,15,17,21-hexaen-9-one;

4-ethyl-8,14-dioxa-5,10,19,20,23-pentaazatetracyclo[13.5.2.$1^{2,5}$.$0^{18,21}$]tricosa-1(20), 2(23),15,17,21-pentaen-9-one;

(13R)-23-fluoro-13-methyl-8,14-dioxa-10,19,20-triazatetracyclo[13.5.2.$1^{2,6}$.$0^{18,21}$]tricosa-1(20),2,4,6(23),15,17,21-heptaen-9-one;

9,14-dioxa-4,5,11,19,20-pentaazatetracyclo[13.5.2.$1^{2,5}$.$0^{18,21}$]tricosa-1(20),2(23), 3,15,17,21-hexaen-10-one;

4-ethyl-8,14-dioxa-5,10,19,20,23-pentaazatetracyclo[13.5.2.$1^{2,5}$.$0^{18,21}$]tricosa-1(20), 2(23),3,15,17,21-hexaen-9-one;

3,9,15-trioxa-4,11,20,21-tetraazatetracyclo[14.5.2.$1^{2,5}$.$0^{19,22}$]tetracosa-1(21),2(24), 4,16,18,22-hexaen-10-one;

(13R)-16-fluoro-13-methyl-8,14-dioxa-4,10,19,20-tetraazatetracyclo[13.5.2.$1^{2,6}$.$0^{18,21}$]tricosa-1(20),2,4,6(23),15,17,21-heptaen-9-one;

(13R)-4-chloro-13-methyl-8,14-dioxa-10,19,20,23-tetraazatetracyclo[13.5.2.$1^{2,6}$.$0^{18,21}$]tricosa-1(20),2(23),3,5,15(22),16,18(21)-heptaen-9-one;

8,14-dioxa-2,4,10,19,20-pentaazatetracyclo[13.5.2.$1^{2,5}$.$0^{18,21}$]tricosa-1(20),3,5(23), 15(22),16,18(21)-hexaen-9-one;

(13R)-4-methoxy-13-methyl-8,14-dioxa-10,19,20,23-tetraazatetracyclo[13.5.2.$1^{2,6}$.$0^{18,21}$]tricosa-1(20),2,4,6(23),15,17,21-heptaen-9-one;

(13R)-13-methyl-9-oxo-8,14-dioxa-10,19,20-triazatetracyclo[13.5.2.$1^{2,6}$.$0^{18,21}$]tricosa-1(20),2,4,6(23),15,17,21-heptaene-5-carbonitrile;

(13R)-13-methyl-4-(pyrrolidin-1-yl)-8,14-dioxa-5,10,19,20,23-pentaazatetracyclo[13.5.2.$1^{2,6}$.$0^{18,21}$]tricosa-1(20),2,4,6(23),15,17,21-heptaen-9-one;

(7S,13R)-7,13-dimethyl-8,14-dioxa-5,10,19,20,23-pentaazatetracyclo[13.5.2.$1^{2,6}$.$0^{18,21}$]tricosa-1(20),2,4,6(23),15,17,21-heptaen-9-one;

(7R,13R)-7,13-dimethyl-8,14-dioxa-5,10,19,20,23-pentaazatetracyclo[13.5.2.$1^{2,6}$.$0^{18,21}$]tricosa-1(20),2,4,6(23),15,17,21-heptaen-9-one;

(13R)-16-fluoro-13-methyl-8,14-dioxa-10,19,20-triazatetracyclo[13.5.2.$1^{2,6}$.$0^{18,21}$]tricosa-1(20),2,4,6(23),15,17,21-heptaen-9-one;

(13R)-13-methyl-8,14-dioxa-4,10,19,20,23-pentaazatetracyclo[13.5.2.$1^{2,6}$.$0^{18,21}$]tricosa-1(20),2,4,6(23),15,17,21-heptaen-9-one;

8,14-dioxa-4-thia-10,19,20,23-tetraazatetracyclo[13.5.2.$1^{2,5}$.$0^{18,21}$]tricosa-1(20),2,5(23), 15,17,21-hexaen-9-one;

8,14-dioxa-3-thia-10,19,20,23-tetraazatetracyclo[13.5.2.$1^{2,5}$.$0^{18,21}$]tricosa-1(20),2(23), 4,15,17,21-hexaen-9-one;

(7R,13R)-7,13-dimethyl-8,14-dioxa-10,19,20,23-tetraazatetracyclo[13.5.2.$1^{2,6}$.$0^{18,21}$]tricosa-1(20),2,4,6(23),15,17,21-heptaen-9-one;

(13R)-4-[(3R)-3-methoxypyrrolidin-1-yl]-13-methyl-8,14-dioxa-5,10,19,20,23-pentaazatetracyclo[13.5.2.$1^{2,6}$.$0^{18,21}$]tricosa-1(20),2,4,6(23),15,17,21-heptaen-9-one;

(13R)-16-chloro-13-methyl-8,14-dioxa-10,19,20-triazatetracyclo[13.5.2.$1^{2,6}$.$0^{18,21}$]tricosa-1(20),2,4,6(23),15,17,21-heptaen-9-one;

(13R)-13,16-dimethyl-8,14-dioxa-10,19,20-triazatetracyclo[13.5.2.$1^{2,6}$.$0^{18,21}$]tricosa-1(20),2,4, 6(23),15,17,21-heptaen-9-one;

(13R)-13-methyl-8,14-dioxa-3,10,19,20,23-pentaazatetracyclo[13.5.2.$1^{2,6}$.$0^{18,21}$]tricosa-1(20),2,4, 6(23),15,17,21-heptaen-9-one;

8-oxa-10,14,19,20-tetraazatetracyclo[13.5.2.$1^{2,6}$.$0^{18,21}$]tricosa-1(20),2(23),3,5,15(22), 16,18(21)-heptaen-9-one hydrochloride;

8-oxa-10,19,20-triazatetracyclo[13.5.2.$1^{2,6}$.$0^{18,21}$]tricosa-1(20),2(23),3,5,15(22),16,18(21)-heptaen-9-one;

(13R)-5-methoxy-13-methyl-8,14-dioxa-4,10,19,20-tetraazatetracyclo[13.5.2.$1^{2,6}$.$0^{18,21}$]tricosa-1(20),2,4,6(23),15,17,21-heptaen-9-one;

(13R)-13-methyl-8,14-dioxa-4,10,19,20-tetraazatetracyclo[13.5.2.$1^{2,6}$.$0^{18,21}$]tricosa-1(20),2, 6(23),15,17,21-hexaene-5,9-dione;

4-methyl-8,14-dioxa-3,4,10,19,20-pentaazatetracyclo[13.5.2.$1^{2,5}$.$0^{18,21}$]tricosa-1(20),2, 5(23),15(22),16,18(21)-hexaen-9-one;

(13R)-16-fluoro-13-methyl-8,14-dioxa-10,19,20,23-tetraazatetracyclo[13.5.2.$1^{2,6}$.$0^{18,21}$]tricosa-1(20),2,4,6(23),15,17,21-heptaen-9-one;

7,13-dioxa-4-thia-9,18,19,22-tetraazatetracyclo[12.5.2.$1^{2,5}$.$0^{17,20}$]docosa-1(19),2,5(22), 14(21),15,17(20)-hexaen-8-one;

(13R)-4,13-dimethyl-8,14-dioxa-5,10,19,20,23-pentaazatetracyclo[13.5.2.$1^{2,6}$.$0^{18,21}$]tricosa-1(20),2(23),3,5,15(22),16,18(21)-heptaen-9-one;

8,14-dioxa-23-thia-4,10,19,20-tetraazatetracyclo[13.5.2.$1^{2,5}$.$0^{18,21}$]tricosa-1(20),2,4,15(22), 16,18(21)-hexaen-9-one;

(7S,13R)-7,13-dimethyl-8,14-dioxa-10,19,20,23-tetraazatetracyclo[13.5.2.$1^{2,6}$.$0^{18,21}$]tricosa-1(20),2(23),3,5,15(22),16,18(21)-heptaen-9-one;

(13R)-13-methyl-9-oxo-8,14-dioxa-5,10,19,20-tetraazatetracyclo[13.5.2.$1^{2,5}$.$0^{18,21}$]tricosa-1(20), 2(23),3,15(22),16,18(21)-hexaene-4-carbonitrile;

12,12-difluoro-8,14-dioxa-10,19,20-triazatetracyclo[13.5.2.$1^{2,6}$.$0^{18,21}$]tricosa-1(20),2(23), 3,5,15(22),16,18(21)-heptaen-9-one;

(13R)-17-fluoro-13-methyl-8,14-dioxa-10,19,20-triazatetracyclo[13.5.2.$1^{2,6}$.$0^{18,21}$]tricosa-1(20),2(23),3,5,15(22),16,18(21)-heptaen-9-one;

(7S,13R)-7,13-dimethyl-8,14-dioxa-4,10,19,20,23-pentaazatetracyclo[13.5.2.$1^{2,6}$.$0^{18,21}$]tricosa-1(20),2(23),3,5,15(22),16,18(21)-heptaen-9-one;

(7R,13R)-7,13-dimethyl-8,14-dioxa-4,10,19,20,23-pentaazatetracyclo[13.5.2.$1^{2,6}$.$0^{18,21}$]tricosa-1(20),2(23),3,5,15(22),16,18(21)-heptaen-9-one;

(13S)-13-methyl-8,14-dioxa-4,10,19,20,23-pentaazatetracyclo[13.5.2.$1^{2,6}$.$0^{18,21}$]tricosa-1(20),2(23),3,5,15(22),16,18(21)-heptaen-9-one;

(13R)-13-methyl-8,14-dioxa-10,19,20,22-tetraazatetracyclo[13.5.2.$1^{2,6}$.$0^{18,21}$]tricosa-1(20), 2(23),3,5,15,17,21-heptaen-9-one;

(12R)-4,12-dimethyl-7,13-dioxa-4,9,18,19,22-pentaazatetracyclo[12.5.2.$1^{2,5}$.$0^{17,20}$]docosa-1(19),2,5(22),14(21),15,17(20)-hexaen-8-one;

(13R)-13-methyl-8,14-dioxa-4,5,10,19,20,23-hexaazatetracyclo[13.5.2.$1^{2,5}$.$0^{18,21}$]tricosa-1(20),2(23),3,15,17,21-hexaen-9-one;

(13R)-13-methyl-8,14-dioxa-23-thia-4,10,19,20-tetraazatetracyclo[13.5.2.$1^{2,5}$.$0^{18,21}$]tricosa-1(20),2,4,15,17,21-hexaen-9-one;

(13R)-4,13-dimethyl-8,14-dioxa-4,10,19,20,23-pentaazatetracyclo[13.5.2.$1^{2,5}$.$0^{18,21}$]tricosa-1(20),2,5(23),15(22),16,18(21)-hexaen-9-one;

(13R)-13-methyl-8,14-dioxa-10,16,19,20-tetraazatetracyclo[13.5.2.$1^{2,6}$.$0^{18,21}$]tricosa-1(20), 2(23),3,5,15(22),16,18(21)-heptaen-9-one;

14-methyl-8-oxa-10,14,19,20-tetraazatetracyclo[13.5.2.$1^{2,6}$.$0^{18,21}$]tricosa-1(20),2(23),3,5,15,17,21-heptaen-9-one;

(13R)-13-methyl-8,14-dioxa-4,10,19,20,22-pentaazatetracyclo[13.5.2.$1^{2,6}$.$0^{18,21}$]tricosa-1(20),2(23),3,5,15,17,21-heptaen-9-one;

(13R)-13-methyl-8,14-dioxa-10,17,19,20-tetraazatetracyclo[13.5.2.$1^{2,6}$.$0^{18,21}$]tricosa-1(20), 2(23),3,5,15(22),16,18(21)-heptaen-9-one;

8,14-dioxa-4,5,10,19,20,23-hexaazatetracyclo[13.5.2.$1^{2,5}$.$0^{18,21}$]tricosa-1(20),2(23),3, 15(22),16,18(21)-hexaen-9-one;

12,12-difluoro-8,14-dioxa-4,5,10,19,20,23-hexaazatetracyclo[13.5.2.$1^{2,5}$.$0^{18,21}$]tricosa-1(20),2(23),3,15(22),16,18(21)-hexaen-9-one);

(12R)-12-fluoro-8,14-dioxa-10,19,20-triazatetracyclo[13.5.2.$1^{2,6}$.$0^{18,21}$]tricosa-1(20),2(23), 3,5,15(22),16,18(21)-heptaen-9-one;

(12S)-12-fluoro-8,14-dioxa-10,19,20-triazatetracyclo[13.5.2.$1^{2,6}$.$0^{18,21}$]tricosa-1(20),2(23), 3,5,15(22),16,18(21)-heptaen-9-one;

12,12-difluoro-8,14-dioxa-4,10,19,20,23-pentaazatetracyclo[13.5.2.$1^{2,6}$.$0^{18,21}$]tricosa-1(20),2(23),3,5,15(22),16,18(21)-heptaen-9-one;

(12S)-12-fluoro-8,14-dioxa-4,10,19,20,23-pentaazatetracyclo[13.5.2.$1^{2,6}$.$0^{18,21}$]tricosa-1(20),2(23),3,5,15,17,21-heptaen-9-one;

(12R)-12-fluoro-8,14-dioxa-4,10,19,20,23-pentaazatetracyclo[13.5.2.$1^{2,6}$.$0^{18,21}$]tricosa-1(20),2(23),3,5,15,17,21-heptaen-9-one;

(12S)-12-fluoro-8,14-dioxa-4,5,10,19,20,23-hexaazatetracyclo[13.5.2.$1^{2,5}$.$0^{18,21}$]tricosa-1(20),2(23),3,15,17,21-hexaen-9-one;

(12R)-12-fluoro-8,14-dioxa-4,5,10,19,20,23-hexaazatetracyclo[13.5.2.$1^{2,5}$.$0^{18,21}$]tricosa-1(20),2(23),3,15,17,21-hexaen-9-one;

8',14'-dioxa-10',19',20'-triazaspiro[cyclopropane-1,13'-tetracyclo[13.5.2.$1^{2,6}$.$0^{18,21}$]tricosane]-1'(20'),2'(23'),3',5',15'(22'),16',18'(21')-heptaen-9'-one.

The invention relates also to a global process for the preparation of compounds of formula (I), which process is characterized that there is used as starting material the compound of formula (I-1):

(I-1)

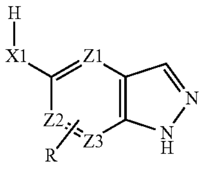

wherein R, X1, Z1, Z2 and Z3 are as defined for formula (I)

on which is condensed first a compound PG1-LG1, then a compound PG2-LG2, or first a compound PG2-LG2 then a compound PG1-LG1 wherein PG1 is a protecting group or, when —X1- is a bond PG1 represents a halogen, and PG2 is a protecting group and LG1 and LG2 are leaving groups, to yield the compound of formula (I-2):

(I-2)

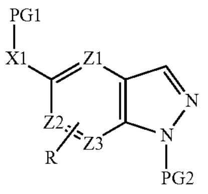

wherein R, X1, Z1, Z2, Z3, PG1 and PG2 are as defined hereinbefore, compound of formula (I-2) on which:

is condensed a leaving group LG3 to yield the compound of formula (I-3):

(I-3)

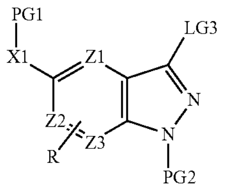

wherein R, X1, Z1, Z2, Z3, PG1, PG2 and LG3 are as defined hereinbefore, compound of formula (I-3):

on which is condensed, after deprotection of X1, a compound LG4-X2-NPG3 wherein LG4 is a leaving group, PG3 is a protecting group and X2 is as defined for formula (I) to yield the compound of formula (I-4):

(I-4)

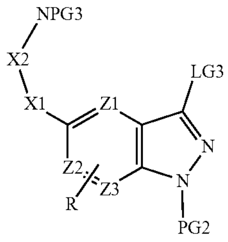

wherein R, X1, X2, Z1, Z2, Z3, PG2, PG3 and LG3 are as defined hereinbefore, compound of formula (I-4) on which is condensed a compound of formula (I-5):

(I-5)

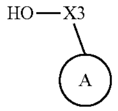

wherein A and X3 are as defined in formula (I), or an organometallic derivative of compound of formula (I-5) such as a boronate, to yield the compound of formula (I-6):

(I-6)

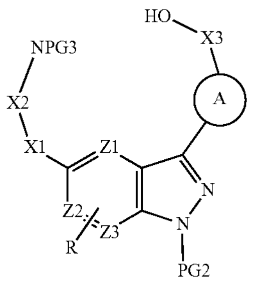

wherein R, X1, X2, X3, A, Z1, Z2, Z3, PG2 and PG3 are as defined hereinbefore, compound of formula (I-6) which is subjected to a deprotection of —X2-NPG3, then to a cyclization to give the compound of formula (I-7):

(I-7)

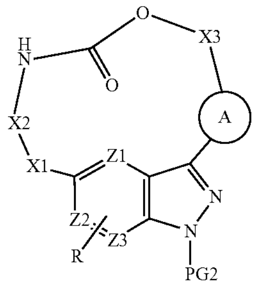

wherein R, X1, X2, X3, A, Z1, Z2, Z3 and PG2 are as defined hereinbefore, compound of formula (I-7) which is optionally alkylated on the carbamate function, and/or optionally substituted on the A ring, then submitted to the deprotection of —N(PG2)- to give the compound of formula (I), or compound of formula (I-3) on which is condensed a compound of formula (I-8):

(I-8)

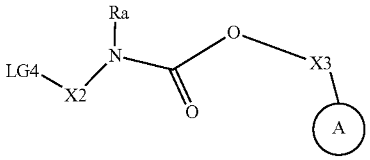

wherein Ra, X2, X3, and A are as defined hereinbefore and LG4 is a leaving group, or an organometallic derivative of compound of formula (I-8) such as a boronate, to yield the compound of formula (I-9):

(I-9)

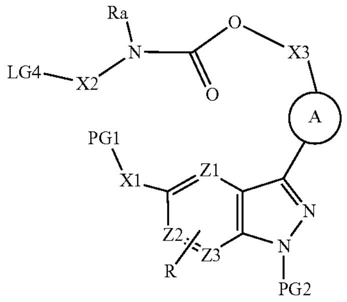

wherein R, Ra, X1, X2, X3, A, Z1, Z2, Z3, PG1, PG2 and LG4 are as defined hereinbefore, compound of formula (I-9) which is subjected, after deprotection of X1, to a cyclization to yield the compound of formula (I-7) as defined above, which, after deprotection of —N(PG2)-, and/or optional substitution on the A ring, gives the compound of formula (I), or compound of formula (I-3) on which is condensed, after deprotection of X1, a compound LG5-X2-NRa-COOBn wherein X2 and Ra are as defined in formula (I) and LG5 is a leaving group, to yield the compound of formula (I-10):

(I-10)

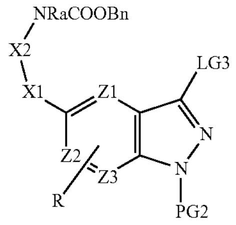

wherein R, Ra, X1, X2, Z1, Z2, Z3, PG2 and LG3 are as defined hereinbefore, compound of formula (I-10) on which is condensed a compound of formula (I-5):

(I-5)

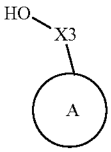

wherein X3 and A are as defined hereinbefore, or an organometallic derivative of compound of formula (I-5) such as a boronate, to yield the compound of formula (I-11):

(I-11)

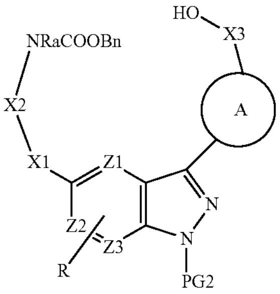

wherein R, Ra, X1, X2, X3, Z1, Z2, Z3, A and PG2 are as defined hereinbefore, compound of formula (I-11) which is subjected to a cyclization to yield the compound of formula (I-7) as defined above, which, after deprotection of —N(PG2)-, and/or optional substitution on the A ring, gives the compound of formula (I), or compound of formula (I-2) on which is condensed, after deprotection of X1, a compound of formula (I-12):

(I-12)

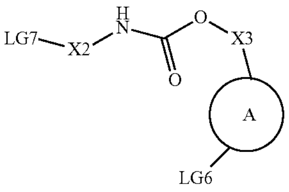

wherein A, X3 and X2 are as defined hereinbefore and LG6 and LG7 are leaving groups, to yield a compound of formula (I-13):

(I-13)

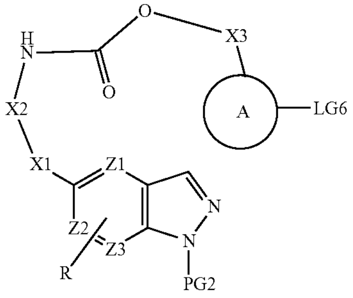

wherein R, X1, X2, X3, A, Z1, Z2, Z3, PG2 and LG6 are as defined hereinbefore, compound of formula (I-13) that is cyclized to yield the compound of formula (I-7) which is optionally alkylated on the carbamate function, then submitted to the deprotection of —N(PG2), and/or optionally substituted on the A ring, to give the compound of formula (I), or compound of formula (I-2) which is transformed in a boronic derivative of formula (I-14):

(I-14)

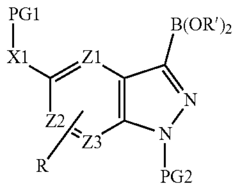

wherein R, X1, Z1, Z2, Z3, PG1 and PG2 are as defined hereinbefore, and R' represents a hydrogen atom or an alkyl group, it being understood that the two R' alkyl group can be linked to form a cyclic structure, compound of formula (I-14) on which is condensed a compound of formula (I-15):

(I-15)

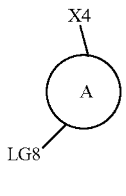

wherein A is as defined herein before, X4 is a carboxylic acid or an ester or a carbonyl derivative of X3, and LG8 is a leaving group, to yield the compound of formula (I-16):

(I-16)

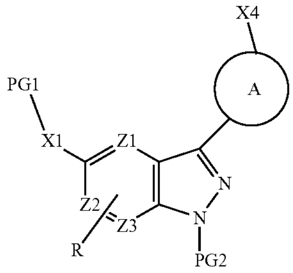

wherein R, X1, Z1, Z2, Z3, X4, PG1 and PG2 are as defined hereinbefore, compound of formula (I-16) on which is condensed, after deprotection of X1 a compound LG5-X2-NRaCOOBn as defined hereinbefore to yield the compound of formula (I-17):

(I-17)

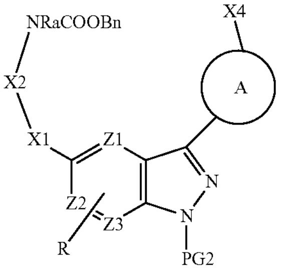

wherein R, Ra, X1, X2, Z1, Z2, Z3, X4 and PG2 are as defined hereinbefore, which is submitted to a reduction to yield the compound of formula (I-11) that is converted to compound of formula (I) as described hereinabove, or compound of formula (I-14) on which is condensed a compound of formula (I-18):

(I-18)

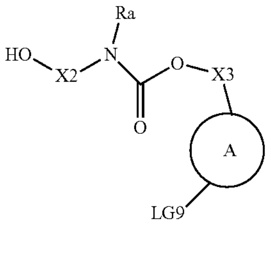

wherein A, X2, X3 and Ra are as defined herein before, and LG9 is a leaving group, to yield the compound of formula (I-19):

(I-19)

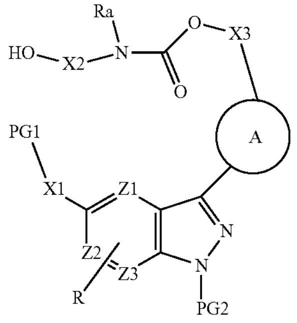

wherein R, Ra, A, X1, X2, X3, Z1, Z2, Z3, PG1 and PG2 are as defined hereinbefore, compound of formula (I-19) on which is introduced a leaving group to yield the compound of formula (I-9) as defined above, that is converted to compound of formula (I) as described above, or compound of formula (I-2) on which is condensed, after deprotection of X1, a compound LG5-X2-NRa-COOBn as defined hereinbefore to yield a compound of formula (I-20):

(I-20)

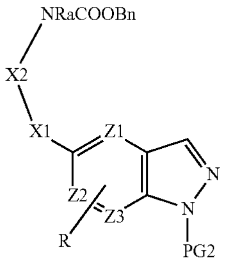

wherein R, Ra, X1, X2, Z1, Z2, Z3 and PG2 are as defined hereinbefore, compound of formula (I-20) which is transformed in a boronic derivative of formula (I-21):

(I-21)

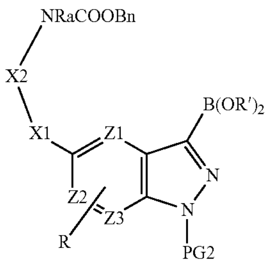

wherein R, Ra, X1, X2, Z1, Z2, Z3, PG2 and R' are as defined hereinbefore, compound of formula (I-21) on which is condensed a compound of formula (I-22):

(I-22)

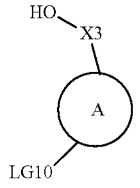

wherein X3 and A are as defined hereinbefore, and LG10 is a leaving group, to yield the compound of formula (I-11) that is converted to compound of formula (I) as described hereinabove, or compound of formula (I-21) on which is condensed a compound of formula (I-15) as defined hereinbefore to yield the compound of formula (I-17) that is converted to compound of formula (I) as described hereinabove, the compound of formula (I), may then be purified according to a conventional separation technique, and is converted, if desired, into its addition salts with a pharmaceutically acceptable acid or base and which is optionally separated into its isomers according to a conventional separation technique, it being understood that at any moment considered appropriate during the course of the process described above, some groups of the starting reagents or of the synthesis intermediates can be protected, subsequently deprotected and functionalized, as required by the synthesis.

The compounds of formulae (I-5), (I-8), (I-12), (I-15), (I-18) and (I-22) are either commercially available or can be obtained by the person skilled in the art using conventional chemical reactions described in the literature.

Pharmacological studies of the compounds of the invention of formula (I) exhibit inhibitory activity against LRRK2 kinase, including LRRK2 mutant kinase, such as mutant p.G2019S. Kinase activity can be determined using a kinase assay, which typically employs a kinase substrate and a phosphate group donor such as ATP (or a derivative thereof). An exemplary kinase assay is described in the Pharmacological Study.

Compounds of formula (I) of the invention or pharmaceutically acceptable salts thereof are inhibitors of LRRK2 kinase activity and are thus believed to be of potential use in the treatment of or prevention of diseases associated with or characterized by LRRK2 kinase activity such as neurological diseases, endosomal-lysosomal disorders, inflammatory diseases, bacterial, viral and parasitic infections, cardiovascular diseases, autoimmune diseases and cancers. Particularly compounds of the invention are useful in the treatment of neurological diseases including but not limited to Parkinson's disease (including sporadic Parkinson's disease patients as well as patients with LRRK2 mutations such as p.G2019S or Rab29/Rab7L1 polymorphisms), Alzheimer's disease, amyotrophic lateral sclerosis (ALS), dementia (including Lewy body dementia and vascular dementia, HIV-induced dementia), diabetic neuropathy, age related memory disfunction, mild cognitive impairment, argyrophilic grain disease, Pick's disease, epilepsy, tauopathies such as progressive supranuclear palsy and corticobasal degeneration, other synucleinopathies such as multiple system atrophy, frontotemporal dementia, inherited frontotemporal dementia and parkinsonism linked to chromosome 17 (FTDP-17), withdrawal symptoms/relapse associated with drug addiction, L-Dopa induced dyskinesia, ischemic stroke, traumatic brain injury, spinal cord injury and multiple sclerosis.

Other diseases potentially treatable by inhibition of LRRK2 activity are endosomal-lysosomal diseases including but not limited to Niemann-Pick Type A, B or C disease, Gaucher's disease, Krabbe's disease, Fabry's disease and disorders with mitochondrial deficits; inflammatory diseases including but not limited to vasculitis, pulmonary diseases such as chronic obstructive pulmonary disease, idiopathic pulmonary fibrosis, inflammatory myopathies, ankylosing spondylitis; autoimmune diseases including but not limited to Crohn's disease, inflammatory bowel disease, rheumatoid arthritis, ulcerative colitis, lupus, autoimmune hemolytic anemia, pure red cell aplasia, idiopathic thrombocytopenic purpura, type 1 diabetes mellitus, obesity, Evans syndrome, bullous skin disorders, Sjogren's syndrome, Devic's disease and leprosy. Compounds of the invention have also anti carcinogenic effects and are potentially useful in the treatment of cancers including but not limited to thyroid cancer, renal cancer (including papillary renal), breast cancer, hormone-related cancer, adeno- and squamous lung cancer, non-small-cell lung cancer, colon cancer, prostate cancers, skin cancers, leukemias (including acute myelogenous leukemia) and lymphomas.

Compounds of the invention are also potentially useful in the treatment of cardiovascular diseases including but not limited to stroke.

Other diseases potentially treatable by compounds of the invention are bacterial infections such as but not limited to leprosy and tuberculosis; viral infections such as but not limited to coronavirus such as SARS-CoV, MERS-CoV and SARS-CoV-2, HIV, West Nile virus and chikungunya virus.

Another aspect of the invention is related to pharmaceutical compositions comprising at least one compound of formula (I) in combination with one or more pharmaceutically acceptable excipients. In particular, these pharmaceutical compositions are interesting for use in the treatment or prevention of diseases associated with or characterized by LRRK2 kinase activity such as but not limited to neurological diseases, endosomal-lysosomal disorders, inflammatory diseases, bacterial, viral and parasitic infections, cardiovascular diseases, autoimmune diseases and cancers. In a specific embodiment, pharmaceutical compositions of the invention are useful for the treatment or prevention of Parkinson's disease (including sporadic Parkinson's disease patients as well as patients with LRRK2 mutations or Rab29/Rab7L1 polymorphisms), Alzheimer's disease, amyotrophic lateral sclerosis (ALS), dementia (including Lewy body dementia and vascular dementia, HIV-induced dementia), diabetic neuropathy, age related memory disfunction, mild cognitive impairment, argyrophilic grain disease, Pick's disease, epilepsy, tauopathies such as progressive supranuclear palsy and corticobasal degeneration, other synucleinopathies such as multiple system atrophy, frontotemporal dementia, inherited frontotemporal dementia and parkinsonism linked to chromosome 17 (FTDP-17), withdrawal symptoms/relapse associated with drug addiction, L-Dopa induced dyskinesia, ischemic stroke, traumatic brain injury, spinal cord injury, multiple sclerosis, Niemann-Pick Type A, B or C disease, Gaucher's disease, Krabbe's disease, Fabry's disease, disorders with mitochondrial deficits, Crohn's disease, inflammatory bowel disease, rheumatoid arthritis, ulcerative colitis, lupus, autoimmune hemolytic anemia, pure red cell aplasia, idiopathic thrombocytopenic purpura, type 1 diabetes mellitus, obesity, Evans syndrome, bullous skin disorders, Sjogren's syndrome, Devic's disease, leprosy, thyroid cancer, renal cancer (including papillary renal), breast cancer, hormone-related cancer, adeno- and squamous lung cancer, non-small-cell lung cancer, colon cancer, prostate cancers, skin cancers, leukemias (including acute myelogenous leukemia), lymphomas, stroke, leprosy, tuberculosis, and SARS-CoV, MERS-CoV, SARS-CoV-2, HIV, West Nile virus and chikungunya virus infections.

Among the pharmaceutical compositions according to the invention there may be mentioned more especially those that are suitable for oral, parenteral, nasal, per- or trans-cutaneous, rectal, perlingual, ocular or respiratory administration, especially tablets or dragées, sublingual tablets, sachets, paquets, capsules, glossettes, lozenges, suppositories, creams, ointments, dermal gels, and drinkable or injectable ampoules.

The pharmaceutical compositions according to the invention comprise one or more excipients or carriers selected from diluents, lubricants, binders, disintegration agents, stabilisers, preservatives, absorbents, colorants, sweeteners, flavourings etc.

By way of non-limiting example there may be mentioned:

as diluents: lactose, dextrose, sucrose, mannitol, sorbitol, cellulose, glycerol, as lubricants: silica, talc, stearic acid and its magnesium and calcium salts, polyethylene glycol, as binders: magnesium aluminium silicate, starch, gelatin, tragacanth, methylcellulose, sodium carboxymethylcellulose and polyvinylpyrrolidone, as disintegrants: agar, alginic acid and its sodium salt, effervescent mixtures.

The dosage varies according to the sex, age and weight of the patient, the administration route, the nature of the therapeutic indication, or of any associated treatments, and ranges from 0.01 mg to 1 g per 24 hours in one or more administrations.

The following Preparations and Examples illustrate the invention but do not limit it in any way. The compounds of this invention can be prepared by any of several standard synthetic processes commonly used by those skilled in the art of organic chemistry. The compounds are generally prepared from starting materials which are either commercially available or prepared by standard means obvious to those skilled in the art.

General Schemes

As indicated herein before, the present invention provides compounds according to formula (I):

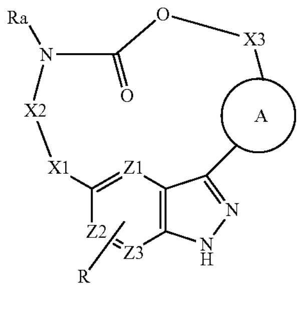

(I)

wherein R, Z1, Z2, Z3, X1, X2, X3, Ra and A are as defined for formula (I).

With reference to the general reaction schemes suitable for preparing said compounds, these compounds can be represented by formula (I), for which the general reaction schemes can be found herein below. In the general schemes below, R, Z1, Z2, Z3, X1, X2, X3, Ra and A will have the same meaning as defined for formula (I).

The fused pyrazolo bicyclic structure containing Z1, Z2, Z3 and R will be referred to as fused pyrazolo structure in the followings.

In the general schemes below, $Lg_1$ and $Lg_2$ each independently represent suitable leaving groups. $Pg_1$ and $Pg_3$ each independently represent a suitable protecting group that can be used to protect X1 and/or X2. $Pg_2$ represents a protective group suitable to protect the NH of the fused pyrazolo structure.

Rb in the schemes below can be either H, alkyl or a cyclic alkyl.

For those compounds for which a transcarbamylation reaction is used, the CbzX2Lg2 moiety can be made either by reaction from the corresponding bromo alkyl amine through reaction with Cbz chloride or by reaction between the hydroxyalkylamine through reaction with Cbz chloride followed by mesylation or tosylation.

In all of the general schemes below, before deprotection of the NH of the fused pyrazolo structure, the carbamate can be optionally substituted by an alkylation reaction to give a compound of formula (XIIIa) after which the NH of the fused pyrazolo structure can be deprotected to result in the final compound of formula (I).

Alternatively, in all of the general schemes below, before deprotection of the NH of the fused pyrazolo structure, an optional cross-coupling reaction such as a Buchwald, Suzuki, Sonogashira reaction or alternatively an O-alkylation or nucleophilic aromatic substitution can be carried out on the (hetero-) aromatic ring which contains a leaving group such as a halide, to form a compound of formula (XIIIa). After the cross-coupling reaction such as a Buchwald, Suzuki, Sonogashira reaction or alternatively an O-alkylation or nucleophilic aromatic substitution, the NH of the fused pyrazolo structure can be deprotected to result in the final compound of formula (I).

The compounds of formula (I) can be prepared as shown in general Scheme A below wherein the compound of formula (II) is converted to a protected compound of formula (III). This compound of formula (III) can be converted to a compound of formula (IV) containing a leaving group on the fused pyrazolo structure and then into a nitrogen protected compound of formula (V). The compound of formula (V) can be converted into a selectively protected fused pyrazolo structure of formula (VI) which is then alkylated with an intermediate of formula (VIII) containing a leaving group resulting in a compound of formula (IX). The compound of formula (VIII) can be prepared from a compound of formula (VII) through a nucleophilic substitution.

The compound of formula (IX) can be coupled via organometallic cross-coupling such as Suzuki or Ullmann coupling with a (hetero-)aryl of formula (X) or (Xa) to form a compound of formula (XI). The compound of formula (XI) can then be selectively deprotected to a compound of formula (XII) before being cyclized to form a compound of formula (XIII). Final deprotection of the nitrogen of the fused pyrazolo structure, either or not after alkylation of the carbamate moiety and/or substitution of the A ring, results in the compound of formula (I).

Scheme A

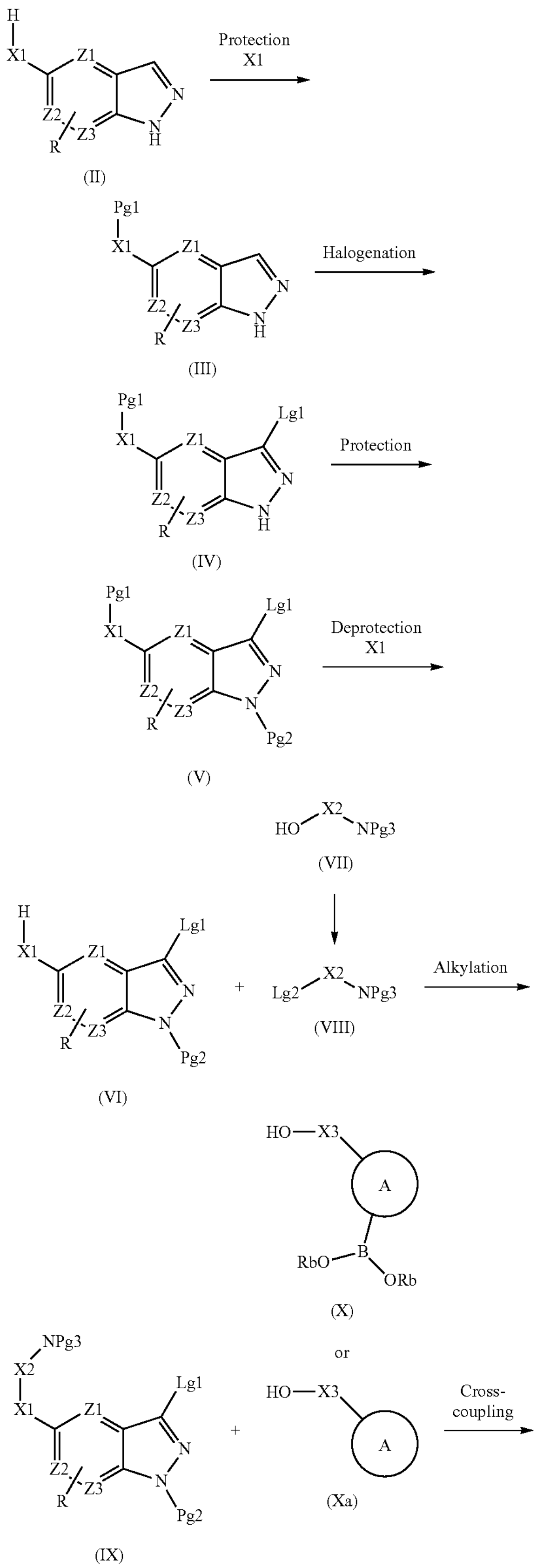

-continued

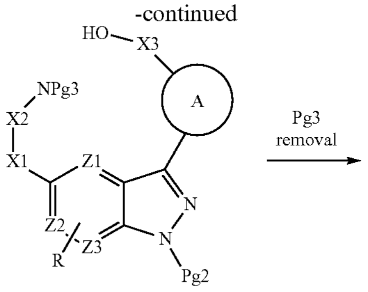

(XI)

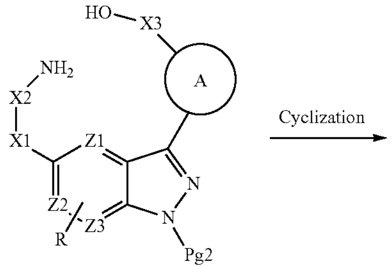

(XII)

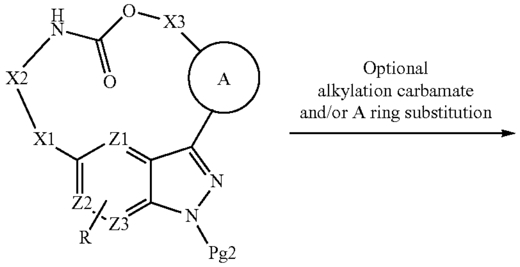

(XIII)

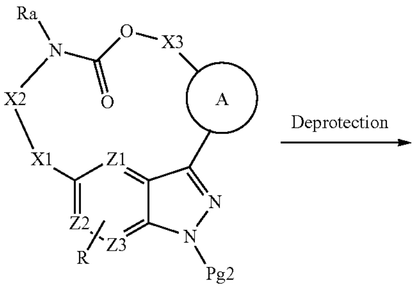

(XIIIa)

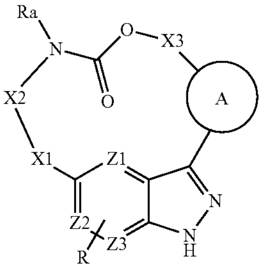

(I)

In the above reaction Scheme A, the reaction between a compound of formula (VI) and a compound of formula (VIII) can be accomplished in a solvent such as N,N-dimethylformamide or acetonitrile and a base such as cesium carbonate or potassium carbonate.

In the above reaction between compound of formula (IX) and compound of formula (X), the leaving groups $Lg_1$ is advantageously a halogen atom such as chlorine, bromine or iodine. Such a halogen displacement reaction can be effected under cross-coupling conditions such as Suzuki conditions using palladium catalysts such as for example tetrakis(triphenylphosphine) palladium(0) combined or not with 2-dicyclohexylphosphino-2',4',6'-triisopropylbiphenyl (Xphos) in the presence of potassium phosphate tribasic in a solvent mixture such as for example 1,4-dioxane/water at an elevated temperature such as for example 90° C. either under microwave conditions or not.

Alternatively, the halogen displacement reaction can be effected under Ullmann conditions using copper iodide in the presence of potassium carbonate and 8-hydroxyquinoline in a solvent such as for example dimethyl sulfoxide at an elevated temperature such as for example 70° C. Suitable compounds of formula (X) or formula (Xa) may be either commercially acquired or obtained through various selective protection and deprotection steps known to the person skilled in the art. For the synthesis of compounds of formula (Xa) a borylation step might be required.

The deprotection of $Pg_3$ results in a compound of formula (XII).

The cyclisation of the compound of formula (XII) to give compound of formula (XIII) can be performed by a method known by the person skilled in the art as a carbamylation reaction, for example by treatment with 1,1'-carbonyldiimidazole and N,N-diisopropylethylamine or sodium hydride in a solvent such as N,N-dimethylacetamide at for example 90° C. Final deprotection of the NH of the fused pyrazolo structure under acidic conditions, either or not after alkylation of the carbamate and/or substitution of the A ring yields the final compound of formula (I).

Alternatively, the compounds of formula (I) can be prepared as shown in general Scheme B below wherein the fused pyrazolo structure of formula (II) is converted to a protected compound of formula (III). The NH of the fused pyrazolo structure can be protected to a compound of formula (XIV). This compound of formula (XIV) can be converted to a boronic acid (or boronate ester) of formula (XV). The compound of formula (XV) can be coupled via organometallic cross-coupling reaction such as Suzuki coupling with a (hetero-)aryl of formula (XVI) to form a compound of formula (XVII). The compound of formula (XVII) can be alkylated with an intermediate of formula (XIX) containing a carbamate such as a benzyl carbamate resulting in a compound of formula (XX). The compound of formula (XIX) can commercially be acquired or being prepared from a compound of formula (XVIII) through a reaction with CbzCl or through the introduction of a leaving group Lg2 on the compound of formula (XVIIIa). The X4 moiety of compound (XX) can be transformed into X3-OH usually by a reduction of a carboxylic acid or a carboxylic ester or a (cyclo)alkyl-carbonyl or a heterocycloalkyl-carbonyl. The compound of formula (XXI) can then be cyclized by a transcarbamylation reaction to form a compound of formula (XIII). Final deprotection of the nitrogen of the fused pyrazolo structure, either or not after alkylation of the carbamate and/or substitution of the A ring results in the compound of formula (I).

Scheme B
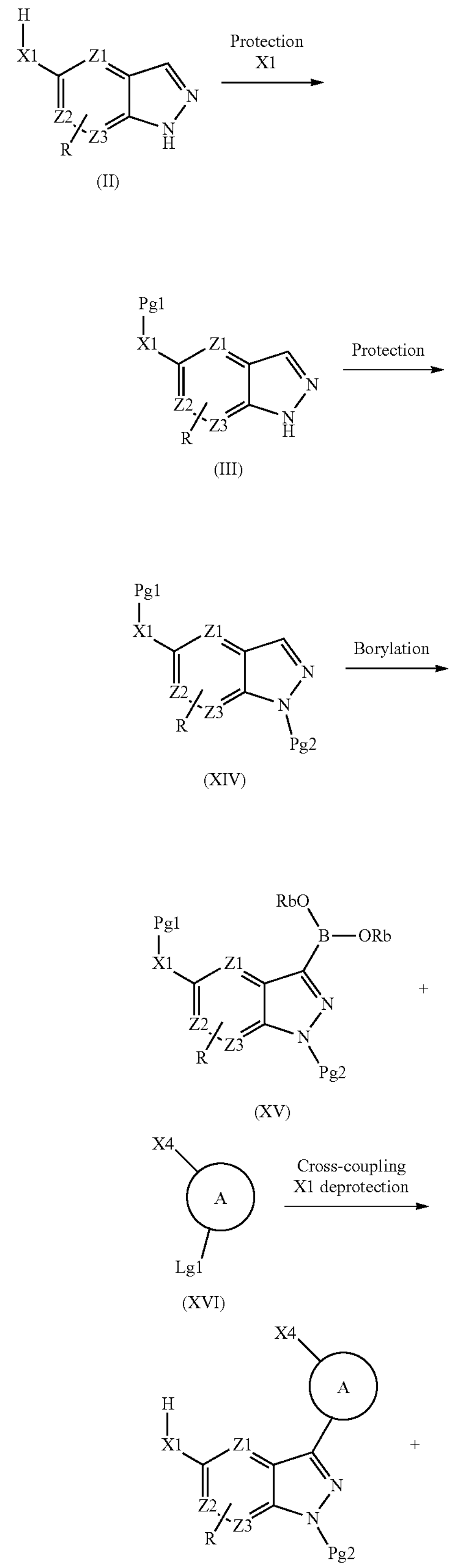
(II)
(III)
(XIV)
(XV)
(XVI)
(XVII)
-continued
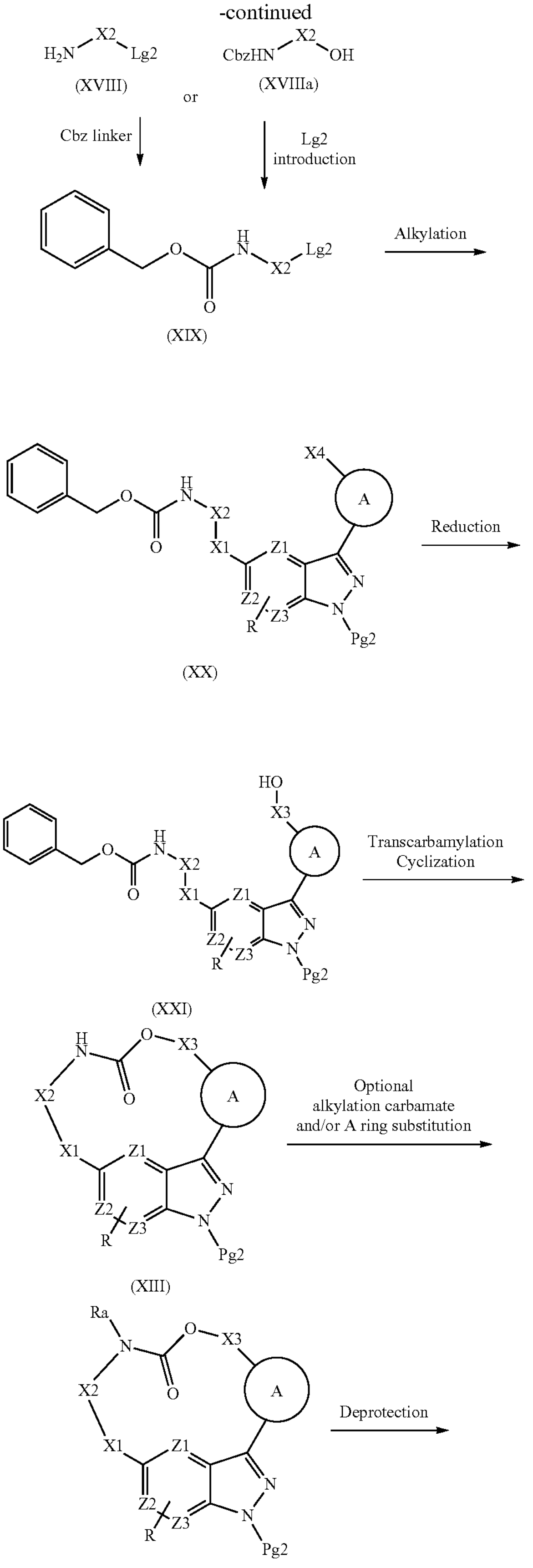
(XVIII)
(XVIIIa)
(XIX)
(XX)
(XXI)
(XIII)
(XIIIa)

-continued

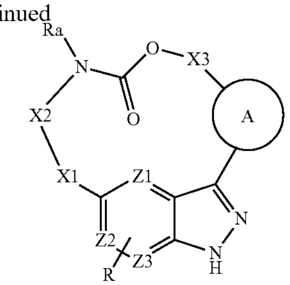

(I)

In the above reaction Scheme B, fused pyrazolo structure borylation of a compound of formula (XV) to the compound of formula (XVI) can be accomplished using an iridium catalyst and bis(pinacolato)diboron in a solvent such as TBME.

In the above reaction between compound of formula (XV) and compound of formula (XVI), the leaving groups $Lg_1$ is advantageously a halogen atom such as chlorine, bromine or iodine. Such a halogen displacement reaction can be affected under cross-coupling conditions such as Suzuki conditions using palladium catalysts such as for example tetrakis(triphenylphosphine) palladium(0) combined or not with 2-dicyclohexylphosphino-2',4',6'-triisopropylbiphenyl (Xphos) in the presence of potassium phosphate tribasic in a solvent mixture such as for example 1,4-dioxane/water at an elevated temperature such as for example 110° C. either under microwave conditions or not.

In the above reaction scheme, the alkylation between a compound of formula (XVII) with a compound of formula (XIX) can be accomplished in a solvent such as N,N-dimethylformamide or acetonitrile and a base such as cesium carbonate or potassium carbonate at an elevated temperature such as 120° C. Suitable compounds of formula (XIX) may be either commercially acquired or obtained through reaction with CbzCl and sodium hydroxide of a compound of formula (XVIII) in water as a solvent. Alternatively, the compound of formula (XIX) can be made by introduction of Lg2 on the compound of the formula (XVIIIa).

X4 in the compound of formula (XX) can be a (cyclo) alkyl-carbonyl, heterocycloalkyl-carbonyl or carboxylic derivative (carboxylic acid or ester) which can be reduced into the corresponding alcohol making use of sodium borohydride or lithium aluminium hydride in a solvent such as THE at an elevated temperature such as 120° C.

The transcarbamylation of the compound of formula (XXI) to the macrocycle of formula (XIII) can be done using potassium carbonate or cesium carbonate or potassium hydroxide in a solvent such as acetonitrile at a temperature ranging from RT to refluxing solvent, or using sodium hydride in a dry solvent such as toluene at a temperature ranging from 0° C. to refluxing solvent, either under microwave conditions or not.

Final deprotection of the nitrogen of the fused pyrazolo structure under acidic conditions, either or not after alkylation of the carbamate and/or substitution of the A ring yields the final compound of formula (I).

Alternatively, the compounds of formula (I) can be prepared as shown in general Scheme C below wherein the fused pyrazolo structure of formula (II) is converted to a protected compound of formula (III). This compound of formula (III) can be converted to a compound of formula (IV) containing a leaving group on the fused pyrazolo structure and then into a nitrogen protected compound of formula (V). The compound of formula (V) can be converted into a selectively protected fused pyrazolo structure of formula (VI) which is then alkylated with an intermediate of formula (XIX) containing a leaving group resulting in a compound of formula (XXII). The compound of formula (XIX) can commercially be acquired or being prepared from a compound of formula (XVIII) through a reaction with CbzCl or through the introduction of a leaving group Lg2 on the compound of formula (XVIIIa). The compound of formula (XXII) can be coupled via organometallic cross coupling reaction such as Suzuki coupling with a (hetero-) aryl of formula (X) to form a compound of formula (XXI). The compound of formula (XXI) can then be cyclized by a transcarbamylation reaction to form a compound of formula (XIII). Final deprotection of the nitrogen of the fused pyrazolo structure, either or not after alkylation of the carbamate and/or substitution of the A ring results in the compound of formula (I).

Scheme C

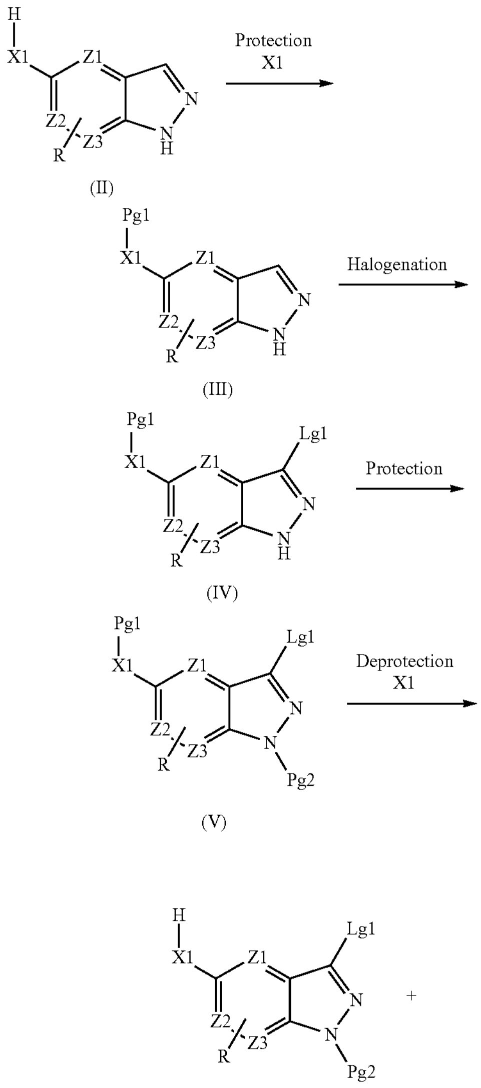

(II)

(III)

(IV)

(V)

+

(VI)

-continued

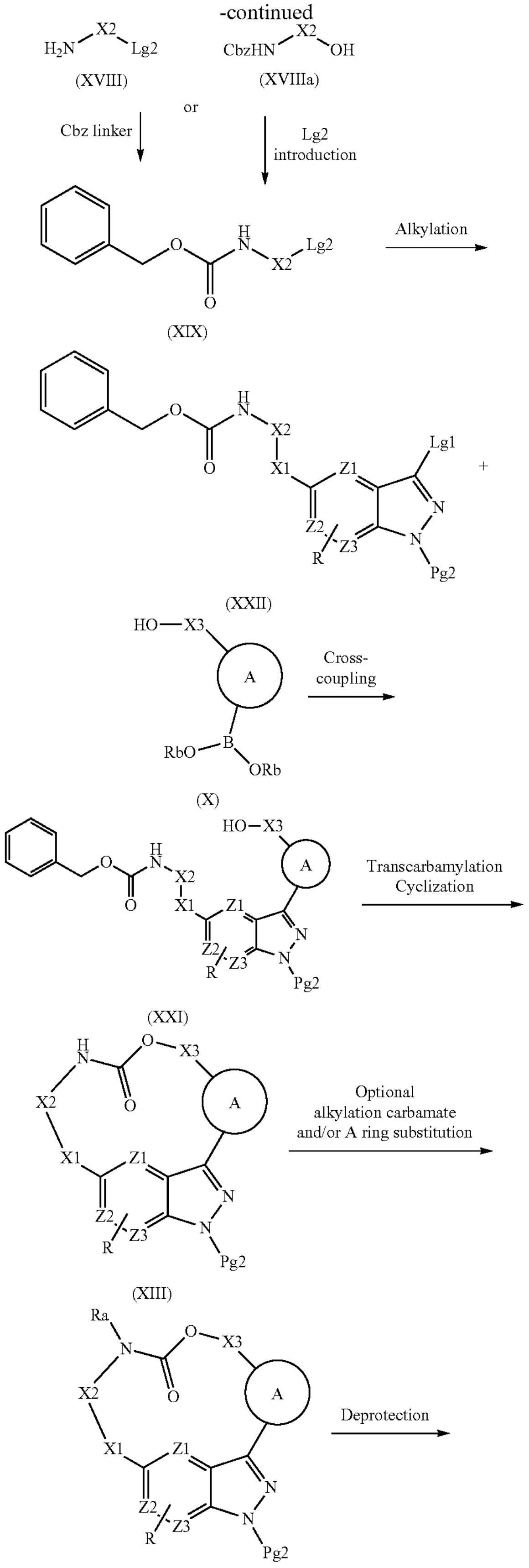

(XVIII) (XVIIIa) (XIX) (XXII) (X) (XXI) (XIII) (XIIIa)

-continued

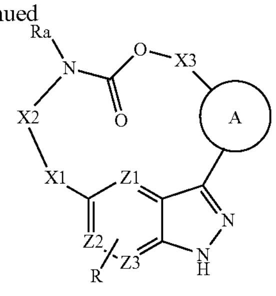

(I)

In the above reaction Scheme C, the alkylation between a compound of formula (VI) with a compound of formula (XIX) can be accomplished in a solvent such as N,N-dimethylformamide or acetonitrile and a base such as cesium carbonate or potassium carbonate at an elevated temperature such as 120° C.

Suitable compounds of formula (XIX) may be either commercially acquired or obtained through reaction with CbzCl and sodium hydroxide of a compound of formula (XVIII) in water as a solvent. Alternatively, the compound of formula (XIX) can be made by introduction of Lg2 on the compound of the formula (XVIIIa).

In the above reaction between compound of formula (XXII) and compound of formula (X), the leaving groups $Lg_1$ is advantageously a halogen atom such as chlorine, bromine or iodine. Such a halogen displacement reaction can be effected under organometallic coupling conditions such as Suzuki conditions using palladium catalysts such as for example tetrakis (triphenylphosphine)palladium(0) combined or not with 2-dicyclohexylphosphino-2',4',6'-triisopropylbiphenyl (Xphos) in the presence of potassium phosphate tribasic in a solvent mixture such as for example 1,4-dioxane/water at an elevated temperature such as for example 110° C. either under microwave conditions or not.

Suitable compounds of formula (X) may be either commercially acquired or obtained through various selective protection and deprotection steps known to the person skilled in the art. A borylation step might be required to obtain compounds of formula (X).

The transcarbamylation of the compound of formula (XXI) to the macrocycle of formula (XIII) can be done using potassium carbonate or cesium carbonate or potassium hydroxide in a solvent such as acetonitrile at a temperature ranging from RT to refluxing solvent, or using sodium hydride in a dry solvent such as toluene at a temperature ranging from 0° C. to refluxing solvent, either under microwave conditions or not.

Final deprotection of the nitrogen of the fused pyrazolo structure under acidic conditions, either or not after alkylation of the carbamate and/or substitution of the A ring yields the final compound of formula (I).

Alternatively, the compounds of formula (I) can be prepared as shown in general Scheme D below wherein the fused pyrazolo structure of formula (II) is converted to a protected compound of formula (III) and then into a nitrogen protected compound of formula (XIV). The compound of formula (XIV) can be converted into a selectively protected fused pyrazolo structure of formula (XXIII) which is then alkylated with a compound of intermediate (XIX) containing a Cbz group to result in a compound of formula (XXIV). Compound of formula (XIX) can be prepared from a compound of formula (XVIII) through a reaction with CbzCl or through the introduction of a leaving group Lg2 on the compound of formula (XVIIIa). The compound of formula (XXIV) can be boronated to a compound of formula (XXV). The boronated compounds of formula (XXV) can be reacted in a cross-coupling reaction such as a Suzuki coupling with a (hetero-)aryl of formula (XXVI) to form a compound of formula (XXI). The compound of formula (XXI) can then be cyclized by a transcarbamylation reaction to form a compound of formula (XIII). Final deprotection of the nitrogen of the fused pyrazolo structure, either or not after alkylation of the carbamate and/or substitution of the A ring results in the compound of formula (I).

Scheme D

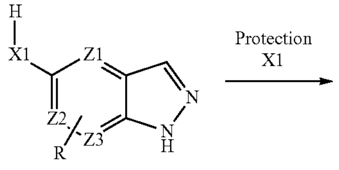

(II)

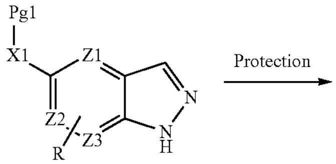

(III)

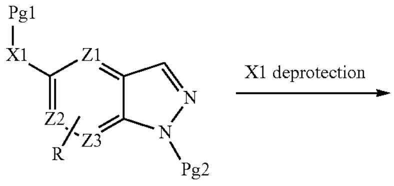

(XIV)

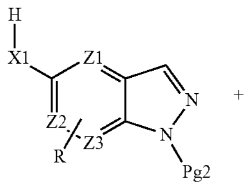

(XXIII)

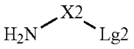

(XVIII)

or

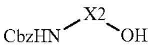

(XVIIIa)

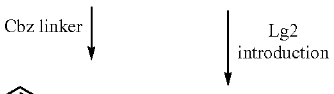

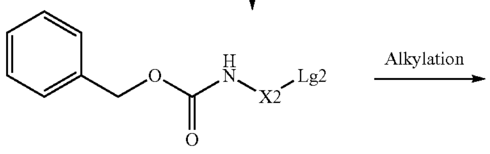

(XIX)

-continued

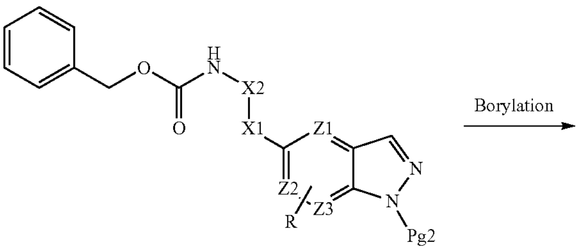

(XXIV)

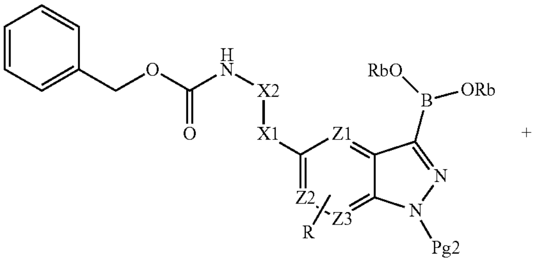

(XXV)

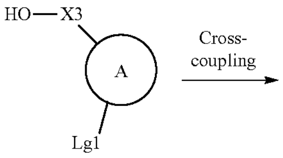

(XXVI)

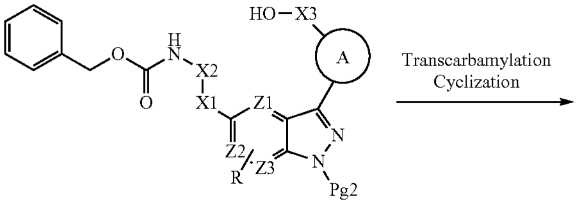

(XXI)

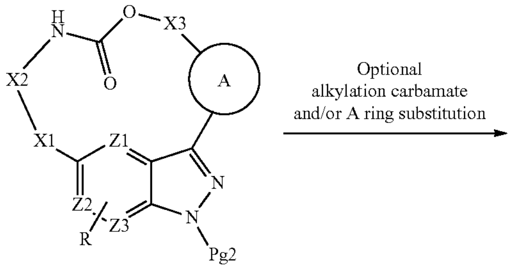

(XIII)

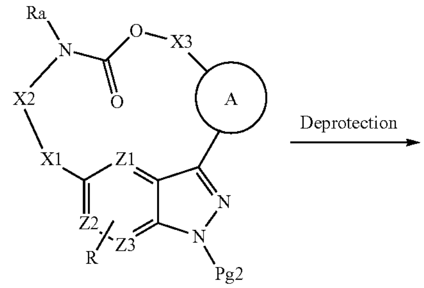

(XIII)

-continued

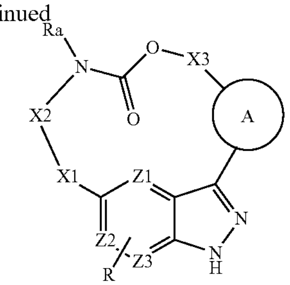

(I)

In the above reaction Scheme D, the reaction between a compound of formula (XXIII) and a compound of formula (XIX) can be accomplished in a solvent such as N,N-dimethylformamide or acetonitrile and a base such as cesium carbonate or potassium carbonate.

Suitable compounds of formula (XIX) may be either commercially acquired or obtained through reaction with CbzCl and sodium hydroxide of a compound of formula (XVIII) in water as a solvent. Alternatively, the compound of formula (XIX) can be made by introduction of Lg2 on the compound of the formula (XVIIIa).

In the above reaction scheme, fused pyrazolo structure borylation of a compound of formula (XXIV) to the compound of formula (XXV) can be accomplished using an iridium catalyst and bis(pinacolato)diboron in a solvent such as TBME.

In the above reaction between compound of formula (XXV) and compound of formula (XXVI), the leaving groups $Lg_1$ is advantageously a halogen atom such as chlorine, bromine or iodine.

Such a halogen displacement reaction can be effected under organometallic cross coupling conditions such as Suzuki conditions using palladium catalysts such as for example tetrakis (triphenylphosphine)palladium(0) combined or not with 2-dicyclohexylphosphino-2',4',6'-triisopropylbiphenyl (Xphos) in the presence of potassium phosphate tribasic in a solvent mixture such as for example 1,4-dioxane/water at an elevated temperature such as for example 90° C. either under microwave conditions or not.

Suitable compounds of formula (XXVI) may be either commercially acquired or obtained through various reactions including selective protection and deprotection steps known to the person skilled in the art.

The transcarbamylation of the compound of formula (XXI) to the macrocycle of formula (XIII) can be done using potassium carbonate or cesium carbonate or potassium hydroxide in a solvent such as acetonitrile at a temperature ranging from RT to refluxing solvent, or using sodium hydride in a dry solvent such toluene at a temperature ranging from 0° C. to refluxing solvent, either under microwave conditions or not.

Final deprotection of the nitrogen of the fused pyrazolo structure under acidic conditions, either or not after alkylation of the carbamate and/or substitution of the A ring yields the final compound of formula (I).

Alternatively, the compounds of formula (I) can be prepared as shown in general Scheme E below wherein the fused pyrazolo structure of formula (II) is converted to a protected compound of formula (III). This compound of formula (III) can be converted to a compound of formula (IV) containing a leaving group on the fused pyrazolo structure and then into a nitrogen protected compound of formula (V). The compound of formula (V) can be converted into a selectively protected fused pyrazolo structure of formula (VI) which is then coupled in a cross-coupling reaction such as a Suzuki coupling with a (hetero-)aryl of formula (XXVII) to form a compound of formula (XXVIII). The X4 moiety in the compound of formula (XXVII) contains a carbonyl precursor such as (cyclo)alkyl-carbonyl, heterocycloalkyl-carbonyl, carboxylic acid or ester which can be reduced into a compound of formula (XXIX). The compound of formula (XXIX) is then alkylated with an intermediate of formula (XIX) containing a leaving group resulting in a compound of formula (XXI). The compound of formula (XIX) can commercially be acquired or being prepared from a compound of formula (XVIII) through a reaction with CbzCl or through the introduction of a leaving group Lg2 on the compound of formula (XVIIIa). The compound of formula (XXI) can then be cyclized by a transcarbamylation reaction to form a compound of formula (XIII). Final deprotection of the nitrogen fused pyrazolo structure, either or not after alkylation of the carbamate and/or substitution of the A ring results in the compound of formula (I).

Scheme E

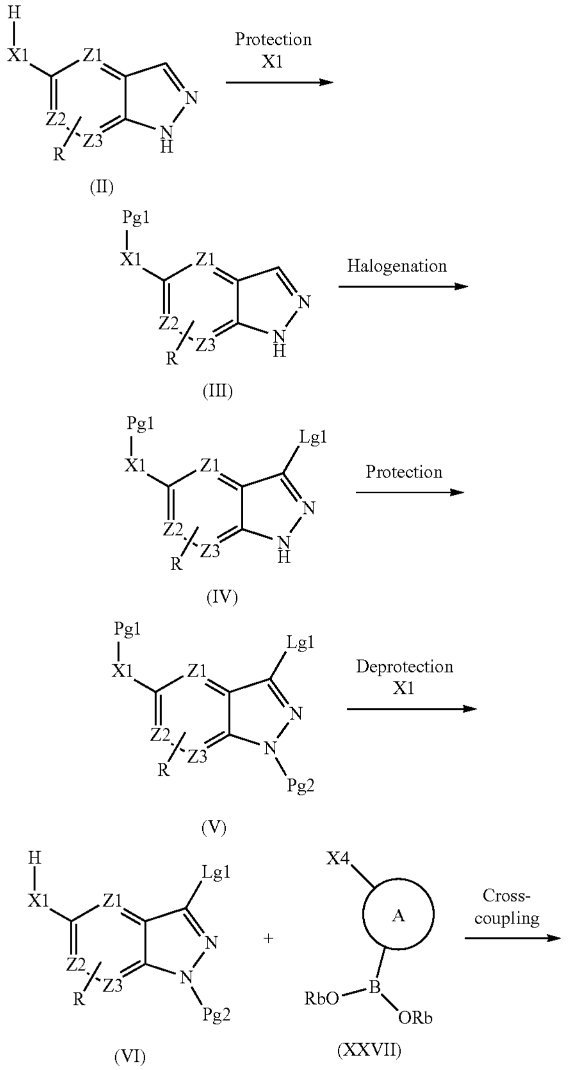

-continued

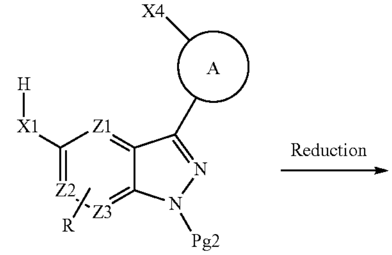

(XXVIII)

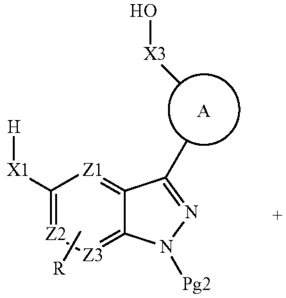

(XXIX)

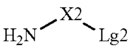

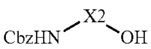

(XVIII) or (XVIIIa)

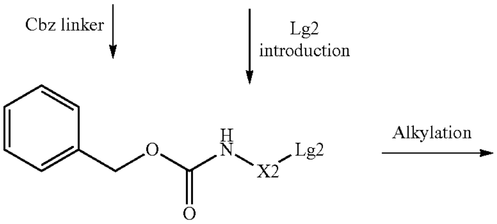

(XIX)

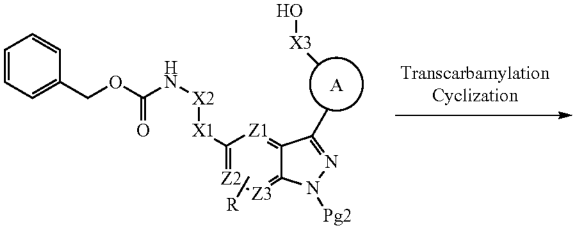

(XXI)

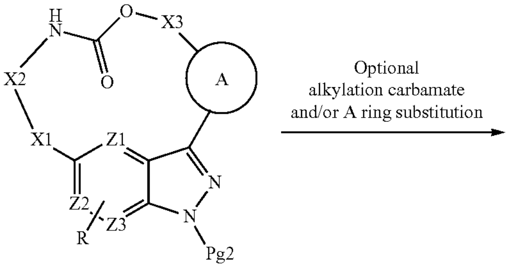

(XIII)

-continued

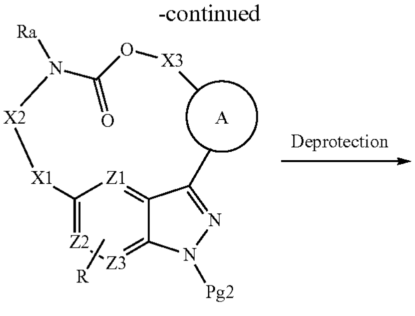

(XIIIa)

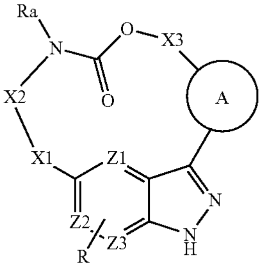

(I)

In the above Scheme E, reaction between compounds of formula (VI), the leaving groups $Lg_1$ is advantageously a halogen atom such as chlorine, bromine or iodine. Such a halogen displacement reaction can be affected under organometallic cross coupling conditions such as Suzuki conditions using palladium catalysts such as for example tetrakis (triphenylphosphine) palladium(0) combined or not with 2-dicyclohexylphosphino-2',4',6'-triisopropylbiphenyl (Xphos) in the presence of potassium phosphate tribasic in a solvent mixture such as for example 1,4-dioxane/water at an elevated temperature such as for example 110° C. either under microwave conditions or not.

Suitable compounds of formula (XXVII) contain a precursor moiety of the alcohol such as an ester or a carboxylic acid. Compounds of formula (XXVII) may be either commercially acquired or obtained through various reactions including selective protection and deprotection steps known to the person skilled in the art. For the compounds of formula (XXVII) a borylation step might be required.

Reduction of the X4 carbonyl in the compound of formula (XXVIII) results in a compound of formula (XXIX).

In the above reaction scheme, the alkylation between a compound of formula (XXIX) with a compound of formula (XIX) can be accomplished in a solvent such as N,N-dimethylformamide or acetonitrile and a base such as cesium carbonate or potassium carbonate at an elevated temperature such as 120° C.

Suitable compounds of formula (XIX) may be either commercially acquired or obtained through reaction with CbzCl and sodium hydroxide of a compound of formula (XVIII) in water as a solvent. Alternatively, the compound of formula (XIX) can be made by introduction of Lg2 on the compound of the formula (XVIIIa).

The transcarbamylation of the compound of formula (XXI) to the macrocycle of formula (XIII) can be done using potassium carbonate or cesium carbonate or potassium hydroxide in a solvent such as acetonitrile at a temperature ranging from RT to refluxing solvent, or using sodium hydride in a dry solvent such as toluene at a temperature ranging from 0° C. to refluxing solvent, either under microwave conditions or not.

Final deprotection of the nitrogen of the fused pyrazolo structure under acidic conditions, either or not after alkylation of the carbamate and/or substitution of the A ring yields the final compound of formula (I).

Alternatively, the compounds of formula (I) can be prepared as shown in general Scheme F below wherein the fused pyrazolo structure of formula (II) is converted to a protected compound of formula (III). This compound of formula (III) can be converted to a compound of formula (IV) containing a leaving group on the fused pyrazolo structure and then into a nitrogen protected compound of formula (V). The compound of formula (V) can be converted into a selectively protected fused pyrazolo structure of formula (VI) which is then alkylated with an intermediate of formula (XIX) containing a leaving group resulting in a compound of formula (XXII). The compound of formula (XIX) can commercially be acquired or being prepared from a compound of formula (XVIII) through a reaction with CbzCl or through the introduction of a leaving group Lg2 on the compound of formula (XVIIIa). The compound of formula (XXII) can be coupled via organometallic cross coupling reaction such as Suzuki coupling with a (hetero-) aryl of formula (XXVII) to form a compound of formula (XX). The X4 moiety in the compound of formula (XX) contains a carbonyl precursor such as (cyclo)alkyl-carbonyl, heterocycloalkyl-carbonyl, carboxylic acid or ester which can be reduced into a compound of formula (XXI). The compound of formula (XXI) can then be cyclized by a transcarbamylation reaction to form a compound of formula (XIII). Final deprotection of the nitrogen of the fused pyrazolo structure, either or not after alkylation of the carbamate and/or substitution of the A ring results in the compound of formula (I).

Scheme F

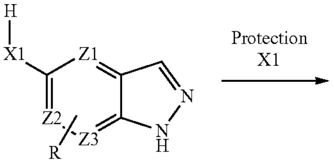

(II)

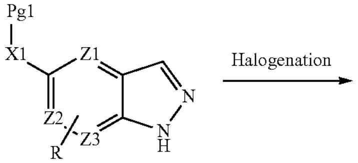

(III)

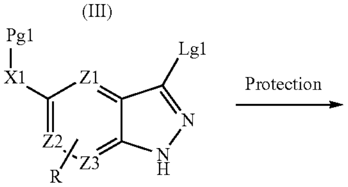

(IV)

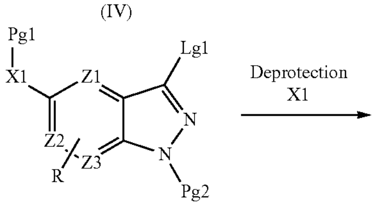

(V)

-continued

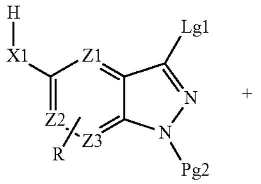

(VI)

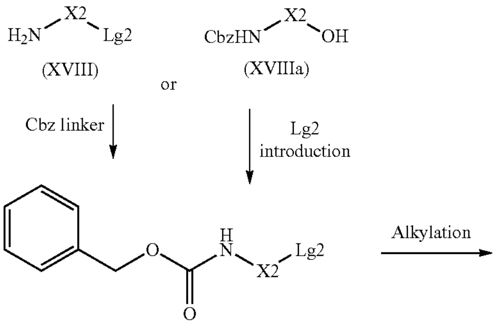

(XVIII) or (XVIIIa)

(XIX)

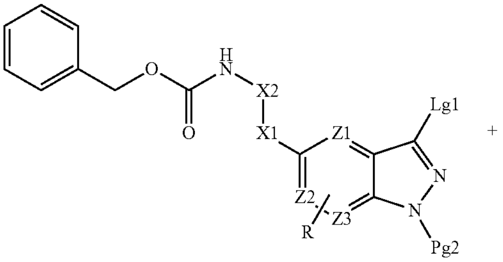

(XXII)

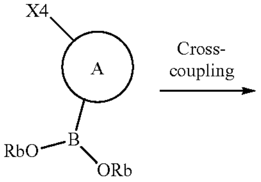

(XXVII)

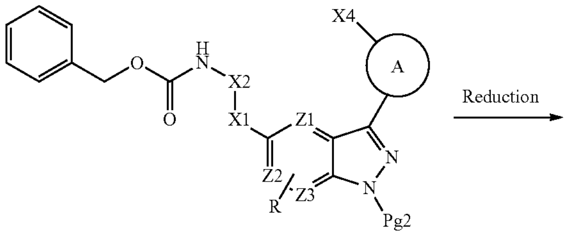

(XX)

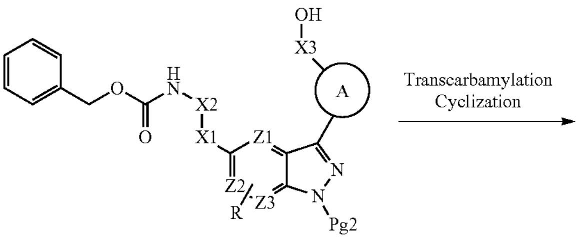

(XXI)

-continued

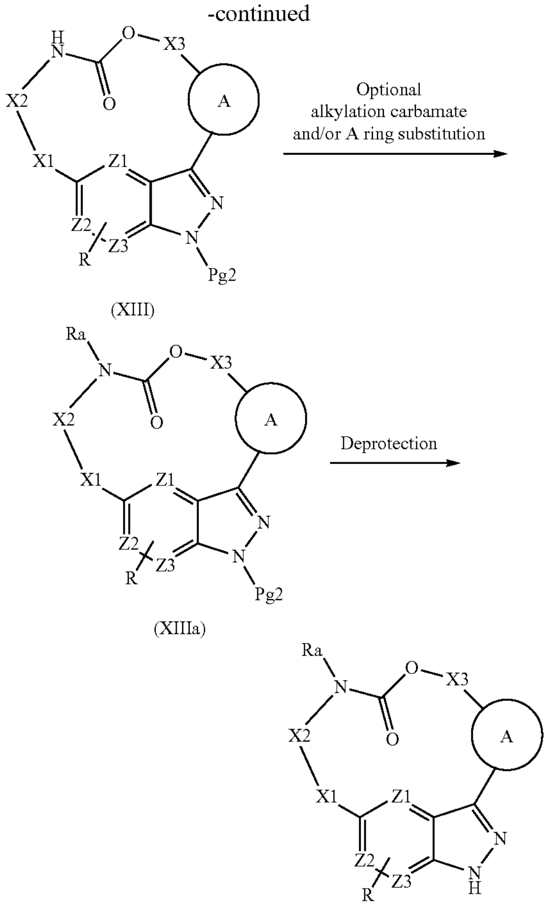

(XIII)

(XIIIa)

(I)

In the above reaction Scheme F, the alkylation between a compound of formula (VI) with a compound of formula (XIX) can be accomplished in a solvent such as N,N-dimethylformamide or acetonitrile and a base such as cesium carbonate or potassium carbonate at an elevated temperature such as 120° C.

Suitable compounds of formula (XIX) may be either commercially acquired or obtained through reaction with CbzCl and sodium hydroxide of a compound of formula (XVIII) in water as a solvent. Alternatively, the compound of formula (XIX) can be made by introduction of Lg2 on the compound of the formula (XVIIIa).

In the above reaction between compound of formula (XXII) and compound of formula (XXVII), the leaving groups $Lg_1$ is advantageously a halogen atom such as chlorine, bromine or iodine. Such a halogen displacement reaction can be affected under cross-coupling conditions such as Suzuki conditions using palladium catalysts such as for example tetrakis(triphenylphosphine)palladium(0) combined or not with 2-dicyclohexylphosphino-2',4',6'-triisopropylbiphenyl (Xphos) in the presence of potassium phosphate tribasic in a solvent mixture such as for example 1,4-dioxane/water at an elevated temperature such as for example 110° C. either under microwave conditions or not.

Suitable compounds of formula (XXVII) may be either commercially acquired or obtained through various reactions including selective protection and deprotection steps known to the person skilled in the art. For the compounds of formula (XXVII) a borylation step might be required.

Reduction of the X4 carbonyl in the compound of formula (XX) results in a compound of formula (XXI).

Transcarbamylation of the compound of formula (XXI) to the macrocycle of formula (XIII) can be achieved using sodium hydride in dry toluene at an elevated temperature such as ranging from 130° C. or 150° C. Alternatively, the transcarbamylation can be done using potassium carbonate or KOH in a solvent such as acetonitrile at an elevated temperature such as 140° C. Final deprotection of the nitrogen of the fused pyrazolo structure under acidic conditions, either or not after alkylation of the carbamate and/or substitution of the A ring yields the final compound of formula (I).

Alternatively, the compounds of formula (I) can be prepared as shown in general Scheme G below wherein the fused pyrazolo structure of formula (II) is converted to a protected compound of formula (III) and then into a nitrogen protected compound of formula (XIV). The compound of formula (XIV) can be converted into a selectively protected fused pyrazolo structure of formula (XXIII) which is then alkylated with a compound of intermediate (XIX) containing a Cbz group to result in a compound of formula (XXIV). Compound of formula (XIX) can be prepared from a compound of formula (XVIII) through a reaction with CbzCl or through the introduction of a leaving group Lg2 on the compound of formula (XVIIIa). The compound of formula (XXIV) can be boronated to a compound of formula (XXV). The boronated compounds of formula (XXV) can be reacted in a cross-coupling such as a Suzuki coupling with a (hetero-)aryl of formula (XVI) to form a compound of formula (XX). The X4 moiety in the compound of formula (XX) contains a carbonyl precursor such as (cyclo)alkyl-carbonyl, heterocycloalkyl-carbonyl, carboxylic acid or ester which can be reduced into a compound of formula (XXI). The compound of formula (XXI) can then be cyclized by a transcarbamylation reaction to form a compound of formula (XIII). Final deprotection of the nitrogen of the fused pyrazolo structure, either or not after alkylation of the carbamate and/or substitution of the A ring results in the compound of formula (I).

Scheme G

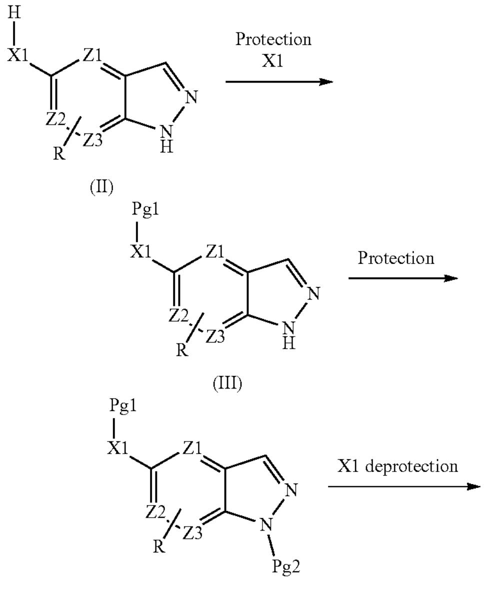

(II)

(III)

(XIV)

-continued

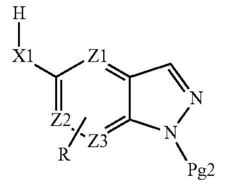

(XXIII)

+

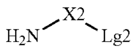

(XVIII)

or

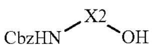

(XVIIIa)

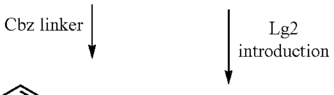

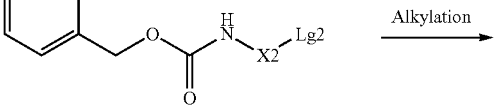

(XIX)

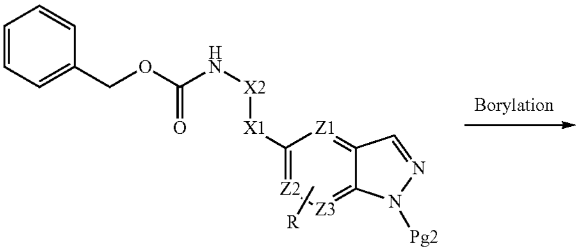

(XXIV)

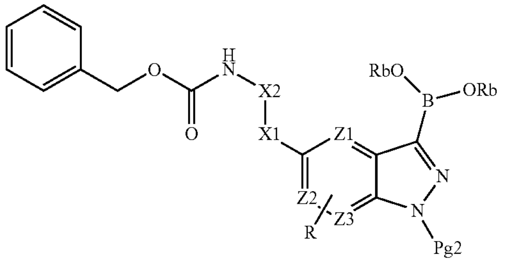

(XXV)

+

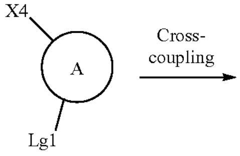

(XIV)

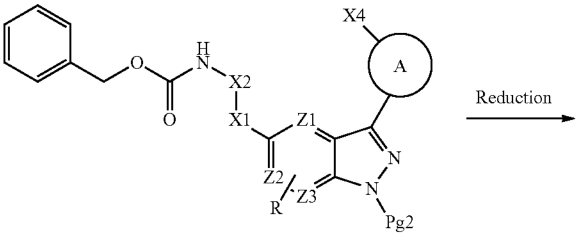

(XX)

-continued

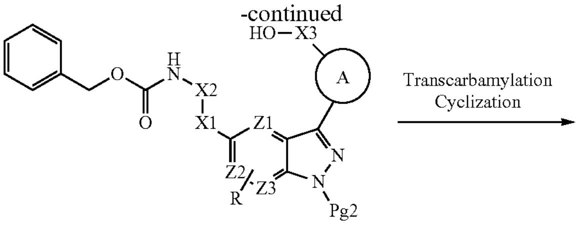

(XXI)

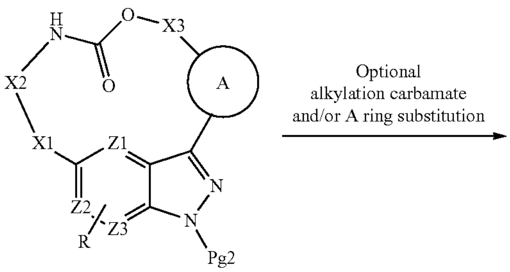

(XIII)

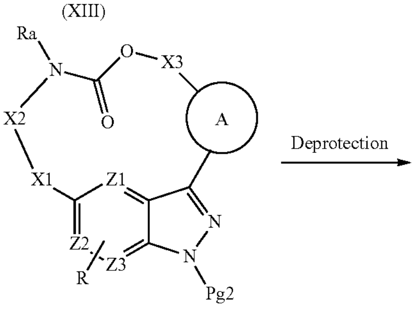

(XIIIa)

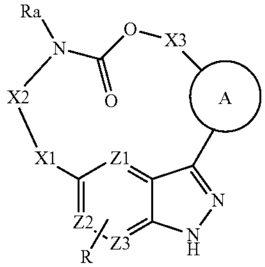

(I)

In the above reaction Scheme G, the reaction between a compound of formula (XXIII) and a compound of formula (XIX) can be accomplished in a solvent such as N,N-dimethylformamide or acetonitrile and a base such as cesium carbonate or potassium carbonate.

Suitable compounds of formula (XIX) may be either commercially acquired or obtained through reaction with CbzCl and sodium hydroxide of a compound of formula (XVIII) in water as a solvent. Alternatively, the compound of formula (XIX) can be made by introduction of Lg2 on the compound of the formula (XVIIIa).

In the above reaction scheme, fused pyrazolo structure borylation of a compound of formula (XXIV) to a compound of formula (XXV) can be accomplished using an iridium catalyst and bis(pinacolato)diboron in a solvent such as TBME.

In the above reaction between compound of formula (XXV) and compound of formula (XVI), the leaving groups $Lg_1$ is advantageously a halogen atom such as chlorine, bromine or iodine. Such a halogen displacement reaction can be affected under cross-coupling conditions such as Suzuki conditions using palladium catalysts such as for example tetrakis(triphenylphosphine) palladium(0) combined or not with 2-dicyclohexylphosphino-2',4',6'-triisopropylbiphenyl (Xphos) in the presence of potassium phosphate tribasic in a solvent mixture such as for example 1,4-dioxane/water at an elevated temperature such as for example 90° C. either under microwave conditions or not.

Suitable compounds of formula (XVI) may be either commercially acquired or obtained through various reactions including selective protection and deprotection steps known to the person skilled in the art.

The carbonyl moiety of X4 in the compound of formula (XX) can be reduced into the corresponding alcohol making use of, for instance, sodium borohydride or lithium aluminium hydride in a solvent such as THE at an elevated temperature such as 120° C.

The transcarbamylation of the compound of formula (XXI) to the macrocycle of formula (XIII) can be done using potassium carbonate or cesium carbonate or potassium hydroxide in a solvent such as acetonitrile at a temperature ranging from RT to refluxing solvent, or using sodium hydride in a dry solvent such toluene at a temperature ranging from 0° C. to refluxing solvent, either under microwave conditions or not.

Final deprotection of the nitrogen of the fused pyrazolo structure under acidic conditions, either or not after alkylation of the carbamate and/or substitution of the A ring yields the final compound of formula (I).

Alternatively, the compounds of formula (I) can be prepared as shown in general Scheme H below wherein the fused pyrazolo structure of formula (II) is converted to a protected compound of formula (III) and then into a nitrogen protected compound of formula (XIV). The compound of formula (XIV) can be converted into a selectively protected fused pyrazolo structure of formula (XXIII) which is then alkylated with a compound of intermediate (XXX) containing a (hetero-)aromatic group to result in a compound of formula (XXXI). Compound of formula (XXX) can be prepared using different reaction steps known to the person skilled in the art and is in detail described for the exemplified compounds. The compound of formula (XXXI) can be macrocyclized through a CH-activation reaction. Final deprotection of the nitrogen of the fused pyrazolo structure, either or not after alkylation of the carbamate and/or substitution of the A ring results in the compound of formula (I).

Scheme H

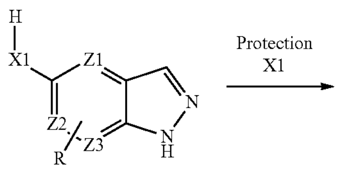

(II)

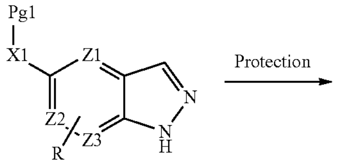

(III)

-continued

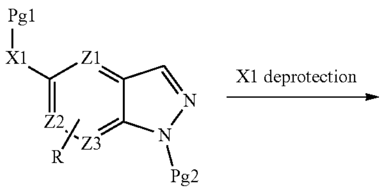

(XIV)

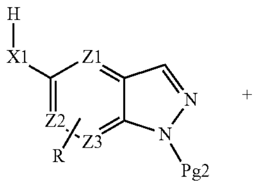

(XXIII)

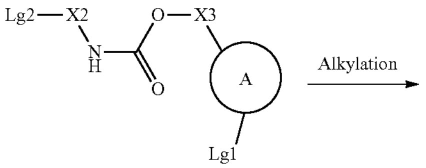

(XXX)

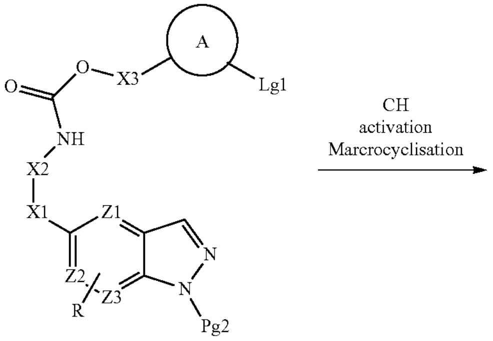

(XXXI)

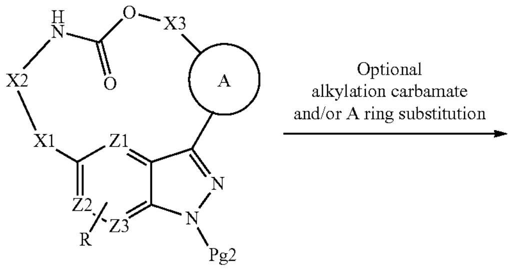

(XIII)

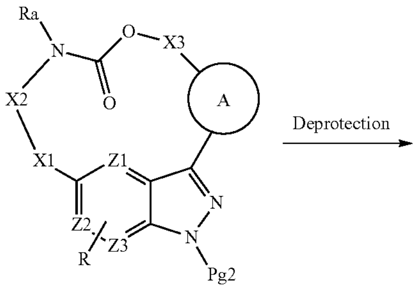

(XIIIa)

-continued

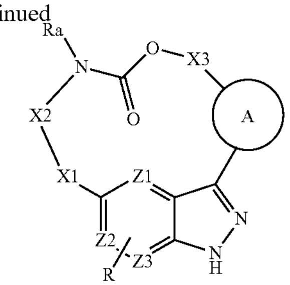

(I)

In the above reaction Scheme H, the alkylation between a compound of formula (XXIII) with a compound of formula (XXX) can be accomplished in a solvent such as N,N-dimethylformamide or acetonitrile and a base such as cesium carbonate or potassium carbonate at an elevated temperature such as 80° C.

Suitable compounds of formula (XXX) may be either commercially acquired or obtained through synthesis routes available in the literature. In the above reaction between compound of formula (XXX) and compound of formula (XXIII), the leaving groups $Lg_2$ is advantageously a mesylate group.

CH activation of the compound of formula (XXXI) to the macrocycle of formula (XIII) can be achieved using Cat-aCXium, palladium acetate and potassium acetate in dry toluene under microwave conditions at an elevated temperature such as 140° C. The leaving group $Lg_1$ is advantageously a halogen atom such as chlorine, bromine or iodine. Final deprotection of the nitrogen of the fused pyrazolo structure under acidic conditions, either or not after alkylation of the carbamate and/or substitution of the A ring yields the final compound of formula (I).

Alternatively, the compounds of formula (I), a particular case of compounds of formula (I) wherein X1 is NR'a can be prepared as shown in general Scheme I below wherein the fused pyrazolo structure of formula (XXXII) in which X5 is for instance a nitro group is converted to a protected compound of formula (XXXIII) and then into a nitrogen protected compound of formula (XXXIV). The compound of formula (XXXIV) can be converted into a selectively protected fused pyrazolo structure of formula (VI) which is then alkylated with a compound of formula (VIII) containing a protecting group Pg3. After alkylation, deprotection of X2 results in a compound of formula (XXXVI) which is then coupled in a cross-coupling reaction such as a Suzuki reaction with a compound of formula (X). The resulting compound of formula (XII) can be macrocyclized affording a compound of formula (XIII). Final deprotection of the nitrogen of the fused pyrazolo structure, either or not after alkylation of the carbamate and/or substitution of the A ring results in the compound of formula (I).

Scheme I

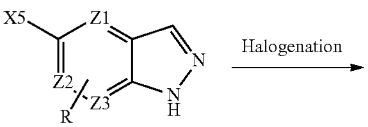

(XXXII)

-continued

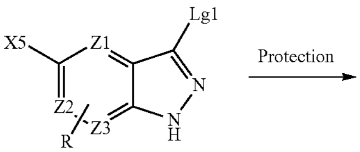

(XXXIII)

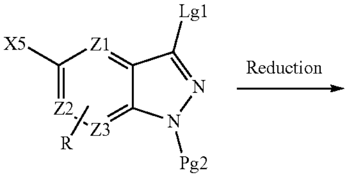

(XXXIV)

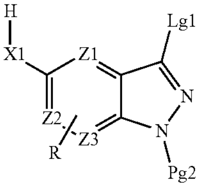

+

(VI)

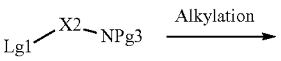

(VIII)

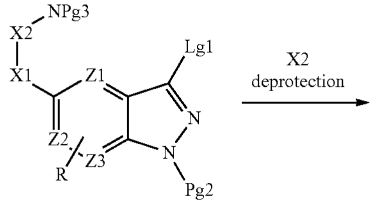

(IX)

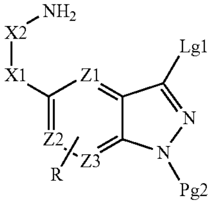

+

(XXXVI)

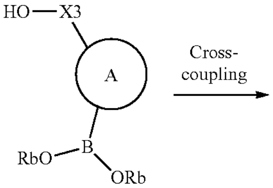

(X)

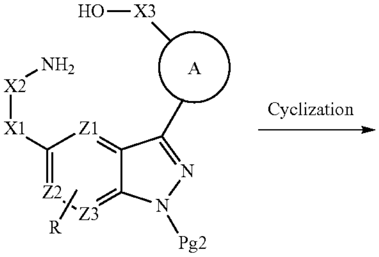

(XII)

-continued

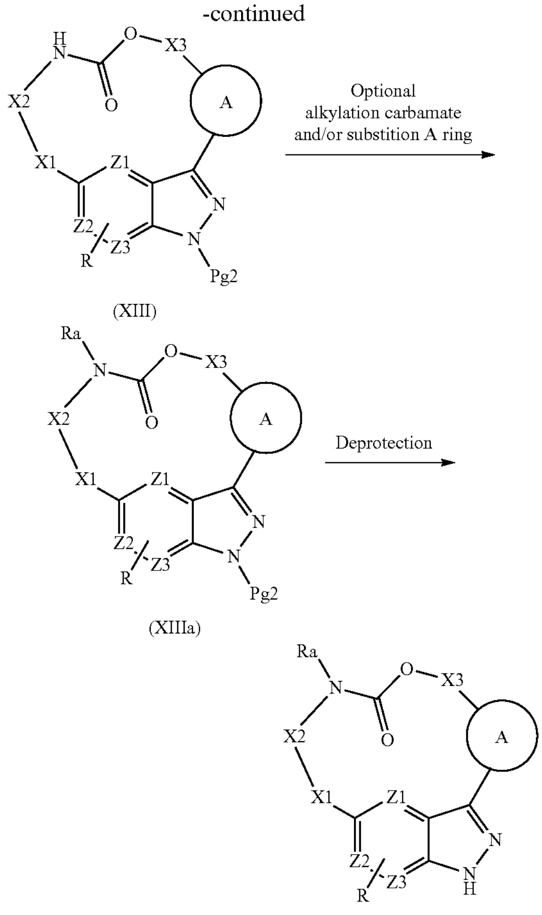

(XIII)

(XIIIa)

(I)

In the above reaction Scheme I, X5 is a nitro group and X1 is in this scheme particularly NR'a. Halogenation of the fused pyrazolo structure can be achieved using for example iodine and potassium hydroxide in a solvent such as N,N-dimethylformamide at an elevated temperature such as 60° C.

Reduction of the nitro group can be obtained using iron in the presence of ammonia chloride in a mixture of solvents such as EtOH, THE and water at an elevated temperature such as 80° C. to yield a compound of formula (VI).

The alkylation between a compound of formula (VI) with a compound of formula (VIII) can be accomplished in a solvent such as N,N-dimethylformamide or acetonitrile and a base such as cesium carbonate or potassium carbonate at an elevated temperature such as 80 or 90° C. The compound of formula (VIII) contains a protecting group Pg3, which can be a phthalimide group. Deprotection of X2-NPg3 in a compound of formula (IX) can be achieved using a reagent such as hydrazine in a solvent such as EtOH at an elevated temperature such as 60° C.

Organometallic cross coupling such as Suzuki coupling of the compound of formula (XXXVI) with a compound of formula (X) can be done using palladium catalysts such as for example tetrakis(triphenylphosphine)palladium(0) combined or not with 2-dicyclohexylphosphino-2',4',6'-triisopropylbiphenyl (Xphos) in the presence of potassium phosphate tribasic in a solvent mixture such as for example 1,4-dioxane/water at an elevated temperature such as for example 120° C. either under microwave conditions or not.

The cyclisation of the compound of formula (XII) to give compound of formula (XIII) can be performed by a method known by the person skilled in the art as a carbamylation reaction, for example by treatment with 1,1'-carbonyldiimidazole and N,N-diisopropylethylamine in a solvent such as N,N-dimethylacetamide at for example 90° C. Final deprotection of the nitrogen of the fused pyrazolo structure under acidic conditions, either or not after alkylation of the carbamate and/or substitution of the A ring yields the final compound of formula (I).

Alternatively, the compounds of formula (I) can be prepared as shown in general Scheme J below wherein the fused pyrazolo structure of formula (II) is converted to a protected compound of formula (III). This compound of formula (III) can be converted to a compound of formula (IV) containing a leaving group on the fused pyrazolo structure and then into a nitrogen protected compound of formula (V). The compound of formula (V) can be converted into a selectively protected fused pyrazolo structure of formula (VI) in which then X1 is protected to form a compound of formula (XXXVII). The compound of formula (XXXVII) can be coupled via organometallic cross coupling such as Suzuki coupling with a (hetero-)aryl of formula (XXXVIII) to form a compound of formula (XXXIX). Alkylation of the (hetero-)aromatic ring gives rise to a compound of formula (XL). Deprotection of X1 followed by alkylation with a compound of formula (XIX) results in a compound of formula (XLII). The compound of formula (XIX) can commercially be acquired or being prepared from a compound of formula (XVIII) through a reaction with CbzCl or through the introduction of a leaving group Lg2 on the compound of formula (XVIIIa). Deprotection of X3 leads to a compound of formula (XXI).

The compound of formula (XXI) can then be cyclized by a transcarbamylation reaction to form a compound of formula (XIII). Final deprotection of the nitrogen of the fused pyrazolo structure, either or not after alkylation of the carbamate and/or substitution of the A ring results in the compound of formula (I).

Scheme J

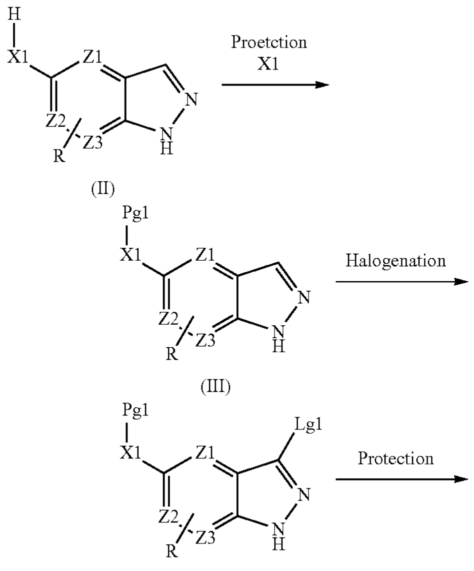

(II)

(III)

(IV)

-continued
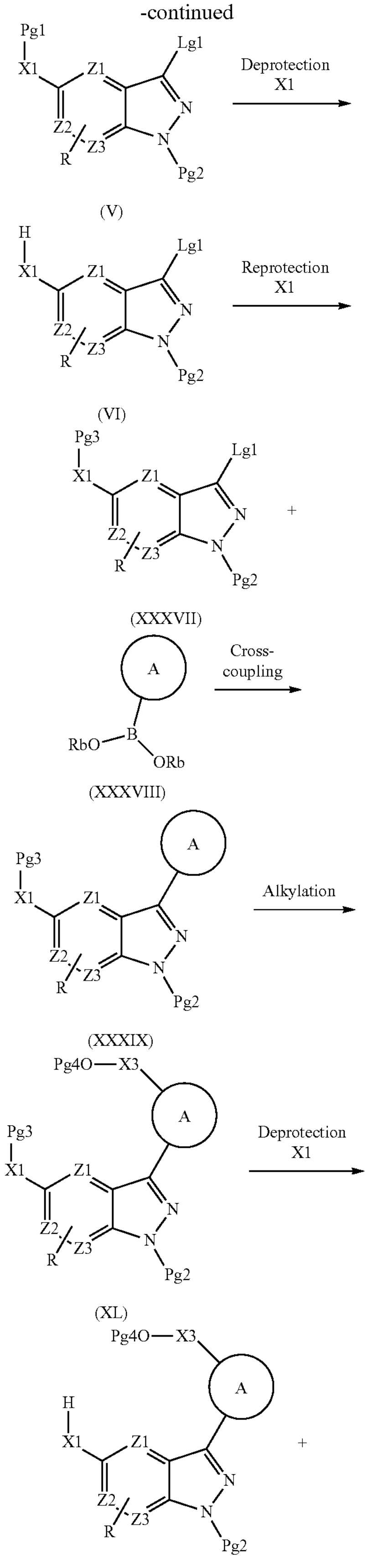
(V)
(VI)
(XXXVII)
(XXXVIII)
(XXXIX)
(XL)
(XLI)
-continued
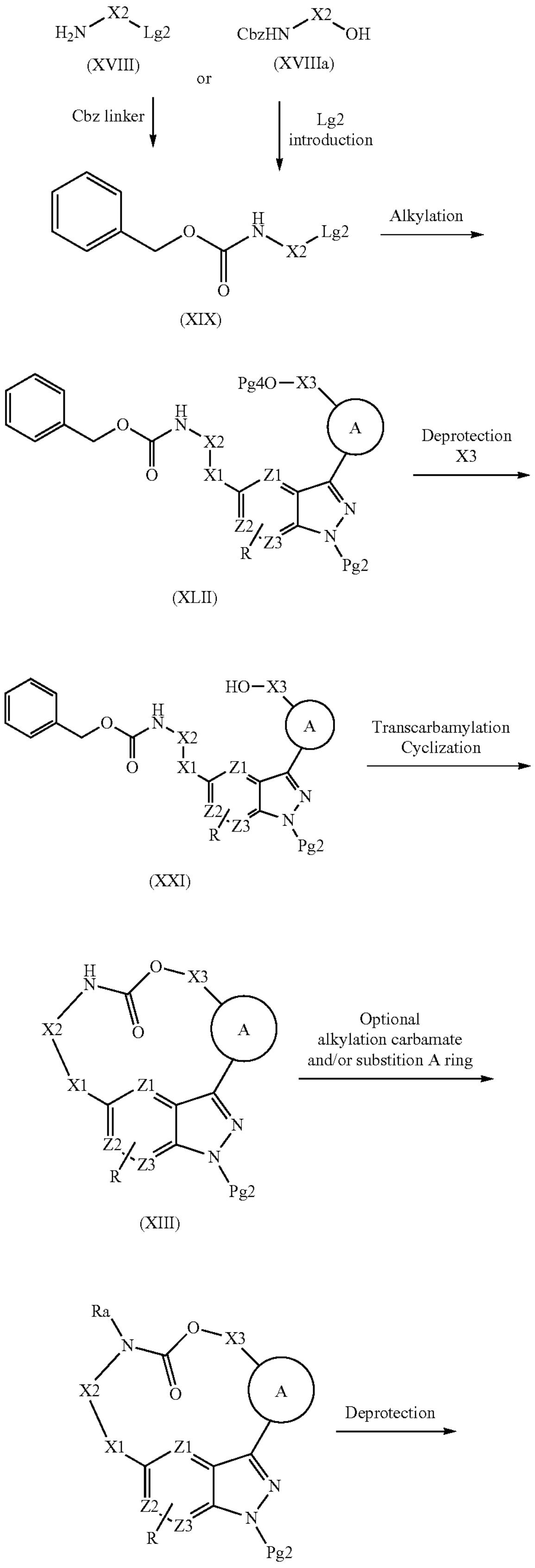
(XVIII)
(XVIIIa)
(XIX)
(XLII)
(XXI)
(XIII)
(XIIIa)

-continued

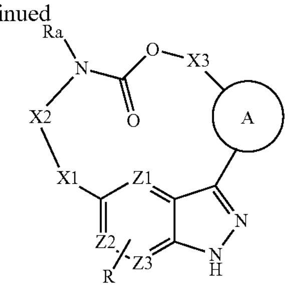

(I)

In the above reaction Scheme J, the protection of X1 of compound of formula (VI) can be accomplished with benzyl chloride in a solvent such as N,N-dimethylformamide or acetonitrile and a base such as cesium carbonate or potassium carbonate at room temperature or at an elevated temperature.

In the above reaction between compound of formula (XXXVII) and compound of formula (XXXVIII), the leaving groups $Lg_1$ is advantageously a halogen atom such as chlorine, bromine or iodine. Such a halogen displacement reaction can be effected via organometallic cross coupling conditions such as Suzuki conditions using palladium catalysts such as for example tetrakis(triphenylphosphine)palladium(0) combined or not with 2-dicyclohexylphosphino-2',4',6'-triisopropylbiphenyl (Xphos) in the presence of potassium phosphate tribasic in a solvent mixture such as for example 1,4-dioxane/water at an elevated temperature such as for example 110° C. either under microwave conditions or not.

Suitable compounds of formula (XXXVIII) may be either commercially acquired or obtained through various reactions including selective protection and deprotection steps known to the person skilled in the art. For the compounds of formula (XXXVIII) a borylation step might be required.

In the above reaction scheme, the alkylation of compound of formula (XXXIX) can be accomplished using (2-bromoethoxy)(tert-butyl)dimethylsilane in a solvent such as N,N-dimethylformamide and a base such as sodium hydride at 0° C. or at room temperature.

Deprotection of X1 in the compound of formula (XL) can be accomplished using hydrogen gas in the presence of Pd/C in a solvent such as EtOH at room temperature.

The alkylation between a compound of formula (XLI) with a compound of formula (XIX) can be accomplished in a solvent such as N,N-dimethylformamide or acetonitrile and a base such as cesium carbonate or potassium carbonate at an elevated temperature such as 120° C.

Suitable compounds of formula (XIX) may be either commercially acquired or obtained through reaction with CbzCl and sodium hydroxide of a compound of formula (XVIII) in water as a solvent. Alternatively, the compound of formula (XIX) can be made by introduction of Lg2 on the compound of the formula (XVIIIa).

Deprotection of X3-OPg4 in the compound of formula (XLII) can be done using TBAF in a solvent such as THE at room temperature.

The transcarbamylation of the compound of formula (XXI) to the macrocycle of formula (XIII) can be done using potassium carbonate or cesium carbonate or potassium hydroxide in a solvent such as acetonitrile at a temperature ranging from RT to refluxing solvent, or using sodium hydride in a dry solvent such toluene at a temperature ranging from 0° C. to refluxing solvent, either under microwave conditions or not.

Final deprotection of the nitrogen of the fused pyrazolo structure under acidic conditions, either or not after alkylation of the carbamate and/or substitution of the A ring yields the final compound of formula (I).

Alternatively, the compounds of formula (I) can be prepared as shown in general Scheme K below wherein the fused pyrazolo structure of formula (II) is converted to a protected compound of formula (III). The NH of the fused pyrazolo structure can be protected to a compound of formula (XIV). This compound of formula (XIV) can be converted to a boronic acid (or boronate ester) of formula (XV). The compound of formula (XV) can be coupled via organometallic cross coupling such as Suzuki coupling with a (hetero-)aryl of formula (XLIII) or of formula (XXVI) to form a compound of formula (XLIV) or a compound of formula (XLIVa). Deprotection of X1 results in a compound of formula (XLV) or a compound of formula (XLVa). The compound of formula (XLV) or the compound of formula (XLVa) can be alkylated with an intermediate of formula (XIX) containing a carbamate resulting in a compound of formula (XLVI) or in a compound of formula (XXI). Deprotection of X3-OPg4 in the compound of formula (XLVI) results in the compound of formula (XXI). The compound of formula (XXI) can then be cyclized by a transcarbamylation reaction to form a compound of formula (XIII). Final deprotection of the nitrogen of the fused pyrazolo structure, either or not after alkylation of the carbamate and/or substitution of the A ring results in the compound of formula (I).

Scheme K

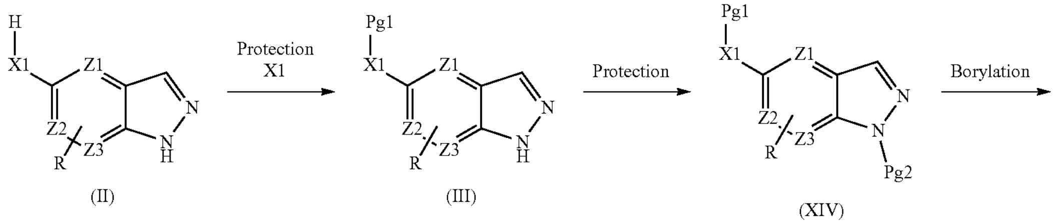

(II) (III) (XIV)

-continued
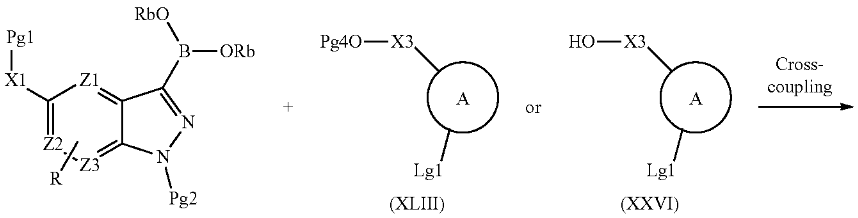
(XV) (XLIII) (XXVI)
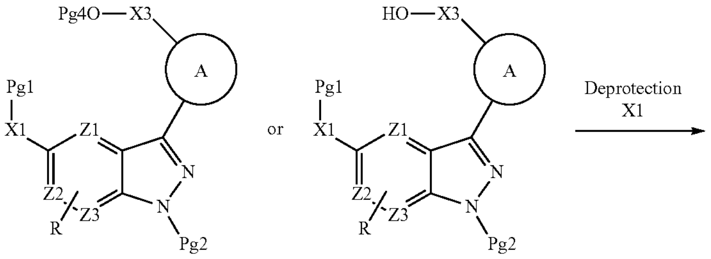
(XLIV) (XLIVa)
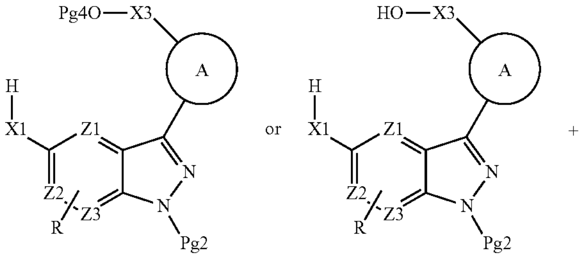
(XLV) (XLVa)
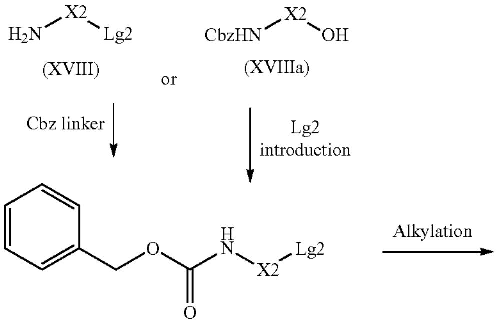
(XVIII) (XVIIIa)
(XIX)

-continued

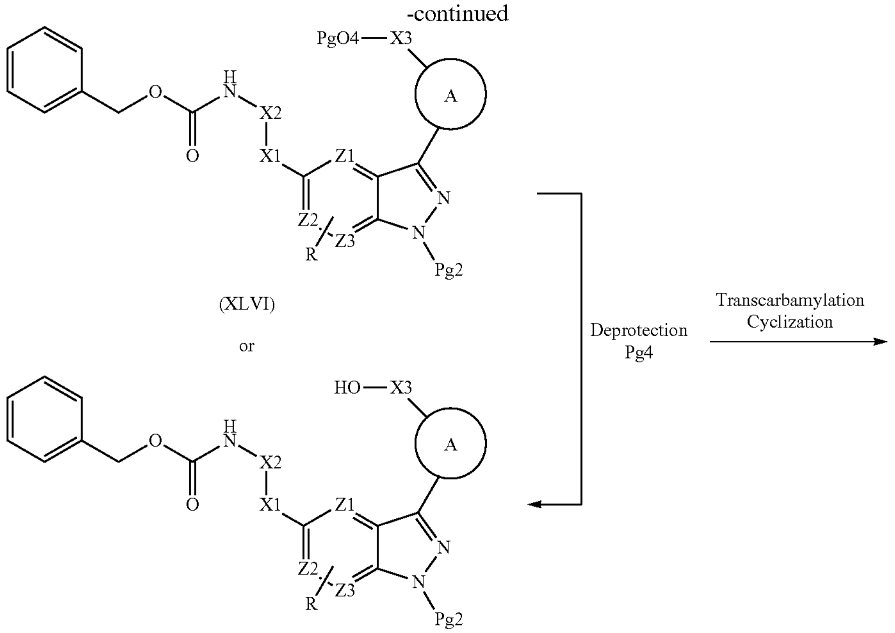

(XLVI)

or (XXI)

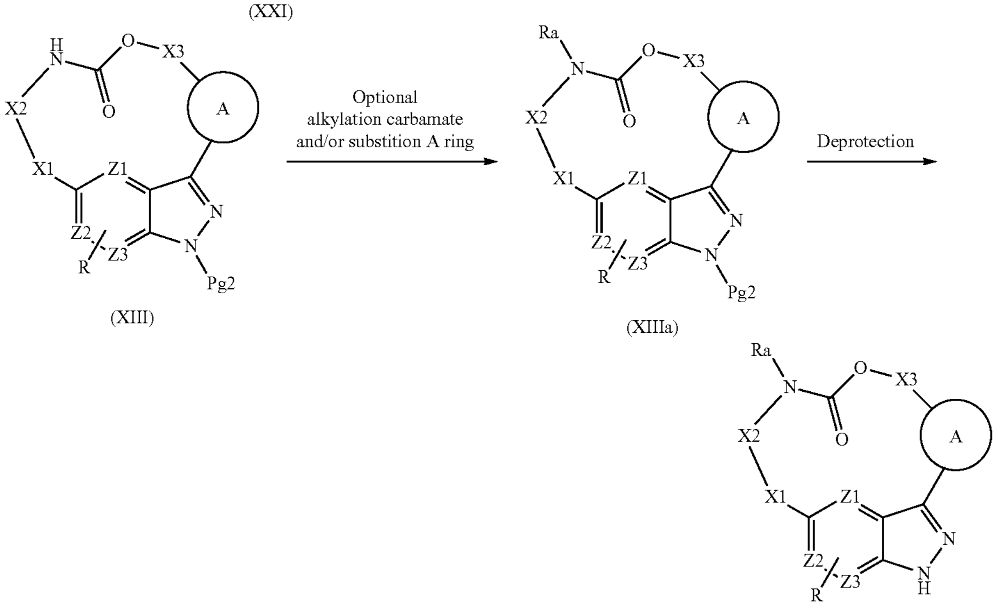

(XIII)

(XIIIa)

(I)

In the above reaction Scheme K, fused pyrazolo structure borylation of a compound of formula (XIV) to a compound of formula (XV) can be accomplished using an iridium catalyst and bis(pinacolato)diboron in a solvent such as TBME.

In the above reaction between compound of formula (XV) and compound of formula (XLIII) or compound of formula (XXVI), the leaving groups $Lg_1$ is advantageously a halogen atom such as chlorine, bromine or iodine. Such a halogen displacement reaction can be affected under cross-coupling conditions such as Suzuki conditions using palladium catalysts such as for example tetrakis(triphenylphosphine)palladium(0) combined with 2-dicyclohexylphosphino-2',4',6'-triisopropylbiphenyl (Xphos) in the presence of potassium phosphate tribasic in a solvent mixture such as for example 1,4-dioxane/water at an elevated temperature such as for example 90° C. either under microwave conditions or not.

Deprotection of X1 in the compound of formula (XLIV) or in the compound of formula (XLIVa) can be achieved using a reagent such as TBAF in a solvent such as THF at room temperature.

In the above reaction scheme, the alkylation between a compound of formula (XLV) or a compound of formula (XLVa) with a compound of formula (XIX) can be accomplished in a solvent such as N,N-dimethylformamide or acetonitrile and a base such as cesium carbonate or potassium carbonate at an elevated temperature such as 50° C. Suitable compounds of formula (XIX) may be either commercially acquired or obtained through reaction with CbzCl and sodium hydroxide of a compound of formula (XVIII) in water as a solvent. Alternatively, the compound of formula (XIX) can be made by introduction of Lg2 on the compound of the formula (XVIIIa).

Deprotection of X3-OPg4 in the compound of formula (XLVI) can be achieved using conditions such as potassium carbonate in a solvent such as MeOH at room temperature.

The transcarbamylation of the compound of formula (XXI) to the macrocycle of formula (XIII) can be done using potassium carbonate or cesium carbonate or potassium hydroxide in a solvent such as acetonitrile at a temperature ranging from RT to refluxing solvent, or using sodium hydride in a dry solvent such toluene at a temperature ranging from 0° C. to refluxing solvent, either under micro-wave conditions or not.

Final deprotection of the nitrogen of the fused pyrazolo structure under acidic conditions, either or not after alkylation of the carbamate and/or substitution of the A ring yields the final compound of formula (I).

Alternatively, the compounds of formula (I) can be prepared as shown in general Scheme L below wherein the fused pyrazolo structure of formula (II) is converted to a protected compound of formula (III). The NH of the fused pyrazolo structure can be protected to a compound of formula (XIV). This compound of formula (XIV) can be converted to a boronic acid (or boronate ester) of formula (XV). The compound of formula (XV) can be coupled in a cross coupling reaction such as a Suzuki coupling with a (hetero-)aryl of formula (XLVIII) to form a compound of formula (XLIX). Introduction of a leaving group on X2 results in a compound of formula (L). Deprotection of X1 results in a compound of formula (LI). The compound of formula (LI) can then be cyclized by a nucleophilic substitution to form a compound of formula (XIII). Final deprotection of the nitrogen of the fused pyrazolo structure, either or not after alkylation of the carbamate and/or substitution of the A ring results in the compound of formula (I).

Scheme L

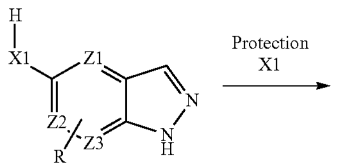

(II)

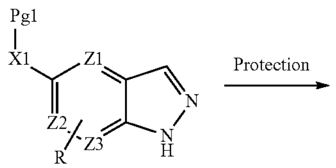

(III)

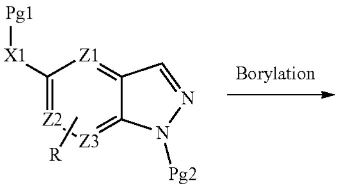

(XIV)

-continued

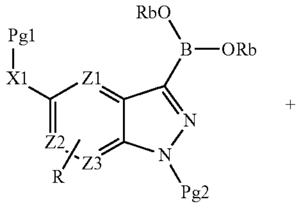

(XV)

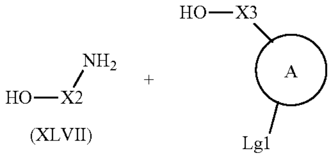

(XLVII)

(XXVI)

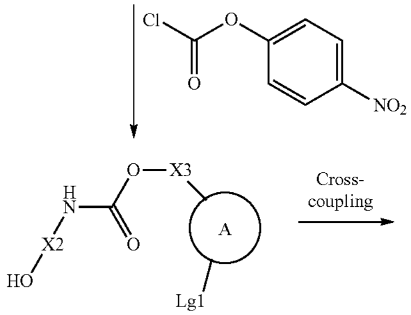

(XLVIII)

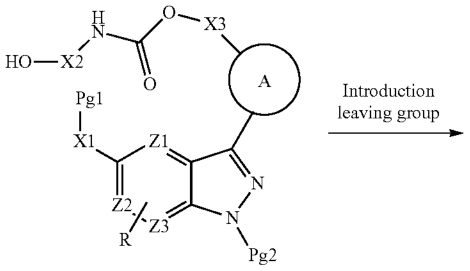

(XLIX)

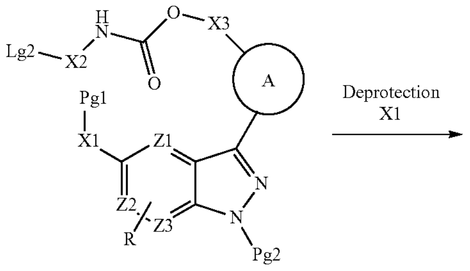

(L)

-continued

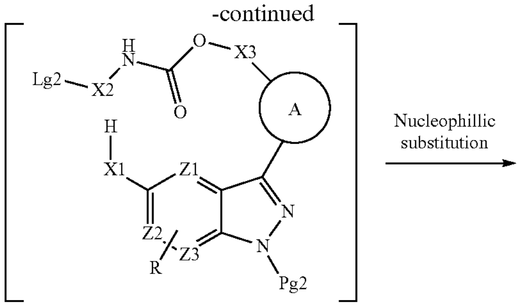

(LI)

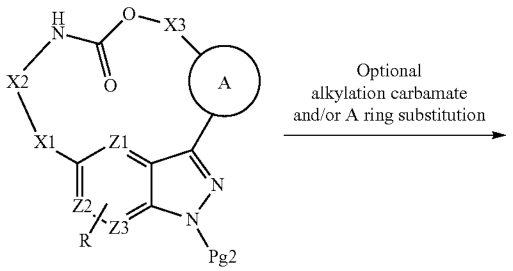

(XIII)

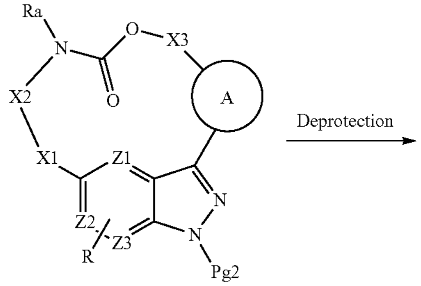

(XIIIa)

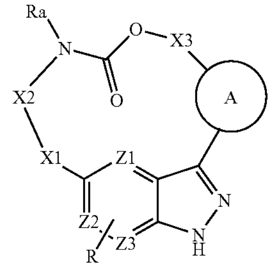

(I)

In the above reaction Scheme L, fused pyrazolo structure borylation a compound of formula (XIV) to a compound of formula (XV) can be accomplished using an iridium catalyst and bis(pinacolato)diboron in a solvent such as TBME.

In the above reaction between compound of formula (XV) and compound of formula (XLVIII), the leaving groups $Lg_1$ is advantageously a halogen atom such as chlorine, bromine or iodine. Such a halogen displacement reaction can be effected via organometallic cross coupling conditions such as Suzuki conditions using palladium catalysts such as for example tetrakis(triphenylphosphine)palladium(0) combined or not with 2-dicyclohexylphosphino-2',4',6'-triisopropylbiphenyl (Xphos) in the presence of potassium phosphate tribasic in a solvent mixture such as for example 1,4-dioxane/water at an elevated temperature such as for example 90° C. either under microwave conditions or not.

The compound of formula (XLVIII) can be made from a reaction of an alcohol of formula (XXVI), a chloroformate such as nitro-phenyl chloroformate and an amine of formula (XLVII). Introduction of a leaving group on X2 such as a mesylate on the compound of formula (XLIX) can be achieved using mesyl chloride in the presence of a base such as trimethylamine in a solvent such as DCM at room temperature and results in a compound of formula (L).

Deprotection of X1 to the compound of formula (LI) can be achieved using a reagent such as TBAF in a solvent such as THE at room temperature.

The macrocyclization of the compound of formula (LI) by nucleophilic substitution can be done on using cesium carbonate in a solvent such as N,N-dimethylformamide at an elevated temperature such as 80° C. and results in a compound of formula (XIII).

Final deprotection of the nitrogen of the fused pyrazolo structure under acidic conditions, either or not after alkylation of the carbamate and/or substitution of the A ring yields the final compound of formula (I).

Alternatively, the compounds of formula (I) can be prepared as shown in general Scheme M below wherein the fused pyrazolo structure of formula (II) is converted to a protected compound of formula (III). This compound of formula (III) can be converted to a compound of formula (IV) containing a leaving group on the fused pyrazolo structure and then into a nitrogen protected compound of formula (V). The compound of formula (V) can be converted into a selectively protected fused pyrazolo structure of formula (VI) which is then alkylated with an intermediate of formula (XIX) containing a leaving group resulting in a compound of formula (XXII). The compound of formula (XIX) can commercially be acquired or being prepared from a compound of formula (XVIII) through a reaction with CbzCl or through the introduction of a leaving group Lg2 on the compound of formula (XVIIIa). The compound of formula (XXII) can be coupled in a copper mediated coupling with a protected alkyne (LII) to form a compound of formula (LIII).

Deprotection of the alkyne leads to a compound of formula (LIV). From the alkyne the (hetero-)aromatic ring can be formed resulting in a compound of formula (XLII). Deprotection of X3-OPg4 results in a compound of formula (XXI). The compound of formula (XXI) can then be cyclized by a transcarbamylation reaction to form a compound of formula (XIII). Final deprotection of the nitrogen of the fused pyrazolo structure, either or not after alkylation of the carbamate and/or substitution of the A ring results in the compound of formula (I).

Scheme M

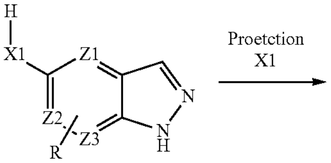

(II)

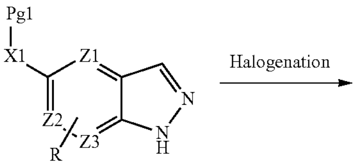

(III)

-continued
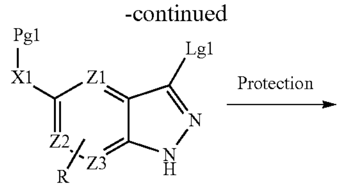
(IV)
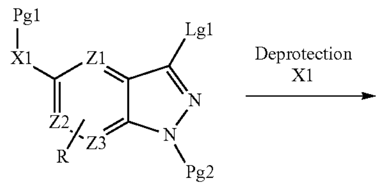
(V)
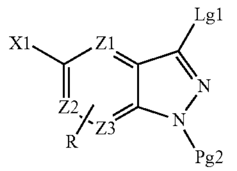
+
(VI)
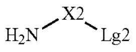
(XVIII)
or
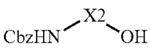
(XVIIIa)
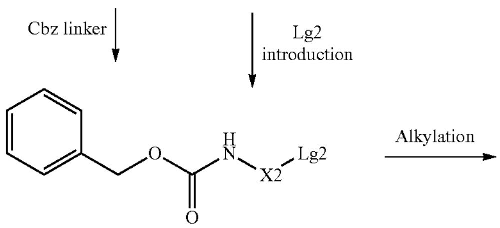
(XIX)
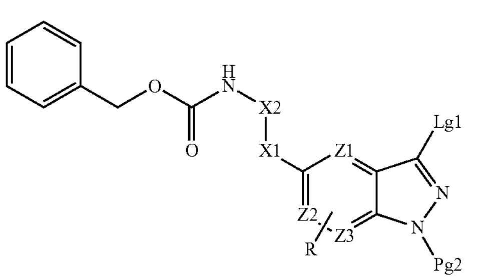
+
(XXII)
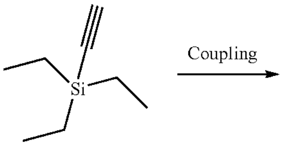
(LII)
-continued
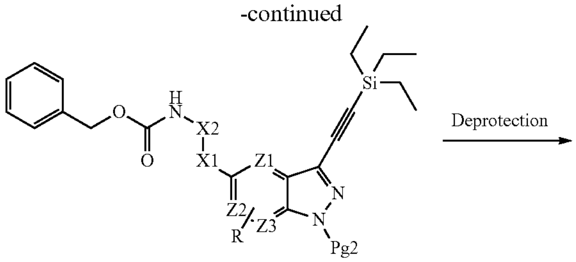
(LIII)
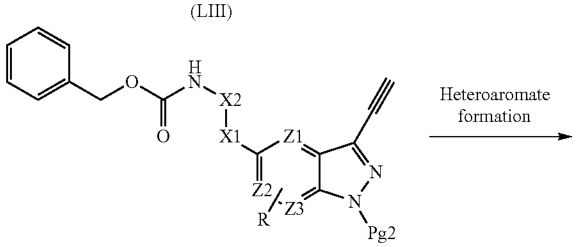
(LIV)
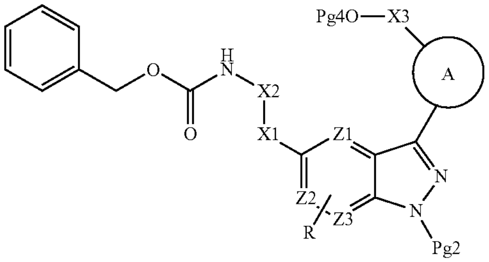
(XLII)
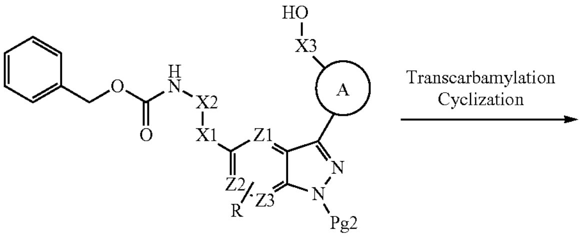
(XXI)
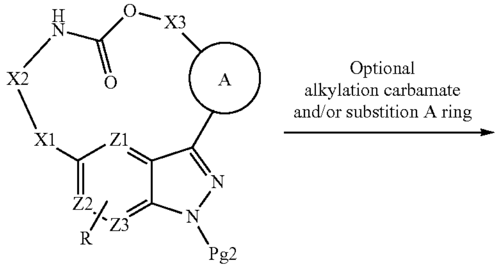
(XIII)
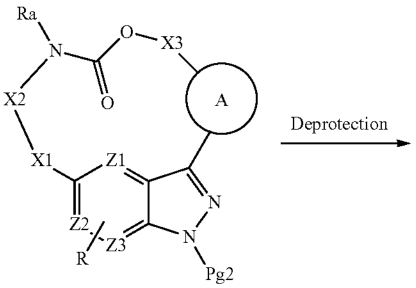
(XIIIa)

-continued

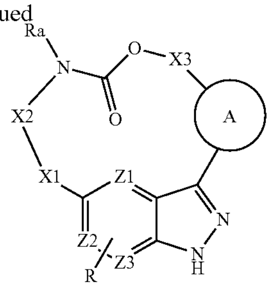

(I)

In the above Scheme M, A is a 5-membered aromatic cyclic group as define in formula (a) with A4 is a carbon atom and A5 represent a carbon atom optionally substituted.

In the above reaction scheme, the alkylation between a compound of formula (VI) with a compound of formula (XIX) can be accomplished in a solvent such as N,N-dimethylformamide or acetonitrile and a base such as cesium carbonate or potassium carbonate at an elevated temperature such as 120° C.

Suitable compounds of formula (XIX) may be either commercially acquired or obtained through reaction with CbzCl and sodium hydroxide of a compound of formula (XVIII) in water as a solvent. Alternatively, the compound of formula (XIX) can be made by introduction of Lg2 on the compound of the formula (XVIIIa).

In the above reaction between compound of formula (XXII) and compound of formula (LII), the leaving groups $Lg_1$ is advantageously a halogen atom such as chlorine, bromine or iodine. Such a halogen displacement reaction can be effected under conditions using palladium catalysts such as for example tetrakis(triphenylphosphine)palladium (0) combined or not with CuI in the presence of triethylamine in a solvent such as for example THE at an elevated temperature such as for example 80° C.

Alkyne deprotection can be achieved using TBAF in a solvent such as THE at room temperature giving a compound of formula (LIV).

Heteroaromatic ring formation to a compound of formula (XLII) can be effected through reaction with a reagent such as tert-butyl-(3-nitropropoxy)-diphenyl-silane in the presence of PhNCO and trimethylamine in a solvent such as THE at an elevated temperature such as 80° C. Deprotection of X3-OPg4 in compound (XLII) can be done using TBAF in a solvent such as THE at room temperature giving a compound of formula (XXI).

The transcarbamylation of the compound of formula (XXI) to the macrocycle of formula (XIII) can be done using potassium carbonate or cesium carbonate or potassium hydroxide in a solvent such as acetonitrile at a temperature ranging from RT to refluxing solvent, or using sodium hydride in a dry solvent such toluene at a temperature ranging from 0° C. to refluxing solvent, either under microwave conditions or not.

Final deprotection of the nitrogen of the fused pyrazolo structure under acidic conditions, either or not after alkylation of the carbamate and/or substitution of the A ring yields the final compound of formula (I).

Alternatively, the compounds of formula (I) can be prepared as shown in general Scheme N below wherein the fused pyrazolo structure of formula (II) is converted to a protected compound of formula (III). This compound of formula (III) can be converted to a compound of formula (IV) containing a leaving group on the fused pyrazolo structure and then into a nitrogen protected compound of formula (V). The compound of formula (V) can be converted into a selectively protected fused pyrazolo structure of formula (VI). The compound of formula (VI) is alkylated with a compound of formula (VIIIa) to form a compound of formula (LV). Deprotection of X2-N(Ra)Pg3 results in a compound of formula (LVI). The compound of formula (LVI) can be coupled to the (hetero-)aromatic compound of formula (LVII) through a reaction with CDI. The compound of formula (LVIII) can then be cyclized by a CH activation reaction to form a compound of formula (XIII). Final deprotection of the nitrogen of the fused pyrazolo structure, either or not after alkylation of the carbamate and/or substitution of the A ring results in the compound of formula (I).

Scheme N

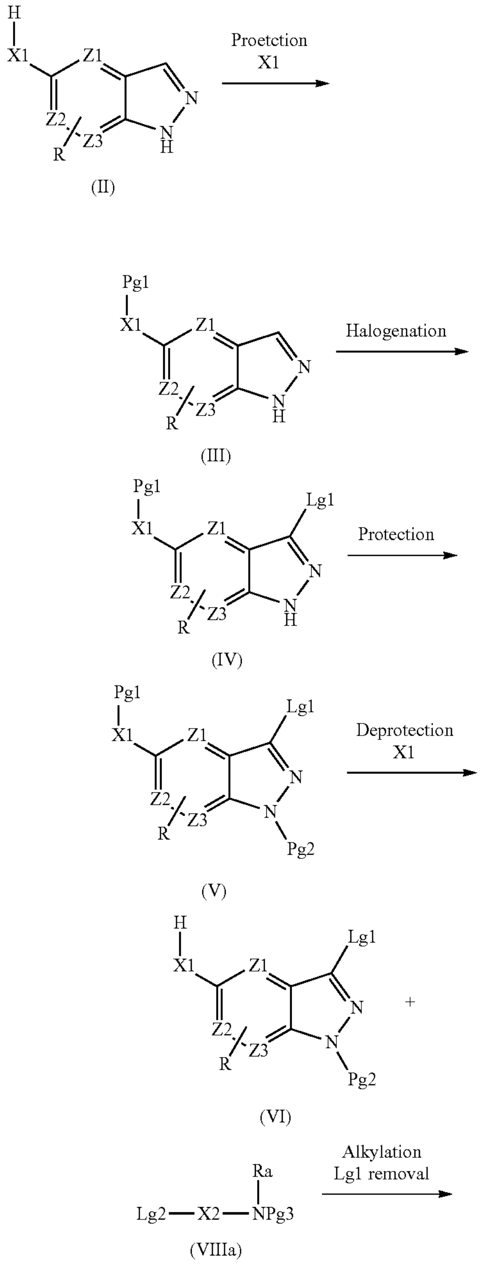

(II)

(III)

(IV)

(V)

(VI)

(VIIIa)

-continued

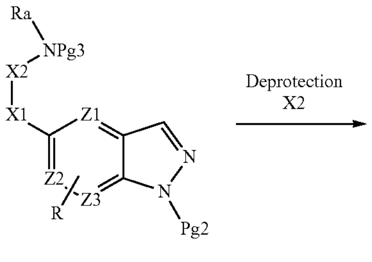

(LV)

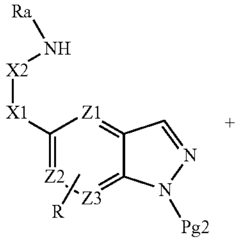

(LVI)

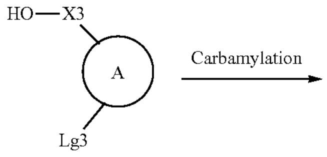

(LVII)

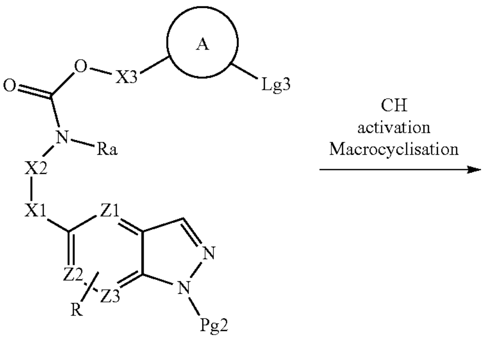

(LVIII)

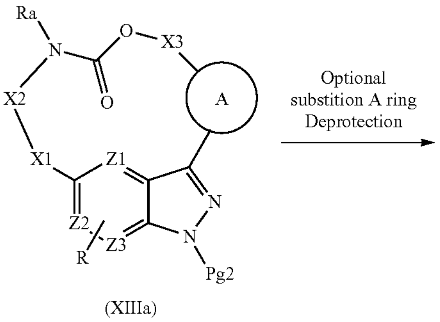

(XIIIa)

-continued

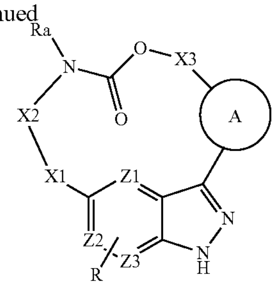

(I)

In the above reaction Scheme N, the alkylation between a compound of formula (VI) with a compound of formula (VIIIa) can be accomplished in a solvent such as N,N-dimethylformamide or acetonitrile and a base such as cesium carbonate or potassium carbonate at room temperature or at an elevated temperature. Suitable compounds of formula (VIIIa) may be either commercially acquired or obtained through various selective protection and deprotection steps known to the person skilled in the art.

Deprotection of the compound of formula (LV) can be affected using palladium over carbon on charcoal and hydrogen gas at room temperature in a solvent such as MeOH.

Coupling of the (hetero-)aromatic part on formula (LVI) can be achieved at room temperature using 1,1'-carbonyldiimidazole and a base such as cesium carbonate in a solvent such as N,N-dimethylacetamide Ring closure through CH activation of the compound of formula (LVIII) to the macrocycle of formula (XIII) can be achieved using cataCXium, palladium acetate and potassium acetate in dry toluene under microwave conditions at an elevated temperature such as 150° C.

Final deprotection of the nitrogen of the fused pyrazolo structure under acidic conditions, either or not after alkylation of the carbamate and/or substitution of the A ring yields the final compound of formula (I).

Alternatively, the compounds of formula (I) can be prepared as shown in general Scheme O below wherein the fused pyrazolo structure of formula (II) is converted to a protected compound of formula (III). The NH of the fused pyrazolo structure can be protected to a compound of formula (XIV). This compound of formula (XIV) can be converted to a boronic acid (or boronate ester) of formula (XV). The compound of formula (XV) can be coupled via organometallic cross coupling such as Suzuki coupling with a (hetero-)aryl of formula (XLIII) or of formula (XXVI) to form a compound of formula (XLIV) or a compound of formula (XLIVa), which can then be alkylated with a compound of formula (XIX) and cyclized by a transcarbamylation reaction in a one-pot reaction to form a compound of formula (XIII). Alternatively the compound of formula (XLIVa) can be first deprotected to a compound of formula (XLIVb) before the one-pot alkylation and cyclisation. Final deprotection of the nitrogen of the fused pyrazolo structure, either or not after alkylation of the carbamate and/or substitution of the A ring results in the compound of formula (I).

Scheme O
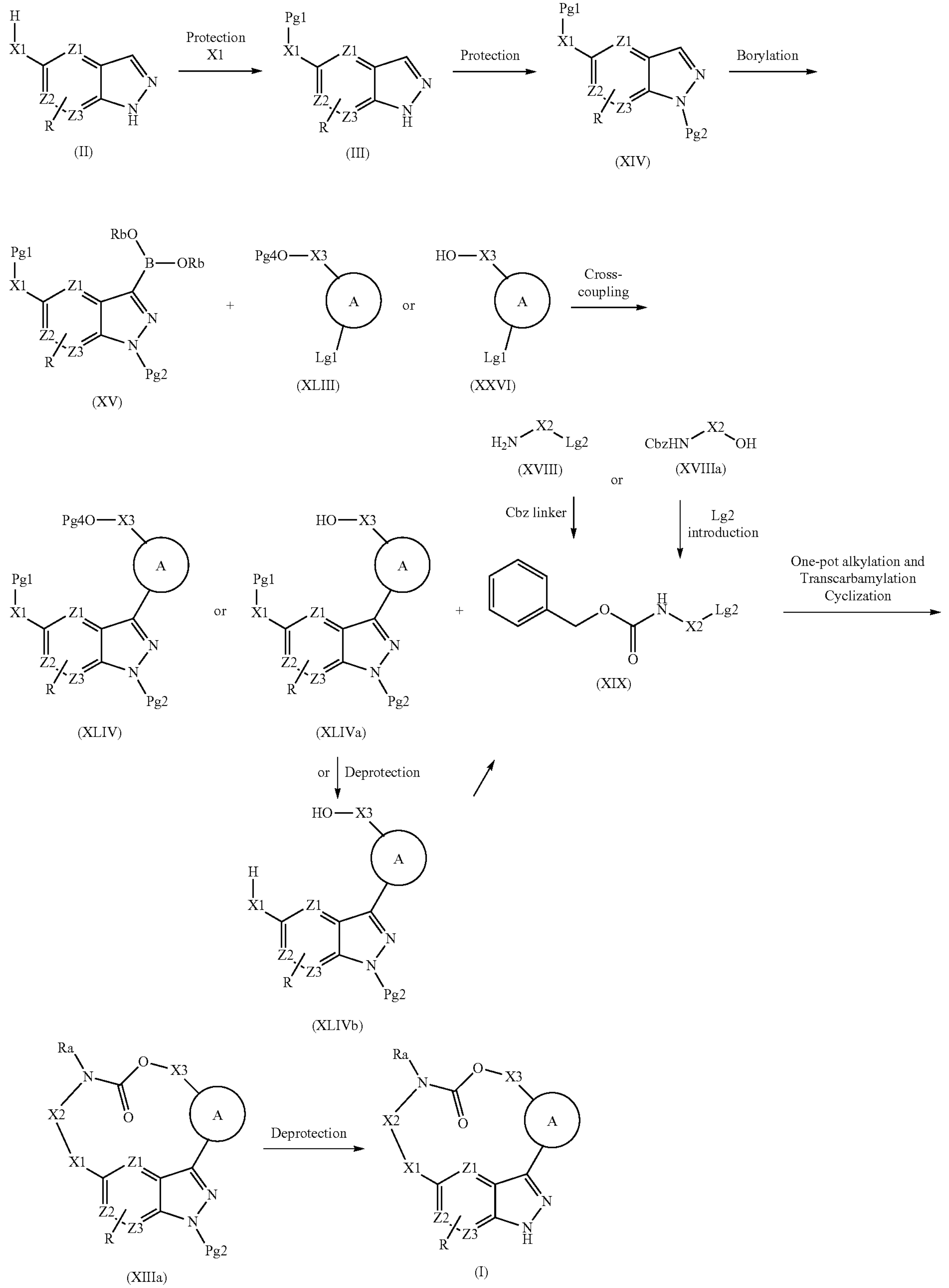

In the above reaction Scheme O, fused pyrazolo structure borylation of a compound of formula (XIV) to a compound of formula (XV) can be accomplished using an iridium catalyst and bis(pinacolato)diboron in a solvent such as TBME.

In the above reaction between compound of formula (XV) and compound of formula (XLIII) or compound of formula (XXVI), the leaving groups $Lg_1$ is advantageously a halogen atom such as chlorine, bromine or iodine. Such a halogen displacement reaction can be affected under cross-coupling conditions such as Suzuki conditions using palladium catalysts such as for example tetrakis(triphenylphosphine)palladium(0) combined with 2-dicyclohexylphosphino-2',4',6'-triisopropylbiphenyl (Xphos) in the presence of potassium phosphate tribasic in a solvent mixture such as for example 1,4-dioxane/water at an elevated temperature such as for example 90° C. either under microwave conditions or not.

The possibly deprotection of X1 can be done using TBAF in a solvent such as THF at a temperature such as room temperature.

The possibly one-pot alkylation with a compound of formula (XIX) and transcarbamylation to the macrocycle of formula (XIII) can be done using cesium carbonate in a solvent such as acetonitrile at a temperature ranging from RT to 80° C.

Final deprotection of the nitrogen of the fused pyrazolo structure under acidic conditions, either or not after alkylation of the carbamate and/or substitution of the A ring yields the final compound of formula (I).

Alternatively, the compounds of formula (I) can be prepared as shown in general Scheme P below wherein the fused pyrazolo structure of formula (II) is converted to a protected compound of formula (III). The NH of the fused pyrazolo structure can be protected to a compound of formula (XIV). This compound of formula (XIV) can be converted to a boronic acid (or boronate ester) of formula (XV). The compound of formula (XV) can be coupled via organometallic cross coupling such as Suzuki coupling with a (hetero-)aryl of formula (XXVI) to form a compound of formula (XLIVa), which can then be alkylated with a compound of formula (XLVI) and cyclized by a carbamylation reaction to form a compound of formula (XLVIII). Final deprotection of the nitrogen of the fused pyrazolo structure, either or not after alkylation of the carbamate and/or substitution of the A ring results in the compound of formula (I).

Scheme P

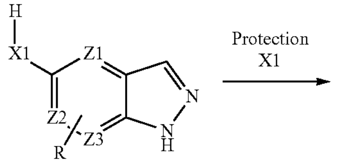

(II)

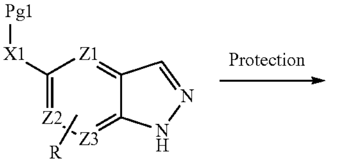

(III)

-continued

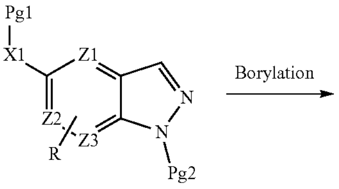

(XIV)

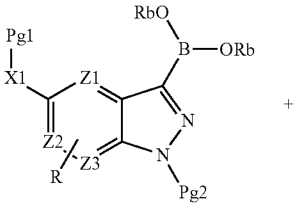

(XV)

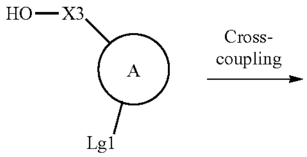

(XXVI)

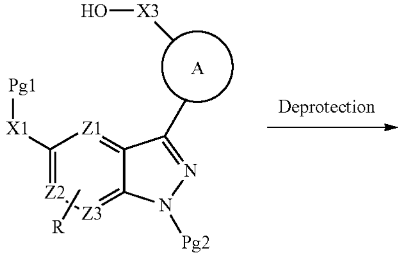

(XLIVa)

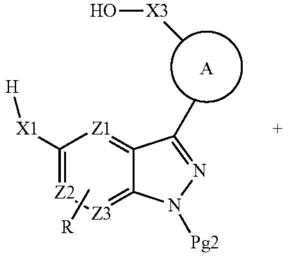

(XLV)

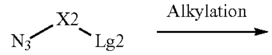

(XLVI)

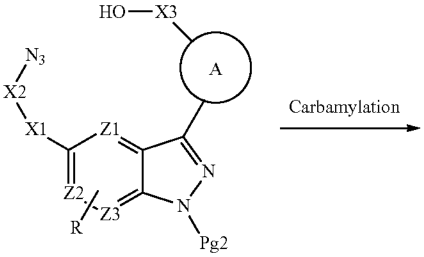

(XLVII)

-continued

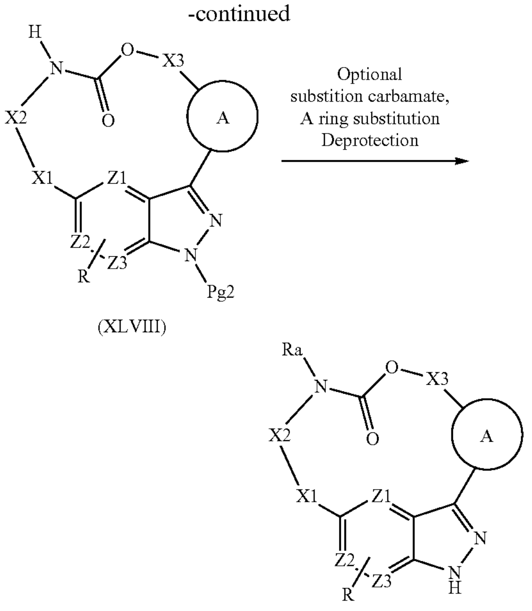

(XLVIII)

(I)

In the above reaction Scheme P, fused pyrazolo structure borylation of a compound of formula (XIV) to a compound of formula (XV) can be accomplished using an iridium catalyst and bis(pinacolato)diboron in a solvent such as TBME.

In the above reaction between compound of formula (XV) and compound of formula (XXVI), the leaving groups $Lg_1$ is advantageously a halogen atom such as chlorine, bromine or iodine. Such a halogen displacement reaction can be affected under cross-coupling conditions such as Suzuki conditions using palladium catalysts such as for example tetrakis(triphenylphosphine)palladium(0) combined with 2-dicyclohexylphosphino-2',4',6'-triisopropylbiphenyl (Xphos) in the presence of potassium phosphate tribasic in a solvent mixture such as for example 1,4-dioxane/water at an elevated temperature such as for example 90° C. either under microwave conditions or not.

The alkylation of the compound of formula (XLV) with a compound of formula (XLVI) can be done using cesium carbonate in a solvent such as acetonitrile at a temperature ranging from RT to 80° C.

Carbamylation of the compound of formula (XLVIII) can be achieved using a reagent such as CDI, $COCl_2$, $CO_2$ or CO.

Final deprotection of the nitrogen of the fused pyrazolo structure under acidic conditions, either or not after alkylation of the carbamate and/or substitution of the A ring yields the final compound of formula (I).

EXAMPLES

IUPAC names of compounds of the invention were generated using the following software:

Product version: MarvinSketch 18.3.0
Build Date: 2018 Jan. 26
Internal Build id: 18.3.0-7913
Operating System: amd64 Windows 10.10.0
Character encoding: windows-1252
Java: Jeroen Frijters Java 1.8.0
Memory: 43.8M total, 10.0M free
Environment: Application
.NET Version: v2.0.50727
IKVM Version: 8.10.1.2
JChem NET API Assembly Version: 18.3.07913
JChem NET API File Version: 18.3.0.7913
Marvin .NET Version: 18.3.0.137
Process type: x64
http://www.chemaxon.com In case of a discrepancy between the drawn chemical structures and the corresponding chemical names, the drawn chemical structures will be considered as true structures.

To prepare the compounds described in the examples, the following experimental protocols were followed unless otherwise indicated.

Unless otherwise stated, reaction mixtures were stirred magnetically at room temperature. When organic solutions were "dried", they were generally dried over a drying agent such as sodium sulfate or magnesium sulfate. When mixtures, solutions and extracts were "concentrated", they were typically concentrated on a rotary evaporator under reduced pressure.

All intermediates and final exemplified compounds were analyzed by high-performance liquid chromatography (HPLC) following one of the described methods below.

LCMS Method A

Analyses were carried out on a Thermo Scientific Accucore C18 (50 mm long×2.1 mm I.D., 2.6 μm) at 35° C., with a flow rate of 1.50 mL/min. A gradient elution was performed from 95% (Water+0.1% Formic acid)/5% Acetonitrile to 5% (Water+0.1% Formic acid)/95% Acetonitrile in 1.30 minutes; the resulting composition was held for 0.5 min; then the final mobile phase composition; from 5% (Water+0.1% Formic acid)/95% Acetonitrile to 90% (Water+0.1% Formic acid)/10% Acetonitrile in 0.10 minutes. The injection volume was 1 μL. MS acquisition range and UV detector were set to 100-1000 m/z and 190-400 nm respectively.

LCMS Method B

Analyses were carried out on a Phenomenex Kinetex OOB-4475-AN C18 column (50 mm long×2.1 mm I.D.; 1.7 μm particles) at 60° C., with a flow rate of 1.5 mL/min. A gradient elution was performed from 90% (Water+0.1% Formic acid)/10% Acetonitrile to 10% (Water+0.1% Formic acid)/90% Acetonitrile in 1.50 minutes; the resulting composition was held for 0.40 min; then the final mobile phase composition; from 10% (Water+0.1% Formic acid)/90% Acetonitrile to 90% (Water+0.1% Formic acid)/10% Acetonitrile in 0.10 minutes. The injection volume was 2 μL with Agilent autosampler injector or 5 μL with Gerstel MPS injector. MS acquisition range and DAD detector were set to 100-800 m/z and 190-400 nm respectively.

LCMS Method C

Analyses were carried out on an YMC pack ODS-AQ C18 column (50 mm long×4.6 mm ID.; 3 μm particle size) at 35° C., with a flow rate of 2.6 mL/min. A gradient elution was performed from 95% (Water+0.1% Formic acid)/5% Acetonitrile to 5% (Water+0.1% Formic acid)/95% Acetonitrile in 4.8 min; the resulting composition was held for 1.0 min; from 5% (Water+0.1% formic acid)/95% Acetonitrile to 95% (Water+0.1% formic acid)/5% Acetonitrile in 0.2 min. The standard injection volume was 2 μL. Acquisition ranges were set to 190-400 nm for the UV-PDA detector and 100-1400 m/z for the TOF-LCMS detector. Total run time: 6.2 minutes.

LCMS Method D

Analyses were carried out on a Phenomenex Kinetex C18 column (50 mm long×2.1 mm I.D.; 2.6 μm particle size) at 35° C., with a flow rate of 0.7 mL/min. A gradient elution was performed from 95% (Water+50 mM Ammonium Acetate)/5% Acetonitrile to 5% (Water+50 mM Ammonium Acetate)/95% Acetonitrile in 4.8 min; the resulting composition was held for 1.0 min; from 5% (Water+50 mM Ammonium Acetate)/95% Acetonitrile to 95% (Water+50 mM Ammonium Acetate)/5% Acetonitrile in 0.2 min. The standard injection volume was 2 μL. Acquisition ranges were set to 190-400 nm for the UV-PDA detector and 100-1400 m/z for the MS detector. Total run time: 6.2 minutes.

LCMS Method E

Analyses were carried out on an YMC pack ODS-AQ C18 column (50 mm long×4.6 mm ID.; 3 μm particle size) at 35° C., with a flow rate of 2.6 mL/min. A gradient elution was performed from 95% (Water+0.1% Formic acid)/5% Acetonitrile to 5% (Water+0.1% Formic acid)/95% Acetonitrile in 4.8 min; the resulting composition was held for 1.0 min; from 5% (Water+0.1% formic acid)/95% Acetonitrile to 95% (Water+0.1% formic acid)/5% Acetonitrile in 0.2 min. The standard injection volume was 2 μL. Acquisition ranges were set to 190-400 nm for the UV-PDA detector and 100-1400 m/z for the MS detector.

LCMS Method F

Analytical HPLC was conducted on a X-Select CSH C18 XP column (2.5 μm 30×4.6 mm id) eluting with 0.1% formic acid in water (solvent A) and 0.1% formic acid in acetonitrile (solvent B), using the following elution gradient 0-3 minutes: 5% to 100% B, 3-4 minutes 100% B, at a flow rate of 1.8 mL/minute at 40° C. The mass spectra (MS) were recorded on a Waters ZQ mass spectrometer (scan 200-900 uma) using electrospray positive ionisation[ES+ to give $[M+H]^+$ molecular ions] or electrospray negative ionisation [ES− to give $[M-H]^-$ molecular ions] modes with a 20 V cone voltage.

LCMS Method G

Analytical HPLC was conducted on a X-Select CSH C18 XP column (2.5 μm 30×4.6 mm id) eluting with $(NH_4)_2CO_3$ aq. 2 g/L in water (solvent A) and acetonitrile (solvent B), using the following elution gradient 0-3 minutes: 5% to 100% B, 3-4 minutes 100% B, at a flow rate of 1.8 mL/minute at 40° C. The mass spectra (MS) were recorded on a Waters ZQ mass spectrometer (scan 200-900 uma) using electrospray positive ionisation[ES+ to give $[M+H]^+$ molecular ions] or electrospray negative ionisation [ES− to give $[M-H]^-$ molecular ions] modes with a 20 V cone voltage.

LCMS Method H

Analytical HPLC was conducted on a X-Select CSH C18 XP column (2.5 μm 30×4.6 mm id) eluting with 0.1% formic acid in water (solvent A) and 0.1% formic acid in acetonitrile (solvent B), using the following elution gradient 0-4 minutes: 0% to 50% B at a flow rate of 1.8 mL/minute at 40° C. The mass spectra (MS) were recorded on a Waters ZQ mass spectrometer (scan 200-900 uma) using electrospray positive ionisation [ES+ to give $[M+H]^+$ molecular ions] or electrospray negative ionisation [ES− to give $[M-H]^-$ molecular ions] modes with a 20 V cone voltage.

LCMS Method I

Analytical HPLC was conducted on a X-Select CSH C18 XP column (2.5 μm 30×4.6 mm id) eluting with 0.1% formic acid in water (solvent A) and 0.1% formic acid in acetonitrile (solvent B), using the following elution gradient 0-4 minutes: 40% to 100% B, 4-5 min: 100% B at a flow rate of 1.8 mL/minute at 40° C. The mass spectra (MS) were recorded on a Waters ZQ mass spectrometer (scan 200-900 uma) using electrospray positive ionisation [ES+ to give $[M+H]^+$ molecular ions] or electrospray negative ionisation [ES− to give $[M-H]^-$ molecular ions] modes with a 20 V cone voltage.

LCMS Method J

Analytical HPLC was conducted on a X-Select CSH C18 XP column (2.5 μm 30×4.6 mm id) eluting with 0.1% formic acid in water (solvent A) and 0.1% formic acid in acetonitrile (solvent B), using the following elution gradient 0-6 minutes: 5% to 100% B, 6-7 min: 100% B at a flow rate of 1.8 mL/minute at 40° C. The mass spectra (MS) were recorded on a Waters ZQ mass spectrometer (scan 200-900 uma) using electrospray positive ionisation [ES+ to give $[M+H]^+$ molecular ions] or electrospray negative ionisation [ES− to give $[M-H]^-$ molecular ions] modes with a 20 V cone voltage.

Chiral analytical SFC was conducted on a Whelk O1 (R,R) column (1.8 μm 100×4.6 mmid) eluting with CO2/methanol (70/30) at a flow rate of 2.5 mL/minute at 35° C.

All final exemplified compounds were analysed by proton NMR.

$^1$H NMR spectra were recorded in either $CDCl_3$, d6-DMSO or $CD_3OD$ on a Bruker Avance 400 MHz or were recorded on a Bruker Ultrashield AV300 MHz spectrometer, with a Bruker 5 mm BBI 1H/D-BB Z-GRD probe, using a BACS-60 sample changer, and registered with Bruker Topspin 2.1 software. Chemical shifts are reported in parts per million (ppm) relative to the residual protiated solvent (7.26 ppm for $CDCl_3$, 2.50 ppm for d6-DMSO and 3.31 ppm for $CD_3OD$). For $^1$H NMR spectra, multiplicities, coupling constants in hertz and numbers of protons are indicated parenthetically. Abbreviations for NMR data are as follows: s=singlet, d=doublet, t=triplet, q=quadruplet, m=multiplet, br s=broad singlet.

Alternatively, the $^1$H-NMR measurements were performed on Bruker Avance III 500 MHz spectrometer, using DMSO-d6 (hexadeutero-dimethylsulfoxide) or $CDCl_3$ (deuterochloroform) as solvent. $^1$H-NMR data is in the form of delta values, given in part per million (ppm), using the residual peak of the solvent (2.50 ppm for DMSO-d6 and 7.26 ppm for $CDCl_3$) as internal standard. Splitting patterns are designated as: s (singlet), 2s (2×singlet), d (doublet), 2d (2×doublet), t (triplet), 2t (2×triplet), q (quartet), 2q (2×quartet), quint (quintet), sept (septet), m (multiplet), 2m (2×multiplet), brs (broad singlet), brd (broad doublet), brt (broad triplet), brq (broad quartet), brm (broad multiplet), vbrs (very broad singlet), dd (doublet of doublets), td (triplet of doublets), dt (doublet of triplets), dq (doublet of quartet), ddd (doublet of doublet of doublets), dm (doublet of multiplets), tm (triplet of multiplets), qm (quartet of multiplets).

Abbreviations

The following abbreviations are employed herein:

Ph=phenyl
Ac=acetate
Bn=benzyl
t-Bu=tert-butyl
n-Bu=linear butyl
Me=methyl
Et=ethyl
Pr=propyl
iPr=isopropyl
Bu=butyl
TMS=trimethylsilyl
TBS=tert-butyldimethylsilyl
TFA=trifluoroacetic acid
i-$Pr_2$NEt or DIPEA=N,N-diisopropylethylamine TEA=triethylamine
DMAP=4-dimethylaminopyridine
Pd/C=palladium on carbon
KOH=potassium hydroxide
NaOH=sodium hydroxide
LiGH=lithium hydroxide
Ar=argon
$N_2$=nitrogen
$H_2$=hydrogen
LAH=lithium Aluminium Hydride
Boc=tert-butoxycarbonyl
Cbz=carboxybenzyl
LDA=lithium diisopropylamide
NBS=N-bromosuccinimide
NIS=N-iodosuccinimide
ACN=acetonitrile
PTSA=p-toluenesulfonic acid
THF=tetrahydrofuran
DCM=dichloromethane
DMF=N,N-dimethylformamide
AA=acetic acid
TBME=methyl tert-butyl ether
Hept=heptane
EtOAc=ethyl acetate
DHP=3,4-Dihydro-2H-pyran
THP=Tetrahydropyran
TBAF=tetrabutylammonium fluoride
cataCXium=di(1-adamantyl)-n-butylphosphine
XPhos=2-Dicyclohexylphosphino-2',4',6'-triisopropylbiphenyl
dppf=1,1'-Bis(diphenylphosphino)ferrocene
wt %=weight %
e.e. =enantiomeric excess
min=minute(s)
h or hr=hour(s)
L=liter(s)
mL=milliliter(s)
μL=microliter(s)
g=gram(s)
mg=milligram(s)
mol=moles
mmol=millimole(s)
RT=room temperature
$t_R$=retention time
sat=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
ppm=parts per million Example 1: 8,14-dioxa-4,10,19,20-tetraazatetracyclo $[13.5.2.1^{2,6}.0^{18,21}]$tricosa-1(20),2,4, 6(23),15,17,21-heptaen-9-one

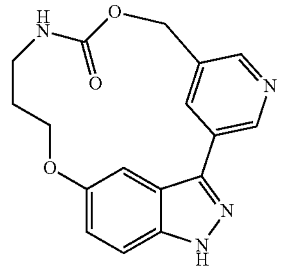 [SMILES: O=C1NCCCOc2ccc3[nH]nc(c3c2)-c2cncc(c2)CO1]

Example 1 is prepared according to the synthesis route described in general Scheme A.

Preparation of Intermediate 1: 5-((tert-butyldimethylsilyl)oxy)-1H-indazole

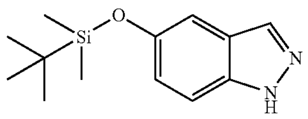 [SMILES: CC(C)(C)[Si](C)(C)Oc1ccc2[nH]ncc2c1]

1H-indazol-5-ol (19 g, 141.643 mmol) was dissolved in 425 mL of DCM, then imidazole (11.572 g, 169.972 mmol) and tert-butylchlorodimethylsilane (23.485 g, 155.807 mmol) were added and the mixture was stirred at RT for 16 hours. A saturated $NaHCO_3$ solution was added and the reaction mixture was extracted with DCM (2×). The combined organic layers were dried over $MgSO_4$, filtered and the solvent was removed under reduced pressure. The crude product was purified by flash chromatography on silica gel using Hept/EtOAc (100:0 to 70:30). The desired fractions were combined and concentrated under reduced pressure yielding 5-((tert-butyldimethylsilyl)oxy)-1H-indazole 1 as a salmon solid.

LCMS method A: $[M+H]^+$=249.0, $t_R$=0.997 min

Preparation of Intermediate 2: 5-((tert-butyldimethylsilyl)oxy)-3-iodo-1H-indazole

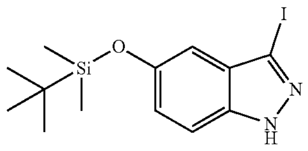 [SMILES: CC(C)(C)[Si](C)(C)Oc1ccc2[nH]nc(I)c2c1]

5-((tert-butyldimethylsilyl)oxy)-3-iodo-1H-indazole 1 (20 g, 80.515 mmol) was dissolved in 240 mL of DCM, N-iodosuccinimide (19.021 g, 84.541 mmol) was added and the mixture was stirred at RT for 16 hours. The reaction mixture was diluted with DCM and a saturated $NaHCO_3$ solution was added. The two layers were separated and the water layer was extracted with DCM (2×). The combined organic layers were dried over $MgSO_4$, filtered and the solvent was removed under reduced pressure affording the crude product which was purified by flash chromatography on silica gel using Hept/EtOAc (100:0 to 80:20) as eluents. The desired fractions were combined and the solvent was removed under reduced pressure yielding 5-((tert-butyldimethylsilyl)oxy)-3-iodo-1H-indazole 2 as a light brown solid.

LCMS method A: $[M+H]^+$=374.9, $t_R$=1.156 min

Preparation of Intermediate 3: 5-((tert-butyldimethylsilyl)oxy)-3-iodo-1-(tetrahydro-2H-pyran-2-yl)-H-indazole

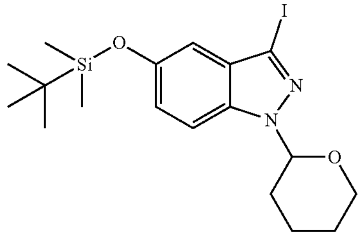 [SMILES: CC(C)(C)[Si](C)(C)Oc1ccc2c(c1)c(I)nn2C1CCCCO1]

To a solution of 5-((tert-butyldimethylsilyl)oxy)-3-iodo-1H-indazole 2 (27.960 g, 74.699 mmol) in 224 mL of DCM, 4-methylbenzenesulfonic acid monohydrate (1.421 g, 7.470 mmol) and 3,4-dihydro-2H-pyran (20.490 mL, 224.097 mmol) were added. The reaction mixture was stirred at RT for 16 hours. The mixture was diluted with DCM and a saturated $NaHCO_3$ solution was added. The two layers were separated and the water layer was extracted with DCM (2×). The combined organic layers were dried over $MgSO_4$, filtered and the solvent was removed under reduced pressure. The concentrated was purified by flash chromatography (silica; Heptane/EtOAc 100:0 to 95:5). The desired fractions were combined and the solvent was removed under reduced pressure affording 5-((tert-butyldimethylsilyl)oxy)-3-iodo-1-(tetrahydro-2H-pyran-2-yl)-1H-indazole 3 as a light orange oil.

LCMS method A: $[M+H]^+$=458.9, $t_R$=1.377 min

Preparation of Intermediate 4: 3-iodo-1-(tetrahydro-pyran-2-yl)-1H-indazol-5-ol

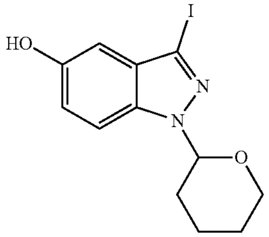 [SMILES: Oc1ccc2c(c1)c(I)nn2C1CCCCO1]

5-((tert-butyldimethylsilyl)oxy)-3-iodo-1-(tetrahydro-2H-pyran-2-yl)-1H-indazole 3 (10.000 g, 21.814 mmol) was dissolved in 62 mL of THF. TBAF [1M] in THE (32.8 mL, 32.800 mmol) was added at 0° C. The reaction was stirred at RT for 16 h. A saturated $NaHCO_3$ solution was added and the two layers were separated. The water layer was extracted with DCM (2×). The combined organic layers were dried over $MgSO_4$, filtered and the solvent was removed under reduced pressure. The crude was purified by flash chromatography (silica; Heptane/EtOAc 100:0 to 60:40). The fractions containing the desired product were combined and the solvent was evaporated under reduced pressure to yield 3-Iodo-1-(tetrahydro-pyran-2-yl)-1H-indazol-5-ol 4 as a creamy solid.

LCMS method B: $[M+H]^+$=345.0, $t_R$=0.767 min

Preparation of Intermediate 5: 3-(dibenzylamino)propan-1-ol

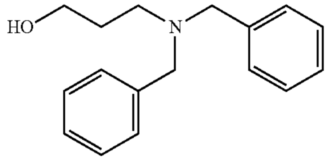 [SMILES: OCCCN(Cc1ccccc1)Cc1ccccc1]

To a solution of 3-aminopropan-1-ol (5 g, 66.569 mmol) in 200 mL of EtOH, potassium carbonate (18.861 g, 136.466 mmol) and benzyl bromide (17.395 mL, 146.452 mmol) were carefully added and the resulting mixture was stirred at 70° C. under reflux for 4 hours. The mixture was filtered and the filtrate was washed with water. The aqueous layer was extracted with EtOAc (2×) and the combined organic layers were dried over MgSO4, filtered and concentrated under reduced pressure giving the crude product which was purified by flash chromatography on silicagel using Hept/EtOAc (100:0 to 80:20) as eluents. The desired fractions were combined and the solvent was removed under reduced pressure yielding 3-(dibenzylamino)propan-1-ol 5 as a yellowish oil.

LCMS method B: no m/z detected, $t_R$=0.248 min

Preparation of Intermediate 6: 3-(dibenzylamino)propyl methane sulfonate

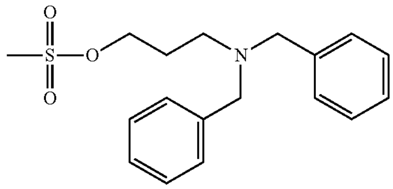 [SMILES: CS(=O)(=O)OCCCN(Cc1ccccc1)Cc1ccccc1]

3-(dibenzylamino)propan-1-ol 5 (5.000 g, 19.580 mmol) was dissolved in 60 mL of DCM and triethylamine (8.187 mL, 58.740 mmol) was added. The mixture was cooled to 0° C. and methane sulfonyl chloride (1.970 mL, 25.454 mmol) was added. The mixture was stirred at RT for 16 hours. DCM and a saturated solution of $NaHCO_3$ were added. The two layers were separated and the mixture was extracted with DCM (×2). The combined organic layers were dried over $MgSO_4$, filtered and the solvent under reduced pressure yielding 3-(dibenzylamino)propyl methane sulfonate 6 as a yellow oil which was used in the next step without purification.

LCMS method B: no m/z detected, $t_R$=0.380 min

Preparation of Intermediate 7. N,N-dibenzyl-3-((3-iodo-1-(tetrahydro-2H-pyran-2-yl)-1H-indazol-5-yl)oxy)propan-1-amine

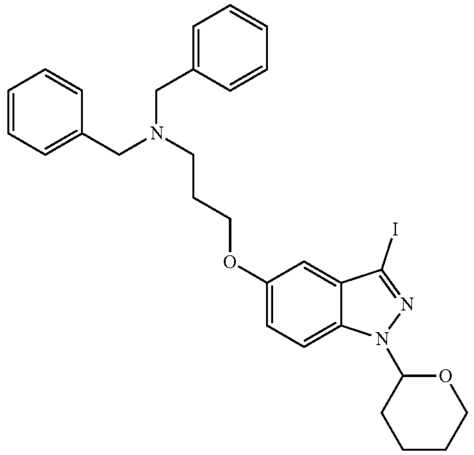 [SMILES: Ic1nn(C2CCCCO2)c2ccc(OCCCN(Cc3ccccc3)Cc3ccccc3)cc12]

3-(dibenzylamino)propyl methane sulfonate 6 (crude, 6.298 g, 18.888 mmol) dissolved in 10 mL of N,N-dimethylformamide and was added to a stirred mixture of 3-iodo-1-(tetrahydro-pyran-2-yl)-1H-indazol-5-ol 4 (5.000 g, 14.529 mmol) and cesium carbonate (7.101 g, 21.794 mmol) in 40 mL of N,N-dimethylformamide. The reaction was stirred at RT for 30 minutes and then heated at 85° C. for 2 hours. The mixture was diluted with EtOAc and water was added.

The two layers were separated and the water layer was extracted with DCM (×2). The combined organic layers were dried over $MgSO_4$, filtered and concentrated under reduced pressure. The crude was purified by flash chromatography on silica gel, using Hept/EtOAc, (100:0 to 80:20).

The fractions containing the desired compound were combined and the solvent is removed under reduced pressure to yield N,N-dibenzyl-3-((3-iodo-1-(tetrahydro-2H-pyran-2-yl)-1H-indazol-5-yl)oxy)propan-1-amine 7 as a yellowish oil.

LCMS method B: $[M+H]^+$=582.2, $t_R$=0.890 min

Preparation of Intermediate 8: (5-(hydroxymethyl)pyridin-3-yl)boronic acid

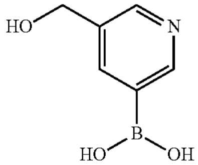 [SMILES: OCc1cncc(B(O)O)c1]

(5-bromopyridin-3-yl)methanol (3.000 g, 15.956 mmol), bis(pinacolato)diboron (4.862 g, 19.147 mmol) and potassium acetate (4.698 g, 47.868 mmol) were dissolved in 50 mL of 1,4-dioxane. After degassing with N2 for 5 minutes, Pd(dppf)$Cl_2$·DCM (1.303 g, 1.596 mmol) was added and the reaction mixture was stirred at 110° C. for 4 hours. The mixture was diluted with EtOAc and filtered over a pad of celite. The solvent was evaporated under reduced pressure, yielding (5-(hydroxymethyl)pyridin-3-yl)boronic acid 8 as a dark brown solid. The crude was used in the next step without purification.

LCMS method B: $[M+H]^+$=154.1, $t_R$=0.107 min

Preparation of Intermediate 9: {5-[5-(3-dibenzylamino-propoxy)-1-(tetrahydro-pyran-2-yl)-1H-indazol-3-yl]-pyridin-3-yl}-methanol

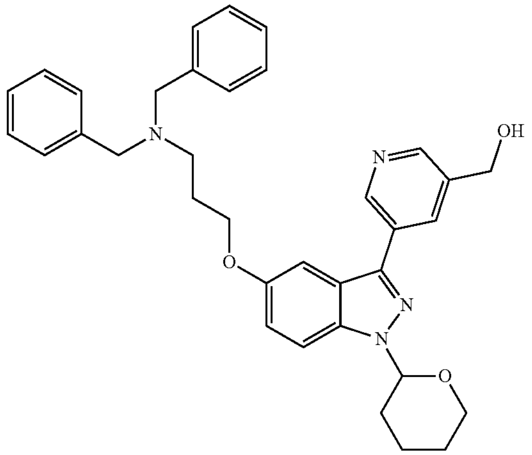 [SMILES: OCc1cncc(-c2nn(C3CCCCO3)c3ccc(OCCCN(Cc4ccccc4)Cc4ccccc4)cc23)c1]

Tetrakis(triphenylphosphine)palladium(0) (1.411 g, 1.221 mmol) and XPhos (0.291 g, 0.611 mmol) were added to a mixture of N,N-dibenzyl-3-((3-iodo-1-(tetrahydro-2H-pyran-2-yl)-1H-indazol-5-yl)oxy)propan-1-amine 7 (7.100 g, 12.210 mmol), (5-(hydroxymethyl)pyridin-3-yl)boronic acid 8 (crude, 8.84 g, 15.873 mmol) and potassium phosphate tribasic (7.77 g, 36.63 mmol) in 122.00 mL of 1,4-dioxane/$H_2O$ (3:1). The mixture was degassed with $N_2$ for 5 min and stirred at 90° C. for 16 hours. The mixture was diluted with EtOAc and water was added. The two layers were separated and the water layer was extracted with DCM (×2). The combined organic layers were dried over $MgSO_4$, filtered and concentrated under reduced pressure. The crude was purified by flash chromatography on silica gel, using DCM:MeOH (100:0 to 98:2). The desired fractions were combined and the solvent was removed under reduced pressure to obtain {5-[5-(3-dibenzylamino-propoxy)-1-(tetrahydro-pyran-2-yl)-1H-indazol-3-yl]-pyridin-3-yl}-methanol 9 as a yellow oil.

LCMS method B: $[M+H]^+$=563.3, $t_R$=0.749 min

Preparation of Intermediate 10: {5-[5-(3-amino-propoxy)-1-(tetrahydro-pyran-2-yl)-1H-indazol-3-yl]-pyridin-3-yl}-methanol

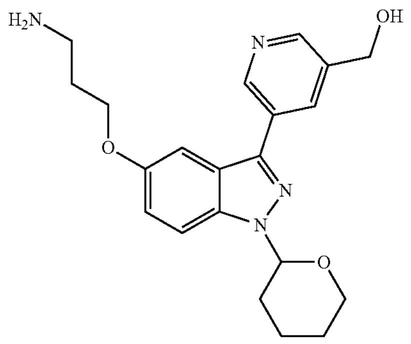 [SMILES: NCCCOc1ccc2c(c1)c(-c1cncc(CO)c1)nn2C1CCCCO1]

{5-[5-(3-Dibenzylamino-propoxy)-1-(tetrahydro-pyran-2-yl)-1H-indazol-3-yl]-pyridin-3-yl}-methanol 9 (6.000 g, 10.662 mmol) was dissolved in 106 mL of EtOAc, degassed with N2. Pd/C 10% w/w (6.000 g) was added and the reaction mixture was stirred under H2 atmosphere with a balloon at RT for 66 hours. The reaction mixture was filtered over a pad of celite and washed with a mixture of DCM:MeOH:DMA (9:1:1). The filtrate was concentrated under reduced pressure to afford the crude product which was purified by flash chromatography (silica gel, DCM/MeOH/MeOH (NH3) (100:0:0 to 90:9:1). The desired fractions were combined and the solvent was removed under reduced pressure to yield {5-[5-(3-amino-propoxy)-1-(tetrahydro-pyran-2-yl)-1H-indazol-3-yl]-pyridin-3-yl}-methanol 10 as a cream solid.

LCMS method B: $[M+H]^+$=383.3, $t_R$=0.316 min

Preparation of Intermediate 11: 19-(oxan-2-yl)-8,14-dioxa-4,10,19,20-tetraazatetracyclo[13.5.2.$1^{2,6}$.$0^{18,21}$]tricosa-1(20),2,4,6(23),15,17,21-heptaen-9-one

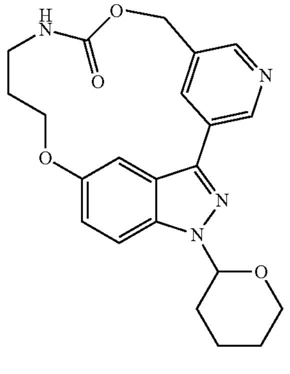 [SMILES: O=C1NCCCOc2ccc3c(c2)c(nn3C2CCCCO2)-c2cncc(c2)CO1]

CDI (0.103 g, 0.633 mmol) was added to a solution of (5-(5-(3-aminopropoxy)-1-(tetrahydro-2H-pyran-2-yl)-1H-indazol-3-yl)pyridin-3-yl)methanol 10 (0.220 g, 0.575 mmol) in 133 mL of DMA. The mixture was stirred at RT for 2 hours and at 90° C. for 72 hours. The reaction was diluted with EtOAc, cooled to 0° C. and a saturated solution of $NaHCO_3$ was added. The two layers were separated and the water layer was extracted with EtOAc (×2). The combined organic layers were dried over $MgSO_4$, filtered and concentrated under reduced pressure. The product was purified by flash chromatography (silica gel, DCM:MeOH 100:0 to 97.5:2.5). The desired fractions were combined and the solvent was removed under reduced pressure to afford 19-(oxan-2-yl)-8,14-dioxa-4,10,19,20-tetraazatetracyclo[13.5.2.$1^{2,6}$.$0^{18,21}$]tricosa-1(20),2,4, 6(23),15,17,21-heptaen-9-one 11 as a colorless foam.

LCMS method B: $[M+H]^+$=409.1, $t_R$=0.753 min

Preparation of Example 1: 8,14-dioxa-4,10,19,20-tetraazatetracyclo[13.5.2.$1^{2,6}$.$0^{18,21}$]tricosa-1(20),2,4, 6(23),15,17,21-heptaen-9-one

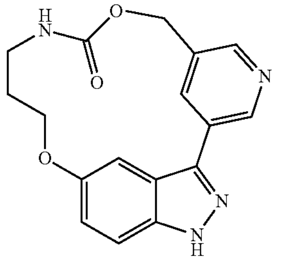 [SMILES: O=C1NCCCOc2ccc3[nH]nc(c3c2)-c2cncc(c2)CO1]

A mixture of 19-(oxan-2-yl)-8,14-dioxa-4,10,19,20-tetraazatetracyclo[13.5.2.$1^{2,6}$.$0^{18,21}$]tricosa-1(20),2,4,6(23),15,17,21-heptaen-9-one 11 (0.135 g, 0.331 mmol) in HCl in 1,4-dioxane[4N] (33 mL) was stirred at RT for 2 hours. The mixture was cooled to 0° C., diluted with DCM and quenched carefully with a saturated solution of $NaHCO_3$. The two layers were separated and the water layer was extracted with DCM (×2). The combined organic layers were dried over $MgSO_4$, filtered and concentrated under reduced pressure. The product was purified by flash chromatography on silica gel (DCM:MeOH, 100:0 to 94:6). The desired fractions were combined and the solvent was removed under reduced pressure yielding 8,14-dioxa-4,10,19,20-tetraazatetracyclo[13.5.2.$1^{2,6}$.$0^{18,21}$]tricosa-1(20),2,4,6(23),15,17,21-heptaen-9-one example 1 as a white solid.

LCMS method C: $[M+H]^+$=325.05, $t_R$=2.020 min

LCMS method D: $[M+H]^+$=325.1, $t_R$=3.945 min $^1H$ NMR (300 MHz, DMSO) δ 13.32 (s, 1H), 9.03 (s, 1H), 8.53 (s, 1H), 8.15 (s, 1H), 7.99 (t, J=5.9 Hz, 1H), 7.54 (d, J=9.0 Hz, 1H), 7.21 (s, 1H), 7.01 (d, J=8.9 Hz, 1H), 5.28 (brs, 2H), 4.29 (t, J=8.3 Hz, 2H), 3.17 (d, J=4.6 Hz, 2H), 1.97 (brs, 2H) ppm.

Example 2: 10-methyl-8,14-dioxa-4,10,19,20-tetraazatetracyclo[13.5.2.$1^{2,6}$.$0^{18,21}$]tricosa-1(20),2,4,6(23),15,17,21-heptaen-9-one

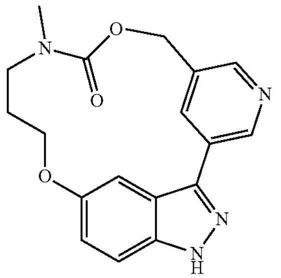 [SMILES: CN1CCCOc2ccc3[nH]nc(c3c2)-c2cncc(c2)COC1=O]

Example 2 is prepared according to the synthesis route described in general Scheme A.

Preparation of Intermediate 12: 10-methyl-19-(oxan-2-yl)-8,14-dioxa-4,10,19,20-tetraazatetracyclo [13.5.2.1$^{2,6}$.0$^{18,21}$]tricosa-1(20),2,4,6(23),15,17,21-heptaen-9-one

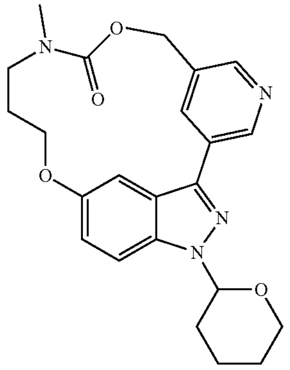 [SMILES: CN1CCCOc2ccc3c(c2)c(nn3C2CCCCO2)-c2cncc(c2)COC1=O]

To a solution of intermediate 11 (0.05 g, 0.12 mmol) in 5 mL of dry N,N-dimethylformamide, under nitrogen atmosphere, at 0° C., sodium hydride 60% in mineral oil (0.007 g, 0.15 mmol) was added. The mixture was stirred at 0° C. for 15 minutes, then iodomethane (0.02 mL, 0.33 mmol) was added and the mixture was stirred at RT for 15 minutes. The mixture was cooled to 0° C., diluted with EtOAc and quenched carefully with water. The two layers were separated and the water layer was extracted with EtOAc (×2). The combined organic layers were washed with brine, dried over $MgSO_4$, filtered and the solvent was removed under reduced pressure. The product was purified by flash chromatography on silica gel (DCM:MeOH 100:0 to 97.5:2.5). The desired fractions were combined and the solvent was removed under reduced pressure affording 10-methyl-19-(oxan-2-yl)-8,14-dioxa-4,10,19,20-tetraazatetracyclo [13.5.2.1$^{2,6}$.0$^{18,21}$]tricosa-1(20),2,4,6(23),15,17,21-heptaen-9-one 12 as a yellow oil.

LCMS method B: $[M+H]^+$=423.1, $t_R$=0.897 min

Preparation of Example 2: 10-methyl-8,14-dioxa-4,10,19,20-tetraazatetracyclo[13.5.2.1$^{2,6}$.0$^{18,21}$]tricosa-1(20),2,4,6(23),15,17,21-heptaen-9-one

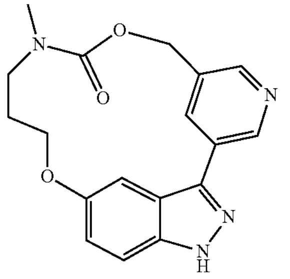 [SMILES: CN1CCCOc2ccc3[nH]nc(c3c2)-c2cncc(c2)COC1=O]

A mixture of 10-methyl-19-(oxan-2-yl)-8,14-dioxa-4,10,19,20-tetraazatetracyclo[13.5.2.1$^{2,6}$.0$^{18,21}$]tricosa-1(20),2,4,6(23),15,17,21-heptaen-9-one 12 (0.042 g, 0.099 mmol) in HCl in 1,4-dioxane[4N] (5.0 mL) was stirred at RT for 2 h. The mixture was cooled at 0° C., diluted with DCM and quenched carefully with a saturated solution of $NaHCO_3$. The two layers were separated and the water layer was extracted with DCM (×2). The combined organic layers were dried over $MgSO_4$, filtered and the solvent was removed under reduced pressure. The product was purified by flash chromatography on silica gel (DCM:MeOH, 100:0 to 94:6). The desired fractions were combined and the solvent was removed under reduced pressure to afford 10-methyl-8,14-dioxa-4,10,19,20-tetraazatetracyclo [13.5.2.1$^{2,6}$.0$^{18,21}$]tricosa-1(20),2,4,6(23), 15,17,21-heptaen-9-one example 2 as a white solid.

LCMS method E: $[M+H]^+$=339.1, $t_R$=2.298 min

LCMS method D: $[M+H]^+$=339.1, $t_R$=3.425 min $^1$H NMR (300 MHz, 100° C., d6-DMSO) δ 13.00 (s, 1H), 9.03 (s, 1H), 8.55 (s, 1H), 8.28 (s, 1H), 7.52 (d, J=9.0 Hz, 1H), 7.20 (s, 1H), 7.02 (dd, J=9.0, 2.3 Hz, 1H), 5.40 (brs, J=17.6 Hz, 2H), 4.32 (t, J=8.4 Hz, 2H), 3.68-3.21 (m, 2H), 3.03 (s, 3H), 2.33-2.04 (m, 2H) ppm.

Example 3: 4-fluoro-8,14-dioxa-10,19,20-triazatetracyclo[13.5.2.1$^{2,6}$.0$^{18,21}$]tricosa-1(20), 2,4,6(23),15,17,21-heptaen-9-one

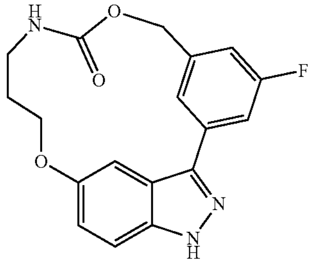 [SMILES: O=C1NCCCOc2ccc3[nH]nc(c3c2)-c2cc(F)cc(c2)CO1]

Example 3 is prepared according to the synthesis route described in general Scheme A.

Preparation of Intermediate 13: 2-[3-(3-iodo-1-tetrahydropyran-2-yl-indazol-5-yl)oxy propyl]isoindoline-1,3-dione

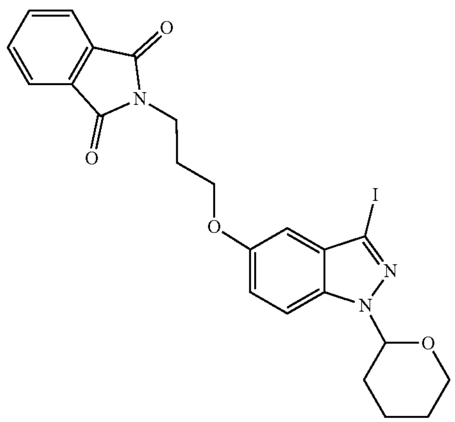 [SMILES: O=C1c2ccccc2C(=O)N1CCCOc1ccc2c(c1)c(I)nn2C1CCCCO1]

A suspension of 3-iodo-1-tetrahydropyran-2-yl-indazol-5-ol 4 (4 g, 11.63 mmol), cesium carbonate (7.560 g, 23.26 mmol) and N-(3-bromopropyl)phthalimide (4.679 g, 17.45 mmol) in N,N-dimethylformamide (48 mL) was heated at 60° C. for 16 h. The reaction mixture was concentrated under reduced pressure. The resulting white solid was triturated with ethyl acetate and recovered. The recovered filtrate was washed with water. The aqueous layer was extracted with ethyl acetate (3×). The combined organic layer was washed with water then brine, dried over sodium sulfate, filtered and evaporated under vacuum to give a cream solid. Both white and cream solids were gathered to give 2-[3-(3-iodo-1-tetrahydropyran-2-yl-indazol-5-yl)oxypropyl]isoindoline-1,3-dione 13 as a cream solid.

LCMS method F: $[M+H]^+$=532, $t_R$=3.12 min

Preparation of Intermediate 14: 3-(3-iodo-1-tetrahydropyran-2-yl-indazol-5-yl)oxypropan-1-amine

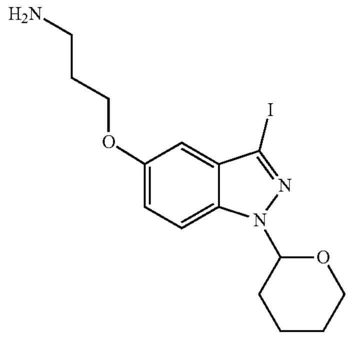 [SMILES: NCCCOc1ccc2c(c1)c(I)nn2C1CCCCO1]

A mixture of 2-[3-(3-iodo-1-tetrahydropyran-2-yl-indazol-5-yl)oxypropyl]isoindoline-1,3-dione 13 (6.176 g, 11.63 mmol) and hydrazine monohydrate (2.04 mL, 58.15 mmol) in EtOH (40 mL) was heated to 50° C. for 16 h. The reaction mixture was evaporated under reduced pressure and EtOH was added to the white solid. The solid was filtrated, washed with EtOH (3×) and the filtrate was evaporated under reduced pressure to give 3-(3-iodo-1-tetrahydropyran-2-yl-indazol-5-yl)oxypropan-1-amine 14 as a pale brown oil.

LCMS method F: $[M+H]^+$=402, $t_R$=1.65 min

Preparation of Intermediate 15: [3-[5-(3-aminopropoxy)-1-tetrahydropyran-2-yl-indazol-3-yl]-5-fluoro-phenyl]methanol

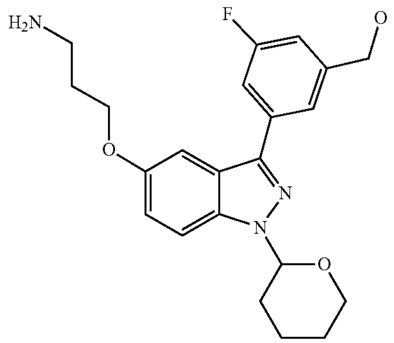

To a degassed solution of 3-(3-iodo-1-tetrahydropyran-2-yl-indazol-5-yl)oxypropan-1-amine 14 (200 mg, 0.500 mmol), 3-fluoro-5-(hydroxymethyl)phenylboronic acid (127 mg, 0.750 mmol), tripotassium phosphate (318 mg, 1.500 mmol) and xPhos (24 mg, 0.050 mmol) in 1,4-dioxane (3.2 mL) and water (1.4 mL) was added tetrakis(triphenylphosphine)palladium(0) (29 mg, 0.025 mmol). The reaction mixture was irradiated under μ-waves (Biotage initiator+), absorption level: high at 120° C. for 1 h. The reaction mixture was filtered through a celite bed then the celite was washed with ethyl acetate. The filtrate was diluted with water and extracted with ethyl acetate (3×). The organic layer was washed with water then brine, dried over sodium sulfate and concentrated under reduced pressure to give [3-[5-(3-aminopropoxy)-1-tetrahydropyran-2-yl-indazol-3-yl]-5-fluoro-phenyl]methanol 15 as a pale yellow oil.

LCMS method F: $[M+H]^+$=400, $t_R$=1.76 min

Preparation of Intermediate 16: 4-fluoro-19-(oxan-2-yl)-8,14-dioxa-10,19,20-triazatetra cyclo [$13.5.2.1^{2,6}.0^{18,21}$]tricosa-1(20),2(23),3,5,15(22),16,18(21)-heptaen-9-one

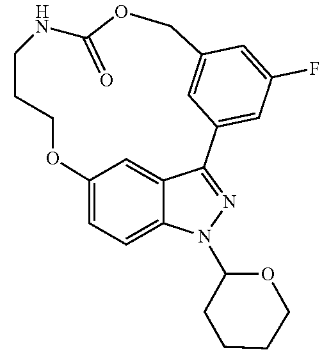 [SMILES: O=C1NCCCOc2ccc3c(c2)c(nn3C2CCCCO2)-c2cc(F)cc(c2)CO1]

To a solution of [3-[5-(3-aminopropoxy)-1-tetrahydropyran-2-yl-indazol-3-yl]-5-fluoro-phenyl]methanol 15 (199 mg, 0.499 mmol) in DMA (150 mL) was added 1,1'-carbonyldiimidazole (89 mg, 0.549 mmol). The reaction mixture was stirred at RT for 2 hours then heated to 90° C. for 48 hours. The reaction was concentrated under vacuum then ethyl acetate and a saturated aqueous solution of $NaHCO_3$ were added. The mixture was extracted with ethyl acetate (2×). The combined organic layers were washed with water then brine, dried over sodium sulfate, filtered and the solvent was removed under reduced pressure. The crude product was purified by column chromatography eluting with cyclohexane/EtOAc/EtOH (3-1): 100/0 to 70/30 to give 4-fluoro-19-(oxan-2-yl)-8,14-dioxa-10,19,20-triazatetracyclo[$13.5.2.1^{2,6}.0^{18,21}$]tricosa-1(20),2(23),3,5,15(22),16,18(21)-heptaen-9-one 16 as a white solid.

LCMS method F: $[M+H]^+$=426, $t_R$=2.84 min

Preparation of Example 3: 4-fluoro-8,14-dioxa-10,19,20-triazatetracyclo[13.5.2.1$^{2,6}$.0$^{18,21}$]tricosa-1(20), 2,4,6(23),15,17,21-heptaen-9-one

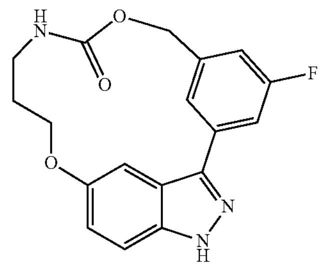 [SMILES: O=C1NCCCOc2ccc3[nH]nc(c3c2)-c2cc(F)cc(c2)CO1]

To a solution of 4-fluoro-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one 16 (92 mg, 0.217 mmol) in 1,4-dioxane (2.6 mL) was added 4M HCl in 1,4-dioxane (0.54 mL, 2.17 mmol) and the reaction was stirred at RT for 1 h 30. The reaction mixture was heated to 50° C. for 60 hours. The solvent was removed under reduced pressure and the cream solid was recrystallized with acetonitrile to give 4-fluoro-8,14-dioxa-10,19,20-triazatetracyclo[13.5.2.1$^{2,6}$.0$^{18,21}$]tricosa-1(20),2,4,6(23),15,17,21-heptaen-9-one example 3 as a white solid.

LCMS method F: $[M+H]^+$=342, $t_R$=2.16 min

LCMS method G: $[M+H]^+$=342, $t_R$=2.24 min $^1$H NMR (400 MHz, d6-DMSO) δ 13.06 (1H, s), 7.74 (2H, m), 7.62-7.58 (1H, m), 7.52-7.49 (1H, m), 7.35 (1H, m), 7.14-7.11 (1H, m), 7.00 (1H, m), 5.29 (2H, s), 4.33 (2H, t), 3.22-3.18 (2H, m), 2.06-2.05 (2H, m) ppm.

Example 4: 8,14-dioxa-10,19,20,23-tetraazatetracyclo[13.5.2.1$^{2,6}$.0$^{18,21}$]tricosa-1(20),2,4, 6(23),15,17, 21-heptaen-9-one

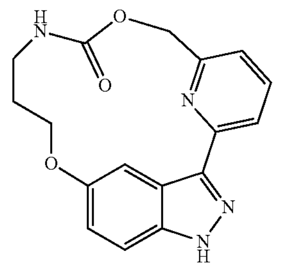 [SMILES: O=C1NCCCOc2ccc3[nH]nc(c3c2)-c2cccc(n2)CO1]

Example 4 is prepared according to the synthesis route described in general Scheme B.

Preparation of Intermediate 17: tert-butyl-dimethyl-(1-tetrahydropyran-2-ylindazol-5-yl)oxy-silane

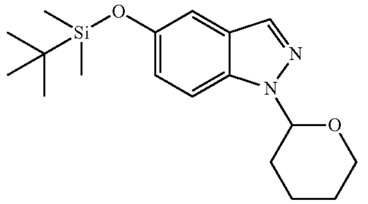 [SMILES: CC(C)(C)[Si](C)(C)Oc1ccc2c(cnn2C2CCCCO2)c1]

To a solution of tert-butyl-(1H-indazol-5-yloxy)-dimethyl-silane 1 (15.95 g, 64.28 mmol) in DCM (200 mL) and THF (100 mL) was added at RT methane sulfonic acid (0.834 mL, 12.86 mmol) and DHP (17.59 mL, 192.84 mmol). The resulting reaction mixture was stirred at RT overnight. The residue was diluted with saturated sodium bicarbonate solution and extracted with EtOAc twice. The combined organic layers were dried over anhydrous sodium sulfate and concentrated under reduced pressure. The residue was purified by flash-column chromatography (120 g silica Biotage) chromatography (cyclohexane-ethyl acetate, 1:0 to 90/10). The desired fractions were combined and the solvent was removed under reduced pressure to give tert-butyl-dimethyl-(1-tetrahydropyran-2-ylindazol-5-yl)oxy-silane 17 as white crystals.

LCMS method F: $[M+H]^+$=333.2, $t_R$=3.53 min

Preparation of Intermediate 18: [5-[tert-butyl(dimethyl)silyl]oxy-1-tetrahydropyran-2-yl-indazol-3-yl] boronic acid and 5-[(tert-butyldimethylsilyl)oxy]-1-(oxan-2-yl)-3-(tetramethyl-1,3,2-dioxaborolan-2-yl)-1H-indazole

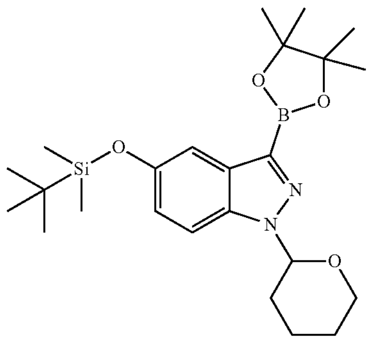

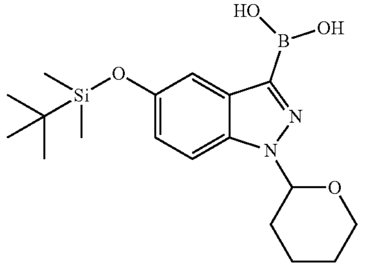

In a sealed tube was added tert-butyl-dimethyl-(1-tetrahydropyran-2-ylindazol-5-yl)oxy-silane 17 (3 g; 9.03 mmol), TBME (15 mL), 4,4,5,5-tetramethyl-2-(4,4,5,5-tetramethyl-1,3,2-dioxaborolan-2-yl)-1,3,2-dioxaborolane (2.3 g; 9.03 mmol), 4,4'-di-tert-butyl-2,2'-bipyridine (145 mg; 0.54 mmol) and (1,5-cyclooctadiene)(methoxy)iridium (I) dimer (119 mg; 0.18 mmol). The reaction was degassed with Argon during 10 min then it was put to react overnight at 80° C. The solvent was removed under reduced pressure, then the oil was dissolved with ethyl acetate and water. The layers were separated and the aqueous layer was extracted twice with ethyl acetate. The organic layers were combined and the solvent was removed under reduced pressure to give a mixture of [5-[tert-butyl(dimethyl)silyl]oxy-1-tetrahydropyran-2-yl-indazol-3-yl]boronic acid and 5-[(tert-butyldimethylsilyl)oxy]-1-(oxan-2-yl)-3-(tetramethyl-1,3,2-dioxaborolan-2-yl)-1H-indazole 18 as a brown oil. The product was used in next step without further purification.

LCMS method F: $[M+H]^+$=459, $t_R$=3.80 min

LCMS method G: $[M+H]^+$=377.2, $t_R$=3.15 min

Preparation of Intermediate 19: 2-(5-hydroxy-1-tetrahydropyran-2-yl-indazol-3-yl)pyridine-4-carboxylate

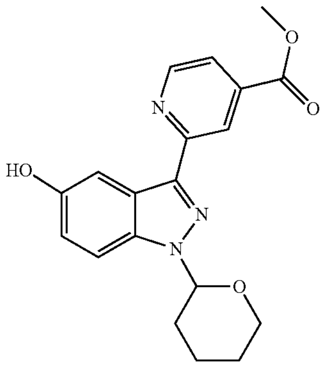 [SMILES: COC(=O)c1ccnc(-c2nn(C3CCCCO3)c3ccc(O)cc23)c1]

To a solution of [5-[tert-butyl(dimethyl)silyl]oxy-1-tetrahydropyran-2-yl-indazol-3-yl]boronic acid and 5-[(tert-butyldimethylsilyl)oxy]-1-(oxan-2-yl)-3-(tetramethyl-1,3,2-dioxaborolan-2-yl)-1H-indazole 18 (1.5 g, 3.99 mmol) in N,N-dimethylformamide (5 mL) were added at RT methyl 6-bromopyridine-2-carboxylate (1.030 g, 4.78 mmol), cesium carbonate (3.8 g, 11.96 mmol) and $PdCl_2$dppf·DCM (163 mg, 0.2 mmol). The resulting reaction mixture was stirred at 110° C. overnight. The solvent was removed under reduced pressure and the oil was dissolved in EtOAc and water. The two layers were separated and the aqueous phase was extracted with ethyl acetate twice. The combined organic layers were dried over anhydrous sodium sulfate and concentrated under reduced pressure. The residue was purified by flash-column chromatography (30 g silica BIOTAGE) chromatography (cyclohexane-ethyl acetate, 100/0 to 50/50) affording methyl 2-(5-hydroxy-1-tetrahydropyran-2-yl-indazol-3-yl)pyridine-4-carboxylate 19 as a yellow powder.

LCMS method F: $[M+H]^+$=354.1, $t_R$=2.59 min

Preparation of Intermediate 20: benzyl N-(3-bromopropyl)carbamate

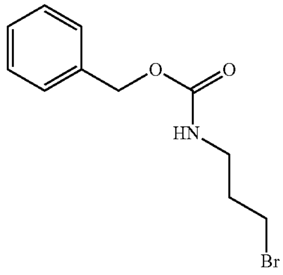 [SMILES: O=C(NCCCBr)OCc1ccccc1]

To a solution of 3-bromopropylamine hydrochloride (6 g, 27 mmol) in aqueous NaOH 10% (40 mL) at 0° C. were added slowly CbzCl (4.3 mL, 30 mmol) and NaOH 10% (40 mL). After 12 h, the reaction mixture was diluted with DCM. The aqueous layer was extracted two times with DCM (100 mL). The combined organic layers were washed with brine, dried over magnesium sulfate, filtered and concentrated under reduced pressure. This residue was purified by flash chromatography on silica gel (Macherey Nagel, 80 g) with gradient elution: cyclohexane/EtOAc 0-20% to give benzyl N-(3-bromopropyl)carbamate 20 as a transparent oil.

LCMS method F: $[M+H]^+$=274, $t_R$=2.41 min

Preparation of Intermediate 21: methyl 6-[5-(3-{[(benzyloxy)carbonyl]amino}propoxy)-1-(oxan-2-yl)-1H-indazol-3-yl]pyridine-2-carboxylate

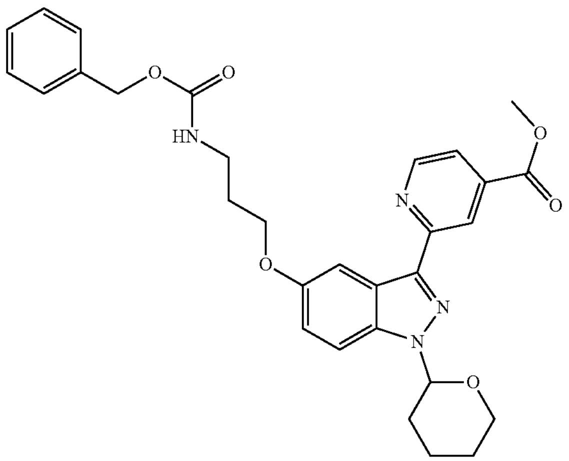 [SMILES: COC(=O)c1ccnc(-c2nn(C3CCCCO3)c3ccc(OCCCNC(=O)OCc4ccccc4)cc23)c1]

To a solution of methyl 6-[5-hydroxy-1-(oxan-2-yl)-1H-indazol-3-yl]pyridine-2-carboxylate 19 (1 g, 2.82 mmol) in N,N-dimethylformamide (100 mL), cesium carbonate (1.83 g, 5.6 mmol) and benzyl N-(3-bromopropyl)carbamate 20 (0.765 g, 2.82 mmol) were added. The reaction was stirred at 120° C. for 16 hours. The mixture was concentrated under reduced pressure. Water (200 mL) was added and the resulting mixture was extracted with EtOAc (4×100 mL). The combined organic layers were washed with brine (2×50 mL). The organic layer was dried over sodium sulfate, filtered off and evaporated under reduced pressure to afford brown/orange oil.

This residue was purified by flash chromatography on silica gel (Macherey Nagel, 120 g) with gradient elution: cyclohexane/EtOAc 0-70% to give methyl 6-[5-(3-{[(benzyloxy)carbonyl]amino}propoxy)-1-(oxan-2-yl)-1H-indazol-3-yl]pyridine-2-carboxylate 21 as a white solid.

LCMS method F: $[M+H]^+$=545.2, $t_R$=3.21 min

Preparation of Intermediate 22: benzyl N-[3-({3-[6-(hydroxymethyl)pyridin-2-yl]-1-(oxan-2-yl)-1H-indazol-5-yl}oxy)propyl]carbamate

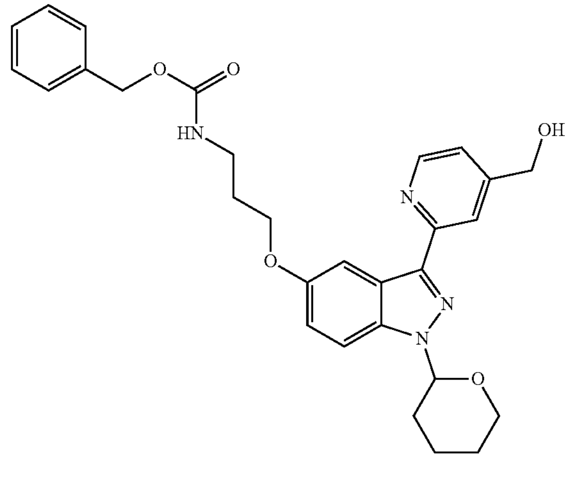 [SMILES: O=C(NCCCOc1ccc2c(c1)c(-c1cc(CO)ccn1)nn2C1CCCCO1)OCc1ccccc1]

To methyl 6-[5-(3-{[(benzyloxy)carbonyl]amino}propoxy)-1-(oxan-2-yl)-1H-indazol-3-yl]pyridine-2-carboxylate 21 (1.2 g, 2.2 mmol) in THF (50 mL) was added a 1 M solution of lithium aluminium tetrahydride (4.4 mL, 4.2 mmol) at 0° C. The mixture was stirred at 0° C. for 1 hour. To the reaction mixture, EtOAc (10 mL) was added at 0° C. and poured in a 10% solution of Rochelle's salt (100 mL) and EtOAc (100 mL). The mixture was stirred at RT for 2 hours. After separation, the aqueous layer was extracted with EtOAc (2×50 mL). The combined organic layers were washed with brine, dried over sodium sulfate and concentrated under reduced pressure to brown/orange oil. This residue was purified by flash chromatography on silica gel (Macherey Nagel, 120 g) with gradient elution: cyclohexane/EtOAc 0-100% to give benzyl N-[3-({3-[6-(hydroxymethyl)pyridin-2-yl]-1-(oxan-2-yl)-1H-indazol-5-yl}oxy)propyl]carbamate 22 as a yellow oil.

LCMS method F: $[M+H]^+$=517.3, $t_R$=2.76 min

Preparation of Intermediate 23: 19-(oxan-2-yl)-8,14-dioxa-10,19,20,23-tetraazatetracyclo[13.5.2.1$^{2,6}$.0$^{18,21}$]tricosa-1(20),2,4,6(23),15,17,21-heptaen-9-one

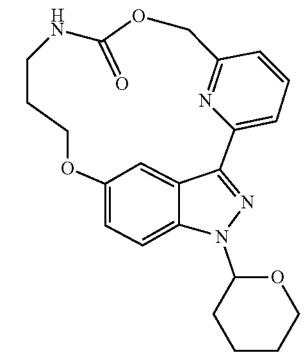 [SMILES: O=C1NCCCOc2ccc3c(c2)c(nn3C2CCCCO2)-c2cccc(n2)CO1]

A solution of benzyl N-[3-({3-[6-(hydroxymethyl)pyridin-2-yl]-1-(oxan-2-yl)-1H-indazol-5-yl}oxy)propyl]carbamate 22 (0.4 g; 0.775 mmol) in 100 mL of toluene was added over 30 min to a solution a solution of sodium hydride (60% suspension in paraffin oil) (310 mg, 7.75 mmol) in 100 mL of toluene at room temperature. The reaction mixture was stirred at RT for 5 min and then one hour at 130° C. The reaction is allowed to cool down and then 10 mL of EtOH is added carefully. 100 mL of water in added. After separation, the aqueous layer was extracted with ethyl acetate (2×100 mL). The combined organic layers were washed with brine, dried over sodium sulfate and concentrated under reduced pressure to give an orange oil. A purification by column chromatography (DCM/MeOH 0-10%) afforded pure 19-(oxan-2-yl)-8,14-dioxa-10,19,20,23-tetraazatetracyclo[13.5.2.1$^{2,6}$.0$^{18,21}$]tricosa-1(20),2,4,6(23),15,17,21-heptaen-9-one 23 as a whitish solid.

LCMS method F: $[M+H]^+$=409.2, $t_R$=2.53 min

Preparation of Example 4: 8,14-dioxa-10,19,20,23-tetraazatetracyclo[13.5.2.1$^{2,6}$.0$^{18,21}$]tricosa-1(20),2,4, 6(23),15,17,21-heptaen-9-one

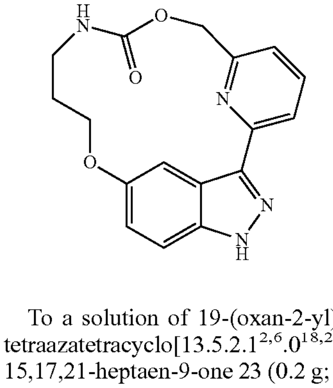

To a solution of 19-(oxan-2-yl)-8,14-dioxa-10,19,20,23-tetraazatetracyclo[13.5.2.1$^{2,6}$.0$^{18,21}$]tricosa-1(20),2,4,6(23),15,17,21-heptaen-9-one 23 (0.2 g; 0.489 mmol) in DCM (20 mL) was added Trifluoroacetic acid (0.38 mL, 4.89 mmol) at room temperature. The mixture was stirred at 50° C. for 24 hours. The reaction is allowed to cool down. 50 mL of toluene were added to the solution and the reaction mixture was concentrated under reduced pressure to give an orange oil. 25 mL of water and 25 mL of DCM and a 25 wt % aqueous solution of ammonia (1.5 mL) were added. After separation, the aqueous layer was extracted with DCM (2×20 mL). The combined organic layers were washed with brine, dried over sodium sulfate and concentrated under reduced pressure to give an orange oil. A purification by column chromatography (DCM/MeOH 0-5%) afforded pure 8,14-dioxa-10,19,20,23-tetraazatetracyclo[13.5.2.1$^{2,6}$.0$^{18,21}$]tricosa-1(20),2,4,6(23),15,17,21-heptaen-9-one example 4 as a whitish solid.

LCMS method F: $[M+H]^+$=325.2, $t_R$=1.93 min

LCMS method G: $[M+H]^+$=325.2, $t_R$=1.94 min $^1$H NMR (400 MHz, d6-DMSO) δ 13.2 (1H, m), 8.08 (1H, d, J=9.7 Hz), 7.90 (1H, d, J=3.5 Hz), 7.83 (1H, t, J=8.3 Hz), 7.75 (1H, t, J=5.9 Hz), 7.47 (1H, d, J=8.3 Hz), 7.26 (1H, d, J=8.3 Hz), 6.97 (1H, dd, J=2.5, 9.1 Hz), 5.31 (2H, m), 4.31 (2H, dd, J=7.7, 8.6 Hz), 3.11-3.09 (2H, m), 1.97-2.03 (2H, m) ppm.

Example 5: 8,14-dioxa-10,19,20-triazatetracyclo [13.5.2.1$^{2,6}$.0$^{18,21}$]tricosa-1(20),2,4,6(23), 15,17,21-heptaen-9-one

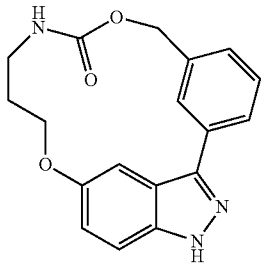 [SMILES: O=C1NCCCOc2ccc3[nH]nc(c3c2)-c2cccc(c2)CO1]

Example 5 is prepared according to the synthesis route described in general Scheme A.

Preparation of Intermediate 24: [3-[5-(3-amino-propoxy)-1-tetrahydropyran-2-yl-indazol-3-yl]phenyl]methanol

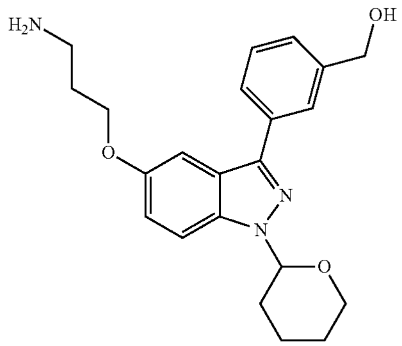 [SMILES: NCCCOc1ccc2c(c1)c(-c1cccc(CO)c1)nn2C1CCCCO1]

To a degassed solution of 3-(3-iodo-1-tetrahydropyran-2-yl-indazol-5-yl)oxypropan-1-amine 14 (400 mg, 0.998 mmol), 3-(Hydroxymethyl)phenylboronic acid (227 mg, 1.497 mmol), tripotassium phosphate (636 mg, 2.994 mmol) and xPhos (48 mg, 0.100 mmol) in dioxane (6.4 mL) and water (2.8 mL) was added tetrakis(triphenylphosphine)palladium(0) (58 mg, 0.050 mmol). The reaction mixture was heated under microwave conditions (Biotage initiator+) at 120° C. for 1 h. The reaction mixture was filtered through celite bed then the celite was washed with ethyl acetate. The filtrate was then diluted with water and extracted with ethyl acetate (3×). The organic layer was washed with water then brine, dried over sodium sulfate and concentrated under reduced pressure to give [3-[5-(3-aminopropoxy)-1-tetrahydropyran-2-yl-indazol-3-yl]phenyl]methanol 24 as a pale yellow oil.

LCMS method F: $[M+H]^+$=382, $t_R$=1.64 min

Preparation of Intermediate 25: 19-(oxan-2-yl)-8,14-dioxa-10,19,20-triazatetracyclo [13.5.2.1$^{2,6}$.0$^{18,21}$]tricosa-1(20),2,4,6(23),15,17,21-heptaen-9-one

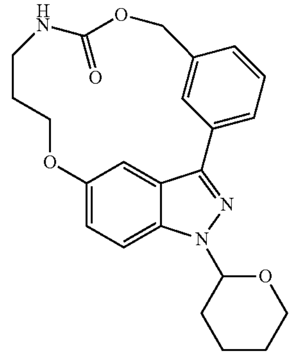 [SMILES: O=C1NCCCOc2ccc3c(c2)c(nn3C2CCCCO2)-c2cccc(c2)CO1]

To a solution of [3-[5-(3-aminopropoxy)-1-tetrahydropyran-2-yl-indazol-3-yl]phenyl]methanol 24 (380 mg, 0.998 mmol) in DMA (300 mL) was added 1,1'-Carbonyldiimidazole (178 mg, 1.100 mmol). The reaction mixture was stirred at RT for 2 h then 90° C. for 64 h. The reaction was concentrated under vacuum then ethyl acetate and a saturated aqueous solution of $NaHCO_3$ were added. The mixture was extracted with ethyl acetate (2×). The combined organic layers were washed with water then brine, dried over sodium sulfate, filtered and concentrated under reduced pressure. The crude product was purified by column chromatography eluting with cyclohexane/ethyl acetate-EtOH (3-1): 100/0 to 70/30 to give a white solid. The solid was recrystallized with acetonitrile to give 19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one 25 as a white solid.

LCMS method F: $[M+H]^+$=408, $t_R$=2.76 min

Preparation of Example 5: 8,14-dioxa-10,19,20-triazatetracyclo[13.5.2.1$^{2,6}$.0$^{18,21}$]tricosa-1(20),2,4,6 (23), 15,17,21-heptaen-9-one

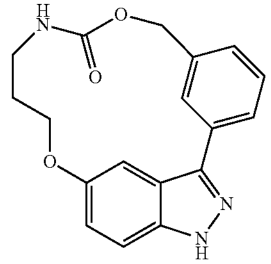 [SMILES: O=C1NCCCOc2ccc3[nH]nc(c3c2)-c2cccc(c2)CO1]

To a solution of 19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one 25 (81 mg, 0.199 mmol) in dioxane (2.4 mL) was added 4M HCl in dioxane (0.75 mL, 2.985 mmol) and the reaction was heated to 50° C. for 24 h. The reaction mixture was cooled down to RT and the solid was filtered then rinsed with diisopropyl ether (3×) to give 8,14-dioxa-10,19,20-triazatetracyclo[13.5.2.1$^{2,6}$.0$^{18,21}$]tricosa-1(20),2,4,6(23),15,17,21-heptaen-9-one example 5 as a white solid.

LCMS method F: $[M+H]^+$=324, $t_R$=2.02 min

LCMS method G: $[M+H]^+$=324, $t_R$=2.10 min $^1$H NMR (400 MHz, d6-DMSO) δ 7.93-7.87 (2H, m), 7.69-7.66 (1H, m), 7.50-7.44 (2H, m), 7.36 (1H, d, J=2.3 Hz), 7.28-7.25 (1H, m), 6.98 (1H, dd, J=2.3, 8.9 Hz), 5.33-5.29 (3H, m), 4.32 (2H, m), 3.18 (2H, m), 2.04 (2H, m) ppm.

Example 6: 10-(propan-2-yl)-8,14-dioxa-4,10,19,20-tetraazatetracyclo[13.5.2.1$^{2,6}$.0$^{18,21}$]tricosa-1(20),2,4,6(23),15,17,21-heptaen-9-one

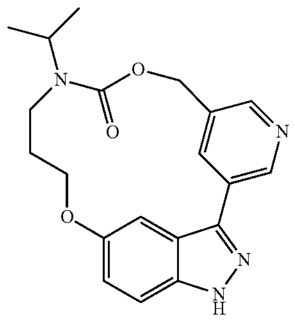 [SMILES: CC(C)N1CCCOc2ccc3[nH]nc(c3c2)-c2cncc(c2)COC1=O]

Example 6 is prepared according to the synthesis route described in general Scheme A.

Example 6 is made using analog conditions as for example 2. 2-Iodopropane is used for the alkylation step of the carbamate to yield 10-(propan-2-yl)-8,14-dioxa-4,10,19,20-tetraazatetracyclo[13.5.2.1$^{2,6}$.0$^{18,21}$]tricosa-1(20),2,4,6(23),15,17,21-heptaen-9-one example 6.

LCMS method E: $[M+H]^+$=367.2, $t_R$=2.829 min

LCMS method D: $[M+H]^+$=367.2, $t_R$=3.832 min $^1$H NMR (300 MHz, 100° C., d6-DMSO) δ 12.96 (s, 1H), 9.01 (s, 1H), 8.54 (s, 1H), 8.39 (t, J=2.1 Hz, 1H), 7.50 (d, J=9.0 Hz, 1H), 7.23 (s, 1H), 6.99 (dd, J=9.0, 2.3 Hz, 1H), 5.36 (brs, 2H), 4.28 (t, J=8.6 Hz, 2H), 4.20-4.04 (m, 1H), 3.32 (brt, J=7.3 Hz, 2H), 2.19 (brs, 2H), 1.18 (s, 3H), 1.15 (s, 3H) ppm.

Example 7: 8,14-dioxa-5,10,19,20-tetraazatetracyclo[13.5.2.1$^{2,6}$.0$^{18,21}$]tricosa-1(20),2,4, 6(23),15,17,21-heptaen-9-one

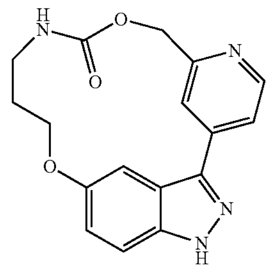 [SMILES: O=C1NCCCOc2ccc3[nH]nc(c3c2)-c2ccnc(c2)CO1]

Example 7 is prepared according to the synthesis route described in general Scheme B.

Example 7 is made using analog conditions as for example 4. Methyl 4-bromopyridine-2-carboxylate is used for the Suzuki reaction to give 8,14-dioxa-5,10,19,20-tetraazatetracyclo[13.5.2.1$^{2,6}$.0$^{18,21}$]tricosa-1(20),2,4,6(23),15,17,21-heptaen-9-one example 7.

LCMS method F: $[M+H]^+$=325.1, $t_R$=1.58 min

LCMS method G: $[M+H]^+$=325.2, $t_R$=1.83 min $^1$H NMR (400 MHz, d6-DMSO) δ 13.28 (1H, s), 8.59-8.57 (1H, m), 7.86 (2H, m), 7.83 (1H, dd, J=2.1, 5.5 Hz), 7.55 (1H, d, J=9.0 Hz), 7.44 (1H, d, J=2.1 Hz), 7.03 (1H, dd, J=2.1, 9.0 Hz), 5.32-5.31 (2H, m), 4.37 (2H, dd, J=8.3, 8.6 Hz), 3.19-3.18 (2H, m), 2.10-2.05 (2H, m) ppm.

Example 8: 4-methoxy-8,14-dioxa-10,19,20-triazatetracyclo[13.5.2.1$^{2,6}$.0$^{18,21}$]tricosa-1(20),2,4,6(23),15,17,21-heptaen-9-one

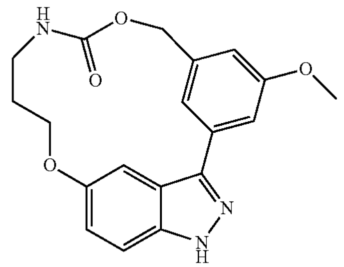 [SMILES: COc1cc2cc(c1)-c1n[nH]c3ccc(cc13)OCCCNC(=O)OC2]

Example 8 is prepared according to the synthesis route described in general Scheme C.

Preparation of Intermediate 26: benzyl N-[3-(3-iodo-1-tetrahydropyran-2-yl-indazol-5-yl)oxypropyl]carbamate

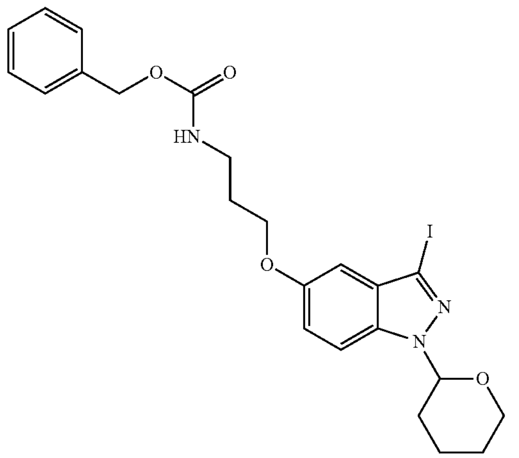 [SMILES: O=C(NCCCOc1ccc2c(c1)c(I)nn2C1CCCCO1)OCc1ccccc1]

A suspension of 3-iodo-1-tetrahydropyran-2-yl-indazol-5-ol 4 (17.012 g, 49.453 mmol), cesium carbonate (32.144 g, 98.906 mmol) and benzyl N-(3-bromopropyl)carbamate 20 (10.6 mL, 54.398 mmol) in N,N-dimethylformamide (250 mL) was heated at 60° C. for 20 h. The reaction mixture was filtered and rinsed with acetonitrile. The filtrate crystallized and it was filtered to give a white solid which was rinsed with water (3×). The filtrate was recovered and evaporated under reduced pressure to give a pink solid. It was solubilized with DCM and water was added. It was extracted with DCM (2×) then the combined organic layers were dried over anhydrous sodium sulfate and concentrated under reduced pressure to give a pale pink solid. The solid was recrystallized from acetonitrile to give benzyl N-[3-(3-iodo-1-tetrahydropyran-2-yl-indazol-5-yl)oxypropyl]carbamate 26 as a white solid.

LCMS method F: $[M+H]^+$=536.0, $t_R$=3.11 min

Preparation of Intermediate 27: benzyl N-[3-[3-[3-(hydroxymethyl)-5-methoxy-phenyl]-1-tetrahydropyran-2-yl-indazol-5-yl]oxypropyl]carbamate

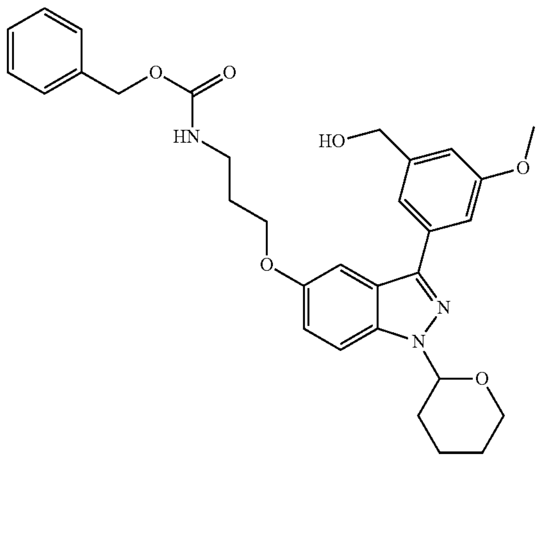 [SMILES: COc1cc(CO)cc(-c2nn(C3CCCCO3)c3ccc(OCCCNC(=O)OCc4ccccc4)cc23)c1]

To a degassed solution of benzyl N-[3-(3-iodo-1-tetrahydropyran-2-yl-indazol-5-yl)oxypropyl]carbamate 26 (600 mg, 1.12 mmol), [3-Methoxy-5-(tetramethyl-1,3,2-dioxaborolan-2-yl)phenyl]methanol (444 mg, 1.68 mmol), tripotassium phosphate (713 mg, 3.36 mmol) and xPhos (53 mg, 0.112 mmol) in 1,4-dioxane (7 mL) and water (4.8 mL) was added tetrakis(triphenylphosphine)palladium(0) (65 mg, 0.056 mmol). The reaction mixture was irradiated under μ-waves (Biotage initiator+), absorption level: high at 120° C. for 1 h. The reaction mixture was filtered through celite bed then the celite was washed with ethyl acetate. The filtrate was then diluted with water and extracted with ethyl acetate (3×). The organic layer was washed with water then brine, dried over sodium sulfate and concentrated under reduced pressure. The crude was purified by column chromatography eluting with DCM/Ethyl acetate, 100/0 to 70/30 to give benzyl N-[3-[3-[3-(hydroxymethyl)-5-methoxy-phenyl]-1-tetrahydropyran-2-yl-indazol-5-yl]oxypropyl]carbamate 27 as a colorless oil.

LCMS method F: $[M+H]^+$=546, $t_R$=2.89 min

Preparation of Intermediate 28: 4-methoxy-19-(oxan-2-yl)-8,14-dioxa-10,19,20-triazatetra cyclo[13.5.2.$1^{2,6}$.$0^{18,21}$]tricosa-1(20),2,4,6(23),15,17,21-heptaen-9-one

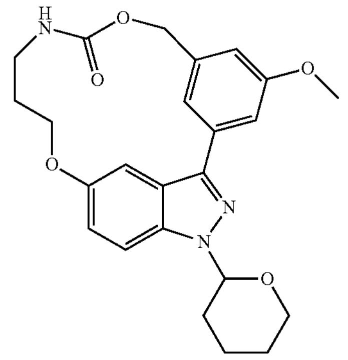 [SMILES: COc1cc2cc(c1)-c1nn(C3CCCCO3)c3ccc(cc13)OCCCNC(=O)OC2]

To a suspension of potassium carbonate (80 mg, 0.582 mmol) in acetonitrile (12 mL) was dropwise added a solution of benzyl N-[3-[3-[3-(hydroxymethyl)-5-methoxy-phenyl]-1-tetrahydropyran-2-yl-indazol-5-yl]oxypropyl]carbamate 27 (53 mg, 0.097 mmol) in acetonitrile (7 mL) at RT. The reaction mixture was heated under microwave conditions at 140° C. for 6 h. The reaction mixture was filtered and directly purified by column chromatography eluting with DCM/Ethyl acetate, 100/0 to 80/20 to 4-methoxy-19-(oxan-2-yl)-8,14-dioxa-10,19,20-triazatetracyclo[13.5.2.$1^{2,6}$.$0^{18,21}$]tricosa-1(20),2,4,6(23),15,17,21-heptaen-9-one 28 as a colorless oil.

LCMS method F: $[M+H]^+$=438, $t_R$=2.76 min

Preparation of Example 8: 4-methoxy-8,14-dioxa-10,19,20-triazatetracyclo[13.5.2.$1^{2,6}$.$0^{18,21}$]tricosa-1(20),2,4,6(23),15,17,21-heptaen-9-one

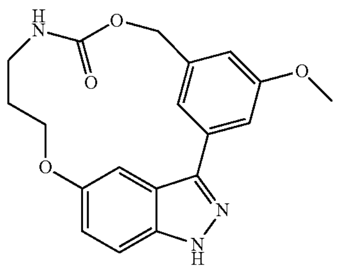 [SMILES: COc1cc2cc(c1)-c1n[nH]c3ccc(cc13)OCCCNC(=O)OC2]

To a solution of 4-methoxy-19-(oxan-2-yl)-8,14-dioxa-10,19,20-triazatetracyclo[13.5.2.$1^{2,6}$.$0^{18,21}$]tricosa-1(20),2,4,6(23),15,17,21-heptaen-9-one 28 (23 mg, 0.053 mmol) in DCM (4 mL) was added trifluoro acetic acid (80 μL, 1.06 mmol) at RT. The reaction mixture was irradiated under μ-waves (Biotage initiator+), absorption level: high at 80° C. for 1 h 30. The crude reaction mixture was purified by flash-column chromatography eluting with DCM/Ethyl acetate: 100/0 to 80/20, to give 4-methoxy-8,14-dioxa-10,19,20-triazatetracyclo[13.5.2.$1^{2,6}$.$0^{18,21}$]tricosa-1(20),2,4,6(23),15,17,21-heptaen-9-one example 8 as a white solid.

LCMS method F: $[M+H]^+$=354, $t_R$=2.07 min

LCMS method G: $[M+H]^+$=354, $t_R$=2.09 min $^1$H NMR (400 MHz, d6-DMSO) δ 12.89 (1H, s), 7.67 (1H, m), 7.52-7.47 (2H, m), 7.42-7.34 (2H, m), 6.99-6.96 (1H, m), 6.88 (1H, m), 5.25 (2H, m), 4.31 (2H, t), 3.86 (3H, s), 3.17 (2H, m), 2.03 (2H, m) ppm.

Example 9: 4-bromo-8,14-dioxa-10,19,20-triazatetracyclo[13.5.2.$1^{2,6}$.$0^{18,21}$]tricosa-1(20), 2,4,6(23),15,17,21-heptaen-9-one

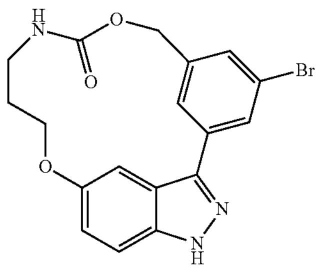 [SMILES: O=C1NCCCOc2ccc3[nH]nc(c3c2)-c2cc(Br)cc(c2)CO1]

Example 9 can be prepared according to the synthesis route described in general Scheme A, C and D.

Preparation of Intermediate 29: 1-tetrahydropyran-2-ylindazol-5-ol

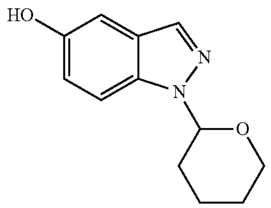 [SMILES: Oc1ccc2c(cnn2C2CCCCO2)c1]

To a solution of tert-butyl-dimethyl-(1-tetrahydropyran-2-ylindazol-5-yl)oxy-silane 17 (12.58 g, 37.8 mmol) in tetrahydrofuran (100 mL) was added by portions tetra-n-butylammonium fluoride 1.0 M in THE (47.58 mL, 47.58 mmol) at RT. The reaction mixture was stirred at RT for 1 h. The reaction mixture was poured into ice water (300 mL) and stirred for 1 h. The aqueous phase was extracted with ethyl acetate (2×150 mL). The combined organic layers were washed with brine (150 mL), dried over magnesium sulfate anhydrous and concentrated under reduced pressure. Purification on silica column (RS SiOH 80 g) using cyclohexane/ethyl acetate as eluent from 90/10 to 80/20 gave 1-tetrahydropyran-2-ylindazol-5-ol 29 as a colorless oil.

LCMS method F: $[M+H]^+$=219, $t_R$=1.81 min

Preparation of Intermediate 30: benzyl N-[3-(1-tetrahydropyran-2-ylindazol-5-yl)oxypropyl]carbamate

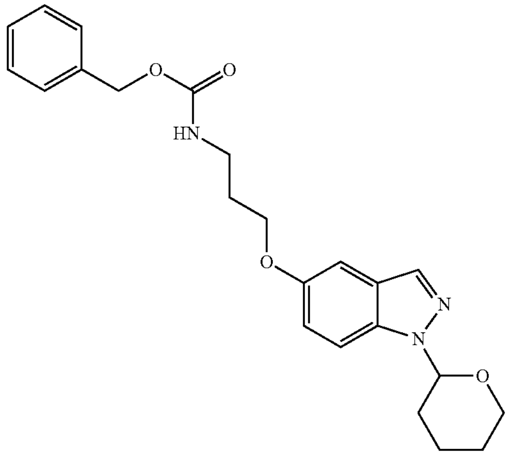 [SMILES: O=C(NCCCOc1ccc2c(cnn2C2CCCCO2)c1)OCc1ccccc1]

To a solution of 1-tetrahydropyran-2-ylindazol-5-ol 29 (7.06 g, 32.3 mmol) in N,N-dimethylformamide (110 mL) was added cesium carbonate (21.0 g, 64.6 mmol) and benzyl N-(3-bromopropyl)carbamate 20 (10.14 g, 37.3 mmol) at RT. The mixture was stirred at 80° C. overnight. The reaction mixture was concentrated under reduced pressure. Water (100 mL) and ethyl acetate (200 mL) were added to the residue. After separation, the aqueous layer was extracted with ethyl acetate (2×50 mL). The combined organic layers were washed with brine (100 mL), dried over sodium sulfate anhydrous and concentrated under reduced pressure to dryness.

Purification on silica column (RS SiOH 200 g) using Cyclohexane/Ethyl acetate from 80/20 to 60/40 as eluent gave benzyl N-[3-(1-tetrahydropyran-2-ylindazol-5-yl)oxypropyl]carbamate 30 as a beige solid.

LCMS method F: $[M+H]^+$=410.2, $t_R$=2.77 min (current 20V)

Preparation of Intermediate 31: benzyl N-[3-[1-tetrahydropyran-2-yl-3-(4,4,5,5-tetramethyl-1,3,2-dioxaborolan-2-yl)indazol-5-yl]oxypropyl]carbamate

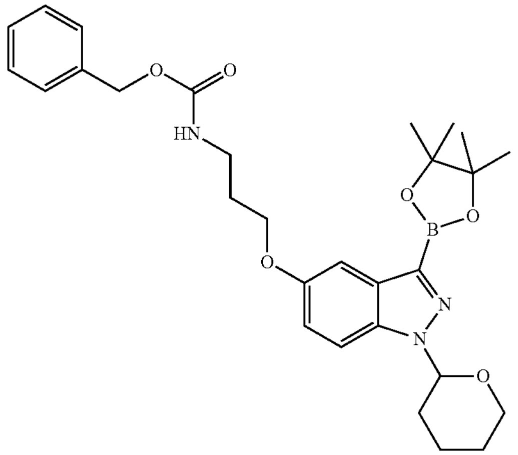 [SMILES: CC1(C)OB(c2nn(C3CCCCO3)c3ccc(OCCCNC(=O)OCc4ccccc4)cc23)OC1(C)C]

To a solution of benzyl N-[3-(1-tetrahydropyran-2-ylindazol-5-yl)oxypropyl]carbamate 30 (11.42 g, 27.9 mmol) in TBME/THF (500/100 mL) was added 4,4,5,5-tetramethyl-2-(4,4,5,5-tetramethyl-1,3,2-dioxaborolan-2-yl)-1,3,2-dioxaborolane (7.79 g, 30.69 mmol) and 4,4'-di-tert-butyl-2,2'-bipyridine (450 mg, 1.67 mmol). The reaction mixture was degassed by bubbling nitrogen for 15 min and (1,5-cyclooctadiene)(methoxy)iridium(I) dimer (370 mg, 0.56 mmol) was added. The reaction mixture was stirred at 80° C. overnight under atmosphere of nitrogen. The solvent was removed under reduced pressure, then the oil was dissolved with ethyl acetate and water. The layers were separated and the aqueous layer was extracted twice with ethyl acetate. The organic layers were combined and the solvent was removed under reduced pressure to give benzyl N-[3-[1-tetrahydropyran-2-yl-3-(4,4,5,5-tetramethyl-1,3,2-dioxaborolan-2-yl)indazol-5-yl]oxypropyl]carbamate 31 as a brown oil. The product was used in next step without further purification.

LCMS method F: $[M+H]^+$=536.2, $t_R$=3.18 min (current 20V)

Preparation of Intermediate 32: (3-bromo-5-iodo-phenyl)methanol

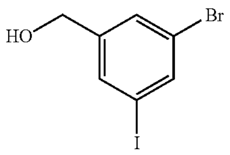

To a solution of 3-bromo-5-iodo-benzoic acid (10.0 g, 30.6 mmol) in THE (450 mL) was slowly added solid sodium borohydride (3.47 g, 91.8 mmol) at 0° C. After the end of the gas release (i.e. 5 min), boron trifluoride diethyl etherate (11.3 mL, 91.8 mmol) was dropwise added at 0° C. The reaction mixture was allowed to warm to RT and stirred at RT overnight. The reaction mixture was cooled to 0° C. and an aqueous 1 M solution of sodium hydroxide (100 mL) was slowly added. The reaction mixture was filtered off under celite pad and eluted with ethyl acetate. The solution was washed with water (100 mL) and with brine (100 mL). The organic layer was dried with sodium sulfate anhydrous, filtered off and the dried under reduced pressure to afford clean (3-bromo-5-iodo-phenyl)methanol 32 as a beige solid.

LCMS method F: $[M+H]^+$=not detected, $t_R$=2.54 min (current 20V)

Preparation of Intermediate 33: benzyl N-[3-[3-[3-bromo-5-(hydroxymethyl)phenyl]-1-tetrahydropyran-2-yl-indazol-5-yl]oxypropyl]carbamate

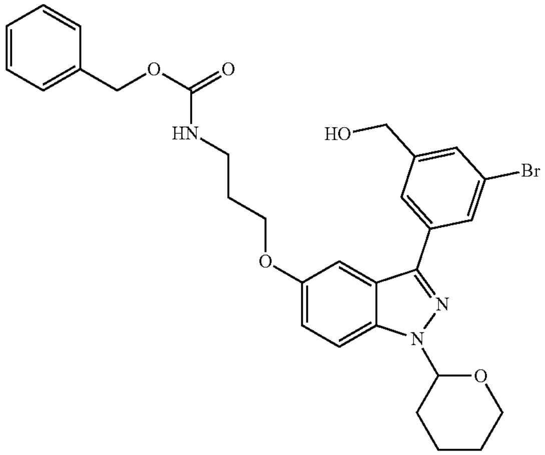 [SMILES: O=C(NCCCOc1ccc2c(c1)c(-c1cc(Br)cc(CO)c1)nn2C1CCCCO1)OCc1ccccc1]

To a solution of benzyl N-[3-[1-tetrahydropyran-2-yl-3-(4,4,5,5-tetramethyl-1,3,2-dioxaborolan-2-yl)indazol-5-yl]oxypropyl]carbamate 32 (1.870 g, 3.50 mmol) in N,N-dimethylformamide (15 mL) was added at RT (3-bromo-5-iodo-phenyl)methanol 31 (1.314 g, 4.20 mmol) and $Cs_2CO_3$ (3.421 g, 10.50 mmol). The reaction mixture was degassed by bubbling nitrogen for 15 min and $PdCl_2$ dppf (0.128 g, 0.18 mmol) was added. The resulting mixture was stirred at 110° C. under microwave irradiation for 50 min. The reaction mixture was filtered over celite and washed with ethyl acetate. The solvent was removed under reduced pressure and the oil was dissolved in EtOAc and water. The two layers were separated and the aqueous phase was extracted with ethyl acetate twice. The combined organic layers were dried over anhydrous sodium sulfate and concentrated under reduced pressure. Purification by flash-column chromatography (40 g RS SiOH) chromatography (cyclohexane-ethyl acetate, 100/0 to 50/50) gave benzyl N-[3-[3-[3-bromo-5-(hydroxymethyl)phenyl]-1-tetrahydropyran-2-yl-indazol-5-yl]oxypropyl]carbamate 33 as an orange oil.

LCMS method F: $[M+H]^+$=596.1, $t_R$=3.07 min (current 20V)

Preparation of Intermediate 34: 4-bromo-19-(oxan-2-yl)-8,14-dioxa-10,19,20-triazatetra cyclo [$13.5.2.1^{2,6}.0^{18,21}$]tricosa-1(20),2,4,6(23),15,17,21-heptaen-9-one

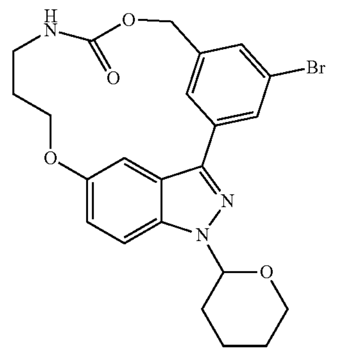 [SMILES: O=C1NCCCOc2ccc3c(c2)c(nn3C2CCCCO2)-c2cc(Br)cc(c2)CO1]

To a solution of benzyl N-[3-[3-[3-bromo-5-(hydroxymethyl)phenyl]-1-tetrahydropyran-2-yl-indazol-5-yl]oxypropyl]carbamate 33 (288 mg, 0.48 mmol) in dry toluene (300 mL) was added sodium hydride 60% in oil (480 mg, 12 mmol) at RT. The reaction mixture was stirred at 130° C. for 1 h. The reaction was then stirred at RT overnight and sodium hydride 60% in oil (192 mg, 4.8 mmol) was added. The reaction mixture was stirred at 130° C. for 3 h. More sodium hydride 60% in oil (192 mg, 4.8 mmol) was added and the reaction mixture was stirred at 140° C. for overnight. More sodium hydride 60% in oil (192 mg, 4.8 mmol) was added and the reaction mixture was stirred at 140° C. for 5 h. Again sodium hydride 60% in oil (192 mg, 4.8 mmol) was added and the reaction mixture was stirred at 140° C. for 1 h till completion of the reaction. The reaction mixture was allowed to RT and cooled in an ice bath. EtOH (50 mL) was slowly added. The reaction mixture was diluted with ethyl acetate (200 mL) and water was added (200 mL). After separation, the aqueous layer was extracted with ethyl acetate (x3 50 mL). The combined organic layers were washed with brine (150 mL), dried over sodium sulfate, filtered and dried under reduced pressure to afford an orange oil.

Purification on silica column (RS SiOH 80 g) using cyclohexane/ethyl acetate from 100/0 to 0/100 as and DCM/MeOH 90/10 as eluent gave 60 mg of the intended product. The impure fractions were pooled and the solvent was removed under reduced pressure. The residue was purified on silica column (RS SiOH 40 g) using clyclohexane/ethyl acetate from 100/0 to 50/50 as eluent gave 4-bromo-19-(oxan-2-yl)-8,14-dioxa-10,19,20-triazatetracyclo [$13.5.2.1^{2,6}.0^{18,21}$]tricosa-1(20),2,4,6(23),15,17,21-heptaen-9-one 34 as a white solid.

LCMS method F: $[M+H]^+$=487.7, $t_R$=3.05 min

Preparation of Example 9: 4-bromo-8,14-dioxa-10,19,20-triazatetracyclo[$13.5.2.1^{2,6}.0^{18,21}$]tricosa-1(20), 2,4,6(23),15,17,21-heptaen-9-one

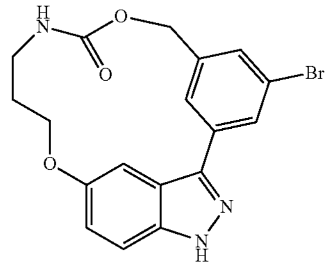 [SMILES: O=C1NCCCOc2ccc3[nH]nc(c3c2)-c2cc(Br)cc(c2)CO1]

To a solution of 4-bromo-19-(oxan-2-yl)-8,14-dioxa-10,19,20-triazatetracyclo[$13.5.2.1^{2,6}.0^{18,21}$]tricosa-1(20),2,4,6(23),15,17,21-heptaen-9-one 34 (30 mg, 0.062 mmol) in DCM (3 mL) was added trifluoroacetic acid (95 μL, 1.24 mmol). The reaction mixture was stirred at 80° C. under microwave irradiation for 2 h. The reaction mixture was diluted with DCM (20 mL). Water (50 mL) and ammonium hydroxide 25% weight aqueous solution (3 mL) were added. After separation, the aqueous layer was extracted with DCM (x3 10 mL). The combined organic layers were washed with saturated sodium carbonate aqueous solution (30 mL) and brine (30 mL). The organic layer was dried over sodium sulfate, filtered and dried under reduced pressure to afford a beige solid. DCM was added to the solid. The precipitate was filtered and the filtrate was purified on preparative TLC using cyclohexane/ethyl acetate; 50/50 as eluent. The resulting product was purified a second time on preparative TLC using cyclohexane/ethyl acetate; 50/50 as eluent to give 4-bromo-8,14-dioxa-10,19,20-triazatetracyclo[$13.5.2.1^{2,6}.0^{18,21}$]tricosa-1(20),2,4,6(23),15,17,21-heptaen-9-one example 9 as a beige solid.

LCMS method F: $[M+H]^+$=403, $t_R$=2.40 min

LCMS method G: $[M+H]^+$=403, $t_R$=2.38 min $^1H$ NMR (400 MHz, d6-DMSO) δ 13.07 (1H, s), 8.02 (1H, s), 7.87 (1H, s), 7.74 (1H, s), 7.51 (2H, q, J=2.8 Hz), 7.32 (1H, d, J=2.7 Hz), 7.00 (1H, dd, J=2.3, 8.9 Hz), 5.29 (2H, m), 4.32 (2H, m), 3.18 (2H, m, J=8.1 Hz), 2.03 (2H, m) ppm.

Example 10: 5-fluoro-8,14-dioxa-10,19,20-triazatetracyclo[$13.5.2.1^{2,6}.0^{18,21}$]tricosa-1(20), 2,4,6(23),15,17,21-heptaen-9-one

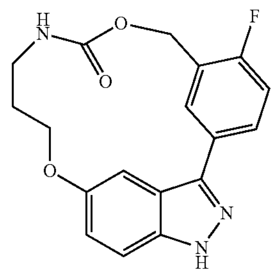 [SMILES: O=C1NCCCOc2ccc3[nH]nc(c3c2)-c2ccc(F)c(c2)CO1]

Example 10 is prepared according to the synthesis route described in general Scheme E.

Preparation of Intermediate 35: 2-fluoro-5-[5-hydroxy-1-(oxan-2-yl)-1H-indazol-3-yl]benzoic acid

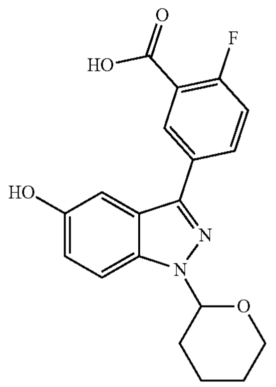 [SMILES: O=C(O)c1cc(-c2nn(C3CCCCO3)c3ccc(O)cc23)ccc1F]

To solution of 3-iodo-1-(oxan-2-yl)-1H-indazol-5-ol 4 (1 g, 2.90 mmol), 2-fluoro-5-(tetramethyl-1,3,2-dioxaborolan-2-yl)benzoic acid (0.925 g, 2.52 mmol) in dioxane/water; 70/30 (12 mL) was added tripotassium phosphate (1.84 g, 8.7 mmol). The mixture was degassed by bubbling nitrogen for 15 minutes. Xphos (0.138 g, 0.29 mmol) and palladium-tetrakis(triphenylphosphine) (0.167 g, 0.145 mmol) were added. The mixture was heated at 120° C. for 2 hours under microwaves irradiations (BIOTAGE). The reaction mixture was filtered over celite pad and eluted with ethyl acetate. The solution was washed with water (50 mL) and with brine (50 mL). The organic layer was dried with sodium sulfate and the solvent was removed under reduced pressure to afford a brown oil. Purification on silica column on Biotage using cyclohexane/ethyl acetate from 100/0 to 20/80 as eluent gave 2-fluoro-5-[5-hydroxy-1-(oxan-2-yl)-1H-indazol-3-yl] benzoic acid 35 as a white powder.

LCMS method F: $[M+H]^+$=357.1, $t_R$=2.34 min

Preparation of Intermediate 36: 3-[4-fluoro-3-(hydroxymethyl)phenyl]-1-(oxan-2-yl)-1H-indazol-5-ol

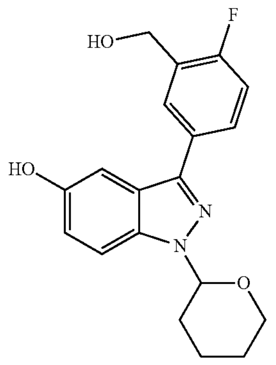 [SMILES: OCc1cc(-c2nn(C3CCCCO3)c3ccc(O)cc23)ccc1F]

To a solution 2-fluoro-5-[5-hydroxy-1-(oxan-2-yl)-1H-indazol-3-yl]benzoic acid 35 (0.2 g, 0.56 mmol) in THE (25 mL) was added solid sodium borohydride (0.062 g, 1.68 mmol) at RT. After the end of the gas release (i.e. 5 min), the reaction mixture was cooled to 0° C. and neat boron trifluoride diethyl etherate (0.163 mL, 1.68 mmol) was added dropwise over 1 h. The reaction mixture was allowed to warm to RT and stirred at 65° C. for 2 h. The reaction mixture was cooled to 0° C. and an aqueous 1 M solution of sodium hydroxide (50 mL) was added. The mixture was stirred at RT for 2 h. The reaction mixture was filtered over celite and eluted with ethyl acetate. The solution was washed with water (50 mL) and with brine (50 mL). The organic layer was dried with sodium sulfate and the solvent was removed under reduced pressure to afford a brown oil. Purification (Biotage) on silica column using cyclohexane/ethyl acetate from 100/00 to 50/50 as eluent 3-[4-fluoro-3-(hydroxymethyl)phenyl]-1-(oxan-2-yl)-1H-indazol-5-ol 36 as a white powder.

LCMS method F: $[M+H]^+$=343.1, $t_R$=2.27 min

Preparation of Intermediate 37: benzyl N-[3-({3-[4-fluoro-3-(hydroxymethyl)phenyl]-1-(oxan-2-yl)-1H-indazol-5-yl}oxy)propyl]carbamate

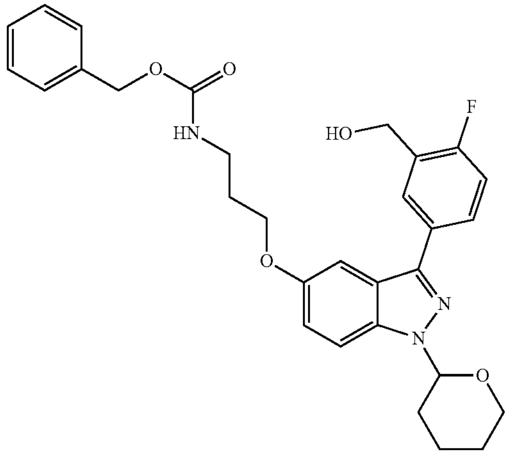 [SMILES: O=C(NCCCOc1ccc2c(c1)c(-c1ccc(F)c(CO)c1)nn2C1CCCCO1)OCc1ccccc1]

To a solution 3-[4-fluoro-3-(hydroxymethyl)phenyl]-1-(oxan-2-yl)-1H-indazol-5-ol 36 (0.18 g, 0.52 mmol) in N,N-dimethylformamide (10 mL), cesium carbonate (0.338 g, 1.04 mmol) and tert-butyl 3-[(methanesulfonyloxy)methyl] pyrrolidine-1-carboxylate 20 (0.169 gr, 0.624 mmol) was added. The reaction was stirred at 80° C. for 16 hours. The mixture was concentrated under reduced pressure. Water (50 mL) was added and the resulting mixture was extracted with EtOAc (4×100 mL). Combined organic layers were washed with saturated brine (2×50 mL). The organic layer was dried over sodium sulfate and the solvent was removed under reduced pressure to afford brown/orange oil. The residue was purified by flash chromatography on silica gel (Macherey Nagel, 12 g) with gradient elution: cyclohexane/EtOAc 0-70% to give benzyl N-[3-({3-[4-fluoro-3-(hydroxymethyl)phenyl]-1-(oxan-2-yl)-1H-indazol-5-yl}oxy)propyl] carbamate 37 as a white solid.

LCMS method F: $[M+H]^+$=534.2, $t_R$=2.90 min

Preparation of Intermediate 38: 5-fluoro-19-(oxan-2-yl)-8,14-dioxa-10,19,20-triazatetra cyclo [13.5.2.1$^{2,6}$.0$^{18,21}$]tricosa-1(20),2,4,6(23),15,17,21-heptaen-9-one

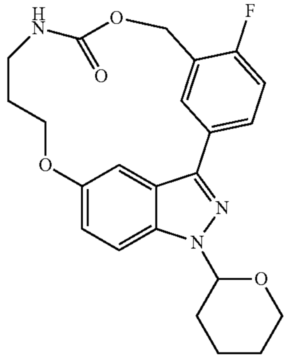 [SMILES: O=C1NCCCOc2ccc3c(c2)c(nn3C2CCCCO2)-c2ccc(F)c(c2)CO1]

A solution of benzyl N-[3-({3-[4-fluoro-3-(hydroxymethyl)phenyl]-1-(oxan-2-yl)-1H-indazol-5-yl}oxy)propyl] carbamate 37 (0.153 g; 0.28 mmol) in 50 mL of toluene was added to a solution of sodium hydride (60% suspension in paraffin oil) (114 mg, 24 mmol) in 50 mL of toluene at room temperature. The reaction mixture was stirred at RT for 5 min and then one hour at 130° C. The reaction is allowed to cool down and then 10 mL of EtOH is added carefully. 100 mL of water in added. After separation, the aqueous layer was extracted with ethyl acetate (2×100 mL). The combined organic layers were washed with a saturated brine, dried over sodium sulfate and the solvent was removed under reduced pressure to give an orange oil. A purification by column chromatography (DCM/MeOH 0-10%) afforded pure 5-fluoro-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one 38 as a whitish solid.

LCMS method F: $[M+H]^+$=426.2, $t_R$=2.78 min

Preparation of Example 10: 5-fluoro-8,14-dioxa-10,19,20-triazatetracyclo[13.5.2.1$^{2,6}$.0$^{18,21}$]tricosa-1(20), 2,4,6(23),15,17,21-heptaen-9-one

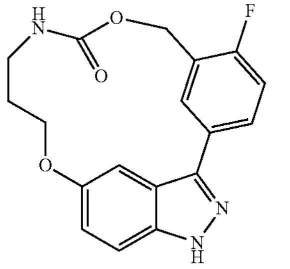 [SMILES: O=C1NCCCOc2ccc3[nH]nc(c3c2)-c2ccc(F)c(c2)CO1]

To a solution of 5-fluoro-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one 38 (35 mg, 0.082 mmol) in DCM (5 mL) was added trifluoroacetic acid (63 μL, 0.82 mmol). The reaction mixture was stirred at RT for 6 h and at 30° C. overnight. More trifluoroacetic acid (32 μL, 0.41 mmol) was added and the reaction mixture was stirred at 50° C. for 5 h. Again more trifluoroacetic acid (32 μL, 0.41 mmol) was added and the reaction mixture was stirred at 50° C. for another 2 h. The reaction mixture was evaporated to dryness and co-evaporated with toluene. DCM (40 mL), water (125 mL) and ammonium hydroxide 25% weight aqueous solution (3 mL) were added. After separation, the aqueous layer was extracted with DCM (3×20 mL). The combined organic layers were washed with saturated sodium carbonate solution (100 mL) and brine (100 mL), dried over sodium sulfate anhydrous and the solvent was removed under reduced pressure to afford a beige solid.

Trituration of the residue one time in acetonitrile, five times in DCM and two times in EtOH gave 5-fluoro-8,14-dioxa-10,19,20-triazatetracyclo[13.5.2.1$^{2,6}$.0$^{18,21}$]tricosa-1(20),2,4,6(23), 15,17,21-heptaen-9-one example 10 as a white powder.

LCMS method F: $[M+H]^+$=342.1, $t_R$=2.18 min

LCMS method G: $[M+H]^+$=342.1, $t_R$=2.36 min $^1$H NMR (400 MHz, d6-DMSO) δ 12.95 (1H, s), 7.93 (2H, m), 7.81 (1H, s), 7.89 (1H, d, J=9.0 Hz), 7.33 (2H, m), 6.99 (1H, dd, J=9.1 Hz), 5.35 (2H, s), 4.33 (2H, m), 3.19 (2H, m), 2.03 (2H, m) ppm.

Example 11: 5-methyl-8,14-dioxa-10,19,20-triazatetracyclo[13.5.2.1$^{2,6}$.0$^{18,21}$]tricosa-1(20),2,4,6(23), 15,17,21-heptaen-9-one

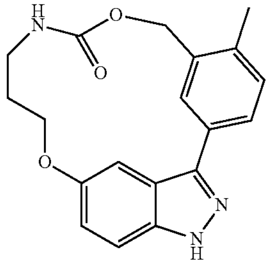 [SMILES: Cc1ccc2cc1COC(=O)NCCCOc1ccc3[nH]nc-2c3c1]

Example 11 is prepared according to the synthesis route described in general Scheme F.

Preparation of Intermediate 39: methyl 5-[5-[3-(benzyloxycarbonylamino)propoxy]-1-tetrahydropyran-2-yl-indazol-3-yl]-2-methyl-benzoate

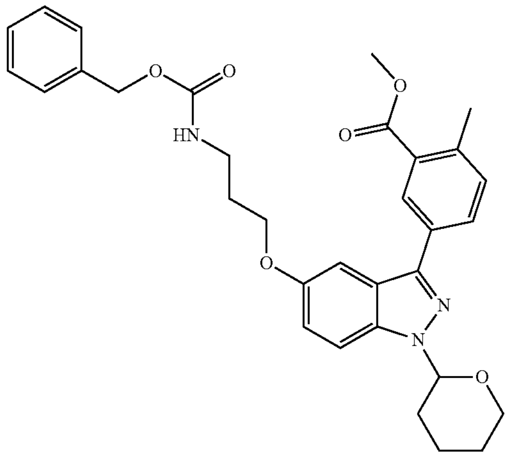 [SMILES: COC(=O)c1cc(-c2nn(C3CCCCO3)c3ccc(OCCCNC(=O)OCc4ccccc4)cc23)ccc1C]

A solution of benzyl N-[3-(3-iodo-1-tetrahydropyran-2-yl-indazol-5-yl)oxypropyl]carbamate 26 (1.2 g, 2.2 mmol postulated), (3-methoxycarbonyl-4-methyl-phenyl)boronic acid (467 mg, 2.42 mmol), potassium phosphate tribasic (1.4 g, 6.6 mmol) and triethylamine (1.4 mL, 9.9 mmol) in THF/$H_2O$ (6.5/3.2 mL) was degassed for 15 minutes. Pd(dppf)$Cl_2$·DCM (179 mg, 0.22 mmol) was added and the reaction mixture was stirred under nitrogen atmosphere at 100° C. for 17 hours. The reaction mixture was filtered over celite and washed with EtOAc. The filtrate was diluted with water (100 mL) and extracted with EtOAc (2×50 mL). The combined organic layers were washed with brine (2×50 mL), dried over sodium sulfate, filtered and the solvent was removed under reduced pressure. The residue was purified by column (Macherey Nagel, 40 g) chromatography with eluent cyclohexane/EtOAc (100/0 to 80/20). The desired fractions were collected and the solvent was removed under reduced pressure to give methyl 5-[5-[3-(benzyloxycarbonylamino)propoxy]-1-tetrahydropyran-2-yl-indazol-3-yl]-2-methyl-benzoate 39 (1.04 g, 1.87 mmol) as a white solid.

LCMS method F: $[M+H]^+$=558, $t_R$=3.33 min

Preparation of Intermediate 40: benzyl N-[3-[3-[3-(hydroxymethyl)-4-methyl-phenyl]-1-tetrahydropyran-2-yl-indazol-5-yl]oxypropyl]carbamate

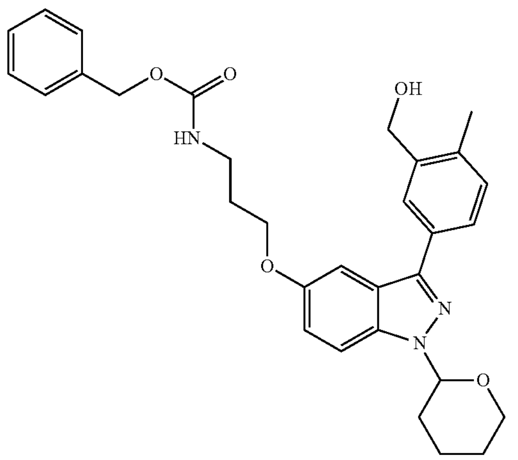 [SMILES: Cc1ccc(-c2nn(C3CCCCO3)c3ccc(OCCCNC(=O)OCc4ccccc4)cc23)cc1CO]

To a solution of methyl 5-[5-[3-(benzyloxycarbonylamino)propoxy]-1-tetrahydropyran-2-yl-indazol-3-yl]-2-methyl-benzoate 39 (1 g, 1.8 mmol) in THE (6 mL) under $N_2$, LAH 1 M in THF (2.2 mL, 2.2 mmol) was added at 0° C. The reaction was stirred at 0° C. for 2 hours and 30 minutes. The mixture was quenched with water (1 mL), NaOH 10% (0.2 mL) and water (0.5 mL). The mixture was filtered and washed with EtOAc. The filtrate was diluted with water (50 mL) and extracted with EtOAc (3×50 mL). The combined organic layers were washed with brine (2×50 mL), dried with anhydrous sodium sulfate and the solvent was removed under reduced pressure. The crude was purified by pad of silica with cyclohexane/EtOAc (60/40) as eluent to give benzyl N-[3-[3-[3-(hydroxymethyl)-4-methyl-phenyl]-1-tetrahydropyran-2-yl-indazol-5-yl]oxypropyl]carbamate 40 as a white oil.

LCMS method F: $[M+H]^+$=530, $t_R$=2.90 min

Preparation of Intermediate 41: 5-methyl-19-(oxan-2-yl)-8,14-dioxa-10,19,20-triazatetra cyclo [13.5.2.1$^{2,6}$.0$^{18,21}$]tricosa-1(20),2,4,6(23),15,17,21-heptaen-9-one

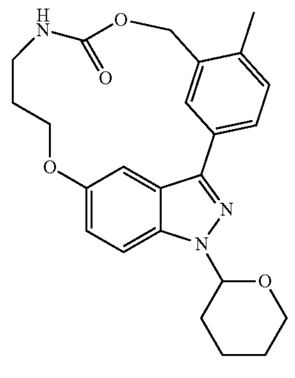 [SMILES: Cc1ccc2cc1COC(=O)NCCCOc1ccc3c(c1)c-2nn3C1CCCCO1]

To a solution of benzyl N-[3-[3-[3-(hydroxymethyl)-4-methyl-phenyl]-1-tetrahydropyran-2-yl-indazol-5-yl]oxypropyl]carbamate 40 (120 mg, 0.23 mmol) in acetonitrile (40 mL), potassium carbonate (190 mg, 1.38 mmol) was added. The mixture was divided in two vials then heated in microwaves at 140° C. for 4 hours and 30 minutes. The two vials was heated again in microwaves at 140° C. for 4 hours. The mixture was filtered to removed potassium carbonate and the solvent was evaporated under reduced pressure to give 5-methyl-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one 41 as a white powder. The crude was used in the next step without further purification.

LCMS method F: $[M+H]^+$=422, $t_R$=2.87 min

Preparation of Example 11: 5-methyl-8,14-dioxa-10,19,20-triazatetracyclo[13.5.2.1$^{2,6}$.0$^{18,21}$]tricosa-1(20),2,4,6(23),15,17,21-heptaen-9-one

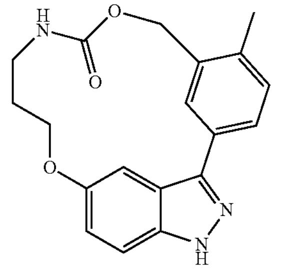 [SMILES: Cc1ccc2cc1COC(=O)NCCCOc1ccc3[nH]nc-2c3c1]

To a solution of 5-methyl-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one 41 (84 mg, 0.2 mmol) in DCM (15 mL) was added trifluoro acetic acid (306 μL, 4 mmol). The mixture was heated in microwaves at 80° C. for 1 hour. The solvent was removed under reduced pressure to afford an oily residue, which was dissolved in DCM (20 mL). A precipitate was formed and filtered. The solid was dissolved in DCM/MeOH (15 mL), then $NaHCO_3$ saturated was added (15 mL). After separation, the aqueous layer was extracted with DCM (3×10 mL). The combined organic layers were washed with brine (20 mL), dried over anhydrous sodium sulfate, filtered and the solvent was removed under reduced pressure to give 5-methyl-8,14-dioxa-10,19,20-triazatetracyclo[13.5.2.1$^{2,6}$.0$^{18,21}$]tricosa-1(20),2,4,6(23),15,17,21-heptaen-9-one example 11 as a white solid.

LCMS method F: $[M+H]^+=338$, $t_R=2.32$ min

LCMS method G: $[M+H]^+=338$, $t_R=2.35$ min $^1$H NMR (400 MHz, d6-DMSO) δ 12.86-12.79 (1H, m), 7.84 (1H, m), 7.82 (1H, m), 7.74 (1H, s), 7.46 (1H, d, J=8.9 Hz), 7.42 (1H, m), 7.28 (1H, dd, J=0.6, 8.3 Hz), 6.98 (1H, dd, J=2.4, 9.0 Hz), 5.28 (2H, s), 4.34 (2H, dd, J=8.2, 8.5 Hz), 3.2 (2H, m), 2.32 (3H, s), 2.04-1.99 (2H, m) ppm.

Example 12: 4-(pyrrolidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one

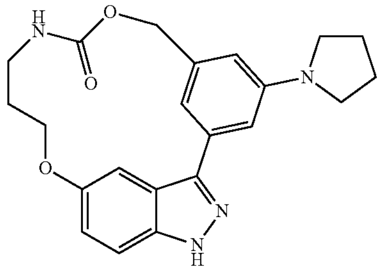 [SMILES: O=C1NCCCOc2ccc3[nH]nc(c3c2)-c2cc(cc(N3CCCC3)c2)CO1]

Example 12 is prepared according to the synthesis route described in general Scheme C. Pyrrolidine is used for the Buchwald reaction with the bromide intermediate 34.

Preparation of Intermediate 42: 19-(oxan-2-yl)-4-(pyrrolin-8,14-dioxa-10,19,20-triazatetracyclo[13.5.2.1$^{2,6}$.0$^{18,21}$]tricosa-1(20),2,4,6(23),15,17,21-heptaen-9-one

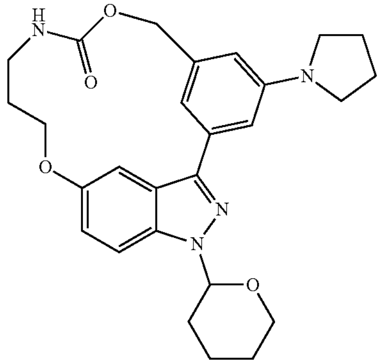 [SMILES: O=C1NCCCOc2ccc3c(c2)c(nn3C2CCCCO2)-c2cc(cc(N3CCCC3)c2)CO1]

To a degassed solution of 4-bromo-10-methyl-19-(oxan-2-yl)-7-oxa-10,13,19,20-tetraazatetracyclo[13.5.2.12,6.018, 21] tricosa-1(20),2,4,6(23),15(22), 16,18(21)-heptaen-14-one example 9 (100 mg, 0.206 mmol), pyrrolidine (19 al, 0.227 mmol), tBuONa (40 mg, 0.412 mmol) and SPhos (3 mg, 0.008 mmol) in dioxane (2.5 mL) was added Pd-dba$_3$ (4 mg, 0.004 mmol) at RT. The reaction mixture was stirred under microwave irradiation for 45 min at 60° C. More pyrrolidine (2 μl; 0.021 mmol) was added and the reaction was stirred under microwave irradiation during 20 min at 60° C. After being cooled to RT, the reaction mixture was diluted with water and extracted with ethyl acetate twice. The combined organic layer was washed with brine, dried over anhydrous sodium sulfate and concentrated under reduced pressure. The residue was purified by flash-column (5 g $SiO_2$) chromatography (cyclohexane/Ethyl acetate, 1:0 to 50/50) affording 19-(oxan-2-yl)-4-(pyrrolidin-1-yl)-8,14-dioxa-10,19,20-triazatetracyclo[13.5.2.1$^{2,6}$.0$^{18,21}$]tricosa-1(20),2,4,6(23),15,17,21-heptaen-2-one 42 as a white powder.

LCMS method F: $[M+H]^+=477.2$, $t_R=3.00$ min

Preparation of Example 12: 4-(pyrrolidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one

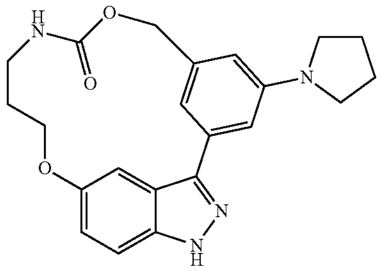 [SMILES: O=C1NCCCOc2ccc3[nH]nc(c3c2)-c2cc(cc(N3CCCC3)c2)CO1]

To a mixture of 19-(oxan-2-yl)-4-(pyrrolidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one 42 (60 mg; 0.126 mmol) in DCM (2.5 mL) was added TFA (48 μl; 0.630 mmol). The reaction mixture was stirred under microwaves irradiation at 80° C. during 30 min. The solvent was removed under reduced pressure, the mixture was dissolved in EtOAc and washed with 1N NaOH (pH=7), then with water. The organic layer was concentrated under reduced pressure and the product was purified by chromatography using a 4 g SiO2 column eluted with DCM/MeOH 100/0 to 90/10. The desired fractions were combined to give 4-(pyrrolidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one example 12 as a yellow powder.

LCMS method F: $[M+H]^+=393.1$, $t_R=2.39$ min (current 20V)

LCMS method G: $[M+H]^+=393.1$, $t_R=2.47$ min (pH10 current 20V)

1H NMR (400 MHz, d6-DMSO) δ 7.61 (1H, m), 7.47-7.44 (1H, m), 7.36 (1H, d, J=2.7 Hz), 7.20 (1H, s), 7.04 (1H, t, J=1.9 Hz), 6.95 (1H, dd, J=2.4, 9.0 Hz), 6.50 (1H, s), 5.22-5.20 (2H, m), 4.30 (2H, d, J=16.9 Hz), 3.32 (4H, m), 3.17-3.15 (2H, m), 2.03-1.99 (6H, m), 1.07 (1H, d, J=6.1 Hz) ppm.

Example 13: 4-[4-(propan-2-yl)piperazin-1-yl]-8,14-dioxa-10,19,20-triazatetracyclo[13.5.2.1$^{2,6}$.0$^{18,21}$]tricosa-1(20),2,4,6(23),15,17,21-heptaen-9-one

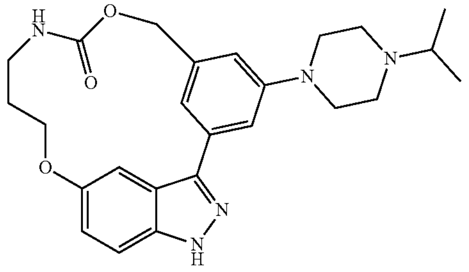 [SMILES: CC(C)N1CCN(c2cc3cc(c2)-c2n[nH]c4ccc(cc24)OCCCNC(=O)OC3)CC1]

Example 13 is prepared according to the synthesis route described in general Scheme C and procedures analogous to those used to obtain example 12. 1-(propan-2-yl)piperazine is used for the Buchwald reaction with the bromide intermediate 34 to give 4-[4-(propan-2-yl)piperazin-1-yl]-8,14-dioxa-10,19,20-triazatetracyclo[13.5.2.1$^{2,6}$.0$^{18,21}$]tricosa-1(20),2,4,6(23),15,17,21-heptaen-9-one example 13.

LCMS method F: $[M+H]^+$=450.2, $t_R$=1.54 min

LCMS method G: $[M+H]^+$=450.2, $t_R$=2.26 min $^1$H NMR (400 MHz, d6-DMSO, 80° C.) δ 12.80 (1H, s), 7.68-7.57 (1H, m), 7.46 (1H, d, J=9.3 Hz), 7.37-7.34 (3H, m), 6.96 (1H, dd, J=2.4, 8.8 Hz), 6.87 (1H, s), 5.23 (2H, s), 4.28 (2H, s), 3.25-3.22 (4H, m), 3.17 (2H, s), 2.76-2.67 (1H, m), 2.66-2.61 (4H, m), 2.02 (2H, s), 1.05 (6H, d, J=6.5 Hz) ppm.

Example 14: 4-{2-oxa-6-azaspiro[3.4]octan-6-yl}-8,14-dioxa-10,19,20-triazatetracyclo[13.5.2.1$^{2,6}$.0$^{18,21}$]tricosa-1(20),2,4,6(23),15,17,21-heptaen-9-one

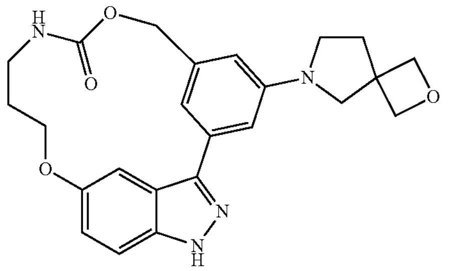 [SMILES: O=C1NCCCOc2ccc3[nH]nc(c3c2)-c2cc(cc(N3CCC4(COC4)C3)c2)CO1]

Example 14 is prepared according to the synthesis route described in general Scheme C and procedures analogous to those used to obtain example 12. 2-Oxa-6-azaspiro[3.4]octane is used for the Buchwald reaction with the bromide intermediate 34 to give 4-{2-oxa-6-azaspiro[3.4]octan-6-yl}-8,14-dioxa-10,19,20-triazatetracyclo[13.5.2.1$^{2,6}$.0$^{18,21}$]tricosa-1(20),2,4,6(23),15,17,21-heptaen-9-one example 14.

LCMS method F: $[M+H]^+$=435, $t_R$=2.16 min

LCMS method G: $[M+H]^+$=435, $t_R$=2.20 min $^1$H NMR (400 MHz, d6-DMSO, 80° C.) δ 12.77 (1H, s), 7.61 (1H, m), 7.46 (1H, d, J=9.2 Hz), 7.36 (1H, m), 7.22 (1H, m), 7.04 (1H, m), 6.96 (1H, m), 6.51 (1H, m), 5.22 (2H, m), 4.64-4.56 (4H, m), 4.30 (2H, m), 3.60 (2H, s), 3.35 (2H, t), 3.16 (2H, m), 2.31 (2H, m), 2.02 (2H, m) ppm.

Example 15: 4-[4-(oxetan-3-yl)piperazin-1-yl]-8,14-dioxa-10,19,20-triazatetracyclo[13.5.2.1$^{2,6}$.0$^{18,21}$]tricosa-1(20),2,4,6(23),15,17,21-heptaen-9-one

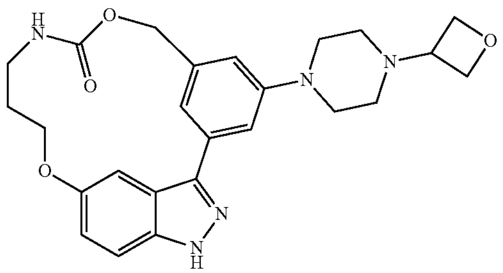 [SMILES: O=C1NCCCOc2ccc3[nH]nc(c3c2)-c2cc(cc(N3CCN(C4COC4)CC3)c2)CO1]

Example 15 is prepared according to the synthesis route described in general Scheme C and and procedures analogous to those used to obtain example 12. 1-(oxetan-3-yl)piperazine is used for the Buchwald reaction with the bromide intermediate 34 to give 4-[4-(oxetan-3-yl)piperazin-1-yl]-8,14-dioxa-10,19,20-triazatetracyclo[13.5.2.1$^{2,6}$.0$^{18,21}$]tricosa-1(20),2,4, 6(23),15,17,21-heptaen-9-one example 15.

LCMS method F: $[M+H]^+$=464.2, $t_R$=1.47 min

LCMS method G: $[M+H]^+$=464.2, $t_R$=2.00 min $^1$H NMR (400 MHz, d6-DMSO, 80° C.) δ 12.81 (1H, s), 7.64 (1H, s), 7.48-7.45 (1H, d, J=9.0 Hz), 7.39-7.34 (3H, m), 6.96 (1H, dd, J=2.2, 8.8 Hz), 6.89 (1H, m), 5.23 (2H, s), 4.62-4.57 (2H, t, J=6.5 Hz), 4.55-4.51 (2H, m), 4.33-4.27 (2H, t, J=8.6 Hz), 3.58-3.51 (1H, q, J=6.2 Hz), 3.30-3.26 (4H, m), 3.17-3.11 (2H, m), 2.10-1.99 (2H, m) ppm. 4 protons were located under the DMSO peak and are not reported here.

Example 16: 4-(morpholin-4-yl)-8,14-dioxa-10,19,20-triazatetracyclo[13.5.2.1$^{2,6}$.0$^{18,21}$]tricosa-1(20),2,4,6(23),15,17,21-heptaen-9-one

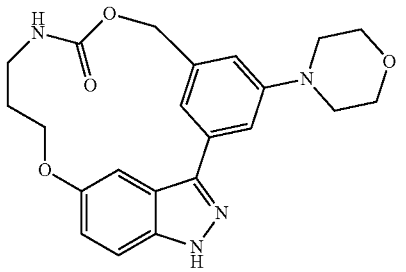 [SMILES: O=C1NCCCOc2ccc3[nH]nc(c3c2)-c2cc(cc(N3CCOCC3)c2)CO1]

Example 16 is prepared according to the synthesis route described in general Scheme C and procedures analogous to those used to obtain example 12. Morpholine is used for the Buchwald reaction with the bromide intermediate 34 to give 4-(morpholin-4-yl)-8,14-dioxa-10,19,20-triazatetracyclo[13.5.2.1$^{2,6}$.0$^{18,21}$]tricosa-1(20),2,4,6(23),15,17,21-heptaen-9-one example 16.

LCMS method F: $[M+H]^+$=409.2, $t_R$=2.13 min

LCMS method G: $[M+H]^+$=409.2, $t_R$=2.15 min $^1$H NMR (400 MHz, d6-DMSO, 80° C.) δ 12.82 (1H, s), 7.63 (1H, m), 7.48-7.45 (1H, d, J=9.0 Hz), 7.40 (2H, m), 7.34 (1H, m), 6.97 (1H, dd, J=2.3, 8.9 Hz), 6.89 (1H, s), 5.23

(2H, s), 4.33-4.28 (2H, t, J=8.32), 3.82-3.76 (4H, t, J=4.8 Hz), 3.23-3.20 (4H, t, J=4.9 Hz), 3.17 (2H, s), 2.02 (2H, s) ppm.

Example 17: 4-[(2R,6S)-2,6-dimethylmorpholin-4-yl]-8,14-dioxa-10,19,20-triazatetra cyclo [13.5.2.1$^{2,6}$.0$^{18,21}$]tricosa-1(20),2,4,6(23),15,17,21-heptaen-9-one

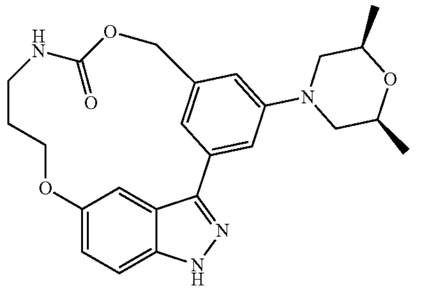 [SMILES: C[C@@H]1CN(c2cc3cc(c2)-c2n[nH]c4ccc(cc24)OCCCNC(=O)OC3)C[C@H](C)O1]

Example 17 is prepared according to the synthesis route described in general Scheme C and procedures analogous to those used to obtain example 12. Cis-2,6-dimethylmorpholine is used for the Buchwald reaction with the bromide intermediate 34 to give 4-[(2R,6S)-2,6-dimethylmorpholin-4-yl]-8,14-dioxa-10,19,20-triazatetracyclo[13.5.2.1$^{2,6}$.0$^{18,21}$]tricosa-1(20), 2,4,6(23),15,17,21-heptaen-9-one example 17.

LCMS method F: $[M+H]^+$=437.1, $t_R$=2.30 min

LCMS method G: $[M+H]^+$=437.2, $t_R$=2.36 min $^1$H NMR (400 MHz, d6-DMSO, 80° C.) δ 12.81 (1H, s), 7.63 (1H, s), 7.48-7.45 (1H, m), 7.39-7.34 (3H, m), 6.98-6.90 (2H, m), 5.23 (2H, s), 4.30 (2H, m), 3.80-3.73 (2H, m), 3.64 (2H, dd, J=1.5, 12.1 Hz), 3.17 (2H, s), 2.41-2.35 (2H, m), 2.06-2.05 (2H, m), 1.21 (6H, d, J=6.3 Hz) ppm.

Example 18: 4-methyl-8,14-dioxa-10,19,20-triaza-tetracyclo[13.5.2.1$^{2,6}$.0$^{18,21}$]tricosa-1(20),2,4,6(23),15,17,21-heptaen-9-one

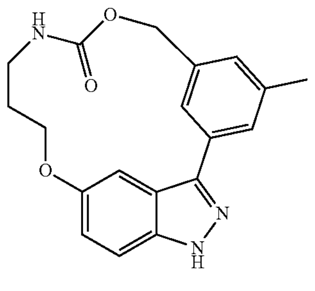 [SMILES: Cc1cc2cc(c1)-c1n[nH]c3ccc(cc13)OCCCNC(=O)OC2]

Example 18 is prepared according to the synthesis route described in general Scheme F and procedures analogous to those used to obtain example 11. (3-Methoxycarbonyl-5-methyl-phenyl)boronic acid is used for the Suzuki coupling with intermediate 26 to give 4-methyl-8,14-dioxa-10,19,20-triazatetracyclo[13.5.2.1$^{2,6}$.0$^{18,21}$]tricosa-1(20),2,4,6(23),15,17,21-heptaen-9-one example 18.

LCMS method F: $[M+H]^+$=338, $t_R$=2.25 min

LCMS method G: $[M+H]^+$=338, $t_R$=2.30 min $^1$H NMR (400 MHz, d6-DMSO) δ 7.73-7.65 (3H, m), 7.49-7.45 (1H, m), 7.34 (1H, d, J=2.1 Hz), 7.10-7.07 (1H, m), 6.97 (1H, dd, J=2.2, 9.0 Hz), 5.26-5.25 (2H, m), 4.34-4.28 (2H, m), 3.17 (2H, m), 2.41 (3H, s), 2.04-2.01 (2H, m) ppm. The indazole NH proton was not visible in this solvent.

Example 19: 5-methoxy-8,14-dioxa-10,19,20-triaza-tetracyclo[13.5.2.1$^{2,6}$.0$^{18,21}$]tricosa-1(20),2,4,6(23),15,17,21-heptaen-9-one

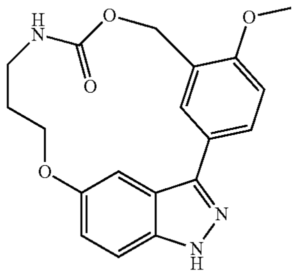 [SMILES: COc1ccc2cc1COC(=O)NCCCOc1ccc3[nH]nc-2c3c1]

Example 19 is prepared according to the synthesis route described in general Scheme F and procedures analogous to those used to obtain example 11. (4-Methoxy-3-methoxycarbonyl-phenyl)boronic acid is used for the Suzuki coupling with intermediate 26 to give 5-methoxy-8,14-dioxa-10,19,20-triazatetracyclo[13.5.2.1$^{2,6}$.0$^{18,21}$]tricosa-1(20),2,4,6(23),15,17,21-heptaen-9-one example 19.

LCMS method F: $[M+H]^+$=354, $t_R$=2.19 min

LCMS method G: $[M+H]^+$=354, $t_R$=2.17 min $^1$H NMR (400 MHz, d6-DMSO) δ 12.75 (1H, s), 7.91 (1H, dd, J=2.2, 8.6 Hz), 7.83 (1H, m), 7.72 (1H, m), 7.45 (1H, d, J=8.9 Hz), 7.37 (1H, d, J=2.2 Hz), 7.15 (1H, d, J=8.5 Hz), 6.97 (1H, dd, J=2.4, 9.0 Hz), 5.26 (2H, s), 4.33 (2H, m), 3.90 (3H, s), 3.18 (2H, m), 2.02 (2H, m) ppm.

Example 20: 4-(4,4-difluoropiperidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one

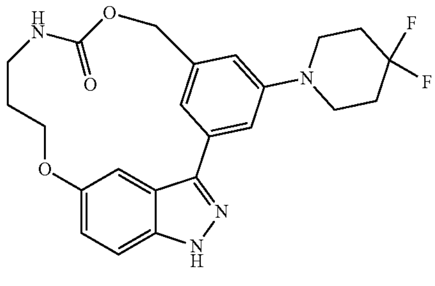 [SMILES: O=C1NCCCOc2ccc3[nH]nc(c3c2)-c2cc(cc(N3CCC(F)(F)CC3)c2)CO1]

Example 20 is prepared according to the synthesis route described in general Scheme C and procedures analogous to those used to obtain example 12. 4,4-Difluoropiperidine is used for the Buchwald reaction with the bromide intermediate 34 to give 4-(4,4-difluoropiperidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one example 20.

LCMS method F: $[M+H]^+$=443.1, $t_R$=2.46 min

LCMS method G: $[M+H]^+$=443.1, $t_R$=2.49 min $^1$H NMR (400 MHz, d6-DMSO, 80° C.) δ 12.83 (1H, s), 7.64 (1H, s), 7.49-7.43 (2H, m), 7.39 (1H, s), 7.36-7.33 (1H, m), 5.24 (2H, s), 4.36-4.27 (2H, m), 3.46-3.42 (4H, m), 3.17 (4H, s), 2.17-1.98 (6H, m) ppm.

Example 21: 4-(3,3-difluoropyrrolidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one

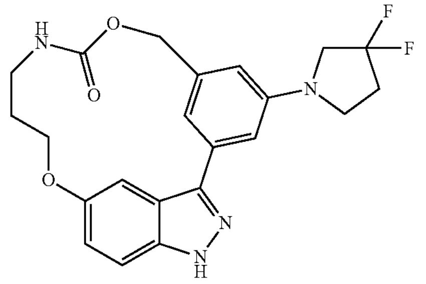 [SMILES: O=C1NCCCOc2ccc3[nH]nc(c3c2)-c2cc(cc(N3CCC(F)(F)C3)c2)CO1]

Example 21 is prepared according to the synthesis route described in general Scheme C and procedures analogous to those used to obtain example 12. 3,3-Difluoropyrrolidine is used for the Buchwald reaction with the bromide intermediate 34 to give 4-(3,3-difluoropyrrolidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one example 21.

LCMS method F: [M+H]$^+$=429.1, $t_R$=2.46 min

LCMS method G: [M+H]$^+$=429.1, $t_R$=2.48 min $^1$H NMR (400 MHz, d6-DMSO, 80° C.) δ 12.82 (1H, s), 7.63 (1H, s,), 7.47 (1H, d, J=8.9 Hz), 7.36-7.31 (2H, m), 7.10-7.08 (1H, m), 6.96 (1H, dd, J=2.4, 9.0 Hz), 6.59-6.58 (1H, m), 5.23 (2H, s), 4.33-4.27 (2H, m), 3.37 (2H, t, J=13.7 Hz), 3.58 (2H, t, J=7.2 Hz), 3.16 (2H, s), 2.63-2.53 (2H, m) 2.02 (2H, m) ppm.

Example 22: 7-methyl-8,14-dioxa-10,19,20-triazatetracyclo[13.5.2.1$^{2,6}$.0$^{18,21}$]tricosa-1(20), 2,4,6(23),15,17,21-heptaen-9-one

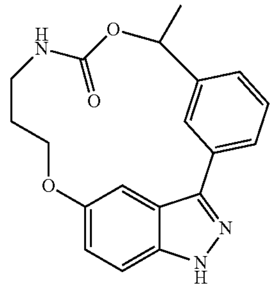 [SMILES: CC1OC(=O)NCCCOc2ccc3[nH]nc(c3c2)-c2cccc1c2]

Example 22 is prepared according to the synthesis route described in general Scheme C and procedures analogous to those used to obtain example 8. (3-(1-Hydroxyethyl)phenyl) boronic acid is used for the Suzuki coupling to give 7-methyl-8,14-dioxa-10,19,20-triazatetracyclo[13.5.2.1$^{2,6}$.0$^{18,21}$]tricosa-1(20),2,4,6(23),15,17,21-heptaen-9-one example 22.

LCMS method F: [M+H]$^+$=338, $t_R$=2.22 min

LCMS method G: [M+H]$^+$=338, $t_R$=2.25 min $^1$H NMR (400 MHz, d6-DMSO) δ 13.12 (1H, s), 7.95-7.92 (1H, m), 7.86-7.83 (2H, m), 7.50-7.46 (2H, m), 7.35 (1H, m), 7.31-7.29 (1H, m), 7.00-6.97 (1H, m), 5.95-5.90 (1H, m), 4.37-4.25 (2H, m), 3.56-3.49 (1H, m), 2.77-2.68 (1H, m), 2.24-2.15 (1H, m), 1.77-1.69 (1H, m), 1.59 (3H, d, J=6.7 Hz) ppm.

Example 23: 4-[4-(2-methoxyethyl)piperidin-1-yl]-8,14-dioxa-10,19,20-triazatetracyclo[13.5.2.1$^{2,6}$.0$^{18,21}$]tricosa-1(20),2,4,6(23),15,17,21-heptaen-9-one

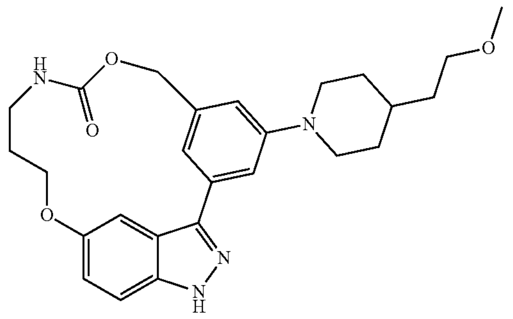 [SMILES: COCCC1CCN(c2cc3cc(c2)-c2n[nH]c4ccc(cc24)OCCCNC(=O)OC3)CC1]

Example 23 is prepared according to the synthesis route described in general Scheme C and procedures analogous to those used to obtain example 12. 4-(2-Methoxyethyl)piperidine is used for the Buchwald reaction with the bromide intermediate 34 to give 4-[4-(2-methoxyethyl)piperidin-1-yl]-8,14-dioxa-10,19,20-triazatetracyclo[13.5.2.1$^{2,6}$.0$^{18,21}$]tricosa-1(20),2,4,6(23),15,17,21-heptaen-9-one example 23.

LCMS method F: [M+H]$^+$=465.2, $t_R$=1.81 min

LCMS method G: [M+H]$^+$=465.2, $t_R$=2.53 min $^1$H NMR (400 MHz, d6-DMSO, 80° C.) δ 12.79 (1H, br. s), 7.63-7.59 (1H, m), 7.46 (1H, d, J=9.2 Hz), 7.37 (1H, d, J=2.0 Hz), 7.34 (1H, d, J=2.0 Hz), 7.32 (1H, s), 6.96 (1H, dd, J=2.3, 8.9 Hz), 6.86 (1H, s), 5.22-5.19 (2H, m), 4.33-4.28 (2H, m), 3.77-3.73 (2H, m), 3.43 (2H, t, J=8.0 Hz), 3.21-3.16 (2H, m), 3.09-3.06 (3H, br. s), 2.78 (2H, dt, J=4.0, 11.2 Hz), 2.05-2.01 (2H, m), 1.82-1.77 (2H, m), 1.58-1.49 (3H, m), 1.38-1.27 (2H, m) ppm.

Example 24: 9,14-dioxa-11,19,20-triazatetracyclo[13.5.2.1$^{2,6}$.0$^{18,21}$]tricosa-1(20),2,4, 6(23),15,17,21-heptaen-10-one

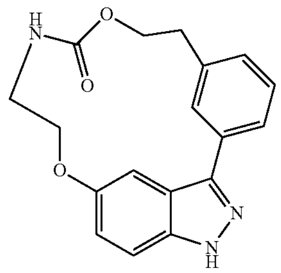 [SMILES: O=C1NCCOc2ccc3[nH]nc(c3c2)-c2cccc(c2)CCO1]

Example 24 is prepared according to the synthesis route described in general Scheme C and procedures analogous to those used to obtain example 8. 2-[3-(4,4,5,5-tetramethyl-1,3,2-dioxaborolan-2-yl)phenyl]ethan-1-ol is used for the Suzuki coupling to give 9,14-dioxa-11,19,20-triazatetracyclo[13.5.2.$1^{2,6}$.$0^{18,21}$]tricosa-1(20),2,4,6(23),15,17,21-heptaen-10-one example 24.

LCMS method F: $[M+H]^+$=324.1, $t_R$=2.14 min

LCMS method G: $[M+H]^+$=324.1, $t_R$=2.19 min $^1H$ NMR (400 MHz, d6-DMSO) δ 13.05-13.03 (1H, m), 7.99 (1H, t, J=5.9 Hz), 7.82 (1H, s), 7.68 (1H, d, J=7.6 Hz), 7.58 (1H, d, J=1.9 Hz), 7.46-7.41 (2H, m), 7.28-7.25 (1H, m), 7.04 (1H, dd, J=2.2, 9.0 Hz), 4.33-4.21 (4H, m), 3.40-3.3 (2H, m), 3.01 (2H, t, J=5.0 Hz) ppm.

Example 25: 4-[(3R)-3-hydroxypyrrolidin-1-yl]-8,14-dioxa-10,19,20-triazatetracyclo[13.5.2.$1^{2,6}$.$0^{18,21}$]tricosa-1(20),2,4,6(23),15,17,21-heptaen-9-one

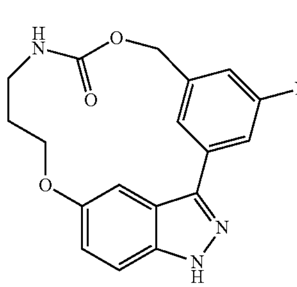

Example 25 is prepared according to the synthesis route described in general Scheme C and procedures analogous to those used to obtain example 12. (3R)-Pyrrolidin-3-ol is used for the Buchwald reaction with the bromide intermediate 34 to give 4-[(3R)-3-hydroxypyrrolidin-1-yl]-8,14-dioxa-10,19,20-triazatetracyclo[13.5.2.$1^{2,6}$.$0^{18,21}$]tricosa-1(20),2,4,6(23),15,17,21-heptaen-9-one example 25.

LCMS method F: $[M+H]^+$=409. 1, $t_R$=1.96 min

LCMS method G: $[M+H]^+$=409.2, $t_R$=2.04 min $^1H$ NMR (400 MHz, d6-DMSO) δ 7.65-7.56 (1H, m), 7.48-7.45 (1H, m), 7.36 (1H, d, J=2.5 Hz), 7.19 (1H, s), 7.01 (1H, s), 6.93 (1H, dd, J=2.3, 9.1 Hz), 6.46 (1H, s), 5.22 (2H, s), 4.48-4.43 (1H, m), 4.32-4.27 (2H, m), 3.53-3.32 (3H, m), 3.18-3.13 (2H, m), 3.11-2.99 (2H, m), 2.15-2.07 (1H, m), 2.07-1.97 (2H, m), 1.97-1.92 (1H, m) ppm. The indazole NH proton was not visible in this solvent.

Example 26: 4-[(2-methoxyethyl)(methyl)amino]-8,14-dioxa-10,19,20-triazatetracyclo[13.5.2.$1^{2,6}$.$0^{18,21}$]tricosa-1(20),2,4,6(23),15,17,21-heptaen-9-one

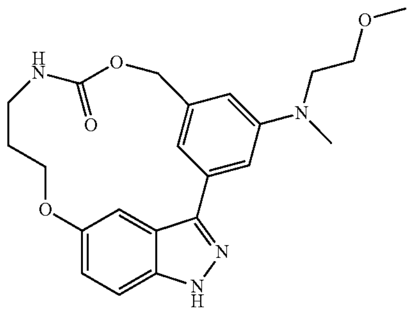 [SMILES: COCCN(C)c1cc2cc(c1)-c1n[nH]c3ccc(cc13)OCCCNC(=O)OC2]

Example 26 is prepared according to the synthesis route described in general Scheme C and procedures analogous to those used to obtain example 12. 2-Methoxy-N-methylethanamine is used for the Buchwald reaction with the bromide intermediate 34 to give 4-[(2-methoxyethyl)(methyl)amino]-8,14-dioxa-10,19,20-triazatetracyclo[13.5.2.$1^{2,6}$.$0^{18,21}$]tricosa-1(20),2,4,6(23),15,17,21-heptaen-9-one example 26.

LCMS method F: $[M+H]^+$=411.2, $t_R$=2.07 min

LCMS method G: $[M+H]^+$=411.2, $t_R$=2.32 min $^1H$ NMR (400 MHz, d6-DMSO) δ 12.74 (1H, s), 7.48-7.45 (1H, m), 7.36 (1H, d, J=2.3 Hz), 7.23-7.19 (2H, m), 6.96 (1H, dd, J=2.4, 9.0 Hz), 6.67 (1H, dd, J=1.3, 2.5 Hz), 5.22 (1H, t, J=9.7 Hz), 4.30 (2H, d, J=16.7 Hz), 3.31-3.31 (3H, m), 3.11-3.04 (8H, s), 3.01 (3H, s), 2.01-2.02 (2H, m) ppm.

Example 27: 4-chloro-8,14-dioxa-10,19,20-triazatetracyclo[13.5.2.$1^{2,6}$.$0^{18,21}$]tricosa-1(20), 2,4,6(23),15,17,21-heptaen-9-one

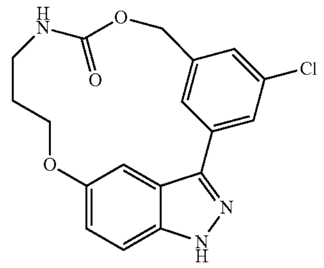 [SMILES: O=C1NCCCOc2ccc3[nH]nc(c3c2)-c2cc(Cl)cc(c2)CO1]

Example 27 is prepared according to the synthesis route described in general Scheme F and procedures analogous to those used to obtain example 11. (3-Chloro-5-methoxycarbonyl-phenyl)boronic acid is used for the Suzuki coupling with intermediate 26 to give 4-chloro-8,14-dioxa-10,19,20-triazatetracyclo[13.5.2.$1^{2,6}$.$0^{18,21}$]tricosa-1(20),2,4,6(23),15,17,21-heptaen-9-one example 27.

LCMS method F: $[M+H]^+$=358.0, $t_R$=2.38 min

LCMS method G: $[M+H]^+$=358.1, $t_R$=2.52 min $^1H$ NMR (400 MHz, d6-DMSO, 80° C.) δ 13.08 (1H, s), 7.85 (2H, d, J=15.0 Hz), 7.77-7.75 (1H, m), 7.50 (1H, d, J=8.0 Hz), 7.36 (1H, s), 7.32 (1H, d, J=2.4 Hz), 7.00 (1H, dd, J=2.3, 8.9 Hz), 5.29-5.25 (2H, m), 4.35-4.30 (2H, m), 3.23-3.12 (2H, m), 2.06-2.00 (2H, m) ppm.

Example 28: 4-fluoro-5-methyl-8,14-dioxa-10,19,20-triazatetracyclo[13.5.2.$1^{2,6}$.$0^{18,21}$]tricosa-1(20),2,4,6(23),15,17,21-heptaen-9-one

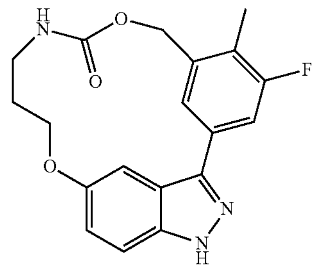 [SMILES: Cc1c(F)cc2cc1COC(=O)NCCCOc1ccc3[nH]nc-2c3c1]

Example 28 is prepared according to the synthesis route described in general Scheme G.

Preparation of Intermediate 43: methyl 5-[5-(3-{[(benzyloxy)carbonyl]amino}propoxy)-1-(oxan-2-yl)-H-indazol-3-yl]-3-fluoro-2-methylbenzoate

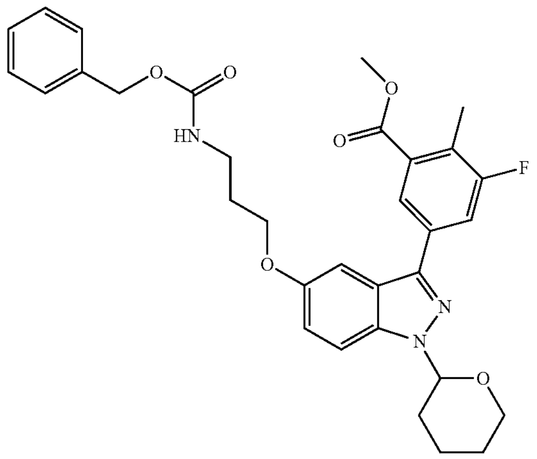 [SMILES: COC(=O)c1cc(-c2nn(C3CCCCO3)c3ccc(OCCCNC(=O)OCc4ccccc4)cc23)cc(F)c1C]

To a solution of benzyl N-(3-{[1-(oxan-2-yl)-3-(tetramethyl-1,3,2-dioxaborolan-2-yl)-1H-indazol-5-yl]oxy}propyl)carbamate 31 (0.6 g, 1.12 mmol) in N,N-dimethylformamide (15 mL) was added at RT (methyl 5-bromo-3-fluoro-2-methylbenzoate (0.332 g, 1.35 mmol), $Cs_2CO_3$ (1.096 g, 3.36 mmol) and $PdCl_2$(dppf)DCM (0.041 g, 0.06 mmol). The resulting mixture was degassed by bubbling nitrogen for 10 minutes and stirred at 110° C. under microwave irradiation for 50 min. The solvent was removed under reduced pressure and the oil was dissolved in EtOAc and water. The two layers were separated and the aqueous phase was extracted twice with ethyl acetate. The combined organic layers were dried over sodium sulfate and the solvent was removed under reduced pressure. The residue was purified by flash-column chromatography (25 g silica BIOTAGE) chromatography (cyclohexane-ethyl acetate, 100/0 to 50/50) affording methyl 5-[5-(3-{[(benzyloxy)carbonyl]amino}propoxy)-1-(oxan-2-yl)-1H-indazol-3-yl]-3-fluoro-2-methylbenzoate 43 as a yellow powder.

LCMS method F: $[M+H]^+$=576.2, $t_R$=3.48 min

Preparation of Intermediate 44: benzyl N-[3-({3-[3-fluoro-5-(hydroxymethyl)-4-methyl phenyl]-1-(oxan-2-yl)-1H-indazol-5-yl}oxy)propyl]carbamate

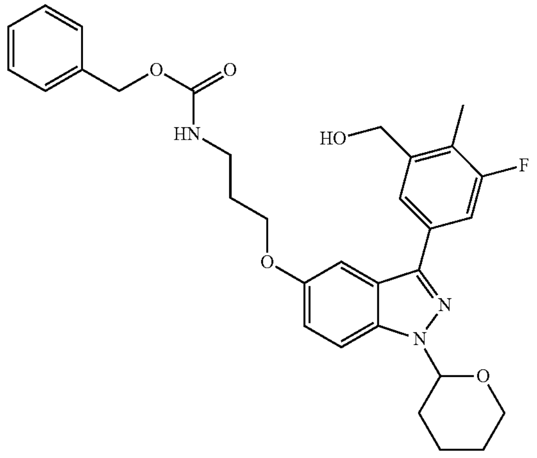 [SMILES: Cc1c(F)cc(-c2nn(C3CCCCO3)c3ccc(OCCCNC(=O)OCc4ccccc4)cc23)cc1CO]

To a methyl 5-[5-(3-{[(benzyloxy)carbonyl]amino}propoxy)-1-(oxan-2-yl)-1H-indazol-3-yl]-3-fluoro-2-methylbenzoate 43 (0.225 g, 0.39 mmol) in THE (50 mL) was added a 1M solution of Lithium aluminium tetrahydride (0.78 mL, 0.78 mmol) at 0° C. The mixture was stirred at 0° C. for 1 hour. To the reaction mixture, EtOAc (10 mL) was added at 0° C. and poured in a 10% solution of Rochelle's salt (100 mL) and EtOAc (100 mL). The mixture was stirred at RT for 2 hours. After separation, the aqueous layer was extracted with EtOAc (2×50 mL). The combined organic layers were washed with brine, dried over sodium sulfate and the solvent was removed under reduced pressure to a brown/orange oil. This residue was purified by flash chromatography on silica gel (Macherey Nagel, 25 g) with gradient elution: cyclohexane/EtOAc 0-100% to give benzyl N-[3-({3-[3-fluoro-5-(hydroxymethyl)-4-methylphenyl]-1-(oxan-2-yl)-1H-indazol-5-yl}oxy)propyl]carbamate 44 as a yellow oil.

LCMS method F: $[M+H]^+$=548.2, $t_R$=3.10 min

Preparation of Intermediate 45: 4-fluoro-5-methyl-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one

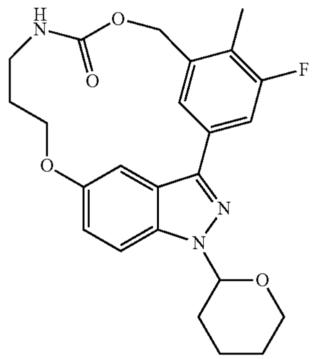 [SMILES: Cc1c(F)cc2cc1COC(=O)NCCCOc1ccc3c(c1)c-2nn3C1CCCCO1]

To a solution of benzyl-N-[3-({3-[3-fluoro-5-(hydroxymethyl)-4-methylphenyl]-1-(oxan-2-yl)-1H-indazol-5-yl}oxy)propyl]carbamate 44 (0.125 g, 0.23 mmol) in anhydrous acetonitrile (33 mL) was added at RT cesium carbonate (0.447 g, 1.37 mmol). The resulting reaction mixture was stirred at 90° C. for 1 h 30. The reaction mixture was filtered, the solvent was removed under reduced pressure and the residue was purified by flash-column (15 g silica Macherey Nagel) chromatography (DCM-ethyl acetate, 1:0 to 8:2) affording 4-fluoro-5-methyl-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one 45 as a white foam.

LCMS method F: $[M+H]^+$=440.2, $t_R$=3.03 min

Preparation of Example 28: 4-fluoro-5-methyl-8,14-dioxa-10,19,20-triazatetracyclo[13.5.2.$1^{2,6}$.$0^{18,21}$]tricosa-1(20),2,4,6(23),15,17,21-heptaen-9-one

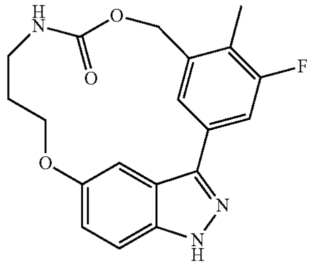 [SMILES: Cc1c(F)cc2cc1COC(=O)NCCCOc1ccc3[nH]nc-2c3c1]

To a solution of 4-fluoro-5-methyl-19-(oxan-2-yl)-8,14-dioxa-10,19,20-triazatetracyclo[13.5.2.$1^{2,6}$.$0^{18,21}$]tricosa-1(20),2,4,6(23),15,17,21-heptaen-9-one 45 (0.066 g, 0.15 mmol) in DCM (3 mL) was added at RT TFA (0.143 mL, 1.92 mmol). The resulting reaction mixture was stirred under microwave irradiation at 80° C. for 1 h 30. The reaction mixture was concentrated under reduced pressure, diluted with saturated sodium bicarbonate solution and extracted twice with ethyl acetate. The combined organic layers were dried over anhydrous sodium sulfate and the solvent was removed under reduced pressure. The residue was purified by flash-column (5 g silica Macherey Nagel) chromatography (DCM-ethyl acetate, 1:0 to 4:6) to give a solid, which was triturated in acetonitrile and filtered affording 4-fluoro-5-methyl-8,14-dioxa-10,19,20-triazatetracyclo[13.5.2.$1^{2,6}$.$0^{18,21}$]tricosa-1(20),2,4,6(23),15,17,21-heptaen-9-one example 28 as a white solid.

LCMS method F: $[M+H]^+$=356.2, $t_R$=2.36 min

LCMS method G: $[M+H]^+$=356.2, $t_R$=2.39 min $^1H$ NMR (400 MHz, d6-DMSO) δ 7.80 (1H, s), 7.67 (1H, s), 7.63 (1H, d, J=11.2 Hz), 7.48 (1H, dd, J=0.6, 9.1 Hz), 7.40 (1H, d, J=2.4 Hz), 6.96 (1H, dd, J=2.3, 8.9 Hz), 5.29 (2H, s), 4.35 (2H, t, J=8.1 Hz), 3.24-3.17 (2H, m), 2.22 (3H, d, J=1.7 Hz), 2.06-2.05 (2H, m) ppm.

The indazole NH proton was not visible in this solvent.

Example 29: 4,5-difluoro-8,14-dioxa-10,19,20-triazatetracyclo[13.5.2.$1^{2,6}$.$0^{18,21}$]tricosa-1(20),2,4,6(23),15,17,21-heptaen-9-one

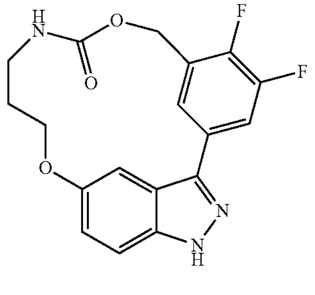 [SMILES: O=C1NCCCOc2ccc3[nH]nc(c3c2)-c2cc(F)c(F)c(c2)CO1]

Example 29 is prepared according to the synthesis route described in general Scheme F and procedures analogous to those used to obtain example 11. Methyl 2,3-difluoro-5-(4,4,5,5-tetramethyl-1,3,2-dioxaborolan-2-yl)benzoate is used for the Suzuki coupling with intermediate 26 to give 4,5-difluoro-8,14-dioxa-10,19,20-triazatetracyclo[13.5.2.$1^{2,6}$.$0^{18,21}$]tricosa-1(20),2,4,6(23),15,17,21-heptaen-9-one example 29.

LCMS method F: $[M+H]^+$=360, $t_R$=2.47 min

LCMS method G: $[M+H]^+$=360, $t_R$=2.52 min $^1H$ NMR (400 MHz, d6-DMSO, 80° C.) δ 13.06 (1H, s), 7.84-7.78 (2H, m), 7.71-7.69 (1H, m), 7.51 (1H, d, J=9.1 Hz), 7.31 (1H, d, J=2.1 Hz), 7.01 (1H, dd, J=2.4, 9.0 Hz), 5.38 (2H, m), 4.34 (2H, dd, J=8.1, 8.8 Hz), 3.18 (2H, m), 2.03 (2H, m) ppm.

Example 30: 5-bromo-8,14-dioxa-10,19,20-triazatetracyclo[13.5.2.$1^{2,6}$.$0^{18,21}$]tricosa-1(20),2,4,6(23),15,17,21-heptaen-9-one

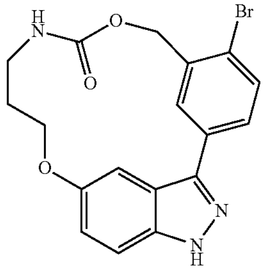 [SMILES: O=C1NCCCOc2ccc3[nH]nc(c3c2)-c2ccc(Br)c(c2)CO1]

Example 30 is prepared according to the synthesis route described in general Scheme C and procedures analogous to those used to obtain example 8.

Preparation of Intermediate 46: [3-bromo-5-(hydroxymethyl)phenyl]boronic acid

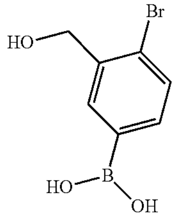 [SMILES: OCc1cc(B(O)O)ccc1Br]

A solution of borane tetrahydrofuran complex (1.0 M in THF, 8.2 mL, 8.2 mmol) was slowly added to a solution of 3-borono-6-bromo-benzoic acid (500 mg, 2.05 mmol) in THE (30 mL) at 0° C. The reaction mixture was allowed to reach room temperature and stirred for 16 hours. MeOH (25 mL) was added at 0° C. to quench the reaction until no gas was produced. The solvent was evaporated, and the residue was partitioned between ethyl acetate (50 mL) and water (50 mL). After separation, the aqueous layer was extracted with ethyl acetate (2×50 mL). The combined organic layers were washed with brine (50 mL), dried over anhydrous sodium magnesium sulfate, filtered and concentrated under reduced pressure to give [3-bromo-5-(hydroxymethyl)phenyl]boronic acid 46 as a white solid.

LCMS method F: no m/z detected, $t_R$=1.58 min

Preparation of Intermediate 47: benzyl N-[3-[3-[4-bromo-3-(hydroxymethyl)phenyl]-1-tetrahydropyran-2-yl-indazol-5-yl]oxypropyl]carbamate

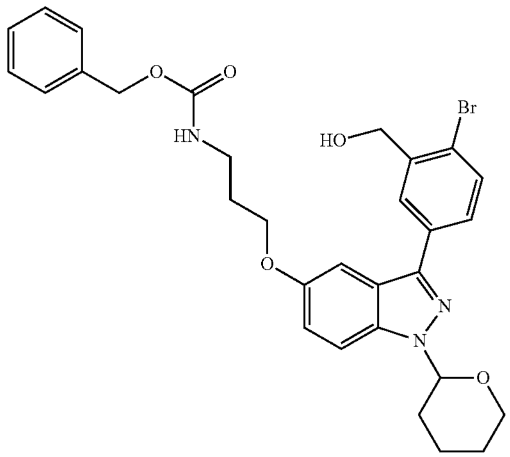 [SMILES: O=C(NCCCOc1ccc2c(c1)c(-c1ccc(Br)c(CO)c1)nn2C1CCCCO1)OCc1ccccc1]

To a solution of benzyl-N-[3-(3-iodo-1-tetrahydropyran-2-yl-indazol-5-yl)oxypropyl]carbamate 26 (692 mg, 1.29 mmol), [4-bromo-3-(hydroxymethyl)phenyl]boronic acid 46 (357 mg, 1.55 mmol) and a 1M solution of $Na_2CO_3$ (3.9 mL, 3.87 mmol) in DME (13 mL) was added palladium-tetrakis(triphenylphosphine) (75 mg, 0.065 mmol, 5 mol %). The reaction mixture was stirred at 80° C. for 16 hours. After being cooled to room temperature, the reaction mixture was diluted with water (20 mL), extracted twice with ethyl acetate (2×50 mL). The combined organic layer was washed with brine, dried over anhydrous sodium sulfate, filtered and concentrated under reduced pressure to afford a yellow solid. The crude was purified by flash chromatography (CyH/EtOAc 0 to 100% EtOAc) with a 24 g Redisep to afford benzyl N-[3-[3-[4-bromo-3-(hydroxymethyl)phenyl]-1-tetrahydropyran-2-yl-indazol-5-yl]oxypropyl]carbamate 47 as a white solid.

LCMS method F: $[M+H]^+$=594, $t_R$=3.12 min

Preparation of Intermediate 48: 5-bromo-19-(oxan-2-yl)-8,14-dioxa-10,19,20-triaza tetracyclo [13.5.2.1$^{2,6}$.0$^{18,21}$]tricosa-1(20),2,4,6(23),15,17,21-heptaen-9-one

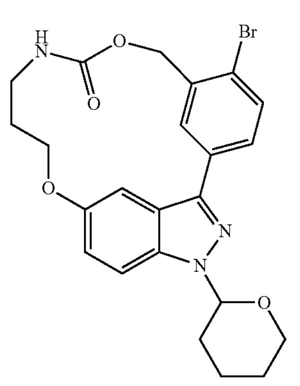 [SMILES: O=C1NCCCOc2ccc3c(c2)c(nn3C2CCCCO2)-c2ccc(Br)c(c2)CO1]

A suspension of benzyl N-[3-[3-[4-bromo-5-(hydroxymethyl)phenyl]-1-tetrahydropyran-2-yl-indazol-5-yl]oxypropyl]carbamate 47 (590 mg, 0.99 mmol) and cesium carbonate (1.94 g, 5.96 mmol) in acetonitrile (200 mL) was heated to 90° C. for 2 h. The reaction mixture was cooled to RT then filtered and concentrated under reduced pressure. The obtained solid was triturated with acetonitrile to give 5-bromo-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one 48 as a white solid.

LCMS method F: $[M+H]^+$=486/488, $t_R$=3.25 min

Preparation of Example 30: 5-bromo-8,14-dioxa-10,19,20-triazatetracyclo[13.5.2.1$^{2,6}$.0$^{18,21}$]tricosa-1(20),2,4,6(23),15,17,21-heptaen-9-one

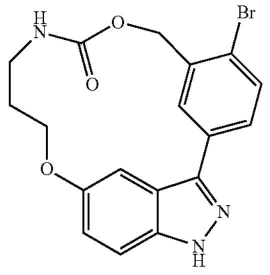 [SMILES: O=C1NCCCOc2ccc3[nH]nc(c3c2)-c2ccc(Br)c(c2)CO1]

To a solution of 5-bromo-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one 48 (50 mg, 0.10 mmol) in DCM (3 mL) was added trifluoroacetic acid (157 μL, 2.05 mmol). The reaction mixture was stirred at RT for 4 h. The reaction mixture was diluted with DCM (20 mL). Water (20 mL) and ammonium hydroxide 25% weight aqueous solution (3 mL) were added. A white precipitate was presented in organic layer, and not soluble in DCM. The solid was filtered and dried under reduced pressure to afford 5-bromo-8,14-dioxa-10,19,20-triazatetracyclo[13.5.2.1$^{2,6}$.0$^{18,21}$]tricosa-1(20),2,4,6(23),15,17,21-heptaen-9-one example 30 as a white solid.

LCMS method F: $[M+H]^+$=403, $t_R$=2.58 min

LCMS method G: $[M+H]^+$=403, $t_R$=2.48 min $^1$H NMR (400 MHz, d6-DMSO) δ 13.05 (1H, s), 7.91-7.87 (3H, m), 7.73-7.69 (1H, m), 7.52-7.49 (1H, m), 7.37 (1H, d, J=1.7 Hz), 7.01 (1H, dd, J=2.3, 8.9 Hz), 5.27 (2H, s), 4.37-4.33 (2H, m), 3.19 (2H, m), 2.02-1.99 (2H, m) ppm.

Example 31: 4-(4-methylpiperazin-1-yl)-8,14-dioxa-10,19,20-triazatetracyclo[13.5.2.1$^{2,6}$.0$^{18,21}$]tricosa-1(20),2,4,6(23),15,17,21-heptaen-9-one

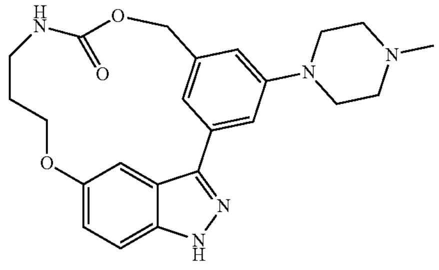 [SMILES: CN1CCN(c2cc3cc(c2)-c2n[nH]c4ccc(cc24)OCCCNC(=O)OC3)CC1]

Example 31 is prepared according to the synthesis route described in general Scheme C and procedures analogous to those used to obtain example 12. 1-Methylpiperazine is used for the Buchwald reaction with the bromide intermediate 34 to give 4-(4-methylpiperazin-1-yl)-8,14-dioxa-10,19,20-triazatetracyclo[13.5.2.$1^{2,6}$.$0^{18,21}$]tricosa-1(20),2,4,6(23),15,17,21-heptaen-9-one example 31.

LCMS method F: $[M+H]^+$=422, $t_R$=1.44 min

LCMS method G: $[M+H]^+$=422, $t_R$=2.02 min $^1$H NMR (400 MHz, d6-DMSO) δ 12.80 (1H, s), 7.62 (1H, m), 7.46 (1H, d, J=9.2 Hz), 7.38 (1H, m), 7.35 (2H, m), 6.98-6.95 (1H, m), 6.88 (1H, m), 5.23 (2H, m), 4.32-4.28 (2H, m), 3.25 (4H, m), 3.16 (2H, m), 2.53 (4H, m), 2.28 (3H, s), 2.04 (2H, m) ppm.

Example 32: 4-(3-methoxyazetidin-1-yl)-8,14-dioxa-10,19,20-triazatetracyclo[13.5.2.$1^{2,6}$.$0^{18,21}$]tricosa-1(20),2,4,6(23),15,17,21-heptaen-9-one

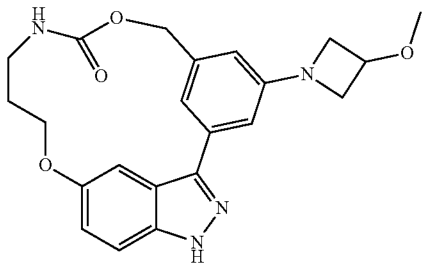 [SMILES: COC1CN(c2cc3cc(c2)-c2n[nH]c4ccc(cc24)OCCCNC(=O)OC3)C1]

Example 32 is prepared according to the synthesis route described in general Scheme C and procedures analogous to those used to obtain example 12. 3-methoxyazetidine hydrochloride is used for the Buchwald reaction with the bromide intermediate 34 to give 4-(3-methoxyazetidin-1-yl)-8,14-dioxa-10,19,20-triazatetracyclo[13.5.2.$1^{2,6}$.$0^{18,21}$]tricosa-1(20),2,4,6(23),15,17,21-heptaen-9-one example 32.

LCMS method F: $[M+H]^+$=409.2, $t_R$=2.15 min

LCMS method G: $[M+H]^+$=409.1, $t_R$=2.13 min $^1$H NMR (400 MHz, d6-DMSO, 80° C.) δ 12.85 (1H, br s), 7.61 (1H, br s), 7.48-7.45 (1H, m), 7.36-7.34 (1H, m), 7.27 (1H, s), 6.95 (1H, dd, J=2.4, 9.2 Hz), 6.90 (1H, t, J=2.0 Hz), 6.37 (1H, dd, J=1.5, 2.1 Hz), 5.20 (2H, s), 4.40-4.27 (3H, m), 4.15-4.11 (2H, m), 3.69 (2H, dd, J=4.3, 8.6 Hz), 3.30 (3H, s), 3.22-3.12 (2H, m), 2.09-1.96 (2H, m) ppm.

Example 33: 1-{9-oxo-8,14-dioxa-10,19,20-triazatetracyclo[13.5.2.$1^{2,6}$.$0^{18,21}$]tricosa-1(20),2,4,6(23),15,17,21-heptaen-4-yl}piperidine-4-carbonitrile

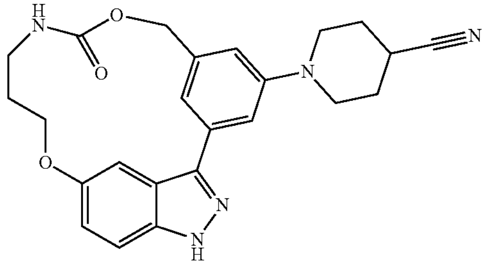 [SMILES: N#CC1CCN(c2cc3cc(c2)-c2n[nH]c4ccc(cc24)OCCCNC(=O)OC3)CC1]

Example 33 is prepared according to the synthesis route described in general Scheme C and procedures analogous to those used to obtain example 12. Piperidine-4-carbonitrile is used for the Buchwald reaction with the bromide intermediate 34 to give 1-{9-oxo-8,14-dioxa-10,19,20-triazatetracyclo[13.5.2.$1^{2,6}$.$0^{18,21}$]tricosa-1(20),2,4,6(23),15,17,21-heptaen-4-yl}piperidine-4-carbonitrile example 33.

LCMS method F: $[M+H]^+$=432, $t_R$=2.15 min

LCMS method G: $[M+H]^+$=432, $t_R$=2.21 min $^1$H NMR (400 MHz, d6-DMSO) δ 12.82 (1H, s), 7.63 (1H, m), 7.48-7.46 (1H, m), 7.40-7.35 (3H, m), 7.98-7.95 (1H, m), 7.90 (1H, m), 5.23 (2H, m), 4.30 (2H, m), 3.50-3.44 (2H, m), 3.22-3.15 (4H, m), 2.08-2.00 (4H, m), 1.92-1.84 (2H, m), 1.07 (1H, d, J=5.9 Hz) ppm.

Example 34: 4-[4-(pyrrolidin-1-yl)piperidin-1-yl]-8,14-dioxa-10,19,20-triazatetracyclo[13.5.2.$1^{2,6}$.$0^{18,21}$]tricosa-1(20),2,4,6(23),15,17,21-heptaen-9-one

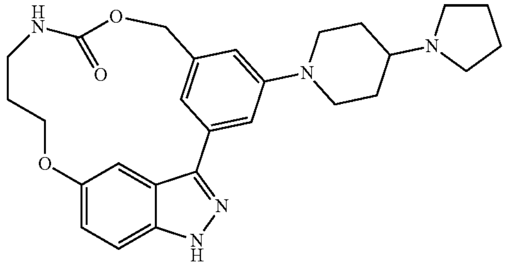 [SMILES: O=C1NCCCOc2ccc3[nH]nc(c3c2)-c2cc(cc(N3CCC(N4CCCC4)CC3)c2)CO1]

Example 34 is prepared according to the synthesis route described in general Scheme C and procedures analogous to those used to obtain example 12. 4-Pyrrolidin-1-ylpiperidine is used for the Buchwald reaction with the bromide intermediate 34 to give 4-[4-(pyrrolidin-1-yl)piperidin-1-yl]-8,14-dioxa-10,19,20-triazatetracyclo[13.5.2.$1^{2,6}$.$0^{18,21}$]tricosa-1(20),2,4, 6(23),15,17,21-heptaen-9-one example 34.

LCMS method F: $[M+H]^+$=476, $t_R$=1.59 min

LCMS method G: $[M+H]^+$=476, $t_R$=1.51 min $^1$H NMR (400 MHz, DMSO) δ 12.85 (1H, m), 7.47 (1H, d, J=8.7 Hz), 7.37 (3H, t, J=13.0 Hz), 6.98-6.92 (2H, m), 5.28 (2H, m), 4.30 (2H, s), 3.85 (2H, m), 3.42 (1H, q, J=7.0 Hz), 3.18 (3H, s), 2.88-2.82 (2H, m), 2.14 (2H, s), 2.04 (10H, m) ppm. Two protons were located under the DMSO peak and are not reported here.

Example 35: 4-(azetidin-1-yl)-8,14-dioxa-10,19,20-triazatetracyclo[13.5.2.$1^{2,6}$.$0^{18,21}$]tricosa-1(20),2,4,6(23),15,17,21-heptaen-9-one

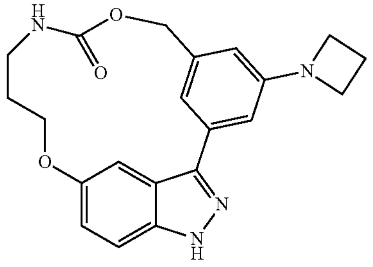 [SMILES: O=C1NCCCOc2ccc3[nH]nc(c3c2)-c2cc(cc(N3CCC3)c2)CO1]

Example 35 is prepared according to the synthesis route described in general Scheme C and procedures analogous to those used to obtain example 12. Azetidine is used for the Buchwald reaction with the bromide intermediate 34 to give 4-(azetidin-1-yl)-8,14-dioxa-10,19,20-triazatetracyclo$[13.5.2.1^{2,6}.0^{18,21}]$tricosa-1(20),2,4,6(23),15,17,21-heptaen-9-one example 35.

LCMS method F: $[M+H]^+$=379, $t_R$=2.08 min

LCMS method G: $[M+H]^+$=379, $t_R$=2.23 min $^1H$ NMR (400 MHz, d6-DMSO) δ 12.78 (1H, m), 7.59 (1H, m), 7.48-7.44 (1H, m), 7.35 (1H, s), 7.25 (1H, s), 6.98-6.94 (1H, m), 6.88-6.87 (1H, m), 6.34 (1H, s), 5.20 (2H, s), 4.32-4.27 (2H, m), 3.90 (3H, t, J=7.2 Hz), 3.15 (3H, m), 2.39-2.32 (2H, m), 2.06 (2H, s) ppm.

Example 36: 4-(piperidin-1-yl)-8,14-dioxa-10,19,20-triazatetracyclo$[13.5.2.1^{2,6}.0^{18,21}]$tricosa-1(20),2,4,6(23),15,17,21-heptaen-9-one

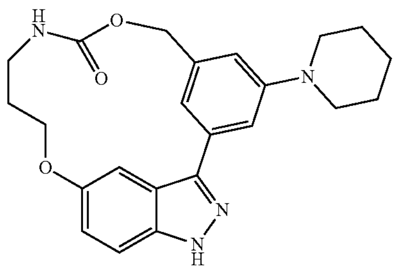 [SMILES: O=C1NCCCOc2ccc3[nH]nc(c3c2)-c2cc(cc(N3CCCCC3)c2)CO1]

Example 36 is prepared according to the synthesis route described in general Scheme A.

Piperidine is used for the Buchwald reaction with the bromide intermediate 34 to give 4-(piperidin-1-yl)-8,14-dioxa-10,19,20-triazatetracyclo$[13.5.2.1^{2,6}.0^{18,21}]$tricosa-1(20),2,4,6(23), 15,17,21-heptaen-9-one example 36.

LCMS method F: $[M+H]^+$=407.2, $t_R$=1.65 min

LCMS method G: $[M+H]^+$=407.2, $t_R$=2.48 min $^1H$ NMR (400 MHz, d6-DMSO, 80° C.) δ 12.79 (1H, s), 7.64-7.62 (1H, m), 7.48-7.44 (1H, d, J=8.4 Hz), 7.38-7.32 (3H, m), 6.96 (1H, dd, J=2.3, 9.1 Hz), 6.87-6.86 (1H, m), 5.22 (2H, s), 4.30 (2H, dd, J=7.6, 10.0 Hz), 3.27-3.21 (4H, m), 3.20-3.11 (2H, m), 2.06-1.97 (2H, m), 1.71-1.64 (4H, m), 1.63-1.58 (2H, m) ppm.

Example 37: 4-(2,5-dihydrofuran-3-yl)-8,14-dioxa-10,19,20-triazatetracyclo$[13.5.2.1^{2,6}.0^{18,21}]$tricosa-1(20),2,4,6(23),15,17,21-heptaen-9-one

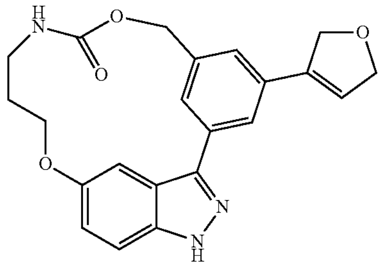 [SMILES: O=C1NCCCOc2ccc3[nH]nc(c3c2)-c2cc(cc(C3=CCOC3)c2)CO1]

Example 37 is prepared according to the synthesis route described in general Scheme A. 2-(2,5-Dihydrofuran-3-yl)-4,4,5,5-tetramethyl-1,3,2-dioxaborolane is used for the Suzuki reaction with the bromide intermediate 34 to give 4-(2,5-dihydrofuran-3-yl)-8,14-dioxa-10,19,20-triazatetracyclo$[13.5.2.1^{2,6}.0^{18,21}]$tricosa-1(20),2,4,6(23),15,17,21-heptaen-9-one example 37.

LCMS method F: $[M+H]^+$=392.2, $t_R$=2.19 min

LCMS method G: $[M+H]^+$=392.2, $t_R$=2.19 min $^1H$ NMR (400 MHz, d6-DMSO, 80° C.) δ 12.94 (1H, s), 7.85 (2H, d, J=6.3 Hz), 7.69 (1H, s), 7.50 (1H, d, J=9.6 Hz), 7.37 (1H, s), 7.33 (1H, d, J=2.0 Hz), 6.99 (1H, dd, J=2.3, 8.9 Hz), 6.55-6.52 (1H, m), 5.33-5.30 (2H, m), 5.00-4.96 (2H, m), 4.80-4.77 (2H, m), 4.35-4.29 (2H, m), 3.19-3.17 (2H, m), 1.99 (2H, s) ppm.

Example 38: 4-[4-(morpholin-4-yl)piperidin-1-yl]-8,14-dioxa-10,19,20-triazatetracyclo$[13.5.2.1^{2,6}.0^{18,21}]$tricosa-1(20),2,4,6(23),15,17,21-heptaen-9-one

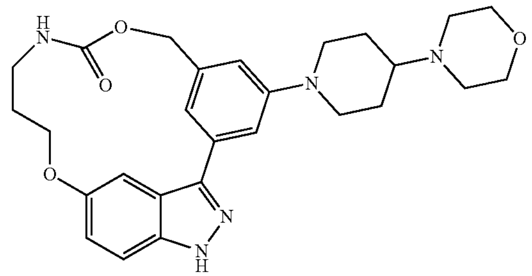 [SMILES: O=C1NCCCOc2ccc3[nH]nc(c3c2)-c2cc(cc(N3CCC(N4CCOCC4)CC3)c2)CO1]

Example 38 is prepared according to the synthesis route described in general Scheme C and procedures analogous to those used to obtain example 12. 4-(4-Piperidyl)morpholine is used for the Buchwald reaction with the bromide intermediate 34 to give 4-[4-(morpholin-4-yl)piperidin-1-yl]-8,14-dioxa-10,19,20-triazatetracyclo$[13.5.2.1^{2,6}.0^{18,21}]$tricosa-1(20),2,4, 6(23),15,17,21-heptaen-9-one example 38.

LCMS method F: $[M+H]^+$=492.2, $t_R$=1.48 min

LCMS method G: $[M+H]^+$=492.2, $t_R$=2.07 min $^1H$ NMR (400 MHz, d6-DMSO) δ 12.79 (1H, s), 7.61 (1H, s), 7.47 (1H, d, J=5.8 Hz), 7.39-7.29 (3H, m), 6.97 (1H, dd, J=2.2, 9.1 Hz), 6.89 (1H, s), 5.22 (2H, s), 4.36-4.26 (2H, m), 3.87-3.75 (2H, m), 3.64-3.54 (4H, m), 3.23-3.12 (2H, m), 2.88-2.76 (2H, m), 2.57-2.52 (4H, m), 2.41-2.29 (1H, m), 2.09-1.88 (4H, m), 1.63-1.5 (2H, m) ppm.

Example 39: 4-(1-methyl-1,2,3,6-tetrahydropyridin-4-yl)-8,14-dioxa-10,19,20-triazatetra cyclo$[13.5.2.1^{2,6}.0^{18,21}]$tricosa-1(20),2,4,6(23),15,17,21-heptaen-9-one

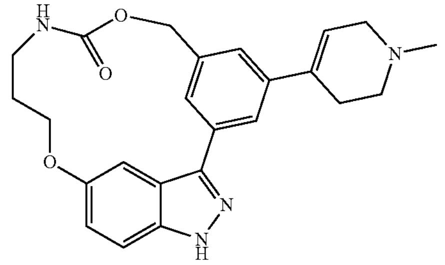 [SMILES: CN1CC=C(c2cc3cc(c2)-c2n[nH]c4ccc(cc24)OCCCNC(=O)OC3)CC1]

Example 39 is prepared according to the synthesis route described in general Scheme A. 1-methyl-4-(4,4,5,5-tetramethyl-1,3,2-dioxaborolan-2-yl)-3,6-dihydro-2H-pyridine is used for the Suzuki reaction with the bromide intermediate 34 to give 4-(1-methyl-1,2,3,6-tetrahydropyridin-4-yl)-8,14-dioxa-10,19,20-triazatetracyclo[13.5.2.$1^{2,6}$.$0^{18,21}$]tricosa-1(20),2,4,6(23),15,17,21-heptaen-9-one example 39.

LCMS method F: $[M+H]^+$=419.2, $t_R$=1.49 min

LCMS method G: $[M+H]^+$=419.2, $t_R$=2.16 min $^1$H NMR (400 MHz, d6-DMSO, 80° C.) δ 12.95 (1H, s), 7.97 (1H, s), 7.87 (1H, s), 7.71-7.69 (1H, m), 7.50 (1H, d, J=8.0 Hz), 7.40 (1H, s), 7.34 (1H, d, J=1.5 Hz), 7.00 (1H, dd, J=2.3, 8.9 Hz), 6.28-6.25 (1H, m), 5.35-5.32 (2H, m), 4.32 (2H, dd, J=8.1, 9.0 Hz), 3.94-3.91 (2H, m), 3.55-3.41 (2H, m), 3.25-3.17 (2H, m), 2.92 (3H, s), 2.90-2.84 (2H, m), 2.10-1.99 (2H, m) ppm.

Example 40: 4-[(2S,5S)-2,5-dimethylmorpholin-4-yl]-8,14-dioxa-10,19,20-triazatetracyclo[13.5.2.$1^{2,6}$.$0^{18,21}$]tricosa-1(20),2,4,6(23),15,17,21-heptaen-9-one

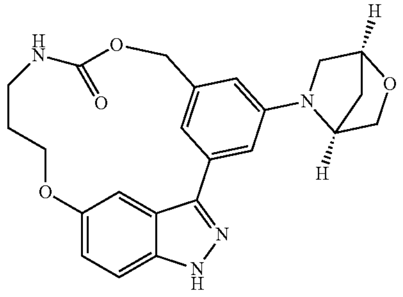 [SMILES: O=C1NCCCOc2ccc3[nH]nc(c3c2)-c2cc(cc(N3C[C@@H]4C[C@H]3CO4)c2)CO1]

Example 40 is prepared according to the synthesis route described in general Scheme C and procedures analogous to those used to obtain example 12. (1S,4S)-2-Oxa-5-azabicyclo[2.2.1]heptane hydrochloride is used for the Buchwald reaction with the bromide intermediate 34 to give 4-[(2S,5S)-2,5-dimethylmorpholin-4-yl]-8,14-dioxa-10,19,20-triazatetracyclo[13.5.2.$1^{2,6}$.$0^{18,21}$]tricosa-1(20),2,4,6(23),15,17,21-heptaen-9-one example 40.

LCMS method F: $[M+H]^+$=421.1, $t_R$=2.06 min

LCMS method G: $[M+H]^+$=421.2, $t_R$=2.06 min $^1$H NMR (400 MHz, d6-DMSO) δ 12.78 (1H, s), 7.62 (1H, m), 7.46 (1H, d, J=9.1 Hz), 7.36 (1H, s), 7.23 (1H, s), 7.06 (1H, s), 6.97-6.95 (1H, m), 6.58 (1H, s), 5.21 (2H, m), 4.63 (2H, d, J=17.5 Hz), 4.32-4.28 (2H, m), 3.82 (1H, m), 3.76 (1H, m), 3.58-3.56 (1H, m), 3.16 (2H, m), 3.10 (1H, m), 2.03 (2H, m), 1.98-1.95 (1H, m), 1.90-1.88 (1H, m) ppm.

Example 41: 4-[(morpholin-4-yl)methyl]-8,14-dioxa-10,19,20-triazatetracyclo[13.5.2.$1^{2,6}$.$0^{18,21}$]tricosa-1(20),2,4,6(23),15,17,21-heptaen-9-one

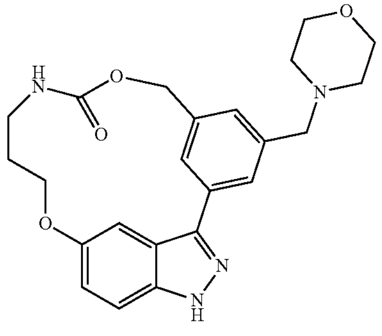 [SMILES: O=C1NCCCOc2ccc3[nH]nc(c3c2)-c2cc(cc(CN3CCOCC3)c2)CO1]

Example 41 is prepared according to the synthesis route described in general Scheme C.

Preparation of Intermediate 49: 4-[(morpholin-4-yl)methyl]-19-(oxan-2-yl)-8,14-dioxa-10,19,20-triazatetracyclo[13.5.2.$1^{2,6}$.$0^{18,21}$]tricosa-1(20),2,4,6(23),15,17,21-heptaen-9-one

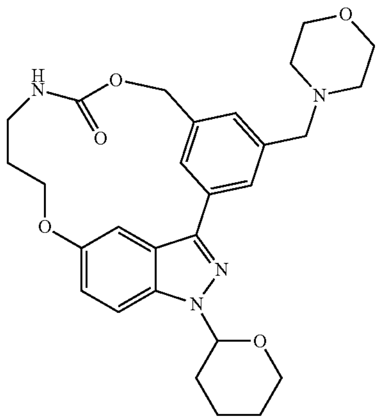 [SMILES: O=C1NCCCOc2ccc3c(c2)c(nn3C2CCCCO2)-c2cc(cc(CN3CCOCC3)c2)CO1]

In a sealed tube, to a solution of 4-bromo-19-(oxan-2-yl)-8,14-dioxa-10,19,20 triazatetracyclo[13.5.2.$1^{2,6}$.$0^{18,21}$]tricosa-1(20),2(23),3,5,15(22),16,18(21)-heptaen-9-one example 12 (100 mg, 0.21 mmol) in THF/H2O 9/1 (4 mL) was added potassium 1-trifluoroboratomethylmorpholine (87 mg, 0.42 mmol) and cesium carbonate (205 mg, 0.63 mmol) at RT. The reaction mixture was degassed for 15 min by bubbling nitrogen gas through the solution, then palladium acetate (2 mg, 0.01 mmol) and Xphos (10 mg, 0.02 mmol) were added and the reaction mixture was stirred at 100° C. for 18 hours. The reaction mixture was allowed to cool to RT and the solvent was removed under reduced pressure. EtOAc (50 mL) was added to the residue and the suspension was filtered over celite. The filtrate was extracted with EtOAc (2×20 mL), washed with brine, dried over sodium sulfate and the solvent was removed under reduced pressure to afford a yellow oil. The oil was triturated with acetonitrile and diethyl ether to afford 4-[(morpholin-4-yl)methyl]-19-(oxan-2-yl)-8,14-dioxa-10,19,20-triazatetracyclo[13.5.2.$1^{2,6}$.$0^{18,21}$]tricosa-1(20),2,4,6(23),15,17,21-heptaen-9-one 49 as a beige powder.

LCMS method F: $[M+H]^+$=507, $t_R$=1.74 min

Preparation of Example 41: 4-[(morpholin-4-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one

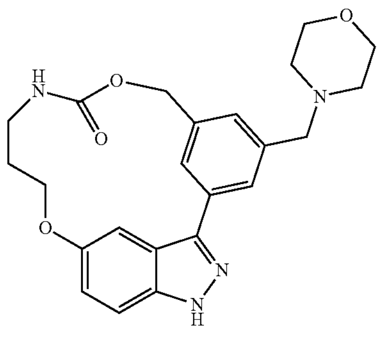 [SMILES: O=C1NCCCOc2ccc3[nH]nc(c3c2)-c2cc(cc(CN3CCOCC3)c2)CO1]

To a solution of 4-[(morpholin-4-yl)methyl]-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one 49 (60 mg, 0.13 mmol) in DCM (2 mL) was stirred at RT for 6 hours. The reaction mixture was evaporated under reduced pressure to give a brown oil. dDCM (20 mL) and a saturated solution of bicarbonate (10 mL) was added to the residue, after separation, the organic layer was extracted with DCM (2×10 mL), washed with brine, dried over sodium sulfate and evaporated under reduced pressure to give an yellow oil. Some acetonitrile and diethyl ether was added to the oil, the precipitate formed was filtered to afford 4-[(morpholin-4-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one example 41 as a beige solid.

LCMS method F: $[M+H]^+=423$, $t_R=1.42$ min

LCMS method G: $[M+H]^+=423$, $t_R=2.03$ min

1H NMR (400 MHz, DMSO) δ 12.89 (1H, s), 7.81 (2H, d, J=11.8 Hz), 7.66 (1H, s), 7.50-7.47 (1H, m), 7.35 (1H, d, J=1.9 Hz), 7.22 (1H, s), 6.98 (1H, dd, J=2.4, 9.0 Hz), 5.29-5.26 (2H, m), 4.34-4.28 (2H, m), 3.63 (4H, m), 3.56 (2H, s), 3.18 (2H, s), 2.46 (4H, m), 2.06-2.03 (2H, m) ppm.

Example 42: 4-[(pyrrolidin-1-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one

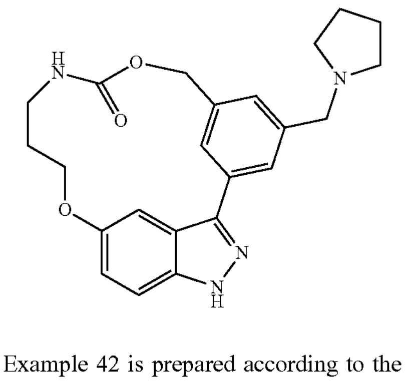

Example 42 is prepared according to the synthesis route described in general Scheme C and procedures analogous to those used to obtain example 41. Potassium trifluoro[(pyrrolidin-1-yl)methyl]borate was used for the Suzuki coupling with the bromide intermediate 34 to give 4-[(pyrrolidin-1-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one example 42.

LCMS method F: $[M+H]^+=407$, $t_R=1.44$ min

LCMS method G: $[M+H]^+=407$, $t_R=2.12$ min $^1$H NMR (400 MHz, d6-DMSO) δ 12.88 (1H, s), 7.84 (1H, s), 7.79 (1H, s), 7.66 (1H, m), 7.48 (1H, d, J=8.8 Hz), 7.35 (1H, d, J=1.7 Hz), 7.22 (1H, s), 6.98 (1H, dd, J=2.3, 8.9 Hz), 5.28 (2H, s), 4.32 (2H, dd, J=8.1, 8.6 Hz), 3.69 (2H, s), 3.17 (2H, m), 2.54 (4H, m), 2.03 (2H, m), 1.75 (4H, m) ppm.

Example 43: 4-[(pyrrolidin-1-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one

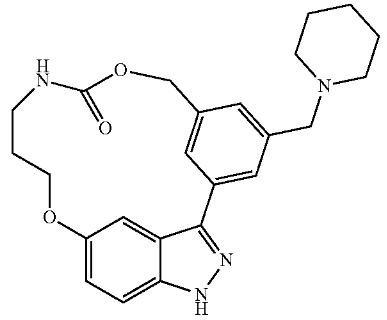 [SMILES: O=C1NCCCOc2ccc3[nH]nc(c3c2)-c2cc(cc(CN3CCCCC3)c2)CO1]

Example 43 is prepared according to the synthesis route described in general Scheme C and procedures analogous to those used to obtain example 41. Potassium trifluoro[(piperidin-1-yl)methyl]borate was used for the Suzuki coupling with the bromide intermediate 34 to give 4-[(pyrrolidin-1-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one example 43.

LCMS method F: $[M+H]^+=421$, $t_R=1.49$ min

LCMS method G: $[M+H]^+=421$, $t_R=2.33$ min $^1$H NMR (400 MHz, d6-DMSO, 80° C.) δ 12.86 (1H, s), 7.86 (2H, m), 7.59 (1H, m), 7.48 (1H, d, J=8.4 Hz), 7.37 (1H, d, J=2.1 Hz), 7.25 (1H, m), 6.99 (1H, dd, J=2.3, 8.9 Hz), 5.30 (2H, s), 4.32 (2H, m), 3.19 (2H, m), 2.05 (2H, m), 1.62 (4H, m), 1.48 (2H, m) ppm. Some protons are not visible due to different conformations. Structure confirmed by COSY.

Example 44: 4-[(4-methylpiperazin-1-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one

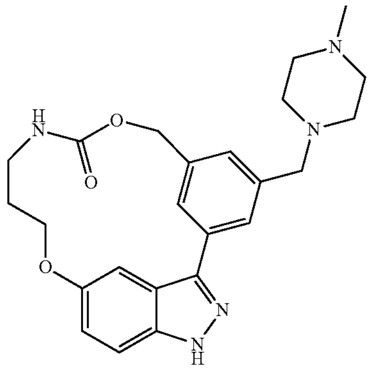 [SMILES: CN1CCN(Cc2cc3cc(c2)-c2n[nH]c4ccc(cc24)OCCCNC(=O)OC3)CC1]

Example 44 is prepared according to the synthesis route described in general Scheme C and procedures analogous to those used to obtain example 41. Potassium trifluoro[(4-methylpiperazin-1-yl)methyl]borate was used for the Suzuki coupling with the bromide intermediate 34 to give 4-[(4-methylpiperazin-1-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one example 44.

LCMS method F: $[M+H]^+$=436, $t_R$=1.36 min (current 20V)

LCMS method G: $[M+H]^+$=436, $t_R$=1.95 min (pH10 current 20V)

$^1$H NMR (400 MHz, d6-DMSO, 80° C.) δ 12.89 (1H, s), 7.81 (1H, s), 7.79 (1H, s), 7.66 (1H, m), 7.48 (1H, d, J=8.8 Hz), 7.35 (1H, m), 7.20 (1H, m), 6.98 (1H, dd, J=2.3, 9.1 Hz), 5.28 (2H, s), 4.31 (2H, m), 3.55 (2H, s), 3.17 (2H, m), 2.46-2.37 (8H, m), 2.20 (3H, s), 2.04 (2H, m) ppm.

Example 45: 5-(morpholin-4-yl)-8,14-dioxa-10,19,20-triazatetracyclo[13.5.2.1$^{2,6}$.0$^{18,21}$]tricosa-1(20),2,4,6(23),15,17,21-heptaen-9-one

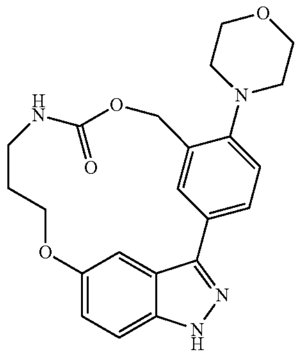 [SMILES: O=C1NCCCOc2ccc3[nH]nc(c3c2)-c2ccc(N3CCOCC3)c(c2)CO1]

Example 45 is prepared according to the synthesis route described in general Scheme C. Morpholine was used for the Buchwald coupling with the bromide intermediate 48 to give 5-(morpholin-4-yl)-8,14-dioxa-10,19,20-triazatetracyclo[13.5.2.1$^{2,6}$.0$^{18,21}$]tricosa-1(20),2,4, 6(23),15,17,21-heptaen-9-one example 45.

LCMS method F: $[M+H]^+$=409, $t_R$=2.17 min

LCMS method G: $[M+H]^+$=409, $t_R$=2.16 min $^1$H NMR (400 MHz, d6-DMSO) δ 12.80 (1H, s), 7.89-7.86 (2H, m), 7.68 (1H, s), 7.49-7.45 (1H, m), 7.35 (1H, d, J=1.3 Hz), 7.29-7.25 (1H, m), 6.97 (1H, dd, J=2.3, 8.9 Hz), 5.37 (2H, s), 4.31 (2H, dd, J=8.3, 8.6 Hz), 3.78 (4H, m), 3.17 (2H, s), 2.91 (4H, m), 2.05 (2H, s) ppm.

Example 46: 4-[4-(2-methoxyethyl)piperazin-1-yl]-8,14-dioxa-10,19,20-triazatetracyclo[13.5.2.1$^{2,6}$.0$^{18,21}$]tricosa-1(20),2,4,6(23),15,17,21-heptaen-9-one

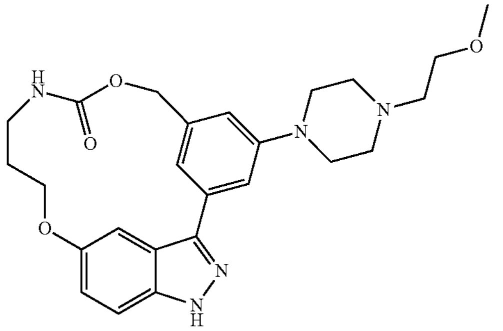 [SMILES: COCCN1CCN(c2cc3cc(c2)-c2n[nH]c4ccc(cc24)OCCCNC(=O)OC3)CC1]

Example 46 is prepared according to the synthesis route described in general Scheme A. 1-(2-methoxyethyl)piperazine is used for the Buchwald reaction with the bromide intermediate 34 to give 4-[4-(2-methoxyethyl)piperazin-1-yl]-8,14-dioxa-10,19,20-triazatetracyclo[13.5.2.1$^{2,6}$.0$^{18,21}$]tricosa-1(20),2,4,6(23),15,17,21-heptaen-9-one example 46.

LCMS method F: $[M+H]^+$=466.2, $t_R$=1.48 min

LCMS method G: $[M+H]^+$=466.2, $t_R$=2.06 min $^1$H NMR (400 MHz, d6-DMSO, 80° C.) δ 12.83 (1H, s), 7.64 (1H, s), 7.49-7.46 (1H, m), 7.40 (2H, s), 7.34 (1H, s), 6.99-6.91 (2H, m), 5.24 (2H, s), 4.33-4.27 (2H, m), 3.67-3.63 (2H, m), 3.17-3.08 (15H, m), 2.10-1.99 (2H, m) ppm.

Example 47: 4-(diethylamino)-8,14-dioxa-10,19,20-triazatetracyclo[13.5.2.1$^{2,6}$.0$^{18,21}$]tricosa-1(20),2,4,6(23),15,17,21-heptaen-9-one

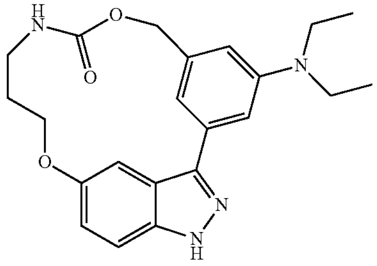 [SMILES: CCN(CC)c1cc2cc(c1)-c1n[nH]c3ccc(cc13)OCCCNC(=O)OC2]

Example 47 is prepared according to the synthesis route described in general Scheme A. Diethylamine is used for the Buchwald reaction with the bromide intermediate 34 to give 4-(diethylamino)-8,14-dioxa-10,19,20-triazatetracyclo[13.5.2.1$^{2,6}$.0$^{18,21}$]tricosa-1(20),2,4, 6(23),15,17,21-heptaen-9-one example 47.

LCMS method F: $[M+H]^+$=395.2, $t_R$=1.57 min

LCMS method G: $[M+H]^+$=395.2, $t_R$=2.48 min $^1$H NMR (400 MHz, d6-DMSO, 80° C.) δ 12.73 (1H, br s), 7.59 (1H, br s), 7.46 (1H, d, J=9.3 Hz), 7.36 (1H, d, J=2.1 Hz), 7.18-7.16 (2H, m), 6.95 (1H, dd, J=2.4, 8.8 Hz), 6.63

(1H, s), 5.21-5.20 (2H, m), 4.32-4.27 (2H, m), 3.42 (4H, q, J=7.0 Hz), 3.21-3.10 (2H, m), 2.08-1.96 (2H, m), 1.17 (6H, t, J=6.9 Hz) ppm.

Example 48: 4-cyclopropyl-8,14-dioxa-10,19,20-triazatetracyclo[13.5.2.1$^{2,6}$.0$^{18,21}$]tricosa-1(20),2,4,6(23),15,17,21-heptaen-9-one

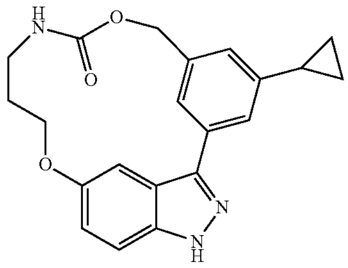 [SMILES: O=C1NCCCOc2ccc3[nH]nc(c3c2)-c2cc(cc(C3CC3)c2)CO1]

Example 48 is prepared according to the synthesis route described in general Scheme C. Potassium trifluoro[cyclopropyl]borate was used for the Suzuki coupling with the bromide intermediate 34 to give 4-cyclopropyl-8,14-dioxa-10,19,20-triazatetracyclo[13.5.2.1$^{2,6}$.0$^{18,21}$]tricosa-1(20),2,4,6(23),15,17,21-heptaen-9-one example 48.

LCMS method F: $[M+H]^+$=364, $t_R$=2.40 min

LCMS method G: $[M+H]^+$=364, $t_R$=2.39 min $^1$H NMR (400 MHz, d6-DMSO, 80° C.) δ 12.87 (1H, s), 7.68 (1H, s), 7.64 (1H, m), 7.60 (1H, s), 7.47 (1H, d, J=9.1 Hz), 7.33 (1H, d, J=2.1 Hz), 6.99 (1H, s), 6.97 (1H, dd, J=9.0, 2.3 Hz), 5.24 (2H, m), 4.30 (2H, m), 3.17 (2H, m), 2.03 (3H, m), 1.00 (2H, m), 0.74 (2H, m) ppm.

Example 49: 5-(4-methylpiperazin-1-yl)-8,14-dioxa-10,19,20-triazatetracyclo[13.5.2.1$^{2,6}$.0$^{18,21}$]tricosa-1(20),2,4,6(23),15,17,21-heptaen-9-one

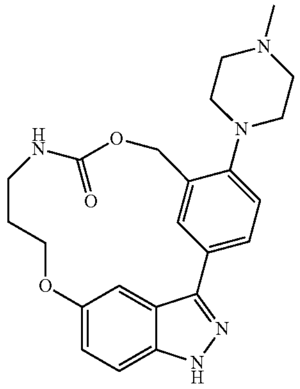 [SMILES: CN1CCN(c2ccc3cc2COC(=O)NCCCOc2ccc4[nH]nc-3c4c2)CC1]

Example 49 is prepared according to the synthesis route described in general Scheme C. 4-Methylpiperazine was used for the Buchwald coupling with the bromide intermediate 48 to give 5-(4-methylpiperazin-1-yl)-8,14-dioxa-10,19,20-triazatetracyclo[13.5.2.1$^{2,6}$.0$^{18,21}$]tricosa-1(20),2,4,6(23),15,17,21-heptaen-9-one example 49.

LCMS method F: $[M+H]^+$=422, $t_R$=1.44 min

LCMS method G: $[M+H]^+$=422, $t_R$=2.13 min $^1$H NMR (400 MHz, $CD_3OD$) δ 8.01-7.99 (1H, m), 7.92 (1H, dd, J=2.1, 8.4 Hz), 7.79 (1H, t, J=6.1 Hz), 7.49-7.34 (4H, m), 7.04 (1H, dd, J=2.3, 9.1 Hz), 5.51-5.47 (2H, m), 4.36 (2H, m), 3.74-3.63 (2H, m), 3.42 (4H, m), 3.21 (4H, m), 3.03 (3H, s), 2.12 (2H, m) ppm.

Example 50: 13-methyl-8,14-dioxa-10,19,20-triazatetracyclo[13.5.2.1$^{2,6}$.0$^{18,21}$]tricosa-1(20),2,4,6(23),15,17,21-heptaen-9-one

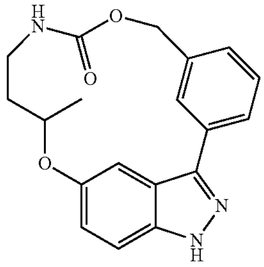 [SMILES: CC1CCNC(=O)OCc2cccc(c2)-c2n[nH]c3ccc(cc23)O1]

Example 50 is prepared according to the synthesis route described in general scheme C and procedures analogous to those used to obtain example 8.

To a solution of 13-methyl-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one (330 mg, 0.78 mmol) in dichloromethane (12 mL) was added trifluoroacetic acid (1.19 mL, 15.65 mmol) at RT. The solution was then irradiated under micro-waves (Biotage initiator+) for 2 h. The reaction mixture was concentrated under vacuo and the residue was dissolved in EtOAc. The organic phase was washed with a saturated aqueous solution of sodium hydrogen carbonate, with brine, dried over $Na_2SO_4$, filtered and evaporated under reduced pressure. The solid obtained was triturated in diisopropyl ether and dried to give the expected compound 13-methyl-8,14-dioxa-10,19,20-triazatetracyclo[13.5.2.1$^{2,6}$.0$^{18,21}$]tricosa-1(20),2,4,6(23),15,17,21-heptaen-9-one example 50 as a pale yellow solid.

LCMS method F: $[M+H]^+$=338, $t_R$=2.25 min

LCMS method G: $[M+H]^+$=338, $t_R$=2.24 min $^1$H NMR (400 MHz, d6-DMSO) δ 13.12 (1H, s), 7.93-7.84 (3H, m), 7.47 (2H, dd, J=8.5, 15.8 Hz), 7.27 (2H, d, J=7.0 Hz), 6.97 (1H, dd, J=2.1, 8.9 Hz), 5.75 (1H, d, J=12.1 Hz), 4.81 (1H, d, J=12.5 Hz), 4.57 (1H, dd, J=6.0, 9.2 Hz), 3.59-3.54 (1H, m), 2.93-2.86 (1H, m), 2.47-2.33 (1H, m), 1.41-1.38 (4H, m) ppm.

Example 51: 8,14-dioxa-4,5,10,19,20-pentaazatetracyclo[13.5.2.1$^{2,5}$.0$^{18,21}$]tricosa-1(20),2(23),3,15(22),16,18(21)-hexaen-9-one

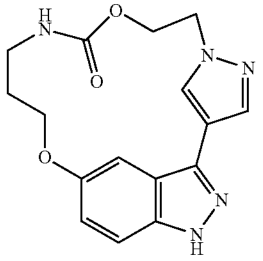 [SMILES: O=C1NCCCOc2ccc3[nH]nc(c3c2)-c2cnn(c2)CCO1]

Example 51 is prepared according to the synthesis route described in general Scheme C.

Preparation of Intermediate 50: benzyl N-[3-({3-[1-(2-hydroxyethyl)-1H-pyrazol-4-yl]-1-(oxan-2-yl)-1H-indazol-5-yl}oxy) propyl]carbamate

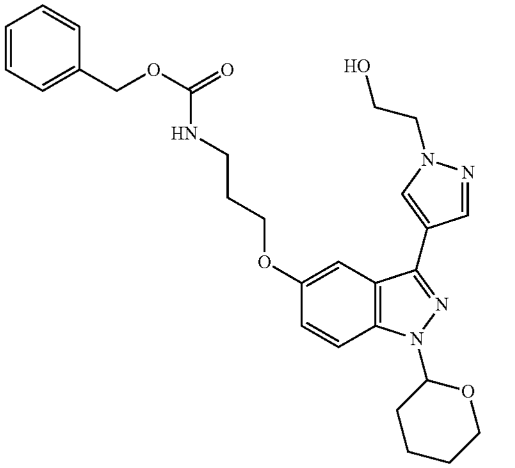 [SMILES: O=C(NCCCOc1ccc2c(c1)c(-c1cnn(CCO)c1)nn2C1CCCCO1)OCc1ccccc1]

To a solution of benzyl-N-(3-{[3-iodo-1-(oxan-2-yl)-1H-indazol-5-yl]oxy}propyl)carbamate 26 (0.535 g, 1.0 mmol) in dioxane (3 mL) and water (1 mL) was added at RT 1-(2-hydroxyethyl)-1H-pyrazole-4-boronic acid pinacol ester (0.286 g, 1.2 mmol), $K_3PO_4$ (0.637 g, 3.0 mmol), XPhos (0.048 g, 0.1 mmol) and $Pd(PPh_3)_4$(0.058 g, 0.05 mmol). The resulting reaction mixture was stirred under microwave irradiation at 120° C. for 1 h. The residue was diluted with saturated sodium chloride solution and extracted with ethyl acetate twice. The combined organic layers were dried over anhydrous sodium sulfate and the solvent was removed under reduced pressure. The residue was purified by flash-column (25 g silica Macherey Nagel) chromatography (cyclohexane-ethyl acetate 3/EtOH 1, 1:0 to 1:1) affording benzyl N-[3-({3-[1-(2-hydroxyethyl)-1H-pyrazol-4-yl]-1-(oxan-2-yl)-1H-indazol-5-yl}oxy) propyl] carbamate 50 as a yellow oil.

LCMS method F: $[M+H]^+$=520.2, $t_R$=2.56 min

Preparation of Intermediate 51

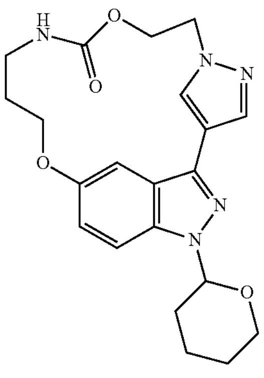 [SMILES: O=C1NCCCOc2ccc3c(c2)c(nn3C2CCCCO2)-c2cnn(c2)CCO1]

To a solution of benzyl N-[3-({3-[1-(2-hydroxyethyl)-1H-pyrazol-4-yl]-1-(oxan-2-yl)-1H-indazol-5-yl}oxy)propyl] carbamate 50 (0.380 g, 0.73 mmol) in anhydrous acetonitrile (146 mL) was added at RT cesium carbonate (1.430 g, 4.39 mmol). The resulting reaction mixture was stirred at 90° C. for 36 h. The reaction mixture was filtered and the filtrate was concentrated under reduced pressure. The residue was purified by flash-column (15 g silica Macherey Nagel) chromatography (cyclohexane-ethyl acetate 3/EtOH 1, 1:0 to 3:7) affording 19-(oxan-2-yl)-8,14-dioxa-4,5,10,19,20-pentaazatetracyclo[$13.5.2.1^{2,5}.0^{18,21}$]tricosa-1(20),2(23),3, 15(22), 16,18(21)-hexaen-9-one 51 as a white solid.

LCMS method F: $[M+H]^+$=412.2, $t_R$=2.20 min

Preparation of Example 51: 8,14-dioxa-4,5,10,19, 20-pentaazatetracyclo[$13.5.2.1^{2,5}.0^{18,21}$]tricosa-1 (20),2(23), 3,15(22),16,18(21)-hexaen-9-one

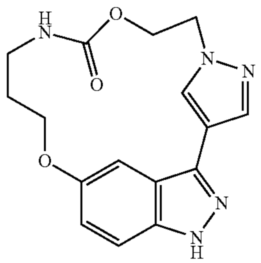 [SMILES: O=C1NCCCOc2ccc3[nH]nc(c3c2)-c2cnn(c2)CCO1]

To a solution of 19-(oxan-2-yl)-8,14-dioxa-4,5,10,19,20-pentaazatetracyclo[$13.5.2.1^{2,5}.0^{18,21}$]tricosa-1(20),2(23),3, 15(22),16,18(21)-hexaen-9-one 51 (0.155 g, 0.38 mmol) in DCM (3 mL) was added at RT TFA (0.561 mL, 7.53 mmol). The resulting reaction mixture was stirred under microwave irradiation at 80° C. for 1 h 30. The reaction mixture was concentrated under reduced pressure, diluted with saturated sodium bicarbonate solution and extracted with ethyl acetate twice. The combined organic layers were dried over anhydrous sodium sulfate and concentrated under reduced pressure. The residue was purified by flash-column (15 g silica Macherey Nagel) chromatography (cyclohexane-ethyl acetate 3/EtOH 1, 9:1 to 0:1) to give a solid (70 mg), which was triturated in diisopropyl ether and filtered affording 8,14-dioxa-4,5,10,19,20-pentaazatetracyclo[$13.5.2.1^{2,5}.0^{18,21}$]tricosa-1(20),2(23), 3,15(22),16,18(21)-hexaen-9-one example 51 as a white solid.

LCMS method F: $[M+H]^+$=328.1, $t_R$=1.68 min

LCMS method G: $[M+H]^+$=328.1, $t_R$=1.68 min $^1$H NMR (400 MHz, d6-DMSO) δ 12.82 (1H, s), 8.09 (1H, s), 7.86 (1H, t, J=6.1 Hz), 7.77 (1H, d, J=0.6 Hz), 7.44-7.41 (1H, m), 7.07 (1H, d, J=2.3 Hz), 6.94 (1H, dd, J=2.3, 8.9 Hz), 4.53-4.49 (2H, m), 4.38-4.28 (4H, m), 3.14-3.09 (2H, m), 1.86 (2H, q, J=8.7 Hz) ppm.

Example 52: 4-[methyl(oxetan-3-yl)amino]-8,14-dioxa-10,19,20-triazatetracyclo[13.5.2.1$^{2,6}$.0$^{18,21}$]tricosa-1(20),2,4,6(23),15,17,21-heptaen-9-one

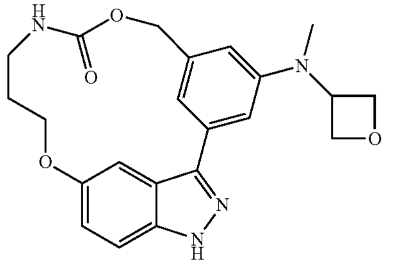 [SMILES: CN(c1cc2cc(c1)-c1n[nH]c3ccc(cc13)OCCCNC(=O)OC2)C1COC1]

Example 52 is prepared according to the synthesis route described in general Scheme C. N-methyloxetan-3-amine is used for the Buchwald reaction with the bromide intermediate 34 to give 4-[methyl(oxetan-3-yl)amino]-8,14-dioxa-10,19,20-triazatetracyclo[13.5.2.1$^{2,6}$.0$^{18,21}$]tricosa-1(20),2,4,6(23),15,17,21-heptaen-9-one example 52.

LCMS method F: [M+H]$^+$=409, $t_R$=2.04 min

LCMS method G: [M+H]$^+$=409, $t_R$=2.06 min $^1$H NMR (400 MHz, d6-DMSO) δ 12.81 (1H, s), 7.62 (1H, s), 7.46 (1H, d), 7.34 (2H, s), 7.13 (1H, s), 6.98-6.95 (1H, m), 6.64 (1H, s), 5.22 (2H, m), 4.84-4.81 (2H, m), 4.77-4.74 (1H, m), 4.65-4.64 (2H, m), 4.32-4.28 (2H, m), 3.16 (2H, m), 2.96 (3H, s), 2.03 (2H, m) ppm.

Example 53: 4-[(dimethylamino)methyl]-8,14-dioxa-10,19,20-triazatetracyclo[13.5.2.1$^{2,6}$.0$^{18,21}$]tricosa-1(20),2,4,6(23),15,17,21-heptaen-9-one

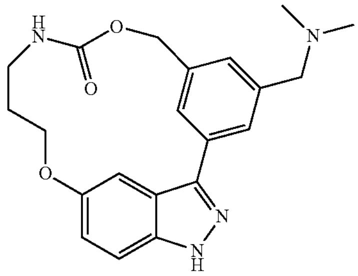 [SMILES: CN(C)Cc1cc2cc(c1)-c1n[nH]c3ccc(cc13)OCCCNC(=O)OC2]

Example 53 is prepared according to the synthesis route described in general Scheme C. Potassium (dimethylamino)methyltrifluoroborate was used for the Suzuki coupling with the bromide intermediate 34 to give 4-[(dimethylamino)methyl]-8,14-dioxa-10,19,20-triazatetracyclo[13.5.2.1$^{2,6}$.0$^{18,21}$]tricosa-1(20),2,4,6(23),15,17,21-heptaen-9-one example 53.

LCMS method F: [M+H]$^+$=381, $t_R$=1.39 min

LCMS method G: [M+H]$^+$=381, $t_R$=2.03 min $^1$H NMR (400 MHz, d6-DMSO) δ 12.93 (1H, s), 7.87 (2H, m), 7.70-7.66 (1H, m), 7.51-7.47 (1H, m), 7.36 (1H, d, J=2.1 Hz), 7.25 (1H, s), 6.99 (1H, dd, J=2.3, 9.1 Hz), 5.30-5.26 (2H, m), 4.34-4.30 (2H, m), 3.73 (2H, m), 3.17 (2H, s), 2.40-2.33 (6H, m), 2.06 (2H, s) ppm.

Example 54: 4,10-dimethyl-8,14-dioxa-10,19,20-triazatetracyclo[13.5.2.1$^{2,6}$.0$^{18,21}$]tricosa-1(20),2,4,6(23),15,17,21-heptaen-9-one

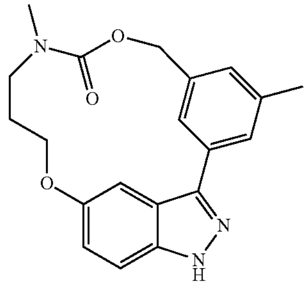 [SMILES: Cc1cc2cc(c1)-c1n[nH]c3ccc(cc13)OCCCN(C)C(=O)OC2]

Example 54 is prepared according to the synthesis route described in general Scheme F.

Preparation of Intermediate 52: 4,10-dimethyl-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one

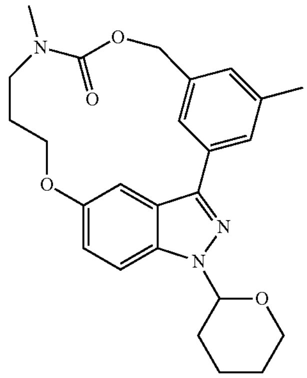 [SMILES: Cc1cc2cc(c1)-c1nn(C3CCCCO3)c3ccc(cc13)OCCCN(C)C(=O)OC2]

To a mixture of 4-methyl-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one example 18 (115 mg, 0.273 mmol) in THF (2.5 mL) at 0° C. was added NaH 60% in oil dispersion (8 mg, 0.328 mmol) and MeI (20 μL, 0.328 mmol). The reaction mixture was stirred overnight at RT. More NaH 60% in oil dispersion (8 mg, 0.328 mmol) and MeI (20 μL, 0.328 mmol) were added. The reaction mixture was stirred overnight at RT. The solvent was removed under reduced pressure, EtOAc and water were added. The layers were separated, the aqueous one was extracted with ethyl acetate. The organic layers were combined and the solvent was removed under reduced pressure to give 4,10-dimethyl-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one 52 as a colorless oil.

LCMS method F: [M+H]$^+$=436.2, $t_R$=3.15 min

Preparation of Example 54: 4,10-dimethyl-8,14-dioxa-10,19,20-triazatetracyclo[13.5.2.1$^{2,6}$.0$^{18,21}$]tricosa-1(20),2,4,6(23),15,17,21-heptaen-9-one

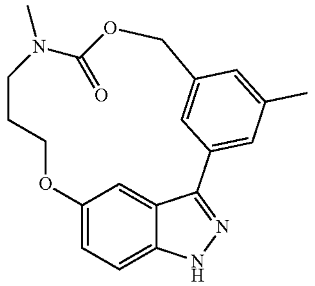 [SMILES: Cc1cc2cc(c1)-c1n[nH]c3ccc(cc13)OCCCN(C)C(=O)OC2]

To a mixture of 4,10-dimethyl-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one 52 (150 mg; 0.345 mmol) in DCM (2.5 mL) was added TFA (132 μl, 1.723 mmol). The reaction mixture was stirred under microwave conditions at 80° C. during 60 min. The solvent was removed under reduced pressure, the mixture was dissolved in EtOAc and washed with a saturated solution of 1 N $NaHCO_3$ (pH=7), then with water. The organic layer was concentrated under reduced pressure the oil was purified by chromatography using a 10 g $SiO_2$ column eluted with DCM/MeOH 100/0 to 95/5. The desired fractions were combined but the product is not enough pure it was re-purified by chromatography using a 10 g $SiO_2$ column eluted with cyclohexane/Ethyl acetate 70/30 to 50/50. The desired fractions were combined, and the solvent was removed under reduced pressure then the oil was triturated with pentane. The solid was filtered and boiled in hot water, it was filtered and dried under high vacuum to give 4,10-dimethyl-8,14-dioxa-10,19,20-triazatetracyclo[13.5.2.1$^{2,6}$.0$^{18,21}$]tricosa-1(20),2,4,6(23),15,17,21-heptaen-9-one example 54 as a white powder.

LCMS method F: $[M+H]^+$=352.2, $t_R$=2.49 min

LCMS method G: $[M+H]^+$=352.2, $t_R$=2.49 min

The $^1$H NMR analysis showed the presence of rotamers. $^1$H NMR (400 MHz, d6-DMSO) δ 13.11-13.05 (1H, m), 7.68 (2H, d, J=13.7 Hz), 7.51-7.47 (1H, m), 7.20-7.12 (2H, m), 6.99 (1H, dd, J=2.2, 9.0 Hz), 5.82 (0.75H, d, J=13.3 Hz), 5.15 (0.25H, s), 4.78 (0.75H, d, J=13.5 Hz), 4.43-4.35 (0.75H, m), 4.28-4.12 (1.25H, m), 3.94-3.84 (0.75H, m), 3.47-3.39 (0.25H, m), 3.04-3.03 (3H, m), 2.91-2.82 (1.25H, m), 2.41-2.39 (4H, m), 2.27-2.16 (0.25H, m), 1.77-1.70 (0.75H, m) ppm.

Example 55: 4-(propan-2-yloxy)-8,14-dioxa-10,19,20-triazatetracyclo[13.5.2.1$^{2,6}$.0$^{18,21}$]tricosa-1(20),2,4,6(23),15,17,21-heptaen-9-one

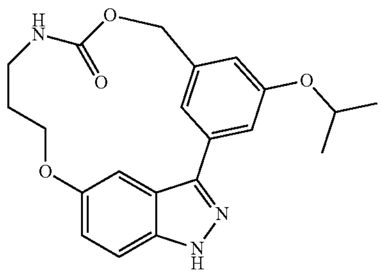 [SMILES: CC(C)Oc1cc2cc(c1)-c1n[nH]c3ccc(cc13)OCCCNC(=O)OC2]

Example 54 is prepared according to the synthesis route described in general Scheme F.

Preparation of Intermediate 53: methyl 3-[5-[3-(benzyloxycarbonylamino)propoxy]-1-tetrahydropyran-2-yl-indazol-3-yl]-5-hydroxy-benzoate

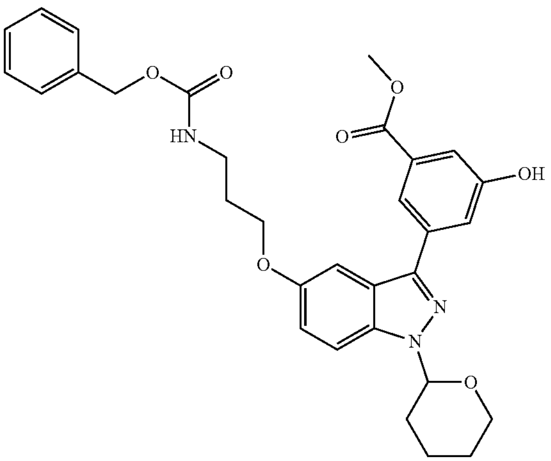 [SMILES: COC(=O)c1cc(O)cc(-c2nn(C3CCCCO3)c3ccc(OCCCNC(=O)OCc4ccccc4)cc23)c1]

To a degassed solution of benzyl N-[3-(3-iodo-1-tetrahydropyran-2-yl-indazol-5-yl)oxypropyl]carbamate 26 (2.876 g, 5.372 mmol), methyl 3-hydroxy-5-(4,4,5,5-tetramethyl-1,3,2-dioxaborolan-2-yl)benzoate (2.988 g, 10.473 mmol), XPhos (256 mg, 0.537 mmol) and $K_3PO_4$ (3.421 g, 16.116 mmol) in dioxane (40.0 mL) and water (10.0 mL) was added $Pd(PPh_3)_4$ (311 mg, 0.269 mmol). The resulting cloudy brown solution was degassed with nitrogen gas for 5 minutes and separated in three batches, sealed and heated to 120° C. under microwave irradiation for 1 h each. The mixture was poured into water (50 mL), EtOAc (100 mL) was added and the phases were separated. The aqueous layer was extracted with EtOAc (3×100 mL) and the combined organic extracts were washed with a saturated aqueous NaCl solution (1×50 mL), dried over anhydrous $Na_2SO_4$, filtered and concentrated under reduced pressure. The resulting crude material (brown oil, 4.1 g) was purified by column chromatography (220 g Macherey Nagel $SiO_2$, 100 mL/min, CyH/EtOAc 100:0 to 60:40) to afford methyl 3-[5-[3-(benzyloxycarbonylamino)propoxy]-1-tetrahydropyran-2-yl-indazol-3-yl]-5-hydroxy-benzoate 53 as a brown oil.

LCMS method F: $[M+H]^+$=560.1, $t_R$=2.97 min

Preparation of Intermediate 54: methyl 3-[5-[3-(benzyloxycarbonylamino)propoxy]-1-tetrahydropyran-2-yl-indazol-3-yl]-5-isopropoxy-benzoate

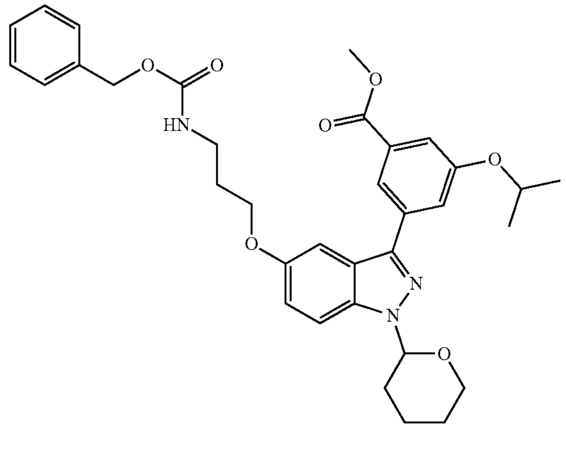 [SMILES: COC(=O)c1cc(OC(C)C)cc(-c2nn(C3CCCCO3)c3ccc(OCCCNC(=O)OCc4ccccc4)cc23)c1]

To a solution of methyl 3-[5-[3-(benzyloxycarbonylamino)propoxy]-1-tetrahydropyran-2-yl-indazol-3-yl]-5-hydroxy-benzoate 53 (2.800 g, 5.004 mmol) and $K_2CO_3$ (1.729 g, 12.510 mmol) in N,N-dimethylformamide (25.0 mL) was added 2-bromopropane (940 μL, 1.231 mg, 10.008 mmol). The resulting cloudy brown solution was heated to 70° C. for 2 h. The reaction was quenched with water (20 mL), EtOAc (50 mL) was added and phases were separated. The aqueous layer was extracted with EtOAc (3×50 mL) and the combined organic extracts were washed with saturated aqueous NaCl solution (1×20 mL), dried over anhydrous $Na_2SO_4$, filtered and the solvent was removed under reduced pressure. The resulting crude material (brown solid, 3.5 g) was purified by column chromatography (120 g Macherey Nagel $SiO_2$, CyH/EtOAc 100:0 to 70:30) to afford methyl 3-[5-[3-(benzyloxycarbonylamino)propoxy]-1-tetrahydropyran-2-yl-indazol-3-yl]-5-isopropoxy-benzoate 54 as a brown solid.

LCMS method F: $[M+H]^+$=602.3, $t_R$=3.48 min

Preparation of Intermediate 55: benzyl N-[3-[3-[3-(hydroxymethyl)-5-isopropoxy-phenyl]-1-tetrahydropyran-2-yl-indazol-5-yl]oxypropyl]carbamate

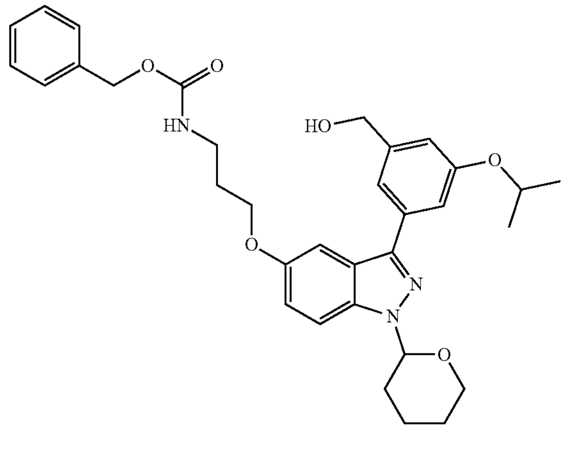 [SMILES: CC(C)Oc1cc(CO)cc(-c2nn(C3CCCCO3)c3ccc(OCCCNC(=O)OCc4ccccc4)cc23)c1]

To a solution of methyl 3-[5-[3-(benzyloxycarbonylamino)propoxy]-1-tetrahydropyran-2-yl-indazol-3-yl]-5-isopropoxy-benzoate 54 (3.000 g, 4.986 mmol) in THF (50.0 mL) at 0° C. was added dropwise $LiAlH_4$ (1.0 M in THF, 9.97 mL, 9.972 mmol). The resulting brown solution was stirred at 0° C. for 15 minutes, then at room temperature for 1 h. The reaction was carefully quenched with saturated aqueous Rochelle's salt (20 mL), EtOAc (50 mL) was added and the phases were separated. The aqueous layer was extracted with EtOAc (3×50 mL) and the combined organic extracts were washed with a saturated aqueous NaCl solution (1×50 mL), dried over anhydrous $Na_2SO_4$, filtered and concentrated under reduced pressure to afford crude benzyl N-[3-[3-[3-(hydroxymethyl)-5-isopropoxy-phenyl]-1-tetrahydropyran-2-yl-indazol-5-yl]oxypropyl]carbamate 55 as a brown oil which was used in the next step without further purification.

LCMS method F: $[M+H]^+$=574.2, $t_R$=3.06 min

Preparation of Intermediate 56: 19-(oxan-2-yl)-4-(propan-2-yloxy)-8,14-dioxa-10,19,20-triazatetracyclo[13.5.2.1$^{2,6}$.0$^{18,21}$]tricosa-1(20),2,4,6(23),15,17,21-heptaen-9-one

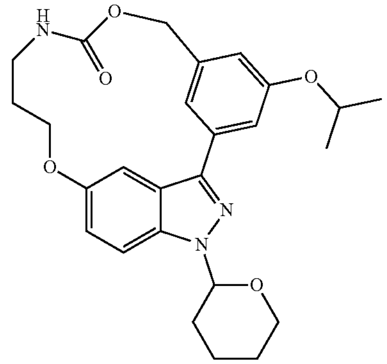 [SMILES: CC(C)Oc1cc2cc(c1)-c1nn(C3CCCCO3)c3ccc(cc13)OCCCNC(=O)OC2]

To a solution of benzyl N-[3-[3-[3-(hydroxymethyl)-5-isopropoxy-phenyl]-1-tetrahydropyran-2-yl-indazol-5-yl]oxypropyl]carbamate 55 (100 mg, 0.174 mmol) in MeCN (18.0 mL) was added $Cs_2CO_3$ (341 mg, 1.046 mmol). The resulting cloudy yellow mixture was heated under reflux for 5 h. The mixture was cooled to room temperature, filtered and concentrated under reduced pressure. The resulting crude material (yellow oil, 100 mg) was purified by column chromatography (4 g Macherey Nagel $SiO_2$, 15 mL/min, $CH_2Cl_2$/MeOH 100:0 to 98:2) to afford 19-(oxan-2-yl)-4-(propan-2-yloxy)-8,14-dioxa-10,19,20-triazatetracyclo[13.5.2.1$^{2,6}$.0$^{18,21}$]tricosa-1(20),2,4,6(23),15,17,21-heptaen-9-one 56 as a transparent oil.

LCMS method F: $[M+H]^+$=466.2, $t_R$=3.03 min

Preparation of Example 55: 4-(propan-2-yloxy)-8,14-dioxa-10,19,20-triazatetracyclo[13.5.2.1$^{2,6}$.0$^{18,21}$]tricosa-1(20),2,4,6(23),15,17,21-heptaen-9-one

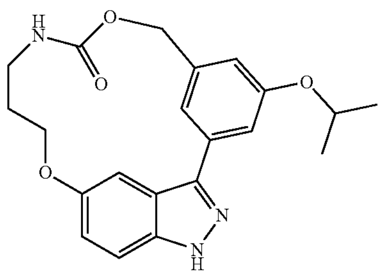 [SMILES: CC(C)Oc1cc2cc(c1)-c1n[nH]c3ccc(cc13)OCCCNC(=O)OC2]

To a solution of 19-(oxan-2-yl)-4-(propan-2-yloxy)-8,14-dioxa-10,19,20-triazatetracyclo[13.5.2.1$^{2,6}$.0$^{18,21}$]tricosa-1(20),2,4,6(23),15,17,21-heptaen-9-one 56 (54 mg, 0.116 mmol) in $CH_2Cl_2$ (5.0 mL) was added TFA (300 µL, 447 mg, 3.920 mmol). The vial containing the resulting clear yellow solution was sealed and heated to 50° C. under microwave irradiation for 3 h. Saturated aqueous $NaHCO_3$ (1 mL) was added and phases were separated. The aqueous layer was extracted with $CH_2Cl_2$ (3×5 mL) and the combined organic extracts were washed with water (1×5 mL), dried over anhydrous $Na_2SO_4$, filtered and concentrated under reduced pressure. The resulting crude material (pale yellow oil, 49 mg) was triturated with $iPr_2O$ to afford 4-(propan-2-yloxy)-8,14-dioxa-10,19,20-triazatetracyclo[13.5.2.1$^{2,6}$.0$^{18,21}$]tricosa-1(20),2,4,6(23),15,17,21-heptaen-9-one example 55 as a white amorphous solid.

LCMS method F: $[M+H]^+$=382.1, $t_R$=2.41 min

LCMS method G: $[M+H]^+$=382.2, $t_R$=2.40 min $^1$H NMR (400 MHz, d6-DMSO, 80° C.) δ 7.66 (brs, 1H), 7.49-7.46 (m, 2H), 7.39-7.34 (m, 2H), 6.98 (dd, J=2.4, 9.0 Hz, 1H), 6.85 (brs, 1H), 5.24 (brs, 1H), 4.72-4.63 (sept, J=5.9 Hz, 1H), 4.33-4.29 (m, 2H), 3.19-3.15 (m, 2H), 2.04-2.02 (m, 2H), 1.35-1.33 (m, 6H) ppm.

Two labile protons were not visible in this solvent.

Example 56: 4-fluoro-7-methyl-8,14-dioxa-10,19,20-triazatetracyclo[13.5.2.1$^{2,6}$.0$^{18,21}$]tricosa-1(20),2,4,6(23),15,17,21-heptaen-9-one

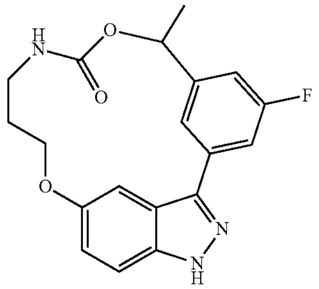 [SMILES: CC1OC(=O)NCCCOc2ccc3[nH]nc(c3c2)-c2cc(F)cc1c2]

Example 56 is prepared according to the synthesis route described in general Scheme A.

Preparation of Intermediate 57: 1-(3-bromo-5-fluoro-phenyl)ethanol

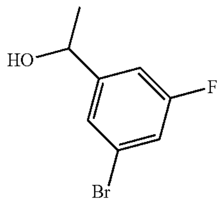

To a cooled solution of 3-bromo-5-fluorobenzaldehyde (1.5 g, 7.389 mmol) in dry tetrahydrofuran (19 mL) was added dropwise methylmagnesium bromide solution 3M in diethyl ether (4.93 mL, 14.778 mmol) at 0° C. The reaction mixture was stirred at 0° C. for 20 min then RT for 16 h. The reaction mixture was quenched with a saturated aqueous solution of $NH_4Cl$ then extracted with ethyl acetate (2×). The combined organic layers were washed with water then brine, dried over sodium sulfate and concentrated under reduced pressure. The crude product was purified by flash-column chromatography eluting with Cyclohexane/Ethyl acetate-EtOH (3-1): 100/0 to 80/20, to give 1-(3-bromo-5-fluoro-phenyl)ethanol 57 as a colorless oil.

LCMS method F: $[M+H]^+$=mass not detected, $t_R$=2.32 min

Preparation of Intermediate 58: 1-[3-fluoro-5-(4,4,5,5-tetramethyl-1,3,2-dioxaborolan-2-yl)phenyl]ethanol

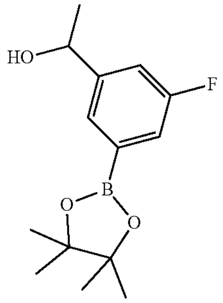 [SMILES: CC(O)c1cc(F)cc(B2OC(C)(C)C(C)(C)O2)c1]

To a degassed solution in a sealed tube of 1-(3-bromo-5-fluoro-phenyl)ethanol 57 (1.196 g, 5.461 mmol), bis(pinacolato)diboron (2.080 g, 8.192 mmol) and potassium acetate (2.144 g, 21.844 mmol) in dioxane (17 mL) was added $PdCl_2(dppf)$-$CH_2Cl_2$ (0.446 g, 0.546 mmol). The reaction mixture was heated at 90° C. for 24 h. The reaction mixture was filtered over celite on Whatman paper and rinsed with ethyl acetate. The reaction mixture was diluted with water and extracted with ethyl acetate (3×). The combined organic layers were washed with water and brine, dried over anhydrous sodium sulfate and concentrated under reduced pressure to give 1-[3-fluoro-5-(4,4,5,5-tetramethyl-1,3,2-dioxaborolan-2-yl)phenyl]ethanol 58 as a black oil.

LCMS method F: no m/z detected, $t_R$=2.65 min.

Preparation of Intermediate 59: benzyl N-[3-[3-[3-fluoro-5-(1-hydroxyethyl)phenyl]-1-tetrahydropyran-2-yl-indazol-5-yl]oxypropyl]carbamate

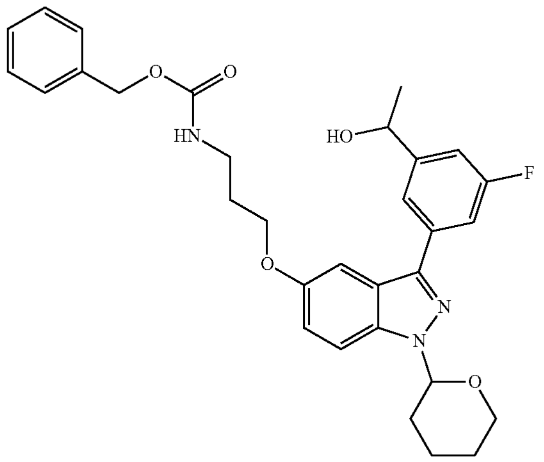 [SMILES: CC(O)c1cc(F)cc(-c2nn(C3CCCCO3)c3ccc(OCCCNC(=O)OCc4ccccc4)cc23)c1]

To a degassed solution of benzyl N-[3-(3-iodo-1-tetrahydropyran-2-yl-indazol-5-yl)oxypropyl]carbamate 26 (1.462 g, 2.734 mmol), 1-[3-fluoro-5-(4,4,5,5-tetramethyl-1,3,2-dioxaborolan-2-yl)phenyl]ethanol 58 (1.453 g, 5.466 mmol), tripotassium phosphate (1.742 g, 8.202 mmol) and xPhos (0.130 g, 0.274 mmol) in dioxane (14.6 mL) and water (8.8 mL) was added tetrakis(triphenylphosphine)palladium(0) (0.158 g, 0.137 mmol). The reaction mixture was irradiated under microwaves (Biotage initiator+) at 120° C. for 1 h. The reaction mixture was filtered over celite and the celite was washed with ethyl acetate. The filtrate was then diluted with water and extracted with ethyl acetate (3×). The combined organic layers were washed with water and brine, dried over sodium sulfate and concentrated under reduced pressure.

The crude was purified by column chromatography eluting with DCM/ethyl acetate, 100/0 to 80/20 to give benzyl N-[3-[3-[3-fluoro-5-(1-hydroxyethyl)phenyl]-1-tetrahydropyran-2-yl-indazol-5-yl]oxypropyl]carbamate 59 as a cream solid.

Yield: 780 mg of intermediate 59 (50%)

LCMS method F: $[M+H]^+=548$, $t_R=3.07$ min

Preparation of Intermediate 60: 1-[3-[5-(3-aminopropoxy)-1-tetrahydropyran-2-yl-indazol-3-yl]-5-fluoro-phenyl]ethanol and 4-fluoro-7-methyl-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one

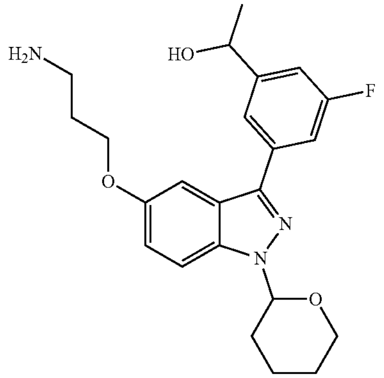

-continued

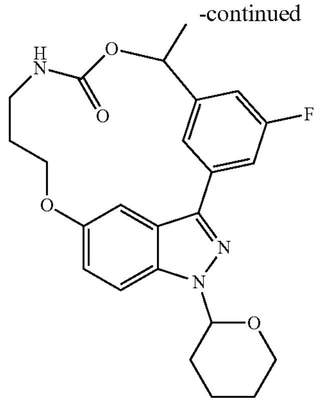

A suspension of benzyl N-[3-[3-[3-fluoro-5-(1-hydroxyethyl)phenyl]-1-tetrahydropyran-2-yl-indazol-5-yl]oxypropyl]carbamate 59 (0.780 g, 1.426 mmol) and cesium carbonate (2.781 g, 8.556 mmol) in acetonitrile (300 mL) was heated to 90° C. for 16 h. LCMS analysis showed formation of the desired product but starting material remained and the formation of 1-[3-[5-(3-aminopropoxy)-1-tetrahydropyran-2-yl-indazol-3-yl]-5-fluoro-phenyl]ethanol was observed. The reaction mixture was heated to 90° C. for 16 h. The reaction mixture was cooled to RT then filtered and concentrated under reduced pressure to give a mix of 1-[3-[5-(3-aminopropoxy)-1-tetrahydropyran-2-yl-indazol-3-yl]-5-fluoro-phenyl]ethanol (66%) and 4-fluoro-7-methyl-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one (26%) (0.667 g, 1.426 mmol (postulated)) as an orange oil. The crude product was not purified, it was engaged in the next step without further purification.

Preparation of Intermediate 61: 4-fluoro-7-methyl-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one

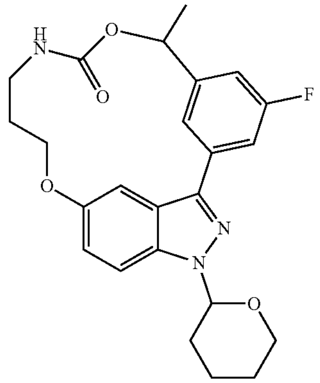 [SMILES: CC1OC(=O)NCCCOc2ccc3c(c2)c(nn3C2CCCCO2)-c2cc(F)cc1c2]

To a solution of 1-[3-[5-(3-aminopropoxy)-1-tetrahydropyran-2-yl-indazol-3-yl]-5-fluoro-phenyl]ethanol and 4-fluoro-7-methyl-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one 60 (0.567 g, 1.373 mmol) in DMA (350 mL) was added 1,1'-carbonyldiimidazole (0.245 g, 1.510 mmol). The reaction mixture was stirred at RT for 2 h then 90° C. for 22 h. The reaction mixture was concentrated under reduced pressure and ethyl acetate and a saturated aqueous solution of $NaHCO_3$ were added. The mixture was extracted with ethyl acetate (2×). The combined organic layers were washed with water and brine, dried over sodium sulfate, filtered and concentrated under reduced pressure.

The crude product was purified by column chromatography eluting with Cyclohexane/Ethyl acetate-EtOH (3-1): 100/0 to 70/30 to give a cream solid. The solid was triturated from diisopropyl ether to give 4-fluoro-7-methyl-19-(oxan-2-yl)-8,14-dioxa-10,19,20-triazatetracyclo[13.5.2.$1^{2,6}$.$0^{18,21}$]tricosa-1(20),2,4,6(23),15,17,21-heptaen-9-one 61 as a white solid.

Yield: 100 mg of intermediate 61 (14%)

LCMS method F: $[M+H]^+$=440, $t_R$=2.96 min

Preparation of Example 56: 4-fluoro-7-methyl-8,14-dioxa-10,19,20-triazatetracyclo[13.5.2.$1^{2,6}$.$0^{18,21}$]tricosa-1(20),2,4,6(23),15,17,21-heptaen-9-one

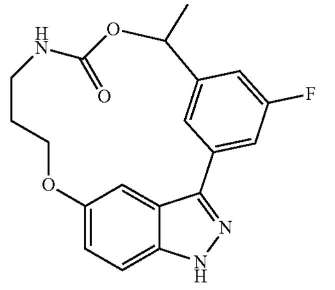 [SMILES: CC1OC(=O)NCCCOc2ccc3[nH]nc(c3c2)-c2cc(F)cc1c2]

To a solution of 4-fluoro-7-methyl-19-(oxan-2-yl)-8,14-dioxa-10,19,20-triazatetracyclo[13.5.2.$1^{2,6}$.$0^{18,21}$]tricosa-1(20),2,4,6(23),15,17,21-heptaen-9-one 61 (100 mg, 0.228 mmol) in DCM (16 mL) was added trifluoro acetic acid (350 µL, 4.560 mmol) at RT. The reaction mixture was irradiated under microwave conditions (Biotage initiator). The solid was triturated from diisopropyl ether to give 4-fluoro-7-methyl-8,14-dioxa-10,19,20-triazatetracyclo[13.5.2.$1^{2,6}$.$0^{18,21}$]tricosa-1(20),2,4,6(23),15,17,21-heptaen-9-one example 56 as a cream solid.

LCMS method F: $[M+H]^+$=356, $t_R$=2.33 min

LCMS method G: $[M+H]^+$=356, $t_R$=2.32 min $^1H$ NMR (400 MHz, d6-DMSO) δ 13.26 (1H, s), 8.01-7.98 (1H, m), 7.69 (1H, s), 7.59-7.56 (1H, m), 7.53-7.50 (1H, m), 7.33 (1H, m), 7.22-7.18 (1H, m), 7.02-6.99 (1H, m), 5.91-5.86 (1H, m), 4.35-4.28 (2H, m), 3.56-3.49 (1H, m), 2.79-2.72 (1H, m), 2.21-2.16 (1H, m), 1.77-1.71 (1H, m), 1.61-1.58 (3H, d) ppm.

Example 57: 4-[1-(oxetan-3-yl)-1,2,3,6-tetrahydropyridin-4-yl]-8,14-dioxa-10,19,20-triazatetracyclo[13.5.2.$1^{2,6}$.$0^{18,21}$]tricosa-1(20),2,4,6(23),15,17,21-heptaen-9-one

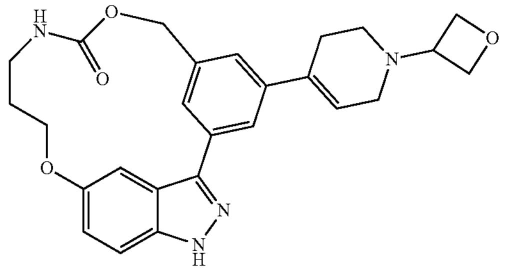 [SMILES: O=C1NCCCOc2ccc3[nH]nc(c3c2)-c2cc(cc(C3=CCN(C4COC4)CC3)c2)CO1]

Example 57 is prepared according to the synthesis route described in general Scheme C.

Preparation of Intermediate 62: 1-(oxetan-3-yl)-4-(4,4,5,5-tetramethyl-1,3,2-dioxaborolan-2-yl)-3,6-dihydro-2H-pyridine

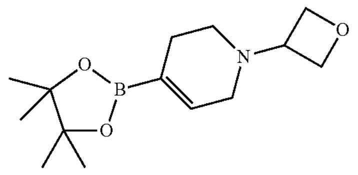 [SMILES: CC1(C)OB(C2=CCN(C3COC3)CC2)OC1(C)C]

To a solution of 4-(4,4,5,5-tetramethyl-1,3,2-dioxaborolan-2-yl)-1,2,3,6-tetrahydropyridine (370 mg, 1.77 mmol) in DCM (9 mL), triethylamine (245 µL, 1.77 mmol) and 3-bromooxetane (750 mg, 5.5 mmol) were added. The resulting mixture was stirred at room temperature for 2 days. The reaction mixture was evaporated under reduced pressure to give 1-(oxetan-3-yl)-4-(4,4,5,5-tetramethyl-1,3,2-dioxaborolan-2-yl)-3,6-dihydro-2H-pyridine 62 (500 mg, 1.77 postulated) as an orange oil. The compound was used without further purification in the next step.

Preparation of Intermediate 63: 19-(oxan-2-yl)-4-(1,2,3,6-tetrahydropyridin-4-yl)-8,14-dioxa-10,19,20-triazatetracyclo[13.5.2.$1^{2,6}$.$0^{18,21}$]tricosa-1(20),2,4,6(23),15,17,21-heptaen-9-one

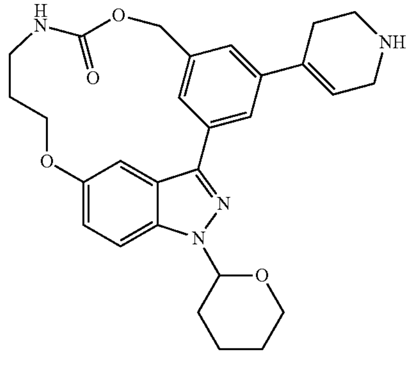 [SMILES: O=C1NCCCOc2ccc3c(c2)c(nn3C2CCCCO2)-c2cc(cc(C3=CCNCC3)c2)CO1]

To a solution of 4-bromo-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one intermediate 34 (260 mg, 0.53 mmol) in dioxane/water (15/1.5 mL), 1-(oxetan-3-yl)-4-(4,4,5,5-tetramethyl-1,3,2-dioxaborolan-2-yl)-3,6-dihydro-2H-pyridine 62 (300 mg, 1.06 mmol postulated) and $K_3PO_4$ (337 mg, 1.59 mmol) were added. The mixture was degassed during 10 minutes, then Pd(dppf)$Cl_2$. DCM (17 mg, 0.021 mmol) was added. The mixture was heated at 90° C. for 20 hours. Monitoring by LCMS analysis showed formation of the expected product without oxetane. The reaction mixture was cooled to room temperature, then more 1-(oxetan-3-yl)-4-(4,4,5,5-tetramethyl-1,3,2-dioxaborolan-2-yl)-3,6-dihydro-2H-pyridine (200 mg, 0.71 mmol postulated) and $K_3PO_4$ (168 mg, 0.79 mmol) were added. The mixture was degassed during 10 minutes and more Pd(dppf)$Cl_2$. DCM (8 mg, 0.0098 mmol) was added. The mixture was heated at 90° C. for 1 days. The reaction mixture was filtered over celite, diluted with EtOAc (50 mL) and water (50 mL). After separation, the aqueous layer was extracted with EtOAc (2×50 mL).

The combined organic layers were washed with brine (50 mL), dried over anhydrous sodium sulfate, filtered and concentrated under reduced pressure. The crude was purified by column (Macherey Nagel, 25 g) chromatography with DCM/(MeOH/NH3) (100/0 to 90/10). The desired fractions were collected, combined and evaporated to give 19-(oxan-2-yl)-4-(1,2,3,6-tetrahydropyridin-4-yl)-8,14-dioxa-10,19,20-triazatetracyclo[13.5.2.1$^{2,6}$.0$^{18,21}$]tricosa-1(20),2,4,6(23),15,17,21-heptaen-9-one 63 as an orange solid.

LCMS method F: $[M+H]^+$=489, $t_R$=1.81 min

Preparation of Intermediate 64: 19-(oxan-2-yl)-4-[1-(oxetan-3-yl)-1,2,3,6-tetrahydropyridin-4-yl]-8,14-dioxa-10,19,20-triazatetracyclo[13.5.2.1$^{2,6}$.0$^{18,21}$]tricosa-1(20),2,4,6(23),15,17,21-heptaen-9-one

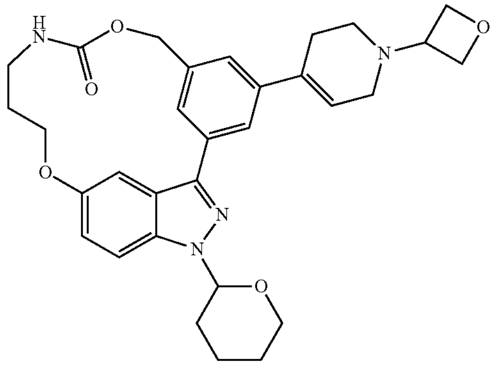 [SMILES: O=C1NCCCOc2ccc3c(c2)c(nn3C2CCCCO2)-c2cc(cc(C3=CCN(C4COC4)CC3)c2)CO1]

To a solution of 19-(oxan-2-yl)-4-(1,2,3,6-tetrahydropyridin-4-yl)-8,14-dioxa-10,19,20-triazatetracyclo[13.5.2.1$^{2,6}$.0$^{18,21}$]tricosa-1(20),2,4,6(23),15,17,21-heptaen-9-one 63 (289 mg, 0.59 mmol) in dry THF (15 mL), oxetan-3-one (212 mg, 2.95 mmol) was added. The mixture was cooled to 0° C. then sodium tris(acetoxy)borohydride (248 mg, 1.18 mmol) was added. The reaction mixture was stirred at room temperature for 18 hours. The reaction mixture was quenched with $Na_2CO_3$ 1M (~7 mL, pH=8), then the mixture was diluted with EtOAc (50 mL). After separation, the aqueous layer was extracted with EtOAc (3×50 mL). The combined organic layers were washed with brine (50 mL), dried over anhydrous sodium sulfate, filtered and concentrated under reduced pressure. The crude was purified by column (Macherey Nagel, 15 g) flash chromatography with DCM/MeoH (100/0 to 97/3) as eluent, to give 19-(oxan-2-yl)-4-[1-(oxetan-3-yl)-1,2,3,6-tetrahydropyridin-4-yl]-8,14-dioxa-10,19,20-triazatetracyclo[13.5.2.1$^{2,6}$.0$^{18,21}$]tricosa-1(20),2,4,6(23),15,17,21-heptaen-9-one 64 as a white crystals.

LCMS method F: $[M+H]^+$=545, $t_R$=1.84 min

Preparation of Example 57: 4-[1-(oxetan-3-yl)-1,2,3,6-tetrahydropyridin-4-yl]-8,14-dioxa-10,19,20-triazatetracyclo[13.5.2.1$^{2,6}$.0$^{18,21}$]tricosa-1(20),2,4,6(23),15,17,21-heptaen-9-one

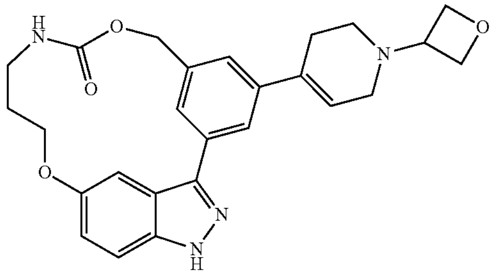 [SMILES: O=C1NCCCOc2ccc3[nH]nc(c3c2)-c2cc(cc(C3=CCN(C4COC4)CC3)c2)CO1]

To a solution of 19-(oxan-2-yl)-4-[1-(oxetan-3-yl)-1,2,3,6-tetrahydropyridin-4-yl]-8,14-dioxa-10,19,20-triazatetracyclo[13.5.2.1$^{2,6}$.0$^{18,21}$]tricosa-1(20),2,4,6(23),15,17,21-heptaen-9-one 64 (82 mg, 0.15 mmol) in DCM (4 mL) was added trifluoro acetic acid (107 μL, 1.4 mmol). The mixture was stirred at room temperature for 24 hours. The reaction mixture was then heated at 40° C. for 4 hours. More trifluoro acetic acid (26 μL, 0.35 mmol) was added and the reaction mixture was heated at 40° C. for 3 hours and at room temperature overnight. The reaction mixture was diluted with DCM (25 mL) and a saturated $NaHCO_3$ solution (25 mL). After separation, the aqueous layer was extracted with DCM (3×20 mL). The combined organic layers were washed with brine (25 mL), dried over anhydrous sodium sulfate, filtered and the solvent was removed under reduced pressure. The crude was triturated in acetonitrile, filtered and the solid was washed several times with acetonitrile to give 4-[1-(oxetan-3-yl)-1,2,3,6-tetrahydropyridin-4-yl]-8,14-dioxa-10,19,20-triazatetracyclo[13.5.2.1$^{2,6}$.0$^{18,21}$]tricosa-1(20),2,4,6(23),15,17,21-heptaen-9-one example 57 as a cream powder.

LCMS method F: $[M+H]^+$=461, $t_R$=1.49 min

LCMS method G: $[M+H]^+$=461, $t_R$=2.19 min $^1H$ NMR (400 MHz, d6-DMSO, 80° C.) δ 12.89 (1H, m), 7.90 (1H, s), 7.80 (1H, s), 7.67 (1H, m), 7.48 (1H, d, J=9.5 Hz), 7.35 (2H, m), 6.98 (1H, dd, J=1.5, 8.9 Hz), 6.23 (1H, m), 5.29 (2H, m), 4.61 (2H, t, J=6.5 Hz), 4.55 (2H, t, J=5.9 Hz), 4.31 (2H, t, J=9.3 Hz), 3.65 (1H, t, J=6.1 Hz), 3.18 (2H, m), 3.09 (2H, m), 2.61 (2H, m), 2.57 (2H, m), 2.04 (2H, m) ppm.

Example 58: 4-(3-methylpiperidin-1-yl)-8,14-dioxa-10,19,20-triazatetracyclo[13.5.2.$1^{2,6}$.$0^{18,21}$]tricosa-1(20),2,4,6(23),15,17,21-heptaen-9-one

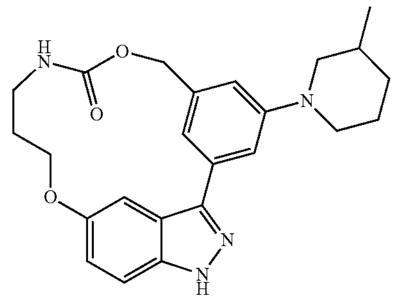 [SMILES: CC1CCCN(c2cc3cc(c2)-c2n[nH]c4ccc(cc24)OCCCNC(=O)OC3)C1]

Example 58 is prepared according to the synthesis route described in general Scheme C. 3-Methylpiperidine is used for the Buchwald reaction with the bromide intermediate 34 to give 4-(3-methylpiperidin-1-yl)-8,14-dioxa-10,19,20-triazatetracyclo[13.5.2.$1^{2,6}$.$0^{18,21}$]tricosa-1(20),2,4,6(23),15,17,21-heptaen-9-one example 58.

LCMS method F: $[M+H]^+$=421.2, $t_R$=1.88 min

LCMS method G: $[M+H]^+$=421.2, $t_R$=2.66 min $^1H$ NMR (400 MHz, d6-DMSO) δ 7.69-7.56 (1H, m), 7.48-7.45 (1H, m), 7.38-7.31 (3H, m), 6.95 (1H, dd, J=2.4, 9.0 Hz), 6.87-6.86 (1H, m), 5.24-5.20 (2H, m), 4.30 (2H, dd, J=8.0, 9.1 Hz), 3.22-3.1 (2H, m), 3.07 (6H, s), 2.79-2.68 (1H, m), 2.07-1.98 (2H, m) 1.83-1.74 (3H, m), 1.7-1.55 (1H, m), 1.19-1.05 (1H, m) ppm. The indazole NH proton was not visible in this solvent.

Example 59: 4-[(3S)-3-hydroxypyrrolidin-1-yl]-8,14-dioxa-10,19,20-triazatetracyclo[13.5.2.$1^{2,6}$.$0^{18,21}$]tricosa-1(20),2,4,6(23),15,17,21-heptaen-9-one

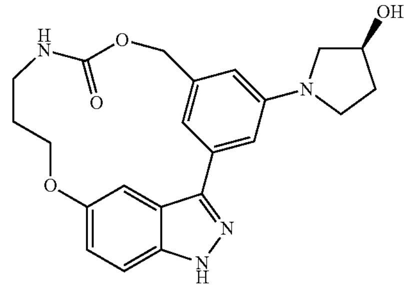 [SMILES: O=C1NCCCOc2ccc3[nH]nc(c3c2)-c2cc(cc(N3CC[C@H](O)C3)c2)CO1]

Example 59 is prepared according to the synthesis route described in general Scheme C. (3S)-pyrrolidin-3-ol is used for the Buchwald reaction with the bromide intermediate 34 to give 4-[(3S)-3-hydroxypyrrolidin-1-yl]-8,14-dioxa-10,19,20-triazatetracyclo[13.5.2.$1^{2,6}$.$0^{18,21}$]tricosa-1(20),2,4,6(23),15,17,21-heptaen-9-one example 59.

LCMS method F: $[M+H]^+$=409.2, $t_R$=1.98 min

LCMS method G: $[M+H]^+$=409.2, $t_R$=1.96 min $^1H$ NMR (400 MHz, d6-DMSO) δ 12.84 (1H, m), 7.61-7.60 (1H, m), 7.48-7.45 (1H, m), 7.36 (1H, d, J=2.1 Hz), 7.21-6.93 (3H, m), 6.47 (1H, s), 5.25-5.21 (2H, m), 4.88-4.66 (1H, m) 4.48-4.45 (1H, m), 4.32-4.27 (2H, m), 3.53-3.32 (3H, m), 3.20-3.16 (3H, m), 2.16-2.07 (1H, m), 2.02-1.94 (3H, m) ppm.

Example 60: 4-fluoro-8,14-dioxa-10,19,20-triazapentacyclo[13.5.2.$1^{2,6}$.$1^{7,10}$.$0^{18,21}$]tetracosa-1(20),2(24),3,5,15(22),16,18(21)-heptaen-9-one

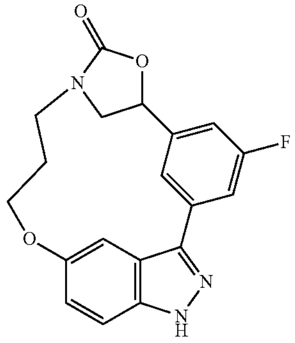 [SMILES: O=C1OC2CN1CCCOc1ccc3[nH]nc(c3c1)-c1cc(F)cc2c1]

Example 60 is prepared according to the synthesis route described below.

Preparation of Intermediate 65: 1-(3-bromo-5-fluorophenyl)-2-nitroethan-1-ol

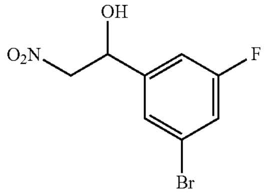 [SMILES: O=[N+]([O-])CC(O)c1cc(F)cc(Br)c1]

To a stirred solution of 3-bromo-5-fluorobenzaldehyde (2 g, 10 mmol) in THE (20 mL) was added dropwise at 0° C., nitromethane (0.536 mL, 10 mmol) and then dropwise sodium hydroxide solution 1N (10 mL, 10 mmol). The solution was stirred at 0° C. for 15 min. The solution was quenched with a solution of acetic acid (12 mL). To the resulting mixture was added water (25 mL). The water layer was extracted with EtOAc (4×50 mL). The combined organic layers were washed with saturated brine (2×50 mL). The organic layer was dried over sodium sulfate, filtered and the solvent was removed under reduced pressure to afford brown/orange oil. This residue was purified by flash chromatography on silica gel (Macherey Nagel, 120 g) with gradient elution: cyclohexane/EtOAc 0-30% to give 1-(3-bromo-5-fluorophenyl)-2-nitroethan-1-ol 65 as a white solid.

LCMS method F: $[M-H]^-$=262.2, $t_R$=2.28 min

Preparation of Intermediate 66: 2-amino-1-(3-bromo-5-fluorophenyl) ethan-1-ol

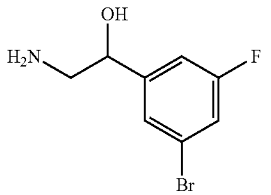 [SMILES: NCC(O)c1cc(F)cc(Br)c1]

To a solution of 1-(3-bromo-5~fluorophenyl)-2-nitro-ethan-1-ol 65 (6.2 g, 15.2 mmol) in EtOH (100 mL) was added Raney-Nickel (2 g) and 0.5 mL of acetic acid. Dihydrogen was bubbled in the mixture for 5 min. The reaction mixture was stirred for 16 h under dihydrogen atmosphere. The reaction mixture was filtered over celite and the solvent of the filtrate was removed under reduced pressure to give was 2-amino-1-(3-bromo-5-fluorophenyl) ethan-1-ol 66 which is directly used in the next step without purification.

LCMS method F: $[M+H]^+$=236, $t_R$=1.12 min

Preparation of Intermediate 67: 5-(3-bromo-5-fluorophenyl)-1,3-oxazolidin-2-one

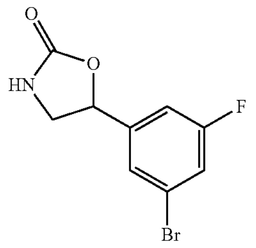 [SMILES: O=C1NCC(c2cc(F)cc(Br)c2)O1]

To a solution of 2-amino-1-(3-bromo-5-fluorophenyl) ethan-1-ol 66 (1.75 g, 1.75 mmol) in THE (100 mL) were added 1,1'-carbonyldiimidazole (1.34 g, 8.25 mmol) and imidazole (0.561 g, 8.25 mmol). The reaction mixture was stirred at RT for 16 h. To the reaction mixture was added a saturated aqueous solution of $NH_4Cl$ (100 mL). The mixture was extracted with ethyl acetate (2×50 mL). The combined organic layers were washed with water and brine, dried over sodium sulfate, filtered and concentrated under reduced pressure. The crude product was purified by column chromatography on a Biotage eluting with cyclohexane/ethyl acetate (3-1): 100/0 to 70/30 to give a white solid as 5-(3-bromo-5-fluorophenyl)-1,3-oxazolidin-2-one 67.

LCMS method F: $[M+H]^+$=262.0, $t_R$=2.07 min

Preparation of Intermediate 68: 5-(3-bromo-5-fluorophenyl)-3-{3-[(tert-butyldimethylsilyl)oxy]propyl}-1,3-oxazolidin-2-one

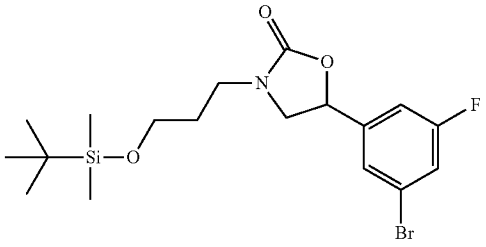 [SMILES: CC(C)(C)[Si](C)(C)OCCCN1CC(c2cc(F)cc(Br)c2)OC1=O]

To a stirred solution of 5-(3-bromo-5-fluorophenyl)-1,3-oxazolidin-2-one 67 (1.6 g, 6.1 mmol) in THE (10 mL) was added sodium hydride (0.366 g, 9.1 mmol) at 0° C. The solution was stirred at 0° C. for 10 min. Then a solution of (3-bromopropoxy)(tert-butyl)dimethylsilane (1.5 g, 6.1 mmol) in THF (10 mL) was added to the mixture. The mixture was stirred at room temperature for 16 h. The solution is quenched with a solution of saturated chloride ammonium (25 mL).

The resulting mixture was extracted with EtOAc (4×100 mL). Combined organic layers were washed with saturated brine (2×50 mL). The organic layer was dried over sodium sulfate, filtered and the solvent was removed under reduced pressure to afford a brown/orange oil. This residue was purified by flash chromatography on silica gel (Macherey Nagel, 24 g) with gradient elution: cyclohexane/EtOAc 0-50% to give 5-(3-bromo-5-fluorophenyl)-3-{3-[(tert-butyldimethylsilyl)oxy]propyl}-1,3-oxazolidin-2-one 68 as a yellow oil.

LCMS method F: $[M+H]^+$=434.0, $t_R$=3.42 min

Preparation of Intermediate 69: 5-(3-bromo-5-fluorophenyl)-3-(3-hydroxypropyl)-1,3-oxazolidin-2-one

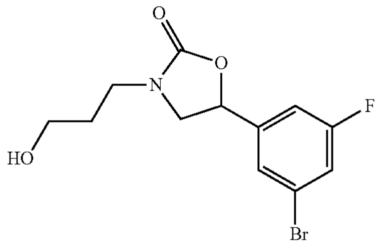 [SMILES: O=C1OC(c2cc(F)cc(Br)c2)CN1CCCO]

To a solution of 5-(3-bromo-5-fluorophenyl)-3-{3-[(tert-butyldimethylsilyl)oxy]propyl}-1,3-oxazolidin-2-one 68 (0.8 g, 1.85 mmol postulated) in tetrahydrofuran (50 mL) was added portion wise tetra-n-butylammonium fluoride 1.0 M in THE (1.85 mL, 1.85 mmol) at RT. The reaction mixture was stirred at RT for 3 h. The reaction mixture was poured into ice water (100 mL) and stirred for 10 min. The aqueous phase was extracted with ethyl acetate (2×100 mL).

The combined organic layers were washed with brine (100 mL), dried over magnesium sulfate and concentrated under reduces pressure. The residue was purified by flash-column chromatography (24 g silica BIOTAGE) chromatography (cyclohexane-ethyl acetate, 100/0 to 50/50) affording 5-(3-bromo-5-fluorophenyl)-3-(3-hydroxypropyl)-1,3-oxazolidin-2-one 69 a beige powder.

LCMS method F: $[M+H]^+$=320.0, $t_R$=2.02 min

Preparation of Intermediate 70: 3-[5-(3-bromo-5-fluorophenyl)-2-oxo-1,3-oxazolidin-3-yl]propyl methane sulfonate

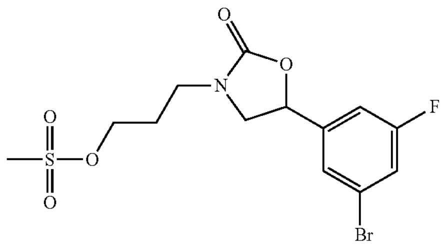 [SMILES: CS(=O)(=O)OCCCN1CC(c2cc(F)cc(Br)c2)OC1=O]

To a solution of 5-(3-bromo-5-fluorophenyl)-3-(3-hydroxypropyl)-1,3-oxazolidin-2-one 69 (0.5 g, 1.57 mmol) and diisopropylethylamine (0.545 mL, 3.14 mmol) in dichoromethane (50 mL) at 0° C., was added dropwise methanesulfonyl chloride (0.145 mL, 1.88 mmol). The reaction mixture was stirred at room temperature for 4 hours.

The reaction mixture was washed with a saturated solution of ammonium chloride, with a saturated solution of sodium bicarbonate and brine, filtered and the solvent was removed under reduced pressure to give 3-[5-(3-bromo-5-fluorophenyl)-2-oxo-1,3-oxazolidin-3-yl]propyl methane sulfonate 70 as a colorless oil.

LCMS method F: $[M+H]^+$=397.9, $t_R$=2.36 min

Preparation of Intermediate 71: 5-(3-bromo-5-fluorophenyl)-3-(3-{[1-(oxan-2-yl)-1H-indazol-5-yl]oxy}propyl)-1,3-oxazolidin-2-one

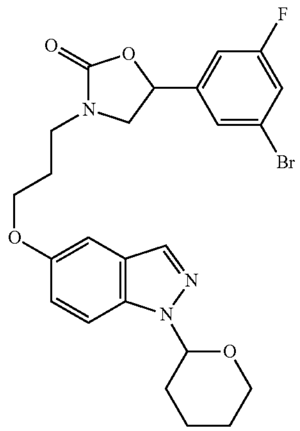 [SMILES: O=C1OC(c2cc(F)cc(Br)c2)CN1CCCOc1ccc2c(cnn2C2CCCCO2)c1]

To a solution of 3-[5-(3-bromo-5-fluorophenyl)-2-oxo-1,3-oxazolidin-3-yl]propyl methane sulfonate 70 (0.618 g, 1.57 mmol) in N,N-dimethylformamide (100 mL), cesium carbonate (1.02 g, 3.14 mmol) and 1-(oxan-2-yl)-1H-indazol-5-ol 29 (0.343 g, 1.57 mmol) were added. The reaction was stirred at 80° C. for 16 hours. The mixture was concentrated under reduced pressure. Water (200 mL) was added and the resulting mixture was extracted with EtOAc (4×100 mL). The combined organic layers were washed with brine (2×50 mL). The organic layers were dried over sodium sulfate, filtered and concentrated under reduced pressure to afford a brown/orange oil. This residue was purified by flash chromatography on silica gel (Macherey Nagel, 120 g) with gradient elution. cyclohexane/EtOAc 0-70% to give 5-(3-bromo-5-fluorophenyl)-3-(3-{[1-(oxan-2-yl)-1H-indazol-5-yl]oxy}propyl)-1,3-oxazolidin-2-one 71 as a white solid.

LCMS method F: $[M+H]^+$=520.0, $t_R$=2.91 min

Preparation of Intermediate 72: 4-fluoro-19-(oxan-2-yl)-8,14-dioxa-10,19,20-triazapenta cyclo [$13.5.2.1^{2,6}.1^{7,10}.0^{18,21}$]tetracosa-1(20),2(24), 3,5,15 (22),16,18(21)-heptaen-9-one

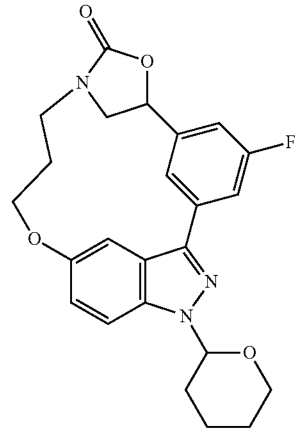 [SMILES: O=C1OC2CN1CCCOc1ccc3c(c1)c(nn3C1CCCCO1)-c1cc(F)cc2c1]

To a solution of 5-(3-bromo-5-fluorophenyl)-3-(3-{[1-(oxan-2-yl)-1H-indazol-5-yl]oxy}propyl)-1,3-oxazolidin-2-one 71 (50 mg, 0.0963 mmol) in 15 mL of toluene was added reagent potassium acetate (113 mg, 1.156 mmol) 2 eq) at room temperature. The mixture was degassed by bubbling nitrogen for 15 minutes. Palladium acetate (25 mg, 0.115 mmol, 0.2 eq) and cataxium (41 mg, 0.115 mmol, 0.2 eq) were added. The mixture was heated at 140° C. for 2 hours under microwaves conditions. The reaction mixture was filtered over celite and 20 mL of water was added to the filtrate. The aqueous layer was extracted with ethyl acetate (2×20 mL). The combined organic layers were washed with a brine, dried over sodium sulfate and concentrated under reduced pressure to an orange oil. A purification by column chromatography on a Biotage (cyclohexane/ethyl acetate 0-100%) afforded pure 4-fluoro-19-(oxan-2-yl)-8,14-dioxa-10,19,20-triazapentacyclo[$13.5.2.1^{2,6}.1^{7,10}$. $0^{18,21}$]tetracosa-1(20),2(24), 3,5,15(22),16,18(21)-heptaen-9-one 72 as a whitish solid.

LCMS method F: $[M+H]^+$=438.1, $t_R$=2.77 min

Preparation of Example 60: 4-fluoro-8,14-dioxa-10,19,20-triazapentacyclo[$13.5.2.1^{2,6}.1^{7,10}.0^{18,21}$]tetracosa-1(20),2(24),3,5,15(22),16,18(21)-heptaen-9-one

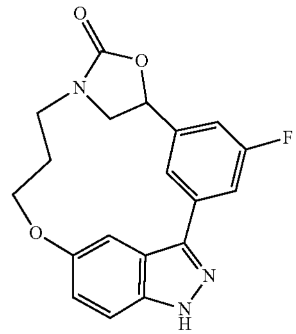 [SMILES: O=C1OC2CN1CCCOc1ccc3[nH]nc(c3c1)-c1cc(F)cc2c1]

To a solution of 4-fluoro-19-(oxan-2-yl)-8,14-dioxa-10,19,20-triazapentacyclo[13.5.2.1$^{2,6}$.1$^{7,10}$.0$^{18,21}$]tetracosa-1(20),2(24),3,5,15(22),16,18(21)-heptaen-9-one 72 (0.113 g; 0.258 mmol) in DCM (20 mL) was added trifluoroacetic acid (0.2 mL, 2.58 mmol) at room temperature. The mixture was stirred at room temperature for 24 h. The reaction is allowed to cool down to room temperature and toluene (50 mL) was added. The reaction mixture was concentrated under reduced pressure to give an orange oil. Water (25 mL), DCM (25 mL) and a 25 wt % aqueous solution of ammonia (1.5 mL) were added. After separation, the aqueous layer was extracted with DCM (2×20 mL). The combined organic layers were washed with brine, dried over sodium sulfate and concentrated under reduced pressure to an orange oil. A purification by column chromatography on a Biotage (DCM/MeOH 0-5%) afforded pure 4-fluoro-8,14-dioxa-10,19,20-triazapentacyclo[13.5.2.1$^{2,6}$.1$^{7,10}$.0$^{18,21}$]tetracosa-1(20),2(24),3,5, 15(22),16,18(21)-heptaen-9-one example 60 as a whitish solid.

LCMS method F: $[M+H]^+$=354.1, $t_R$=2.22 min

LCMS method G: $[M+H]^+$=354.2, $t_R$=2.22 min $^1$H NMR (400 MHz, d6-DMSO) δ 13.26-13.24 (1H, m), 8.22 (1H, s), 7.59 (1H, ddd, J=1.5, 2.5, 9.9 Hz), 7.52 (1H, d, J=8.9 Hz), 7.49 (1H, d, J=2.1 Hz), 7.36 (1H, td, J=1.8, 9.4 Hz), 7.02 (1H, dd, J=2.3, 9.3 Hz), 5.69 (1H, dd, J=2.8, 9.0 Hz), 4.47-4.38 (1H, m), 4.22 (1H, q, J=3.9 Hz), 4.17 (1H, t, J=6.0 Hz), 4.02-3.96 (1H, m), 3.57-3.46 (1H, m), 3.08 (1H, dd, J=4.6, 14.4 Hz), 2.36-2.25 (1H, m), 1.98-1.88 (1H, m) ppm.

Example 61: 4-(oxolan-3-yl)-8,14-dioxa-10,19,20-triazatetracyclo[13.5.2.1$^{2,6}$.0$^{18,21}$]tricosa-1(20),2,4,6(23),15,17,21-heptaen-9-one

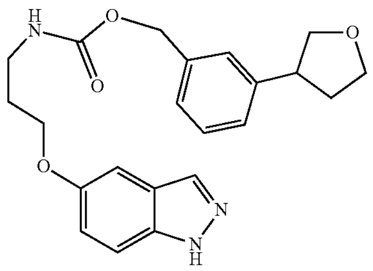 [SMILES: O=C(NCCCOc1ccc2[nH]ncc2c1)OCc1cccc(C2CCOC2)c1]

Example 61 is prepared according to the synthesis route described in general Scheme A.

Preparation of Intermediate 73: 4-(2,5-dihydrofuran-3-yl)-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one

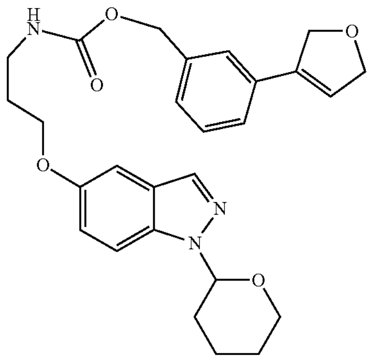 [SMILES: O=C(NCCCOc1ccc2c(cnn2C2CCCCO2)c1)OCc1cccc(C2=CCOC2)c1]

To a degassed solution of 4-bromo-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one 34 (125 mg, 0.25 mmol), 2-(2,5-dihydrofuran-3-yl)-4,4,5,5-tetramethyl-1,3,2-dioxaborolane (100 mg, 0.50 mmol), potassium phosphate tribasic (160 mg, 0.765 mmol) in dioxane/water (9/1, 5.0 mL) was added [1,1'-bis(diphenylphosphino)ferrocene] dichloropalladium(II) (18.5 mg, 0.025 mmol, 10 mol %) under argon at room temperature. The reaction mixture was stirred for 5 hours at 90° C. The reaction mixture was diluted with water (10 mL) and extracted with ethyl acetate (3×15 mL). The combined organic layers were washed with brine (15 mL), dried over anhydrous sodium magnesium sulfate, filtered and the solvent was removed under reduced pressure to afford 4-(2,5-dihydrofuran-3-yl)-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one 73 as an orange foam. The crude product was used in the next step without any further purification.

LCMS method F: $[M+H]^+$=476.1, $t_R$=2.74 min

Preparation of Intermediate 74: 19-(oxan-2-yl)-4-(oxolan-3-yl)-8,14-dioxa-10,19,20-triazatetracyclo[13.5.2.1$^{2,6}$.0$^{18,21}$]tricosa-1(20),2,4,6(23),15,17,21-heptaen-9-one

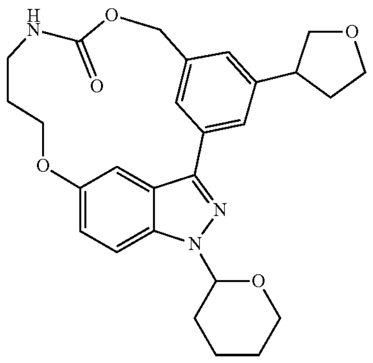 [SMILES: O=C1NCCCOc2ccc3c(c2)c(nn3C2CCCCO2)-c2cc(cc(C3CCOC3)c2)CO1]

To a stirred solution of 4-(2,5-dihydrofuran-3-yl)-19-(oxan-2-yl)-8,14-dioxa-10,19,20-triazatetracyclo

[13.5.2.1$^{2,6}$.0$^{18,21}$]tricosa-1(20),2,4,6(23),15,17,21-heptaen-9-one 73 (59 mg, 0.125 mmol) in 1.75 mL MeOH and 0.2 mL acetic acid was added 10% palladium on charcoal (1.5 mg, 0.0013 mmol, 10 mol %) and the mixture was stirred for 20 minutes at room temperature under an atmosphere of hydrogen. The mixture was then filtered, washing with DCM, and the solvent of the filtrate was removed under reduced pressure to afford 19-(oxan-2-yl)-4-(oxolan-3-yl)-8,14-dioxa-10,19,20-triazatetracyclo[13.5.2.1$^{2,6}$.0$^{18,21}$]tricosa-1(20),2,4,6(23),15,17,21-heptaen-9-one 74 as a colorless oil.

LCMS method F: $[M+H]^+$=478.1, $t_R$=2.71 min

Preparation of Example 61: 4-(oxolan-3-yl)-8,14-dioxa-10,19,20-triazatetracyclo[13.5.2.1$^{2,6}$.0$^{18,21}$]tricosa-1(20),2,4,6(23),15,17,21-heptaen-9-one

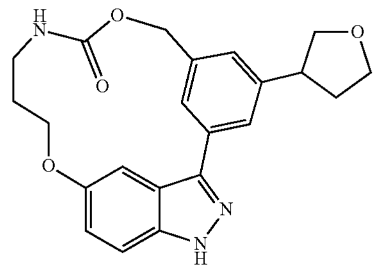 [SMILES: O=C1NCCCOc2ccc3[nH]nc(c3c2)-c2cc(cc(C3CCOC3)c2)CO1]

To a solution of 19-(oxan-2-yl)-4-(oxolan-3-yl)-8,14-dioxa-10,19,20-triazatetracyclo[13.5.2.1$^{2,6}$.0$^{18,21}$]tricosa-1(20),2,4,6(23),15,17,21-heptaen-9-one 74 (0.019 g, 0.039 mmol) in DCM (3 mL) was added trifluoro acetic acid (0.06 mL, 0.78 mmol). The mixture was heated under microwave conditions at 80° C. for 1 h. The solvent was removed under reduced pressure.

The crude residue was purified on preparative TLC (DCM/MeOH/$NH_3$: 90/9/1) to afford 4-(oxolan-3-yl)-8,14-dioxa-10,19,20-triazatetracyclo[13.5.2.1$^{2,6}$.0$^{18,21}$]tricosa-1(20),2,4,6(23), 15,17,21-heptaen-9-one example 61 as a white solid.

LCMS method F: $[M+H]^+$=394.1, $t_R$=2.13 min

LCMS method G: $[M+H]^+$=394.2, $t_R$=2.13 min $^1$H NMR (400 MHz, d6-DMSO, 80° C.) δ 12.88 (1H, br. s), 7.77 (2H, m), 7.65 (1H, br. s), 7.50-7.47 (1H, m), 7.35-7.33 (1H, m), 7.19 (1H, s), 6.99-6.96 (1H, dd, J=2.0, 8.8 Hz), 5.28 (2H, s), 4.34-4.28 (2H, m), 4.12-4.07 (1H, m), 4.03-3.97 (1H, m), 3.88-3.82 (1H, m), 3.67 (1H, t, J=5.2 Hz), 3.53-3.44 (1H, m), 3.22-3.11 (2H, m), 2.43-2.33 (1H, m), 2.06-1.96 (3H, m) ppm.

Example 62: (13S)-13-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

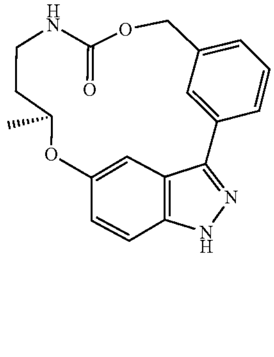 [SMILES: C[C@H]1CCNC(=O)OCc2cccc(c2)-c2n[nH]c3ccc(cc23)O1]

Example 62 is prepared according to the synthesis route described in general Scheme C and by chiral HPLC separation of example 50. The chiral separation is done on a Chiralpak IA column 20×250 mm 5 μm, eluent [C7/EtOH]+0.1% DEA [90/10] run time 40 min, 19 mL/min RT to give (13S)-13-methyl-8,14-dioxa-10,19,20-triazatetracyclo[13.5.2.1$^{2,6}$.0$^{18,21}$]tricosa-1(20),2(23), 3,5,15(22),16,18(21)-heptaen-9-one example 62.

LCMS method F: $[M+H]^+$=338.1, $t_R$=2.24 min

LCMS method G: $[M+H]^+$=338.1, $t_R$=2.25 min $^1$H NMR (400 MHz, d6-DMSO) δ 13.11 (1H, s), 7.93-7.84 (3H, m), 7.47 (2H, dd, J=8.4, 15.7 Hz), 7.29-7.25 (2H, m), 6.97 (1H, dd, J=2.2, 9.0 Hz), 5.77-5.71 (1H, m), 4.83-4.79 (1H, m), 4.59-4.53 (1H, m), 3.58 (1H, m), 2.94-2.85 (1H, m), 1.41-1.38 (4H, m), 1.25-1.14 (1H, m) ppm.

Chiral HPLC e.e. 98.2%

Example 63: (13R)-13-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

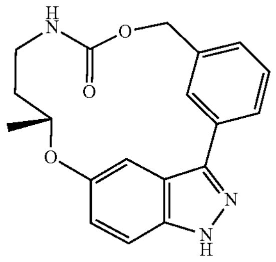 [SMILES: C[C@@H]1CCNC(=O)OCc2cccc(c2)-c2n[nH]c3ccc(cc23)O1]

Example 63 is prepared according to the synthesis route described in general Scheme C and by chiral HPLC separation of example 50. The chiral separation is done on a Chiralpak IA column 20×250 mm 5 μm, eluent [C7/EtOH]+0.1% DEA [90/10] run time 40 min, 19 mL/min RT to give (13R)-13-methyl-8,14-dioxa-10,19,20-triazatetracyclo[13.5.2.1$^{2,6}$.0$^{18,21}$]tricosa-1(20),2(23), 3,5,15(22),16,18(21)-heptaen-9-one example 63.

LCMS method F: $[M+H]^+$=338.2, $t_R$=2.25 min

LCMS method G: $[M+H]^+$=338.2, $t_R$=2.23 min $^1$H NMR (400 MHz, d6-DMSO) δ 13.11 (1H, s), 7.93-7.84 (3H, m), 7.47 (2H, dd, J=8.6, 15.1 Hz), 7.29-7.25 (2H, m), 6.97 (1H, dd, J=2.2, 9.0 Hz), 5.77-5.74 (1H, m), 4.83-4.79 (1H, m), 4.59-4.53 (1H, m), 3.59-3.54 (1H, m), 2.96-2.86 (1H, m), 1.42-1.38 (4H, m), 1.25-1.14 (1H, m) ppm.

Chiral HPLC e.e. 98.8%

Example 64: 4-(1-methyl-1H-pyrazol-3-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one

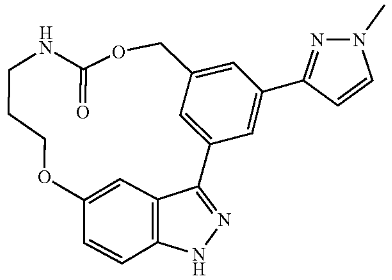 [SMILES: Cn1ccc(-c2cc3cc(c2)-c2n[nH]c4ccc(cc24)OCCCNC(=O)OC3)n1]

Example 64 is prepared according to the synthesis route described in general Scheme C. 1-Methyl-1H-pyrazole-3-boronic acid pinacol ester was used for the Suzuki coupling with the bromide intermediate 34 to give 4-(1-methyl-1H-pyrazol-3-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one example 64.

LCMS method F: $[M+H]^+$=404, $t_R$=2.12 min

LCMS method G: $[M+H]^+$=404, $t_R$=2.12 min $^1$H NMR (400 MHz, d6-DMSO) δ 12.93 (1H, s), 8.30 (1H, s), 7.82 (1H, s), 7.73-7.68 (3H, m), 7.51-7.49 (1H, d), 7.38 (1H, m), 7.01-6.98 (1H, dd), 6.71 (1H, d, J=2.3 Hz), 5.34 (2H, m), 4.35-4.31 (2H, m), 3.93 (3H, s), 3.19 (2H, m), 2.05 (2H, m) ppm.

Example 65: (7S)-7-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

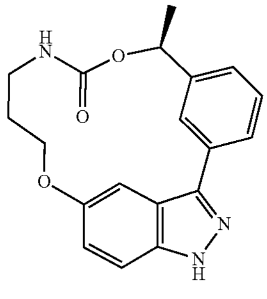 [SMILES: C[C@@H]1OC(=O)NCCCOc2ccc3[nH]nc(c3c2)-c2cccc1c2]

Example 65 is prepared according to the synthesis route described in general Scheme C. (1S)-1-[3-(4,4,5,5-tetramethyl-1,3,2-dioxaborolan-2-yl)phenyl]ethanol is used for the Suzuki coupling with intermediate 26 to give (7S)-7-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one example 65.

LCMS method F: $[M+H]^+$=338, $t_R$=2.19 min

LCMS method G: $[M+H]^+$=338, $t_R$=2.19 min $^1$H NMR (400 MHz, d6-DMSO) δ 13.12 (1H, s), 7.94 (1H, m), 7.86-7.84 (2H, m), 7.50-7.46 (2H, m), 7.35-7.29 (2H, m), 7.00-6.98 (1H, dd), 5.95-5.90 (1H, q), 4.38-4.23 (2H, m), 3.56-3.49 (1H, m), 2.78-2.70 (1H, m), 2.25-2.15 (1H, m), 1.77-1.69 (1H, m), 1.59 (3H, d) ppm.

Example 66: 4-[2-(morpholin-4-yl)ethoxy]-8,14-dioxa-10,19,20-triazatetracyclo[13.5.2.1$^{2,6}$.0$^{18,21}$]tricosa-1(20),2(23),3,5,15(22),16,18(21)-heptaen-9-one

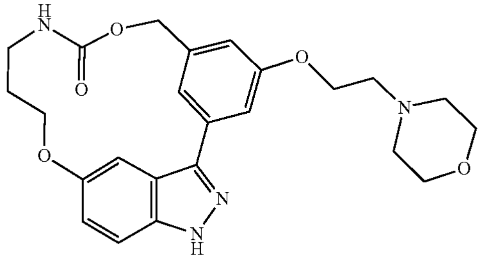 [SMILES: O=C1NCCCOc2ccc3[nH]nc(c3c2)-c2cc(cc(OCCN3CCOCC3)c2)CO1]

Example 66 is prepared according to the synthesis route described in general Scheme F.

Preparation of Intermediate 75: methyl 3-[5-[3-(benzyloxycarbonylamino)propoxy]-1-tetrahydropyran-2-yl-indazol-3-yl]-5-(2-morpholinoethoxy)benzoate

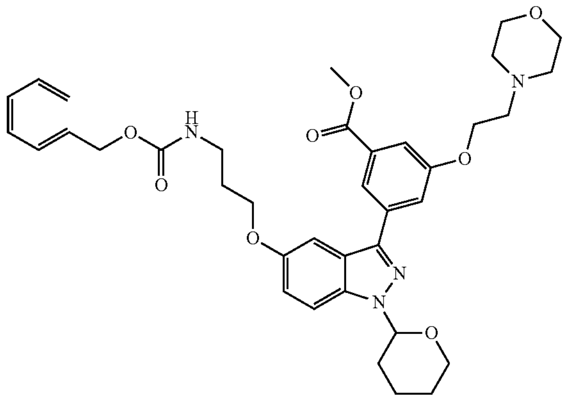 [SMILES: C=C/C=C\C=C\COC(=O)NCCCOc1ccc2c(c1)c(-c1cc(OCCN3CCOCC3)cc(C(=O)OC)c1)nn2C1CCCCO1]

To a solution of methyl 3-[5-[3-(benzyloxycarbonylamino)propoxy]-1-tetrahydropyran-2-yl-indazol-3-yl]-5-hydroxy-benzoate 53 (400 mg, 0.715 mmol), 2-morpholinoethanol (131 μL, 141 mg, 1.073 mmol) and $PPh_3$ (281 mg, 1.073 mmol) in THF (5.0 mL) was added dropwise a solution of DMEAD (251 mg, 1.073 mmol) in THE (2.5 mL). The resulting clear yellow solution was stirred at room temperature for 16 h. The solvents were evaporated under reduced pressure and the residue was partitioned between EtOAc (20 mL) and water (20 mL). The aqueous phase was extracted with EtOAc (3×20 mL) and the combined organic layers were washed with brine (1×20 mL), dried over anhydrous $Na_2SO_4$, filtered and concentrated under reduced pressure. The resulting crude material (yellow oil, 700 mg) was purified by column chromatography (40 g Macherey Nagel $SiO_2$, 30 mL/min, CyH/EtOAc 100:0 to 80:20 then $CH_2Cl_2$/MeOH 95:5) to afford methyl 3-[5-[3-(benzyloxycarbonylamino)propoxy]-1-tetrahydropyran-2-yl-indazol-3-yl]-5-(2-morpholinoethoxy)benzoate 75 as a pale yellow oil.

LCMS method F: $[M+H]^+$=673.3, $t_R$=2.24 min

Preparation of Intermediate 76: benzyl N-[3-[3-[3-(hydroxymethyl)-5-(2-morpholinoethoxy)phenyl]-1-tetrahydropyran-2-yl-indazol-5-yl]oxypropyl]carbamate

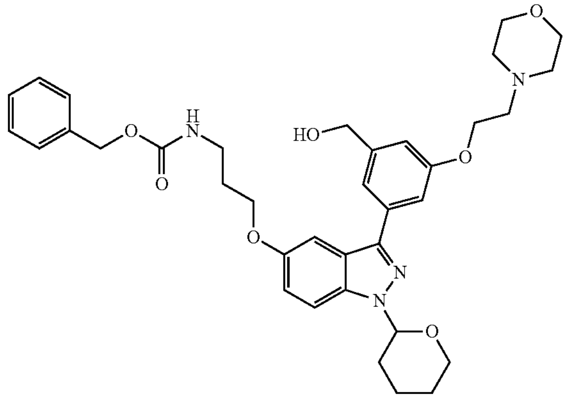 [SMILES: O=C(NCCCOc1ccc2c(c1)c(-c1cc(CO)cc(OCCN3CCOCC3)c1)nn2C1CCCCO1)OCc1ccccc1]

To a solution of methyl 3-[5-[3-(benzyloxycarbonylamino)propoxy]-1-tetrahydropyran-2-yl-indazol-3-yl]-5-(2-morpholinoethoxy)benzoate 75 (451 mg, 0.670 mmol) in THE (6.5 mL) at 0° C. was added dropwise $LiAlH_4$ (1.0 M solution in THF, 1.34 mL, 1.340 mmol). The resulting cloudy white solution was stirred at 0° C. for 1 h. The reaction was quenched with saturated aqueous Rochelle's salt (5 mL), EtOAc (20 mL) was added and the two layers were separated. The aqueous layer was extracted with EtOAc (3×10 mL) and the combined organic layers were washed with brine (1×5 mL), dried over anhydrous $Na_2SO_4$, filtered and the solvent was removed under reduced pressure to afford crude benzyl N-[3-[3-[3-(hydroxymethyl)-5-(2-morpholinoethoxy)phenyl]-1-tetrahydropyran-2-yl-indazol-5-yl]oxypropyl]carbamate 76 as a transparent oil which was used in the next step without further purification.

LCMS method F: $[M+H]^+$=645.3, $t_R$=2.07 min

Preparation of Intermediate 77: 4-[2-(morpholin-4-yl)ethoxy]-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one

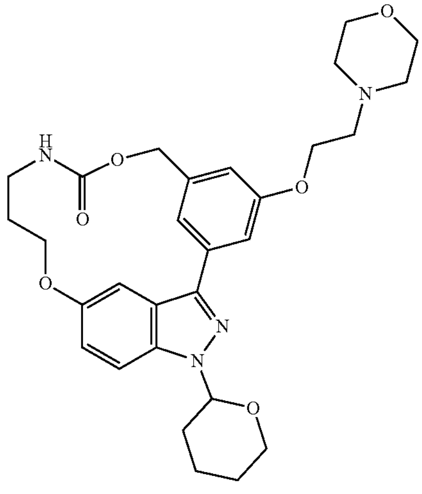 [SMILES: O=C1NCCCOc2ccc3c(c2)c(nn3C2CCCCO2)-c2cc(cc(OCCN3CCOCC3)c2)CO1]

To a solution of benzyl N-[3-[3-[3-(hydroxymethyl)-5-(2-morpholinoethoxy)phenyl]-1-tetrahydropyran-2-yl-indazol-5-yl]oxypropyl]carbamate 76 (200 mg, 0.310 mmol) in degassed MeCN (30.0 mL) was added $Cs_2CO_3$ (606 mg, 1.860 mmol). The resulting cloudy yellow solution was heated under reflux for 5 h. The mixture was cooled to room temperature, filtered and the solvent was removed under reduced pressure to afford crude 4-[2-(morpholin-4-yl)ethoxy]-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one 77 as a brown solid which was used in the next step without further purification.

LCMS method F: $[M+H]^+$=537.2, $t_R$=1.82 min

Preparation of Example 66: 4-[2-(morpholin-4-yl)ethoxy]-8,14-dioxa-10,19,20-triazatetracyclo[13.5.2.1$^{2,6}$.0$^{18,21}$]tricosa-1(20),2(23),3,5,15(22),16,18(21)-heptaen-9-one

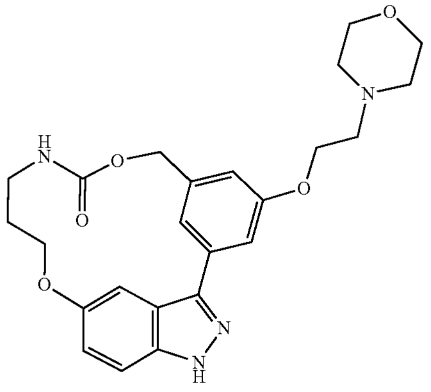 [SMILES: O=C1NCCCOc2ccc3[nH]nc(c3c2)-c2cc(cc(OCCN3CCOCC3)c2)CO1]

To a solution of crude 4-[2-(morpholin-4-yl)ethoxy]-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one 77 (189 mg, 0.310 mmol postulated) in $CH_2Cl_2$ (6.0 mL) was added TFA (475 μL, 707 mg, 6.200 mmol). The resulting clear yellow solution was stirred at room temperature for 6 h. Saturated aqueous $NaHCO_3$ (5 mL) was added and the two layers were separated. The aqueous layer was extracted with $CH_2Cl_2$ (3×5 mL) and the combined organic layers were washed with water (1×5 mL), dried over anhydrous $Na_2SO_4$, filtered and concentrated under reduced pressure. The residue was purified by preparative reverse-phase chromatography (Column XSELECT PHENYL-HEXYL 19*100 mm 5 μm, $[(NH_4)_2CO_3$ aq. 2 g/L/ACN]35% B to 55% B in 7 min, 19 mL/min RT) to afford 4-[2-(morpholin-4-yl)ethoxy]-8,14-dioxa-10,19,20-triazatetracyclo[13.5.2.1$^{2,6}$.0$^{18,21}$]tricosa-1(20),2(23),3,5,15(22),16,18(21)-heptaen-9-one example 66 as a pale orange solid.

LCMS method F: $[M+H]^+$=453.3, $t_R$=1.79 min

LCMS method G: $[M+H]^+$=453.3, $t_R$=2.80 min $^1$H NMR (400 MHz, d6-DMSO, 80° C.) δ 12.90 (brs, 1H), 7.67 (brs, 1H), 7.51 (brs, 1H), 7.48 (d, J=8.6 Hz, 1H), 7.42-7.40 (m, 1H), 7.36-7.34 (m, 1H), 6.98 (dd, J=8.6, 2.0 Hz, 1H), 6.90-6.88 (m, 1H), 5.25 (brs, 1H), 4.34-4.31 (m, 2H), 4.20 (t, J=5.7 Hz, 2H), 3.63-3.59 (m, 4H), 3.17 (brs, 2H), 2.77 (t, J=5.7 Hz, 2H), 2.55-2.52 (m, 4H), 2.03 (brs, 2H) ppm.

Example 67: 4-(2-methoxyethyl)-8,14-dioxa-10,19,20-triazatetracyclo[13.5.2.1$^{2,6}$.0$^{18,21}$]tricosa-1(20),2(23),3,5,15(22),16,18(21)-heptaen-9-one

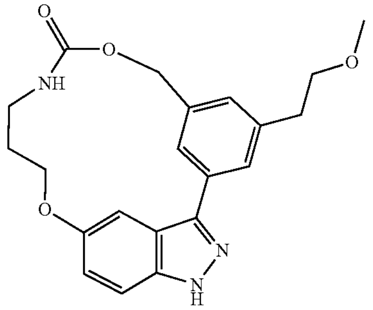 [SMILES: COCCc1cc2cc(c1)-c1n[nH]c3ccc(cc13)OCCCNC(=O)OC2]

Example 67 is prepared according to the synthesis route described in general Scheme A. Potassium (2-methoxyethyl) trifluoroborate is used for the Suzuki coupling with intermediate 26 to give 4-(2-methoxyethyl)-8,14-dioxa-10,19,20-triazatetracyclo[13.5.2.1$^{2,6}$.0$^{18,21}$]tricosa-1(20),2(23),3,5,15(22),16,18(21)-heptaen-9-one example 67.

LCMS method F: $[M+H]^+$=382.2, $t_R$=2.17 min

LCMS method G: $[M+H]^+$=382.2, $t_R$=2.18 min $^1$H NMR analysis indicated the presence of two rotamers.

$^1$H NMR (400 MHz, d6-DMSO, 80° C.) δ 12.87 (1H, br. s), 7.82 (0.4H, d, J=1.6 Hz, rot. 2), 7.74 (1.6H, d, J=4.9 Hz, rot. 1), 7.67-7.63 (1H, m), 7.50-7.46 (1H, m), 7.34 (1H, d, J=1.9 Hz), 7.22 (0.2H, s, rot. 2), 7.14 (0.8H, s, rot. 1), 6.99-6.96 (1H, m), 5.31-5.26 (2H, m), 4.34-4.28 (2H, m), 3.65 (2H, t, J=6.80 Hz), 3.30 (3H, s), 3.20-3.11 (2H, m), 2.91 (2H, t, J=6.7 Hz), 2.07-1.99 (3H, m) ppm.

Example 68: (7R)-7-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

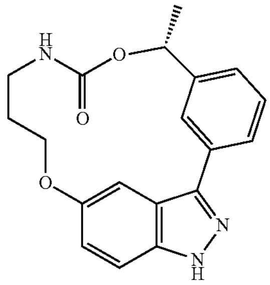 [SMILES: C[C@H]1OC(=O)NCCCOc2ccc3[nH]nc(c3c2)-c2cccc1c2]

Example 68 is prepared according to the synthesis route described in general Scheme C. (1R)-1-[3-(4,4,5,5-tetramethyl-1,3,2-dioxaborolan-2-yl)phenyl]ethanol is used for the Suzuki coupling with intermediate 26 to give (7R)-7-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one example 68.

LCMS method F: $[M+H]^+$=338.2, $t_R$=2.18 min

LCMS method G: $[M+H]^+$=338.2, $t_R$=2.19 min $^1$H NMR (400 MHz, d6-DMSO) δ 13.13-13.11 (1H, m), 7.94 (1H, dd, J=4.7, 7.4 Hz), 7.87-7.83 (2H, m), 7.51-7.46 (2H, m), 7.36-7.29 (2H, m), 6.99 (1H, dd, J=2.3, 9.1 Hz), 5.93 (1H, q, J=6.8 Hz), 4.38-4.23 (2H, m), 3.56-3.49 (1H, m), 2.78-2.70 (1H, m), 2.25-2.15 (1H, m), 1.78-1.69 (1H, m), 1.61-1.58 (3H, m) ppm.

Example 69: 5-cyclopropyl-8,14-dioxa-10,19,20-triazatetracyclo[13.5.2.1$^{2,6}$.0$^{18,21}$]tricosa-1(20),2,4,6(23),15,17,21-heptaen-9-one

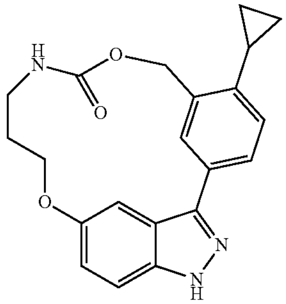 [SMILES: O=C1NCCCOc2ccc3[nH]nc(c3c2)-c2ccc(C3CC3)c(c2)CO1]

Example 69 is prepared according to the synthesis route described in general Scheme C. Potassium cyclopropyl (trifluoro)borate was used for the Suzuki coupling with the bromide intermediate 48 to give 5-cyclopropyl-8,14-dioxa-10,19,20-triazatetracyclo[13.5.2.1$^{2,6}$.0$^{18,21}$]tricosa-1(20),2,4,6(23),15,17,21-heptaen-9-one example 69.

LCMS method F: $[M+H]^+$=364, $t_R$=2.40 min

LCMS method G: $[M+H]^+$=364, $t_R$=2.40 min $^1$H NMR (400 MHz, d6-DMSO) δ 7.86-7.83 (2H, m), 7.74 (1H, s), 7.50-7.37 (3H, m), 7.16-7.13 (1H, m), 6.99-6.96 (1H, m), 5.48 (2H, s), 4.37-4.32 (2H, m), 3.20 (2H, s), 2.00 (1H, m), 1.92 (1H, m), 1.16 (1H, m), 1.02-0.97 (2H, m), 0.73-0.68 (2H, m) ppm.

Example 70: 4-(2-methoxyethoxy)-8,14-dioxa-10,19,20-triazatetracyclo[13.5.2.1$^{2,6}$.0$^{18,21}$]tricosa-1(20),2,4,6(23),15,17,21-heptaen-9-one

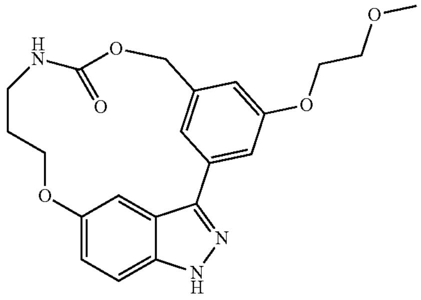 [SMILES: COCCOc1cc2cc(c1)-c1n[nH]c3ccc(cc13)OCCCNC(=O)OC2]

Example 70 is prepared according to the synthesis route described in general Scheme F and procedures analogous to those used to obtain example 66 to give 4-(2-methoxyethoxy)-8,14-dioxa-10,19,20-triazatetracyclo[13.5.2.1$^{2,6}$.0$^{18,21}$]tricosa-1(20),2,4,6(23),15,17,21-heptaen-9-one example 70.

LCMS method F: $[M+H]^+$=398.2, $t_R$=2.89 min

LCMS method G: $[M+H]^+$=398.2, $t_R$=2.13 min $^1$H NMR (400 MHz, d6-DMSO, 80° C.) δ 12.89 (brs, 1H), 7.67 (brs, 1H), 7.52 (s, 1H), 7.48 (d, J=8.9 Hz, 1H), 7.42-7.41 (m, 1H), 7.36 (d, J=1.9 Hz, 1H), 6.98 (dd, J=8.9, 1.9 Hz, 1H), 6.89 (s, 1H), 5.25 (brs, 2H), 4.34-4.29 (m, 2H), 4.21 (t, J=4.5 Hz, 2H), 3.72 (t, J=4.5 Hz, 2H), 3.37 (s, 3H), 3.22-3.12 (m, 2H), 2.08-1.98 (m, 2H) ppm.

Example 71: 4-fluoro-13-methyl-8,14-dioxa-10,19,20-triazatetracyclo[13.5.2.$1^{2,6}$.$0^{18,21}$]tricosa-1(20),2,4,6(23),15,17,21-heptaen-9-one

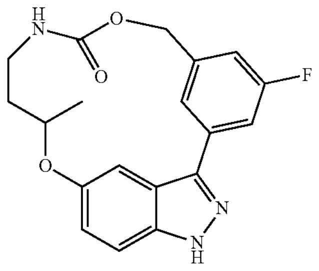 [SMILES: CC1CCNC(=O)OCc2cc(F)cc(c2)-c2n[nH]c3ccc(cc23)O1]

Example 71 is prepared according to the synthesis route described in general Scheme C to give 4-fluoro-13-methyl-8,14-dioxa-10,19,20-triazatetracyclo[13.5.2.$1^{2,6}$.$0^{18,21}$]tricosa-1(20),2,4, 6(23),15,17,21-heptaen-9-one example 71.

LCMS method F: $[M+H]^+$=356.1, $t_R$=2.37 min

LCMS method G: $[M+H]^+$=356.2, $t_R$=2.33 min $^1H$ NMR (400 MHz, d6-DMSO) δ 13.26 (1H, m), 8.01-7.96 (1H, m), 7.68 (1H, s), 7.61-7.50 (2H, m), 7.27 (1H, d, J=1.9 Hz), 7.17 (1H, ddd, J=1.4, 2.4, 9.5 Hz), 6.99 (1H, dd, J=2.2, 9.0 Hz), 5.71 (1H, d, J=13.7 Hz), 4.89-4.83 (1H, m), 4.62-4.54 (1H, m), 3.61-3.50 (1H, m), 2.94-2.86 (1H, m), 2.43-2.36 (1H, m), 1.42-1.39 (4H, m) ppm.

Example 72: 11-methyl-8,14-dioxa-10,19,20-triazatetracyclo[13.5.2.$1^{2,6}$.$0^{18,21}$]tricosa-1(20),2,4,6(23),15,17,21-heptaen-9-one

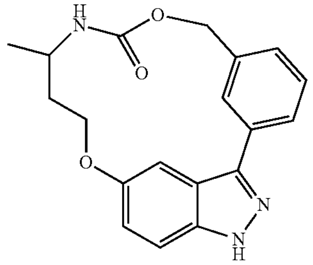 [SMILES: CC1CCOc2ccc3[nH]nc(c3c2)-c2cccc(c2)COC(=O)N1]

Example 72 is prepared according to the synthesis route described in general Scheme C to give 11-methyl-8,14-dioxa-10,19,20-triazatetracyclo[13.5.2.$1^{2,6}$.$0^{18,21}$]tricosa-1(20),2,4,6(23),15,17,21-heptaen-9-one example 72.

LCMS method F: $[M+H]^+$=338, $t_R$=2.26 min

LCMS method G: $[M+H]^+$=338, $t_R$=2.25 min $^1H$ NMR (400 MHz, d6-DMSO) δ 12.92-12.85 (1H, m), 7.95 (1H, s), 7.86 (1H, d, J=7.4 Hz), 7.56 (1H, s), 7.50-7.43 (2H, m), 7.35 (1H, d, J=2.1 Hz), 7.28-7.26 (1H, m), 6.99 (1H, dd, J=2.3, 8.9 Hz), 5.68 (1H, s), 4.94-4.89 (1H, m), 4.41-4.34 (2H, m), 3.88-3.81 (1H, m), 2.19 (1H, s), 1.97-1.95 (1H, m), 1.25-1.22 (3H, m) ppm.

Example 73: 4-(3-oxomorpholin-4-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one

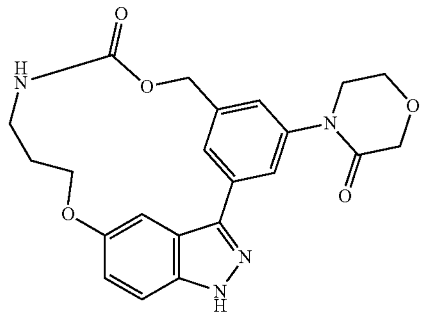 [SMILES: O=C1NCCCOc2ccc3[nH]nc(c3c2)-c2cc(cc(N3CCOCC3=O)c2)CO1]

Example 73 is prepared according to the synthesis route described in general Scheme C and analogues procedures have been used as to obtain example 12. Morpholin-3-one is used for the Buchwald reaction with the bromide intermediate 34 to give 4-(3-oxomorpholin-4-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one example 73.

LCMS method F: $[M+H]^+$=423, $t_R$=1.88 min

LCMS method G: $[M+H]^+$=423, $t_R$=1.87 min $^1H$ NMR (400 MHz, d6-DMSO) δ 12.99 (1H, s), 7.87 (1H, s), 7.80 (1H, s), 7.72 (1H, s), 7.48 (1H, s), 7.34 (2H, d, J=10.8 Hz), 6.99 (1H, dd, J=2.1, 8.9 Hz), 5.31 (2H, s), 4.35-4.30 (2H, m), 4.24 (2H, s), 4.03 (2H, t, J=5.1 Hz), 3.82 (2H, t, J=5.0 Hz), 3.18 (2H, s), 2.06 (2H, s) ppm.

Example 74: 4-(2-oxopyrrolidin-1-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one

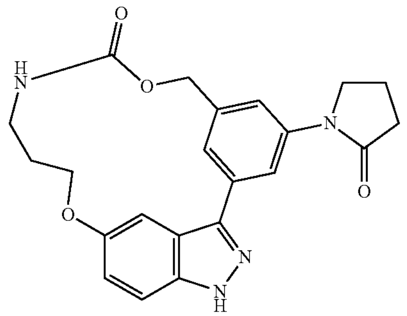 [SMILES: O=C1NCCCOc2ccc3[nH]nc(c3c2)-c2cc(cc(N3CCCC3=O)c2)CO1]

Example 74 is prepared according to the synthesis route described in general Scheme C and procedures analogous to those used to obtain example 12. Pyrrolidin-2-one is used for the Buchwald reaction with the bromide intermediate 34 to give 4-(2-oxopyrrolidin-11-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one example 74.

LCMS method F: $[M+H]^+$=407, $t_R$=2.02 min

LCMS method G: $[M+H]^+$=407, $t_R$=2.01 min $^1H$ NMR (400 MHz, d6-DMSO) δ 12.93 (1H, s), 8.14 (1H, s), 7.69 (2H, s), 7.59 (1H, s), 7.48 (1H, d, J=9.54 Hz), 7.35 (1H, s), 6.98 (1H, dd, J=2.4, 9.0 Hz), 5.28 (2H, s), 4.32 (2H, m), 3.93 (2H, m), 3.17 (2H, m), 3.53 (2H, m), 3.13 (2H, m), 2.03 (2H, m) ppm.

Example 75: 5-(2-oxopyrrolidin-1-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one

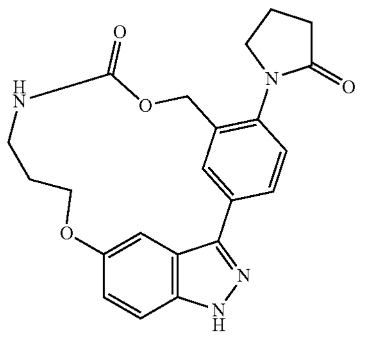 [SMILES: O=C1NCCCOc2ccc3[nH]nc(c3c2)-c2ccc(N3CCCC3=O)c(c2)CO1]

Example 75 is prepared according to the synthesis route described in general Scheme C and procedures analogous to those used to obtain example 12. Pyrrolidin-2-one is used for the Buchwald reaction with the bromide intermediate 48 to give 5-(2-oxopyrrolidin-1-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one example 75.

LCMS method F: $[M+H]^+$=407, $t_R$=1.92 min

LCMS method G: $[M+H]^+$=407, $t_R$=1.92 min $^1$H NMR (400 MHz, d6-DMSO) δ 12.95 (1H, s), 7.97-7.93 (2H, m), 7.71 (1H, s), 7.48 (1H, s), 7.40-7.37 (2H, m), 6.99 (1H, dd, J=2.2, 8.8 Hz), 5.11 (2H, s), 4.36-4.31 (2H, m), 3.81 (2H, t, J=6.9 Hz), 3.17 (2H, s), 3.06 (2H, m hidden), 2.23-2.18 (2H, m), 2.03 (2H, m) ppm.

Example 76: 4-(2-methylpyrrolidin-1-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one

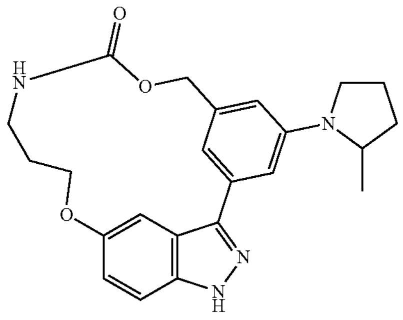 [SMILES: CC1CCCN1c1cc2cc(c1)-c1n[nH]c3ccc(cc13)OCCCNC(=O)OC2]

Example 76 is prepared according to the synthesis route described in general Scheme C and procedures analogous to those used to obtain example 12. 2-Methylpyrrolidine is used for the Buchwald reaction with the bromide intermediate 34 to give 4-(2-methylpyrrolidin-1-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one example 76.

LCMS method F: $[M+H]^+$=407, $t_R$=2.27 min

LCMS method G: $[M+H]^+$=407, $t_R$=2.56 min $^1$H NMR (400 MHz, d6-DMSO) δ 12.75 (1H, m), 7.61-7.58 (1H, m), 7.47-7.44 (1H, m), 7.36 (1H, d, J=2.3 Hz), 7.18 (1H, s), 7.05 (1H, s), 6.95 (1H, dd, J=2.4, 9.0 Hz), 6.50 (1H, s), 5.24-5.21 (2H, m), 4.32-4.27 (2H, m), 3.98-3.95 (1H, m), 3.48-3.43 (1H, m), 3.19 (2H, m), 2.12-1.97 (6H, m), 1.73-1.70 (1H, m), 1.19 (3H, d, J=6.1 Hz) ppm.

Example 77: 2-{9-oxo-8,14-dioxa-10,19,20-triazatetracyclo[13.5.2.1$^{2,6}$.0$^{18,21}$]tricosa-1(20),2(23),3,5,15(22),16,18(21)-heptaen-4-yl}acetonitrile

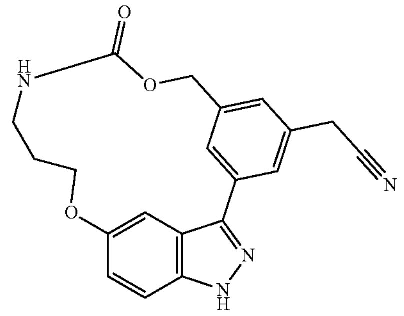 [SMILES: N#CCc1cc2cc(c1)-c1n[nH]c3ccc(cc13)OCCCNC(=O)OC2]

Example 77 is prepared according to the synthesis route described in general Scheme C.

Preparation of Intermediate 78: 2-[19-(oxan-2-yl)-9-oxo-8,14-dioxa-10,19,20-triazatetra cyclo [13.5.2.1$^{2,6}$.0$^{18,21}$]tricosa-1(20),2(23),3,5,15(22),16,18(21)-heptaen-4-yl]acetonitrile

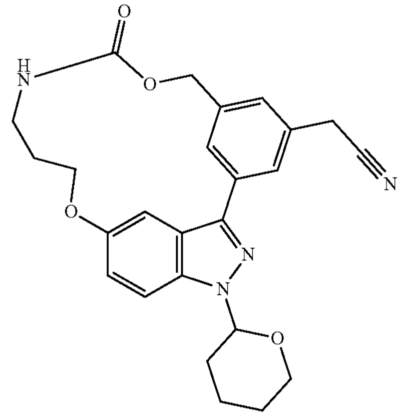 [SMILES: N#CCc1cc2cc(c1)-c1nn(C3CCCCO3)c3ccc(cc13)OCCCNC(=O)OC2]

To a solution of 4-bromo-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one 34 (100 mg, 0.21 mmol) in DMSO (2 mL) was added isoxazol-3-ylboronic acid (49 mg, 0.25 mmol) and a 1 M solution of potassium fluoride (0.63 mL, 0.63 mmol) at RT. The reaction mixture was degassed for 15 min by bubbling nitrogen gas, then[1,1'-Bis(diphenylphosphino)ferrocene]dichloropalladium(II) (15 mg, 0.02 mmol) was added the reaction mixture was stirred at 130° C. for 18 hours. The reaction mixture was filtered over celite, washed with ethyl acetate and concentrated under reduced pressure. EtOAc (30 mL) and water (10 mL) were added, the mixture was filtered over celite. The two layers were separated, the organic layer was extracted with EtOAc (2×20 mL), washed with brine, dried over sodium sulfate, filtered and concentrated under reduced pressure to give a black oil. The residue was purified by flash chromatography (CyH/AE 5/5) to afford 2-[19-(oxan-2-yl)-9-oxo-8,14-dioxa-10,19,20-triazatetracyclo[13.5.2.1$^{2,6}$.0$^{18,21}$]tricosa-1(20),2(23),3,5,15(22),16,18(21)-heptaen-4-yl]acetonitrile 78 as a white solid.

LCMS method F: $[M+H]^+$=447, $t_R$=2.64 min

Preparation of Example 77: 2-{9-oxo-8,14-dioxa-10,19,20-triazatetracyclo[13.5.2.1$^{2,6}$.0$^{18,21}$]tricosa-1(20),2(23),3,5,15(22),16,18(21)-heptaen-4-yl}acetonitrile

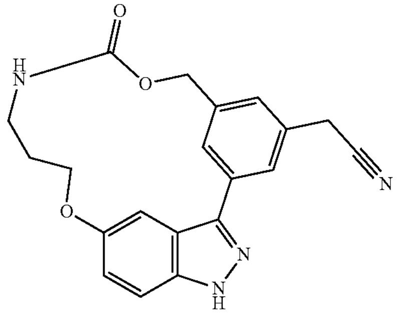 [SMILES: N#CCc1cc2cc(c1)-c1n[nH]c3ccc(cc13)OCCCNC(=O)OC2]

To a solution of 2-[19-(oxan-2-yl)-9-oxo-8,14-dioxa-10,19,20-triazatetracyclo[13.5.2.1$^{2,6}$.0$^{18,21}$]tricosa-1(20),2(23),3,5,15(22),16,18(21)-heptaen-4-yl]acetonitrile 78 (38 mg, 0.085 mmol) in DCM (2 mL) was added TFA (130 µL, 1.70 mmol) and the reaction mixture was stirred at RT for 12 hours. To the reaction mixture was added a saturated solution sodium bicarbonate (10 mL) and DCM (10 mL). The two layers were separated, the organic layer was extracted twice with DCM (10 mL), washed with brine, dried over sodium sulfate, filtered and concentrated under reduced pressure to give a yellow oil. The residue was put in diethyl ether and water, the precipitate was filtered to afford 2-{9-oxo-8,14-dioxa-10,19,20-triazatetracyclo[13.5.2.1$^{2,6}$.0$^{18,21}$]tricosa-1(20),2(23),3,5,15(22),16,18(21)-heptaen-4-yl}acetonitrile example 77 as a white solid.

LCMS method F: $[M+H]^+$=363, $t_R$=2.08 min

LCMS method G: $[M+H]^+$=363, $t_R$=2.08 min $^1$H NMR (400 MHz, d6-DMSO) δ 12.97 (1H, s), 7.90-7.85 (2H, m), 7.73-7.69 (1H, m), 7.52-7.48 (1H, m), 7.35 (1H, d, J=1.9 Hz), 7.25 (1H, s), 6.99 (1H, dd, J=2.3, 8.9 Hz), 5.30 (2H, s), 4.32 (2H, dd, J=7.6, 8.7 Hz), 4.10 (2H, s), 3.17 (2H, s), 2.02 (2H, s) ppm.

Example 78: (11R) or (11S)-11-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

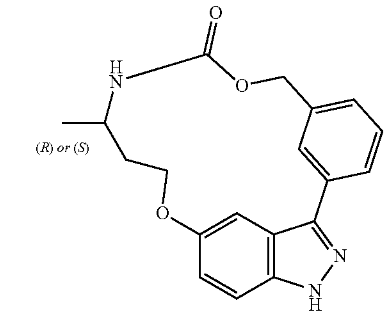 [SMILES: CC1CCOc2ccc3[nH]nc(c3c2)-c2cccc(c2)COC(=O)N1]

Example 78 is prepared according to the synthesis route described in general Scheme C and by chiral HPLC separation of the two enantiomers of example 72. The chiral separation is done on a Chiralpak IA column 20×250 mm 5 µm, eluent [C7/EtOH]+0.1% DEA [90/10] run time 40 min, 19 mL/min RT to give (11R) or (11S)-11-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one example 78.

LCMS method F: $[M+H]^+$=338, $t_R$=2.27 min

LCMS method G: $[M+H]^+$=338, $t_R$=2.27 min $^1$H NMR (400 MHz, d6-DMSO) δ 12.90 (1H, s), 7.94 (1H, s), 7.84 (1H, d, J=7.8 Hz), 7.57 (1H, s), 7.50-7.43 (2H, m), 7.36 (1H, s), 7.28-7.26 (1H, m), 6.99 (1H, dd, J=2.3, 8.9 Hz), 5.67 (1H, m), 4.90 (1H, m), 4.39-4.34 (2H, m), 3.82 (1H, s), 2.20 (1H, m), 1.93 (1H, m), 1.25-1.22 (3H, m) ppm.

Chiral HPLC e.e. 98.2%

The compound is a pure enantiomer, but the absolute stereochemistry of the chiral center is unknown.

Example 79: (11R) or (11S)-11-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

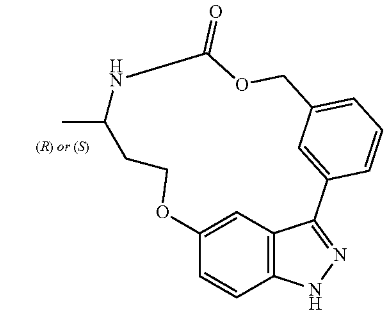 [SMILES: CC1CCOc2ccc3[nH]nc(c3c2)-c2cccc(c2)COC(=O)N1]

Example 79 is prepared according to the synthesis route described in general Scheme C and by chiral HPLC separation of the two enantiomers. The chiral separation is done on a Chiralpak IA column 20×250 mm 5 µm, eluent [C7/EtOH]+0.1% DEA [90/10] run time 40 min, 19 mL/min RT to give (11R) or (11S)-11-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one example 79.

LCMS method F: $[M+H]^+$=338, $t_R$=2.27 min

LCMS method G: $[M+H]^+=338$, $t_R=2.26$ min $^1H$ NMR (400 MHz, DMSO) δ 12.89 (1H, s), 7.94 (1H, s), 7.87-7.84 (1H, m), 7.55 (1H, m), -7.47 (2H, m), 7.35 (1H, m), 7.28-7.26 (1H, m), 7.01-6.97 (1H, m), 5.66 (1H, m), 4.90 (1H, m), 4.41-4.34 (2H, m), 3.87-3.81 (1H, m), 2.22 (1H, m), 1.93 (1H, m), 1.25-1.22 (3H, m) ppm.

Chiral HPLC e.e. 98.5%

The compound is a pure enantiomer, but the absolute stereochemistry of the chiral center is unknown.

Example 80: 4-ethynyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

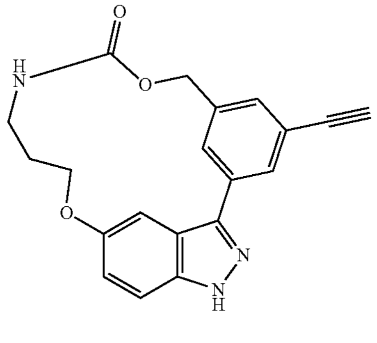 [SMILES: C#Cc1cc2cc(c1)-c1n[nH]c3ccc(cc13)OCCCNC(=O)OC2]

Example 80 is prepared according to the synthesis route described in general Scheme C.

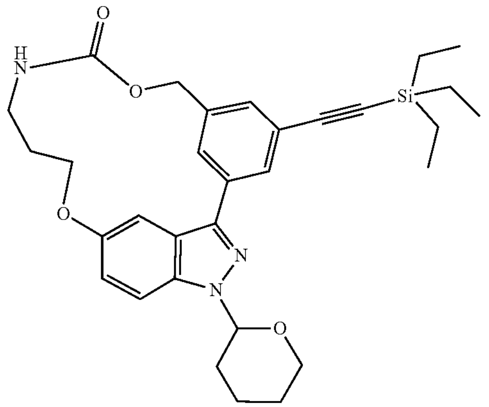 [SMILES: CC[Si](C#Cc1cc2cc(c1)-c1nn(C3CCCCO3)c3ccc(cc13)OCCCNC(=O)OC2)(CC)CC]

Preparation of Intermediate 79: 19-(oxan-2-yl)-4-[2-(triethylsilyl)ethynyl]-8,14-dioxa-10,19,20-triazatetracyclo[13.5.2.1$^{2,6}$.0$^{18,21}$]tricosa-1(20),2(23),3,5,15(22),16,18(21)-heptaen-9-one To a solution of intermediate 34 (100 mg, 0.21 mmol) in THF (2 mL) in a sealed tube were added triethyl(ethynyl) silane (44.1 mg, 0.31 mmol) and triethylamine (63.63 mg, 0.63 mmol). The reaction mixture was degassed for 15 min by bubbling nitrogen gas and $Pd(PPh_3)_4$(12 mg, 0.01 mmol) and copper iodide (0.4 mg, 0.0021 mmol) were added. The reaction mixture was stirred at 80° C. for 12 hours. The reaction mixture was concentrated under reduced pressure to give a yellow oil. To the residue were added EtOAc (20 mL) and water (10 mL), after separation of the two layers, the organic layer was extracted twice with EtOAc (10 mL), washed with brine, dried over sodium sulfate, filtered and the solvent was removed under reduced pressure to give an off-white solid. Diethyl ether was added to the residue, the beige precipitate was filtered, washed with water, to afford 19-(oxan-2-yl)-4-[2-(triethylsilyl)ethynyl]-8,14-dioxa-10,19,20-triazatetracyclo[13.5.2.1$^{2,6}$.0$^{18,21}$]tricosa-1(20),2(23),3,5,15(22),16,18(21)-heptaen-9-one 79 as a beige solid.

LCMS method F: $[M+H]^+=546$, $t_R=3.88$ min

Preparation of Intermediate 80: 4-ethynyl-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one

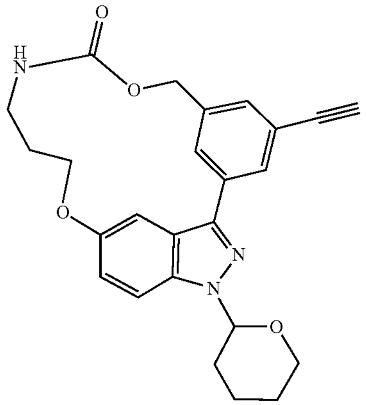 [SMILES: C#Cc1cc2cc(c1)-c1nn(C3CCCCO3)c3ccc(cc13)OCCCNC(=O)OC2]

To a solution of 19-(oxan-2-yl)-4-[2-(triethylsilyl)ethynyl]-8,14-dioxa-10,19,20-triazatetra cyclo[13.5.2.1$^{2,6}$.0$^{18,21}$]tricosa-1(20),2(23),3,5,15(22),16,18(21)-heptaen-9-one 79 (97 mg, 0.21 mmol) in MeOH (2 mL) was added potassium carbonate (87 mg, 0.63 mmol). The resulting reaction mixture was stirred at 60° C. for 3 h. The reaction mixture was filtered and washed with water to afford 4-ethynyl-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one 80 as a white solid.

LCMS method F: $[M+H]^+=432$, $t_R=2.93$ min (current 20V)

Preparation of Example 80: 4-ethynyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

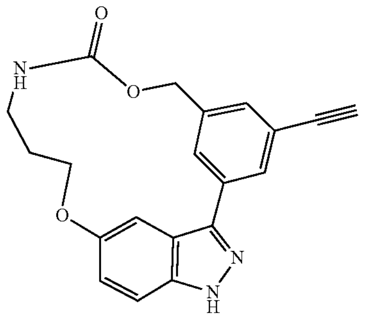 [SMILES: C#Cc1cc2cc(c1)-c1n[nH]c3ccc(cc13)OCCCNC(=O)OC2]

To a solution of 4-ethynyl-19-(oxan-2-yl)-8,14-dioxa-10,19,20-triazatetracyclo[13.5.2.1$^{2,6}$.0$^{18,21}$]tricosa-1(20),2(23), 3,5,15(22),16,18(21)-heptaen-9-one 80 (45 mg, 0.10 mmol) in DCM (2 mL) was added TFA (147 μL, 2.00 mmol) and stirred at RT for 12 hours. To the reaction mixture was added a saturated solution sodium bicarbonate (10 mL) and DCM (10 mL). The two layers were separated and the water layer was extracted twice with DCM (10 mL). The combined organic layers were washed with brine, dried over sodium sulfate, filtered and concentrated under reduced pressure to give a yellow oil. The residue was purified by flash chromatography (CyH/AE 5/5) to afford 4-ethynyl-8,14-dioxa-10,19,20-triazatetracyclo[13.5.2.1$^{2,6}$.0$^{18,21}$]tricosa-1(20),2(23),3,5,15(22),16,18(21)-heptaen-9-one example 80 as a white solid.

LCMS method F: $[M+H]^+$=348, $t_R$=2.30 min

LCMS method G: $[M+H]^+$=348, $t_R$=2.30 min $^1$H NMR (400 MHz, d6-DMSO) δ 13.02 (1H, s), 7.93 (2H, d, J=16.3 Hz), 7.74-7.72 (1H, m), 7.52-7.48 (1H, m), 7.39 (1H, s), 7.32 (1H, d, J=1.9 Hz), 7.00 (1H, dd, J=2.3, 9.1 Hz), 5.29-5.27 (2H, m), 4.35-4.29 (2H, m), 4.08-4.07 (1H, m), 3.18 (2H, s), 2.02 (2H, s) ppm.

Example 81: 4-(piperazin-1-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one

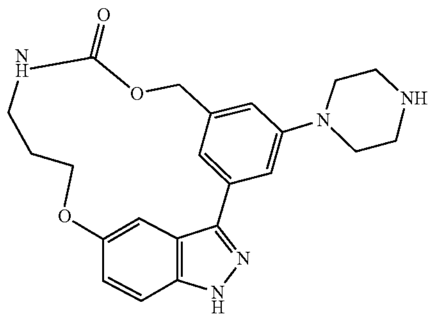 [SMILES: O=C1NCCCOc2ccc3[nH]nc(c3c2)-c2cc(cc(N3CCNCC3)c2)CO1]

Example 81 is prepared according to the synthesis route described in general Scheme A. Tert-butyl piperazine-1-carboxylate is used for the Buchwald reaction with the bromide intermediate 34 to give 4-(piperazin-1-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one example 81.

LCMS method F: $[M+H]^+$=408.2, $t_R$=1.45 min

LCMS method G: $[M+H]^+$=408.2, $t_R$=1.85 min $^1$H NMR (400 MHz, d6-DMSO, 80° C.) δ 12.82 (1H, s), 7.62 (1H, s), 7.47 (1H, d, J=9.3 Hz), 7.39-7.33 (3H, m), 6.96 (1H, dd, J=2.3, 8.9 Hz), 6.88-6.86 (1H, m), 5.23-5.22 (2H, m), 4.33-4.27 (2H, m), 3.21-3.16 (7H, m), 2.96-2.92 (4H, m), 2.06-1.99 (2H, m) ppm.

Example 82: 4-(1,2,3,6-tetrahydropyridin-4-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one

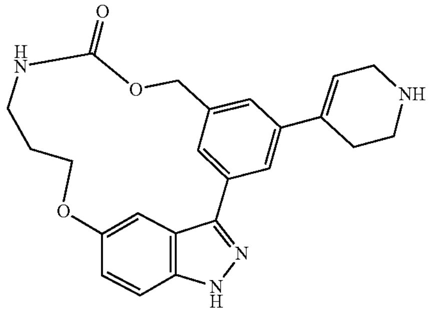 [SMILES: O=C1NCCCOc2ccc3[nH]nc(c3c2)-c2cc(cc(C3=CCNCC3)c2)CO1]

Example 82 is prepared according to the synthesis route described in general Scheme A. Tert-butyl 4-(4,4,5,5-tetramethyl-1,3,2-dioxaborolan-2-yl)-3,6-dihydro-2H-pyridine-1-carboxylate is used for the Suzuki coupling with the bromide intermediate 34 to give 4-(1,2,3,6-tetrahydropyridin-4-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one example 82.

LCMS method F: $[M+H]^+$=405.2, $t_R$=1.49 min

LCMS method G: $[M+H]^+$=405.2, $t_R$=1.95 min $^1$H NMR (400 MHz, d6-DMSO, 80° C.) δ 12.95 (1H, s), 7.89 (1H, s), 7.79 (1H, s), 7.70-7.65 (1H, m), 7.50-7.47 (1H, m), 7.35-7.32 (2H, m), 6.98 (1H, dd, J=2.4, 9.2 Hz), 6.29-6.25 (1H, m), 5.37-5.30 (2H, m), 4.34-4.28 (2H, m), 3.50-3.44 (2H, m), 3.14-3.00 (5H, m), 2.48-2.41 (2H, m), 2.06-2.03 (2H, m) ppm.

Example 83: 11-(methoxymethyl)-8,14-dioxa-10,19,20-triazatetracyclo[13.5.2.1$^{2,6}$.0$^{18,21}$]tricosa-1(20),2(23),3,5,15(22),16,18(21)-heptaen-9-one

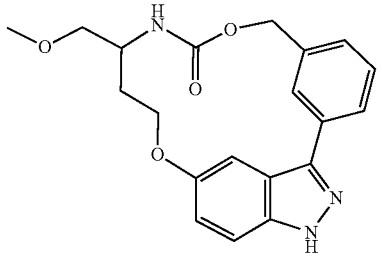 [SMILES: COCC1CCOc2ccc3[nH]nc(c3c2)-c2cccc(c2)COC(=O)N1]

Example 83 is prepared according to the synthesis route described in general Scheme C.

Preparation of Intermediate 81: 3-benzylamino-4-methoxy-but-2-enoic acid methyl ester

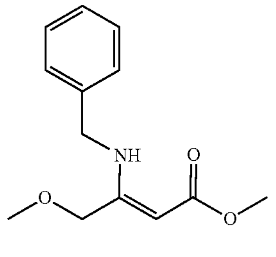

A solution of methyl-4-methoxyacetoacetate (5.00 g, 34.24 mmol), benzylamine (3.73 mL, 34.24 mmol) and acetic acid (0.097 mL, 1.71 mmol) in toluene (24 mL) was heated at 60° C. for 6 hours. The mixture was concentrated under reduced pressure to give 3-benzylamino-4-methoxy-but-2-enoic acid methyl ester 81 as an orange oil. The crude was used in the next step without purification.

Preparation of Intermediate 82: methyl 3-(benzylamino)-4-methoxy-butanoate

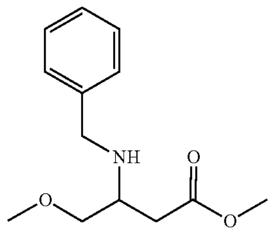

To a solution of 3-benzylamino-4-methoxy-but-2-enoic acid methyl ester 81 (8.66 g, 34.24 mmol postulated) in DCE (80 mL) were added at 0° C., acetic acid (9.77 mL, 171 mmol) and sodium tris(acetoxy)borohydride (21.67 g, 102.72 mmol). The reaction mixture was allowed to warm up to room temperature, then stirred at room temperature for 17 hours. The mixture was diluted with DCM (30 mL), quenched with a saturated solution of $NaHCO_3$ (40 mL). Water (50 mL) was added and the aqueous layer was extracted with DCM (2×70 mL). The combined organic layers were washed with brine (100 mL), dried over anhydrous sodium sulfate, filtered and concentrated under reduced pressure. The crude was purified by column (Macherey Nagel, 330 g) chromatography with cyclohexane/EtOAc (100/0 to 0/100) as eluent. DCM/MeOH (90/10) was used to elute the product. The desired fractions were combined and evaporated under reduced pressure to give methyl 3-(benzylamino)-4-methoxy-butanoate 82 as a brown oil.

LCMS method F: $[M+H]^+=238$, $t_R=0.94$ min

Preparation of Intermediate 83: 3-(benzylamino)-4-methoxy-butan-1-ol

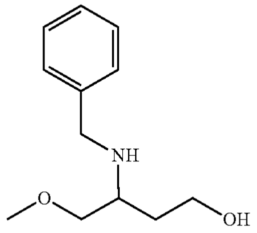

To a solution of methyl 3-(benzylamino)-4-methoxy-butanoate 82 (3.97 g, 16.8 mmol) in THE (70 mL) under $N_2$, LAH 1 M in THE (20.2 mL, 20.2 mmol) was added at 0° C. The reaction was stirred at 0° C. for 18 hours. The mixture was quenched with water (1.8 mL), NaOH 10% (1.8 mL) and water (1.8 mL). The mixture was filtered with EtOAc as eluent. The filtrate was diluted with water (50 mL) and extracted with EtOAc (3×50 mL). Combined organic layers were washed with brine (100 mL), dried with anhydrous sodium sulfate, filtered and evaporated under reduced pressure to give 3-(benzylamino)-4-methoxy-butan-1-ol 83 as a brown oil. The crude was used in the next step without further purification.

LCMS method H: $[M+H]^+=210$, $t_R=0.48$ min

Preparation of Intermediate 84: 3-amino-4-methoxy-butan-1-ol; 2,2,2-trifluoroacetic acid

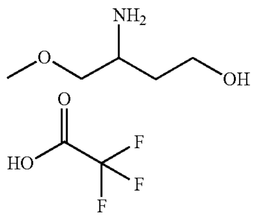

To a solution of 3-(benzylamino)-4-methoxy-butan-1-ol 83 (2.44 g, 11.7 mmol) in MeOH (200 mL), TFA (2.42 mL, 31.59 mmol) was added. The resulting mixture was degassed under $N_2$ during 15 min. $Pd(OH)_2$ (819 mg, 5.85 mmol) was added and the reaction mixture was heated at 50° C. under $H_2$ for 19 hours. The mixture was filtered over celite and the solvent was removed under reduced pressure to give 3-amino-4-methoxy-butan-1-ol; 2,2,2-trifluoroacetic acid 84 as a yellow oil. The crude was used in the next step without further purification.

Preparation of Intermediate 85: benzyl N-[3-hydroxy-1-(methoxymethyl)propyl]carbamate

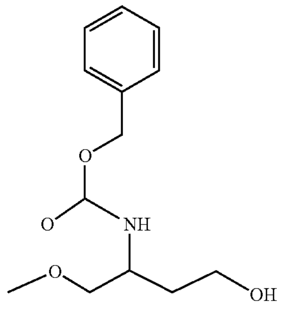 [SMILES: COCC(CCO)NC(O)OCc1ccccc1]

To a solution of 3-amino-4-methoxy-butan-1-ol; 2,2,2-trifluoroacetic acid 84 (3.32 g, 13 mmol postulated) in THE (18 mL)/water (18 mL), was added at room temperature $NaHCO_3$ (3.28 g, 39 mmol). The reaction was stirred at room temperature during 15 minutes, then at 0° C. was slowly added CbzCl (1.85 mL, 13 mmol). The resulting mixture was stirred at room temperature overnight. The mixture was diluted with water (50 mL) and EtOAc (50 mL). After separation, the aqueous layer was extracted with EtOAc (3×50 mL). The combined organic layers were washed with brine (100 mL), dried over anhydrous sodium sulfate, filtered and concentrated under reduced pressure. The crude was purified by column (Macherey Nagel, 120 g) chromatography with cyclohexane/EtOAc (100/0 to 0/100), then DCM/MeOH (90/10) as eluent. The desired fractions were collected, combined and the solvent was removed under reduced pressure to give benzyl N-[3-hydroxy-1-(methoxymethyl)propyl]carbamate 85 as a colorless oil.

LCMS method F: $[M+H]^+$=254, $t_R$=1.86 min

Preparation of Intermediate 86: [3-(benzyloxycarbonylamino)-4-methoxy-butyl]methane

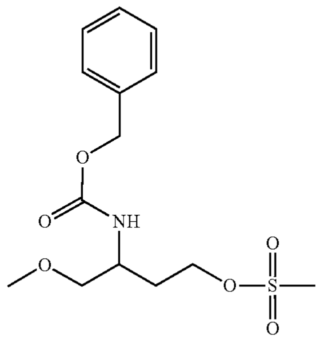

To a solution of benzyl N-[3-hydroxy-1-(methoxymethyl)propyl]carbamate 85 (1.94 g, 7.67 mmol) and diisopropylethylamine (2.66 mL, 15.34 mmol) in dichoromethane (70 mL) at 0° C., was added dropwise methanesulfonyl chloride (0.71 mL, 9.20 mmol). The reaction mixture was stirred at room temperature for 2 hours. The mixture was diluted with water (100 mL) and DCM (100 mL). The water layer was extracted with DCM (2×100 mL). The combined organic layers were washed with brine (150 mL), dried over anhydrous sodium sulfate, filtered and the solvent was removed under reduced pressure to afford [3-(benzyloxycarbonylamino)-4-methoxy-butyl]methane sulfonate 86 as an orange viscous oil. The crude was used in the next step without further purification.

LCMS method F: $[M+H]^+$=332, $t_R$=2.18 min

Preparation of Intermediate 87: benzyl N-[3-(3-iodo-1-tetrahydropyran-2-yl-indazol-5-yl)oxy-1-(methoxymethyl)propyl]carbamate

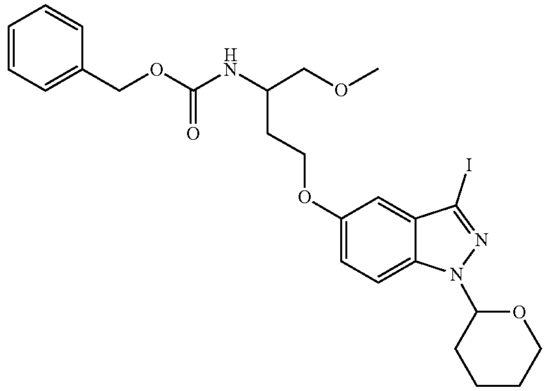 [SMILES: COCC(CCOc1ccc2c(c1)c(I)nn2C1CCCCO1)NC(=O)OCc1ccccc1]

To a solution of 3-iodo-1-tetrahydropyran-2-yl-indazol-5-ol 86 (2.33 g, 6.77 mmol) in N,N-dimethylformamide (60 mL) were added cesium carbonate (6.21 g, 19.1 mmol) and [3-(benzyloxycarbonylamino)-4-methoxy-butyl]methane sulfonate (2.53 g, 7.64 mmol). The resulting mixture was heated at 60° C. overnight. The mixture was filtered and concentrated under reduced pressure. The residue was diluted with water (100 mL) and EtOAc (100 mL). After separation, the aqueous layer was extracted with EtOAc (2×100 mL). The combined organic layers were washed with brine (150 mL), dried over anhydrous sodium sulfate, filtered and evaporated under reduced pressure to afford a red oil. The crude was purified by column (Macherey Nagel, 120 g) flash chromatography with cyclohexane/EtOAc (100/0 to 80/20) as eluent. The desired fractions were collected, combined and the solvent was removed under reduced pressure to afford benzyl N-[3-(3-iodo-1-tetrahydropyran-2-yl-indazol-5-yl)oxy-1-(methoxymethyl)propyl]carbamate 87 as a white oil.

LCMS method F: $[M+H]^+$=580, $t_R$=3.13 min

Preparation of Intermediate 88: benzyl N-[3-[3-[3-(hydroxymethyl)phenyl]-1-tetrahydropyran-2-yl-indazol-5-yl]oxy-1-(methoxymethyl)propyl]carbamate

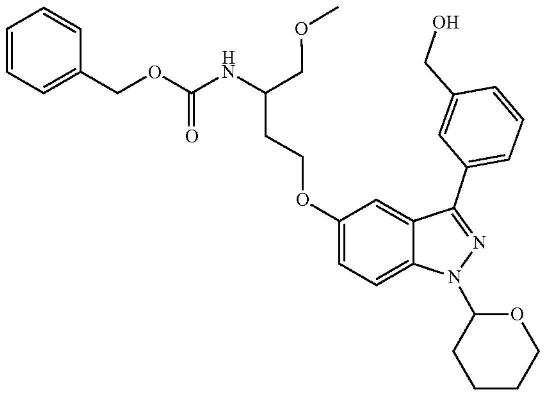 [SMILES: COCC(CCOc1ccc2c(c1)c(-c1cccc(CO)c1)nn2C1CCCCO1)NC(=O)OCc1ccccc1]

To a degassed solution of benzyl N-[3-(3-iodo-1-tetrahydropyran-2-yl-indazol-5-yl)oxy-1-(methoxymethyl)propyl] carbamate 87 (2.81 g, 4.85 mmol), [3-(hydroxymethyl) phenyl]boronic acid (1.11 g, 7.28 mmol) and a 1M solution of $Na_2CO_3$ (14.55 mL, 14.55 mmol) in DME (50 mL) was added palladium-tetrakis(triphenylphosphine) (277 mg, 0.24 mmol, 5 mol %). The reaction mixture was stirred at 80° C. for 2 days. More [3-(hydroxymethyl)phenyl]boronic acid (72 mg, 0.48 mmol), 1M solution of $Na_2CO_3$ (1.45 mL, 1.45 mmol) and palladium-tetrakis(triphenylphosphine) (56 mg, 0.049 mmol, 1 mol %) were added and the reaction mixture was stirred at 80° C. for 4 hours. After being cooled to room temperature, the reaction mixture was filtered over celite and the filtrate was diluted with water (100 mL) and extracted with EtOAc (3×100 mL). The combined organic layers were washed with brine (150 mL), dried over anhydrous sodium sulfate, filtered and concentrated under reduced pressure. The crude was purified by column (Macherey Nagel, 120 g) flash chromatography with cyclohexane/EtOAc (100/0 to 60/40) as eluent. The desired fractions were collected, combined and the solvent was removed under reduced pressure to afford benzyl N-[3-[3-[3-(hydroxymethyl)phenyl]-1-tetrahydropyran-2-yl-indazol-5-yl]oxy-1-(methoxymethyl)propyl]carbamate 88 as a yellow viscous oil.

LCMS method F: $[M+H]^+$=560, $t_R$=2.90 min

Preparation of Intermediate 89: 11-(methoxymethyl)-19-(oxan-2-yl)-8,14-dioxa-10,19,20-triazatetracyclo[13.5.2.$1^{2,6}$.$0^{18,21}$]tricosa-1(20),2(23),3,5,15(22),16, 18(21)-heptaen-9-one

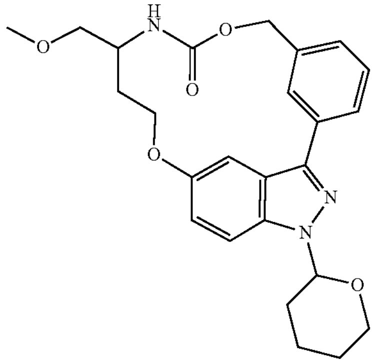 [SMILES: COCC1CCOc2ccc3c(c2)c(nn3C2CCCCO2)-c2cccc(c2)COC(=O)N1]

A suspension of benzyl N-[3-[3-[3-(hydroxymethyl)phenyl]-1-tetrahydropyran-2-yl-indazol-5-yl]oxy-1-(methoxymethyl)propyl]carbamate 88 (1.5 g, 2.68 mmol) and cesium carbonate (5.23 g, 16.08 mmol) in acetonitrile (600 mL) was heated to 90° C. for 6 hours. The reaction mixture was filtered at 90° C., cooled to room temperature and concentrated under reduced pressure. The crude was purified by column (Macherey Nagel, 80 g) chromatography with cyclohexane/EtOAc (100/0 to 60/40) as eluent. The desired fractions were collected, combined and the solvent was removed under reduced pressure to give 11-(methoxymethyl)-19-(oxan-2-yl)-8,14-dioxa-10,19,20-triazatetracyclo [13.5.2.$1^{2,6}$.$0^{18,21}$]tricosa-1(20),2(23),3,5,15(22),16, 18(21)-heptaen-9-one 89 (757 mg, 1.67 mmol) as a white powder.

LCMS method F: $[M+H]^+$=452, $t_R$=2.87 min

Preparation of Example 83: 11-(methoxymethyl)-8, 14-dioxa-10,19,20-triazatetracyclo[13.5.2.$1^{2,6}$.$0^{18,21}$] tricosa-1(20),2(23),3,5,15(22),16,18(21)-heptaen-9-one

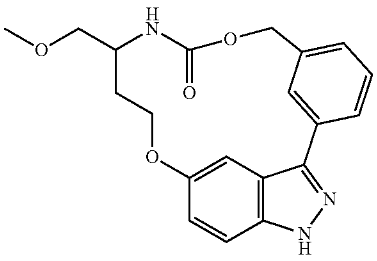 [SMILES: COCC1CCOc2ccc3[nH]nc(c3c2)-c2cccc(c2)COC(=O)N1]

To a solution of 11-(methoxymethyl)-19-(oxan-2-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one 89 (100 mg, 0.22 mmol) in DCM (15 mL) was added trifluoro acetic acid (0.34 mL, 4.4 mmol).

The mixture was heated under microwave conditions at 80° C. for 1 hour. The solvent was removed under reduced pressure to afford an oily residue, which was dissolved in DCM (20 mL) and a saturated solution of $NaHCO_3$ (20 mL) was added. After separation, the aqueous layer was extracted with DCM (3×10 mL). The combined organic layers were washed with brine (20 mL), dried over anhydrous sodium sulfate, filtered and evaporated under reduced pressure. The crude was triturated in acetonitrile but the resulting solid was not clean. The crude was solubilized in DCM and combined with the filtrate. The solvent was removed under reduced pressure. The crude was purified by column (Macherey Nagel, 15 g) flash chromatography with cyclohexane/EtOAc (100/0 to 60/40) as eluent. The desired fractions was collected, combined and the solvent was removed under reduced pressure under reduced pressure to give 11-(methoxymethyl)-8,14-dioxa-10,19,20-triazatetracyclo[13.5.2.$1^{2,6}$.$0^{18,21}$]tricosa-1(20),2(23),3,5,15(22),16, 18(21)-heptaen-9-one example 83 as a pale yellow powder.

LCMS method F: $[M+H]^+$=368, $t_R$=2.21 min

LCMS method G: $[M+H]^+$=368, $t_R$=2.20 min $^1$H NMR (400 MHz, d6-DMSO, 80° C.) δ 12.9 (1H, m), 7.94 (1H, s), 7.86 (1H, m), 7.58 (1H, m), 7.47 (2H, m), 7.37 (1H, d, J=2.1 Hz), 7.27 (1H, m), 6.99 (1H, dd, J=2.3, 8.9 Hz), 5.61 (1H, m), 4.96 (1H, m), 4.33 (2H, m), 3.81 (1H, m), 3.51 (1H, m), 3.43 (1H, dd, J=6.6, 10.0 Hz), 3.32 (3H, s), 2.15 (1H, m), 2.0 (1H, m) ppm.

Example 84: 8,14-dioxa-5,10,19,20,23-pentaazatetracyclo[13.5.2.1$^{2,5}$.0$^{18,21}$]tricosa-1(20),2(23),3,15(22),16,18(21)-hexaen-9-one

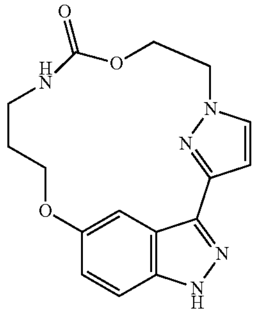 [SMILES: O=C1NCCCOc2ccc3[nH]nc(c3c2)-c2ccn(n2)CCO1]

Example 84 is prepared according to the synthesis route described in general Scheme K.

Preparation of Intermediate 90: 2-(3-bromopyrazol-1-yl)ethanol

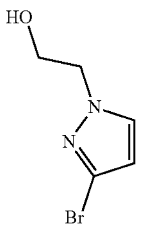

To a solution of 3-bromopyrazole (1 g, 6.807 mmol) in N,N-dimethylformamide (60 mL) was added potassium tert-butoxide solution (1M in THF) (10.2 mL, 10.211 mmol) at RT. The reaction mixture was stirred at RT for 10 min then 1,3,2-Dioxathiolane 2,2-dioxide (1.267 g, 10.211 mmol) was added. The reaction mixture was stirred at RT for 4 h 30. Concentrated hydrochloric acid (6 mL) was added to the reaction mixture and it was stirred at RT for 16 h. The reaction mixture was concentrated under reduced pressure and diluted with ethyl acetate. A saturated solution of $NaHCO_3$ was added and it was extracted with ethyl acetate (3×). The combined organic layers were washed with water then brine, dried over sodium sulfate, filtered and concentrated under reduced pressure. The crude product was purified by flash column chromatography eluting with Cyclohexane/Ethyl acetate-EtOH (3-1), 100/0 to 60/40 to give 2-(3-bromopyrazol-1-yl)ethanol 90 as a colorless oil.

LCMS method F: $[M+H]^+$=193, $t_R$=1.25 min

Preparation of Intermediate 91: 2-[3-[5-[tert-butyl(dimethyl)silyl]oxy-1-tetrahydropyran-2-yl-indazol-3-yl]pyrazol-1-yl]ethanol

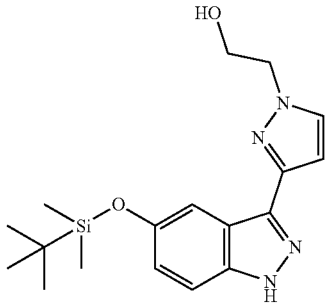 [SMILES: CC(C)(C)[Si](C)(C)Oc1ccc2[nH]nc(-c3ccn(CCO)n3)c2c1]

To a degassed solution of [5-[tert-butyl(dimethyl)silyl]oxy-1-tetrahydropyran-2-yl-indazol-3-yl]boronic acid (563 mg, 1.496 mmol), 2-(3-bromopyrazol-1-yl)ethanol (300 mg, 1.571 mmol), tripotassium phosphate (953 mg, 4.488 mmol), xPhos (71.5 mg, 0.150 mmol) in dioxane (4.52 mL) and water (1.51 mL) was added tetrakis(triphenylphosphine)palladium(0) (86.7 mg, 0.075 mmol). The reaction mixture was irradiated under microwave conditions (Biotage initiator+) at 100° C. for 1 h. The reaction mixture was filtered over celite and washed with ethyl acetate. The filtrate was diluted with water and extracted with ethyl acetate (3×). The combined organic layers were washed with water and brine, dried over sodium sulfate and concentrated under reduced pressure. The crude product was purified by column chromatography eluting with Cyclohexane/Ethyl acetate-EtOH (3-1), 100/0 to 70/30 to give 2-[3-[5-[tert-butyl(dimethyl)silyl]oxy-1-tetrahydropyran-2-yl-indazol-3-yl]pyrazol-1-yl]ethanol 91 as an orange oil.

LCMS method F: $[M+H]^+$=443, $t_R$=3.25 min

Preparation of Intermediate 92: 3-[1-(2-hydroxyethyl)pyrazol-3-yl]-1-tetrahydropyran-2-yl-indazol-5-ol

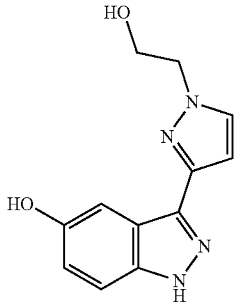 [SMILES: OCCn1ccc(-c2n[nH]c3ccc(O)cc23)n1]

To a solution of 2-[3-[5-[tert-butyl(dimethyl)silyl]oxy-1-tetrahydropyran-2-yl-indazol-3-yl]pyrazol-1-yl]ethanol 91 (406 mg, 0.919 mmol) in THE (2 mL) was added a solution of tetrabutylammonium fluoride 1M in THE (1 mL, 1.012 mmol). The reaction mixture was stirred at room temperature for 16 h. Ice water was added and the reaction mixture was stirred for 20 min. The aqueous phase was extracted with EtOAc (3×) and the combined organic layers were washed with brine, dried over $Na_2SO_4$, filtered and evaporated under reduced pressure. The crude product was purified by flash column chromatography eluting with Cyclohexane/Ethyl acetate-EtOH (3-1), 100/0 to 60/40 to give 3-[1-(2-hydroxyethyl)pyrazol-3-yl]-1-tetrahydropyran-2-yl-indazol-5-ol 92 as a yellow oil.

LCMS method F: $[M+H]^+=329$, $t_R=1.92$ min

Preparation of Intermediate 93: benzyl N-[3-[3-[1-(2-hydroxyethyl)pyrazol-3-yl]-1-tetrahydropyran-2-yl-indazol-5-yl]oxypropyl]carbamate

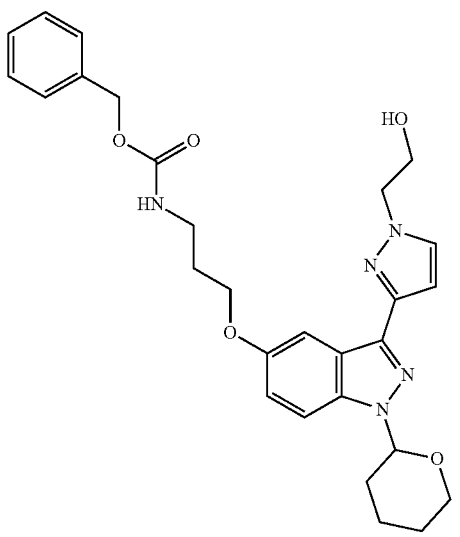 [SMILES: O=C(NCCCOc1ccc2c(c1)c(-c1ccn(CCO)n1)nn2C1CCCCO1)OCc1ccccc1]

A suspension of 3-[1-(2-hydroxyethyl)pyrazol-3-yl]-1-tetrahydropyran-2-yl-indazol-5-ol 92 (150 mg, 0.457 mmol), cesium carbonate (297 mg, 0.914 mmol) and benzyl N-(3-bromopropyl)carbamate (98 µL, 0.503 mmol) in dry acetonitrile (4 mL) was stirred at RT for 16 h. More benzyl N-(3-bromopropyl)carbamate (25 µL, 0.091 mmol, 0.2 eq) in dry acetonitrile (1 mL) was added and the reaction mixture was stirred at RT for 32 h. The reaction mixture was filtered and rinsed with ethyl acetate. Water was added and it was extracted with ethyl acetate (3×). The combined organic layers were washed with water and brine, dried over sodium sulfate, filtered and concentrated under reduced pressure. The crude product was purified by flash column chromatography eluting with Cyclohexane/Ethyl acetate-EtOH (3-1), 100/0 to 60/40, to give benzyl N-[3-[3-[1-(2-hydroxyethyl)pyrazol-3-yl]-1-tetrahydropyran-2-yl-indazol-5-yl]oxypropyl]carbamate 93 as a white solid.

LCMS method F: $[M+H]^+=520$, $t_R=2.64$ min

Preparation of Intermediate 94: 19-(oxan-2-yl)-8,14-dioxa-5,10,19,20,23-pentaazatetracyclo[13.5.2.1$^{2,5}$.0$^{18,21}$]tricosa-1(20),2(23),3,15(22),16,18(21)-hexaen-9-one

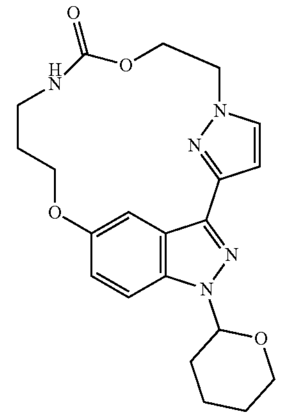 [SMILES: O=C1NCCCOc2ccc3c(c2)c(nn3C2CCCCO2)-c2ccn(n2)CCO1]

A solution of benzyl N-[3-[3-[1-(2-hydroxyethyl)pyrazol-3-yl]-1-tetrahydropyran-2-yl-indazol-5-yl]oxypropyl]carbamate 93 (187 mg, 0.360 mmol, 1 eq) and cesium carbonate (702 mg, 2.160 mmol, 6 eq) in acetonitrile (54 mL) was stirred at 85° C. for 16 h. The reaction mixture was cooled to RT, filtered, rinsed with ethyl acetate and evaporated under reduced pressure. The crude product was purified by column chromatography eluting with DCM/Ethyl acetate: 100/0 to 60/40 to give the expected product 19-(oxan-2-yl)-8,14-dioxa-5,10,19,20,23-pentaazatetracyclo[13.5.2.1$^{2,5}$.0$^{18,21}$]tricosa-1(20),2(23),3,15(22),16,18(21)-hexaen-9-one 94 as a white solid.

LCMS method F: $[M+H]^+=412$, $t_R=2.28$ min

Preparation of Example 84: 8,14-dioxa-5,10,19,20,23-pentaazatetracyclo[13.5.2.1$^{2,5}$.0$^{18,21}$]tricosa-1(20),2(23),3,15(22),16,18(21)-hexaen-9-one

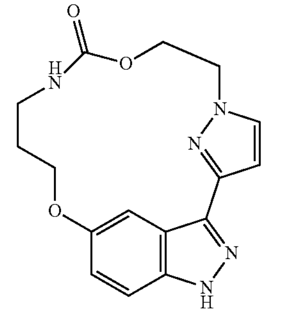 [SMILES: O=C1NCCCOc2ccc3[nH]nc(c3c2)-c2ccn(n2)CCO1]

To a solution of 19-(oxan-2-yl)-8,14-dioxa-5,10,19,20,23-pentaazatetracyclo[13.5.2.1$^{2,5}$.0$^{18,21}$]tricosa-1(20),2(23),3,15(22),16,18(21)-hexaen-9-one 94 (51 mg, 0.124 mmol, 1 eq) in DCM (5 mL) was added trifluoroacetic acid (190 µL, 2.480 mmol, 20 eq) at RT. The solution was heated under microwave conditions at 80° C. for 2 h. The reaction mixture was concentrated under reduced pressure and the brown residue was dissolved in ethyl acetate. A saturated aqueous solution of sodium hydrogen carbonate was added and it was extracted with ethyl acetate (3×). The combined organic layers were washed with water and brine, dried over sodium sulfate, filtered and the solvent was removed under reduced pressure. The crude product was purified by flash column chromatography eluting with Cyclohexane/Ethyl acetate-EtOH (3-1), 100/0 to 50/50. The desired fractions were collected and the solvent was removed under reduced pressure. The compound was triturated with diisopropyl ether to give 8,14-dioxa-5,10,19,20,23-pentaazatetracyclo[13.5.2.1$^{2,5}$.0$^{18,21}$]tricosa-1(20),2(23),3,15(22),16,18(21)-hexaen-9-one example 84 as a white solid.

LCMS method F: $[M+H]^+$=328, $t_R$=1.69 min

LCMS method G: $[M+H]^+$=328, $t_R$=1.66 min $^1$H NMR (400 MHz, d6-DMSO) δ 12.83 (1H, s), 7.82 (1H, d), 7.65 (1H, m), 7.61-7.58 (1H, m), 7.40 (1H, d), 6.95-6.92 (1H, dd), 6.63 (1H, d), 4.52-4.50 (2H, m), 4.42-4.40 (2H, m), 4.28-4.24 (2H, m), 3.11-3.07 (2H, m), 1.90-1.84 (2H, m) ppm.

Example 85: 11-methyl-8,14-dioxa-4,5,10,19,20-pentaazatetracyclo[13.5.2.1$^{2,5}$.0$^{18,21}$]tricosa-1(20),2(23),3,15(22),16,18(21)-hexaen-9-one

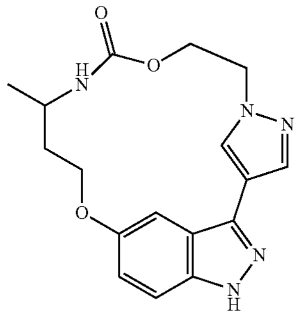 [SMILES: CC1CCOc2ccc3[nH]nc(c3c2)-c2cnn(c2)CCOC(=O)N1]

Example 85 is prepared according to the synthesis route described in general Scheme C to give 11-methyl-8,14-dioxa-4,5,10,19,20-pentaazatetracyclo[13.5.2.1$^{2,5}$.0$^{18,21}$]tricosa-1(20),2(23), 3,15(22),16,18(21)-hexaen-9-one example 85.

LCMS method F: $[M+H]^+$=342, $t_R$=1.83 min

LCMS method G: $[M+H]^+$=342, $t_R$=1.83 min $^1$H NMR (400 MHz, d6-DMSO) δ 12.82-12.79 (1H, m), 8.10 (1H, s), 7.76-7.71 (2H, m), 7.44-7.39 (1H, m), 7.08 (1H, d, J=0.9 Hz), 6.94 (1H, dd, J=1.7, 8.9 Hz), 4.68-4.62 (1H, m), 4.55-4.41 (3H, m), 4.35-4.26 (1H, m), 4.08-4.03 (1H, m), 3.82-3.76 (1H, m), 1.98 (1H, s), 1.80 (1H, s), 1.14-1.04 (3H, m) ppm.

Example 86: 12-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

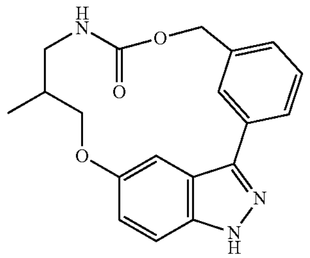 [SMILES: CC1CNC(=O)OCc2cccc(c2)-c2n[nH]c3ccc(cc23)OC1]

Example 86 is prepared according to the synthesis route described in general Scheme E to give 12-methyl-8,14-dioxa-10,19,20-triazatetracyclo[13.5.2.1$^{2,6}$.0$^{18,21}$]tricosa-1(20),2(23),3, 5, 15(22),16,18(21)-heptaen-9-one example 86.

LCMS method F: $[M+H]^+$=338.2, $t_R$=3.12 min

LCMS method G: $[M+H]^+$=338.2, $t_R$=3.09 min $^1$H NMR (400 MHz, d6-DMSO) δ 13.13 (brs, 1H), 8.04-7.99 (m, 1H), 7.88-7.83 (m, 2H), 7.52-7.44 (m, 2H), 7.31-7.27 (m, 2H), 7.02 (dd, J=2.5, 9.0 Hz, 1H), 5.78 (d, J=14.3 Hz, 1H), 4.80 (d, J=14.3 Hz, 1H), 4.53 (d, J=12.0 Hz, 1H), 3.75 (t, J=12.0 Hz, 1H), 3.32-3.30 (m, 1H), 0.96 (d, J=6.5 Hz, 3H) ppm. Two protons were located under the DMSO peak and are not reported here.

Example 87: 11-ethyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

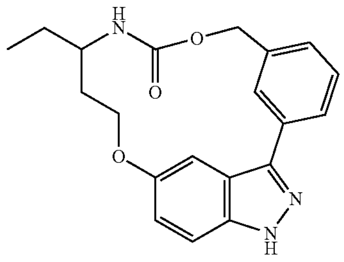 [SMILES: CCC1CCOc2ccc3[nH]nc(c3c2)-c2cccc(c2)COC(=O)N1]

Example 87 is prepared according to the synthesis route described in general Scheme E to give 11-ethyl-8,14-dioxa-10,19,20-triazatetracyclo[13.5.2.1$^{2,6}$.0$^{18,21}$]tricosa-1(20),2(23),3,5, 15(22),16,18(21)-heptaen-9-one example 87.

LCMS method F: $[M+H]^+$=352, $t_R$=2.44 min

LCMS method G: $[M+H]^+$=352, $t_R$=2.38 min $^1$H NMR (400 MHz, d6-DMSO, 80° C.) δ 12.87 (1H, m), 7.95 (1H, m), 7.86 (1H, m), 7.46 (3H, m), 7.37 (1H, d, J=2.1 Hz), 7.27 (1H, dd, J=0.7, 7.5 Hz), 6.98 (1H, dd, J=2.3, 8.9 Hz), 5.67 (1H, m), 4.91 (1H, m), 4.35 (2H, m), 3.55 (1H, m), 2.21 (1H, m), 1.96 (1H, m), 1.57 (2H, m), 0.95 (3H, t, J=7.5 Hz) ppm.

Example 88: 4-fluoro-5,7-dimethyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

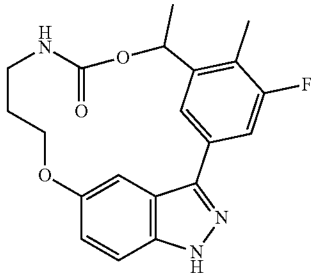 [SMILES: Cc1c(F)cc2cc1C(C)OC(=O)NCCCOc1ccc3[nH]nc-2c3c1]

Example 88 is prepared according to the synthesis route described in general Scheme A.

Preparation of Intermediate 95: (5-bromo-3-fluoro-2-methyl-phenyl)methanol

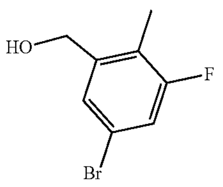

To a mixture of methyl 5-bromo-3-fluoro-2-methyl-benzoate (3.00 g, 12.14 mmol) in THE (35 mL) at 0° C., was added a solution of DIBAL-H (30.4 mL, 30.36 mmol, 1.0 M solution in THF). The reaction mixture was stirred at room temperature for 16 hours. The reaction mixture was diluted with ethyl acetate and cold 1 N HCl was added. The organic layer was washed with 1 N HCl and brine, dried over $MgSO_4$, filtered and the solvent was removed under reduced pressure to afford (5-bromo-3-fluoro-2-methyl-phenyl) methanol 95 as a white solid. The crude product was used in the next step without any further purification.

LCMS method F: $[M-H_2O+H]^+$=201.0, $t_R$=2.35 min

Preparation of Intermediate 96: 5-bromo-3-fluoro-2-methyl-benzaldehyde

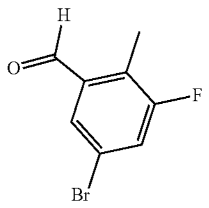

To a solution of (5-bromo-3-fluoro-2-methyl-phenyl) methanol 95 (2.66 g, 12.14 mmol) in DCM (160 mL) was added portion wise manganese dioxide (10.56 g, 121.4 mmol). After stirring for 18 h at room temperature, the suspension was filtered through a sinter funnel. The filtrate was dried over anhydrous magnesium sulfate, filtered and the solvent was removed under reduced pressure to give 5-bromo-3-fluoro-2-methyl-benzaldehyde 96 as a slightly yellow. The crude product was used in the next step without any further purification.

LCMS method F: no m/z detected, $t_R$=2.67 min (current 20V)

Preparation of Intermediate 97: 1-(5-bromo-3-fluoro-2-methyl-phenyl)ethanol

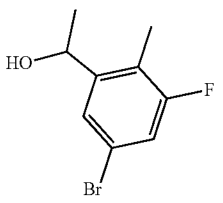

To a cooled solution of 5-bromo-3-fluoro-2-methyl-benzaldehyde 96 (2.43 g, 11.20 mmol) in dry tetrahydrofuran (30 mL) was added dropwise at 0° C. a 3M methylmagnesium bromide solution in diethyl ether (7.5 mL, 22.40 mmol). The reaction mixture was stirred at 0° C. for 20 min and allowed to reach room temperature for 16 hours. The reaction mixture was quenched with a saturated aqueous solution of $NH_4Cl$ then extracted with ethyl acetate (2×100 mL). The organic layer was washed with water the brine, dried over magnesium sulfate, filtered and concentrated under reduced pressure. The crude product was purified by flash-column chromatography eluting with Cyclohexane/Ethyl acetate-EtOH (3-1): 100/0 to 80/20, to give 1-(5-bromo-3-fluoro-2-methyl-phenyl)ethanol 97 as a colorless oil.

LCMS method F: $[M-H_2O+H]^+$=217.0, $t_R$=2.50 min

Preparation of Intermediate 98: 1-[3-fluoro-2-methyl-5-(4,4,5,5-tetramethyl-1,3,2-dioxaborolan-2-yl)phenyl]ethanol

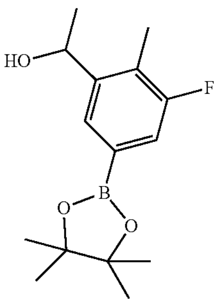 [SMILES: Cc1c(F)cc(B2OC(C)(C)C(C)(C)O2)cc1C(C)O]

To a degassed solution in a sealed tube of 1-(5-bromo-3-fluoro-2-methyl-phenyl)ethanol 97 (2.49 g, 10.66 mmol), bis(pinacolato)diboron (4.06 g, 15.99 mmol) and potassium acetate (4.18 g, 42.64 mmol) in dioxane (30 mL) was added [1,1'-bis(diphenylphosphino)ferrocene]dichloropalladium (II), complex with DCM (0.874 g, 1.07 mmol). The reaction mixture was stirred under argon atmosphere at 100° C. for 16 hours. The reaction mixture was filtered over celite on Whatman paper and rinsed with ethyl acetate. The reaction mixture was diluted with water and extracted with ethyl acetate (3×100 mL). The combined organic layers were washed with water then brine, dried over anhydrous magnesium sulfate and concentrated under reduced pressure to afford 1-[3-fluoro-2-methyl-5-(4,4,5,5-tetramethyl-1,3,2-dioxaborolan-2-yl)phenyl]ethanol 98 as a dark brown oil. The crude product was used in the next step without any purification.

LCMS method F: $[M-H_2O+H]^+$=263.2, $t_R$=2.77 min

Preparation of Intermediate 99: benzyl N-[3-[3-[3-fluoro-5-(1-hydroxyethyl)-4-methyl-phenyl]-1-tetrahydropyran-2-yl-indazol-5-yl]oxypropyl]carbamate

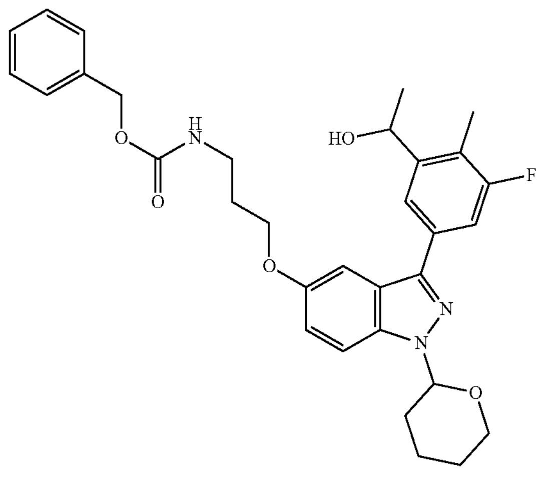 [SMILES: Cc1c(F)cc(-c2nn(C3CCCCO3)c3ccc(OCCCNC(=O)OCc4ccccc4)cc23)cc1C(C)O]

A solution of benzyl N-[3-(3-iodo-1-tetrahydropyran-2-yl-indazol-5-yl)oxypropyl]carbamate 26 (700 mg, 1.31 mmol), 1-[3-fluoro-2-methyl-5-(4,4,5,5-tetramethyl-1,3,2-dioxaborolan-2-yl)phenyl]ethanol 98 (403 mg, 1.44 mmol), potassium phosphate tribasic (833 mg, 3.93 mmol), Xphos (62 mg, 0.13 mmol) and palladium-tetrakis(triphenylphosphine) (75 mg, 0.065 mmol, 5 mol %) in a mixture of dioxane (22 mL) and water (5 mL) was heated at 110° C. for 2 days. The solution was diluted with water and extracted twice with EtOAc. The combined organic layers were washed with brine, dried over magnesium sulfate, filtered and concentrated under reduced pressure. The crude was purified by chromatography on silica gel (DCM/MeOH: 100/0 to 95/5) to give benzyl N-[3-[3-[3-fluoro-5-(1-hydroxyethyl)-4-methyl-phenyl]-1-tetrahydropyran-2-yl-indazol-5-yl]oxypropyl]carbamate 99 as a slightly yellow oil.

LCMS method F: $[M+H]^+=562.3$, $t_R=3.15$ min

Preparation of Intermediate 100: 4-fluoro-5,7-dimethyl-19-(oxan-2-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one and 1-[5-[5-(3-aminopropoxy)-1-tetrahydropyran-2-yl-indazol-3-yl]-3-fluoro-2-methyl-phenyl]

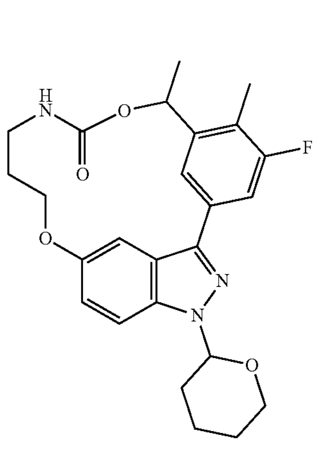

-continued

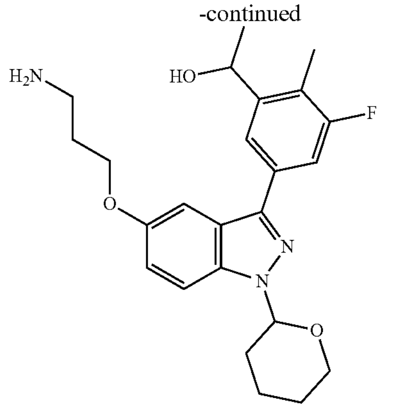

To a solution of benzyl N-[3-[3-[3-fluoro-5-(1-hydroxyethyl)-4-methyl-phenyl]-1-tetrahydropyran-2-yl-indazol-5-yl]oxypropyl]carbamate 99 (594 mg, 1.06 mmol) in anhydrous acetonitrile (200 mL) at room temperature was added cesium carbonate (861 mg, 2.65 mmol). The resulting reaction mixture was stirred at 90° C. for 17 h 30. LCMS showed the formation the expected macrocycle (40% by LCMS) and a side-product arising from the carbamate hydrolysis (42% by LCMS). The reaction mixture was filtered and concentrated under reduced pressure to afford a mixture of 4-fluoro-5,7-dimethyl-19-(oxan-2-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one and 1-[5-[5-(3-aminopropoxy)-1-tetrahydropyran-2-yl-indazol-3-yl]-3-fluoro-2-methyl-phenyl]ethanol 100 as a yellow solid. The crude mixture was used in the next step (CDI, DMA, 90° C.) without any purification.

LCMS method F: expected macrocycle $[M+H]^+=454.2$, $t_R=3.01$ min

LCMS method F: hydrolyzed product $[M+H]^+=428.2$, $t_R=1.94$ min

Preparation of Intermediate 101: 4-fluoro-5,7-dimethyl-19-(oxan-2-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one

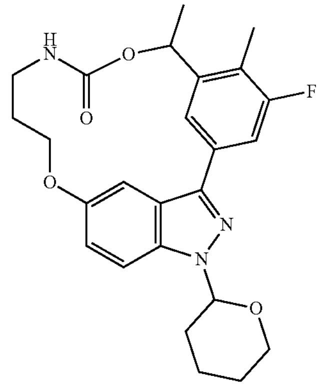 [SMILES: Cc1c(F)cc2cc1C(C)OC(=O)NCCCOc1ccc3c(c1)c-2nn3C1CCCCO1]

To a solution of 4-fluoro-5,7-dimethyl-19-(oxan-2-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one and 1-[5-[5-(3-aminopropoxy)-1-tetrahydropyran-2-yl-indazol-3-yl]-3-fluoro-2-methyl-phenyl]ethanol 100 (0.452 g, 1.06 mmol) in dimethylacetamide (350 mL) was added 1,1'-carbonyldiimidazole (0.188 g, 1.16 mmol). The reaction mixture was stirred at room temperature for 16 hours. The mixture was diluted in water and extracted three times with ethyl acetate (3×100 mL). The combined organic layers were washed with water, then brine, dried over anhydrous magnesium sulfate, filtered and concentrated under reduced pressure. The crude product was purified by silica gel column chromatography (eluent: DCM/MeOH from 100/0 to 95/5) to afford 4-fluoro-5,7-dimethyl-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one 101 as a colorless oil.

LCMS method F: $[M+H]^+$=454.1, $t_R$=2.99 min (current 20V)

Preparation of Example 88: 4-fluoro-5,7-dimethyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

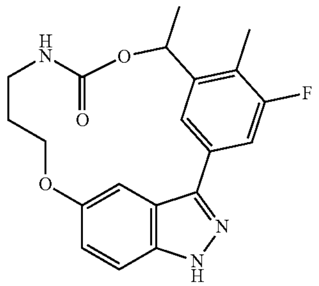 [SMILES: Cc1c(F)cc2cc1C(C)OC(=O)NCCCOc1ccc3[nH]nc-2c3c1]

To a solution of 4-fluoro-5,7-dimethyl-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one 101 (0.080 g, 0.176 mmol) in DCM (15 mL) was added trifluoroacetic acid (0.27 mL, 3.52 mmol). The mixture was heated under microwave conditions at 80° C. for 1 h 15. The solvent was removed under reduced pressure to give a mixture of a yellow solid in an oily residue. The solid residue appeared to be the expected product, which was not soluble enough for column chromatography purification. In order to remove impurities from this solid, the crude mixture was suspended in MeOH (3 mL) and refluxed for 3 hours. The suspension was filtered and the filter cake was rinsed with MeOH. This filter cake was suspended again in MeOH (3 mL) and refluxed for 3 hours. After filtration, the residual solid was suspended in water (3 mL) and reflux for 2 hours. After filtration of the resulting suspension, the solid was collected and dried under reduced pressure at 60° C. to afford 4-fluoro-5,7-dimethyl-8,14-dioxa-10,19,20-triazatetracyclo[13.5.2.1$^{2,6}$.0$^{18,21}$]tricosa-1(20),2(23),3,5,15(22),16,18(21)-heptaen-9-one example 88 as a white solid.

LCMS method F: $[M+H]^+$=370.2, $t_R$=2.38 min

LCMS method G: $[M+H]^+$=370.2, $t_R$=2.35 min $^1$H NMR (400 MHz, d6-DMSO, 80° C.) δ 12.89 (1H, br. s), 7.70-7.67 (2H, m), 7.49-7.42 (2H, m), 7.36 (1H, s), 7.00-6.97 (1H, m), 5.81-5.68 (1H, m), 4.35-4.25 (2H, m), 3.52 (1H, br. s), 2.77 (1H, br. s), 2.27 (3H, d, J=1.9 Hz), 2.12 (1H, br. s), 1.75 (1H, br. s), 1.50 (3H, d, J=7.2 Hz) ppm.

Example 89: 4-fluoro-5-methoxy-7-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

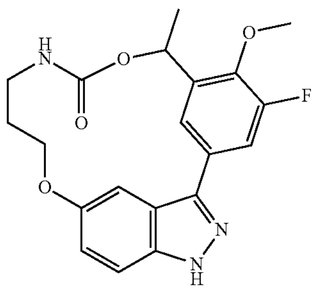 [SMILES: COc1c(F)cc2cc1C(C)OC(=O)NCCCOc1ccc3[nH]nc-2c3c1]

Example 89 is prepared according to the synthesis route described in general Scheme A and according to the procedures described to obtain example 88 to give 4-fluoro-5-methoxy-7-methyl-8,14-dioxa-10,19,20-triazatetracyclo[13.5.2.1$^{2,6}$.0$^{18,21}$]tricosa-1(20),2(23),3,5,15(22), 16,18(21)-heptaen-9-one example 89.

LCMS method F: $[M+H]^+$=386.2, $t_R$=2.40 min

LCMS method G: $[M+H]^+$=386.2, $t_R$=2.37 min $^1$H NMR (400 MHz, d6-DMSO, 80° C.) δ 12.95 (1H, br. s), 7.74 (1H, s), 7.64 (1H, s), 7.55 (1H, d, J=13.1 Hz), 7.49-7.46 (1H, m), 7.34 (1H, s), 7.01-6.97 (1H, m), 5.80 (1H, s), 4.38-4.27 (2H, m), 4.00-3.99 (3H, m), 3.53 (1H, br. s), 2.78 (1H, br. s), 2.15 (1H, br. s), 1.76 (1H, br. s), 1.54 (3H, d, J=6.6 Hz) ppm.

Example 90: 5-fluoro-4,7-dimethyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

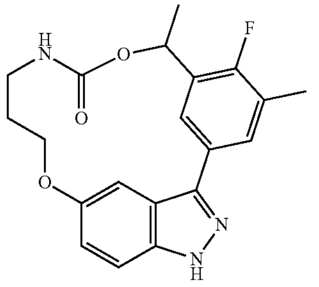 [SMILES: Cc1cc2cc(c1F)C(C)OC(=O)NCCCOc1ccc3[nH]nc-2c3c1]

Example 90 is prepared according to the synthesis route described in general Scheme A and according to the procedures described to obtain example 88 to give 5-fluoro-4,7-dimethyl-8,14-dioxa-10,19,20-triazatetracyclo[13.5.2.1$^{2,6}$.0$^{18,21}$]tricosa-1(20),2(23),3,5,15(22),16,18(21)-heptaen-9-one example 90.

LCMS method F: $[M+H]^+$=370.2, $t_R$=2.44 min

LCMS method G: $[M+H]^+$=370.2, $t_R$=2.43 min $^1$H NMR (400 MHz, d6-DMSO, 80° C.) δ 12.83 (1H, s), 7.73-7.69 (3H, m), 7.48-7.44 (1H, m), 7.37-7.35 (1H, m), 6.98 (1H, dd, J=2.3, 8.9 Hz), 5.88-5.82 (1H, m), 4.38-4.25 (2H, m), 3.56 (1H, br. s), 2.81-2.76 (1H, m), 2.36-2.33 (3H, m), 2.19-2.14 (1H, m), 1.80-1.73 (1H, m), 1.58 (3H, d, J=6.8 Hz) ppm.

Example 91: 8,14-dioxa-10,19,20-triazapentacyclo [13.5.2.1$^{2,6}$.1$^{7,10}$.0$^{18,21}$]tetracosa-1(20),2(24),3,5,15 (22),16,18(21)-heptaen-9-one

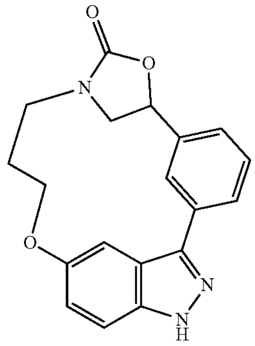 [SMILES: O=C1OC2CN1CCCOc1ccc3[nH]nc(c3c1)-c1cccc2c1]

Example 91 is prepared according to the synthesis route described below.

Preparation of Intermediate 102: 1-(3-bromophenyl)-2-nitro-ethanol

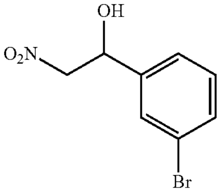 [SMILES: O=[N+]([O-])CC(O)c1cccc(Br)c1]

In a round bottom flask, to a stirred solution of 3-bromobenzaldehyde (1.850 g, 10.00 mmol) in THF (50.0 ml) was added dropwise at 0° C., nitromethane (535 μL, 10.00 mmol) and then sodium hydroxide solution 1N (10.00 ml, 10.00 mmol). The mixture was stirred during 1 h.

LC/MS analysis indicated 70% formation of required product and 50% starting material. The orange mixture was stirred during 3 h at room temperature. The solution was carefully quenched with a solution of acetic acid (10 ml) and water (20 ml). Phases were separated and the aqueous layer was extracted with AcOEt (3×35 ml). Combined organic layer were washed with brine (30 ml), and dried over MgSO4, filtered and concentrated under reduce pressure to afford a crude material (1.720 g). The crude was purified by chromatography column by solid deposit (Macherey Nagel, 4 g, Cyclohexane/AcOEt:90/10 to 70/30). Solvent was evaporated to afford 1-(3-bromophenyl)-2-nitro-ethanol 102 as a yellow pale oil.

LCMS method F: $[M-H]^-$=246.1, $t_R$=2.24 min

Preparation of Intermediate 103: 2-amino-1-(3-bromophenyl)ethanol

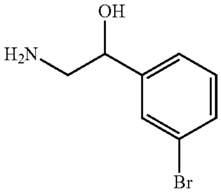

The reaction was divided in 2 batches of 730 mg (2.97 mmol) of 1-(3-bromophenyl)-2-nitro-ethanol 102. To a solution of 1-(3-bromophenyl)-2-nitro-ethanol (0.730 g, 2.97 mmol) in EtOH/water (2:1 v:v) were added iron powder (0.829 g, 29.67 mmol) and ammonium chloride (4.758 g, 177.90 mmol). The resulting brown mixture was stirred during 16 h at room temperature. The solution was filtered to remove iron. Solvent was concentrated and to the residue was added water and EtOAc (50 ml) and phases were separated and extracted with EtOAc (3×50 ml). Organic phases were gathered and washed with brine, dried with $MgSO_4$, filtered and concentrated under reduce pressure to afford 2-amino-1-(3-bromophenyl)ethanol 103 as a pale yellow oil which was used in the next step without further purification.

LCMS method H: $[M+H]^+$=216.0, $t_R$=1.02 min

Preparation of Intermediate 104: 5-(3-bromophenyl)oxazolidin-2-one

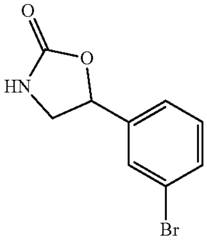 [SMILES: O=C1NCC(c2cccc(Br)c2)O1]

To a solution of 2-amino-1-(3-bromophenyl)ethanol 103 (0.710 g, 3.29 mmol) in THF (33.0 mL) was added 1,1'-Carbonyldiimidazole (0.587 g, 3.62 mmol) and imidazole (0.246 g, 3.62 mmol). The reaction mixture was stirred at RT for 16 h. To the reaction mixture was added saturated aqueous solution of $NH_4Cl$ (30 ml). The mixture was extracted with ethyl acetate (3×30 ml). The combined organic layer was washed with water then brine, dried over sodium sulfate, filtered and concentrated under reduced pressure. The crude product was purified by column chromatography on a biotage eluting with cyclohexane/ethyl acetate: 100/0 to 70/30 to give 5-(3-bromophenyl)oxazolidin-2-one 104.

Preparation of Intermediate 105: 5-(3-bromophenyl)-3-[3-[tert-butyl(dimethyl)silyl]oxypropyl]oxazolidin-2-one

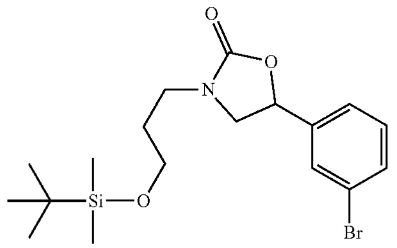 [SMILES: CC(C)(C)[Si](C)(C)OCCCN1CC(c2cccc(Br)c2)OC1=O]

To a solution of 5-(3-bromophenyl)oxazolidin-2-one 104 (0.580 g, 2.40 mmol) in dry THF (25.0 ml) at 0° C. was added sodium hydride (0.115 g, 4.80 mmol). The reaction was stirred 30 min at 0° C., then tetrabutylammonium iodide (0.044 g, 0.120 mmol) and 3-bromopropoxy-tert-butyl-dimethyl-silane (0.669 g, 612 μL, 2.64 mmol) were added. The resulting yellow mixture was stirred at 60° C. during 2 days. It was quenched with a saturated solution of $NaHCO_3$ (25 ml) and extracted with EtOAc (3×50 ml). Organic phase was washed with brine (25 ml), then dried with MgSO4, filtered and concentrated under reduce pressure to afford crude (1.200 g) which was purified by chromatography column by solid deposit (Macherey Nagel 24 g, Cyclohexane/AcOEt 90/10 to 70/30). Solvent was evaporated to afford 5-(3-bromophenyl)-3-[3-[tert-butyl(dimethyl)silyl]oxypropyl] oxazolidin-2-one 105 as a pale yellow oil.

LCMS method F: $[M+H]^+$=416.1, $t_R$=3.41 min

Preparation of Intermediate 106: 5-(3-bromophenyl)-3-(3-hydroxypropyl)oxazolidin-2-one

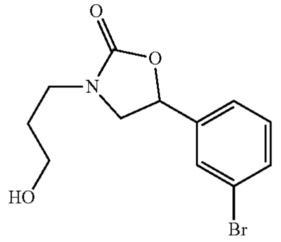 [SMILES: O=C1OC(c2cccc(Br)c2)CN1CCCO]

To a solution of 5-(3-bromophenyl)-3-[3-[tert-butyl(dimethyl)silyl]oxypropyl]oxazolidin-2-one 105 (0.650 g, 1.57 mmol) in dry THE (31.0 ml) at room temperature was added tetra-n-butylammonium fluoride (1.57 ml, 1.57 mmol, 1.0 M in THF). The reaction was stirred at room temperature during 16 h. The mixture was poured into ice water (20 ml) and stirred for 15 min.

The aqueous phase was extracted with ethyl acetate (3×25 ml). The combined organic layers were washed with brine (25 ml), dried over $MgSO_4$, filtered and concentrated under reduce pressure to afford 5-(3-bromophenyl)-3-(3-hydroxypropyl)oxazolidin-2-one 106 as pale yellow oil.

LCMS method F: $[M+H]^+$=302.0, $t_R$=2.00 min

Preparation of Intermediate 107: 3-[5-(3-bromophenyl)-2-oxo-oxazolidin-3-yl]propyl methanesulfonate

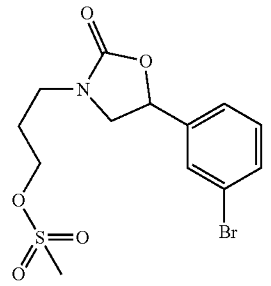 [SMILES: CS(=O)(=O)OCCCN1CC(c2cccc(Br)c2)OC1=O]

To a solution of 5-(3-bromophenyl)-3-(3-hydroxypropyl) oxazolidin-2-one 106 (0.420 g, 1.40 mmol) and diisopropylethylamine (0.487 mL, 2.80 mmol) in DCM (15.0 mL) at 0° C., was added dropwise methanesulfonyl chloride (0.130 mL, 1.68 mmol). The reaction mixture was stirred at room temperature for 3 h. LC/MS analysis indicated the reaction was completed. The organic phase was washed with a saturated solution of ammonium chloride, with a saturated solution of sodium bicarbonate and brine, dried with $MgSO_4$, filtered and evaporated under reduced pressure to afford 3-[5-(3-bromophenyl)-2-oxo-oxazolidin-3-yl]propyl methanesulfonate 107 as a pale yellow oil, which was used in the next step without further purification.

LCMS method F: $[M+H]^+$=380.1, $t_R$=2.28 min

Preparation of Intermediate 108: 5-(3-bromophenyl)-3-[3-(1-tetrahydropyran-2-ylindazol-5-yl)oxypropyl]oxazolidin-2-one

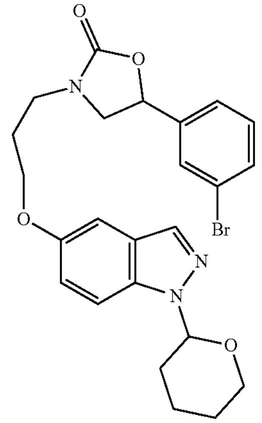 [SMILES: O=C1OC(c2cccc(Br)c2)CN1CCCOc1ccc2c(cnn2C2CCCCO2)c1]

To a solution of 3-[5-(3-bromophenyl)-2-oxo-oxazolidin-3-yl]propyl methanesulfonate 107 (0.912 g, 1.40 mmol) in DMF (28.0 mL), cesium carbonate (0.913 g, 2.80 mmol) and 1-tetrahydropyran-2-ylindazol-5-ol (0.305 g, 1.40 mmol) were added. The reaction was stirred at 60° C. during 1 h 30. The mixture was concentrated under reduced pressure. Water (50 mL) was added and the resulting mixture was extracted with AcOEt (4×30 mL). Combined organic layers were washed with saturated brine (30 mL). The organic layer was dried over sodium sulfate, filtered off and evaporated under reduced pressure to afford brown oil. This residue was purified by flash chromatography on silica gel (Macherey Nagel, 24 g, with gradient elution: Cyclohexane/AcOEt: 100/0 to 70/30) to give 5-(3-bromophenyl)-3-[3-(1-tetrahydropyran-2-ylindazol-5-yl)oxypropyl]oxazolidin-2-one 108 as a yellow oil.

LCMS method F: $[M+H]^+$=502.0, $t_R$=2.45 min

Preparation of Intermediate 109: 19-(oxan-2-yl)-8,14-dioxa-10,19,20-triazapentacyclo[13.5.2.$1^{2,6}$.$1^{7,10}$.$0^{18,21}$]tetracosa-1(20),2(24),3,5,15(22),16,18(21)-heptaen-9-one

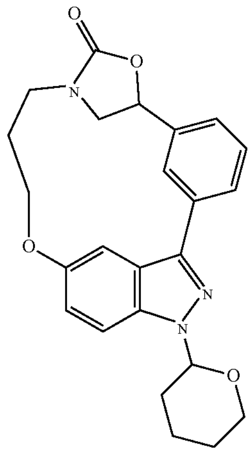 [SMILES: O=C1OC2CN1CCCOc1ccc3c(c1)c(nn3C1CCCCO1)-c1cccc2c1]

To a solution of 5-(3-bromophenyl)-3-[3-(1-tetrahydropyran-2-ylindazol-5-yl)oxypropyl]oxazolidin-2-one 108 (0.300 g, 0.600 mmol) in 10.0 ml of toluene was added reagent potassium acetate (0.118 g, 1.200 mmol) at room temperature. The mixture was degassed by bubbling nitrogen for 15 minutes. Palladium acetate (0.027 g, 0.120 mmol) and cataCXium A (0.043 g, 0.120 mmol) were then added. The mixture was heated at 120° C. for 1 h under microwaves irradiations (BIOTAGE), then 1 h 30 at 130° C. and 45 min at 140° C. The reaction mixture was filtered over celite and 20 ml of water were added to the filtrate. The aqueous layer was extracted with ethyl acetate (2×20 ml). The combined organic layer was washed with a saturated brine, dried over $MgSO_4$ and evaporated in vacuo to give crude (0.280 g), which was purified by column chromatography (Macherey Nagel, 12 g, DCM/MeOH ammoniac. 100/0 to 95/5). Solvents were evaporated to afford 19-(oxan-2-yl)-8,14-dioxa-10,19,20-triazapentacyclo[13.5.2.$1^{2,6}$.$1^{7,10}$.$0^{18,21}$]tetracosa-1(20),2(24),3,5,15(22),16,18(21)-heptaen-9-one 109 as a yellow powder.

LCMS method F: $[M+H]^+$=420.2, $t_R$=2.57 min Preparation of Example 91: 8,14-dioxa-10,19,20-triazapentacyclo[13.5.2.$1^{2,6}$.$1^{7,10}$.$0^{18,21}$]tetracosa-1(20),2(24),3,5,15(22),16,18(21)-heptaen-9-one

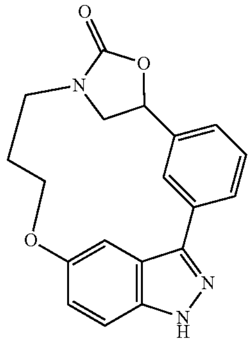 [SMILES: O=C1OC2CN1CCCOc1ccc3[nH]nc(c3c1)-c1cccc2c1]

In a vial, 19-(oxan-2-yl)-8,14-dioxa-10,19,20-triazapentacyclo[13.5.2.$1^{2,6}$.$1^{7,10}$.$0^{18,21}$]tetracosa-1(20),2(24),3,5,15(22),16,18(21)-heptaen-9-one 109 (0.195 g, 0.465 mmol) was dissolved in $CH_2Cl_2$ (9.0 mL) and TFA (0.1 M in $CH_2Cl_2$, 80 μL) was added. The resulting clear yellow solution was stirred at room temperature for 3 days. The reaction was quenched with saturated aqueous $NaHCO_3$ (10 mL) and EtOAc (10 mL) was added. The aqueous phase was extracted with EtOAc (3×15 mL) and the combined organic extracts were washed with saturated aqueous $NaHCO_3$ (15 mL) and saturated aqueous NaCl (15 mL), dried over anhydrous $MgSO_4$, filtered and concentrated under reduced pressure to afford crude (0.195 g) which purified by preparative reverse-phase chromatography (Column XSELECT PHENYL-HEXYL 19*100 mm 5 μm $[(NH4)_2CO3$ aq 2 g/LACN]30% B to 40% B in 7 min 19 mL/min R.T.). Solvent was removed and an other purification was done (0.015 g crude) by chromatography column (Macherey Nagel 4 g, DCM/MeOH: 100/0 to 96/4) to give 8,14-dioxa-10,19,20-triazapentacyclo[13.5.2.$1^{2,6}$.$1^{7,10}$.$0^{18,21}$]tetracosa-1(20),2(24),3,5,15(22),16,18(21)-heptaen-9-one example 91.

LCMS method F: $[M+H]^+$=336.2, $t_R$=1.97 min

LCMS method G: $[M+H]^+$=336.2, $t_R$=1.96 min $^1H$ NMR (400 MHz, d6-DMSO) δ 12.86 (1H, s), 8.39 (1H, t, J=1.7 Hz), 7.92-7.86 (1H, m), 7.58-7.41 (4H, m), 7.01-6.97 (1H, m), 5.69-5.69 (2H, m), 4.46-4.37 (1H, m), 4.30-4.23 (1H, m), 4.12-3.99 (2H, m), 3.61-3.40 (1H, m), 2.35-2.24 (1H, m), 2.04-1.92 (1H, m) ppm.

Example 92: 13-methyl-8,14-dioxa-10,19,20,23-tetraazatetracyclo[13.5.2.$1^{2,6}$.$0^{18,21}$]tricosa-1(20),2(23),3,5,15(22),16,18(21)-heptaen-9-one

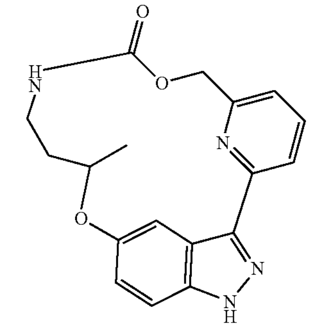 [SMILES: CC1CCNC(=O)OCc2cccc(n2)-c2n[nH]c3ccc(cc23)O1]

Example 92 is prepared according to the synthesis route described in general Scheme B to give 13-methyl-8,14-dioxa-10,19,20,23-tetraazatetracyclo[13.5.2.1$^{2,6}$.0$^{18,21}$]tricosa-1(20),2(23),3,5, 15(22),16,18(21)-heptaen-9-one example 92.

LCMS method F: $[M+H]^+$=339.2, $t_R$=2.09 min

LCMS method G: $[M+H]^+$=339.2, $t_R$=2.07 min $^1$H NMR (400 MHz, d6-DMSO) δ 13.22 (1H, s), 8.09-8.06 (1H, m), 7.90-7.81 (2H, m), 7.74-7.70 (1H, m), 7.48-7.44 (1H, m), 7.26-7.23 (1H, m), 6.95 (1H, dd, J=2.5, 8.9 Hz), 5.58 (1H, s), 5.08-5.04 (1H, m), 4.62 (1H, s), 3.45 (1H, m), 2.92 (1H, s), 2.29-2.25 (1H, m), 1.38-1.35 (4H, m) ppm.

Example 93: 12-methyl-8,14-dioxa-4,5,10,19,20-pentaazatetracyclo[13.5.2.1$^{2,5}$.0$^{18,21}$]tricosa-1(20),2(23),3,15(22),16,18(21)-hexaen-9-one

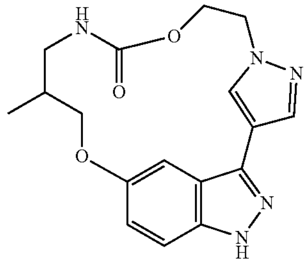 [SMILES: CC1CNC(=O)OCCn2cc(cn2)-c2n[nH]c3ccc(cc23)OC1]

Example 93 is prepared according to the synthesis route described in general Scheme C to give 12-methyl-8,14-dioxa-4,5,10,19,20-pentaazatetracyclo[13.5.2.1$^{2,5}$.0$^{18,21}$]tricosa-1(20),2(23),3, 15(22),16,18(21)-hexaen-9-one example 93.

LCMS method F: $[M+H]^+$=342.1, $t_R$=2.45 min

LCMS method G: $[M+H]^+$=342.2, $t_R$=2.40 min $^1$H NMR (400 MHz, d6-DMSO) δ 12.80 (brs, 1H), 8.08 (s, 1H), 7.95-7.91 (m, 1H), 7.77 (s, 1H), 7.42 (d, J=9.6 Hz, 1H), 7.07 (d, J=2.5 Hz, 1H), 6.99-6.96 (m, 1H), 4.67-4.43 (m, 4H), 4.07 (ddt, J=2.4, 5.6, 6.1 Hz, 1H), 3.70 (dd, J=10.1, 12.7 Hz, 1H), 3.36-3.26 (m, 1H), 2.58-2.53 (m, 1H), 2.22-2.10 (m, 1H), 0.93 (d, J=6.6 Hz, 3H) ppm.

Example 94: 7-methyl-8,14-dioxa-4,5,10,19,20-pentaazatetracyclo[13.5.2.1$^{2,5}$.0$^{18,21}$]tricosa-1(20),2(23),3,15(22),16,18(21)-hexaen-9-one

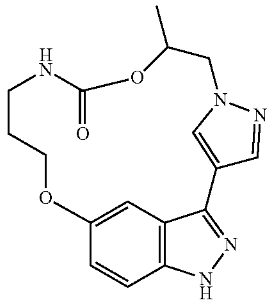 [SMILES: CC1Cn2cc(cn2)-c2n[nH]c3ccc(cc23)OCCCNC(=O)O1]

Example 94 is prepared according to the synthesis route described in general Scheme C.

Preparation of Intermediate 110: 1-[4-(4,4,5,5-tetramethyl-1,3,2-dioxaborolan-2-yl)pyrazol-1-yl]propan-2-ol

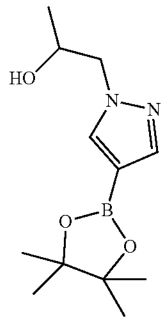 [SMILES: CC(O)Cn1cc(B2OC(C)(C)C(C)(C)O2)cn1]

In a microwave vial, NaH (60% in mineral oil, 480 mg, 12.000 mmol) was suspended in N,N-dimethylformamide (10.0 mL) and a solution of 4-(4,4,5,5-tetramethyl-1,3,2-dioxaborolan-2-yl)-1H-pyrazole (776 mg, 4.000 mmol) in N,N-dimethylformamide (10.0 mL) was added. The resulting cloudy white solution was stirred at room temperature for 15 minutes and rac-propylene oxide (839 μL, 697 mg, 12.000 mmol) was added. The vial containing the resulting cloudy yellow solution was sealed and heated to 80° C. for 2 h. The solvents were evaporated under reduced pressure and the residue was dissolved in $CH_2Cl_2$ (50 mL), filtered through a silica pad and concentrated under reduced pressure to afford crude 1-[4-(4,4,5,5-tetramethyl-1,3,2-dioxaborolan-2-yl)pyrazol-1-yl]propan-2-ol 110 as a brown solid which was used in the next step without further purification.

LCMS method F: $[M+H]^+$=253.2, $t_R$=1.93 min

Preparation of Intermediate 111: benzyl N-[3-[3-[1-(2-hydroxypropyl)pyrazol-4-yl]-1-tetrahydropyran-2-yl-indazol-5-yl]oxypropyl]carbamate

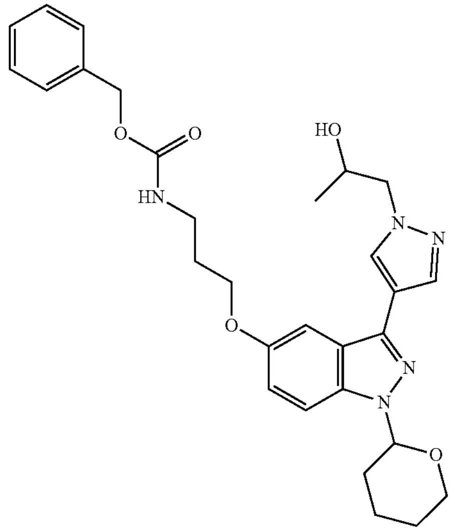 [SMILES: CC(O)Cn1cc(-c2nn(C3CCCCO3)c3ccc(OCCCNC(=O)OCc4ccccc4)cc23)cn1]

In a microwave vial, benzyl N-[3-(3-iodo-1-tetrahydropyran-2-yl-indazol-5-yl)oxypropyl]carbamate 26 (803 mg, 1.500 mmol), 1-[4-(4,4,5,5-tetramethyl-1,3,2-dioxaborolan- 2-yl)pyrazol-1-yl]propan-2-ol 110 (567 mg, 2.250 mmol), XPhos (72 mg, 0.150 mmol) and $K_3PO_4$ (955 mg, 4.500 mmol) were suspended in dioxane (6.0 mL) and water (1.5 mL) and the mixture was degassed with $N_2$ for 15 minutes. $Pd(PPh_3)_4$(87 mg, 0.075 mmol) was added and the resulting cloudy yellow solution was sealed and heated to 120° C. under microwave conditions for 2 h. The mixture was cooled to room temperature and poured in EtOAc (25 mL) and water (25 mL) and the two layers were separated. The aqueous layer was extracted with EtOAc (3×25 mL) and the combined organic layers were washed with saturated aqueous NaCl (1×25 mL), dried over anhydrous $Na_2SO_4$, filtered and concentrated under reduced pressure. The resulting crude material (yellow oil, 900 mg) was purified by column chromatography (40 g Macherey Nagel $SiO_2$, $CH_2Cl_2$/MeOH 100:0 to 95:5) to afford benzyl N-[3-[3-[1-(2-hydroxypropyl)pyrazol-4-yl]-1-tetrahydropyran-2-yl-indazol-5-yl]oxypropyl]carbamate 111 as a yellow solid.

LCMS method F: $[M+H]^+$=534.3, $t_R$=2.66 min

Preparation of Intermediate 112: 7-methyl-19-(oxan-2-yl)-8,14-dioxa-4,5,10,19,20-pentaazazetetra-cyclo[13.5.2.1$^{2,5}$.0$^{18,21}$]tricosa-1(20),2(23),3,15(22),16,18(21)-hexaen-9-one

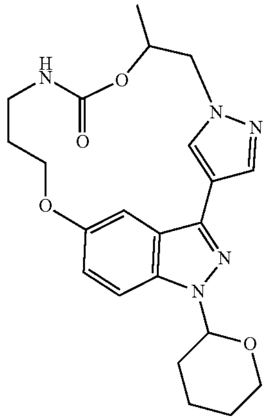 [SMILES: CC1Cn2cc(cn2)-c2nn(C3CCCCO3)c3ccc(cc23)OCCCNC(=O)O1]

To a solution of benzyl N-[3-[3-[1-(2-hydroxypropyl)pyrazol-4-yl]-1-tetrahydropyran-2-yl-indazol-5-yl]oxypropyl]carbamate 111 (180 mg, 0.334 mmol) in MeCN (18.0 mL) was added $Cs_2CO_3$ (659 mg, 2.024 mmol). The resulting cloudy white solution was heated to reflux for 6 h. LC/MS analysis indicated that the reaction was complete. The mixture was cooled to room temperature, filtered and concentrated under reduced pressure. The resulting crude material (pale yellow oil, 180 mg) was purified by column chromatography (4 g Macherey Nagel $SiO_2$, 15 mL/min, CyH/EtOAc 100:0 to 0:100) to afford 7-methyl-19-(oxan-2-yl)-8,14-dioxa-4,5,10,19,20-pentaazatetracyclo[13.5.2.1$^{2,5}$.0$^{18,21}$]tricosa-1(20),2(23),3,15(22),16,18(21)-hexaen-9-one 112 as a white solid.

LCMS method F: $[M+H]^+$=426.2, $t_R$=2.31 min

Preparation of Example 94: 7-methyl-8,14-dioxa-4,5,10,19,20-pentaazatetracyclo[13.5.2.1$^{2,5}$.0$^{18,21}$]tricosa-1(20),2(23),3,15(22),16,18(21)-hexaen-9-one

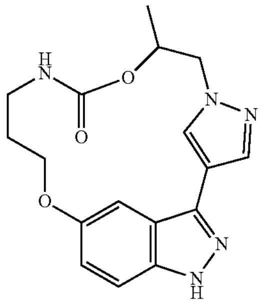 [SMILES: CC1Cn2cc(cn2)-c2n[nH]c3ccc(cc23)OCCCNC(=O)O1]

To a solution of 7-methyl-19-(oxan-2-yl)-8,14-dioxa-4,5,10,19,20-pentaazatetracyclo[13.5.2.1$^{2,5}$.0$^{18,21}$]tricosa-1(20),2(23),3,15(22),16,18(21)-hexaen-9-one 112 (43 mg, 0.101 mmol) in $CH_2Cl_2$ (2.5 mL) was added TFA (0.39 mL, 0.576 mg, 5.050 mmol). The resulting transparent solution was stirred at room temperature for 6 h. The solvent was removed under reduced pressure and the residue was triturated with MeCN and dried (50° C., 5 mbar) for 3 h to afford 7-methyl-8,14-dioxa-4,5,10,19,20-pentaazatetracyclo[13.5.2.1$^{2,5}$.0$^{18,21}$]tricosa-1(20),2(23),3,15(22),16,18(21)-hexaen-9-one example 94 as a white solid.

LCMS method F: $[M+H]^+$=342.2, $t_R$=2.42 min

LCMS method G: $[M+H]^+$=342.2, $t_R$=2.39 min $^1$H NMR (400 MHz, d6-DMSO) δ 12.81 (s, 1H), 8.14 (s, 1H), 7.86-7.82 (m, 1H), 7.77 (s, 1H), 7.42 (d, J=9.0 Hz, 1H), 7.08 (d, J=2.5 Hz, 1H), 6.94 (dd, J=2.7, 9.1 Hz, 1H), 4.96-4.89 (m, 1H), 4.49 (dd, J=2.3, 14.9 Hz, 1H), 4.42 (dd, J=3.6, 12.2 Hz, 1H), 4.30 (dd, J=10.2, 14.5 Hz, 1H), 4.24-4.16 (m, 1H), 3.53-3.47 (m, 1H), 2.78-2.71 (m, 1H), 1.97-1.88 (m, 1H), 1.78-1.68 (m, 1H), 1.31 (d, J=6.3 Hz, 3H) ppm.

Example 95: 5-fluoro-4-methoxy-7-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

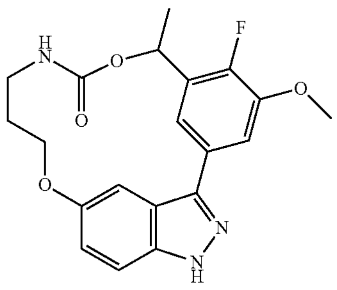 [SMILES: COc1cc2cc(c1F)C(C)OC(=O)NCCCOc1ccc3[nH]nc-2c3c1]

Example 95 is prepared according to the synthesis route described in general Scheme A and according to the procedures described to obtain example 88 to give 5-fluoro-4-methoxy-7-methyl-8,14-dioxa-10,19,20-triazatetracyclo[13.5.2.1$^{2,6}$.0$^{18,21}$]tricosa-1(20),2(23),3,5,15(22), 16,18(21)-heptaen-9-one example 95.

LCMS method F: $[M+H]^+$=386.2, $t_R$=2.41 min

LCMS method G: $[M+H]^+$=386.2, $t_R$=2.40 min $^1H$ NMR (400 MHz, d6-DMSO) δ 13.14 (1H, br. s), 8.07 (1H, dd, J=4.2, 7.8 Hz), 7.52-7.47 (2H, m), 7.43-7.40 (1H, m), 7.33 (1H, d, J=2.1 Hz), 6.99 (1H, dd, J=2.2, 9.0 Hz), 5.84-5.77 (1H, m), 4.37-4.27 (2H, m), 3.93 (3H, s), 3.55-3.48 (1H, m), 2.77-2.67 (1H, m), 2.15-2.07 (1H, m), 1.78-1.69 (1H, m), 1.56-1.53 (3H, d, J=6.4 Hz) ppm.

Example 96: (7R,13R)-7,13-dimethyl-8,14-dioxa-10,19,20-triazatetracyclo[13.5.2.$1^{2,6}$.$0^{18,21}$]tricosa-1(20),2(23),3,5,15(22),16,18(21)-heptaen-9-one

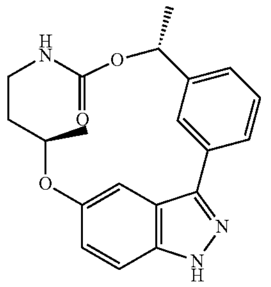 [SMILES: C[C@@H]1CCNC(=O)O[C@H](C)c2cccc(c2)-c2n[nH]c3ccc(cc23)O1]

Example 96 is prepared according to the synthesis route described in general Scheme C and by chiral HPLC purification. The chiral purification is done on a Chiralpak IA column 250×4.6 mm 5 μm, eluent [heptane/EtOH]+0.1% DEA [80/0], 1 mL/min RT to give (7R,13R)-7,13-dimethyl-8,14-dioxa-10,19,20-triazatetracyclo[13.5.2.$1^{2,6}$.$0^{18,21}$]tricosa-1(20),2(23),3,5,15(22), 16,18(21)-heptaen-9-one example 96.

LCMS method F: $[M+H]^+$=352.2, $t_R$=2.47 min

LCMS method G: $[M+H]^+$=352.2, $t_R$=2.44 min $^1H$ NMR (400 MHz, d6-DMSO) δ 12.81-12.77 (1H, m), 7.92 (1H, s), 7.76 (1H, d, J=7.6 Hz), 7.53-7.36 (3H, m), 7.31-7.27 (2H, m), 6.96 (1H, dd, J=2.3, 8.9 Hz), 5.92 (1H, s), 4.64 (1H, s), 3.26-3.22 (1H, m), 3.15-3.05 (1H, m), 2.1-1.86 (1H, m), 1.62 (4H, s), 1.41-1.37 (3H, m) ppm.

Chiral HPLC e.e. 100%

Example 97: (13R)-13-methyl-8,14-dioxa-4,5,10,19,20-pentaazatetracyclo[13.5.2.$1^{2,5}$.$0^{18,12}$]tricosa-1(20),2(23),3,15,17,21-hexaen-9-one

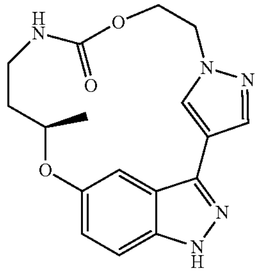 [SMILES: C[C@@H]1CCNC(=O)OCCn2cc(cn2)-c2n[nH]c3ccc(cc23)O1]

Example 97 is prepared according to the synthesis route described in general Scheme C and by chiral HPLC purification. The chiral purification is done on a Chiralpak IB N-5 column 20×250 mm 5 μm, eluent [heptane/EtOH]+0.1% DEA [85/15] run time 20 min, 19 mL/min RT to give (13R)-13-methyl-8,14-dioxa-4,5,10,19,20-pentaazatetracyclo[13.5.2.$1^{2,5}$.$0^{18,21}$]tricosa-1(20),2(23),3,15,17,21-hexaen-9-one example 97.

LCMS method F: $[M+H]^+$=342.3, $t_R$=1.91 min

LCMS method G: $[M+H]^+$=342.2, $t_R$=1.92 min $^1H$ NMR (400 MHz, d6-DMSO) δ 12.80 (1H, s), 8.08 (1H, s), 7.77-7.76 (2H, m), 7.43-7.39 (1H, m), 7.07 (1H, d, J=1.9 Hz), 6.92 (1H, dd, J=2.2, 9.0 Hz), 4.68-4.42 (4H, m), 4.11-4.05 (1H, m), 3.58-3.46 (1H, mm), 2.94-2.86 (1H, m), 2.16-2.08 (1H, m), 1.39-1.36 (4H, m) ppm.

Chiral HPLC e.e. >99%

Example 98: 8,15-dioxa-4,10,20,21-tetraazapentacyclo[14.5.2.$1^{2,6}$.$1^{10,13}$.$0^{19,22}$]pentacosa-1(21),2(25),3,5,16(23),17,19(22)-heptaen-9-one

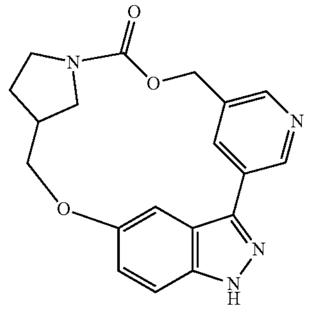 [SMILES: O=C1OCc2cncc(c2)-c2n[nH]c3ccc(cc23)OCC2CCN1C2]

Example 98 is prepared according to the synthesis route described in general Scheme N.

Preparation of Intermediate 113: benzyl 3-(hydroxymethyl)pyrrolidine-1-carboxylate

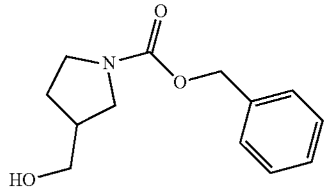 [SMILES: O=C(OCc1ccccc1)N1CCC(CO)C1]

To a solution of 3-bromopropylamine hydrobromide (2.0 g, 19.8 mmol) in aq. NaOH 10% (60 mL) at 0° C. was slowly added benzyl chlorformate (3.1 mL, 21.8 mmol) and the mixture was stirred at RT for 1 hour. The reaction mixture was diluted with DCM (100 mL). The aqueous layer was extracted two times with DCM (50 mL). The combined organic layers were washed with brine (50 mL), dried over sodium sulfate, filtered and concentrated under reduced pressure to give a yellow oil. The residue was purified by flash chromatography (CyH/AE 0 to 100% EtOAc) to afford benzyl 3-(hydroxymethyl)pyrrolidine-1-carboxylate 113 as an yellow oil.

LCMS method F: $[M+H]^+$=236, $t_R$=1.97 min

Preparation of Intermediate 114: benzyl 3-(methylsulfonyloxymethyl)pyrrolidine-1-carboxylate

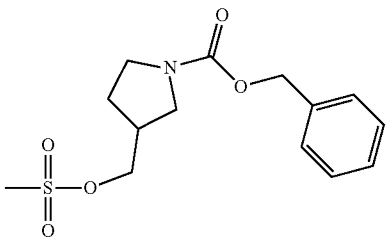 [SMILES: CS(=O)(=O)OCC1CCN(C(=O)OCc2ccccc2)C1]

To a solution of benzyl 3-(hydroxymethyl)pyrrolidine-1-carboxylate 113 (2.90 g, 12.3 mmol) and diisopropylethylamine (4.28 mL, 24.6 mmol) in dichloromethane (20 mL) at 0° C., was added dropwise methanesulfonyl chloride (1.13 mL, 14.8 mmol). The reaction mixture was stirred at room temperature for 4 hours. The organic layer was washed with a saturated solution of ammonium chloride (50 mL), with a saturated solution of sodium bicarbonate (50 mL) and brine, filtered and the solvent was removed under reduced pressure to give benzyl 3-(methylsulfonyloxymethyl)pyrrolidine-1-carboxylate 114 as a yellow oil. The crude product was used in the next step without further purification.

LCMS method F: $[M+H]^+=314$, $t_R=2.29$ min

Preparation of Intermediate 115: benzyl 3-(methylsulfonyloxymethyl)pyrrolidine-1-carboxylate

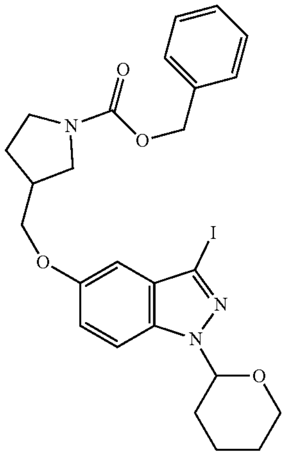 [SMILES: O=C(OCc1ccccc1)N1CCC(COc2ccc3c(c2)c(I)nn3C2CCCCO2)C1]

To a solution of 3-iodo-1-tetrahydropyran-2-yl-indazol-5-ol 4 (4.33 g, 12.6 mmol) in N,N-dimethylformamide (100 mL) was added cesium carbonate (10.27 g, 31.5 mmol). The resulting green solution was stirred at room temperature for 10 minutes. tert-butyl 3-(methylsulfonyloxymethyl)azetidine-1-carboxylate 114 (3.94 g, 12.6 mmol) was added and the mixture was stirred at 60° C. for 12 h. The mixture was cooled to room temperature and concentrated under reduced pressure. The residue was diluted with water (50 mL) and ethyl acetate (100 mL). After separation, the aqueous layer was extracted with ethyl acetate (2×100 mL). The combined organic layers were washed with brine, dried over anhydrous magnesium sulfate, filtered and evaporated under reduced pressure to afford a yellow oil. The oily residue was purified by flash chromatography (CyH/EtOAc 7/3) to afford benzyl 3-(methylsulfonyloxymethyl)pyrrolidine-1-carboxylate 115 as a colorless oil.

LCMS method F: $[M+H]^+=562$, $t_R=3.32$ min

Preparation of Intermediate 116: 5-(pyrrolidin-3-ylmethoxy)-1-tetrahydropyran-2-yl-indazole

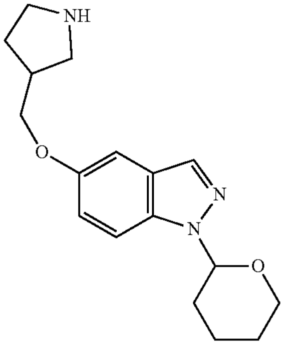 [SMILES: c1cc2c(cnn2C2CCCCO2)cc1OCC1CCNC1]

To a solution of benzyl 3-[(3-iodo-1-tetrahydropyran-2-yl-indazol-5-yl)oxymethyl]pyrrolidine-1-carboxylate 115 (4.00 g, 7.13 mmol) in MeOH (200 mL) were added triethylamine (2.4 mL) and 10% Pd/C (75 mg). The reaction vessel was pressurized to 50 psi (approx. 3-4 bar) for 24 hours in a parr shaker. The mixture was filtered over celite. The filtrate was concentrated under reduced pressure to give 5-(pyrrolidin-3-ylmethoxy)-1-tetrahydropyran-2-yl-indazole 116 as a slightly yellow foam. The crude product was used in the next step without any further purification.

LCMS method F: $[M+H]^+=302.2$, $t_R=1.43$ min

Preparation of Intermediate 117: (5-bromo-3-pyridyl)methyl 3-[(1-tetrahydropyran-2-ylindazol-5-yl)oxymethyl]pyrrolidine-1-carboxylate

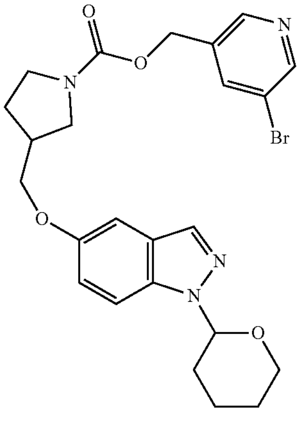 [SMILES: O=C(OCc1cncc(Br)c1)N1CCC(COc2ccc3c(cnn3C3CCCCO3)c2)C1]

To a solution of 5-(pyrrolidin-3-ylmethoxy)-1-tetrahydropyran-2-yl-indazole 116 (0.890 g, 2.95 mmol) in dimethylacetamide (200 mL) was added 1,1'-carbonyldiimidazole (0.526 g, 3.25 mmol). The reaction mixture was stirred at room temperature for 2 hours. The reaction mixture was then added dropwise to a solution of (5-bromo-3-pyridyl)methanol (0.830 g, 4.42 mmol) and cesium carbonate (4.79 g, 14.75 mmol) in DMA (50 mL) at 90° C. and the mixture was stirred at 90° C. for 16 hours. The reaction mixture was allowed to cool down to room temperature and filtered. The filtrate was diluted with water and extracted three times with ethyl acetate (3×100 mL). The combined organic layers were washed with water, brine, dried over anhydrous magnesium sulfate, filtered and concentrated under reduced pressure. The crude product was purified by silica gel column chromatography (eluent: Cyclohexane/EtOAc from 95/5 to 50/50) to afford (5-bromo-3-pyridyl)methyl 3-[(1-tetrahydropyran-2-ylindazol-5-yl)oxymethyl]pyrrolidine-1-carboxylate 117 as a colorless oil.

LCMS method F: $[M+H]^+$=517.1, $t_R$=2.81 min

Preparation of Intermediate 118: 20-(oxan-2-yl)-8,15-dioxa-4,10,20,21-tetraazapentacyclo[14.5.2.1$^{2,6}$.1$^{10,13}$.0$^{19,22}$]pentacosa-1(21),2(25),3,5,16(23),17,19(22)-heptaen-9-one

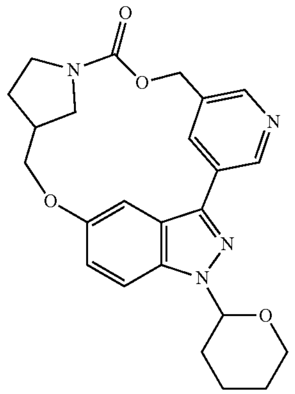 [SMILES: O=C1OCc2cncc(c2)-c2nn(C3CCCCO3)c3ccc(cc23)OCC2CCN1C2]

To a solution of (5-bromo-3-pyridyl)methyl 3-[(1-tetrahydropyran-2-ylindazol-5-yl)oxymethyl]pyrrolidine-1-carboxylate 117 (0.530 g, 1.03 mmol) in toluene (60 mL) was added potassium acetate (0.202 g, 2.06 mmol) at room temperature. The mixture was degassed by bubbling nitrogen for 15 minutes, then, palladium acetate (0.047 g, 0.21 mmol,) and tricyclohexylphosphine (0.059 g, 0.21 mmol) were added. The mixture was heated under microwave conditions at 150° C. for 1 hour and 30 minutes. The reaction mixture was filtered over celite, concentrated under reduced pressure, diluted with DCM, extracted with water, dried over anhydrous magnesium sulfate, filtered and concentrated under reduced pressure. The crude was purified by column chromatography on silica gel (DCM/MeOH: from 10/0 to 9/1) to afford 20-(oxan-2-yl)-8,15-dioxa-4,10,20,21-tetraazapentacyclo[14.5.2.1$^{2,6}$.1$^{10,13}$.0$^{19,22}$]pentacosa-1(21),2(25),3,5,16(23),17,19(22)-heptaen-9-one 118 as a colorless oil.

LCMS method F: $[M+H]^+$=435.3, $t_R$=2.48 min

Preparation of Example 98: 8,15-dioxa-4,10,20,21-tetraazapentacyclo[14.5.2.1$^{2,6}$.1$^{10,13}$.0$^{19,22}$]pentacosa-1(21),2(25),3,5,16(23),17,19(22)-heptaen-9-one

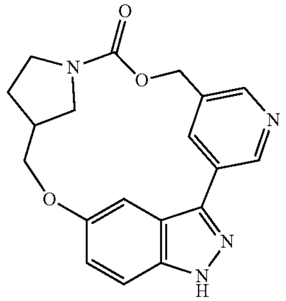 [SMILES: O=C1OCc2cncc(c2)-c2n[nH]c3ccc(cc23)OCC2CCN1C2]

To a solution of 20-(oxan-2-yl)-8,15-dioxa-4,10,20,21-tetraazapentacyclo[14.5.2.1$^{2,6}$.1$^{10,13}$.0$^{19,22}$]pentacosa-1(21),2(25),3,5,16(23),17,19(22)-heptaen-9-one 118 (0.043 g, 0.10 mmol) in DCM (8 mL) was added trifluoroacetic acid (0.15 mL, 2.00 mmol). The mixture was heated under microwave conditions at 80° C. for 1 hour. More trifluoroacetic acid (0.3 mL, 4.00 mmol) was added. The mixture was heated under microwave conditions at 90° C. for 2 more hours. The solvent was evaporated under reduced pressure to give a yellow oily residue. The residue was recrystallized in DCM, filtered and dried under reduced pressure to afford 8,15-dioxa-4,10,20,21-tetraazapentacyclo[14.5.2.1$^{2,6}$.1$^{10,13}$.0$^{19,22}$]pentacosa-1(21),2(25), 3,5,16(23),17,19(22)-heptaen-9-one example 98 as a slightly brown beige solid.

LCMS method F: $[M+H]^+$=351.2, $t_R$=1.75 min

LCMS method G: $[M+H]^+$=351.2, $t_R$=1.96 min

The NMR showed a mixture of rotamers, reported as rot.1 and rot.2 in the NMR description below.

$^1$H NMR (400 MHz, d6-DMSO) δ 13.33 (0.7H, rot.1, br. s), 13.30 (0.3H, rot.2, br. s), 8.95 (0.7H, rot.1, s), 8.89 (0.3H, rot.2, s), 8.60 (0.3H, rot.2, s), 8.56 (0.7H, rot.1, s), 8.29 (0.7H, rot.1, s), 8.26 (0.3H, rot.2, s), 7.52 (0.7H, rot.1, d, J=9.4 Hz), 7.51 (0.3H, rot.2, d, J=9.4 Hz), 7.23-7.05 (2H, rot.1+rot.2, m), 5.75 (0.7H, rot.1, d, J=13.6 Hz), 5.67 (0.3H, rot.2, d, J=14.0 Hz), 5.04 (0.7H, rot.1, d, J=13.6 Hz), 5.02 (0.3H, rot.2, d, J=13.6 Hz), 4.27-4.20 (1H, rot.1+rot.2, m), 4.15-4.01 (1H, rot.1+rot.2, m), 3.89 (1H, rot.1+rot.2, t, J=12.4 Hz), 3.72-3.61 (1H, rot.1+rot.2, m), 3.57-3.47 (2H, rot.1+rot.2, m), 2.80-2.70 (1H, rot.1+rot.2, m), 2.16-1.98 (1H, rot.1+rot.2, m), 1.74-1.64 (1H, rot.1+rot.2, m) ppm.

Example 99: 8,14-dioxa-5,10,19,20-tetraazatetracyclo[13.5.2.1$^{2,5}$.0$^{18,21}$]tricosa-1(20),2(23),3,15(22),16,18(21)-hexaen-9-one

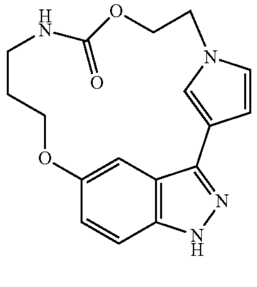 [SMILES: O=C1NCCCOc2ccc3[nH]nc(c3c2)-c2ccn(c2)CCO1]

Example 99 is prepared according to the synthesis route described in general Scheme J.

Preparation of Intermediate 119: 5-(benzyloxy)-3-iodo-1-(oxan-2-yl)-1H-indazole

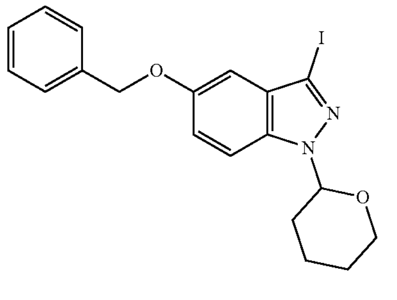 [SMILES: Ic1nn(C2CCCCO2)c2ccc(OCc3ccccc3)cc12]

To a solution of 3-iodo-1-(oxan-2-yl)-1H-indazol-5-ol (3.442 g, 10.0 mmol) in acetonitrile (100 mL) were added at RT cesium carbonate (4.235 g, 13.0 mmol) and benzyl bromide (1.308 mL, 11.0 mmol). The resulting reaction mixture was stirred at RT overnight. The reaction mixture was concentrated under reduced pressure. The residue was diluted with water and brine and extracted twice with ethyl acetate. The combined organic layers were dried over anhydrous sodium sulfate and the solvent was removed under reduced pressure. The residue was triturated in acetonitrile and filtered affording 5-(benzyloxy)-3-iodo-1-(oxan-2-yl)-1H-indazole 119 as a white solid.

LCMS method F: $[M+H]^+$=435.1, $t_R$=3.33 min

Preparation of Intermediate 120: 5-(benzyloxy)-1-(oxan-2-yl)-3-(1H-pyrrol-3-yl)-1H-indazole

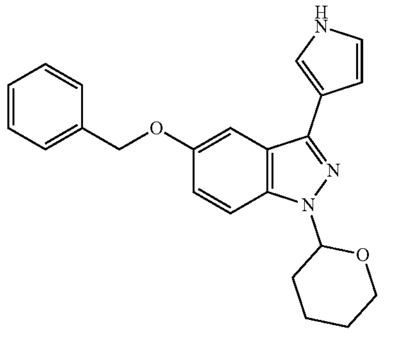 [SMILES: c1ccc(COc2ccc3c(c2)c(-c2cc[nH]c2)nn3C2CCCCO2)cc1]

To a solution of 5-(benzyloxy)-3-iodo-1-(oxan-2-yl)-1H-indazole 119 (1.000 g, 2.3 mmol) in dioxane (6.9 mL) and water (2.3 mL) was added at RT 3-(4,4,5,5-tetramethyl-1,3,2-dioxaborolan-2-yl)-1H-pyrrole (0.534 g, 2.76 mmol), $K_3PO_4$ (1.466 g, 6.91 mmol), XPhos (0.110 g, 0.23 mmol) and $Pd(PPh_3)_4$(0.133 g, 0.12 mmol). The resulting reaction mixture was stirred under microwave conditions at 120° C. for 1 h. The residue was diluted with brine and extracted twice with ethyl acetate. The combined organic layers were dried over anhydrous sodium sulfate and concentrated under reduced pressure. The residue was purified by flash-column (25 g silica Macherey Nagel) chromatography (cyclohexane-ethyl acetate, 1:0 to 6:4) affording 5-(benzyloxy)-1-(oxan-2-yl)-3-(1H-pyrrol-3-yl)-1H-indazole 120 as a yellow oil.

LCMS method F: $[M+H]^+$=374.2, $t_R$=2.95 min

Preparation of Intermediate 121: 5-(benzyloxy)-3-(1-{2-[(tert-butyldimethylsilyl)oxy]ethyl}-1H-pyrrol-3-yl)-1-(oxan-2-yl)-1H-indazole

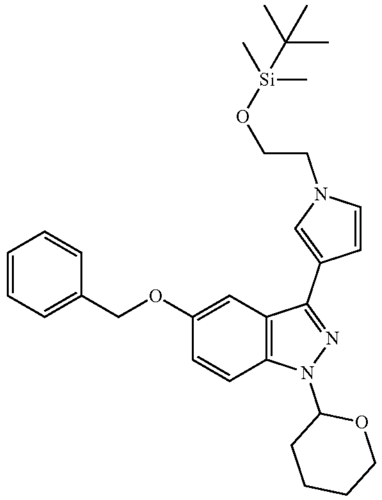 [SMILES: CC(C)(C)[Si](C)(C)OCCn1ccc(-c2nn(C3CCCCO3)c3ccc(OCc4ccccc4)cc23)c1]

To a solution of 5-(benzyloxy)-1-(oxan-2-yl)-3-(1H-pyrrol-3-yl)-1H-indazole 120 (0.740 g, 1.98 mmol) in N,N-dimethylformamide (8 mL) at 0° C. was added portion wise NaH (0.119 g, 2.97 mmol). After 20 min (2-bromoethoxy)(tert-butyl)dimethylsilane (0.850 mL, 3.96 mmol) in N,N-dimethylformamide (2 mL) was added dropwise at 0° C. The resulting reaction mixture was stirred at 0° C. for 10 min and at RT for 2 h. The reaction mixture was quenched by addition of MeOH and it was concentrated under reduced pressure. The residue was diluted with brine and extracted twice with ethyl acetate. The combined organic layers were dried over anhydrous sodium sulfate and concentrated under reduced pressure. The residue was purified by flash-column (25 g silica Macherey Nagel) chromatography (cyclohexane-ethyl acetate, 1:0 to 9:1) affording 5-(benzyloxy)-3-(1-{2-[(tert-butyldimethylsilyl)oxy]ethyl}-1H-pyrrol-3-yl)-1-(oxan-2-yl)-1H-indazole 121 as a yellow oil.

LCMS method F: $[M+H]^+$=532.4, $t_R$=3.80 min

Preparation of Intermediate 122: 3-(1-{2-[(tert-butyldimethylsilyl)oxy]ethyl}-1H-pyrrol-3-yl)-1-(oxan-2-yl)-1H-indazol-5-ol

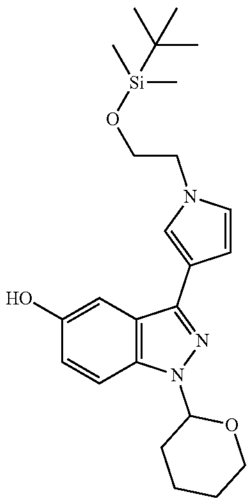 [SMILES: CC(C)(C)[Si](C)(C)OCCn1ccc(-c2nn(C3CCCCO3)c3ccc(O)cc23)c1]

To a solution of 5-(benzyloxy)-3-(1-{2-[(tert-butyldimethylsilyl)oxy]ethyl}-1H-pyrrol-3-yl)-1-(oxan-2-yl)-1H-indazole 121 (0.900 g, 1.69 mmol) in EtOH (15 mL) was added at RT palladium 10% on carbon (90 mg). The reaction mixture was stirred under hydrogen atmosphere at RT overnight. The reaction mixture was filtered and the filtrate was concentrated under reduced pressure. The residue was purified by flash-column (25 g silica Macherey Nagel) chromatography (cyclohexane-ethyl acetate, 1:0 to 8:2) affording 3-(1-{2-[(tert-butyldimethylsilyl)oxy]ethyl}-1H-pyrrol-3-yl)-1-(oxan-2-yl)-1H-indazol-5-ol 122 as a colorless oil.

LCMS method F: $[M+H]^+=442.2$, $t_R=3.27$ min

Preparation of Intermediate 123: benzyl N-(3-{[3-(1-{2-[(tert-butyldimethylsilyl)oxy]ethyl}-1H-pyrrol-3-yl)-1-(oxan-2-yl)-1H-indazol-5-yl]oxy}propyl) carbamate

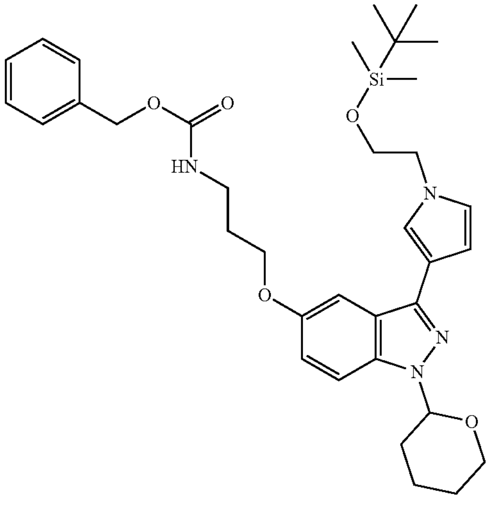 [SMILES: CC(C)(C)[Si](C)(C)OCCn1ccc(-c2nn(C3CCCCO3)c3ccc(OCCCNC(=O)OCc4ccccc4)cc23)c1]

To a solution of 3-(1-{2-[(tert-butyldimethylsilyl)oxy] ethyl}-1H-pyrrol-3-yl)-1-(oxan-2-yl)-1H-indazol-5-ol 122 (0.310 g, 0.70 mmol) in acetonitrile (5 mL) were added at RT cesium carbonate (0.297 g, 0.91 mmol) and benzyl N-(3-bromopropyl)carbamate (0.150 mL, 0.77 mmol). The resulting reaction mixture was stirred at RT overnight. The reaction mixture was concentrated under reduced pressure. The residue was diluted with water and brine and extracted with ethyl acetate twice. The combined organic layers were dried over anhydrous sodium sulfate and concentrated under reduced pressure affording benzyl N-(3-{[3-(1-{2-[(tert-butyldimethylsilyl)oxy]ethyl}-1H-pyrrol-3-yl)-1-(oxan-2-yl)-1H-indazol-5-yl]oxy}propyl) carbamate 123 as a yellow oil. The product was used in the next step without further purification.

LCMS method F: $[M+H]^+=633.3$, $t_R=3.64$ min

Preparation of Intermediate 124: benzyl N-[3-({3-[1-(2-hydroxyethyl)-1H-pyrrol-3-yl]-1-(oxan-2-yl)-1H-indazol-5-yl}oxy)propyl]carbamate

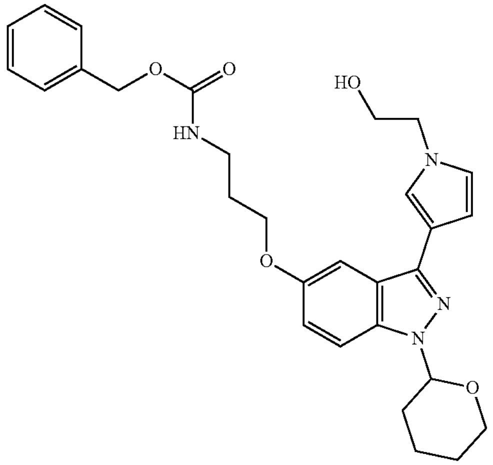 [SMILES: O=C(NCCCOc1ccc2c(c1)c(-c1ccn(CCO)c1)nn2C1CCCCO1)OCc1ccccc1]

To a solution of benzyl N-(3-{[3-(1-{2-[(tert-butyldimethylsilyl)oxy]ethyl}-1H-pyrrol-3-yl)-1-(oxan-2-yl)-1H-indazol-5-yl]oxy}propyl)carbamate 123 (0.444 g, 0.70 mmol) in THE (5 mL) was added at RT tetrabutylammonium fluoride 1M in THE (1.4 mL, 1.40 mmol). The resulting reaction mixture was stirred at RT for 2 h. The reaction mixture was diluted with brine and extracted with ethyl acetate twice. The combined organic layers were dried over anhydrous sodium sulfate and concentrated under reduced pressure. The residue was purified by flash-column (15 g silica Macherey Nagel) chromatography (cyclohexane-ethyl acetate 3/EtOH 1, 1:0 to 7:3) affording benzyl N-[3-({3-[1-(2-hydroxyethyl)-1H-pyrrol-3-yl]-1-(oxan-2-yl)-1H-indazol-5-yl}oxy)propyl]carbamate 124 as a colorless oil.

LCMS method F: $[M+H]^+=519.2$, $t_R=2.72$ min

Preparation of Intermediate 125: 19-(oxan-2-yl)-8,14-dioxa-5,10,19,20-tetraazatetracyclo[13.5.2.1$^{2,5}$.0$^{18,21}$]tricosa-1(20),2(23),3,15(22),16,8(21)-hexaen-9-one

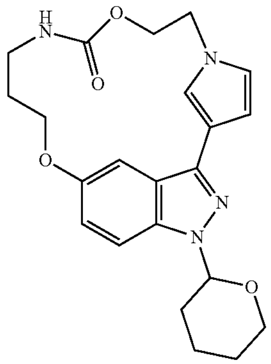 [SMILES: O=C1NCCCOc2ccc3c(c2)c(nn3C2CCCCO2)-c2ccn(c2)CCO1]

To a solution of benzyl N-[3-({3-[1-(2-hydroxyethyl)-1H-pyrrol-3-yl]-1-(oxan-2-yl)-1H-indazol-5-yl}oxy)propyl]carbamate 124 (0.230 g, 0.44 mmol) in anhydrous acetonitrile (88 mL) was added at RT cesium carbonate (0.867 g, 2.66 mmol). The resulting reaction mixture was stirred at 90° C. for 48 h. The reaction mixture was filtered and the filtrate was concentrated under reduced pressure. The residue was purified by flash-column (15 g silica Macherey Nagel) chromatography (cyclohexane-ethyl acetate 3/EtOH 1, 1:0 to 8:2) affording 19-(oxan-2-yl)-8,14-dioxa-5,10,19,20-tetraazatetracyclo[13.5.2.1$^{2,5}$.0$^{18,21}$]tricosa-1(20),2(23),3,15(22), 16,18(21)-hexaen-9-one 125 as a colorless oil.

LCMS method F: $[M+H]^+$=411.2, $t_R$=2.42 min

Preparation of Example 99: 8,14-dioxa-5,10,19,20-tetraazatetracyclo[13.5.2.1$^{2,5}$.0$^{18,21}$]tricosa-1(20),2(23),3,15(22),16,18(21)-hexaen-9-one

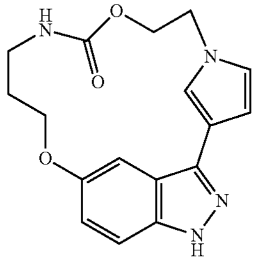 [SMILES: O=C1NCCCOc2ccc3[nH]nc(c3c2)-c2ccn(c2)CCO1]

To a solution of 19-(oxan-2-yl)-8,14-dioxa-5,10,19,20-tetraazatetracyclo[13.5.2.1$^{2,5}$.0$^{18,21}$]tricosa-1(20),2(23),3,15(22),16,18(21)-hexaen-9-one 125 (0.100 g, 0.24 mmol) in DCM (3 mL) was added at RT TFA (0.363 mL, 4.87 mmol). The resulting reaction mixture was stirred under microwave conditions at 80° C. for 20 min. The reaction mixture was concentrated under reduced pressure, diluted with a saturated sodium bicarbonate solution and extracted with ethyl acetate twice. The combined organic layers were dried over anhydrous sodium sulfate and concentrated under reduced pressure. The residue was purified by flash-column (15 g silica Macherey Nagel) chromatography (cyclohexane-ethyl acetate 3/EtOH 1, 1:0 to 7:3) to give the product with some impurities. The product was purified twice by flash-column (2*4 g silica Macherey Nagel) chromatography (DCM-MeOH, 1:0 to 98:2) to give a solid (10 mg), which was triturated in diisopropyl ether and filtered affording 8,14-dioxa-5,10,19,20-tetraazatetracyclo[13.5.2.1$^{2,5}$.0$^{18,21}$]tricosa-1(20),2(23),3,15(22),16,18(21)-hexaen-9-one example 99 as a cream solid.

LCMS method F: $[M+H]^+$=327.2, $t_R$=1.82 min

LCMS method G: $[M+H]^+$=327.3, $t_R$=1.90 min $^1$H NMR (400 MHz, d6-DMSO) δ 12.56 (1H, s); 7.90-7.86 (1H, m), 7.39-7.36 (1H, m), 7.26-7.24 (1H, m), 7.15 (1H, d, J=1.9 Hz), 6.92-6.87 (2H, m), 6.39 (1H, dd, J=1.7, 2.5 Hz), 4.35-4.23 (6H, m), 3.18-3.11 (2H, m), 1.92-1.83 (2H, m) ppm.

Example 100: (13R) or (13S)-4-fluoro-13-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

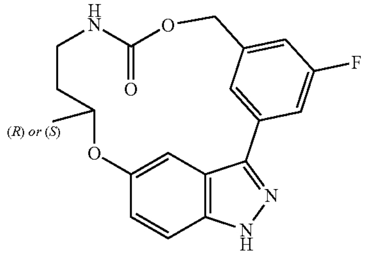 [SMILES: CC1CCNC(=O)OCc2cc(F)cc(c2)-c2n[nH]c3ccc(cc23)O1]

Example 100 is prepared according to the synthesis route described in general Scheme C and by chiral SFC separation of example 71 to give (13R) or (13 S)-4-fluoro-13-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one example 100.

LCMS method F: $[M+H]^+$=356.2, $t_R$=2.46 min

LCMS method G: $[M+H]^+$=356.2, $t_R$=2.46 min $^1$H NMR (400 MHz, d6-DMSO) δ 13.26 (1H, s), 7.99 (1H, dd, J=5.0, 7.3 Hz), 7.67 (1H, s), 7.61-7.50 (2H, m), 7.26 (1H, d, J=1.7 Hz), 7.17 (1H, d, J=9.5 Hz), 6.98 (1H, dd, J=2.3, 8.9 Hz), 5.73 (1H, s), 4.89-4.83 (1H, m), 4.61-4.54 (1H, m), 3.61-3.58 (1H, m), 2.95-2.87 (1H, m), 2.40-2.33 (1H, m), 1.42-1.39 (4H, m) ppm.

Chiral HPLC e.e. >98%

The compound is a pure enantiomer, but the absolute stereochemistry of the chiral center is unknown.

Example 101: (13R) or (13S)-4-fluoro-13-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one Example 101 is prepared according to the synthesis route described in general Scheme C and by chiral SFC separation of example 71 to give (13R) or (13 S)-4-fluoro-13-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one example 101.

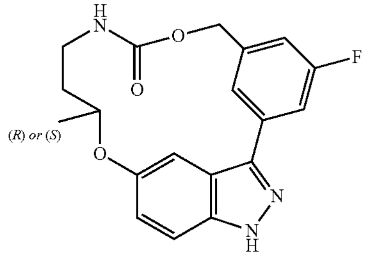 [SMILES: CC1CCNC(=O)OCc2cc(F)cc(c2)-c2n[nH]c3ccc(cc23)O1]

LCMS method F: $[M+H]^+$=356.2, $t_R$=2.47 min

LCMS method G: $[M+H]^+$=356.2, $t_R$=2.46 min $^1$H NMR (400 MHz, d6-DMSO) δ 13.28-13.26 (1H, m), 7.99 (1H, dd, J=5.2, 6.7 Hz), 7.67 (1H, s), 7.61-7.50 (2H, m), 7.26 (1H, d, J=1.9 Hz), 7.19-7.15 (1H, m), 6.98 (1H, dd, J=2.3, 8.9 Hz), 5.74-5.70 (1H, m), 4.89-4.79 (1H, m), 4.61-4.53 (1H, m), 3.59 (1H, s), 2.95-2.86 (1H, m), 2.40-2.33 (1H, m), 1.42-1.39 (4H, m) ppm.

Chiral HPLC e.e. >98%

The compound is a pure enantiomer, but the absolute stereochemistry of the chiral center is unknown

Example 102: (13R)-13-methyl-8,14-dioxa-4,10,19,20-tetraazatetracyclo[13.5.2.1$^{2,6}$.0$^{18,21}$]tricosa-1(20),2(23),3,5,15(22),16,18(21)-heptaen-9-one

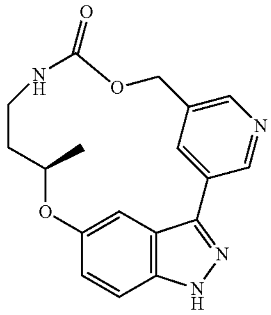 [SMILES: C[C@@H]1CCNC(=O)OCc2cncc(c2)-c2n[nH]c3ccc(cc23)O1]

Example 102 is prepared according to the synthesis route described in general Scheme C and by chiral HPLC purification. The chiral purification is done on a Chiralpak IB N-5 column 250×4.6 mm 5 μm, eluent [C7/EtOH]+0.1% DEA [80/20], 1 mL/min RT to give (13R)-13-methyl-8,14-dioxa-4,10,19,20-tetraazatetracyclo[13.5.2.1$^{2,6}$.0$^{18,21}$]tricosa-1(20),2(23),3,5, 15(22),16,18(21)-heptaen-9-one example 102.

LCMS method F: $[M+H]^+$=339, $t_R$=1.80 min

LCMS method G: $[M+H]^+$=339, $t_R$=2.05 min $^1$H NMR (400 MHz, d6-DMSO) δ 13.32 (1H, s), 9.04 (1H, d), 8.53 (1H, d), 8.15 (1H, m), 8.02-7.99 (1H, m), 7.54 (1H, d), 7.19 (1H, m), 7.01-6.98 (1H, dd, J=2.2, 9.0 Hz), 5.77-5.74 (1H, m), 4.95-4.92 (1H, m), 4.59-4.52 (1H, m), 3.60-3.53 (1H, m), 2.95-2.87 (1H, m), 2.45-2.38 (1H, m), 1.41 (3H, d), 1.38-1.34 (1H, m) ppm.

Chiral HPLC e.e. >99%

Example 103: 6-cyclopropyl-8,14-dioxa-4,5,10,19,20-pentaazatetracyclo[13.5.2.1$^{2,5}$.0$^{18,21}$]tricosa-1(20),2(23),3,15(22),16,18(21)-hexaen-9-one

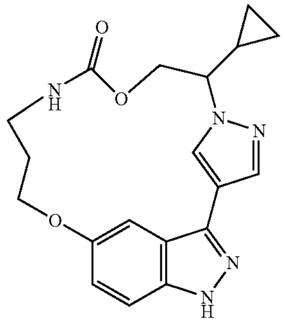 [SMILES: O=C1NCCCOc2ccc3[nH]nc(c3c2)-c2cnn(c2)C(C2CC2)CO1]

Example 103 is prepared according to the synthesis route described in general Scheme B.

Preparation of Intermediate 126: ethyl 2-(4-bromopyrazol-1-yl)-2-cyclopropyl-acetate

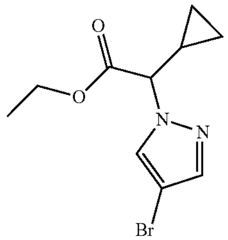

To a solution of 4-bromo-1H-pyrazole (588 mg, 4 mmol) in N,N-dimethylformamide (2 mL) were added ethyl 2-bromo-2-cyclopropyl-acetate (1 g, 4.8 mmol), and potassium carbonate (1.11 g, 8 mmol). The mixture was stirred for 4 hours at 80° C. The reaction was quenched with water (15 mL) and the resulting solution was extracted with EtOAc (20 mL×3). The combined organic layers were washed with brine, dried over anhydrous sodium sulfate, filtered, and concentrated under reduced pressure to give ethyl 2-(4-bromopyrazol-1-yl)-2-cyclopropyl-acetate 126 as a yellow liquid. The crude was used in the next step without any purification.

LCMS method F: $[M+H]^+$=274, $t_R$=2.53 min

Preparation of Intermediate 127: ethyl 2-[4-[5-[tert-butyl(dimethyl)silyl]oxy-1-tetrahydropyran-2-yl-indazol-3-yl]pyrazol-1-yl]-2-cyclopropyl-acetate

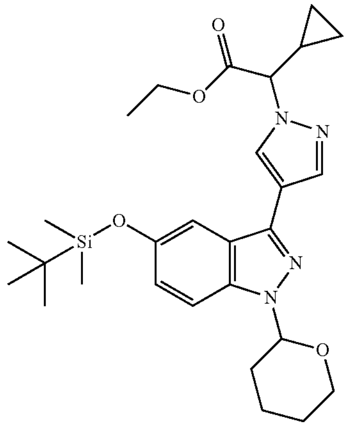 [SMILES: CCOC(=O)C(C1CC1)n1cc(-c2nn(C3CCCCO3)c3ccc(O[Si](C)(C)C(C)(C)C)cc23)cn1]

To a solution of [5-[tert-butyl(dimethyl)silyl]oxy-1-tetrahydropyran-2-yl-indazol-3-yl]boronic acid 18 (1.63 g, 4.35 mmol), ethyl 2-(4-bromopyrazol-1-yl)-2-cyclopropyl-acetate 126 (700 mg, 2.56 mmol), tripotassium phosphate (1.63 g, 7.68 mmol) in dioxane (7.7 mL) and water (2.6 mL) were added XPhos (122 mg, 0.25 mmol) and tetrakis(triphenylphosphine)palladium(0) (147 mg, 0.13 mmol). The reaction mixture was heated at 100° C. under microwave conditions for 1 hour and 30 minutes. The reaction mixture was filtered over celite and the celite was washed with EtOAc. The filtrate was then diluted with water and extracted with EtOAc (3×). The combined organic layers were washed with brine, dried over anhydrous sodium sulfate and concentrated under reduced pressure. The crude product was purified by column (Macherey Nagel, 40 g) chromatography with cyclohexane/EtOAc (100/0 to 80/20) as eluent. The desired fractions were combined and evaporated under reduced pressure to give ethyl 2-[4-[5-[tert-butyl(dimethyl)silyl]oxy-1-tetrahydropyran-2-yl-indazol-3-yl]pyrazol-1-yl]-2-cyclopropyl-acetate 127 as a yellow oil.

LCMS method F: $[M+H]^+$=525, $t_R$=3.76 min

Preparation of Intermediate 128: ethyl 2-cyclopropyl-2-[4-(5-hydroxy-1-tetrahydropyran-2-yl-indazol-3-yl)pyrazol-1-yl]acetate

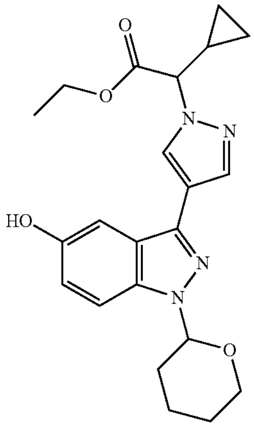 [SMILES: CCOC(=O)C(C1CC1)n1cc(-c2nn(C3CCCCO3)c3ccc(O)cc23)cn1]

To a solution of ethyl 2-[4-[5-[tert-butyl(dimethyl)silyl]oxy-1-tetrahydropyran-2-yl-indazol-3-yl]pyrazol-1-yl]-2-cyclopropyl-acetate 127 (238 mg, 0.45 mmol) in THF (1.8 mL) was added dropwise at room temperature tetrabutylammonium fluoride 1M in THF (0.5 mL, 0.5 mmol).

The resulting reaction mixture was stirred at room temperature overnight. The reaction mixture was poured into ice water and stirred for 20 min. The aqueous phase was extracted twice with EtOAc and the combined organic layers were washed with brine, dried over anhydrous sodium sulfate and concentrated under reduced pressure to give ethyl 2-cyclopropyl-2-[4-(5-hydroxy-1-tetrahydropyran-2-yl-indazol-3-yl)pyrazol-1-yl]acetate 128 as an orange solid.

LCMS method F: $[M+H]^+$=411, $t_R$=2.53 min

Preparation of Intermediate 129: ethyl 2-[4-[5-[3-(benzyloxycarbonylamino)propoxy]-1-tetrahydropyran-2-yl-indazol-3-yl]pyrazol-1-yl]-2-cyclopropyl-acetate

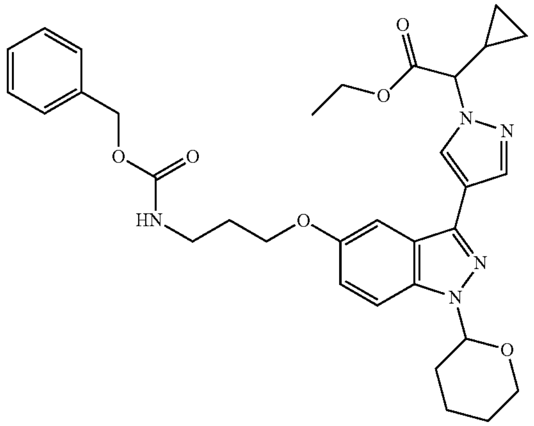 [SMILES: CCOC(=O)C(C1CC1)n1cc(-c2nn(C3CCCCO3)c3ccc(OCCCNC(=O)OCc4ccccc4)cc23)cn1]

To a solution of ethyl 2-cyclopropyl-2-[4-(5-hydroxy-1-tetrahydropyran-2-yl-indazol-3-yl)pyrazol-1-yl]acetate 128 (232 mg, 0.57 mmol,) in acetonitrile (6 mL), were added cesium carbonate (370 mg, 1.14 mmol) and benzyl N-(3-bromopropyl)carbamate (169 mg, 0.62 mmol).

The mixture was stirred at room temperature overnight. The reaction mixture was filtered and rinsed with EtOAc. Water was added and the water layer was extracted with EtOAc (3×). The combined organic layers were washed with brine, dried over sodium sulfate, filtered and concentrated under reduced pressure to afford ethyl 2-[4-[5-[3-(benzyloxycarbonyl amino)propoxy]-1-tetrahydropyran-2-yl-indazol-3-yl]pyrazol-1-yl]-2-cyclopropyl-acetate 129 as a brown oil.

LCMS method F: $[M+H]^+$=602, $t_R$=3.18 min

Preparation of Intermediate 130: benzyl N-[3-[3-[1-(1-cyclopropyl-2-hydroxy-ethyl)pyrazol-4-yl]-1-tetrahydropyran-2-yl-indazol-5-yl]oxypropyl]carbamate

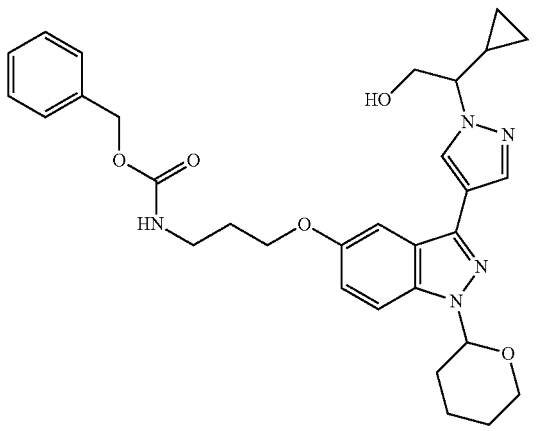 [SMILES: O=C(NCCCOc1ccc2c(c1)c(-c1cnn(C(CO)C3CC3)c1)nn2C1CCCCO1)OCc1ccccc1]

A solution of ethyl 2-[4-[5-[3-(benzyloxycarbonylamino) propoxy]-1-tetrahydropyran-2-yl-indazol-3-yl]pyrazol-1-yl]-2-cyclopropyl-acetate 129 (324 mg, 0.54 mmol) in THF (2.3 mL) was degassed with $N_2$ during 10 minutes, LAH 1 M in THF (0.65 mL, 0.65 mmol) was added at 0° C. and the reaction was stirred at 0° C. for 2 hours and 30 minutes. The mixture was quenched with water (0.2 mL), 10% NaOH (0.2 mL) and water (0.2 mL). The mixture was filtered with EtOAc as eluent. The filtrate was diluted with water and extracted with EtOAc (3×). The combined organic layers were washed with brine, dried with anhydrous sodium sulfate and the solvent was removed under reduced pressure to afford benzyl N-[3-[3-[1-(1-cyclopropyl-2-hydroxy-ethyl)pyrazol-4-yl]-1-tetrahydropyran-2-yl-indazol-5-yl] oxypropyl]carbamate 130 as a colorless oil.

LCMS method F: $[M+H]^+$=560, $t_R$=2.76 min

Preparation of Intermediate 131: 6-cyclopropyl-19-(oxan-2-yl)-8,14-dioxa-4,5,10,19,20-pentaazatetracyclo[13.5.2.1$^{2,5}$.0$^{18,21}$]tricosa-1(20),2(23),3,15(22),16,18(21)-hexaen-9-one

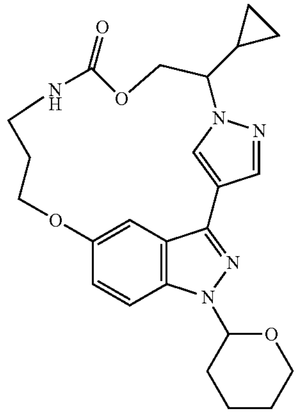 [SMILES: O=C1NCCCOc2ccc3c(c2)c(nn3C2CCCCO2)-c2cnn(c2)C(C2CC2)CO1]

A suspension of benzyl N-[3-[3-[1-(1-cyclopropyl-2-hydroxy-ethyl)pyrazol-4-yl]-1-tetrahydropyran-2-yl-indazol-5-yl]oxypropyl]carbamate 130 (112 mg, 0.2 mmol) and cesium carbonate (390 mg, 1.2 mmol) in acetonitrile (44 mL) was heated to 80° C. for 5 hours. The reaction mixture was filtered at 80° C., cooled to room temperature and concentrated under reduced pressure. The crude was purified by column (Macherey Nagel, 15 g) chromatography with DCM/MeOH (100/0 to 97/3) as eluent. The desired fractions were combined and the solvent was removed under reduced pressure to give 6-cyclopropyl-19-(oxan-2-yl)-8,14-dioxa-4,5,10,19,20-pentaazatetracyclo[13.5.2.1$^{2,5}$.0$^{18,21}$]tricosa-1 (20),2(23),3,15(22),16,18(21)-hexaen-9-one 131 as a colorless solid.

LCMS method F: $[M+H]^+$=452, $t_R$=2.47 min

Preparation of Example 103: 6-cyclopropyl-8,14-dioxa-4,5,10,19,20-pentaazatetracyclo [13.5.2.1$^{2,5}$.0$^{18,21}$]tricosa-1(20),2(23),3,15(22), 16,18(21)-hexaen-9-one

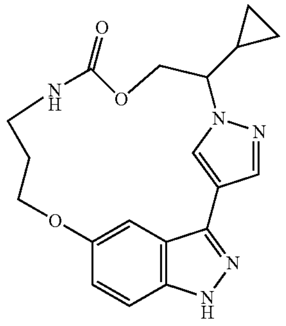 [SMILES: O=C1NCCCOc2ccc3[nH]nc(c3c2)-c2cnn(c2)C(C2CC2)CO1]

To a solution of 6-cyclopropyl-19-(oxan-2-yl)-8,14-dioxa-4,5,10,19,20-pentaazatetracyclo[13.5.2.1$^{2,5}$.0$^{18,21}$]tricosa-1(20),2(23),3,15(22),16,18(21)-hexaen-9-one 131 (46 mg, 0.1 mmol) in DCM (11 mL) was added trifluoro acetic acid (0.16 mL, 2.03 mmol). The mixture was heated at 80° C. under microwave conditions for 1 hour. The reaction mixture was diluted with DCM (25 mL) and a saturated sodium bicarbonate solution (25 mL). After separation, the aqueous layer was extracted with DCM (3×20 mL). The combined organic layers were washed with brine (25 mL), dried over anhydrous sodium sulfate, filtered and concentrated under reduced pressure. The crude was purified by column (Macherey Nagel, 15 g) chromatography with DCM/EtOAc (100/0 to 25/75) as eluent. The desired fractions were combined and the solvent was removed under reduced pressure to afford 6-cyclopropyl-8,14-dioxa-4,5,10,19,20-pentaazatetracyclo[13.5.2.1$^{2,5}$.0$^{18,21}$]tricosa-1(20),2 (23),3,15(22), 16,18(21)-hexaen-9-one example 103 as a white solid.

LCMS method F: $[M+H]^+$=368, $t_R$=2.02 min

LCMS method G: $[M+H]^+$=368, $t_R$=2.03 min $^1$H NMR (400 MHz, d6-DMSO) δ 12.80 (1H, s), 8.17 (1H, s), 7.82 (1H, dd, J=4.6, 7.3 Hz), 7.75 (1H, s), 7.42 (1H, d, J=9 Hz), 7.09 (1H, d, J=2.3 Hz), 6.94 (1H, dd, J=2.3, 8.9 Hz), 4.55 (1H, dd, J=2.5, 11.6 Hz), 4.40 (1H, m), 4.23 (2H, m), 3.90 (1H, m), 2.89 (1H, m), 1.85 (2H, m), 1.58 (1H, m), 0.67 (1H, m), 0.55 (2H, m), 0.44 (1H, m) ppm. One proton was located under the residual water peak and was not reported here.

Example 104: 7-ethyl-8,14-dioxa-10,19,20-triazatetracyclo[13.5.2.$1^{2,6}$.$0^{18,21}$]tricosa-1(20),2,4,6(23),15,17,21-heptaen-9-one

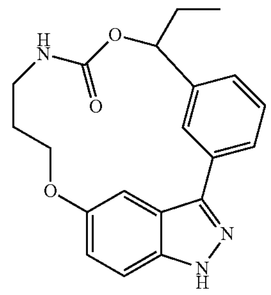 [SMILES: CCC1OC(=O)NCCCOc2ccc3[nH]nc(c3c2)-c2cccc1c2]

Example 104 is prepared according to the synthesis route described in general Scheme G.

Preparation of Intermediate 132: 1-[3-(4,4,5,5-tetramethyl-1,3,2-dioxaborolan-2-yl)phenyl]propan-1-one

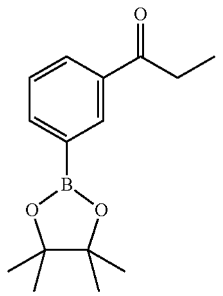 [SMILES: CCC(=O)c1cccc(B2OC(C)(C)C(C)(C)O2)c1]

To a mixture of 1-(3-bromophenyl)propan-1-one (2 g, 9.4 mmol) in dioxane (30 mL) was added 4,4,5,5-tetramethyl-2-(tetramethyl-1,3,2-dioxaborolan-2-yl)-1,3,2-dioxaborolane (2.63 g, 10.3 mmol), $Pd_2dba_3$ (431 mg, 0.471 mmol), KOAc (1.48 g, 15 mmol) and tricyclohexylphosphine (264 mg, 0.94 mmol). The reaction mixture was stirred at 100° C. for 2 h. The solvent was removed under reduced pressure, then it was dissolved in EtOAc and washed with water (×3).

The organic layer was filtered on a Guanidine (SPE) pad. Then the solvent was removed under reduced pressure to give 1-[3-(4,4,5,5-tetramethyl-1,3,2-dioxaborolan-2-yl)phenyl]propan-1-one 132 as a yellow oil.

LCMS method F: $[M+H]^+$=261, $t_R$=2.99 min

Preparation of Example 104: 7-ethyl-8,14-dioxa-10,19,20-triazatetracyclo[13.5.2.$1^{2,6}$.$0^{18,21}$]tricosa-1(20),2,4,6(23),15,17,21-heptaen-9-one

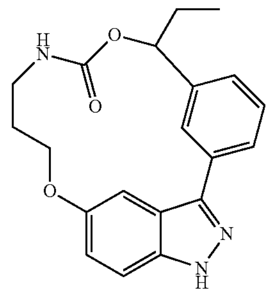 [SMILES: CCC1OC(=O)NCCCOc2ccc3[nH]nc(c3c2)-c2cccc1c2]

To a solution of 7-ethyl-19-(oxan-2-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one 124 (220 mg, 0.51 mmol) in DCM (10 mL) was added trifluoroacetic acid (775 μL, 10.11 mmol). Stirred at 50° C. during 2 h. The reaction mixture was diluted with EtOAc (30 mL) and water (20 mL) After separation, the aqueous layer was extracted with EtOAc (3×10 mL). The combined organic layers were washed with saturated sodium carbonate aqueous solution (30 mL) and brine (30 mL). The organic layer was dried over sodium sulfate anhydrous, filtered off and concentrated to dryness.

The oil was triturated in DCM and the solid was filtered and dried under reduced pressure to give 7-ethyl-8,14-dioxa-10,19,20-triazatetracyclo[13.5.2.$1^{2,6}$.$0^{18,21}$]tricosa-1(20),2,4,6(23),15,17,21-heptaen-9-one 104 as a white powder.

LCMS method F: $[M+H]^+$=352.2, $t_R$=2.41 min (current 20V)

LCMS method G: $[M+H]^+$=352.2, $t_R$=2.38 min (pH10 current 20V)

$^1$H NMR (400 MHz, d6-DMSO) δ 7.96 (1H, dd, J=4.7, 7.6 Hz), 7.85-7.80 (2H, m), 7.50-7.45 (2H, m), 7.37-7.28 (2H, m), 6.99 (1H, dd, J=2.3, 8.9 Hz), 5.68 (1H, dd, J=3.6, 8.5 Hz), 4.41-4.21 (2H, m), 3.56-3.49 (1H, m), 2.78-2.67 (1H, m), 2.23-2.15 (1H, m), 2.10-2.01 (1H, m), 1.89-1.69 (2H, m), 1.00 (3H, t, J=7.3 Hz) ppm.

Example 105: (13R)-13-methyl-8,14-dioxa-5,10,19,20,23-pentaazatetracyclo[13.5.2.$1^{2,6}$.$0^{18,21}$]tricosa-1(20),2,4,6(23),15,17,21-heptaen-9-one

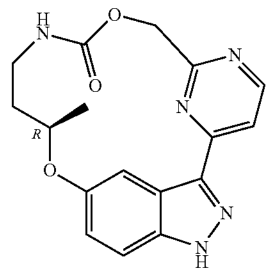

Example 105 is prepared according to the synthesis route described in general Scheme B.

To a solution of (13R)-13-methyl-19-(oxan-2-yl)-8,14-dioxa-5,10,19,20,23-pentaazatetracyclo[13.5.2.$1^{2,6}$.$0^{18,21}$]

tricosa-1(20),2,4,6(23),15,17,21-heptaen-9-one (100 mg, 0.24 mmol) in DCM (2 mL) was added trifluoroacetic acid (362 μL, 4.73 mmol). The mixture was heated under micro-waves irradiation at 80° C. for 45 min. The reaction mixture was diluted with DCM (25 mL) and saturated $NaHCO_3$ (25 mL). A yellow precipitate was appeared and filtered to afford, after dried under vacuum at 60° C. for 12 hours (13R)-13-methyl-8,14-dioxa-5,10,19,20,23-pentaazatetra-cyclo[13.5.2.1$^{2,6}$.0$^{18,21}$]tricosa-1(20),2,4,6(23),15,17,21-heptaen-9-one example 105 as a yellow solid.

LCMS method F: $[M+H]^+$=340, $t_R$=2.00 min

LCMS method G: $[M+H]^+$=340, $t_R$=2.02 min $^1$H NMR (400 MHz, d6-DMSO) δ 13.68-13.67 (1H, m), 8.77-8.74 (1H, m), 8.05 (1H, d, J=5.3 Hz), 7.92-7.87 (2H, m), 7.55-7.52 (1H, m), 7.00 (1H, dd, J=2.3, 9.1 Hz), 5.61-5.55 (1H, m), 5.03-4.97 (1H, m), 4.61 (1H, t, J=6.8 Hz), 3.50 (1H, m), 2.94-2.86 (1H, m), 2.38-2.31 (1H, m), 1.42-1.38 (4H, m) ppm.

Example 106: (7R,13R)-4-fluoro-7,13-dimethyl-8,14-dioxa-10,19,20-triazatetracyclo[13.5.2.1$^{2,6}$.0$^{18,21}$]tricosa-1(20),2,4,6(23),15,17,21-heptaen-9-one

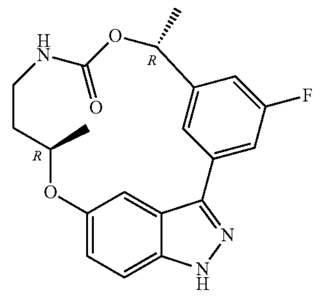

Example 106 is prepared according to the synthesis route described in general Scheme C.

Preparation of Intermediate 133: (1R)-1-[3-fluoro-5-(4,4,5,5-tetramethyl-1,3,2-dioxaborolan-2-yl)phenyl]ethan-1-ol

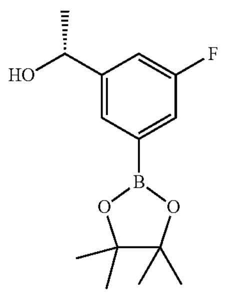 [SMILES: C[C@@H](O)c1cc(F)cc(B2OC(C)(C)C(C)(C)O2)c1]

To a degassed solution of (1R)-1-(3-bromo-5-fluorophenyl)ethan-1-ol (0.500 g, 2.28 mmol) in dioxane (3 mL) was added at RT bis(pinacolato)diboron (0.695 g, 2.74 mmol), KOAc (0.672 g, 6.85 mmol) and $PdCl_2$(dppf)·DCM (0.093 g, 0.11 mmol). The resulting reaction mixture was stirred under microwave irradiation at 100° C. for 2 h. The residue was filtered on celite, diluted with water and extracted with ethyl acetate twice. The combined organic layer was dried over anhydrous sodium sulfate and concentrated in vacuo affording (1R)-1-[3-fluoro-5-(4,4,5,5-tetramethyl-1,3,2-dioxaborolan-2-yl)phenyl]ethan-1-ol 133 as a black oil, used without further purification in the next step.

LCMS method F: $[M-H_2O+H]^+$=249.1, $t_R$=2.68 min

Preparation of Example 106: (7R,13R)-4-fluoro-7,13-dimethyl-8,14-dioxa-10,19,20-triazatetracyclo[13.5.2.1$^{2,6}$.0$^{18,21}$]tricosa-1(20),2,4,6(23),15,17,21-heptaen-9-one

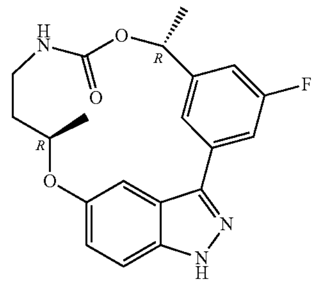

To a solution of (7R,13R)-4-fluoro-7,13-dimethyl-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one (0.530 g, 1.17 mmol) in DCM (10 mL) was added at RT TFA (1.740 mL, 23.37 mmol). The resulting reaction mixture was stirred under microwave irradiation at 80° C. for 1 h. The reaction mixture was concentrated in vacuo, diluted with saturated sodium bicarbonate solution and extracted with ethyl acetate twice. The combined organic layer was dried over anhydrous sodium sulfate and concentrated in vacuo. The residue was purified by flash-column (15 g silica Macherey Nagel) chromatography (cyclohexane-ethyl acetate 3/EtOH 1, 1:0 to 6:4) to give a solid (0.380 g), which was triturated in acetonitrile and filtered affording (7R,13R)-4-fluoro-7,13-dimethyl-8,14-dioxa-10,19,20-triazatetracyclo[13.5.2.1$^{2,6}$.0$^{18,21}$]tricosa-1(20),2,4,6(23),15,17,21-heptaen-9-one example 106 as a white solid.

LCMS method F: $[M+H]^+$=370.1, [M−H]−=368.3, $t_R$=2.51 min

LCMS method G: $[M+H]^+$=370.2, [M−H]−=368.4, $t_R$=2.58 min $^1$H NMR (400 MHz, d6-DMSO, 80° C.) δ 13.22-13.20 (1H, m), 7.78 (1H, dd, J=4.6, 8.0 Hz), 7.65 (1H, d, J=0.8 Hz), 7.52-7.44 (2H, m), 7.23-7.19 (2H, m), 7.00-6.96 (1H, m), 5.88 (1H, q, J=6.6 Hz), 4.65-4.57 (1H, m), 3.24-3.17 (1H, m), 3.10-3.04 (1H, m), 1.83 (1H, dd, J=8.4, 13.1 Hz), 1.72-1.64 (1H, m), 1.62 (3H, d, J=6.6 Hz), 1.38-1.35 (3H, m) ppm.

Example 107: 7-methyl-8,14-dioxa-4,10,19,20-tetraazatetracyclo[13.5.2.1$^{2,6}$.0$^{18,21}$]tricosa-1(20),2,4,6(23),15,17,21-heptaen-9-one

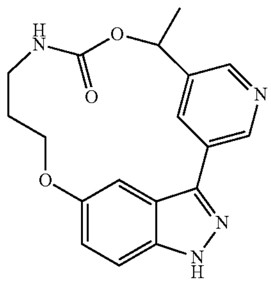 [SMILES: CC1OC(=O)NCCCOc2ccc3[nH]nc(c3c2)-c2cncc1c2]

Example 107 is prepared according to the synthesis route described in general Scheme H.

To a solution of 7-methyl-19-(oxan-2-yl)-8,14-dioxa-4,10,19,20-tetraazatetracyclo[13.5.2.1$^{2,6}$.0$^{18,21}$]tricosa-1(20),2,4,6(23),15,17,21-heptaen-9-one (32 mg, 0.076 mmol, 1 eq) in DCM (1.8 mL) was added trifluoroacetic acid (233 µL, 3.040 mmol, 40 eq) at RT. The solution was heated under microwave conditions at 80° C. for 2 h 40 min. The reaction mixture (brown solution) was evaporated under vacuo, the brown residue was dissolved in EtOAc then a saturated aqueous solution of sodium hydrogen carbonate was added. After separation, the aqueous layer was extracted with ethyl acetate (2×). The combined organic layer was washed with water then brine, dried over sodium sulfate, filtered and evaporated under reduced pressure to give an orange oil. The crude product was purified by column chromatography eluting with Cyclohexane/Ethyl acetate-EtOH (3-1), 100/0 to 60/40 to give the expected product. It was triturated from diisopropyl ether and directly transferred into the brown vial (without filtration due to the low mass), dried under vacuo to give 7-methyl-8,14-dioxa-4,10,19,20-tetraazatetracyclo[13.5.2.1$^{2,6}$.0$^{18,21}$]tricosa-1(20),2,4,6(23),15,17,21-heptaen-9-one example 107 as a white solid.

LCMS method F: $[M+H]^+$=339, $t_R$=1.69 min

LCMS method G: $[M+H]^+$=339, $t_R$=1.98 min $^1$H NMR (400 MHz, d6-DMSO) δ 13.33 (1H, s), 9.03 (1H, d), 8.57 (1H, d), 8.15 (1H, m), 8.04-8.01 (1H, m), 7.55-7.53 (1H, d), 7.28 (1H, m), 7.03-7.01 (1H, dd), 5.98-5.93 (1H, q), 4.37-4.27 (2H, m), 3.55-3.48 (1H, m), 2.80-2.71 (1H, m), 2.23-2.14 (1H, m), 1.78-1.70 (1H, m), 1.65 (3H, d) ppm.

Example 108: (7R)- or (7S)-4-fluoro-7-methyl-8,14-dioxa-10,19,20-triazatetracyclo[13.5.2.1$^{2,6}$.0$^{18,21}$]tricosa-1(20),2,4,6(23),15,17,21-heptaen-9-one

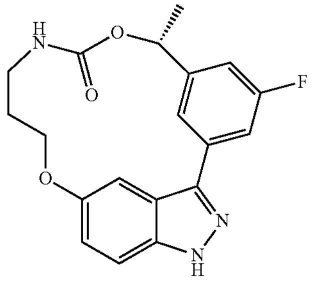 [SMILES: C[C@H]1OC(=O)NCCCOc2ccc3[nH]nc(c3c2)-c2cc(F)cc1c2]

Example 108 is prepared according to the synthesis route described in general Scheme A and by chiral SFC separation to give (7R)- or (7S)-4-fluoro-7-methyl-8,14-dioxa-10,19,20-triazatetracyclo[13.5.2.1$^{2,6}$.0$^{18,21}$]tricosa-1(20),2,4,6(23),15,17,21-heptaen-9-one example 108.

LCMS method F: $[M+H]^+$=356, $t_R$=2.39 min

LCMS method G: $[M+H]^+$=356, $t_R$=2.42 min $^1$H NMR (400 MHz, d6-DMSO) δ 13.28 (1H, s), 8.01-7.97 (1H, m), 7.69 (1H, s), 7.59-7.56 (1H, m), 7.53-7.50 (1H, m), 7.33 (1H, d), 7.21-7.18 (1H, m), 7.02-6.99 (1H, dd), 5.91-5.86 (1H, q), 4.37-4.26 (2H, m), 3.55-3.49 (1H, m), 2.78-2.71 (1H, m), 2.23-2.14 (1H, m), 1.78-1.70 (1H, m), 1.59 (3H, d) ppm.

Chiral HPLC: ee>97.5%

The compound is a pure enantiomer, but the absolute stereochemistry of the chiral center is unknown.

Example 109: (7R)- or (7S)-4-fluoro-7-methyl-8,14-dioxa-10,19,20-triazatetracyclo[13.5.2.1$^{2,6}$.0$^{18,21}$]tricosa-1(20),2,4,6(23),15,17,21-heptaen-9-one

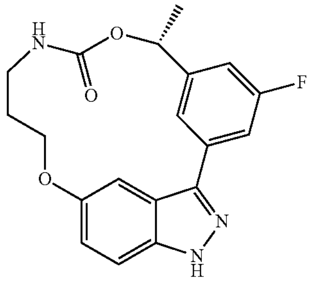 [SMILES: C[C@H]1OC(=O)NCCCOc2ccc3[nH]nc(c3c2)-c2cc(F)cc1c2]

Example 109 is prepared according to the synthesis route described in general Scheme A and by chiral SFC separation to give (7R)- or (7S)-4-fluoro-7-methyl-8,14-dioxa-10,19,20-triazatetracyclo[13.5.2.1$^{2,6}$.0$^{18,21}$]tricosa-1(20),2,4,6(23),15,17,21-heptaen-9-one example 109.

LCMS method F: $[M+H]^+$=356, $t_R$=2.39 min

LCMS method G: $[M+H]^+$=356, $t_R$=2.41 min $^1$H NMR (400 MHz, d6-DMSO) δ 13.27 (1H, s), 8.01-7.98 (1H, m), 7.69 (1H, s), 7.59-7.56 (1H, m), 7.53-7.51 (1H, m), 7.33 (1H, d), 7.21-7.18 (1H, m), 7.01-6.99 (1H, dd), 5.91-5.86 (1H, q), 4.37-4.24 (2H, m), 3.56-3.49 (1H, m), 2.78-2.71 (1H, m), 2.23-2.14 (1H, m), 1.78-1.70 (1H, m), 1.59 (3H, d) ppm.

Chiral HPLC: ee>98.0%

The compound is a pure enantiomer, but the absolute stereochemistry of the chiral center is unknown.

Example 110: 6-methyl-8,14-dioxa-4,5,10,19,20-pentaazatetracyclo[13.5.2.1$^{2,5}$.0$^{18,21}$]tricosa-1(20),2(23),3,15,17,21-hexaen-9-one

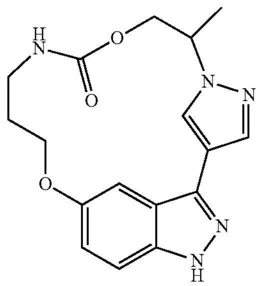 [SMILES: CC1COC(=O)NCCCOc2ccc3[nH]nc(c3c2)-c2cnn1c2]

Example 110 is prepared according to the synthesis route described in general Scheme B.

Preparation of Intermediate 134: ethyl 2-(4-bromopyrazol-1-yl)propanoate

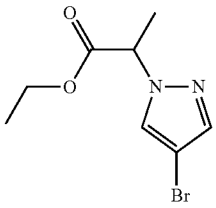

A suspension of 4-bromo-1H-pyrazole (2.00 g, 13.60 mmol), ethyl 2-bromopropanoate (2.1 mL, 16.32 mmol), and potassium carbonate (3.78 g, 27.20 mmol) in N,N-dimethylformamide (8.0 mL) was stirred for 3 h at 80° C. The reaction was quenched by water (30 mL), and the resulting solution was extracted twice with ethyl acetate (50 mL×2). The combined organic layers were dried over anhydrous magnesium sulfate, filtered, and concentrated under reduced pressure to give ethyl 2-(4-bromopyrazol-1-yl)propanoate 134 as a yellow oil.

Yield: 4.58 g of intermediate 134 (quantitative)

LCMS method F: $[M+H]^+=249$, $t_R=2.29$ min

Preparation of Example 110: 6-methyl-8,14-dioxa-4,5,10,19,20-pentaazatetracyclo[13.5.2.1$^{2,5}$.0$^{18,21}$]tricosa-1(20),2(23),3,15,17,21-hexaen-9-one

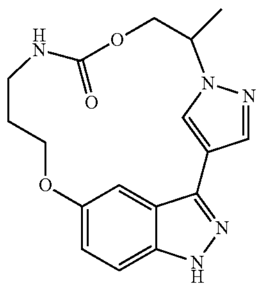 [SMILES: CC1COC(=O)NCCCOc2ccc3[nH]nc(c3c2)-c2cnn1c2]

To a solution of 6-methyl-19-(oxan-2-yl)-8,14-dioxa-4,5,10,19,20-pentaazatetracyclo[13.5.2.1$^{2,5}$.0$^{18,21}$]tricosa-1(20),2(23),3,15,17,21-hexaen-9-one (68 mg, 0.16 mmol) in DCM (2 mL) was added trifluoro acetic acid (245 μL, 3.20 mmol). The mixture was heated in microwaves at 80° C. for 30 min. The reaction mixture was diluted with DCM (25 mL) and $NaHCO_3$ saturated (25 mL). After separation, aqueous layer was extracted with DCM (3×20 mL). The combined organic layer was washed with brine (25 mL), dried over anhydrous sodium sulfate, filtered and evaporated under reduced pressure. The crude was purified by flash chromatography (DCM/MeOH 95/5) to afford 6-methyl-8,14-dioxa-4,5,10,19,20-pentaazatetracyclo[13.5.2.1$^{2,5}$.0$^{18,21}$]tricosa-1(20),2(23),3,15,17,21-hexaen-9-one example 110 as an off-white solid.

LCMS method F: $[M+H]^+=342$, $t_R=1.86$ min

LCMS method G: $[M+H]^+=342$, $t_R=1.89$ min $^1$H NMR (400 MHz, d6-DMSO) δ 12.80-12.79 (1H, m), 8.07 (1H, s), 7.83-7.76 (2H, m), 7.43-7.40 (1H, m), 7.06 (1H, d, J=2.1 Hz), 6.94 (1H, dd, J=2.3, 8.9 Hz), 4.82-4.75 (1H, m), 4.44-4.15 (4H, m), 3.23 (1H, t, J=7.1 Hz), 3.03-2.98 (1H, m), 1.91-1.82 (2H, m), 1.59 (3H, d, J=7.0 Hz) ppm.

Example 111: 7-methyl-8,14-dioxa-10,19,20,23-tetraazatetracyclo[13.5.2.1$^{2,6}$.0$^{18,21}$]tricosa-1(20),2,4,6(23),15,17,21-heptaen-9-one

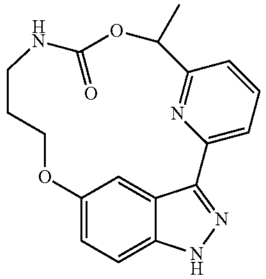 [SMILES: CC1OC(=O)NCCCOc2ccc3[nH]nc(c3c2)-c2cccc1n2]

Example 111 is prepared according to the synthesis route described in general Scheme H using SEM as indazole protecting group.

Preparation of Intermediate 135: 1-(6-bromo-2-pyridyl)ethanol

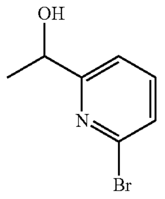

To a cooled solution of 6-bromopyridine-2-carbaldehyde (2.0 g, 10.81 mmol) in dry tetrahydrofuran (28 mL) was dropwise added methylmagnesium bromide solution 3 M in diethyl ether (7.2 mL, 21.62 mmol) at 0° C. The reaction mixture was stirred at 0° C. for 20 min then allowed to reach room temperature for 16 hours. TLC analysis showed total consumption of starting material. The reaction mixture was quenched with a saturated aqueous solution of $NH_4Cl$ then extracted with ethyl acetate (2×100 mL). The organic layer was washed with water the brine, dried over magnesium sulfate, filtered and concentrated under reduced pressure. The crude product was purified by flash-column chromatography eluting with Cyclohexane/Ethyl acetate-EtOH (3-1): 100/0 to 80/20, to give 1-(6-bromo-2-pyridyl)ethanol 135 as a colorless oil.

LCMS method F: $[M+H]^+$=202.0, $t_R$=1.65 min

Preparation of Example 111: 7-methyl-8,14-dioxa-10,19,20,23-tetraazatetracyclo 20 [$13.5.2.1^{2,6}.0^{18,21}$]tricosa-1(20),2,4,6(23),15,17,21-heptaen-9-one

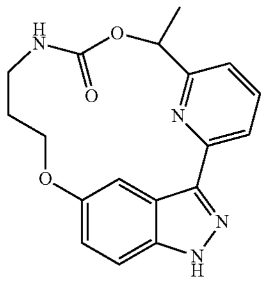 [SMILES: CC1OC(=O)NCCCOc2ccc3[nH]nc(c3c2)-c2cccc1n2]

To a solution of 7-methyl-20-{[2-(trimethylsilyl)ethoxy]methyl}-8,14-dioxa-10,19,20,23-tetraazatetracyclo[$13.5.2.1^{2,6}.0^{18,21}$]tricosa-1(21),2(23),3,5,15(22),16,18-heptaen-9-one (0.037 g, 0.079 mmol) in dichloroethane (2.0 mL) was added an aqueous solution of HCl (6 N, 0.15 mL, 0.95 mmol). The mixture was heated at 70° C. for 16 hours. The mixture was concentrated under reduced pressure and 1,4-dioxane (2.0 mL) and NH40H solution (0.4 mL) were added. The mixture was heated at 75° C. for 3 hours, concentrated under reduced pressure and the residue was suspended in MeOH (0.4 mL) and filtered. The crude product was purified with two successive preparative TLC on silica gel (first using (DCM/MeOH: 95/5) as an eluent, then using Cyclohexane/EtOAc-EtOH: 4/6 (3-1)) to afford 7-methyl-8,14-dioxa-10,19,20,23-tetraazatetracyclo[$13.5.2.1^{2,6}.0^{18,21}$]tricosa-1(20),2,4,6(23),15,17,21-heptaen-9-one example 111 as a white solid.

LCMS method F: $[M+H]^+$=339.2, $t_R$=2.02 min

LCMS method G: $[M+H]^+$=339.3, $t_R$=2.07 min $^1H$ NMR (400 MHz, d6-DMSO) δ 13.27 (1H, s), 8.04 (1H, d, J=8.4 Hz), 7.88-7.84 (2H, m), 7.71 (1H, dd, J=4.5, 7.7 Hz), 7.47 (1H, d, J=8.0 Hz), 7.33 (1H, d, J=7.2 Hz), 6.97 (1H, dd, J=2.8, 9.6 Hz), 5.93 (1H, q, J=6.8 Hz), 4.37-4.24 (2H, m), 3.52-3.40 (1H, m), 2.78-2.67 (1H, m), 2.22-2.12 (1H, m), 1.64-1.61 (4H, m) ppm.

Example 112: 6-(propan-2-yl)-8,14-dioxa-4,5,10,19,20-pentaazatetracyclo[$13.5.2.1^{2,5}.0^{18,21}$]tricosa-1(20),2(23),3,15(22),16,18(21)-hexaen-9-one

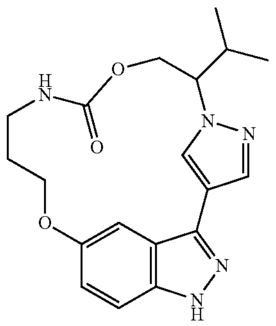 [SMILES: CC(C)C1COC(=O)NCCCOc2ccc3[nH]nc(c3c2)-c2cnn1c2]

Example 112 is prepared according to the synthesis route described in general Scheme B.

Preparation of Intermediate 136: ethyl 2-(4-bromopyrazol-1-yl)-3-methyl-butanoate

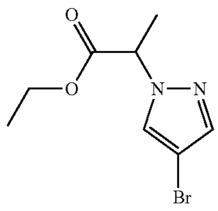

A suspension of 4-Bromo-1H-pyrazole (2.00 g, 13.60 mmol), ethyl 2-bromo-3-methyl-butanoate (2.5 mL, 16.32 mmol), and potassium carbonate (3.78 g, 27.20 mmol) in N,N-dimethylformamide (4.0 mL) was stirred for 3 h at 80° C. The reaction was quenched by water (30 mL), and the resulting solution was extracted twice with ethyl acetate (50 mL×2). The combined organic layers were dried over anhydrous magnesium sulfate, filtered, and concentrated under reduced pressure to give ethyl 2-(4-bromopyrazol-1-yl)-3-methyl-butanoate 136 as a colorless oil.

LCMS method F: $[M+H]^+$=277.1, $t_R$=2.72 min

Preparation of Example 112: 6-(propan-2-yl)-8,14-dioxa-4,5,10,19,20-pentaaza tetracyclo[$13.5.2.1^{2,5}.0^{18,21}$]tricosa-1(20),2(23),3,15(22),16,18(21)-hexaen-9-one

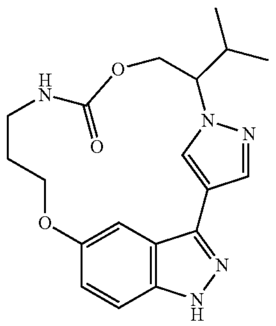 [SMILES: CC(C)C1COC(=O)NCCCOc2ccc3[nH]nc(c3c2)-c2cnn1c2]

To a solution of 19-(oxan-2-yl)-6-(propan-2-yl)-8,14-dioxa-4,5,10,19,20-pentaazatetracyclo[13.5.2.$1^{2,5}$.$0^{18,21}$]tricosa-1(20),2(23),3,15(22),16,18(21)-hexaen-9-one (0.409 g, 0.90 mmol) in DCM (22 mL) was added trifluoroacetic acid (1.37 mL, 18.0 mmol). The reaction mixture was directly heated to 50° C. for 3 hours. LCMS analysis showed formation of the expected product and total consumption of starting material. The reaction mixture (brown solution) was evaporated under reduced pressure. The brown residue was dissolved in EtOAc then a saturated aqueous solution of sodium hydrogen carbonate was added. After separation, the aqueous layer was extracted with ethyl acetate (2×). The combined organic layer was washed with water then brine, dried over sodium sulfate, filtered and evaporated under reduced pressure to give an orange oil. The crude product was purified by column chromatography eluting with Cyclohexane/Ethyl acetate-EtOH (3-1), 100/0 to 70/30. The pure fractions were combined and evaporated under reduced pressure. After evaporation of residual solvent, the product turned out to be less soluble in DCM than before, allowing for recrystallization trials in this solvent. In order to do so, the solid (approx. 160 mg) was stirred in DCM (5 mL) for several minutes, while heating the suspension up to 40° C. After cooling down to room temperature, the solid was isolated by filtration, then recovered and further dried under high vacuum at 60° C. to afford 6-(propan-2-yl)-8,14-dioxa-4,5,10,19,20-pentaazatetracyclo[13.5.2.$1^{2,5}$.$0^{18,21}$]tricosa-1(20),2(23),3,15(22),16,18(21)-hexaen-9-one example 112 as a white solid.

LCMS method F: $[M+H]^+$=370.3, $t_R$=2.05 min

LCMS method G: $[M+H]^+$=370.3, $t_R$=2.12 min $^1$H NMR (400 MHz, d6-DMSO) δ 12.80 (1H, s), 8.17 (1H, s), 7.76-7.75 (2H, m), 7.43-7.40 (1H, m), 7.09 (1H, d, J=1.9 Hz), 6.94 (1H, dd, J=2.3, 8.9 Hz), 4.53 (1H, dd, J=1.6, 11.2 Hz), 4.43 (1H, dt, J=4.4, 12 Hz), 4.29-4.19 (3H, m), 3.44-3.35 (1H, m), 3.30 (1H, s), 2.88-2.81 (1H, m), 1.97-1.85 (1H, m), 1.80-1.75 (1H, m), 1.10 (3H, d, J=6.6 Hz), 0.78 (3H, d, J=6.6 Hz) ppm.

Example 113: (13R)-7,13-dimethyl-8,14-dioxa-4,5,10,19,20-pentaazatetracyclo[13.5.2.$1^{2,5}$.$0^{18,21}$]tricosa-1(20),2(23),3,15(22),16,18(21)-hexaen-9-one

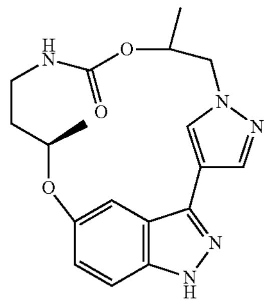 [SMILES: CC1Cn2cc(cn2)-c2n[nH]c3ccc(cc23)O[C@H](C)CCNC(=O)O1]

Example 113 is prepared according to the synthesis route described in general Scheme C.

Preparation of Intermediate 137: 1-[4-(4,4,5,5-tetramethyl-1,3,2-dioxaborolan-2-yl)pyrazol-1-yl]propan-2-ol

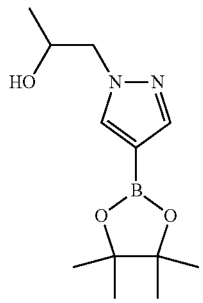 [SMILES: CC(O)Cn1cc(B2OC(C)(C)C(C)(C)O2)cn1]

In a scelled round bottom flask, NaH (60% in mineral oil, 0.990 g, 41.24 mmol) was suspended in N,N-dimethylformamide (100.0 mL) and a solution of 4-(4,4,5,5-tetramethyl-1,3,2-dioxaborolan-2-yl)-1H-pyrazole (4.00 g, 20.62 mmol) was added. The reaction was stirred at room temperature for 15 minutes, then rac-propylene oxide (4.33 mL, 2.40 g, 41.24 mmol) was added. The round bottom flask containing the resulting cloudy brown solution was sealed and heated to 50° C. for 4 h. LC/MS analysis indicated that the reaction was completed. Solvents were evaporated under reduced pressure to afford crude 1-[4-(4,4,5,5-tetramethyl-1,3,2-dioxaborolan-2-yl)pyrazol-1-yl]propan-2-ol 137 as a brown solid which was used in the next step without further purification.

LCMS method F: $[M+H]^+$=253.2, $t_R$=1.92 min

Preparation of Example 113: (13R)-7,13-dimethyl-8,14-dioxa-4,5,10,19,20-pentaazatetra cyclo [13.5.2.$1^{2,5}$.$0^{18,21}$]tricosa-1(20),2(23), 3,15(22),16, 18(21)-hexaen-9-one

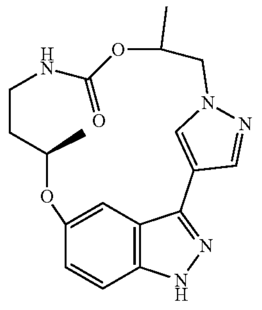 [SMILES: CC1Cn2cc(cn2)-c2n[nH]c3ccc(cc23)O[C@H](C)CCNC(=O)O1]

To a solution of (13R)-7,13-dimethyl-19-(oxan-2-yl)-8,14-dioxa-4,5,10,19,20-pentaazatetra cyclo[13.5.2.$1^{2,5}$.$0^{18,21}$]tricosa-1(20),2(23),3,15(22),16,18(21)-hexaen-9-one (0.090 g, 0.183 mmol) in DCM (3.0 mL) was added trifluoroacetic acid (140 μL, 1.83 mmol). The reaction mixture was stirred at room temperature during 4 h. LCMS analysis showed formation of the expected product. A saturated solution of $NaHCO_3$ (10 mL) was added and phases were separated. The aqueous phase was extracted with DCM (3×10 mL), and organic phase was washed with brine (10 mL), dried with $MgSO_4$, filtered and concentrated under reduce pressure. The crude (120 mg) was purified by chromatography column (Macherey Nagel, 4 g, DCM/MeOH: 100/0 to 90/10). Solvents was evaporated to afford (13R)-7,13-dimethyl-8,14-dioxa-4,5,10,19,20-pentaazatetracyclo [13.5.2.1$^{2,5}$.0$^{18,21}$]tricosa-1(20),2(23), 3,15(22),16,18(21)-hexaen-9-one example 113 as a white powder.

LCMS method F: $[M+H]^+$=356.3, $t_R$=1.96 and 2.02 min, diastereomers

LCMS method G: $[M+H]^+$=356.3, $t_R$=2.03 and 2.08 min, diastereomers $^1$H NMR (400 MHz, d6-DMSO) (mixture of both diastereomers) δ 12.79 (s, 1H), 8.13-8.12 (2H, m), 7.84 (dd, J=3.3, 8.8 Hz, 1H), 7.74 (dd, J=0.7, 16.4 Hz, 2H), 7.61-7.56 (1H, m), 7.43-7.39 (2H, m), 7.08 (d, J=2.5 Hz, 1H), 7.00 (d, J=2.1 Hz, 1H), 6.94-6.90 (2H, m), 5.12-5.04 (1H, m), 4.91-4.86 (1H, m), 4.72-4.64 (1H, m), 4.50-4.43 (2H, m), 4.38-4.25 (2H, m), 3.61-3.51 (2H, m), 3.25-3.18 (1H, m), 2.86 (1H, t, J=11.0 Hz), 2.08 (2H, t, J=12.1 Hz), 1.86 (1H, s), 1.62-1.52 (1H, m), 1.39-1.35 (9H, m), 1.32-1.28 (3H, m) ppm.

Example 114: (13R)-13-methyl-8,14-dioxa-10,19,20,23-tetraazatetracyclo[13.5.2.1$^{2,6}$.0$^{18,21}$]tricosa-1(20),2,4,6(23),15,17,21-heptaen-9-one

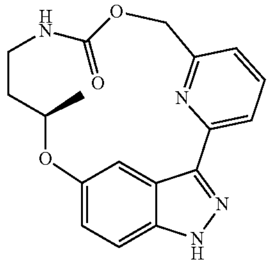 [SMILES: C[C@@H]1CCNC(=O)OCc2cccc(n2)-c2n[nH]c3ccc(cc23)O1]

Example 114 is prepared according to the synthesis route described in general Scheme K.

In 2 µwaves tubes were put a solution of (13R)-13-methyl-19-(oxan-2-yl)-8,14-dioxa-10,19,20,23-tetraazatetracyclo[13.5.2.1$^{2,6}$.0$^{18,21}$]tricosa-1(20),2,4,6(23),15,17,21-heptaen-9-one (300 mg, 0.71 mmol) in DCM (10 mL). To this solution was added trifluoroacetic acid (4.3 mL, 56.84 mmol). The reaction mixture was stirred at 80° C. under microwaves irradiations for 1 h. The solvent was removed under reduced pressure, the oil was dissolved in EtOAc and washed with a saturated solution of $NaHCO_3$. The phase were separated and the organic one was dried with $Na_2SO_4$. The solvent was removed under reduced pressure. The crude was purified by chromatography using a 10 g $SiO_2$ column eluted with cyclohexane/Ethyl acetate 70/30 to 50/50. The good fractions were combined and the solvent was removed under reduced pressure. The oil was triturated in DCM and the solid formed was filtered and dried under reduced pressure to give (13R)-13-methyl-8,14-dioxa-10,19,20,23-tetraazatetracyclo [13.5.2.1$^{2,6}$.0$^{18,21}$]tricosa-1(20),2,4,6(23),15,17,21-heptaen-9-one example 114 as a light yellow powder.

LCMS method F: $[M+H]^+$=339.3, $t_R$=2.17 min

LCMS method G: $[M+H]^+$=339.3, $t_R$=2.16 min $^1$H NMR (400 MHz, d6-DMSO) δ 13.24-13.21 (1H, m), 8.10-8.06 (1H, m), 7.90-7.80 (2H, m), 7.75-7.71 (1H, m), 7.48-7.45 (1H, m), 7.26-7.23 (1H, m), 6.96 (1H, dd, J=2.3, 8.9 Hz), 5.59 (1H, d, J=14.0 Hz), 5.06 (1H, d, J=14.6 Hz), 4.66-4.59 (1H, m), 3.5-3.42 (1H, m), 2.97-2.89 (1H, m), 2.29-2.22 (1H, m), 1.39-1.35 (4H, m) ppm.

Example 115: (7R)- or (7S)-7-ethyl-8,14-dioxa-10,19,20-triazatetracyclo[13.5.2.1$^{2,6}$.0$^{18,21}$]tricosa-1(20),2,4,6(23),15,17,21-heptaen-9-one

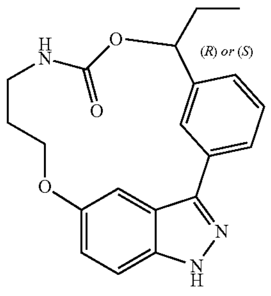 [SMILES: CCC1OC(=O)NCCCOc2ccc3[nH]nc(c3c2)-c2cccc1c2]

Example 115 is prepared according to the synthesis route described in general Scheme G and by chiral HPLC separation of example 104 using Chiralpak IB N-5 20×250 mm 5 µm [C7/EtOH]+0.1% DEA [80/20] run 20 min, 19 mL/min RT to give (7R)- or (7S)-7-ethyl-8,14-dioxa-10,19,20-triazatetracyclo[13.5.2.1$^{2,6}$.0$^{18,21}$]tricosa-1(20),2,4,6(23),15,17,21-heptaen-9-one example 115.

LCMS method F: $[M+H]^+$=352.3, $t_R$=2.42 min

LCMS method G: $[M+H]^+$=352.3, $t_R$=2.41 min $^1$H NMR (400 MHz, d6-DMSO) δ 7.96 (1H, dd, J=5.0, 7.7 Hz), 7.85-7.80 (2H, m), 7.52-7.45 (2H, m), 7.37-7.27 (2H, m), 6.98 (1H, dd, J=2.3, 8.9 Hz), 5.68 (1H, dd, J=3.5, 8.8 Hz), 4.38-4.24 (2H, m), 3.58-3.466 (1H, m), 2.78-2.67 (1H, m), 2.22-2.16 (1H, m), 2.10-2.02 (1H, m), 1.87-1.72 (2H, m), 1.08-0.98 (3H, m) ppm. The indazole NH proton was not visible in this solvent.

Chiral HPLC: ee 100%

The compound is a pure enantiomer, but the absolute stereochemistry of the chiral center is unknown.

Example 116: (7R)- or (7S)-7-ethyl-8,14-dioxa-10,19,20-triazatetracyclo[13.5.2.1$^{2,6}$.0$^{18,21}$]tricosa-1(20),2,4,6(23),15,17,21-heptaen-9-one

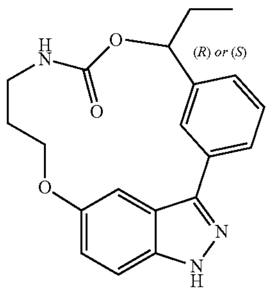 [SMILES: CCC1OC(=O)NCCCOc2ccc3[nH]nc(c3c2)-c2cccc1c2]

Example 116 is prepared according to the synthesis route described in general Scheme G and by chiral HPLC separation of example 104 using Chiralpak IB N-5 20×250 mm 5 µm [C7/EtOH]+0.1% DEA [80/20] run 20 min, 19 mL/min RT to give (7R)- or (7S)-7-ethyl-8,14-dioxa-10,19,20-triazatetracyclo[13.5.2.1$^{2,6}$.0$^{18,21}$]tricosa-1(20),2,4,6(23),15,17,21-heptaen-9-one example 116.

LCMS method F: $[M+H]^+$=352.2, $t_R$=2.42 min

LCMS method G: $[M+H]^+$=352.3, $t_R$=2.41 min $^1$H NMR (400 MHz, d6-DMSO) δ 13.12 (1H, s), 7.96 (1H, dd, J=4.7, 7.8 Hz), 7.85-7.80 (2H, m), 7.51-7.45 (2H, m), 7.37-7.28 (2H, m), 6.99 (1H, dd, J=2.1, 8.9 Hz), 5.68 (1H, dd, J=3.6, 8.7 Hz), 4.39-4.24 (2H, m), 3.56-3.50 (1H, m), 2.78-2.67 (1H, m), 2.22-2.16 (1H, m), 2.10-2.01 (1H, m), 1.87-1.72 (2H, m), 1.00 (3H, t, J=7.2 Hz) ppm.

Chiral HPLC: ee 100%

The compound is a pure enantiomer, but the absolute stereochemistry of the chiral center is unknown.

Example 117: (13R)-13-methyl-8,14-dioxa-5,10,19,20-tetraazatetracyclo[13.5.2.1$^{2,6}$.0$^{18,21}$]tricosa-1(20),2,4,6(23),15,17,21-heptaen-9-one

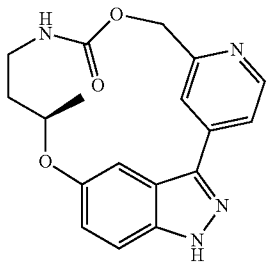 [SMILES: C[C@@H]1CCNC(=O)OCc2cc(ccn2)-c2n[nH]c3ccc(cc23)O1]

Example 117 is prepared according to the synthesis route described in general Scheme K.

In a round bottom flask was added (13R)-13-methyl-19-(oxan-2-yl)-8,14-dioxa-5,10,19,20-tetraazatetracyclo[13.5.2.1$^{2,6}$.0$^{18,21}$]tricosa-1(20),2,4,6(23),15,17,21-heptaen-9-one (0.280 g, 0.663 mmol) in DCM (10.0 mL) and trifluoroacetic acid (2.02 mL, 26.52 mmol). The reaction mixture was stirred at 80° C. under microwaves irradiations during 2 h. LC/MS analysis indicated the reaction was completed. The reaction was quenched with a saturated solution of $NaHCO_3$ (10 mL). Phases were separated and the aqueous phase was extracted with DCM (3×10 mL). Organic phase was washed with a saturated solution of NaCl (10 mL), dried with $MgSO_4$, filtered and concentrated under reduce pressure to afford crude (0.250 g) which was purified by chromatography column (Macherey Nagel 4 g, DCM/MeOH: 100/0 to 90/10). Solvents was removed and the powder was triturated with DCM, to afford (13R)-13-methyl-8,14-dioxa-5,10,19,20-tetraazatetracyclo[13.5.2.1$^{2,6}$.0$^{18,21}$]tricosa-1(20),2,4,6(23),15,17,21-heptaen-9-one example 117 as a yellow powder.

LCMS method F: $[M+H]^+$=339.2, $t_R$=1.83 min

LCMS method G: $[M+H]^+$=339.2, $t_R$=2.07 min $^1$H NMR (400 MHz, d6-DMSO) δ 13.57-13.48 (1H, s), 8.59 (1H, d, J=5.3 Hz), 8.14 (1H, s), 7.86-7.81 (2H, m), 7.58-7.55 (1H, m), 7.37 (1H, d, J=1.9 Hz), 7.02 (1H, dd, J=2.2, 9.0 Hz), 5.72-5.56 (1H, m), 4.99-4.85 (1H, m), 4.62 (1H, dd, J=6.1, 11.2 Hz), 3.00-2.88 (1H, m), 2.70-2.66 (1H, m), 2.35-2.32 (1H, m), 1.43 (3H, d, J=5.9 Hz), 1.06 (1H, t, J=7.0 Hz) ppm.

Example 118: 6-(oxan-4-yl)-8,14-dioxa-4,5,10,19,20-pentaazatetracyclo[13.5.2.1$^{2,5}$.0$^{18,21}$]tricosa-1(20),2(23),3,15,17,21-hexaen-9-one

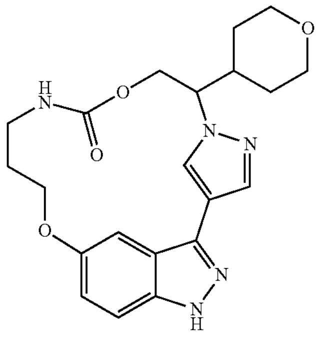 [SMILES: O=C1NCCCOc2ccc3[nH]nc(c3c2)-c2cnn(c2)C(C2CCOCC2)CO1]

Example 118 is prepared according to the synthesis route described in general Scheme B.

Preparation of Intermediate 138: ethyl 2-tetrahydropyran-4-ylideneacetate

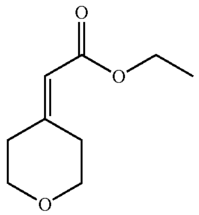

Sodium hydride (60% dispersion in mineral oil, 0.88 g, 22.0 mmol) was suspended in THE (120 mL) and cooled to 0-5° C. in an ice bath. A solution of triethyl phosphonoacetate (4.4 mL, 22.0 mmol) in THF (120 mL) was added dropwise. The mixture was stirred at room temperature for 30 min and a solution of tetrahydro-4H-pyran-4-one (1.9 mL, 20.0 mmol) in THF (120 mL) was added dropwise. The resulting mixture was stirred for additional 6 hours at room temperature, cooled to 0-5° C. and water (500 mL) was added. The mixture was extracted with diethylether (3×250 mL), the combined organic layers were dried over anhydrous magnesium sulfate, filtered and concentrated under reduced pressure to afford ethyl 2-tetrahydropyran-4-ylideneacetate 138 as a colorless oil.

LCMS method F: $[M+H]^+$=171.1, $t_R$=2.08 min

Preparation of Intermediate 139: ethyl 2-tetrahydropyran-4-yl-acetate

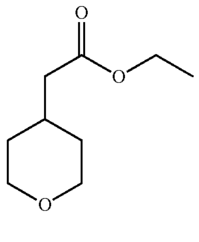

To a solution of ethyl 2-tetrahydropyran-4-ylideneacetate 138 (3.40 g, 20.0 mmol) in MeOH (130 mL) under argon atmosphere, was added 10% Pd/C (0.40 g, 0.40 mmol). The mixture was hydrogenated under a hydrogen atmosphere for 4 hours. The suspension was filtered through a pad of Celite, rinsed with MeOH (100 mL) and the filtrate was evaporated under reduced pressure to give ethyl 2-tetrahydropyran-4-ylacetate 139 as a colorless oil. The crude product was used in the next step without any purification.

Preparation of Intermediate 140: ethyl 2-bromo-2-tetrahydropyran-4-yl-acetate

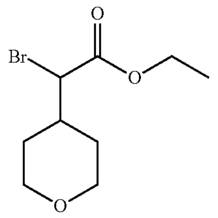

To a solution of lithium diisopropylamide (1.8 M in THF/heptane/ethylbenzene, 10.6 mL, 19.1 mmol) in 30 mL of THE at −78° C. was added trimethylsilyl chloride (4.2 mL, 33.1 mmol) dropwise. Ethyl 2-tetrahydropyran-4-ylacetate 139 (3.000 g, 17.4 mmol) in 15 mL of THE was then added to the mixture dropwise very slowly. The mixture was stirred at −78° C. for 2 hours then N-bromosuccinimide (3.258 g, 18.3 mmol) in 30 mL of THE was added dropwise very slowly. The reaction mixture was allowed to warm slowly to room temperature and was stirred for 16 hours. TLC showed complete reaction. The mixture was concentrated under reduced pressure and the residue was dissolved in 120 mL of ethyl acetate, washed 1×30 mL of water.

The aqueous layer was extracted 3×30 mL of ethyl acetate. The combined organic layers were dried over anhydrous magnesium sulfate, filtered and concentrated under reduced pressure to give a brown oily residue. The crude was purified by column chromatography on silica gel (Cyclohexane: EtOAc from 100:0 to 80:20) to provide ethyl 2-bromo-2-tetrahydropyran-4-yl-acetate 140 as a yellow oil.

LCMS method F: $t_R$=2.36 min, no m/z detected

Preparation of Intermediate 141: ethyl 2-(4-bromopyrazol-1-yl)-2-tetrahydropyran-4-yl-acetate

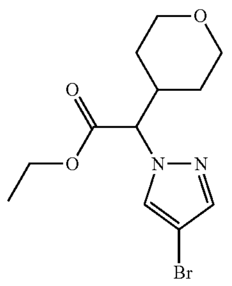 [SMILES: CCOC(=O)C(C1CCOCC1)n1cc(Br)cn1]

A suspension of 4-bromo-1H-pyrazole (1.50 g, 10.20 mmol), ethyl 2-bromo-2-tetrahydropyran-4-yl-acetate 140 (3.07 g, 12.24 mmol), and potassium carbonate (2.83 g, 20.40 mmol) in N,N-dimethylformamide (3.0 mL) was stirred for 3 h at 80° C. The reaction was quenched by water (30 mL), and the resulting solution was extracted twice with ethyl acetate (50 mL×2). The combined organic layers were dried over anhydrous magnesium sulfate, filtered, and concentrated under reduced pressure to give ethyl 2-(4-bromopyrazol-1-yl)-2-tetrahydropyran-4-yl-acetate 141 as a slightly yellow oil.

LCMS method F: $[M+H]^+$=317.0, $t_R$=2.38 min

Preparation of Example 118: 6-(oxan-4-yl)-8,14-dioxa-4,5,10,19,20-pentaazatetracyclo[13.5.2.1$^{2,5}$.0$^{18,21}$]tricosa-1(20),2(23),3,15,17,21-hexaen-9-one

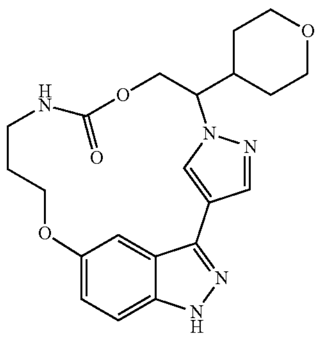 [SMILES: O=C1NCCCOc2ccc3[nH]nc(c3c2)-c2cnn(c2)C(C2CCOCC2)CO1]

To a solution of 19-(oxan-2-yl)-6-(oxan-4-yl)-8,14-dioxa-4,5,10,19,20-pentaazatetracyclo[13.5.2.1$^{2,5}$.0$^{18,21}$]tricosa-1(20),2(23),3,15,17,21-hexaen-9-one (0.115 g, 0.23 mmol) in DCM (6.0 mL) was added trifluoroacetic acid (0.35 mL, 4.60 mmol). The reaction mixture was directly heated to 50° C. for 3 hours. The reaction mixture (brown solution) was evaporated under reduced pressure. The brown residue was dissolved in EtOAc then a saturated aqueous solution of sodium hydrogen carbonate was added. After separation, the aqueous layer was extracted with ethyl acetate (2×). The combined organic layer was washed with water then brine, dried over sodium sulfate, filtered and evaporated under reduced pressure to give an orange oil. The crude product was purified by preparative TLC plate on silica eluting with Cyclohexane/Ethyl acetate-EtOH (3-1), 100/0 to 70/30 to afford 6-(oxan-4-yl)-8,14-dioxa-4,5,10,19,20-pentaazatetracyclo[13.5.2.1$^{2,5}$.0$^{18,21}$]tricosa-1(20),2(23),3,15,17,21-hexaen-9-one example 118 as a white solid.

LCMS method F: $[M+H]^+$=412.3, $t_R$=1.92 min

LCMS method G: $[M+H]^+$=412.3, $t_R$=1.92 min $^1$H NMR (400 MHz, d6-DMSO) δ 12.80 (1H, s), 8.22 (1H, s), 7.83 (1H, dd, J=3.6, 8.0 Hz), 7.77 (1H, s), 7.42 (1H, d, J=9.2 Hz), 7.10 (1H, d, J=1.9 Hz), 6.94 (1H, dd, J=2.3, 8.9 Hz), 4.57 (1H, dd, J=1.8, 12.1 Hz), 4.45 (1H, dt, J=2.8, 12.0 Hz), 4.38 (1H, dq, J=2.0, 10.4 Hz), 4.26-4.15 (2H, m), 3.95 (1H, dd, J=2.8, 11.1 Hz), 3.84-3.80 (1H, m), 3.48-3.39 (1H, m), 3.32-3.28 (1H, m), 3.22 (1H, dt, J=2.4, 11.2 Hz), 2.82 (1H, dt, J=2.8, 11.2 Hz), 2.47-2.36 (1H, m), 1.95-1.88 (1H, m), 1.81-1.75 (2H, m), 1.48 (1H, dq, J=4.8, 12.8 Hz), 1.26 (1H, dq, J=4.8, 12.8 Hz), 1.07 (1H, d, J=12.8 Hz) ppm.

Example 119: 4-ethyl-8,14-dioxa-5,10,19,20,23-pentaazatetracyclo[13.5.2.1$^{2,5}$.0$^{18,21}$]tricosa-1(20),2(23),15,17,21-pentaen-9-one

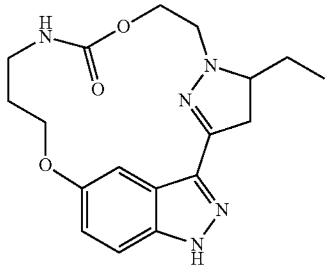 [SMILES: CCC1CC2=NN1CCOC(=O)NCCCOc1ccc3[nH]nc2c3c1]

Example 119 is prepared according to the synthesis route described in general Scheme B.

Preparation of Intermediate 142: 5-ethylpyrazolidin-3-one

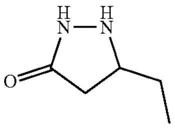

To a solution of hydrazine hydrate 50-60% (1.00 mL, 15.94 mmol) in isopropanol (13 mL), was added a solution of methyl pent-2-enoate (2.000 g, 17.54 mmol) in isopropanol (10 mL) at room temperature. The reaction mixture was stirred at 80° C. for 16 hours. The mixture was evaporated under reduced pressure. Taken in DCM and again evaporated under reduced pressure twice to remove isopropanol affording the crude 5-ethylpyrazolidin-3-one 142 as a pale yellow oil. The crude was used in the next step without further purification.

Yield: 1.940 g of intermediate 142 (quantitative)

Preparation of Intermediate 143: ethyl 2-(5-ethyl-3-oxo-pyrazolidin-1-yl)acetate

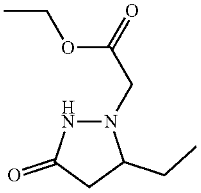

To a solution of 5-ethylpyrazolidin-3-one 142 (1.817 g, 15.94 mmol) and ethyl glyoxylate 50% wt in toluene (3.576 g, 17.53 mmol) in DCM (35 mL) was added at 0° C. sodium triacetoxyborohydride (13.45 g, 63.76 mmol). Gas evolution was observed. The reaction mixture was warmed up to room temperature and stirred for 48 hours. The reaction was quenched by slow addition of an aqueous $NaHCO_3$ solution (50 mL). Gas evolution was observed. The resulting mixture was diluted with DCM (50 mL), followed by an aqueous NaOH 1 M solution until pH ~8/9. After separation, the aqueous layer was extracted with DCM (3×50 mL). The combined organic layer was dried over anhydrous magnesium sulfate, filtered and evaporated under reduced pressure to afford ethyl 2-(5-ethyl-3-oxo-pyrazolidin-1-yl)acetate 143 as a brown oil. The crude product was used in the next step without further purification.

Preparation of Intermediate 144: ethyl 2-(5-bromo-3-ethyl-3,4-dihydropyrazol-2-yl)acetate

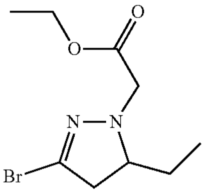

To a mixture of ethyl 2-(5-ethyl-3-oxo-pyrazolidin-1-yl) acetate 143 (1.443 g, 7.21 mmol) and tetraethylammonium bromide (0.453 g, 2.16 mmol) in DCM (3.5 mL) at 20-25° C. was added dropwise triethylamine (0.90 mL, 6.49 mmol) over 2-3 minutes, maintaining the internal temperature below 35° C. The resulting reaction mixture was then cooled to 0-5° C. A solution of phosphorus(V) oxybromide (2.680 g, 9.37 mmol) in DCM (3.7 mL) was added dropwise over 5-10 minutes, maintaining the internal temperature below 20° C. The reaction mixture was warmed to 30° C. and stirred for 5 hours at this temperature. After 5 hours, the reaction mixture was slowly poured into a separate reactor containing a solution of NaOH (1.298 g, 32.44 mmol) in water (26 mL) at 0-5° C. This slow addition was performed using an addition funnel, maintaining the internal temperature below 20° C. The addition funnel was rinsed with DCM (1.1 mL). The resulting biphasic mixture was warmed to 20-25° C., stirred for 3 hours, and the aqueous layer checked by pH. The layers were separated. The organic layer was sequentially washed with a 0.1 M aqueous solution of sodium dihydrogenophosphate ($NaH_2PO_{4(aq)}$, 10 mL) and water (10 mL), then concentrated under reduced pressure. The crude oily residue was purified by column chromatography on silica gel (Cyclochexane/EtOAc: from 10/0 to 9/1) to afford ethyl 2-(5-bromo-3-ethyl-3,4-dihydropyrazol-2-yl) acetate 144 as a yellow oil.

LCMS method F: $[M+H]^+$=265.1, $t_R$=2.42 min

Preparation of Example 119: 4-ethyl-8,14-dioxa-5,10,19,20,23-pentaazatetracyclo[13.5.2.1$^{2,5}$.0$^{18,21}$]tricosa-1(20),2(23),15,17,21-pentaen-9-one

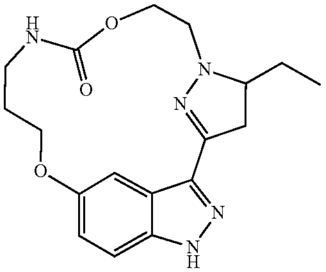 [SMILES: CCC1CC2=NN1CCOC(=O)NCCCOc1ccc3[nH]nc2c3c1]

To a solution of 4-ethyl-19-(oxan-2-yl)-8,14-dioxa-5,10,19,20,23-pentaazatetracyclo[13.5.2.1$^{2,5}$.0$^{18,21}$]tricosa-1(20),2(23),15,17,21-pentaen-9-one (0.052 g, 0.12 mmol) in DCM (3.0 mL) was added trifluoroacetic acid (0.18 mL, 2.40 mmol). The reaction mixture was directly heated to 50° C. for 3 hours. LCMS analysis showed formation of the expected product and total consumption of starting material. The reaction mixture (brown solution) was evaporated under reduced pressure. The brown residue was dissolved in EtOAc then a saturated aqueous solution of sodium hydrogen carbonate was added. After separation, the aqueous layer was extracted with ethyl acetate (2×). The combined organic layer was washed with water then brine, dried over sodium sulfate, filtered and evaporated under reduced pressure to give an orange oil. The crude product was purified over preparative TLC plate on silica eluting with Cyclohexane/Ethyl acetate-EtOHormate (3-1), 100/0 to 70/30. The pure fractions were combined and evaporated under reduced pressure to afford 4-ethyl-8,14-dioxa-5,10,19,20,23-pentaazatetracyclo[13.5.2.1$^{2,5}$.0$^{18,21}$]tricosa-1(20),2(23),15,17,21-pentaen-9-one example 119 as a slightly yellow solid.

LCMS method F: $[M+H]^+$=358.2, $t_R$=2.01 min

LCMS method G: $[M+H]^+$=358.3, $t_R$=2.13 min $^1$H NMR (400 MHz, d6-DMSO, 80° C.) δ 12.70 (1H, br. s), 7.61 (1H, d, J=1.9 Hz), 7.39 (1H, d, J=8.8 Hz), 7.11 (1H, br. s), 6.94 (1H, dd, J=2.8, 8.8 Hz), 4.45-4.17 (4H, m), 3.31-3.07 (5H, m), 2.71-2.59 (1H, m), 1.92-1.80 (3H, m), 1.64-1.52 (1H, m), 1.32-1.27 (1H, m), 0.98 (3H, t, J=7.6 Hz) ppm.

Example 120: (13R)-23-fluoro-13-methyl-8,14-dioxa-10,19,20-triazatetracyclo[13.5.2.1$^{2,6}$.0$^{18,21}$]tricosa-1(20),2,4,6(23),15,17,21-heptaen-9-one

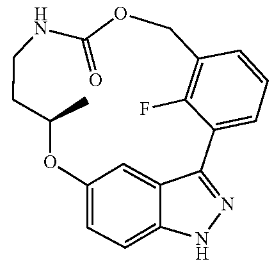 [SMILES: C[C@@H]1CCNC(=O)OCc2cccc(c2F)-c2n[nH]c3ccc(cc23)O1]

Example 120 is prepared according to the synthesis route described in general Scheme C. In a μwave tube was put a solution of (13R)-23-fluoro-13-methyl-19-(oxan-2-yl)-8,14-dioxa-10,19,20-triazatetracyclo[13.5.2.1$^{2,6}$.0$^{18,21}$]tricosa-1(20),2,4,6(23),15,17,21-heptaen-9-one (165 mg, 0.391 mmol) in DCM (10 mL). To this solution was added trifluoroacetic acid (1.2 mL, 15.6 mmol). The reaction mixture was stirred at 80° C. under microwaves irradiations for 1 h. The solvent was removed under reduced pressure, the oil was dissolved in EtOAc and washed with a saturated solution of $NaHCO_3$. The phase were separated and the organic one was dried with $Na_2SO_4$. The solvent was removed under reduced pressure. The crude was triturated in DCM, the solid formed was filtered washed with water and dried to give (13R)-23-fluoro-13-methyl-8,14-dioxa-10,19,20-triazatetracyclo[13.5.2.1$^{2,6}$.0$^{18,21}$]tricosa-1(20),2,4,6(23),15,17,21-heptaen-9-one example 120 as an off white powder.

LCMS method F: $[M+H]^+$=356.2, $t_R$=2.25 min

LCMS method G: $[M+H]^+$=356.2, $t_R$=2.25 min $^1$H NMR (400 MHz, d6-DMSO) δ 13.42-13.11 (1H, s), 7.76-7.68 (2H, m), 7.56-7.45 (2H, m), 7.30 (1H, t, J=7.6 Hz), 6.96-6.90 (2H, m), 6.07-6.02 (1H, m), 4.65 (1H, d, J=12.5 Hz), 4.58-4.54 (1H, m), 3.66-3.58 (1H, m), 2.81-2.68 (1H, m), 2.23-2.16 (1H, m), 1.35-1.31 (4H, m) ppm.

Example 121: 9,14-dioxa-4,5,11,19,20-pentaazatetracyclo[13.5.2.1$^{2,5}$.0$^{18,21}$]tricosa-1(20),2(23),3,15,17,21-hexaen-10-one

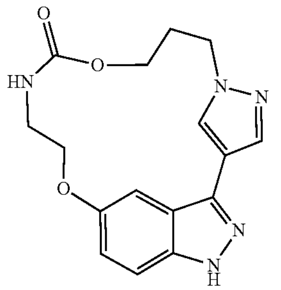 [SMILES: O=C1NCCOc2ccc3[nH]nc(c3c2)-c2cnn(c2)CCCO1]

Example 121 is prepared according to the synthesis route described in general Scheme A.

Preparation of Intermediate 145: 3-[4-(4,4,5,5-tetramethyl-1,3,2-dioxaborolan-2-yl)-1H-pyrazol-1-yl]propan-1-ol

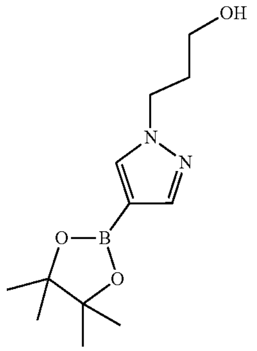 [SMILES: CC1(C)OB(c2cnn(CCCO)c2)OC1(C)C]

To a solution of 4-bromo-1-(3-hydroxypropyl)-1H-pyrazole (0.410 g, 2.0 mmol) in dioxane (4 mL) was added at RT bis(pinacolato)diboron (0.609 g, 2.4 mmol), KOAc (0.589 g, 6.0 mmol) and $PdCl_2$(dppf)DCM (0.082 g, 0.1 mmol). The resulting reaction mixture was stirred under microwave irradiation at 100° C. for 2 h. The residue was diluted with water and extracted with ethyl acetate twice. The combined organic layer was dried over anhydrous sodium sulfate affording 3-[4-(4,4,5,5-tetramethyl-1,3,2-dioxaborolan-2-yl)-1H-pyrazol-1-yl]propan-1-ol 145 as a brown oil, which was used in the next step without further purification.

Yield: 0.504 g of intermediate 145 (quantitative)

LCMS method F: $[M+H]^+$=253.2, $t_R$=1.91 min Preparation of Example 121: 9,14-dioxa-4,5,11,19,20-pentaazatetracyclo[13.5.2.1$^{2,5}$.0$^{18,21}$]tricosa-1(20),2(23),3,15,17,21-hexaen-10-one

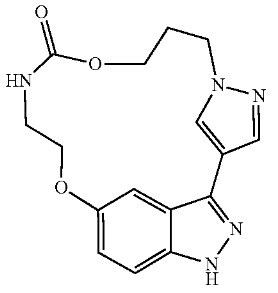 [SMILES: O=C1NCCOc2ccc3[nH]nc(c3c2)-c2cnn(c2)CCCO1]

To a solution of 19-(oxan-2-yl)-9,14-dioxa-4,5,11,19,20-pentaazatetracyclo[13.5.2.$1^{2,5}$.$0^{18,21}$]tricosa-1(20),2(23),3,15,17,21-hexaen-10-one (0.015 g, 0.04 mmol) in DCM (1 mL) was added at RT TFA (0.054 mL, 0.73 mmol). The resulting reaction mixture was stirred under microwave irradiation at 80° C. for 1 h. The reaction mixture was concentrated in vacuo, diluted with saturated sodium bicarbonate solution and extracted with ethyl acetate twice. The combined organic layer was dried over anhydrous sodium sulfate and concentrated in vacuo. The residue was purified by flash-column (4 g silica Macherey Nagel) chromatography (cyclohexane-ethyl acetate 3/EtOH 1, 1:0 to 6:4) affording 9,14-dioxa-4,5,11,19,20-pentaazatetracyclo[13.5.2.$1^{2,5}$.$0^{18,21}$]tricosa-1(20),2(23),3,15,17,21-hexaen-10-one example 121 as a white solid.

LCMS method F: $[M+H]^+$=328.2, $[M-H]^-$=326.3, $t_R$=1.67

LCMS method G: $[M+H]^+$=328.2, $[M-H]^-$=326.4, $t_R$=1.75

$^1$H NMR (400 MHz, d6-DMSO) δ 12.79 (1H, s), 8.31 (1H, s), 7.94 (1H, t, J=5.5 Hz), 7.80 (1H, s), 7.42-7.36 (2H, m), 7.00 (1H, dd, J=2.3, 8.9 Hz), 4.38 (2H, t, J=6.0 Hz), 4.29-4.25 (2H, m), 3.60 (2H, t, J=5.6 Hz), 3.41-3.35 (2H, m) 2.14-2.08 (2H, m) ppm.

Example 122: 4-ethyl-8,14-dioxa-5,10,19,20,23-pentaazatetracyclo[13.5.2.$1^{2,5}$.$0^{18,21}$]tricosa-1(20),2(23),3,15,17,21-hexaen-9-one

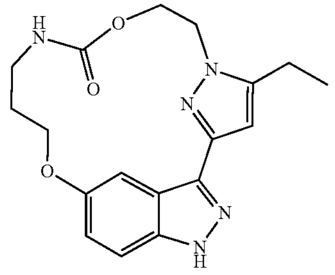 [SMILES: CCc1cc2nn1CCOC(=O)NCCCOc1ccc3[nH]nc-2c3c1]

Example 122 is prepared according to the synthesis route described in general Scheme B.

Preparation of Intermediate 146: ethyl 2-[3-[5-[tert-butyl(dimethyl)silyl]oxy-1-tetrahydropyran-2-yl-indazol-3-yl]-5-ethyl-pyrazol-1-yl]acetate

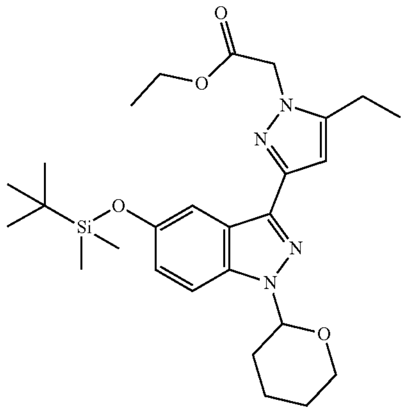 [SMILES: CCOC(=O)Cn1nc(-c2nn(C3CCCCO3)c3ccc(O[Si](C)(C)C(C)(C)C)cc23)cc1CC]

Ethyl 2-[5-[5-[tert-butyl(dimethyl)silyl]oxy-1-tetrahydropyran-2-yl-indazol-3-yl]-3-ethyl-3,4-dihydropyrazol-2-yl]acetate (0.470 g, 0.91 mmol) was diluted in toluene (3.2 mL) and manganese(IV) dioxide (1.193 g, 13.72 mmol) and stirred at 100-105° C. for 24 hours. The reaction mixture was cooled down to room temperature, filtered over a celite pad, rinsed with ethyl acetate, then evaporated under reduced pressure. The crude residue was purified by column chromatography (DCM/EtOAc from 1:0 to 7:3) to afford ethyl 2-[3-[5-[tert-butyl(dimethyl)silyl]oxy-1-tetrahydropyran-2-yl-indazol-3-yl]-5-ethyl-pyrazol-1-yl]acetate 146 as yellow solid.

LCMS method F: $[M+H]^+$=513.4, $t_R$=3.77 min

Preparation of Example 122: 4-ethyl-8,14-dioxa-5,10,19,20,23-pentaazatetracyclo[13.5.2.$1^{2,5}$.$0^{18,21}$]tricosa-1(20),2(23),3,15,17,21-hexaen-9-one

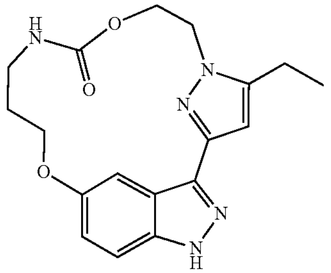 [SMILES: CCc1cc2nn1CCOC(=O)NCCCOc1ccc3[nH]nc-2c3c1]

To a solution of 4-ethyl-19-(oxan-2-yl)-8,14-dioxa-5,10,19,20,23-pentaazatetracyclo[13.5.2.$1^{2,5}$.$0^{18,21}$]tricosa-1(20),2(23),3,15,17,21-hexaen-9-one (0.024 g, 0.054 mmol) in DCM (1.5 mL) was added trifluoroacetic acid (83 μL, 1.09 mmol). The reaction mixture was directly heated to 50° C. (sand bath previously heated to 50° C.) for 6 hours. The reaction mixture (brown solution) was evaporated under reduced pressure. The brown residue was dissolved in EtOAc then a saturated aqueous solution of sodium hydrogen carbonate was added. After separation, the aqueous layer was extracted with ethyl acetate (2×). The combined organic layer was washed with water then brine, dried over sodium sulfate, filtered and evaporated under reduced pressure. The crude product was purified by preparative TLC plate using DCM/MeOH 9/1 as an eluant to give 4-ethyl-8,14-dioxa-5,10,19,20,23-pentaazatetracyclo[13.5.2.$1^{2,5}$.$0^{18,21}$]tricosa-1(20),2(23),3,15,17,21-hexaen-9-one example 122 as an orange solid.

LCMS method F: $[M+H]^+$=356.3, $t_R$=1.99 min

LCMS method G: $[M+H]^+$=356.3, $t_R$=2.03 min $^1$H NMR (400 MHz, d6-DMSO) δ 12.80 (1H, s), 7.64-7.58 (2H, m), 7.38 (1H, d, J=9.2 Hz), 6.92 (1H, dd, J=9.2, 3.2 Hz), 6.44 (1H, s), 4.41 (4H, s), 4.27-4.22 (2H, m), 3.11-3.06 (2H, m), 2.70 (2H, q, J=7.2 Hz), 1.92-1.82 (2H, m), 1.27 (3H, t, J=7.2 Hz) ppm.

Example 123: 3,9,15-trioxa-4,11,20,21-tetraazatetracyclo[14.5.2.$1^{2,5}$.$0^{19,22}$]tetracosa-1(21),2(24),4,16,18,22-hexaen-10-one

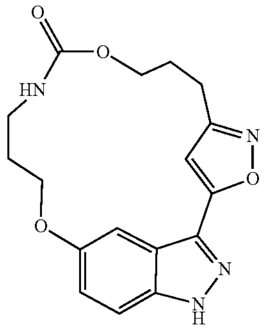 [SMILES: O=C1NCCCOc2ccc3[nH]nc(c3c2)-c2cc(no2)CCCO1]

Example 123 is prepared according to the synthesis route described in general Scheme M.

Preparation of Intermediate 147: benzyl N-[3-[1-tetrahydropyran-2-yl-3-(2-triethylsilylethynyl)indazol-5-yl]oxypropyl]carbamate

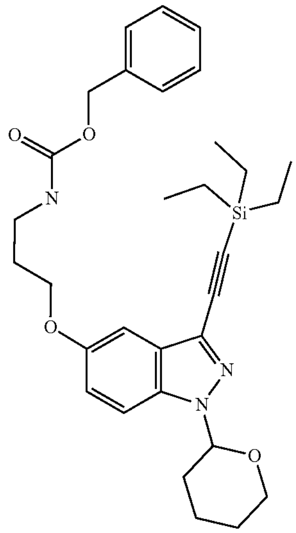

To a degassed solution of benzyl N-[3-(3-iodo-1-tetrahydropyran-2-yl-indazol-5-yl)oxypropyl]carbamate (2.500 g, 4.67 mmol) in THE (15.0 mL), triethylamine (0.754 mL, 5.65 mmol), CuI (0.071 g, 0.374 mmol) and Tetrakis(triphenylphosphine) palladium (0.058 g, 0.050 mmol) was added. Triethylsilylacetylene (1.088 mL, 6.07 mmol) was slowly added and the reaction was heated to 80° C. for 4 h. The reaction mixture was diluted with water (30 mL) and EtOAc (30 mL) and extracted with EtOAc (3×30 mL). The organic layer was combined, washed with saturated brine (30 mL), dried with $MgSO_4$, filtered and concentrated under reduced pressure. The crude material (3.0 g) was purified by column (Macherey Nagel, 40 g, CyH/EtOAc. 90/10 to 70/30). Solvents were evaporated to afford benzyl N-[3-[1-tetrahydropyran-2-yl-3-(2-triethylsilylethynyl)indazol-5-yl]oxypropyl]carbamate 147 as an orange oil.

LCMS method F: $[M+H]^+$=548.4, $t_R$=3.81 min

Preparation of Intermediate 148: benzyl N-[3-(3-ethynyl-1-tetrahydropyran-2-yl-indazol-5-yl)oxypropyl]carbamate

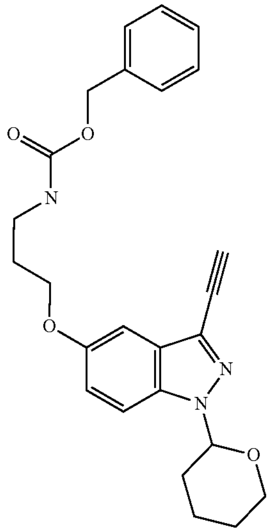

To a solution of benzyl N-[3-[1-tetrahydropyran-2-yl-3-(2-triethylsilylethynyl)indazol-5-yl]oxypropyl]carbamate 147 (2.375 g, 4.36 mmol) in THE (100.0 mL) was added dropwise at room temperature tetrabutylammonium fluoride 1 M in THE (4.77 mL, 4.77 mmol). The resulting mixture was stirred at room temperature during 16 h. Water (35 mL) and EtOAc (35 mL) were added and phases were separated. The aqueous layer was extracted with EtOAc (3×25 mL) and the organic phase was washed with brine (35 mL) and dried with $MgSO_4$, filtered and concentrated. The crude (2.0 g) was purified by chromatography column (Macherey Nagel, 24 g, CyH/EtOAc: 90/10 to 70/30). Solvents were evaporated to afford benzyl N-[3-(3-ethynyl-1-tetrahydropyran-2-yl-indazol-5-yl)oxypropyl]carbamate 148 as a yellow oil.

LCMS method F: $[M+H]^+$=434.3, $t_R$=3.05 min

Preparation of Intermediate 149: tert-butyl-(4-nitrobutoxy)-diphenyl-silane

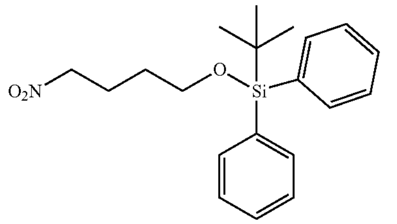 [SMILES: CC(C)(C)[Si](OCCCC[N+](=O)[O-])(c1ccccc1)c1ccccc1]

In a round bottom flask, to a solution of 4-nitrobutan-1-ol (1.00 g, 8.39 mmol) and imidazole (0.686 g, 10.07 mmol) in DCM (85.0 mL) was added slowly tert-butyl(chloro)diphenylsilane (2.18 mL, 8.39 mmol). The mixture was stirred at room temperature during 3 h. Water was added (35 mL) and phases were separated. The aqueous layer was extracted with DCM (3×30 mL), then the organic layer was washed with a saturated solution of NaCl (25 mL), dried with $MgSO_4$, filtered and concentrated under reduced pressure to afford crude tert-butyl-(4-nitrobutoxy)-diphenyl-silane 149 as a colorless oil which was used in the next step without further purification.

LCMS method F: $[M+H]^+$=358.3, $t_R$=3.67 min

Preparation of Intermediate 150: benzyl N-[3-[3-[3-[2-[tert-butyl(diphenyl) silyl]oxyethyl]isoxazol-5-yl]-1-tetrahydropyran-2-yl-indazol-5-yl]oxypropyl] carbamate

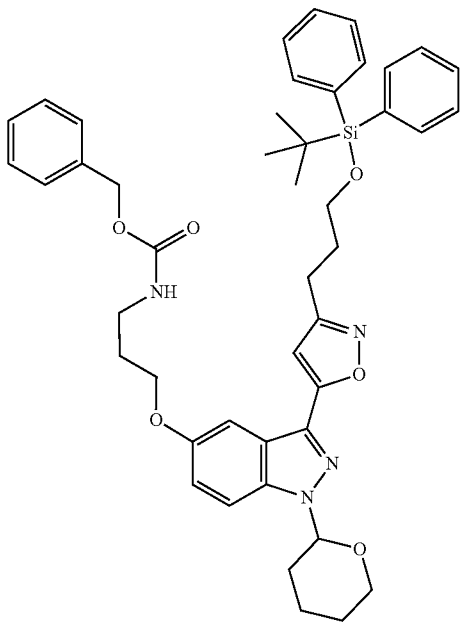 [SMILES: CC(C)(C)[Si](OCCCc1cc(-c2nn(C3CCCCO3)c3ccc(OCCCNC(=O)OCc4ccccc4)cc23)on1)(c1ccccc1)c1ccccc1]

In a round bottom flask, to a solution of tert-butyl-(4-nitrobutoxy)-diphenyl-silane 149 (3.030 g, 8.39 mmol) and benzyl N-[3-(3-ethynyl-1-tetrahydropyran-2-yl-indazol-5-yl)oxypropyl]carbamate 141 (1.000 g, 2.31 mmol) in toluene (25.0 mL), were added phenyl isocyanate (0.276 mL, 2.54 mmol) and triethylamine (0.353 mL, 2.54 mmol). The reaction was stirred during 2 days at 60° C. The precipitate (urea) was filtered and solvent was removed to give crude (4 g) which was purified by chromatography column by solid deposit (Macherey Nagel 40 g, Cyclo/EtOAc: 100/0 to 70/30). Solvents were evaporated to afford benzyl N-[3-[3-[3-[2-[tert-butyl(diphenyl)silyl]oxyethyl]isoxazol-5-yl]-1-tetrahydropyran-2-yl-indazol-5-yl]oxypropyl]carbamate 150 as a yellow solid.

LCMS method I: $[M+H]^+$=773.5, $t_R$=3.71 min

Preparation of Intermediate 151: benzyl N-[3-[3-[3-(3-hydroxypropyl)isoxazol-5-yl]-1-tetrahydropyran-2-yl-indazol-5-yl]oxypropyl]carbamate

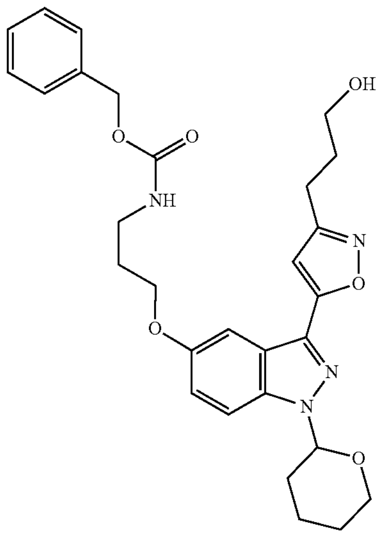 [SMILES: O=C(NCCCOc1ccc2c(c1)c(-c1cc(CCCO)no1)nn2C1CCCCO1)OCc1ccccc1]

In a round bottom flask, to a solution of benzyl N-[3-[3-[3-[3-[tert-butyl(diphenyl) silyl]oxypropyl]isoxazol-5-yl]-1-tetrahydropyran-2-yl-indazol-5-yl]oxypropyl]carbamate 150 (2.00 g, 2.31 mmol) in THE (25.0 mL), was added TBAF (1.0 M in THF), 2.77 mL, 2.77 mmol). The reaction was stirred during 2 h at room temperature. Water (20 mL) and EtOAc (20 mL) were added. Phases were separated and the aqueous phase was extracted with EtOAc (3×25 mL). Then, the organic phase was washed with a saturated solution of NaCl (20 mL), dried with $MgSO_4$, filtered and concentrated under reduced pressure to give crude (1.8 g) which was purified by chromatography column (RediSep 25 g, CyH/EtOAc: 100/0 to 70/30, then DCM/MeOH: 100/0 to 90/10). Solvents was evaporated to afford benzyl N-[3-[3-[3-(3-hydroxypropyl)isoxazol-5-yl]-1-tetrahydropyran-2-yl-indazol-5-yl]oxypropyl]carbamate 151 as an orange oil.

LCMS method F: $[M+H]^+$=535.3, $t_R$=2.85 min

Preparation of Intermediate 152: 20-(oxan-2-yl)-3,9,15-trioxa-4,11,20,21-tetraazatetracyclo[14.5.2.1$^{2,5}$.0$^{19,22}$]tetracosa-1(21),2(24), 4,16,18,22-hexaen-10-one

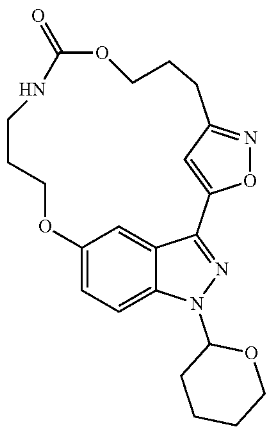 [SMILES: O=C1NCCCOc2ccc3c(c2)c(nn3C2CCCCO2)-c2cc(no2)CCCO1]

The reaction was divided in 2 batches. In a round bottom flask, benzyl N-[3-[3-[3-(3-hydroxypropyl)isoxazol-5-yl]-1-tetrahydropyran-2-yl-indazol-5-yl]oxypropyl]carbamate 151 (0.430 g, 0.805 mmol) in dry MeCN (300.0 mL) was added cesium carbonate (1.572 g, 4.825 mmol). The reaction was stirred during 48 h at 85° C. The mixture was filtered and the filtrate was concentrated under reduce pressure to afford crude (2×400 mg) which were combined and purified by chromatography column by solid deposit (Macherey Nagel 4 g, DCM/MeOH: 100/0 to 95/5). Good fractions were gathered and solvent was removed, to afford 20-(oxan-2-yl)-3,9,15-trioxa-4,11,20,21-tetraazatetracyclo[14.5.2.1$^{2,5}$.0$^{19,22}$]tetracosa-1(21),2(24), 4,16,18,22-hexaen-10-one 152 as a white powder.

LCMS method F: $[M+H]^+$=427.2, $t_R$=2.51 min

Preparation of Example 123: 3,9,15-trioxa-4,11,20,21-tetraazatetracyclo[14.5.2.1$^{2,5}$.0$^{19,22}$]tetracosa-1(21),2(24),4,16,18,22-hexaen-10-one

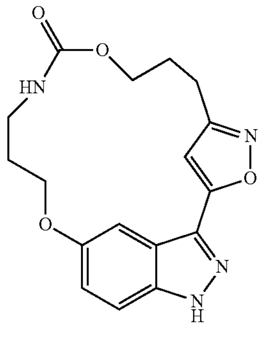 [SMILES: O=C1NCCCOc2ccc3[nH]nc(c3c2)-c2cc(no2)CCCO1]

At 0° C., in a round bottom flask, to a solution of 20-(oxan-2-yl)-3,9,15-trioxa-4,11,20,21-tetraazatetracyclo[14.5.2.1$^{2,5}$.0$^{19,22}$]tetracosa-1(21),2(24),4,16(23),17,19(22)-hexaen-10-one 152 (0.200 g, 0.470 mmol) in DCM (50.0 mL), was added trifluoroacetic acid (1.08 mL, 14.10 mmol). The reaction was stirred at room temperature during 18 h. A saturated solution of $NaHCO_3$ (50 mL) was added and phases were separated. The aqueous phase was extracted with DCM (3×25 mL), dried with $MgSO_4$, filtered and concentrated to afford crude (90 mg) which was purified by preparative reverse-phase chromatography (Column Waters XSELECT C18 19*100 mm, 5 μm $(NH_4)_2CO_3$ aq. 2 g/L MeCN 19 mL/min, RT 25% B to 55% B in 7 min). Solvents were removed to afford 3,9,15-trioxa-4,11,20,21-tetraazatetracyclo[14.5.2.1$^{2,5}$.0$^{19,22}$]tetracosa-1(21),2(24),4,16,18,22-hexaen-10-one example 123 as a white powder.

LCMS method F: $[M+H]^+$=343.3, $t_R$=2.01 min

LCMS method G: $[M+H]^+$=343.2, $t_R$=1.99 min $^1$H NMR (400 MHz, d6-DMSO) δ 13.59 (1H, s), 7.78 (1H, t, J=6.0 Hz), 7.59-7.56 (1H, m), 7.16 (1H, d, J=2.3 Hz), 7.04 (1H, dd, J=2.4, 9.0 Hz), 6.86 (1H, s), 4.39-4.33 (2H, m), 3.85 (2H, t, J=5.6 Hz), 3.08 (2H, dd, J=6.2, 10.0 Hz), 2.93 (2H, t, J=6.5 Hz), 2.02-1.96 (2H, m), 1.86-1.75 (2H, m) ppm.

Example 124: (13R)-16-fluoro-13-methyl-8,14-dioxa-4,10,19,20-tetraazatetracyclo[13.5.2.1$^{2,6}$.0$^{18,21}$]tricosa-1(20),2,4,6(23),15,17,21-heptaen-9-one

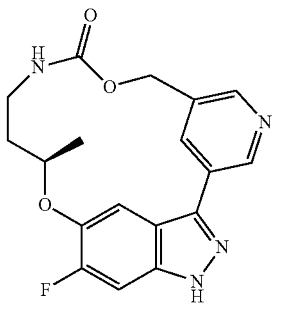 [SMILES: C[C@@H]1CCNC(=O)OCc2cncc(c2)-c2n[nH]c3cc(F)c(cc23)O1]

Example 124 is prepared according to the synthesis route described in general Scheme C.

Preparation of Intermediate 153: benzyl N-[(3R)-3-[(6-fluoro-3-iodo-1H-indazol-5-yl)oxy]butyl]carbamate

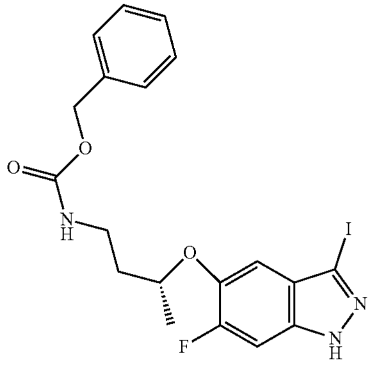 [SMILES: C[C@H](CCNC(=O)OCc1ccccc1)Oc1cc2c(I)n[nH]c2cc1F]

To a solution of benzyl N-[(3R)-3-[(6-fluoro-1H-indazol-5-yl)oxy]butyl]carbamate (1.96 g, 5.49 mmol) in acetone (14 mL) was added portionwise N-Iodosuccinimide (1.35 g, 6.04 mmol) at 0° C. and the reaction mixture was then stirred at room temperature overnight. The reaction mixture was evaporated to dryness and the residue was dissolved in EtOAc (50 mL). The organic phase was washed with a 1 M solution of sodium thiosulfate, with brine, dried over anhydrous sodium sulfate, filtered and evaporated under reduced pressure to give a colorless oil. The residue was purified by flash chromatography (CyH/EtOAc 5/5) to afford benzyl N-[(3R)-3-[(6-fluoro-3-iodo-1H-indazol-5-yl)oxy]butyl] carbamate 153.

LCMS method F: $[M+H]^+$=484, $t_R$=2.82 min

Preparation of Intermediate 154: benzyl N-[(3R)-3-[(6-fluoro-3-iodo-1H-indazol-5-yl)oxy]butyl]carbamate

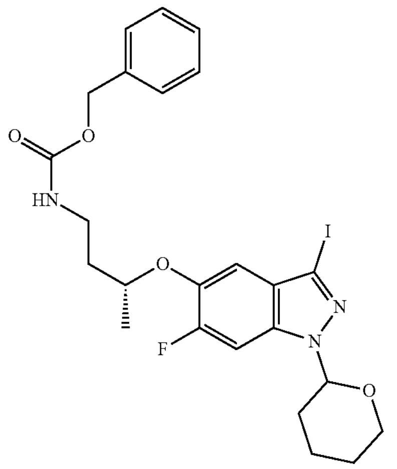 [SMILES: C[C@H](CCNC(=O)OCc1ccccc1)Oc1cc2c(I)nn(C3CCCCO3)c2cc1F]

To a mixture of benzyl benzyl N-[(3R)-3-[(6-fluoro-3-iodo-1H-indazol-5-yl)oxy]butyl]carbamate and benzyl N-[(3R)-3-{[6-fluoro-3-iodo-1-(oxan-2-yl)-1H-indazol-5-yl]oxy}butyl]carbamate (900 mg, 1.59 mmol supposed) in DCM (20 mL) was added trifluoroacetic acid (0.6 mL, 7.95 mmol) and the solution was stirred at room temperature for 4 hours. The residue was diluted with saturated sodium bicarbonate solution (50 mL) and extracted with DCM (3×50 mL). The combined organic layer was washed with brine, dried over $Na_2SO_4$, filtered and evaporated under reduced pressure. The residue was filtered on a silice pad eluting with cyclohexane/EtOAc: 100/0 to 50/50 to afford the expected compound benzyl N-[(3R)-3-[(6-fluoro-3-iodo-1H-indazol-5-yl)oxy]butyl]carbamate 154 as a colorless oil.

LCMS method F: $[M+H]^+$=568, $t_R$=3.25 min

Preparation of Example 124: (13R)-16-fluoro-13-methyl-8,14-dioxa-4,10,19,20-tetraazatetracyclo [13.5.2.1$^{2,6}$.0$^{18,21}$]*tricosa*-1(20),2,4, 6(23),15,17,21-heptaen-9-one

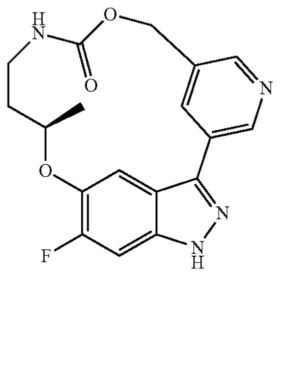 [SMILES: C[C@@H]1CCNC(=O)OCc2cncc(c2)-c2n[nH]c3cc(F)c(cc23)O1]

To a solution of (13R)-16-fluoro-13-methyl-19-(oxan-2-yl)-8,14-dioxa-4,10,19,20-tetraazatetracyclo[13.5.2.1$^{2,6}$.0$^{18,21}$]tricosa-1(20),2,4,6(23),15,17,21-heptaen-9-one (126 mg, 0.29 mmol,) in DCM (3 mL) was added trifluoroacetic acid (438 μL, 5.73 mmol). The mixture was heated under microwave irradiation at 80° C. for 30 min. The reaction mixture was diluted with DCM (25 mL) and $NaHCO_3$ saturated (25 mL). A precipitate was formed between the layers after 2 hours at RT. This precipitate was filtered and washed with diethyl ether twice and dried under vacuum at 60° C. for 12 hours to afford (13R)-16-fluoro-13-methyl-8,14-dioxa-4,10,19,20-tetraazatetracyclo[13.5.2.1$^{2,6}$.0$^{18,21}$] tricosa-1(20),2,4, 6(23),15,17,21-heptaen-9-one example 124 as a white solid.

LCMS method F: $[M+H]^+$=357, $t_R$=1.94 min

LCMS method G: $[M+H]^+$=357, $t_R$=1.93 min $^1$H NMR (400 MHz, d6-DMSO) δ 13.43 (1H, s), 9.04 (1H, d, J=1.1 Hz), 8.57 (1H, s), 8.15 (1H, s), 8.03-8.00 (1H, m), 7.53 (1H, d, J=10.8 Hz), 7.32-7.28 (1H, m), 5.77-5.73 (1H, m), 4.98-4.94 (1H, m), 4.64-4.58 (1H, m), 3.51 (1H, m), 2.93 (1H, dd, J=13.3, 16.9 Hz), 2.41-2.39 (1H, m), 1.44 (4H, m) ppm.

Example 125: (13R)-4-chloro-13-methyl-8,14-dioxa-10,19,20,23-tetraazatetracyclo[13.5.2.1$^{2,6}$.0$^{18,21}$] tricosa-1(20),2(23),3,5,15(22),16,18(21)-heptaen-9-one

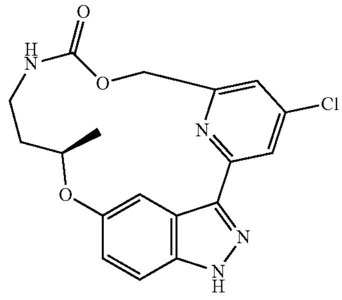 [SMILES: C[C@@H]1CCNC(=O)OCc2cc(Cl)cc(n2)-c2n[nH]c3ccc(cc23)O1]

Example 125 is prepared according to the synthesis route described in general Scheme K.

In a round bottom flask, was added (13R)-4-chloro-13-methyl-19-(oxan-2-yl)-8,14-dioxa-10,19,20,23-tetraazatetracyclo[13.5.2.1$^{2,6}$.0$^{18,21}$]tricosa-1(20),2(23),3,5,15(22),16,18(21)-heptaen-9-one (0.650 g, 1.42 mmol) in DCM (14.5 mL) and trifluoroacetic acid (3.26 mL, 42.60 mmol). The reaction mixture was stirred at 80° C. during 2 h. LC/MS analysis indicated the reaction was completed. The reaction was quenched with a saturated solution of $NaHCO_3$ (15 mL). Phases were separated and the aqueous phase was extracted with DCM (3×10 mL). Organic phase was washed with a saturated solution of NaCl (15 mL), dried with $MgSO_4$, filtered and concentrated under reduce pressure to afford crude (0.600 g) which was purified by chromatography column (Macherey Nagel 12 g, DCM/MeOH: 100/0 to 95/5). Solvents were removed and the powder was triturated with DCM, to afford (13R)-4-chloro-13-methyl-8,14-dioxa-10,19,20,23-tetraazatetracyclo[13.5.2.1$^{2,6}$.0$^{18,21}$]tricosa-1 (20),2(23),3,5,15(22), 16,18(21)-heptaen-9-one example 125 as a white powder.

LCMS method F: $[M+H]^+$=373.2, $t_R$=2.32 min

LCMS method G: $[M+H]^+$=373.2, $t_R$=2.31 min $^1$H NMR (400 MHz, d6-DMSO) δ 13.41 (1H, s), 8.08 (1H, d, J=1.9 Hz), 7.84-7.76 (2H, m), 7.50-7.42 (2H, m), 6.97 (1H, dd, J=2.4, 9.0 Hz), 5.62-5.57 (1H, m), 5.09-5.04 (1H, m), 4.60 (1H, t, J=10.2 Hz), 3.50-3.44 (1H, m), 2.92 (1H, t, J=14.8 Hz), 2.27-2.23 (1H, m), 1.39-1.36 (4H, m) ppm.

Example 126: 8,14-dioxa-2,4,10,19,20-pentaazatetracyclo[13.5.2.1$^{2,5}$.0$^{18,21}$]tricosa-1(20),3,5(23),15(22),16,18(21)-hexaen-9-one

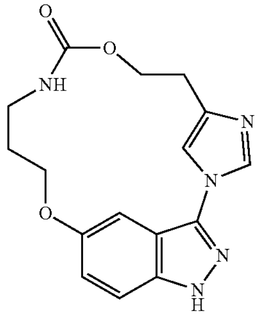 [SMILES: O=C1NCCCOc2ccc3[nH]nc(c3c2)-n2cnc(c2)CCO1]

Example 126 is prepared according to the synthesis route described in general Scheme A.

To a solution of 19-(oxan-2-yl)-8,14-dioxa-2,4,10,19,20-pentaazatetracyclo[13.5.2.1$^{2,5}$.0$^{18,21}$]tricosa-1(20),3,5(23), 15(22),16,18(21)-hexaen-9-one (99 mg, 0.24 mmol) in dioxane (3.8 mL) was added HCl 4 M in dioxane (1.2 mL, 4.82 mmol). The mixture was heated under microwave irradiations at 100° C. for 1 hour and 30 minutes. HCl 4 M in dioxane (0.5 mL, 2 mmol) was added and the reaction was heated under microwave irradiations for 1 hour and 20 minutes. In the reaction mixture a precipitate was formed so it was filtrated and the solid was triturated in acetonitrile. So the solid was dissolved with DCM/MeOH and diluted with $NaHCO_3$ saturated. After separation, aqueous layer was extracted with DCM (3×). The combined organic layer was washed with brine, dried over anhydrous sodium sulfate, filtered and evaporated under reduced pressure to give 8,14-dioxa-2,4,10,19,20-pentaazatetracyclo[13.5.2.1$^{2,5}$.0$^{18,21}$]tricosa-1(20),3,5(23),15(22),16,18(21)-hexaen-9-one example 126 as a white powder.

LCMS method F: $[M+H]^+$=328, $t_R$=1.15 min

LCMS method G: $[M+H]^+$=328, $t_R$=1.62 min $^1$H NMR (400 MHz, d6-DMSO) δ 13.05 (1H, m), 8.02 (1H, d, J=1.3 Hz), 7.69 (1H, t, J=6.1 Hz), 7.50 (1H, m), 7.30 (1H, m), 7.04 (2H, dd, J=2.3, 9.1 Hz), 6.95 (1H, m), 4.38 (2H, m), 4.25 (2H, m), 3.08 (2H, m), 2.95 (2H, t, J=5.3 Hz), 1.85 (1H, m) ppm.

Example 127: (13R)-4-methoxy-13-methyl-8,14-dioxa-10,19,20,23-tetraazatetracyclo[13.5.2.1$^{2,6}$.0$^{18,21}$]tricosa-1(20),2,4,6(23),15,17,21-heptaen-9-one

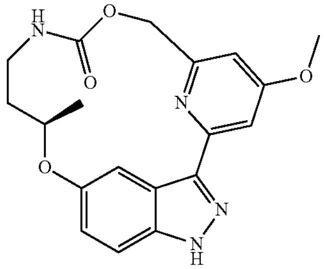 [SMILES: COc1cc2nc(c1)-c1n[nH]c3ccc(cc13)O[C@H](C)CCNC(=O)OC2]

Example 127 is prepared according to the synthesis route described in general Scheme K.

In a microwaves tube was put a solution of (13R)-4-methoxy-13-methyl-19-(oxan-2-yl)-8,14-dioxa-10,19,20,23-tetraazatetracyclo[13.5.2.1$^{2,6}$.0$^{18,21}$]tricosa-1(20),2,4,6(23),15,17,21-heptaen-9-one (60 mg, 0.133 mmol) in DCM (2.5 mL). To this solution was added trifluoroacetic acid (0.813 mL, 10.6 mmol). The reaction mixture was stirred at 80° C. under microwave conditions for 1 h.

The solvent was removed under reduced pressure, the oil was dissolved in EtOAc and washed with a sol. sat. of $NaHCO_3$. The phase were separated and the organic one was dried with $Na_2SO_4$. The solvent was removed under reduced pressure. The crude was purified by chromatography using a 10 g $SiO_2$ column eluted with cyclohexane/Ethyl acetate 70/30 to 50/50. The good fractions were combined and the solvent was removed under reduced pressure. The oil was triturated in DCM and the solid formed was filtered and dried under reduced pressure to give (13R)-4-methoxy-13-methyl-8,14-dioxa-10,19,20,23-tetraazatetracyclo[13.5.2.1$^{2,6}$.0$^{18,21}$]tricosa-1(20),2,4,6(23),15,17,21-heptaen-9-one example 127 as a white fluffy powder.

LCMS method F: $[M+H]^+$=369.3, $t_R$=2.05 min

LCMS method G: $[M+H]^+$=369.3, $t_R$=2.06 min $^1$H NMR (400 MHz, d6-DMSO) δ 13.22-13.20 (1H, m), 7.88 (1H, d, J=1.9 Hz), 7.72 (1H, dd, J=5.4, 6.9 Hz), 7.60 (1H, d, J=2.5 Hz), 7.47-7.44 (1H, m), 6.96-6.88 (2H, m), 5.55 (1H, d, J=14.6 Hz), 5.01-4.96 (1H, m), 4.61 (1H, dd, J=2.9, 3.9 Hz), 3.91 (3H, s), 3.48-3.42 (1H, m), 2.96-2.88 (1H, m), 2.34-2.22 (1H, m), 1.38-1.35 (4H, m) ppm.

Example 128: (13R)-13-methyl-9-oxo-8,14-dioxa-10,19,20-triazatetracyclo[13.5.2.1$^{2,6}$.0$^{18,21}$]tricosa-1(20),2,4,6(23),15,17,21-heptaene-5-carbonitrile

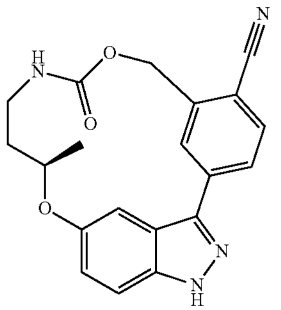 [SMILES: C[C@@H]1CCNC(=O)OCc2cc(ccc2C#N)-c2n[nH]c3ccc(cc23)O1]

Example 128 is prepared according to the synthesis route described in general Scheme B.

Preparation of Intermediate 155: ethyl 5-bromo-2-cyano-benzoate

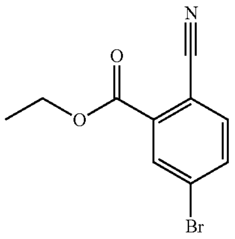

To a solution of 5-bromo-2-cyano-benzoic acid (2.500 g, 11.06 mmol) in ACN (50 mL) were added cesium carbonate (7.207 g, 22.12 mmol) and ethyl iodide (1.33 mL, 16.59 mmol). The mixture was stirred at 90° C. for 30 min. Ethyl iodide (1.33 mL, 16.59 mmol) was added and the reaction was heated at 80° C. After 2 h, ethyl iodide (1.33 mL, 16.59 mmol) was added and the reaction was heated at 80° C. for 3 additional hours. The solvent was evaporated under reduced pressure. The residue was diluted with water and EtOAc and the layers were separated. The aqueous layer was extracted with EtOAc (3x20 mL) and the combined organic layers were dried over anhydrous sodium sulfate, filtered and evaporated under reduced pressure. The residue was purified by silica gel column chromatography (Chromabond Macherey Nagel 80 g) using Cyclohexane/(EtOAc/EtOH 3:1) 100:0 to 80:20 as eluent. The expected fractions were combined and evaporated under reduced pressure to give ethyl 5-bromo-2-cyano-benzoate 155 as a white solid.

LCMS method F: $t_R$=2.53 min, no m/z detected

Preparation of Example 128: (13R)-13-methyl-9-oxo-8,14-dioxa-10,19,20-triazatetra cyclo [13.5.2.1$^{2,6}$.0$^{18,21}$]tricosa-1(20),2,4,6(23),15,17,21-heptaene-5-carbonitrile

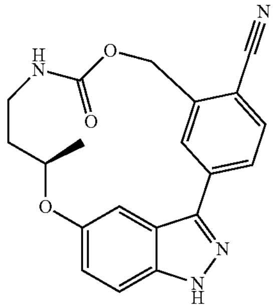 [SMILES: C[C@@H]1CCNC(=O)OCc2cc(ccc2C#N)-c2n[nH]c3ccc(cc23)O1]

To a suspension of (13R)-13-methyl-19-(oxan-2-yl)-9-oxo-8,14-dioxa-10,19,20-triazatetracyclo[13.5.2.1$^{2,6}$.0$^{18,21}$] tricosa-1(20),2,4,6(23),15,17,21-heptaene-5-carbonitrile (102 mg, 0.23 mmol) in DCM (3 mL) was added TFA (0.03 mL, 0.35 mmol). The reaction mixture was stirred at room temperature for 30 min. TFA (0.03 mL, 0.35 mmol) was added and the reaction was stirred for 2 more hours. More TFA (0.03 mL, 0.35 mmol) was added for 3 additional hours. A saturated solution of $NaHCO_3$ was added and the layers were separated. The aqueous layer was extracted with DCM (3x15 mL) and the combined organic layers were dried over anhydrous sodium sulfate, filtered and evaporated under reduced pressure. The residue was purified by preparative HPLC: Column Waters Phenyl-Hexyl C18 19*100 mm, 5 µm/A: $(NH_4)_2CO_3$ aq. 2 g/L/B: ACN/19 mL/min, RT/40% B to 90% B in 7 min. The solvent was evaporated under reduced pressure to give (13R)-13-methyl-9-oxo-8,14-dioxa-10,19,20-triazatetracyclo[13.5.2.1$^{2,6}$.0$^{18,21}$]tricosa-1(20),2,4,6(23),15,17,21-heptaene-5-carbonitrile example 128 as a white solid.

LCMS method F: $[M+H]^+$=363.3, $t_R$=2.28 min

LCMS method G: $[M+H]^+$=363.3, $t_R$=2.26 min $^1$H NMR (400 MHz, d6-DMSO) δ 13.49 (1H, s), 8.19-8.15 (1H, m), 8.11-8.07 (1H, m), 7.97-7.93 (2H, m), 7.58-7.54 (1H, m), 7.29 (1H, s), 7.04-6.99 (1H, m), 5.76-5.71 (1H, m), 5.16-5.10 (1H, m), 4.61-4.57 (1H, m), 3.58-3.55 (1H, m), 2.99-2.90 (1H, m), 2.39-2.33 (1H, m), 1.44-1.40 (4H, m) ppm.

Example 129: (13R)-13-methyl-4-(pyrrolidin-1-yl)-8,14-dioxa-5,10,19,20,23-pentaaza tetracyclo [13.5.2.1$^{2,6}$.0$^{18,21}$]tricosa-1(20),2,4,6(23),15,17,21-heptaen-9-one

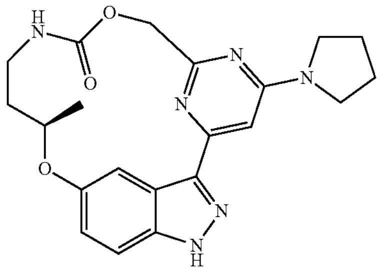 [SMILES: C[C@@H]1CCNC(=O)OCc2nc(cc(N3CCCC3)n2)-c2n[nH]c3ccc(cc23)O1]

Example 129 is prepared according to the synthesis route described below.

Preparation of Intermediate 156: 4-chloro-2-(chloromethyl)-6-pyrrolidin-1-yl-pyrimidine

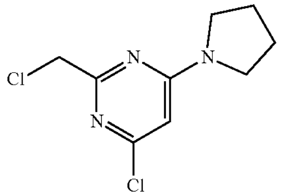 [SMILES: ClCc1nc(Cl)cc(N2CCCC2)n1]

To a solution of 4,6-dichloro-2-(chloromethyl)pyrimidine (0.050 g, 0.253 mmol) in N,N-dimethylformamide (3.0 mL) at 0° C. was added triethylamine (0.048 mL, 0.304 mmol), and the reaction was stirred during 20 minutes. Then, pyrrolidine (0.021 mL, 0.253 mmol) was added and the mixture was stirred during 2 h. Solvent was evaporated. Water (10 mL) and EtOAc (10 mL) were added. The aqueous phase was extracted with EtOAc (3x10 mL), then organic phase was washed with a saturated solution of NaCl (10 mL), dried with $MgSO_4$, filtered and concentrated. The crude (60 mg) was purified by chromatography column (Macherey Nagel 4 g, CyH/EtOAc: 100/0 to 80/20). Solvents were removed to afford 4-chloro-2-(chloromethyl)-6-pyrrolidin-1-yl-pyrimidine 156 as a white powder.

LCMS method F: $[M+H]^{-}$=232.2, $t_R$=2.53 min

Preparation of Intermediate 157: (4-chloro-6-pyrrolidin-1-yl-pyrimidin-2-yl)methyl acetate

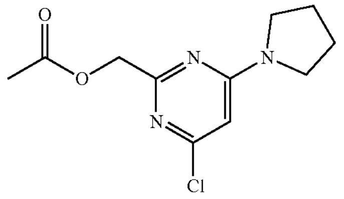 [SMILES: CC(=O)OCc1nc(Cl)cc(N2CCCC2)n1]

To a solution of 4-chloro-2-(chloromethyl)-6-pyrrolidin-1-yl-pyrimidine 156 (0.041 g, 0.177 mmol) in N,N-dimethylformamide (3.0 mL) at 0° C. was added sodium iodide (0.030 g, 0.195 mmol), and potassium acetate (0.035 g, 0.354 mmol) was added and the mixture was stirred during 3 days at room temperature. Solvent was evaporated. Water (10 mL) and EtOAc (10 mL) were added. The aqueous phase was extracted with EtOAc (3×10 mL), then organic phase was washed with a saturated solution of NaCl (10 mL), dried with $MgSO_4$, filtered and concentrated to afford (4-chloro-6-pyrrolidin-1-yl-pyrimidin-2-yl)methyl acetate 157 as a white powder which was used in the next step without further purification.

LCMS method F: $[M+H]^{+}$=256.1, $t_R$=2.28 min

Preparation of Intermediate 158: benzyl N-[(3R)-3-[3-[2-(hydroxymethyl)-6-pyrrolidin-1-yl-pyrimidin-4-yl]-1-tetrahydropyran-2-yl-indazol-5-yl]oxybutyl] carbamate

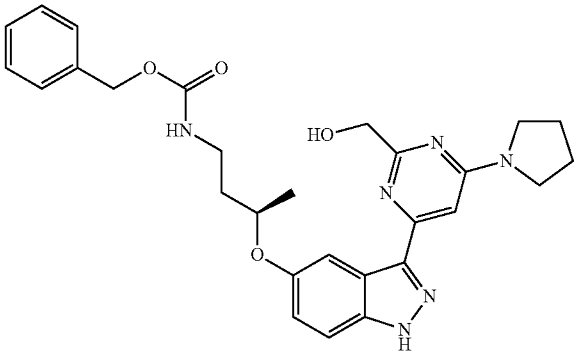 [SMILES: C[C@H](CCNC(=O)OCc1ccccc1)Oc1ccc2[nH]nc(-c3cc(N4CCCC4)nc(CO)n3)c2c1]

To a suspension of [4-[5-[(1R)-3-(benzyloxycarbonylamino)-1-methyl-propoxy]-1-tetrahydropyran-2-yl-indazol-3-yl]-6-pyrrolidin-1-yl-pyrimidin-2-yl]methyl acetate 157 (0.650 g, 1.011 mmol) in MeOH (20.0 mL) was added potassium carbonate (0.168 g, 1.214 mmol).

The reaction was stirred at room temperature during 2 h. The reaction was stopped and filtered and evaporated. The crude (1.0 g) was purified by chromatography column (RediSep, 12 g, DCM/MeOH: 100/0 to 95/5). Solvents was evaporated to afford benzyl N-[(3R)-3-[3-[2-(hydroxymethyl)-6-pyrrolidin-1-yl-pyrimidin-4-yl]-1-tetrahydropyran-2-yl-indazol-5-yl]oxybutyl]carbamate 158 as a yellow solid, which was used in the next step without further purification.

LCMS method F: $[M+H]^{+}$=601.4, $t_R$=2.33 min

Preparation of Example 129: (13R)-13-methyl-4-(pyrrolidin-1-yl)-8,14-dioxa-5,10,19,20,23-pentaazatetracyclo[13.5.2.1$^{2,6}$.0$^{18,21}$]tricosa-1(20),2,4,6(23),15,17,21-heptaen-9-one

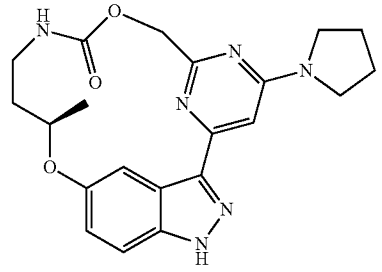 [SMILES: C[C@@H]1CCNC(=O)OCc2nc(cc(N3CCCC3)n2)-c2n[nH]c3ccc(cc23)O1]

In a round bottom flask, was added (13R)-13-methyl-19-(oxan-2-yl)-4-(pyrrolidin-1-yl)-8,14-dioxa-5,10,19,20,23-pentaazatetracyclo[13.5.2.1$^{2,6}$.0$^{18,21}$]tricosa-1(20),2,4,6(23),15,17,21-heptaen-9-one (0.210 g, 0.426 mmol) in DCM (25.0 mL) and trifluoroacetic acid (1.00 mL, 12.79 mmol). The reaction mixture was stirred at 50° C. during 6 h. A saturated solution of $NaHCO_3$ (30 mL) was added and phases were separated. The aqueous phase was washed with DCM (3×25 mL), and organic phase was washed with a saturated solution of NaCl (30 mL), dried with $MgSO_4$, filtered and concentrated under reduce pressure to crude which was triturated with MeOH then dried (speedvac), to afford (13R)-13-methyl-4-(pyrrolidin-1-yl)-8,14-dioxa-5,10,19,20,23-pentaazatetracyclo[13.5.2.1$^{2,6}$.0$^{18,21}$]tricosa-1(20),2,4,6(23),15,17,21-heptaen-9-one example 129 as a white powder.

LCMS method F: $[M+H]^{+}$=409.4, $t_R$=2.03 min

LCMS method G: $[M+H]^{+}$=409.4, $t_R$=2.20 min $^1$H NMR (400 MHz, d6-DMSO) δ 13.35 (1H, s), 7.93 (1H, d, J=2.1 Hz), 7.78 (1H, dd, J=4.4, 7.6 Hz), 7.48-7.45 (1H, m), 7.05 (1H, s), 6.95 (1H, dd, J=2.5, 8.9 Hz), 5.43-5.31 (1H, m), 4.80-4.53 (2H, m), 3.60-3.52 (6H, m), 2.96-2.80 (1H, m), 2.34 (1H, dd, J=1.9, 3.6 Hz), 1.99 (4H, s), 1.37 (3H, d, J=6.1 Hz) ppm.

Example 130: (7R,13R)- or (7S,13R)-7,13-dimethyl-8,14-dioxa-5,10,19,20,23-penta azatetracyclo [13.5.2.1$^{2,6}$.0$^{18,21}$]tricosa-1(20),2,4,6(23),15,17,21-heptaen-9-one

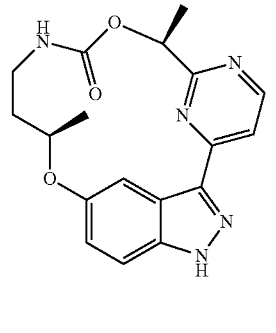 [SMILES: C[C@@H]1CCNC(=O)O[C@@H](C)c2nccc(n2)-c2n[nH]c3ccc(cc23)O1]

Example 130 is prepared according to the synthesis route described below.

Preparation of Intermediate 159: 4-chloro-2-iodopyrimidine

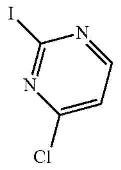

To a mixture of 4-chloropyrimidin-2-amine (50 g, 386.0 mmol), isopentyl nitrite (155.9 mL, 1157.9 mmol) and diiodomethane (139.9 mL, 1736.8 mmol) in 501 mL of THF, was added copper(I) iodide (73.5 g, 386.0 mmol) at room temperature. The mixture was stirred at 85° C. for 6 hours. The mixture was filtered over a pad of celite and concentrated under vacuo. The mixture was diluted with EtOAc and washed with a 10% solution of sodium bisulfite (×2). The organic layers were dried over $MgSO_4$, filtered and concentrated under reduced pressure. The product was purified by flash chromatography on silica gel, using as eluents heptane/ethyl acetate (100:0 to 80:20) to afford 4-chloro-2-iodopyrimidine 159 as a white solid.

LCMS method B: $[M+H]^+$=240.9, $t_R$=0.485 min

Preparation of Intermediate 160: 1-(4-chloropyrimidin-2-yl)ethan-1-ol

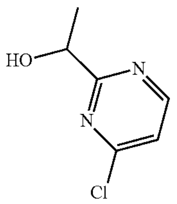

4-chloro-2-iodopyrimidine 159 (6.000 g, 24.955 mmol) was dissolved in 125 mL of dry THF under nitrogen atmosphere. The reaction was cooled at −78° C. and methylmagnesium chloride (3 M in THF) (16.630 mL, 49.910 mmol) was added dropwise and the mixture was stirred at −78° C. for 1 hour. Acetaldehyde (4.185 mL, 74.865 mmol) was added to the mixture and the reaction was warmed at 0° C. over 2.5 hours. The reaction was diluted with EtOAc and a sat. solution of $NH_4Cl$ was added. The organic layer was separated, dried over $MgSO_4$, filtered and concentrated under reduced pressure. The crude was purified by flash chromatography on silica gel, using as eluents heptane/ethyl acetate (100:0 to 65:35) to afford 1-(4-chloropyrimidin-2-yl)ethan-1-ol 160 as a yellow oil.

LCMS method E: $[M+H]^+$=159.0, $t_R$=1.297 min

Preparation of Example 130: (7R,13R)- or (7S,13R)-7,13-dimethyl-8,14-dioxa-5,10,19,20,23-pentaazatetracyclo[13.5.2.1$^{2,6}$.0$^{18,21}$]tricosa-1(20),2,4,6(23),15,17,21-heptaen-9-one

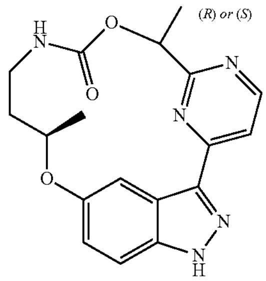 [SMILES: CC1OC(=O)NCC[C@@H](C)Oc2ccc3[nH]nc(c3c2)-c2ccnc1n2]

Example 130 is prepared via chiral HPLC separation of the two diastereoisomers. The chiral separation was done on a Column Waters XSELECT C18 19*100 mm, 5 μm, 35% to 40% MeCN in $(NH_4)_2CO_3$ aq. 2 g/L, 19 mL/min, RT.

To a solution of (13R)-7,13-dimethyl-19-(oxan-2-yl)-8,14-dioxa-5,10,19,20,23-pentaazatetra cyclo[13.5.2.1$^{2,6}$.0$^{18,21}$]tricosa-1(20),2,4,6(23),15,17,21-heptaen-9-one (710 mg, 1.62 mmol) in MeOH (27.8 mL) and water (4.6 mL) was added p-toluenesulfonic acid monohydrate (1.54 g, 8.12 mmol) and the reaction mixture was stirred at 80° C. for 24 h. Then, to the reaction mixture was added p-toluenesulfonic acid monohydrate (308 mg, 1.62 mmol) and stirred for 2 h at 80° C. The reaction mixture was evaporated under vacuo and the residue was dissolved in EtOAc (50 mL) then a saturated aqueous solution of sodium hydrogen carbonate (50 mL) was added. After separation, the aqueous layer was extracted with ethyl acetate (2×). The combined organic layer was washed with brine, dried over sodium sulfate, filtered and evaporated under reduced pressure to give the (7R,13R)- or (7S,13R)-7,13-dimethyl-8,14-dioxa-5,10,19,20,23-pentaazatetracyclo[13.5.2.1$^{2,6}$.0$^{18,21}$]tricosa-1(20),2,4,6(23),15,17,21-heptaen-9-one example 130 as a white solid.

LCMS method F: $[M+H]^+$=354, $t_R$=1.92 min

LCMS method G: $[M+H]^+$=354, $t_R$=1.92 min $^1$H NMR (400 MHz, d6-DMSO) δ 13.63 (1H, m), 8.78 (1H, d, J=5.3 Hz), 8.03 (1H, dd, J=0.7, 5.2 Hz), 7.89-7.86 (2H, m), 7.55-7.52 (1H, m), 7.00 (1H, dd, J=2.5, 8.9 Hz), 5.77 (1H, q, J=6.8 Hz), 4.63-4.57 (1H, m), 3.58-3.50 (1H, m), 2.89-2.80 (1H, m), 2.38-2.29 (1H, m), 1.67 (3H, d, J=7.0 Hz), 1.40-1.37 (4H, m) ppm.

Example 131: (7R,13R)- or (7S,13R)-7,13-dimethyl-8,14-dioxa-5,10,19,20,23-penta azatetracyclo $[13.5.2.1^{2,6}.0^{18,21}]$tricosa-1(20),2,4,6(23),15,17,21-heptaen-9-one

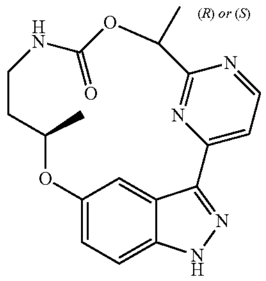 [SMILES: CC1OC(=O)NCC[C@@H](C)Oc2ccc3[nH]nc(c3c2)-c2ccnc1n2]

Example 131 is prepared according to the synthesis route described in general Scheme K and chiral HPLC separation of the two diastereoisomers. The chiral separation was done on a Column Waters XSELECT C18 19*100 mm, 5 μm, 35% to 40% MeCN in $(NH_4)_2CO_3$ aq. 2 g/L, 19 m/min, RT.

The fractions for the second batch was evaporated in vacuo to afford (7R,13R)- or (7S,13R)-7,13-dimethyl-8,14-dioxa-5,10,19,20,23-pentaazatetracyclo$[13.5.2.1^{2,6}.0^{18,21}]$tricosa-1(20),2,4,6(23),15,17,21-heptaen-9-one with a 90% of purity (contained 5% of the other diastereoisomer). So the powder was put in acetonitrile for a recrystallization, the solid obtained was filtered to afford the pure (7R,13R)- or (7S,13R)-7,13-dimethyl-8,14-dioxa-5,10,19,20,23-pentaazatetracyclo$[13.5.2.1^{2,6}.0^{18,21}]$tricosa-1(20),2,4,6(23),15,17,21-heptaen-9-one example 131 as a white powder.

LCMS method F: $[M+H]^+$=354, $t_R$=2.03 min

LCMS method G: $[M+H]^+$=354, $t_R$=2.02 min $^1$H NMR (400 MHz, d6-DMSO) δ 13.62 (1H, s), 8.81-8.78 (1H, m), 8.02-7.98 (2H, m), 7.60-7.49 (2H, m), 7.04-6.97 (1H, m), 6.10 (1H, q, J=6.7 Hz), 4.93-4.85 (1H, m), 3.25 (1H, m), 3.05-2.97 (1H, m), 1.85-1.77 (1H, m), 1.71-1.51 (4H, m), 1.41-1.38 (3H, m) ppm.

Example 132: (13R)-16-fluoro-13-methyl-8,14-dioxa-10,19,20-triazatetracyclo$[13.5.2.1^{2,6}.0^{18,21}]$tricosa-1(20),2,4,6(23),15,17,21-heptaen-9-one

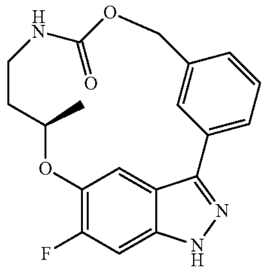 [SMILES: C[C@@H]1CCNC(=O)OCc2cccc(c2)-c2n[nH]c3cc(F)c(cc23)O1]

Example 132 is prepared according to the synthesis route described in general Scheme C.

To a solution of (13R)-16-fluoro-13-methyl-19-(oxan-2-yl)-8,14-dioxa-10,19,20-triazatetracyclo$[13.5.2.1^{2,6}.0^{18,21}]$tricosa-1(20),2,4,6(23),15,17,21-heptaen-9-one (284 mg, 0.65 mmol) in MeOH (11 mL) and water (2 mL) was added p-toluenesulfonic acid monohydrate (615 mg, 3.23 mmol) and the reaction mixture was stirred at 80° C. for 12 h. The reaction mixture was evaporated under vacuo and the residue was dissolved in EtOAc (50 mL) then a saturated aqueous solution of sodium hydrogen carbonate (50 mL) was added. After separation, the aqueous layer was extracted with ethyl acetate (2×). The combined organic layer was washed brine, dried over sodium sulfate, filtered and evaporated under reduced pressure to give an oil. The residue was put in acetonitrile, a solid appeared and was filtered to afford (13R)-16-fluoro-13-methyl-8,14-dioxa-10,19,20-triazatetracyclo$[13.5.2.1^{2,6}.0^{18,21}]$tricosa-1(20),2,4,6(23), 15,17,21-heptaen-9-one example 132 as a white solid.

LCMS method F: $[M+H]^+$=356, $t_R$=2.30 min

LCMS method G: $[M+H]^+$=356, $t_R$=2.38 min $^1$H NMR (400 MHz, d6-DMSO) δ 13.23-13.20 (1H, m), 7.93 (1H, dd, J=4.9, 7.0 Hz), 7.86-7.80 (2H, m), 7.50-7.45 (2H, m), 7.39-7.36 (1H, m), 7.31-7.28 (1H, m), 5.75 (1H, d, J=12.9 Hz), 4.82 (1H, d, J=12.0 Hz), 4.66-4.59 (1H, m), 3.59-3.54 (1H, m), 2.95-2.87 (1H, m), 2.40-2.33 (1H, m), 1.45-1.42 (4H, m) ppm.

Example 133: (13R)-13-methyl-8,14-dioxa-4,10,19,20,23-pentaazatetracyclo$[13.5.2.1^{2,6}.0^{18,21}]$tricosa-1(20),2,4,6(23),15,17,21-heptaen-9-one

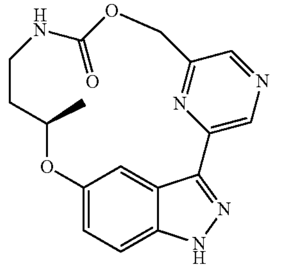 [SMILES: C[C@@H]1CCNC(=O)OCc2cncc(n2)-c2n[nH]c3ccc(cc23)O1]

Example 133 is prepared according to the synthesis route described in general Scheme K.

To a solution of (13R)-13-methyl-19-(oxan-2-yl)-8,14-dioxa-4,10,19,20,23-pentaazatetra cyclo$[13.5.2.1^{2,6}.0^{18,21}]$tricosa-1(20),2,4,6(23),15,17,21-heptaen-9-one (413 mg, 0.98 mmol) in MeOH (16.8 mL) and water (2.8 mL) was added p-toluenesulfonic acid monohydrate (931 mg, 4.88 mmol) and the reaction mixture was stirred at 65° C. overnight. The reaction mixture was diluted with DCM and with a saturated aqueous solution of sodium hydrogen carbonate. After separation, the aqueous layer was extracted with DCM (3×). The combined organic layer was washed brine, dried over sodium sulfate, filtered and evaporated under reduced pressure to give an yellow oil. This oil was triturated in ACN and a cream precipitate was observed. The mixture was filtered and washed with ACN (2×) the cream solid was dried for 1 night to give (13R)-13-methyl-8,14-dioxa-4,10,19,20,23-pentaazatetracyclo$[13.5.2.1^{2,6}.0^{18,21}]$tricosa-1(20),2,4,6(23),15,17,21-heptaen-9-one example 133 as a cream solid.

LCMS method F: $[M+H]^+$=340, $t_R$=1.92 min

LCMS method G: $[M+H]^+$=340, $t_R$=1.98 min $^1$H NMR (400 MHz, d6-DMSO) δ 13.51 (1H, m), 9.27 (1H, s), 8.52 (1H, s), 7.83 (2H, m), 7.52 (1H, d, J=8.9 Hz), 6.99 (1H, dd, J=2.3, 8.9 Hz), 5.69 (1H, d, J=15.0 Hz), 5.16 (1H, d, J=14.8 Hz), 4.60 (1H, m), 3.49 (1H, m), 2.91 (1H, t, J=11.4 Hz), 2.32 (1H, t, J=11.8 Hz), 1.43 (1H, m), 1.38 (3H, d, J=5.9 Hz) ppm.

Example 134: 8,14-dioxa-4-thia-10,19,20,23-tetraazatetracyclo[13.5.2.$1^{2,5}$.$0^{18,21}$]tricosa-1(20),2,5(23),15,17,21-hexaen-9-one

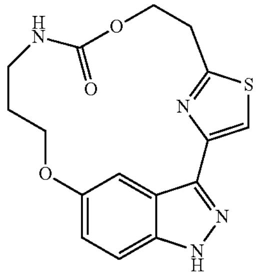 [SMILES: O=C1NCCCOc2ccc3[nH]nc(c3c2)-c2csc(n2)CCO1]

Example 134 is prepared according to the synthesis route described in general Scheme L.

Preparation of Intermediate 161: 2-(4-bromothiazol-2-yl)ethyl N-(3-hydroxypropyl)carbamate

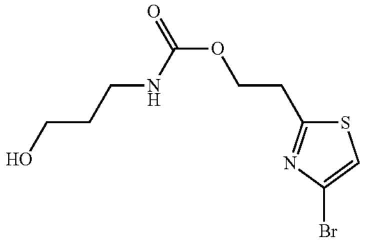 [SMILES: O=C(NCCCO)OCCc1nc(Br)cs1]

To a solution of 4-nitrophenyl chloroformate (0.426 g, 2.11 mmol) and pyridine (0.311 mL, 3.84 mmol) in DCM (10 mL) was added dropwise at RT 2-(4-bromothiazol-2-yl)ethanol (0.400 g, 1.92 mmol) in DCM (5 mL). After 1 h at RT, a mixture of 3-aminopropan-1-ol (0.159 g, 2.11 mmol) and DIPEA (0.668 mL, 3.84 mmol) in DCM (5 mL) was added. The resulting reaction mixture was stirred at RT overnight. The residue was diluted with 0.5 N NaOH solution and extracted with DCM twice. The combined organic layer was washed once again with 0.5 N NaOH solution and dried over anhydrous sodium sulfate and concentrated in vacuo. The residue was purified by flash-column (25 g silica Macherey Nagel) chromatography (DCM-ethyl acetate 1:0 to 3:7) affording 2-(4-bromothiazol-2-yl)ethyl N-(3-hydroxypropyl)carbamate 161 as a colorless oil.

LCMS method F: $[M+H]^+$=309, $t_R$=1.65 min

Preparation of Intermediate 162: 2-[4-[5-[tert-butyl(dimethyl)silyl]oxy-1-tetrahydropyran-2-yl-indazol-3-yl]thiazol-2-yl]ethyl N-(3-hydroxypropyl)carbamate

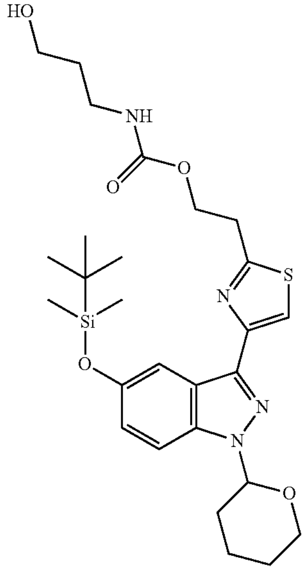 [SMILES: CC(C)(C)[Si](C)(C)Oc1ccc2c(c1)c(-c1csc(CCOC(=O)NCCCO)n1)nn2C1CCCCO1]

To a solution of tert-butyl-dimethyl-[1-tetrahydropyran-2-yl-3-(4,4,5,5-tetramethyl-1,3,2-dioxaborolan-2-yl)indazol-5-yl]oxy-silane (0.700 g, 1.53 mmol) in dioxane (15 mL) and water (1.5 mL) were added at RT 2-(4-bromothiazol-2-yl)ethyl N-(3-hydroxypropyl)carbamate 161 (0.472 g, 1.53 mmol), $K_3PO_4$ (0.972 g, 4.58 mmol), XPhos (0.073 g, 0.15 mmol) and $Pd(PPh_3)_4$ (0.088 g, 0.08 mmol). The resulting reaction mixture was stirred under microwave irradiation at 90° C. for 1 h. The residue was diluted with saturated sodium chloride solution and extracted with ethyl acetate twice. The combined organic layer was dried over anhydrous sodium sulfate and concentrated in vacuo. The residue was purified by flash-column (25 g silica Macherey Nagel) chromatography (cyclohexane-ethyl acetate, 1:0 to 0:1) affording 2-[4-[5-[tert-butyl(dimethyl)silyl]oxy-1-tetrahydropyran-2-yl-indazol-3-yl]thiazol-2-yl]ethyl N-(3-hydroxy propyl)carbamate 162 as a colorless oil.

LCMS method F: $[M+H]^+$=561.3, $t_R$=3.29 min

Preparation of Intermediate 163: 3-[2-[4-[5-[tert-butyl(dimethyl)silyl]oxy-1-tetrahydropyran-2-yl-indazol-3-yl]thiazol-2-yl]ethoxycarbonylamino]propyl methanesulfonate

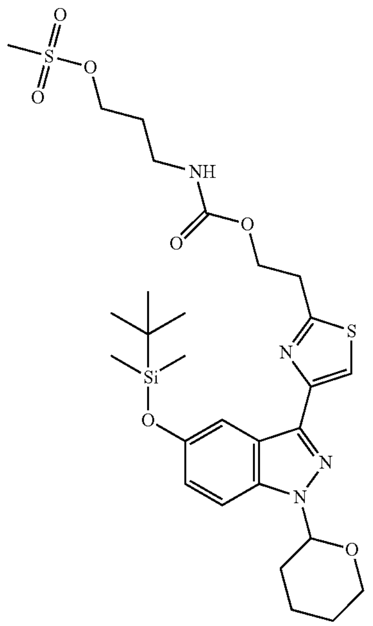 [SMILES: CC(C)(C)[Si](C)(C)Oc1ccc2c(c1)c(-c1csc(CCOC(=O)NCCCOS(C)(=O)=O)n1)nn2C1CCCCO1]

To a solution of 2-[4-[5-[tert-butyl(dimethyl)silyl]oxy-1-tetrahydropyran-2-yl-indazol-3-yl]thiazol-2-yl]ethyl N-(3-hydroxypropyl)carbamate 162 (0.540 g, 0.96 mmol) and triethylamine (0.268 mL, 1.93 mmol) in DCM (18 mL) was added at 0° C. methanesulfonyl chloride (0.097 mL, 1.25 mmol) in DCM (2 mL). The reaction mixture was stirred at RT for 2 h. The residue was diluted with saturated sodium chloride solution and extracted with DCM twice. The combined organic layer was dried over anhydrous sodium sulfate and concentrated in vacuo affording 3-[2-[4-[5-[tert-butyl (dimethyl)silyl]oxy-1-tetrahydropyran-2-yl-indazol-3-yl] thiazol-2-yl]ethoxycarbonylamino]propyl methanesulfonate 163 as a yellow oil, which was used in the next step without further purification.

LCMS method F: $[M+H]^+$=639.3, $t_R$=3.41 min

Preparation of Intermediate 164: 3-[2-[4-(5-hydroxy-1-tetrahydropyran-2-yl-indazol-3-yl)thiazol-2-yl]ethoxycarbonylamino]propyl methanesulfonate

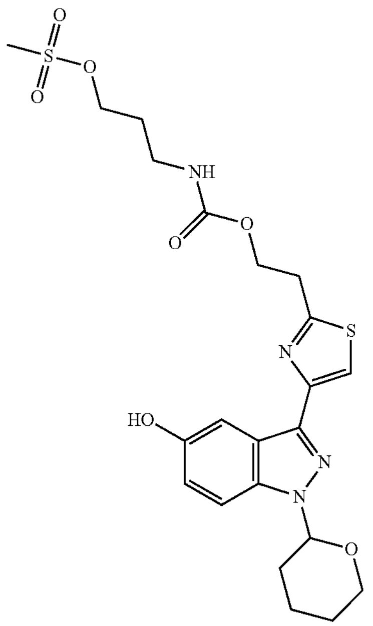 [SMILES: CS(=O)(=O)OCCCNC(=O)OCCc1nc(-c2nn(C3CCCCO3)c3ccc(O)cc23)cs1]

To a solution of 3-[2-[4-[5-[tert-butyl(dimethyl)silyl]oxy-1-tetrahydropyran-2-yl-indazol-3-yl]thiazol-2-yl]ethoxycarbonylamino]propyl methanesulfonate 163 (0.615 g, 0.96 mmol) in THE (10 mL) was added at −10° C. tetrabutylammonium fluoride 1 M in THE (1.06 mL, 1.06 mmol). The resulting reaction mixture was stirred at −10° C. for 5 min. The reaction mixture was diluted with saturated ammonium chloride solution and extracted with ethyl acetate twice. The combined organic layer was dried over anhydrous sodium sulfate and concentrated in vacuo affording 3-[2-[4-(5-hydroxy-1-tetrahydropyran-2-yl-indazol-3-yl)thiazol-2-yl] ethoxy carbonylamino]propyl methanesulfonate 164 as a yellow oil, which was used in the next step without further purification.

LCMS method F: $[M+H]^+$=525.1, $t_R$=2.34 min

Preparation of Intermediate 165: 19-(oxan-2-yl)-8,14-dioxa-4-thia-10,19,20,23-tetraazatetracyclo[13.5.2.1$^{2}$,5s 0$^{18,21}$]tricosa-1(20),2,5(23),15(22),16,18(21)-hexaen-9-one

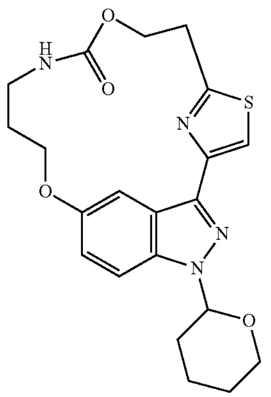 [SMILES: O=C1NCCCOc2ccc3c(c2)c(nn3C2CCCCO2)-c2csc(n2)CCO1]

To a suspension of cesium carbonate (0.941 g, 2.89 mmol) in anhydrous N,N-dimethylformamide (192 mL) at 80° C. was added dropwise (during 2 h) 3-[2-[4-(5-hydroxy-1-tetrahydropyran-2-yl-indazol-3-yl)thiazol-2-yl]ethoxycarbonylamino]propyl methanesulfonate 164 (0.505 g, 0.96 mmol) in N,N-dimethylformamide (192 mL). After addition the resulting reaction mixture was stirred at 80° C. for 2 h. The reaction mixture was filtered and concentrated in vacuo, diluted with saturated sodium chloride solution and extracted with ethyl acetate twice. The combined organic layer was dried over anhydrous sodium sulfate and concentrated in vacuo. The residue was purified by flash-column (25 g silica Macherey Nagel) chromatography (DCM-ethyl acetate, 1:0 to 7:3) affording 19-(oxan-2-yl)-8,14-dioxa-4-thia-10,19,20,23-tetraazatetracyclo[13.5.2.1$^{2,5}$.0$^{18,21}$]tricosa-1(20),2,5(23),15(22),16,18(21)-hexaen-9-one 165 as a white solid.

LCMS method F: $[M+H]^+$=429.4, $t_R$=2.45 min

Preparation of Example 134: 8,14-dioxa-4-thia-10,19,20,23-tetraazatetracyclo[13.5.2.1$^{2,5}$.0$^{18,21}$]tricosa-1(20),2,5(23),15,17,21-hexaen-9-one

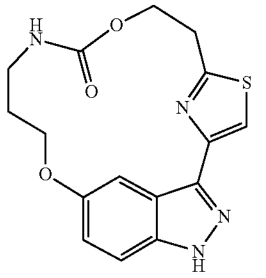 [SMILES: O=C1NCCCOc2ccc3[nH]nc(c3c2)-c2csc(n2)CCO1]

To a suspension of 19-(oxan-2-yl)-8,14-dioxa-4-thia-10,19,20,23-tetraazatetracyclo[13.5.2.1$^{2,5}$.0$^{18,21}$]tricosa-1(20),2,5(23),15(22),16,18(21)-hexaen-9-one 165 (0.150 g, 0.35 mmol) in MeOH (17.5 mL) and water (2.5 mL) was added p-toluenesulfonic acid monohydrate (0.333 g, 1.75 mmol) and the reaction mixture was stirred at 80° C. for 4 h. The reaction mixture was concentrated under vacuo and the residue was neutralized by addition of saturated aqueous solution of sodium hydrogen carbonate. The residue was diluted with EtOAc. The phases were separated and the aqueous phase was extracted with ethyl acetate. The combined organic layer was washed with sodium hydrogen carbonate, brine, dried over sodium sulfate, filtered and evaporated under reduced pressure. The solid was recrystallized in acetonitrile to give 8,14-dioxa-4-thia-10,19,20,23-tetraazatetracyclo[13.5.2.1$^{2,5}$.0$^{18,21}$]tricosa-1(20),2,5(23),15,17,21-hexaen-9-one example 134 as a white solid.

LCMS method F: $[M+H]^+$=345.2, $t_R$=1.79 min

LCMS method G: $[M+H]^+$=345.2, $t_R$=1.78 min, $[M-]H^-$=343.1, $t_R$=1.78 min $^1$H NMR (400 MHz, d6-DMSO) δ 13.05-13.03 (1H, m), 7.83 (1H, s), 7.59-7.51 (2H, m), 7.46-7.43 (1H, m), 6.95 (1H, dd, J=2.4, 9.0 Hz), 4.42 (2H, t, J=5.2 Hz), 4.27-4.22 (2H, m), 3.48 (2H, dd, J=4.6, 5.8 Hz), 3.10-3.05 (2H, m), 1.82 (2H, d, J=8.2 Hz) ppm.

Example 135: 8,14-dioxa-3-thia-10,19,20,23-tetraazatetracyclo[13.5.2.1$^{2,5}$.0$^{18,21}$]tricosa-1(20),2(23),4,15,17,21-hexaen-9-one

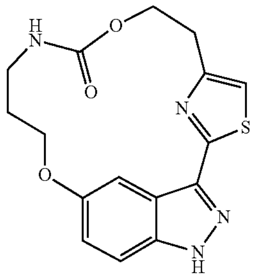 [SMILES: O=C1NCCCOc2ccc3[nH]nc(c3c2)-c2nc(cs2)CCO1]

Example 135 is prepared according to the synthesis route described in general Scheme L.

Preparation of Intermediate 166: 2-(2-bromothiazol-4-yl)ethyl N-(3-hydroxypropyl)carbamate

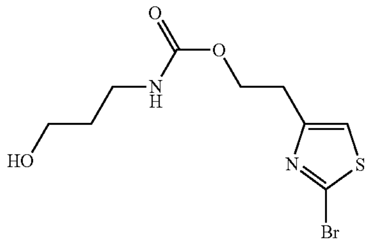 [SMILES: O=C(NCCCO)OCCc1csc(Br)n1]

To a solution of 4-nitrophenyl chloroformate (0.533 g, 2.64 mmol) and pyridine (0.388 mL, 4.81 mmol) in DCM (10 mL) was added dropwise at RT 2-(2-bromothiazol-4-yl)ethanol (0.500 g, 2.40 mmol) in DCM (5 mL). After 1 h at RT, a mixture of 3-aminopropan-1-ol (0.198 g, 2.64 mmol) and DIPEA (0.835 mL, 4.81 mmol) in DCM (5 mL) was added. The resulting reaction mixture was stirred at RT overnight. The residue was diluted with 0.5 N NaOH solution and extracted with DCM twice. The combined organic layer was washed once again with 0.5 N NaOH solution and dried over anhydrous sodium sulfate and concentrated in vacuo. The residue was purified by flash-column (25 g silica Macherey Nagel) chromatography (DCM-ethyl acetate 1:0 to 2:8) affording 2-(2-bromothiazol-4-yl)ethyl N-(3-hydroxypropyl)carbamate 166 as a colorless oil.

LCMS method F: $[M+H]^+$=309, $t_R$=1.60 min

Preparation of Example 135: 8,14-dioxa-3-thia-10,19,20,23-tetraazatetracyclo[13.5.2.$1^{2,5}$.$0^{18,21}$]tricosa-1(20),2(23),4,15,17,21-hexaen-9-one

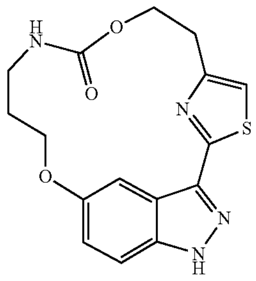 [SMILES: O=C1NCCCOc2ccc3[nH]nc(c3c2)-c2nc(cs2)CCO1]

To a solution of 19-(oxan-2-yl)-8,14-dioxa-3-thia-10,19,20,23-tetraazatetracyclo[13.5.2.$1^{2,5}$.$0^{18,21}$]tricosa-1(20),2(23),4,15,17,21-hexaen-9-one (0.360 g, 0.84 mmol) in MeOH (150 mL) and water (5 mL) was added p-toluenesulfonic acid monohydrate (0.799 g, 4.20 mmol) and the reaction mixture was stirred at 80° C. for 4 days. The reaction mixture was concentrated under vacuo and the residue was neutralized by addition of saturated aqueous solution of sodium hydrogen carbonate. The residue was diluted with EtOAc. The phases were separated and the aqueous phase was extracted with ethyl acetate. The combined organic layer was washed with sodium hydrogen carbonate, brine, dried over sodium sulfate, filtered and evaporated under reduced pressure. The solid was triturated in acetonitrile to give 8,14-dioxa-3-thia-10,19,20,23-tetraazatetracyclo[13.5.2.$1^{2,5}$.$0^{18,21}$]tricosa-1(20),2(23),4,15,17,21-hexaen-9-one example 135 as a white solid.

LCMS method F: $[M+H]^+$=345.2 $t_R$=1.87 min

LCMS method G: $[M+H]^+$=345.2, $t_R$=1.85 min, $[M-H]^-$=343.1, $t_R$=1.85 min $^1$H NMR (400 MHz, d6-DMSO) δ 13.35 (1H, s), 7.69-7.67 (1H, m), 7.56-7.49 (2H, m), 7.35 (1H, s), 7.01 (1H, dd, J=2.4, 9.0 Hz), 4.38-4.26 (4H, m), 3.18-3.05 (4H, m), 1.84 (2H, ddd, J=0.8, 8.9, 17.4 Hz) ppm.

Example 136: (7R,13R)-7,13-dimethyl-8,14-dioxa-10,19,20,23-tetraazatetracyclo[13.5.2.$1^{2,6}$.$0^{18,21}$]tricosa-1(20),2,4,6(23),15,17,21-heptaen-9-one

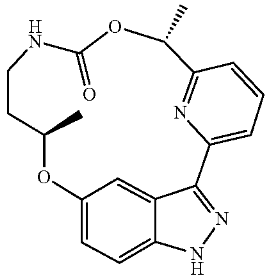 [SMILES: C[C@@H]1CCNC(=O)O[C@H](C)c2cccc(n2)-c2n[nH]c3ccc(cc23)O1]

Example 136 is prepared according to the synthesis route described in general Scheme K.

Preparation of Intermediate 167: [(1R)-1-(6-bromo-2-pyridyl)ethyl]acetate

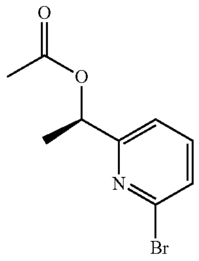

To a stirred solution of 1-(6-bromo-2-pyridyl)ethanol (1 g, 4.94 mmol, 1 eq) in anhydrous diisopropyl ether (120 mL) at 0° C., was added vinyl acetate (2 mL, 21 mmol, 42 eq), 4A molecular sieves (1 g), and Lipase immobilized from *Candida Antarctica* (200 mg) and the reaction mixture was stirred at room temperature for 48 hours. The catalyst and molecular sieves were filtered off and the solvent was concentrated under reduced pressure. The oily residue was purified by column chromatography eluting with cyclohexane/EtOAc: 90/10 to 80/20 to give [(1R)-1-(6-bromo-2-pyridyl)ethyl]acetate 167 as colorless oil.

LCMS method F: $[M+H]^+$=246, $t_R$=2.28 min

Preparation of Intermediate 168: (1R)-1-(6-bromo-2-pyridyl)ethanol

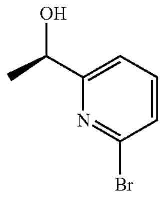

To a solution of [(1R)-1-(6-bromo-2-pyridyl)ethyl]acetate 167 (563 mg, 2.3 mmol, 1 eq) in a mixture of MeOH/water: 1/1 (20 mL) was added potassium carbonate (317 mg, 2.3 mmol, 1 eq) and the solution was stirred at room temperature for 3 hours. MeOH was then evaporated and the aqueous phase was extracted with EtOAc (3×). The combined organic extract was washed with brine, dried over $Na_2SO_4$, filtered and evaporated under reduced pressure to give the expected compound (1R)-1-(6-bromo-2-pyridyl)ethanol 168 as a colorless oil.

LCMS method F: $[M+H]^+$=202, $t_R$=1.69 min

Preparation of Example 136: (7R,13R)-7,13-dimethyl-8,14-dioxa-10,19,20,23-tetraazatetracyclo[13.5.2.1$^{2,6}$.0$^{18,21}$]tricosa-1(20),2,4, 6(23),15,17,21-heptaen-9-one

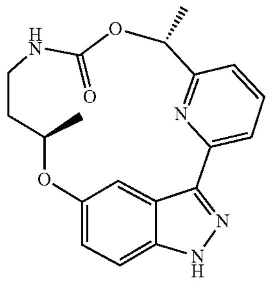 [SMILES: C[C@@H]1CCNC(=O)O[C@H](C)c2cccc(n2)-c2n[nH]c3ccc(cc23)O1]

To a suspension of (7R,13R)-7,13-dimethyl-19-(oxan-2-yl)-8,14-dioxa-10,19,20,23-tetraazatetracyclo[13.5.2.1$^{2,6}$.0$^{18,21}$]tricosa-1(20),2,4,6(23),15,17,21-heptaen-9-one (80 mg, 0.18 mmol, 1 eq) in MeOH/water (14 mL/2 mL) was added para-toluenesulfonic acid monohydrate (174 mg, 0.91 mmol, 5 eq) and the reaction mixture was heated at 65° C. for 24 hours. MeOH was removed partially under reduced pressure and a saturated solution of $NaHCO_3$ was added. The aqueous phase was extracted with EtOAc (2×) and the organic extract was washed with brine, dried over $Na_2SO_4$, filtered and evaporated under reduced pressure. The solid residue was triturated in diisopropyl ether, filtered and dried to give (7R,13R)-7,13-dimethyl-8,14-dioxa-10,19,20,23-tetraazatetracyclo[13.5.2.1$^{2,6}$.0$^{18,21}$]tricosa-1(20),2,4, 6(23), 15,17,21-heptaen-9-one example 136 as a white solid.

LCMS method F: $[M+H]^+$=353.2, $t_R$=2.28 min

LCMS method G: $[M+H]^+$=353.3, $t_R$=2.15 min $^1$H NMR (400 MHz, d6-DMSO, 80° C.) δ 12.93-12.90 (1H, m), 8.11-8.05 (2H, m), 7.85 (1H, t, J=7.7 Hz), 7.46-7.42 (1H, m), 7.34-7.29 (1H, m), 7.22-7.08 (1H, m), 6.97-6.94 (1H, m), 6.2-5.9 (1H, m), 5.05-4.8 (1H, m), 3.4-3.2 (1H, m), 3-2.95 (1H, m), 1.94-1.73 (1H, m), 1.72-1.51 (4H, m), 1.40 (3H, d, J=6.1 Hz) ppm.

Example 137: (13R)-4-[(3R)-3-methoxypyrrolidin-1-yl]-13-methyl-8,14-dioxa-5,10,19,20,23-pentaazatetracyclo[13.5.2.1$^{2,6}$.0$^{18,21}$]tricosa-1(20),2,4,6(23), 15,17,21-heptaen-9-one

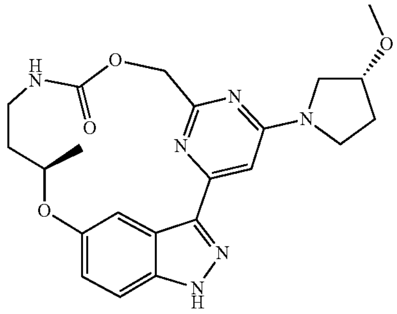 [SMILES: CO[C@@H]1CCN(c2cc3nc(n2)COC(=O)NCC[C@@H](C)Oc2ccc4[nH]nc-3c4c2)C1]

Example 137 is prepared according to the synthesis route described in general Scheme K.

Preparation of Intermediate 169: (4,6-dichloropyrimidin-2-yl)methyl acetate

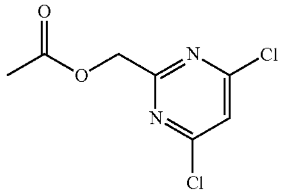

To a solution of 4,6-dichloro-2-(chloromethyl)pyrimidine (0.830 g, 4.23 mmol) in N,N-dimethylformamide (50.0 mL) at 0° C. was added potassium iodide (0.774 g, 4.66 mmol), and potassium acetate (0.457 g, 4.66 mmol) was added and the mixture was stirred during 12 hours at room temperature. Solvent was evaporated. Water (25 mL) and EtOAc (25 mL) were added. Phases were separated and aqueous phase was extracted with EtOAc (3×25 mL), then organic phase was washed with a saturated solution of NaCl (25 mL), dried with $Na_2SO_4$, filtered and concentrated to afford (4,6-dichloropyrimidin-2-yl)methyl acetate 169 as a white powder.

LCMS method F: $[M+H]^+$=221, $t_R$=2.07 min

Preparation of Intermediate 170: [4-[5-[tert-butyl(dimethyl)silyl]oxy-1-tetrahydropyran-2-yl-indazol-3-yl]-6-chloro-pyrimidin-2-yl]methyl acetate

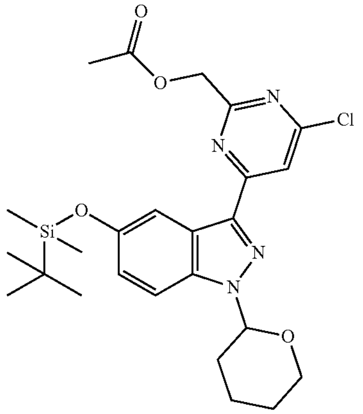 [SMILES: CC(=O)OCc1nc(Cl)cc(-c2nn(C3CCCCO3)c3ccc(O[Si](C)(C)C(C)(C)C)cc23)n1]

To a solution of tert-butyl-dimethyl-[1-tetrahydropyran-2-yl-3-(4,4,5,5-tetramethyl-1,3,2-dioxaborolan-2-yl)indazol-5-yl]oxy-silane (2.5 g, 5.45 mmol) in dioxane (10 mL) and water (1 mL) was added at RT (4,6-dichloropyrimidin-2-yl)methyl acetate 169 (999 mg, 4.54 mmol), Potassium phosphate tribasic (2.89 g, 13.62 mmol). The reaction mixture was degassed by bubbling nitrogen for 15 min, then XPhos (65 mg, 0.14 mmol) and $Pd(PPh_3)_4$(53 mg, 0.045 mmol) were added. The reaction mixture was stirred at 80° C. for 45 min under microwave radiations. The reaction mixture was evaporated in vacuo to give a brown oil. To the reaction mixture was added EtOAc (100 mL) and water (50 mL). After separation, the aqueous layer was extracted with EtOAc (2×50 mL), then the organic layer was washed with brine, dried over sodium sulfate, filtered and evaporated in vacuo. The residue was purified by flash chromatography (CyH/EtOAc 100 to 8/2 CyH/EtOAc) to afford [4-[5-[tert-butyl(dimethyl)silyl]oxy-1-tetrahydropyran-2-yl-indazol-3-yl]-6-chloro-pyrimidin-2-yl]methyl acetate 170 as an yellow oil.

LCMS method F: $[M+H]^+$=517, $t_R$=3.91 min

Preparation of Intermediate 171: [4-chloro-6-(5-hydroxy-1-tetrahydropyran-2-yl-indazol-3-yl)pyrimidin-2-yl]methyl acetate

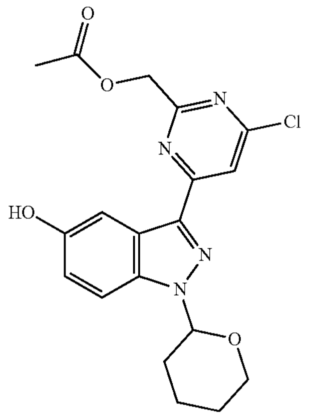 [SMILES: CC(=O)OCc1nc(Cl)cc(-c2nn(C3CCCCO3)c3ccc(O)cc23)n1]

To a solution of [4-[5-[tert-butyl(dimethyl)silyl]oxy-1-tetrahydropyran-2-yl-indazol-3-yl]-6-chloro-pyrimidin-2-yl]methyl acetate 170 (2.34 g, 4.53 mmol) in THE (40 mL) was added dropwise at RT tetrabutylammonium fluoride 1 M in THE (1.3 mL, 4.98 mmol). The resulting reaction mixture was stirred at RT overnight. The reaction mixture was poured into ice water and stirred for 20 min. The aqueous phase was extracted with ethyl acetate (100 mL) twice and the combined organic phase was washed with saturated brine, dried over anhydrous sodium sulfate and concentrated in vacuo to give a brown oil. The residue was purified by flash chromatography CyH/EtOAc 5/5 to afford [4-chloro-6-(5-hydroxy-1-tetrahydropyran-2-yl-indazol-3-yl)pyrimidin-2-yl]methyl acetate 171 as a white solid.

LCMS method F: $[M+H]^+$=403, $t_R$=2.82 min

Preparation of Intermediate 172: benzyl[4-[5-[(1R)-3-(benzyloxycarbonylamino)-1-methyl-propoxy]-1-tetrahydropyran-2-yl-indazol-3-yl]-6-chloro-pyrimidin-2-yl]methyl acetate

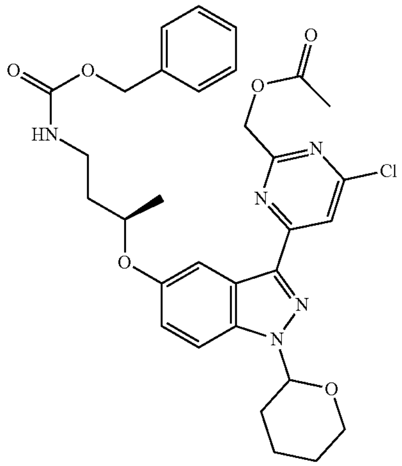 [SMILES: CC(=O)OCc1nc(Cl)cc(-c2nn(C3CCCCO3)c3ccc(O[C@H](C)CCNC(=O)OCc4ccccc4)cc23)n1]

To a mixture of [4-chloro-6-(5-hydroxy-1-tetrahydropyran-2-yl-indazol-3-yl)pyrimidin-2-yl]methyl acetate 171 (945 mg, 2.35 mmol) and cesium carbonate (1.53 g, 4.7 mmol) in acetonitrile (20 mL) and N,N-dimethylformamide (5 mL) was added [(1S)-3-(benzyloxycarbonylamino)-1-methyl-propyl]methanesulfonate (778 mg, 2.59 mmol postulated) and the suspension was heated for 8 hours at RT. The reaction mixture was filtered to removed cesium carbonate and the salts were washed with acetonitrile. The filtrate was evaporated in vacuo to give an yellow oil. The oily residue was put in EtOAc (50 mL) and water (30 mL), the aqueous layer was extracted with EtOAc (2×50 mL), washed with brine, dried over sodium sulfate, filtered and evaporated in vacuo to give an oil. The residue was purified by flash chromatography (CyH/AE 5/5) to afford benzyl[4-[5-[(1R)-3-(benzyloxycarbonylamino)-1-methyl-propoxy]-1-tetrahydropyran-2-yl-indazol-3-yl]-6-chloro-pyrimidin-2-yl]methyl acetate 172 as an off-white solid.

LCMS method I. $[M+H]^+$=608, $t_R$=2.86 min

Preparation of Intermediate 173: [4-[5-[(1R)-3-(benzyloxycarbonylamino)-1-methyl-propoxy]-1-tetrahydropyran-2-yl-indazol-3-yl]-6-[(3R)-3-methoxypyrrolidin-1-yl]pyrimidin-2-yl]methyl acetate

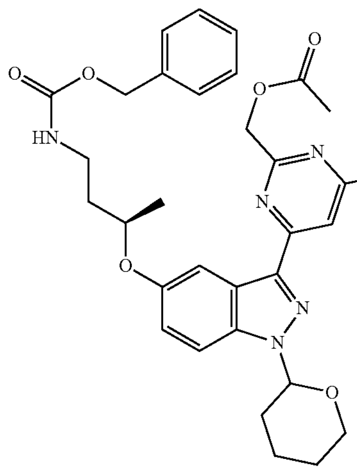

To a mixture of [4-[5-[(1R)-3-(benzyloxycarbonylamino)-1-methyl-propoxy]-1-tetrahydropyran-2-yl-indazol-3-yl]-6-chloro-pyrimidin-2-yl]methyl acetate 172 (103 mg, 0.17 mmol) and potassium carbonate (94 mg, 0.37 mmol) in N,N-dimethylformamide (1.5 mL) was added (3R)-3-methoxypyrrolidine hydrochloride (51 mg, 0.37 mmol) and the suspension was stirred for 8 hours at RT. The reaction mixture was evaporated in vacuo to give an yellow oil.

Then to the residue was added EtOAc (20 mL) and water (10 mL). After separation of the layers, the aqueous layer was extracted with EtOAc (10 mL) twice, then the organic layer was washed with brine, dried over sodium sulfate, filtered and evaporated in vacuo to afford the crude [4-[5-[(1R)-3-(benzyloxycarbonylamino)-1-methyl-propoxy]-1-tetrahydropyran-2-yl-indazol-3-yl]-6-[(3R)-3-methoxypyrrolidin-1-yl]pyrimidin-2-yl]methyl acetate 173 as an yellow oil.

LCMS method F: $[M+H]^+=673$, $t_R=2.89$ min

Preparation of Intermediate 174: benzyl N-[(3R)-3-[3-[2-(hydroxymethyl)-6-pyrrolidin-1-yl-pyrimidin-4-yl]-1-tetrahydropyran-2-yl-indazol-5-yl]oxybutyl] carbamate

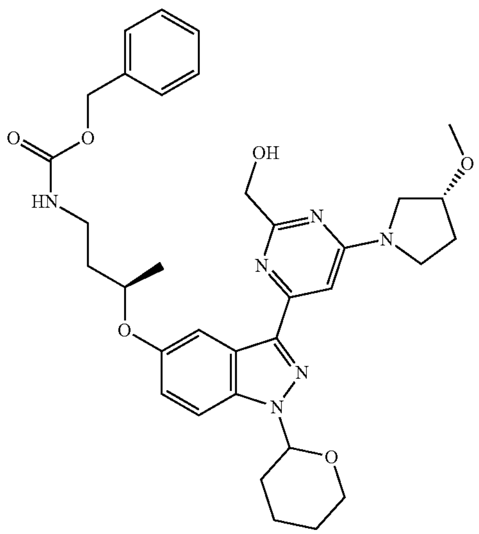 [SMILES: CO[C@@H]1CCN(c2cc(-c3nn(C4CCCCO4)c4ccc(O[C@H](C)CCNC(=O)OCc5ccccc5)cc34)nc(CO)n2)C1]

To a suspension of [4-[5-[(1R)-3-(benzyloxycarbonylamino)-1-methyl-propoxy]-1-tetrahydropyran-2-yl-indazol-3-yl]-6-[(3R)-3-methoxypyrrolidin-1-yl]pyrimidin-2-yl] methyl acetate 173 (0.155 g, 0.23 mmol) in MeOH (2.0 mL) was added potassium carbonate (0.038 g, 0.28 mmol). The reaction was stirred at room temperature during 2 h. The reaction was stopped and filtered and evaporated. The crude was purified by chromatography column (RediSep, 4 g, CyH/EtOAc. 0% to 100% EtOAc) to afford benzyl N-[(3R)-3-[3-[2-(hydroxymethyl)-6-pyrrolidin-1-yl-pyrimidin-4-yl]-1-tetrahydropyran-2-yl-indazol-5-yl]oxybutyl]carbamate 174 as a light yellow oil.

LCMS method F: $[M+H]^+=631$, $t_R=2.23$ min

Preparation of Intermediate 175: (13R)-4-[(3R)-3-methoxypyrrolidin-1-yl]-13-methyl-19-(oxan-2-yl)-8,14-dioxa-5,10,19,20,23-pentaazatetracyclo [13.5.2.1$^{2,6}$.0$^{18,21}$]tricosa-1(20),2(23),3,5,15(22),16,18(21)-heptaen-9-one

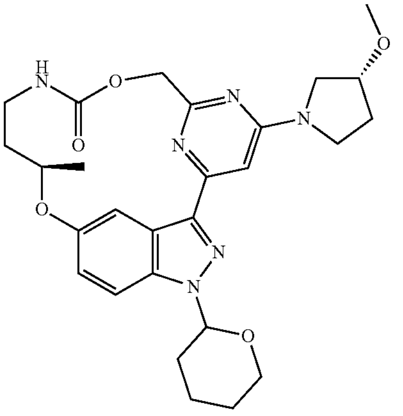 [SMILES: CO[C@@H]1CCN(c2cc3nc(n2)COC(=O)NCC[C@@H](C)Oc2ccc4c(c2)c-3nn4C2CCCCO2)C1]

To a solution of benzyl N-[(3R)-3-[3-[2-(hydroxymethyl)-6-[(3R)-3-methoxypyrrolidin-1-yl]pyrimidin-4-yl]-1-tetrahydropyran-2-yl-indazol-5-yl]oxybutyl]carbamate 174 (121 mg, 0.19 mmol) in dry acetonitrile (10 mL) was added at RT finely powdered potassium hydroxide (54 mg, 0.96 mmol) in one portion. The reaction mixture was stirred at RT for 12 h. The reaction mixture was filtered then rinsed with ethyl acetate and evaporated under reduced pressure to give (13R)-4-[(3R)-3-methoxypyrrolidin-1-yl]-13-methyl-19-(oxan-2-yl)-8,14-dioxa-5,10,19,20,23-pentaazatetracyclo[$13.5.2.1^{2,6}.0^{18,21}$]tricosa-1(20),2(23),3,5,15(22),16,18(21)-heptaen-9-one 175 as a light yellow oil.

LCMS method F: $[M+H]^+$=523, $t_R$=2.68 min

Preparation of Example 137: (13R)-4-[(3R)-3-methoxypyrrolidin-1-yl]-13-methyl-8,14-dioxa-5,10,19,20,23-pentaazatetracyclo[$13.5.2.1^{2,6}.0^{18,21}$]tricosa-1(20),2,4,6(23),15,17,21-heptaen-9-one

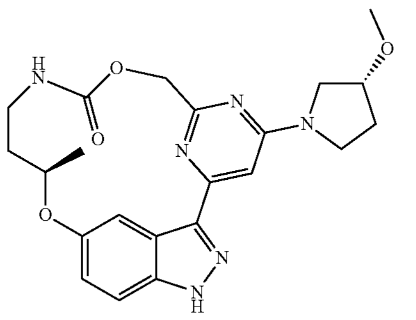 [SMILES: CO[C@@H]1CCN(c2cc3nc(n2)COC(=O)NCC[C@@H](C)Oc2ccc4[nH]nc-3c4c2)C1]

To a solution of (13R)-4-[(3R)-3-methoxypyrrolidin-1-yl]-13-methyl-19-(oxan-2-yl)-8,14-dioxa-5,10,19,20,23-pentaazatetracyclo[$13.5.2.1^{2,6}.0^{18,21}$]tricosa-1(20),2(23),3,5,15(22),16,18(21)-heptaen-9-one 175 (53 mg, 0.10 mmol) in MeOH/$H_2O$ (2/0.3 mL) was added p-toluenesulfonic acid monohydrate (95 mg, 0.5 mmol). The mixture was heated at 80° C. for 5 hours. Then to the reaction mixture was added p-toluenesulfonic acid monohydrate (50 mg, 0.26 mmol) and stirred at 80° C. for 5 hours. The reaction mixture was evaporated in vacuo and a saturated solution of sodium bicarbonate (10 mL) and DCM (10 mL) was added. Then, the aqueous layer was extracted with DCM (2×10 mL), then the organic layer was washed with brine, dried over sodium sulfate, filtered and evaporated in vacuo to give a solid. The solid was purified by flash chromatography (CyH to 100% EtOAc) to afford (13R)-4-[(3R)-3-methoxypyrrolidin-1-yl]-13-methyl-8,14-dioxa-5,10,19,20,23-pentaazatetracyclo[$13.5.2.1^{2,6}.0^{18,21}$]tricosa-1(20),2,4,6(23),15,17,21-heptaen-9-one example 137 as a white powder.

LCMS method F: $[M+H]^+$=439, $t_R$=2.06 min

LCMS method G: $[M+H]^+$=439, $t_R$=2.23 min $^1H$ NMR (400 MHz, d6-DMSO) δ 13.36 (1H, s), 7.93 (1H, d, J=1.9 Hz), 7.79 (1H, dd, J=4.9, 7.4 Hz), 7.49-7.46 (1H, m), 7.06 (1H, s), 6.95 (1H, dd, J=2.4, 9.0 Hz), 5.41-5.36 (1H, m), 4.74 (1H, d, J=15.6 Hz), 4.62-4.56 (1H, m), 4.14-4.07 (1H, m), 3.57 (4H, m), 3.50-3.43 (3H, m), 2.87 (1H, t, J=14.4 Hz), 2.35-2.28 (1H, m), 2.09-2.09 (3H, m), 1.39-1.36 (4H, m) ppm.

Example 138: (13R)-16-chloro-13-methyl-8,14-dioxa-10,19,20-triazatetracyclo[$13.5.2.1^{2,6}.0^{18,21}$]tricosa-1(20),2,4,6(23),15,17,21-heptaen-9-one

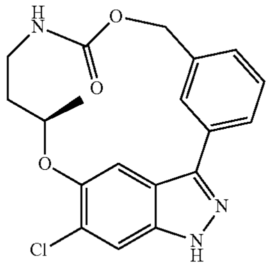 [SMILES: C[C@@H]1CCNC(=O)OCc2cccc(c2)-c2n[nH]c3cc(Cl)c(cc23)O1]

Example 138 is prepared according to the synthesis route described in general Scheme K.

To a solution of (13R)-16-chloro-13-methyl-19-(oxan-2-yl)-8,14-dioxa-10,19,20-triazatetra cyclo[$13.5.2.1^{2,6}.0^{18,21}$]tricosa-1(20),2,4,6(23),15,17,21-heptaen-9-one (376 mg, 0.83 mmol) in MeOH (49 mL) and water (6 mL) was added p-toluenesulfonic acid monohydrate (785 mg, 4.13 mmol) and the reaction mixture was heated to 65° C. for 3 hours and 30 minutes. The reaction mixture was concentrated under vacuo and the crude was neutralized by slow addition of a saturated aqueous sodium hydrogen carbonate solution. It was diluted with EtOAc and after separation, the aqueous layer was extracted with EtOAc (3×). The combined organic layer was washed with brine, dried over sodium sulfate, filtered and evaporated under reduced pressure.

The crude was triturated from ACN then filtrated and washed two times with ACN to give (13R)-16-chloro-13-methyl-8,14-dioxa-10,19,20-triazatetracyclo[$13.5.2.1^{2,6}.0^{18,21}$]tricosa-1(20),2,4,6(23),15,17,21-heptaen-9-one example 138 as a white powder.

LCMS method F: $[M+H]^+$=372, $t_R$=2.42 min

LCMS method G: $[M+H]^+$=372, $t_R$=2.40 min $^1H$ NMR (400 MHz, d6-DMSO) δ 13.24 (1H, m), 7.94 (1H, m), 7.85 (1H, m), 7.80 (1H, m), 7.74 (1H, s), 7.48 (1H, t, J=7.7 Hz), 7.37 (1H, s), 7.29 (1H, m), 5.74 (1H, m), 4.8 (1H, m), 4.63 (1H, m), 3.56 (1H, m), 2.92 (1H, m), 2.37 (1H, m), 1.48 (1H, m), 1.44 (3H, d, J=6 Hz) ppm.

Example 139: (13R)-13,16-dimethyl-8,14-dioxa-10,19,20-triazatetracyclo[$13.5.2.1^{2,6}.0^{18,21}$]tricosa-1(20),2,4,6(23),15,17,21-heptaen-9-one

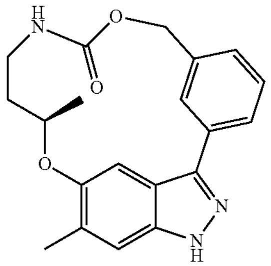 [SMILES: Cc1cc2[nH]nc3c2cc1O[C@H](C)CCNC(=O)OCc1cccc-3c1]

Example 139 is prepared according to the synthesis route described in general Scheme K.

To a solution of (13R)-13,16-dimethyl-19-(oxan-2-yl)-8,14-dioxa-10,19,20-triazatetracyclo[$13.5.2.1^{2,6}.0^{18,21}$]tricosa-1(20),2,4,6(23),15,17,21-heptaen-9-one (537 mg, 1.23 mmol) in MeOH (72 mL) and water (9 mL) was added p-toluenesulfonic acid monohydrate (1.17 g, 6.17 mmol) and the reaction mixture was heated to 65° C. for 3 hours and 30 minutes. The reaction mixture was concentrated under vacuo and the crude was neutralized by slow addition of a saturated aqueous sodium hydrogen carbonate solution. It was diluted with EtOAc and after separation, the aqueous layer was extracted with EtOAc (3×). The combined organic layer was washed with brine, dried over sodium sulfate, filtered and evaporated under reduced pressure.

The crude was triturated from ACN then filtrated and washed two times with ACN to give (13R)-13,16-dimethyl-8,14-dioxa-10,19,20-triazatetracyclo[13.5.2.$1^{2,6}$.$0^{18,21}$]tricosa-1(20),2,4,6(23),15,17,21-heptaen-9-one example 139 as a white powder.

LCMS method F: $[M+H]^+$=352, $t_R$=2.39 min

LCMS method G: $[M+H]^+$=352, $t_R$=2.38 min $^1$H NMR (400 MHz, d6-DMSO) δ=12.97 (1H, s), 7.94 (1H, m), 7.86 (1H, m), 7.84 (1H, m), 7.45 (1H, t, J=7.8 Hz), 7.37 (1H, s), 7.26 (1H, m), 7.24 (1H, m), 5.74 (1H, m), 4.82 (1H, m), 4.58 (1H, m), 3.57 (1H, m), 2.9 (1H, m), 2.41 (1H, m), 2.27 (3H, d, J=0.8 Hz), 1.42 (3H, d, J=5.9 Hz), 1.39 (1H, m) ppm Example 140: (13R)-13-methyl-8,14-dioxa-3,10,19,20,23-pentaazatetracyclo[13.5.2.$1^{2,6}$.$0^{18,21}$]tricosa-1(20),2,4,6(23),15,17,21-heptaen-9-one

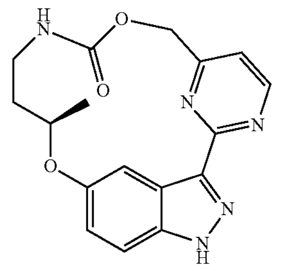 [SMILES: C[C@@H]1CCNC(=O)OCc2ccnc(n2)-c2n[nH]c3ccc(cc23)O1]

Example 140 is prepared according to the synthesis route described in general Scheme B.

To a solution of (13R)-13-methyl-19-(oxan-2-yl)-8,14-dioxa-3,10,19,20,23-pentaazatetracyclo[13.5.2.$1^{2,6}$.$0^{18,21}$]tricosa-1(20),2,4,6(23),15,17,21-heptaen-9-one (77 mg, 0.18 mmol) in MeOH (10.6 mL) and water (1.3 mL) was added p-toluenesulfonic acid monohydrate (173 mg, 0.91 mmol) and the reaction mixture was heated to 65° C. for 3 hours and 30 minutes. The mixture was heated at 65° C. for 1 day. The reaction mixture was concentrated under vacuo and the crude was neutralized by slow addition of a saturated aqueous sodium hydrogen carbonate solution. It was diluted with EtOAc and after separation, the aqueous layer was extracted with EtOAc (3×). The combined organic layer was washed with brine, dried over sodium sulfate, filtered and evaporated under reduced pressure. The crude was triturated from ACN then filtrated and washed two times with ACN to give (13R)-13-methyl-8,14-dioxa-3,10,19,20,23-pentaazatetracyclo[13.5.2.$1^{2,6}$.$0^{18,21}$]tricosa-1(20),2,4,6(23), 15,17,21-heptaen-9-one example 140 as a pale yellow solid.

LCMS method F: $[M+H]^+$=340, $t_R$=1.73 min

LCMS method G: $[M+H]^+$=340, $t_R$=1.74 min $^1$H NMR (400 MHz, d6-DMSO) δ 13.51 (1H, m), 8.81 (1H, d, J=5 Hz), 7.84 (2H, m), 7.5 (1H, m), 7.33 (1H, m), 6.97 (1H, dd, J=1.6, 8.4 Hz), 5.59 (1H, m), 5.07 (111, m), 4.62 (1H, m), 3.48 (1H, m), 2.91 (1H, m), 2.3 (1H, m), 1.41 (1H, m), 1.38 (3H, d, J=5.5 Hz) ppm.

Preparation of Intermediate 176: benzyl N-[(3S)-3-hydroxybutyl]carbamate

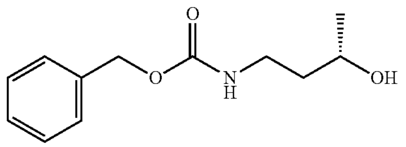 [SMILES: C[C@H](O)CCNC(=O)OCc1ccccc1]

To a solution of (2S)-4-aminobutan-2-ol (10 g, 112.36 mmol) in a mixture of THE (143 mL) and water (143 mL) was added sodium hydrogenocarbonate (10.38 g, 123.59 mmol). The suspension was cooled to 0° C. and benzyl chloroformate (17.64 mL, 123.59 mmol) was added dropwise and the reaction mixture was stirred at room temperature for 16 hours. The solution was diluted with water and extracted with EtOAc (3×). The combined organic layer was washed with brine, dried over sodium sulfate, filtered and evaporated under reduced pressure. The oily residue was purified by column chromatography eluting with dichloromethane/ethyl acetate: 100/0 to 80/20 to give benzyl N-[(3S)-3-hydroxybutyl]carbamate intermediate 176 as a colorless oil.

LCMS method F: $[M+H]^+$=224, $t_R$=1.94 min

Preparation of Intermediate 177: [(1S)-3-(benzyloxycarbonylamino)-1-methyl-propyl]methanesulfonate

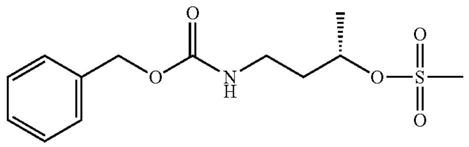 [SMILES: C[C@@H](CCNC(=O)OCc1ccccc1)OS(C)(=O)=O]

To a cooled solution (0° C.) of benzyl N-[(3S)-3-hydroxybutyl]carbamate intermediate 176 (17.06 g, 76.52 mmol) and triethylamine (21.3 mL, 153.04 mmol) in dichloromethane (300 mL) was added dropwise methanesulfonyl chloride (7.7 mL, 99.47 mmol) and the reaction mixture was stirred at room temperature for 19 hours. The reaction mixture was quenched with an aqueous solution of 1N HCl and extracted with dichloromethane (1×). The organic layer was washed with a saturated aqueous solution of $NaHCO_3$ then water and brine, dried over sodium sulfate, filtered and evaporated under reduced pressure to give [(1S)-3-(benzyloxycarbonylamino)-1-methyl-propyl]methanesulfonate intermediate 177 as a yellow oil.

LCMS method F: $[M+H]^+$=302, $t_R$=2.26 min

Preparation of Intermediate 178: benzyl N-[(3R)-3-(3-iodo-1-tetrahydropyran-2-yl-indazol-5-yl)oxy-butyl]carbamate

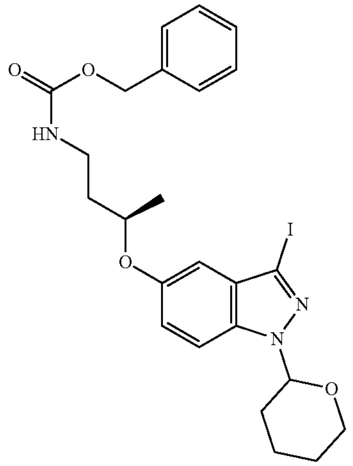 [SMILES: C[C@H](CCNC(=O)OCc1ccccc1)Oc1ccc2c(c1)c(I)nn2C1CCCCO1]

To a solution of 3-iodo-1-tetrahydropyran-2-yl-indazol-5-ol 4 (5.152 g, 14.97 mmol) and cesium carbonate (14.633 g, 44.91 mmol) in DMF (50 mL) was dropwise added a solution of [(1S)-3-(benzyloxycarbonylamino)-1-methyl-propyl]methanesulfonate 177 (5.406 g, 17.96 mmol) in DMF (26 mL) and the reaction mixture was stirred at RT for the week-end. The reaction mixture was filtered then concentrated under reduced pressure. The crude product was diluted with ethyl acetate and a saturated solution of $NaHCO_3$ was added then it was extracted with ethyl acetate (2×). The organic layer was washed with water then brine, dried over sodium sulfate, filtered and concentrated under reduced pressure. The crude product was purified by flash column chromatography eluting with Cyclohexane/Ethyl acetate-Ethanol (3-1), 100/0 to 70/30, to give benzyl N-[(3R)-3-(3-iodo-1-tetrahydropyran-2-yl-indazol-5-yl)oxybutyl]carbamate 178 as a yellow oil.

LCMS method F: $[M+H]^+$=550.1, $t_R$=3.20 min

Preparation of Intermediate 179: benzyl N-(3-hydroxybutyl)carbamate

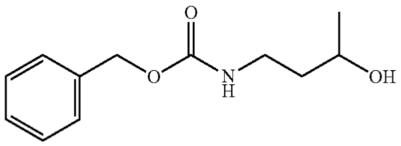 [SMILES: CC(O)CCNC(=O)OCc1ccccc1]

To a solution of 4-aminobutan-2-ol (1.78 g, 20 mmol) in a mixture of THE (30 mL) and water (30 mL) was added sodium hydrogenocarbonate (1.84 g, 22 mmol). The suspension was cooled at 0° C. and benzyl chloroformate (3.15 mL, 22 mmol) was added portionwise and the reaction mixture was stirred at room temperature overnight. The solution was diluted with water and extracted with EtOAc (3×). The combined organic extract was washed with brine, dried over $Na_2SO_4$, filtered and evaporated under reduce pressure. The oily residue was purified by chromatography eluting with cyclohexane/EtOAc: 70/30 to 50/50 to give the expected compound benzyl N-(3-hydroxybutyl)carbamate intermediate 179 as a colorless oil.

LCMS method F: $[M+H]^+$=224.1, $t_R$=1.92 min

Preparation of Intermediate 180: [3-(benzyloxycarbonylamino)-1-methyl-propyl]methane sulfonate

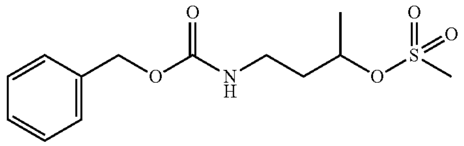 [SMILES: CC(CCNC(=O)OCc1ccccc1)OS(C)(=O)=O]

To a cooled (0° C.) solution of benzyl N-(3-hydroxybutyl) carbamate 179 (1.67 g, 7.5 mmol) and $Et_3N$ (1.56 mL, 11.25 mmol) in dichoromethane (30 mL) was added dropwise methanesulfonyl chloride (638 μL, 8.25 mmol) and the reaction mixture was stirred at room temperature overnight. The organic phase was washed with a 1N HCl solution, with a saturated solution of $NaHCO_3$, with brine, dried over $Na_2SO_4$, filtered and evaporated under reduced pressure to give the expected compound [3-(benzyloxycarbonylamino)-1-methyl-propyl]methanesulfonate 180 as a colorless oil. The crude compound was used in the next step without further purification.

LCMS method F: $[M+H]^+$=302, $t_R$=2.24 min

Preparation of Intermediate 181: N-[3-(3-iodo-1-tetrahydropyran-2-yl-indazol-5-yl)oxybutyl]carbamate

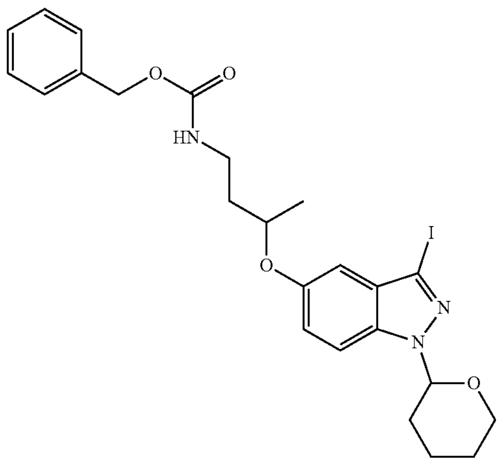 [SMILES: CC(CCNC(=O)OCc1ccccc1)Oc1ccc2c(c1)c(I)nn2C1CCCCO1]

To a solution of 3-iodo-1-tetrahydropyran-2-yl-indazol-5-ol 4 (2 g, 6.08 mmol) and cesium carbonate (5.94 g, 18.25 mmol) in DMF (20 mL) was added dropwise a solution of [3-(benzyloxycarbonylamino)-1-methyl-propyl]methanesulfonate 180 (2.2 g, 7.3 mmol) in DMF (10 mL) and the reaction mixture was stirred at 60° C. overnight. The reaction mixture was cooled to room temperature and water was added. The aqueous phase was extracted with EtOAc (3×) and the organic phase was washed with brine, dried over $Na_2SO_4$, filtered and evaporated under reduced pressure. The residue was purified by chromatography eluting with cyclohexane/EtOAc: 70/30 to give the expected compound N-[3-(3-iodo-1-tetrahydropyran-2-yl-indazol-5-yl)oxybutyl]carbamate 180 as a colorless oil.

LCMS method F: $[M+H]^+$=550.1, $t_R$=3.20 min

Intermediates 179 to 181 are used as intermediates in the synthesis of Examples 50, 71, 92. Examples 62, 63, 96, 97, 100, 101, 102, 105, 106, 113, 114, 117, 120, 125, 127, 128, 129, 130, 131, 133, 136, 137, and 140 can be obtained by chiral HPLC separation of the corresponding racemates, or through a chiral synthesis using intermediates 176 to 178.

Example 141: 8-oxa-10,14,19,20-tetraazatetracyclo [13.5.2.1$^{2,6}$.0$^{18,21}$]tricosa-1(20),2(23), 3,5,15(22),16, 18(21)-heptaen-9-one

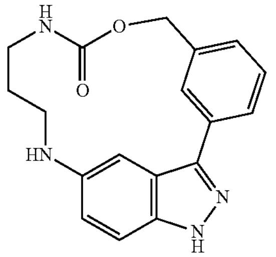 [SMILES: O=C1NCCCNc2ccc3[nH]nc(c3c2)-c2cccc(c2)CO1]

Example 141 is prepared according to the synthesis route described in general Scheme I.

To a solution of 19-(oxan-2-yl)-8-oxa-10,14,19,20-tetraazatetracyclo[13.5.2.1$^{2,6}$.0$^{18,21}$]tricosa-1(20),2(23),3,5,15 (22),16,18(21)-heptaen-9-one (37 mg, 0.09 mmol) in dioxane (7.5 ml) was added HCl 4N dioxane (360 µl, 1.8 mmol). The reaction mixture was stirred overnight at 60° C.

Three drops of HCl 37% were added and the reaction mixture was stirred 1 h at 60° C. The solvent was removed under reduced pressure and the mixture was purified by chromatography using a 4 g SiO2 column eluted with DCM/MeOH 100/0 to 90/10. The desired fractions were combined and the solvent was removed under reduced pressure to give 8-oxa-10,14,19,20-tetraazatetracyclo [13.5.2.1$^{2,6}$.0$^{18,21}$]tricosa-1(20),2(23),3,5,15(22),16,18(21)-heptaen-9-one·hydrochloride example 141 as a cream powder.

LCMS method F: $[M+H]^+$=323.2, $t_R$=1.70 min

LCMS method G: $[M+H]^+$=323.2, $t_R$=1.72 min

1H NMR (400 MHz, d6-DMSO) δ 7.92 (1H, s), 7.85 (2H, d, J=1.5 Hz), 7.53-7.45 (2H, m), 7.35-7.31 (2H, m), 6.54 (1H, q, J=2.9 Hz), 5.3 (1H, m), 4.61 (2H, d, J=6.1 Hz), 3.68 (2H, t, J=5.5 Hz), 3.27 (2H, m), 2.03-1.97 (2H, m), 1.04 (1H, d, J=6.1 Hz) ppm.

Example 142: 8-oxa-10,19,20-triazatetracyclo [13.5.2.1$^{2,6}$.0$^{18,21}$]tricosa-1(20),2(23),3,5, 15(22),16, 18(21)-heptaen-9-one

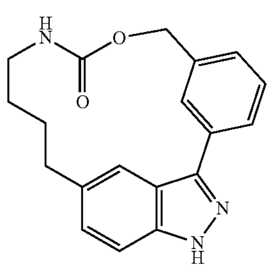 [SMILES: O=C1NCCCCc2ccc3[nH]nc(c3c2)-c2cccc(c2)CO1]

Example 142 is prepared according to the synthesis route described below.

Preparation of Intermediate 182: diisopropylammonium; 4-spiro[7,9-dioxa-8-silanuidabicyclo[4.3.0] nona-1(6),2,4-triene-8,8'-7,9-dioxa-8-silanuidabicyclo[4.3.0]nona-1,3,5-triene]-8-ylbutanenitrile

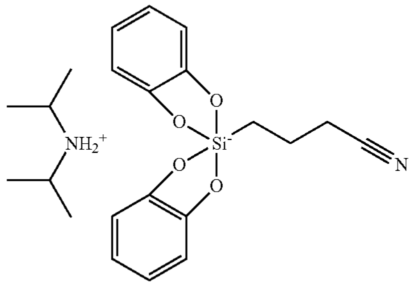

To an oven-dried, 100 mL round bottom flask equipped with a stir bar, reflux condenser, and gas inlet adapter was added catechol (5.67 g, 51.58 mmol) followed by THE (62 mL) and i-$Pr_2NH$ (4.44 mL, 31.74 mmol). The mixture was placed under an argon atmosphere and was allowed to stir at room temperature for 5 minutes. The solution became pale red. 4-Trimethoxysilylbutanenitrile (5.00 g, 26.45 mmol) was added. The solution was heated to reflux in an oil bath and allowed to stir at this temperature for 18 hours. The solvent was removed under reduced pressure. The resulting powder was collected via filtration through a medium porosity fritted funnel. The powder was washed with $Et_2O$ (~100 mL) and pentane (~150 mL). The solid was collected and dried further under reduced pressure to give diisopropylammonium; 4-spiro[7,9-dioxa-8-silanuidabicyclo[4.3.0]nona-1 (6),2,4-triene-8,8'-7,9-dioxa-8-silanuidabicyclo[4.3.0]nona-1,3,5-triene]-8-ylbutanenitrile 182 as a slightly pink powder.

LCMS method F: $[M+H]^-$=not detected, $t_R$=1.01 min

Preparation of Intermediate 183: 4-(1H-indazol-5-yl)butanenitrile

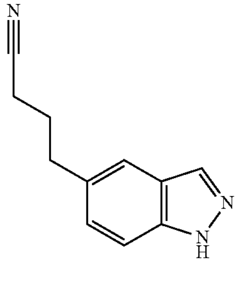 [SMILES: N#CCCCc1ccc2[nH]ncc2c1]

To a 500 mL round bottom flask equipped with a Teflon-coated magnetic stir bar was added 4,4'-di-tert-butyl-2,2'-bipyridine (134 mg, 0.5 mmol), and nickel(II) chloride ethylene glycol dimethyl ether complex (109 mg, 0.5 mmol). The vial was capped and purged with nitrogen, then 30 mL THE was introduced. The resulting suspension was heated briefly with a heat gun until the nickel and ligand were fully solubilized, yielding a pale green solution. The solution was cooled in an ice bath, resulting in the immediate precipitation of an evergreen solid. Solvents were then evaporated under reduced pressure to give a fine coating of the ligated nickel complex.

Once dry, 5-iodo-1H-indazole (2.440 g, 10.0 mmol, 1.0 equiv), diisopropylammonium; 4-spiro[7,9-dioxa-8-silanuidabicyclo[4.3.0]nona-1(6),2,4-triene-8,8'-7,9-dioxa-8-silanuida bicyclo[4.3.0]nona-1,3,5-triene]-8-ylbutanenitrile 182 (8.280 g, 20.0 mmol), and tris(2,2'-bipyridine)ruthenium(II) hexafluorophosphate (172 mg, 0.2 mmol) were added in succession.

The vial was then capped and purged four times. Under inert atmosphere, DMF (100 mL) was introduced. The vial containing all the reagents was further sealed with parafilm and stirred approximately 10 cm away from a PR160L LED PhotoReaction Lighting setup (2 LED with different wavelengths: 390 nm and 456 nm) and was stirred for 24 hours. A fan was blown across the reaction setup to suppress the heat generated by the latter (the reaction temperatures were estimated to be ~30° C.). The reaction mixture was allowed to stir for 24 more hours. The crude reaction mixture was poured in a separatory funnel and diluted with $H_2O$ (120 mL). The resulting suspension was extracted with Et2O (3×180 mL), and the combined organic extracts were washed with a saturated solution of $Na_2CO_3$ (2×120 mL) then $H_2O$ (120 mL), dried over anhydrous magnesium sulfate, filtered and concentrated under reduced pressure. The combined residue was purified by column chromatography on silica gel, eluting with EtOAc and hexanes (from 99/1 to 40/60) to obtain 4-(1H-indazol-5-yl)butanenitrile 183 as a white solid.

LCMS method F: $[M+H]^+$=186.3, $t_R$=1.75 min

Preparation of Intermediate 184: 4-(1-tetrahydropyran-2-ylindazol-5-yl)butanenitrile

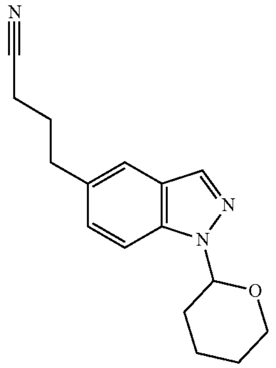 [SMILES: N#CCCCc1ccc2c(cnn2C2CCCCO2)c1]

To a solution of 4-(1H-indazol-5-yl)butanenitrile 183 (1.256 g, 6.79 mmol) in DCM (25 mL), 3,4-dihydro-2H-pyran (1.140 g, 1.24 mL, 13.58 mmol) and p-toluenesulfonic acid monohydrate (0.644 g, 3.39 mmol) were added and the reaction was stirred at room temperature for 24 hours. The residue was dissolved in ethyl acetate (150 mL), quenched with a 1 M aqueous $NaHCO_3$ solution (5 mL), washed with water (25 mL), brine (25 mL), dried over anhydrous magnesium sulfate, filtered and concentrated under reduced pressure. The crude product was purified by flashchromatography using cyclohexane/ethyl acetate (from 99/1 to 70/30) to give 4-(1-tetrahydropyran-2-ylindazol-5-yl)butanenitrile 184 as a colorless oil.

LCMS method F: $[M+H]^+$=not detected, $t_R$=2.36 min

Preparation of Intermediate 185: 4-(1-tetrahydropyran-2-ylindazol-5-yl)butan-1-amine

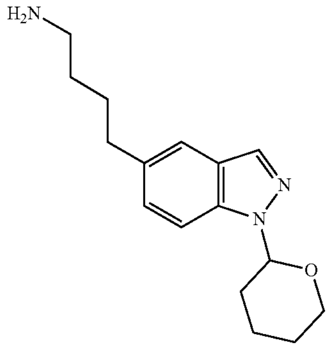 [SMILES: NCCCCc1ccc2c(cnn2C2CCCCO2)c1]

Lithium aluminium hydride 1.0 M solution in THE (14.3 mL, 14.30 mmol) was added dropwise to a solution of 4-(1-tetrahydropyran-2-ylindazol-5-yl)butanenitrile 184 (1.540 g, 5.72 mmol) in THE (20 mL) at 0° C. and stirred at room temperature for 24 hours. The mixture was quenched with a saturated aqueous solution of Rochelle salt (100 mL) and the resulting mixture was stirred overnight to break up the aluminium emulsions. The resulting biphasic medium was extracted with dichloromethane (2×150 mL). Combined organic layers were washed with brine (100 mL), dried over anhydrous magnesium sulfate, filtered and concentrated under reduced pressure to afford 4-(1-tetrahydropyran-2-ylindazol-5-yl)butan-1-amine 185 as a colorless oil.

LCMS method F: $[M+H]^+$=not detected, $t_R$=1.37 min

Preparation of Intermediate 186: (3-bromophenyl)methyl N-[4-(1-tetrahydropyran-2-ylindazol-5-yl)butyl]carbamate

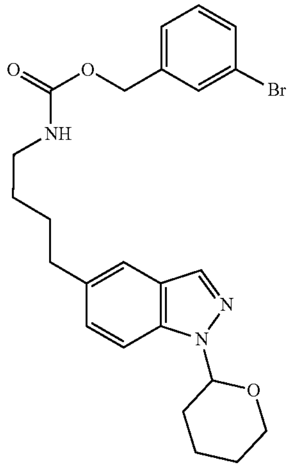 [SMILES: O=C(NCCCCc1ccc2c(cnn2C2CCCCO2)c1)OCc1cccc(Br)c1]

To a solution of 4-(1-tetrahydropyran-2-ylindazol-5-yl)butan-1-amine 185 (1.076 g, 3.94 mmol) in acetonitrile (120 mL) was added 1,1'-carbonyldiimidazole (0.701 g, 4.33 mmol). The reaction mixture was stirred at room temperature for 2 hours. The reaction mixture was then added dropwise to a solution of (3-bromophenyl)methanol (2.36 mL, 19.70 mmol) and cesium carbonate (12.805 g, 39.40 mmol) in acetonitrile (60 mL) at 90° C. The resulting mixture was stirred at the 90° C. for 5 hours. The reaction mixture was allowed to cool down to room temperature and filtered over a celite pad. The filtrate was evaporated under reduced pressure to afford a yellow oil. This residue was partitioned between ethyl acetate (150 mL) and water (100 mL). The organic layer was extracted twice with ethyl acetate (2×100 mL). The combined organic layer was washed with brine, dried over anhydrous magnesium sulfate, filtered and concentrated under reduced pressure. The resulting oil was purified by column chromatography on silica gel, using DCM/MeOH (from 1/0 to 9/1) as an eluant, the desired fractions were combined and the solvent was removed under reduced pressure to afford (3-bromophenyl) methyl N-[4-(1-tetrahydropyran-2-ylindazol-5-yl)butyl]carbamate 186 as a colorless oil.

LCMS method F: $[M+H]^+$=488.1, $t_R$=3.13 min

Preparation of Intermediate 187: 19-(oxan-2-yl)-8-oxa-10,19,20-triazatetracyclo[13.5.2.1$^{2,5}$.0$^{18,21}$]tricosa-1(20),2(23),3,5,15(22),16,18(21)-heptaen-9-one

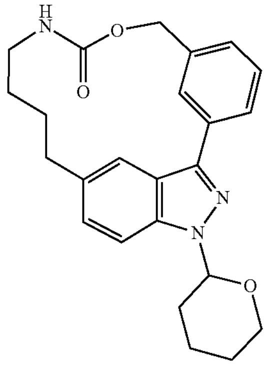 [SMILES: O=C1NCCCCc2ccc3c(c2)c(nn3C2CCCCO2)-c2cccc(c2)CO1]

To a solution of (3-bromophenyl)methyl N-[4-(1-tetrahydropyran-2-ylindazol-5-yl)butyl]carbamate 186 (340 mg, 0.70 mmol) in dry dioxane (68 mL), was added potassium acetate (137 mg, 1.40 mmol). An argon balloon with a long needle was placed in the reaction mixture, bubbling for 15 minutes. Tricyclohexylphosphine (39 mg, 0.14 mmol) and palladium acetate (15 mg, 0.07 mmol) were added and the reaction mixture was placed in a sand bath, pre-heated at 200° C., and stirred at this temperature for 16 hours. The reaction mixture was diluted with water. The aqueous layer was extracted with ethyl acetate (2×20 mL). The combined organic layer was washed with brine, dried over anhydrous magnesium sulfate, filtered and evaporated under reduced pressure. The crude product was purified by column chromatography on silica gel (DCM/MeOH/EtOAc: from 100/0/0 to 95/2.5/2.5) to afford the first fraction of the expected macrocycle (0.015 g) and another fraction which was a mixture of expected macrocycle and dehalogenated side-product benzyl N-[4-(1-tetrahydropyran-2-ylindazol-5-yl) butyl]carbamate (0.119 g). This second fraction was purified again by preparative TLC, using (DCM/MeOH/EtOAc=95/2.5/2.5) as an eluant. Pure macrocycle was recovered from the TLC plate and combined with the first fraction from column chromatography to afford 19-(oxan-2-yl)-8-oxa-10,19,20-triazatetracyclo[13.5.2.1$^{2,6}$.0$^{18,21}$]tricosa-1(20),2(23),3,5,15(22),16,18(21)-heptaen-9-one 187 as a white solid.

LCMS method F: $[M+H]^+$=406.2, $t_R$=2.92 min

Preparation of Example 142: 8-oxa-10,19,20-triazatetracyclo[13.5.2.1$^{2,6}$.0$^{18,21}$]tricosa-1(20),2(23),3,5,15(22),16,18(21)-heptaen-9-one

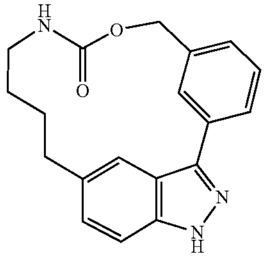 [SMILES: O=C1NCCCCc2ccc3[nH]nc(c3c2)-c2cccc(c2)CO1]

To a solution of 19-(oxan-2-yl)-8-oxa-10,19,20-triazatetracyclo[13.5.2.1$^{2,6}$.0$^{18,21}$]tricosa-1(20),2(23),3,5,15(22),16,18(21)-heptaen-9-one 187 (30 mg, 0.074 mmol) in methanol (4.0 mL) and water (0.4 mL) was added p-toluenesulfonic acid monohydrate (70 mg, 0.36 mmol) and the reaction mixture was heated to 65° C. for 4 hours. The reaction mixture was concentrated under reduced pressure and the crude was neutralized by slow addition of a saturated aqueous sodium hydrogen carbonate solution. The resulting suspension was diluted with ethyl acetate.

After separation, the aqueous layer was extracted with ethyl acetate. The combined organic layers were washed with water and brine, dried over anhydrous magnesium sulfate, filtered and evaporated under reduced pressure. The crude was purified by preparative TLC on silica gel, eluting with DCM/MeOH 95/5, to give the expected product. DCM (5 mL) was added to give a white suspension. The precipitate was filtered off and rinsed with $CH_2Cl_2$ (2×3 mL). The solid was recovered. Remaining solvents were removed under reduced pressure at 40° C. to obtain 8-oxa-10,19,20-triazatetracyclo[13.5.2.1$^{2,6}$.0$^{18,21}$]tricosa-1(20),2(23),3,5,15(22),16,18(21)-heptaen-9-one example 142 as a white solid.

LCMS method F: $[M+H]^+$=322.3, $t_R$=2.25 min

LCMS method G: $[M+H]^+$=322.3, $t_R$=2.25 min $^1$H NMR (400 MHz, d6-DMSO, 80° C.) δ 12.87 (1H, br. s), 7.92 (1H, s), 7.87 (1H, d, J=8.0 Hz), 7.76 (1H, s), 7.54 (1H, br. s), 7.51-7.42 (2H, m), 7.27 (1H, d, J=8.0 Hz), 7.20 (1H, dd, J=1.6, 8.8 Hz), 5.28 (2H, s), 3.22-3.19 (2H, m), 2.92-2.88 (2H, m), 1.95-1.90 (2H, m), 1.72-1.63 (2H, m) ppm.

Example 143: (13R)-5-methoxy-13-methyl-8,14-dioxa-4,10,19,20-tetraazatetracyclo[13.5.2.$1^{2,6}$.$0^{18,21}$]tricosa-1(20),2,4,6(23),15,17,21-heptaen-9-one

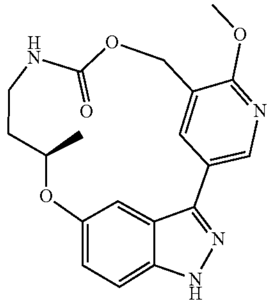 [SMILES: COc1ncc2cc1COC(=O)NCC[C@@H](C)Oc1ccc3[nH]nc-2c3c1]

Example 143 is prepared according to the synthesis route described in general Scheme O.

Preparation of Intermediate 184: 5-bromo-2-methoxy-pyridine-3-carbaldehyde

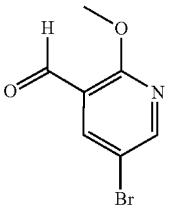

To a solution of 3,5-dibromo-2-methoxy-pyridine (1.62 g, 6.11 mmol) in dry diethyl ether (24 mL) at −78° C. was added dropwise a solution of n-BuLi in hexane (4.16 M titrated) (1.47 mL, 6.11 mmol). The reaction mixture was stirred at −78° C. for 15 min then N,N-dimethylformamide (0.95 mL, 12.22 mmol) was added dropwise and the reaction mixture was stirred at −50° C. for 30 min. The reaction mixture was quenched dropwise with a saturated aqueous ammonium chloride solution at −78° C., warmed to room temperature and stirred for 30 min. Diethyl ether was added to the solution. After separation, the aqueous layer was extracted with diethyl ether.

The organic layer was washed with brine, dried over anhydrous sodium sulfate, filtered and evaporated under reduced pressure to afford a yellow solid which was recrystallized in hexane to afford 5-bromo-2-methoxy-pyridine-3-carbaldehyde intermediate 184 as a yellow powder.

$^1$H NMR (400 MHz, $CDCl_3$) δ 10.32 (1H, s), 8.44 (1H, d, J=2.7 Hz), 8.22 (1H, d, J=2.7 Hz), 4.09 (3H, m) ppm.

Preparation of Intermediate 185: (5-bromo-2-methoxy-3-pyridyl)methanol

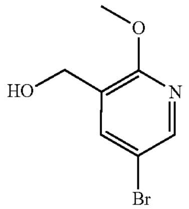

To a solution of 5-bromo-2-methoxy-pyridine-3-carbaldehyde intermediate 184 (997 mg, 4.64 mmol) in methanol (21 mL) at 0° C. was added sodium borohydride (176 mg, 4.64 mmol) in one portion. The reaction mixture was stirred at room temperature for 2 h. The reaction mixture was evaporated under reduced pressure. The residue was diluted with dichloromethane and a sodium bicarbonate saturated solution. After separation, the aqueous layer was extracted with dichloromethane. The organic layer was washed with brine, dried over anhydrous sodium sulfate, filtered and evaporated under reduced pressure. The residue was purified by silica gel column chromatography using cyclohexane/ethyl acetate 100/0 to 50/50 as eluent to afford (5-bromo-2-methoxy-3-pyridyl)methanol intermediate 185 as yellow crystals.

LCMS method F: $[M+H]^+$=218-220, $t_R$=1.81 min

Preparation of Intermediate 186: [5-[5-[tert-butyl (dimethyl)silyl]oxy-1-tetrahydropyran-2-yl-indazol-3-yl]-2-methoxy-3-pyridyl]methanol

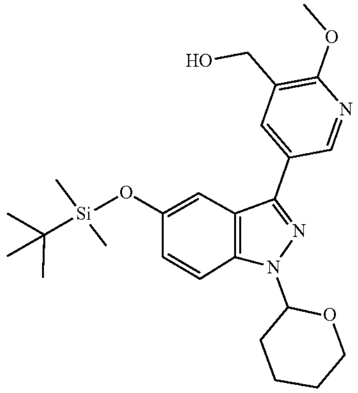 [SMILES: COc1ncc(-c2nn(C3CCCCO3)c3ccc(O[Si](C)(C)C(C)(C)C)cc23)cc1CO]

To a solution of tert-butyl-dimethyl-[1-tetrahydropyran-2-yl-3-(4,4,5,5-tetramethyl-1,3,2-dioxaborolan-2-yl)indazol-5-yl]oxy-silane (1.24 g, 2.71 mmol) in 1,4-dioxane (20 mL) and water (2 mL) at room temperature was added (5-bromo-2-methoxy-3-pyridyl)methanol intermediate 185 (588 mg, 2.71 mmol), potassium phosphate tribasic (1.72 g, 8.13 mmol). The reaction mixture was degassed by bubbling argon for 15 min, then XPhos (388 mg, 0.8 mmol) and tetrakis(triphenylphosphine)-palladium(0) (312 mg, 0.27 mmol) were added. The reaction mixture was stirred at 80° C. for 12 h. The reaction mixture was evaporated under reduced pressure. The residue was diluted with ethyl acetate and. After separation, the aqueous layer was extracted with ethyl acetate. The organic layer was washed with brine, dried over sodium sulfate, filtered and evaporated under reduced pressure. The residue was purified by silica gel column chromatography using cyclohexane/ethyl acetate 100/0 to 0/100 to afford [5-[5-[tert-butyl(dimethyl)silyl]oxy-1-tetrahydropyran-2-yl-indazol-3-yl]-2-methoxy-3-pyridyl] methanol intermediate 186 as a light yellow oil.

LCMS method F: $[M+H]^+$=470.4, $t_R$=3.52 min

Preparation of Intermediate 187: (13R)-5-methoxy-13-methyl-19-(oxan-2-yl)-8,14-dioxa-4,10,19,20-tetraazatetracyclo[13.5.2.1$^{2,6}$.0$^{18,21}$]tricosa-1(20),2,4,6(23),15,17,21-heptaen-9-one

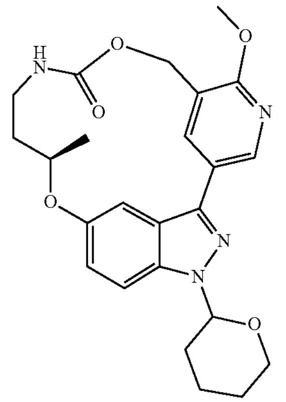 [SMILES: COc1ncc2cc1COC(=O)NCC[C@@H](C)Oc1ccc3c(c1)c-2nn3C1CCCCO1]

To a solution of [5-[5-[tert-butyl(dimethyl)silyl]oxy-1-tetrahydropyran-2-yl-indazol-3-yl]-2-methoxy-3-pyridyl] methanol intermediate 186 (824 mg, 1.76 mmol) in anhydrous acetonitrile (190 mL) was added cesium carbonate (2.86 g, 8.8 mmol) and [(1S)-3-(benzyloxycarbonyl amino)-1-methyl-propyl]methanesulfonate (582 mg, 1.93 mmol) in acetonitrile (10 mL). The reaction mixture was stirred at 80° C. for 24 h. The reaction mixture was filtered and the filtrate was evaporated under reduced pressure. The residue was purified by silica gel column chromatography using cyclohexane/ethyl acetate 50/50 as eluent to afford (13R)-5-methoxy-13-methyl-19-(oxan-2-yl)-8,14-dioxa-4,10,19,20-tetraazatetracyclo[13.5.2.1$^{2,6}$.0$^{18,21}$]tricosa-1(20),2,4,6(23),15,17,21-heptaen-9-one intermediate 187 as a colorless oil.

LCMS method F: $[M+H]^+$=453.4, $t_R$=2.82 min

Preparation of Example 143: (13R)-5-methoxy-13-methyl-8,14-dioxa-4,10,19,20-tetraazatetracyclo[13.5.2.1$^{2,6}$.0$^{18,21}$]tricosa-1(20),2,4,6(23),15,17,21-heptaen-9-one

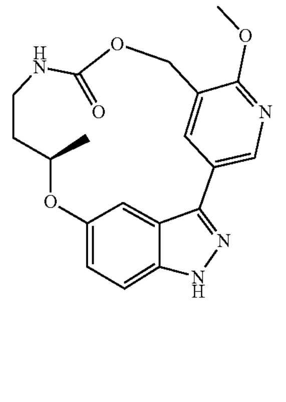 [SMILES: COc1ncc2cc1COC(=O)NCC[C@@H](C)Oc1ccc3[nH]nc-2c3c1]

To a solution of (13R)-5-methoxy-13-methyl-19-(oxan-2-yl)-8,14-dioxa-4,10,19,20-tetraaza tetracyclo[13.5.2.1$^{2,6}$.0$^{18,21}$]tricosa-1(20),2,4,6(23),15,17,21-heptaen-9-one intermediate 187 (170 mg, 0.38 mmol) in methanol (7 mL) and water (1.2 mL) was added p-toluenesulfonic acid monohydrate (357 mg, 1.88 mmol). The reaction mixture was heated at 80° C. for 18 h. The solvent was evaporated under reduced pressure. The residue was dissolved in dichloromethane and a saturated aqueous solution of bicarbonate. After separation, the aqueous layer was extracted with dichloromethane. The organic layer was washed with brine, dried over anhydrous sodium sulfate, filtered and evaporated under reduced pressure. The residue was triturated in diethyl ether, filtered and dried to afford (13R)-5-methoxy-13-methyl-8,14-dioxa-4,10,19,20-tetraazatetracyclo[13.5.2.1$^{2,6}$.0$^{18,21}$]tricosa-1(20),2,4,6(23),15,17,21-heptaen-9-one example 143 as a white solid.

LCMS method F: $[M+H]^+$=369.3, $t_R$=2.15 min

LCMS method G: $[M+H]^+$=369.3, $t_R$=2.13 min $^1$H NMR (400 MHz, d6-DMSO) δ 13.13 (1H, s), 8.67 (1H, d, J=1.7 Hz), 8.11-8.07 (2H, m), 7.52-7.48 (1H, m), 7.24 (1H, d, J=0.8 Hz), 6.98 (1H, dd, J=2.1, 9.1 Hz), 5.45-5.42 (1H, m), 4.95-4.91 (1H, m), 4.60-4.54 (1H, m), 3.98 (3H, s), 3.53 (1H, s), 2.97-2.88 (1H, m), 2.33 (1H, s), 1.41 (4H, d, J=5.9 Hz) ppm.

Example 144: (13R)-13-methyl-8,14-dioxa-4,10,19,20-tetraazatetracyclo[13.5.2.1$^{2,6}$.0$^{18,21}$]tricosa-1(20),2,6(23),15,17,21-hexaene-5,9-dione

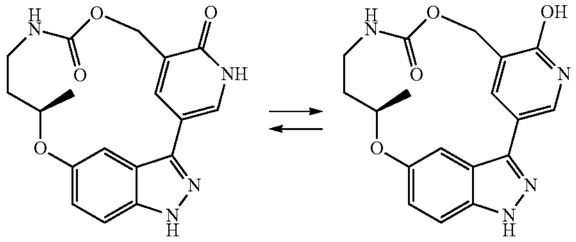 [SMILES: C[C@@H]1CCNC(=O)OCc2cc(c[nH]c2=O)-c2n[nH]c3ccc(cc23)O1 ; C[C@@H]1CCNC(=O)OCc2cc(cnc2O)-c2n[nH]c3ccc(cc23)O1]

Example 144 is prepared by demethylation and concomitant deprotection of intermediate 187. A mixture of (13R)-5-methoxy-13-methyl-19-(oxan-2-yl)-8,14-dioxa-4,10,19,20-tetraazatetracyclo[13.5.2.1$^{2,6}$.0$^{18,21}$]tricosa-1(20),2,4,6(23),15,17,21-heptaen-9-one intermediate 187 (150 mg, 0.33 mmol), sodium iodide (99 mg, 0.66 mmol), chlorotrimethylsilane (83 μL, 0.66 mmol) and acetonitrile (3 mL) was heated at 70° C. for 4 h. The solvent was evaporated under reduced pressure. Ethyl acetate and a saturated aqueous solution of bicarbonate were added. After separation, the aqueous layer was extracted with ethyl acetate. The organic layer was washed with brine, dried over anhydrous sodium sulfate, filtered and evaporated under reduced pressure. The residue was purified by silica gel column chromatography using dichloromethane/methanol 90/10 as eluent to afford (13R)-13-methyl-8,14-dioxa-4,10,19,20-tetraazatetracyclo[13.5.2.1$^{2,6}$.0$^{18,21}$]tricosa-1(20),2,6(23),15,17,21-hexaene-5,9-dione example 144 as a light yellow solid.

LCMS method F: $[M+H]^+$=355.3, $t_R$=1.70 min

LCMS method G: $[M+H]^+$=355.3, $t_R$=1.69 min $^1$H NMR (400 MHz, d6-DMSO) δ13.00 (1H, s), 12.03 (1H, s), 8.01 (1H, t, J=6.2 Hz), 7.90 (1H, s), 7.81 (1H, s), 7.48-7.44 (1H, m), 7.16 (1H, s), 6.96 (1H, dd, J=1.9, 9.1 Hz), 5.25 (1H, m), 4.80 (1H, m), 4.57-4.51 (1H, m), 3.53 (1H, m), 2.91 (1H, s), 2.31 (1H, m), 1.39 (4H, d, J=6.1 Hz) ppm.

Example 145: 4-methyl-8,14-dioxa-3,4,10,19,20-pentaazatetracyclo[13.5.2.1$^{2,5}$.0$^{18,21}$]tricosa-1(20),2,5(23),15(22),16,18(21)-hexaen-9-one

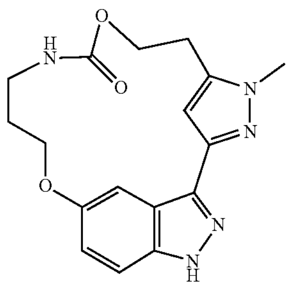 [SMILES: Cn1nc2cc1CCOC(=O)NCCCOc1ccc3[nH]nc-2c3c1]

Example 145 is prepared according to the synthesis route described in general Scheme L.

Preparation of Intermediate 188: (2-(5-bromo-2-methyl-pyrazol-3-yl)ethyl N-(3-hydroxy propyl) carbamate

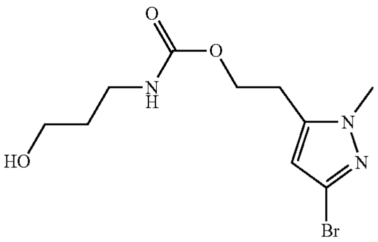 [SMILES: Cn1nc(Br)cc1CCOC(=O)NCCCO]

To a solution of 4-nitrophenyl chloroformate (432 mg, 2.15 mmol) and pyridine (0.315 mL, 3.90 mmol) in dichloromethane (10 mL) at room temperature was added dropwise 2-(5-bromo-2-methyl-pyrazol-3-yl)ethanol (400 mg, 1.95 mmol) in dichloromethane (5 mL). The reaction mixture was stirred at room temperature for 1 h. A mixture of 3-aminopropan-1-ol (161 mg, 2.15 mmol) and DIPEA (0.678 mL, 3.90 mmol) in dichloromethane (5 mL) was added. The reaction mixture was stirred at room temperature for 16 h. The residue was diluted with 0.5N aqueous sodium hydroxide solution and extracted with dichloromethane. The combined organic layers were washed once again with 0.5N aqueous sodium hydroxide solution and dried over anhydrous sodium sulfate and concentrated under reduced pressure. The residue was purified by silica gel column chromatography using dichloromethane/ethyl acetate 100/0 to 0/100 as eluent to afford 2-(5-bromo-2-methyl-pyrazol-3-yl)ethyl N-(3-hydroxypropyl)carbamate intermediate 188 as a colorless oil.

LCMS method F: $[M+H]^+$=306-308, $t_R$=2.25 min

Preparation of Intermediate 189: 2-[5-[5-[tert-butyl(dimethyl)silyl]oxy-1-tetrahydro-pyran-2-yl-indazol-3-yl]-2-methyl-pyrazol-3-yl]ethyl-N-(3-hydroxypropyl)carbamate

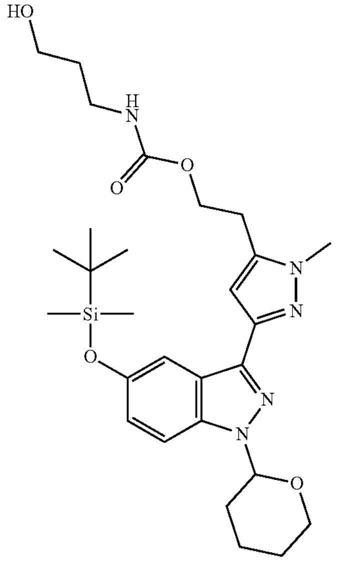 [SMILES: Cn1nc(-c2nn(C3CCCCO3)c3ccc(O[Si](C)(C)C(C)(C)C)cc23)cc1CCOC(=O)NCCCO]

To a solution of tert-butyl-dimethyl-[1-tetrahydropyran-2-yl-3-(4,4,5,5-tetramethyl-1,3,2-dioxaborolan-2-yl)indazol-5-yl]oxy-silane (600 mg, 1.31 mmol) in 1,4-dioxane (13 mL) and water (1.3 mL) at room temperature was added 2-(5-bromo-2-methyl-pyrazol-3-yl)ethyl N-(3-hydroxypropyl)carbamate intermediate 188 (441 mg, 1.44 mmol), potassium phosphate tribasic (833 mg, 3.93 mmol), XPhos (62 mg, 0.13 mmol) and tetrakis(triphenylphosphine)palladium(0) (76 mg, 0.07 mmol). The reaction mixture was stirred under microwave conditioned at 90° C. for 1 h. The residue was diluted with saturated aqueous sodium chloride solution and extracted with ethyl acetate. The combined organic layers were dried over anhydrous sodium sulfate and concentrated under reduced pressure. The residue was purified by silica gel column chromatography using cyclohexane/ethyl acetate 100/0 to 0/100 as eluent to afford 2-[5-[5-[tert-butyl(dimethyl)silyl]oxy-1-tetrahydropyran-2-yl-indazol-3-yl]-2-methyl-pyrazol-3-yl]ethyl N-(3-hydroxypropyl)carbamate intermediate 189 as a colorless oil.

LCMS method F: $[M+H]^+$=558.4, $t_R$=3.17 min

Preparation of Intermediate 190: 3-[2-[5-[5-[tert-butyl(dimethyl)silyl]oxy-1-tetrahydro-pyran-2-yl-indazol-3-yl]-2-methyl-pyrazol-3-yl]ethoxycarbonylamino]propyl methanesulfonate

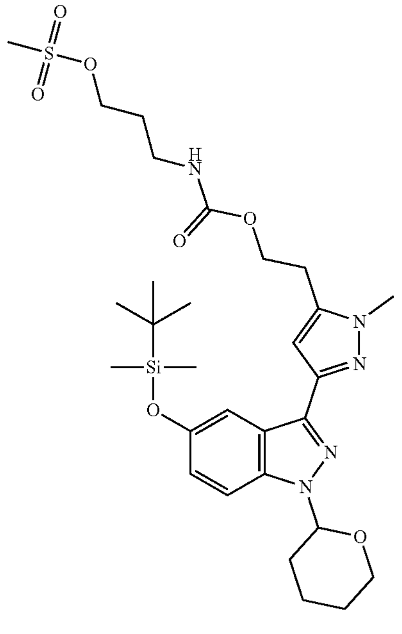

To a solution of 2-[5-[5-[tert-butyl(dimethyl)silyl]oxy-1-tetrahydropyran-2-yl-indazol-3-yl]-2-methyl-pyrazol-3-yl] ethyl N-(3-hydroxypropyl)carbamate intermediate 189 (470 mg, 0.84 mmol) and triethylamine (0.235 mL, 1.69 mmol) in dichloromethane (6 mL) was added at 0° C. methanesulfonyl chloride (0.085 mL, 1.10 mmol) in dichloromethane (2 mL). The reaction mixture was stirred at room temperature for 16 h. The residue was diluted with saturated sodium chloride solution and extracted with dichloromethane. The combined organic layers were dried over anhydrous sodium sulfate and concentrated under reduced pressure to afford 3-[2-[5-[5-[tert-butyl(dimethyl)silyl]oxy-1-tetrahydropyran-2-yl-indazol-3-yl]-2-methyl-pyrazol-3-yl] ethoxycarbonylamino]propyl methanesulfonate intermediate 190 as a yellow oil which was used in the next step without further purification.

LCMS method F: $[M+H]^+$=636.4, $t_R$=3.32 min

Preparation of Intermediate 191: 4-methyl-19-(oxan-2-yl)-8,14-dioxa-3,4,10,19,20-pentaazatetracyclo[13.5.2.1$^{2,5}$.0$^{18,21}$]tricosa-1(20),2,5(23),15(22),16,18(21)-hexaen-9-one

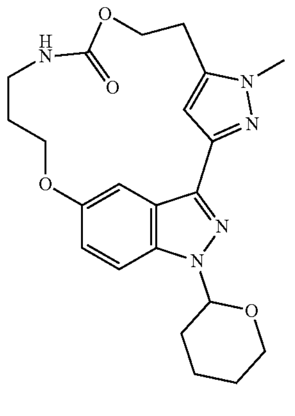 [SMILES: Cn1nc2cc1CCOC(=O)NCCCOc1ccc3c(c1)c-2nn3C1CCCCO1]

To a suspension of cesium carbonate (0.824 g, 2.53 mmol) in anhydrous N,N-dimethylformamide (168 mL) at 80° C. was added dropwise 3-[2-[5-[5-[tert-butyl(dimethyl)silyl] oxy-1-tetrahydropyran-2-yl-indazol-3-yl]-2-methyl-pyrazol-3-yl]ethoxy carbonylamino]propyl methanesulfonate intermediate 190 (0.536 g, 0.84 mmol) in N,N-dimethylformamide (168 mL). The reaction mixture was stirred at 80° C. for 1 h. The reaction mixture was filtered and concentrated under reduced pressure then diluted with saturated aqueous sodium chloride solution and extracted with ethyl acetate. The combined organic layers were dried over anhydrous sodium sulfate and concentrated under reduced pressure. The residue was purified by silica gel column chromatography using dichloromethane/ethyl acetate, 100/0 to 50/50 as eluent to afford 4-methyl-19-(oxan-2-yl)-8,14-dioxa-3,4,10,19,20-pentaazatetracyclo[13.5.2.1$^{2,5}$.0$^{18,21}$]tricosa-1(20),2,5(23),15(22),16,18(21)-hexaen-9-one intermediate 191 as a white solid.

LCMS method F: $[M+H]^+$=426.4, $t_R$=2.10 min

Preparation of Example 145: 4-methyl-8,14-dioxa-3,4,10,19,20-pentaazatetracyclo[13.5.2.1$^{2,5}$.0$^{18,21}$] tricosa-1(20),2,5(23),15(22),16,18(21)-hexaen-9-one

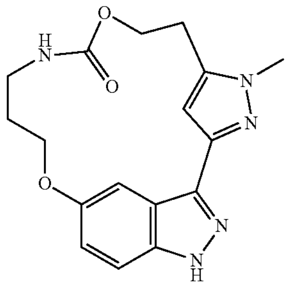 [SMILES: Cn1nc2cc1CCOC(=O)NCCCOc1ccc3[nH]nc-2c3c1]

To a solution of 4-methyl-19-(oxan-2-yl)-8,14-dioxa-3,4,10,19,20-pentaazatetracyclo[13.5.2.1$^{2,5}$.0$^{18,21}$]tricosa-1(20),2,5(23),15(22),16,18(21)-hexaen-9-one intermediate 191 (55 mg, 0.13 mmol) in methanol (3.5 mL) and water (0.5 mL) was added p-toluenesulfonic acid monohydrate (123 mg, 0.65 mmol). The reaction mixture was stirred at 65° C. for 2 h. The reaction mixture was concentrated under reduced pressure and the residue was neutralized by slow addition of saturated aqueous sodium bicarbonate solution. The residue was diluted with ethyl acetate. After separation, the aqueous phase was extracted with ethyl acetate. The combined organic layers were washed with brine, dried over anhydrous sodium sulfate, filtered and evaporated under reduced pressure. The residue was purified by silica gel column chromatography using dichloromethane/methanol 100/0 to 96/4 as eluent. The solid was crystallized in acetonitrile to give 4-methyl-8,14-dioxa-3,4,10,19,20-pentaazatetracyclo[13.5.2.1$^{2,5}$.0$^{18,21}$]tricosa-1(20),2,5(23),15(22),16,18(21)-hexaen-9-one example 145 as a white solid.

LCMS method F: $[M+H]^+$=342.3, $t_R$=1.63 min

LCMS method G: $[M+H]^+$=342.3, $t_R$=1.63 min $^1$H NMR (400 MHz, d6-DMSO) δ 12.91 (1H, s), 7.74 (1H, t, J=6.0 Hz), 7.45-7.41 (1H, m), 7.11 (1H, d, J=1.9 Hz), 6.93 (1H, dd, J=2.2, 8.8 Hz), 6.38 (1H, s), 4.47-4.44 (2H, m), 4.27-4.21 (2H, m), 3.84-3.82 (3H, m), 3.10-3.02 (4H, m), 1.91-1.84 (2H, m) ppm.

Example 146: (13R)-16-fluoro-13-methyl-8,14-dioxa-10,19,20,23-tetraazatetracyclo[13.5.2.1$^{2,6}$.0$^{18,21}$]tricosa-1(20),2,4,6(23),15,17,21-heptaen-9-one

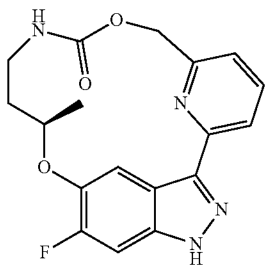 [SMILES: C[C@@H]1CCNC(=O)OCc2cccc(n2)-c2n[nH]c3cc(F)c(cc23)O1]

Example 146 is prepared according to the synthesis route described in general Scheme O.

Preparation of Intermediate 192: tert-butyl-[6-fluoro-1-tetrahydropyran-2-yl-3-(4,4,5,5-tetramethyl-1,3,2-dioxaborolan-2-yl)indazol-5-yl]oxy-dimethyl-silane

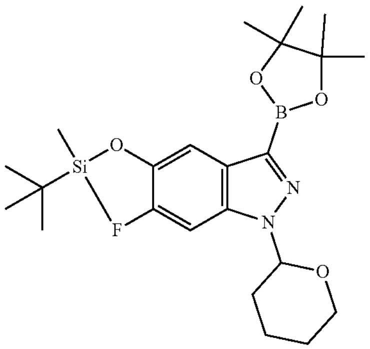

A mixture of tert-butyl-dimethyl-(1-tetrahydropyran-2-ylindazol-5-yl)oxy-silane (500 mg, 1.43 mmol), TBME (dried on 3 A molecular sieves) (6 mL), 4,4,5,5-tetramethyl-2-(4,4,5,5-tetramethyl-1,3,2-dioxaborolan-2-yl)-1,3,2-dioxaborolane (711 mg, 1.43 mmol), 4,4'-di-tert-butyl-2,2'-bipyridine (23 mg, 0.09 mmol) and (1,5-cyclooctadiene)(methoxy)iridium(I) dimer (19 mg, 0.03 mmol) was purged with argon and stirred at 80° C. for 16 h. The solvent was evaporated under reduced pressure and the residue was dissolved with ethyl acetate and water. After separation, the aqueous phase was extracted with ethyl acetate. The organic layers were dried over anhydrous sodium sulfate, filtered and evaporated under reduced pressure to afford tert-butyl-[6-fluoro-1-tetrahydropyran-2-yl-3-(4,4,5,5-tetramethyl-1,3,2-dioxaborolan-2-yl) indazol-5-yl]oxy-dimethyl-silane intermediate 192 as a brown oil which was used in next step without further purification.

LCMS method F: $[M+H]^+$=477.2, $t_R$=3.87 min (major pic observed as boronic acid $[M+H]^+$=395.2, $t_R$=3.18 min)

Preparation of Intermediate 193: [6-[5-[tert-butyl(dimethyl)silyl]oxy-6-fluoro-1-tetrahydro pyran-2-yl-indazol-3-yl]-2-pyridyl]methanol

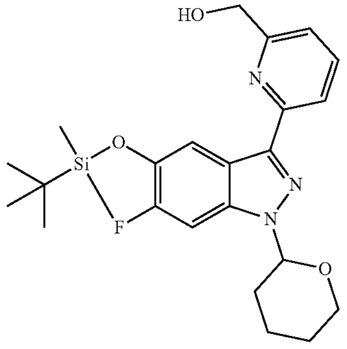

To a solution of tert-butyl-[6-fluoro-1-tetrahydropyran-2-yl-3-(4,4,5,5-tetramethyl-1,3,2-dioxaborolan-2-yl)indazol-5-yl]oxy-dimethyl-silane intermediate 192 (1.00 g, 2.10 mmol) in 1,4-dioxane (10 mL) and water (1 ml) at room temperature was added (6-bromo-2-pyridyl)methanol (302 mg, 1.62 mmol) and potassium phosphate tribasic (1.03 g, 4.86 mmol). The reaction mixture was degassed with argon for 15 min, then XPhos (76 mg, 0.16 mmol) and tetrakis (triphenylphosphine)palladium(0) (56 mg, 0.05 mmol) were added. The reaction mixture was stirred at 80° C. for 45 min under microwave radiations. The solvent was evaporated under reduced pressure. The residue was dissolved in ethyl acetate and water. After separation, the aqueous layer was extracted with ethyl acetate. The organic layer was washed with brine, dried over anhydrous sodium sulfate, filtered and evaporated under reduced pressure. The residue was purified by silica gel column chromatography using cyclohexane/ethyl acetate 50/50 as eluent to afford [6-[5-[tert-butyl(dimethyl)silyl]oxy-6-fluoro-1-tetrahydropyran-2-yl-indazol-3-yl]-2-pyridyl]methanol intermediate 193 as a colorless oil.

LCMS method F: $[M+H]^+$=458.2, $t_R$=3.55 min

Preparation of Intermediate 194: (13R)-16-fluoro-13-methyl-19-(oxan-2-yl)-8,14-dioxa-10,19,20,23-tetraazatetracyclo[13.5.2.1$^{2,6}$.0$^{18,21}$]tricosa-1(20),2,4,6(23),15,17,21-heptaen-9-one

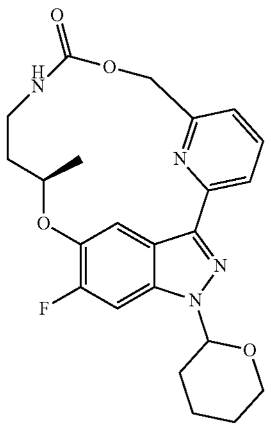 [SMILES: C[C@@H]1CCNC(=O)OCc2cccc(n2)-c2nn(C3CCCCO3)c3cc(F)c(cc23)O1]

To a solution of [6-[5-[tert-butyl(dimethyl)silyl]oxy-6-fluoro-1-tetrahydropyran-2-yl-indazol-3-yl]-2-pyridyl] methanol intermediate 193 (400 mg, 0.87 mmol) in anhydrous acetonitrile (90 mL) was added cesium carbonate (2.83 g, 8.7 mmol) and a solution of [(1S)-3-(benzyloxy carbonylamino)-1-methyl-propyl]methanesulfonate (290 mg, 0.96 mmol) in acetonitrile (10 mL). The reaction mixture was stirred at 80° C. for 24 h. The reaction mixture was filtered and the filtrate was evaporated under reduced pressure. The residue was triturated in diethyl ether, filtered and dried to afford (13R)-16-fluoro-13-methyl-19-(oxan-2-yl)-8,14-dioxa-10,19,20,23-tetraazatetracyclo[13.5.2.1$^{2,6}$.0$^{18,21}$]tricosa-1(20),2,4,6(23),15,17,21-heptaen-9-one intermediate 194 as an off-white powder.

LCMS method F: $[M+H]^+$=441.2, $t_R$=2.78 min

Preparation of Example 146: (13R)-16-fluoro-13-methyl-8,14-dioxa-10,19,20,23-tetraaza tetracyclo [13.5.2.1$^{2,6}$.0$^{18,21}$]tricosa-1(20),2,4,6(23),15,17,21-heptaen-9-one

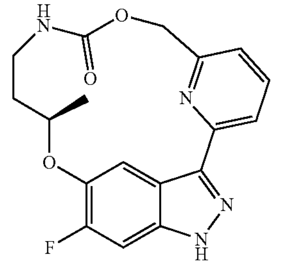 [SMILES: C[C@@H]1CCNC(=O)OCc2cccc(n2)-c2n[nH]c3cc(F)c(cc23)O1]

To a solution of afford (13R)-16-fluoro-13-methyl-19-(oxan-2-yl)-8,14-dioxa-10,19,20,23-tetraazatetracyclo [13.5.2.1$^{2,6}$.0$^{18,21}$]tricosa-1(20),2,4,6(23),15,17,21-heptaen-9-one intermediate 194 (160 mg, 0.36 mmol) in methanol (4 mL) and water (0.7 mL) was added p-toluenesulfonic acid monohydrate (345 mg, 1.82 mmol). The reaction mixture was heated at 80° C. for 18 h. The solvent was evaporated under reduced pressure. The residue was dissolved in dichloromethane (20 mL) and saturated aqueous solution of sodium bicarbonate (20 mL). After separation, the aqueous layer was extracted with dichloromethane (10 mL). The organic layer was washed with brine, dried over anhydrous sodium sulfate, filtered and evaporated under reduced pressure. The residue was triturated with diethyl ether, filtered and dried to afford (13R)-16-fluoro-13-methyl-8,14-dioxa-10,19,20,23-tetraazatetracyclo[13.5.2.1$^{2,6}$.0$^{18,21}$]tricosa-1(20),2,4,6(23),15,17,21-heptaen-9-one example 146 as a white powder.

LCMS method F: $[M+H]^+$=357.1, $t_R$=2.10 min

LCMS method G: $[M+H]^+$=357.2, $t_R$=2.09 min $^1$H NMR (400 MHz, d6-DMSO) δ 13.31 (1H, s), 8.06 (2H, dd, J=8.2, 15.9 Hz), 7.84 (1H, t, J=7.9 Hz), 7.74 (1H, dd, J=4.8, 6.7 Hz), 7.44 (1H, d, J=10.8 Hz), 7.29-7.26 (1H, m), 5.58 (1H, s), 5.10-5.06 (1H, m), 4.64 (1H, s), 3.52-3.50 (1H, m), 2.96 (1H, s), 2.23-2.20 (1H, m), 1.51 (1H, s), 1.40 (3H, d, J=6.1 Hz) ppm.

Example 147: 7,13-dioxa-4-thia-9,18,19,22-tetraaza-tetracyclo[12.5.2.1$^{2,5}$.0$^{17,20}$]docosa-1(19),2,5(22),14(21),15,17(20)-hexaen-8-one

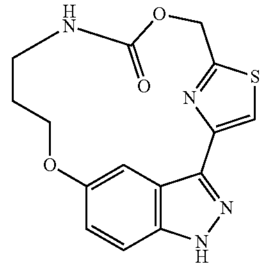 [SMILES: O=C1NCCCOc2ccc3[nH]nc(c3c2)-c2csc(n2)CO1]

Example 147 is prepared according to the synthesis route described in general Scheme L.

Preparation of Intermediate 195: (4-bromothiazol-2-yl)methyl-N-(3-hydroxypropyl) carbamate

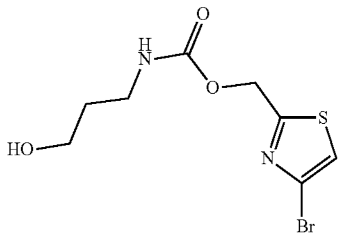 [SMILES: O=C(NCCCO)OCc1nc(Br)cs1]

To a solution of 4-nitrophenyl chloroformate (572 mg, 2.84 mmol) and pyridine (0.416 mL, 5.15 mmol) in dichloromethane (10 mL) was added dropwise at room temperature (4-bromothiazol-2-yl)methanol (500 mg, 2.58 mmol) in dichloromethane (3 mL). The reaction mixture was stirred at room temperature for 1 h. A mixture of 3-aminopropan-1-ol (213 mg, 2.84 mmol) and DIPEA (0.896 mL, 5.15 mmol) in dichloromethane (2 mL) was added. The reaction mixture was stirred at room temperature for 2 h. The residue was diluted with 0.5N aqueous sodium hydroxide solution and extracted with dichloromethane. The combined organic layer was washed once again with 0.5N aqueous sodium hydroxide solution and dried over anhydrous sodium sulfate and concentrated under reduced pressure. The residue was purified by silica gel column chromatography using dichloromethane/ethyl acetate 100/0 to 40/60 as eluent to afford (4-bromothiazol-2-yl)methyl N-(3-hydroxypropyl)carbamate intermediate 195 as a colorless oil which crystallized.

LCMS method F: $[M+H]^+$=295-297, $t_R$=1.51 min

Preparation of Intermediate 196: 2-[4-[5-[tert-butyl(dimethyl)silyl]oxy-1-tetrahydropyran-2-yl-indazol-3-yl]thiazol-2-yl]ethyl-N-(3-hydroxypropyl) carbamate

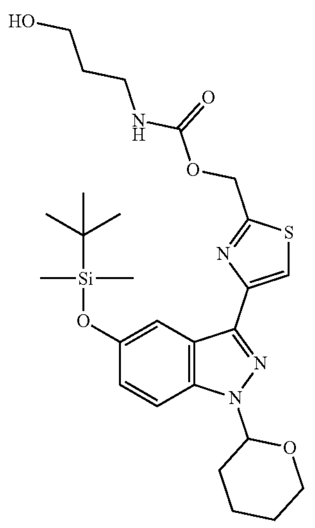 [SMILES: CC(C)(C)[Si](C)(C)Oc1ccc2c(c1)c(-c1csc(COC(=O)NCCCO)n1)nn2C1CCCCO1]

To a solution of tert-butyl-dimethyl-[1-tetrahydropyran-2-yl-3-(4,4,5,5-tetramethyl-1,3,2-dioxaborolan-2-yl)indazol-5-yl]oxy-silane (1.091 g, 2.38 mmol) in 1,4-dioxane (15 mL) and water (1.5 mL) at room temperature was added (4-bromothiazol-2-yl)methyl N-(3-hydroxypropyl)carbamate intermediate 195 (585 mg, 1.98 mmol), potassium phosphate tribasic (1.263 g, 5.95 mmol), XPhos (95 mg, 0.20 mmol) and tetrakis(triphenyl phosphine)palladium(0) (115 mg, 0.10 mmol). The reaction mixture was stirred under microwave irradiations at 90° C. for 1.5 h. The residue was diluted with saturated sodium chloride solution and extracted with ethyl acetate. The combined organic layer was dried over anhydrous sodium sulfate and concentrated under reduced pressure. The residue was purified by silica gel column chromatography cyclohexane/ethyl acetate 100/0 to 0/100 as eluent to afford 2-[4-[5-[tert-butyl(dimethyl)silyl]oxy-1-tetrahydropyran-2-yl-indazol-3-yl]thiazol-2-yl]ethyl-N-(3-hydroxypropyl) carbamate intermediate 196 as a colorless oil.

LCMS method F: $[M+H]^+=547.4$, $t_R=3.27$ min

Preparation of Intermediate 197: 3-[[4-[5-[tert-butyl(dimethyl)silyl]oxy-1-tetrahydro pyran-2-yl-indazol-3-yl]thiazol-2-yl]methoxycarbonylamino]propyl-methanesulfonate

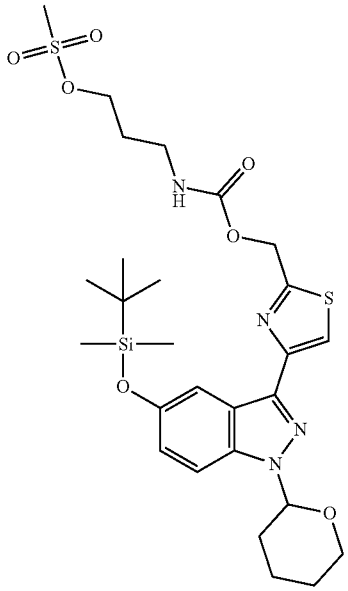 [SMILES: CC(C)(C)[Si](C)(C)Oc1ccc2c(c1)c(-c1csc(COC(=O)NCCCOS(C)(=O)=O)n1)nn2C1CCCCO1]

To a solution of [4-[5-[tert-butyl(dimethyl)silyl]oxy-1-tetrahydropyran-2-yl-indazol-3-yl]thiazol-2-yl]methyl N-(3-hydroxypropyl)carbamate intermediate 196 (500 mg, 0.91 mmol) and triethylamine (0.255 mL, 1.83 mmol) in dichloromethane (6 mL) at 0° C. was added methanesulfonyl chloride (0.092 mL, 1.19 mmol) in dichloromethane (2 mL). The reaction mixture was stirred at room temperature for 16 h. The residue was diluted with saturated aqueous sodium chloride solution and extracted with dichloromethane. The combined organic layers were dried over anhydrous sodium sulfate and concentrated under reduced pressure to afford 3-[[4-[5-[tert-butyl(dimethyl)silyl]oxy-1-tetrahydropyran-2-yl-indazol-3-yl]thiazol-2-yl]methoxycarbonylamino]propyl methanesulfonate intermediate 197 as a yellow oil which was used in the next step without further purification.

LCMS method F: $[M+H]^+=625.4$, $t_R=3.41$ min

Preparation of Intermediate 198: 18-(oxan-2-yl)-7,13-dioxa-4-thia-9,18,19,22-tetraaza tetracyclo[12.5.2.1$^{2,5}$.0$^{17,20}$]docosa-1(19),2,5(22),14(21),15,17(20)-hexaen-8-one

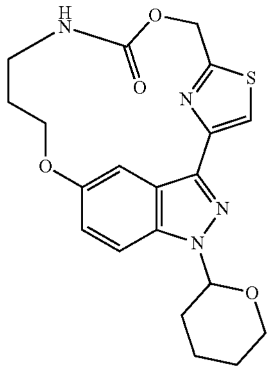 [SMILES: O=C1NCCCOc2ccc3c(c2)c(nn3C2CCCCO2)-c2csc(n2)CO1]

To a suspension of cesium carbonate (532 mg, 1.63 mmol) in anhydrous N,N-dimethylformamide (135 mL) at 85° C. was added dropwise 3-[[4-[5-[tert-butyl(dimethyl) silyl]oxy-1-tetrahydropyran-2-yl-indazol-3-yl]thiazol-2-yl]methoxycarbonylamino]propyl methanesulfonate intermediate 197 (340 mg, 0.54 mmol) in N,N-dimethylformamide (135 mL).

The reaction mixture was stirred at 85° C. for 30 min. The solvent was evaporated under reduced pressure, diluted with saturated aqueous sodium chloride solution and extracted with ethyl acetate. The organic phase was dried over anhydrous sodium sulfate and evaporated under reduced pressure. The residue was purified by silica gel column chromatography using dichloromethane/ethyl acetate, 100/0 to 80/20 as eluent to afford 18-(oxan-2-yl)-7,13-dioxa-4-thia-9,18,19,22-tetraazatetracyclo[12.5.2.1$^{2,5}$.0$^{17,20}$]docosa-1(19),2,5(22),14(21),15,17(20)-hexaen-8-one intermediate 198 as a colorless oil which crystallized.

LCMS method F: $[M+H]^+$=415.1, $t_R$=3.47 min

Preparation of Example 147: 7,13-dioxa-4-thia-9,18,19,22-tetraazatetracyclo[12.5.2.1$^{2,5}$.0$^{17,20}$]docosa-1(19),2,5(22),14(21),15,17(20)-hexaen-8-one

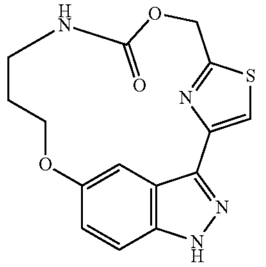 [SMILES: O=C1NCCCOc2ccc3[nH]nc(c3c2)-c2csc(n2)CO1]

To a solution of 18-(oxan-2-yl)-7,13-dioxa-4-thia-9,18,19,22-tetraazatetracyclo[12.5.2.1$^{2,5}$.0$^{17,20}$]docosa-1(19),2,5(22),14(21),15,17(20)-hexaen-8-one intermediate 198 (67 mg, 0.16 mmol) in methanol (3.5 mL) and water (0.5 mL) was added p-toluenesulfonic acid monohydrate (154 mg, 0.81 mmol). The reaction mixture was stirred at 65° C. for 2 h. The solvent was evaporated under reduced pressure and the residue was neutralized by slow addition of saturated aqueous sodium bicarbonate solution. The residue was diluted with ethyl acetate. After separation, the aqueous phase was extracted with ethyl acetate. The organic layers were washed with brine, dried over anhydrous sodium sulfate, filtered and evaporated under reduced pressure. The residue was triturated in acetonitrile, filtered and dried to afford 7,13-dioxa-4-thia-9,18,19,22-tetraazatetracyclo[12.5.2.1$^{2,5}$.0$^{17,20}$]docosa-1(19),2,5(22),14(21),15,17(20)-hexaen-8-one example 147 as a white solid.

LCMS method F: $[M+H]^+$=331.2, $t_R$=1.75 min

LCMS method G: $[M+H]^+$=331.2, $t_R$=1.75 min $^1$H NMR (400 MHz, d6-DMSO) δ 13.04 (1H, s), 8.00-7.94 (3H, m), 7.44-7.41 (1H, m), 6.95 (1H, dd, J=2.6, 9.0 Hz), 5.52 (2H, t, J=17.5 Hz), 4.32-4.26 (2H, m), 3.12 (2H, s), 2.08-1.99 (2H, m) ppm.

Example 148: (13R)-4,13-dimethyl-8,14-dioxa-5,10,19,20,23-pentaazatetracyclo[13.5.2.1$^{2,6}$.0$^{18,21}$]tricosa-1(20),2(23),3,5,15(22),16,18(21)-heptaen-9-one

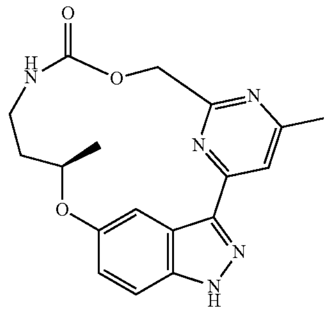 [SMILES: Cc1cc2nc(n1)COC(=O)NCC[C@@H](C)Oc1ccc3[nH]nc-2c3c1]

Example 148 is prepared according to the synthesis route described in general Scheme O.

Preparation of Intermediate 199: [(1S)-3-(benzyloxycarbonylamino)-1-methyl propyl]methane sulfonate

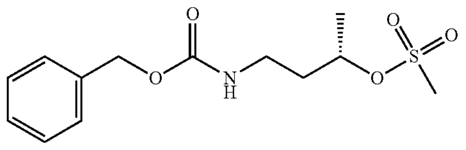 [SMILES: C[C@@H](CCNC(=O)OCc1ccccc1)OS(C)(=O)=O]

To a cooled solution (0° C.) of benzyl N-[(3S)-3-hydroxybutyl]carbamate (17.06 g, 76.52 mmol) and triethylamine (21.3 mL, 153.04 mmol) in dichloromethane (300 mL) was added dropwise methanesulfonyl chloride (7.7 mL, 99.47 mmol) and the reaction mixture was stirred at room temperature for 19 hours. The reaction mixture was quenched with an aqueous solution of 1N HCl and extracted with dichloromethane (1×). The organic layer was washed with a saturated aqueous solution of $NaHCO_3$ then water and brine, dried over sodium sulfate, filtered and evaporated under reduced pressure to give [(1S)-3-(benzyloxycarbonylamino)-1-methyl-propyl]methanesulfonate intermediate 199 as a yellow oil.

LCMS method F: $[M+H]^+$=302, $t_R$=2.26 min

Preparation of Intermediate 200: [4-[5-[tert-butyl (dimethyl)silyl]oxy-1-tetrahydropyran-2-yl-indazol-3-yl]-6-methyl-pyrimidin-2-yl]methyl acetate

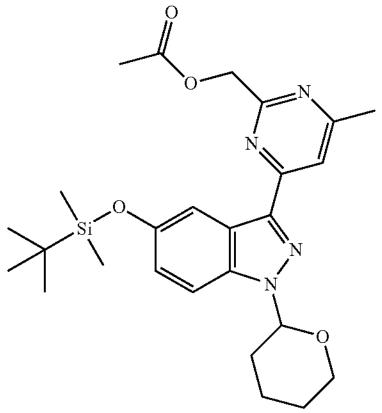 [SMILES: CC(=O)OCc1nc(C)cc(-c2nn(C3CCCCO3)c3ccc(O[Si](C)(C)C(C)(C)C)cc23)n1]

To a solution of tert-butyl-dimethyl-[1-tetrahydropyran-2-yl-3-(4,4,5,5-tetramethyl-1,3,2-dioxaborolan-2-yl)indazol-5-yl]oxy-silane (1.37 g, 3 mmol) in 1,4-dioxane (10 mL) and water (1 mL) at room temperature was added (4-chloro-6-methyl-pyrimidin-2-yl)methyl acetate (499 mg, 2.5 mmol), potassium phosphate tribasic (1.59 g, 7.5 mmol). The reaction mixture was purged with nitrogen for 15 min then XPhos (36 mg, 0.075 mmol) and tetrakis(triphenylphosphine)palladium(0) (29 mg, 0.025 mmol) were added. The reaction mixture was stirred at 80° C. for 45 min under microwave irradiations. The reaction mixture was filtered over Celite pad and the filtrate was diluted with ethyl acetate and water. After separation, the aqueous layer was extracted with ethyl acetate. The organic layers were washed with brine, dried over anhydrous sodium sulfate, filtered and concentrated under reduced pressure. The residue was purified by silica gel column chromatography using cyclohexane/ethyl acetate 100/0 to 80/20 as eluent to afford [4-[5-[tert-butyl(dimethyl)silyl]oxy-1-tetrahydropyran-2-yl-indazol-3-yl]-6-methyl-pyrimidin-2-yl]methyl acetate intermediate 200 as an orange oil.

LCMS method F: $[M+H]^+$=497.3, $t_R$=3.68 min

Preparation of Intermediate 201: 3-[2-(hydroxymethyl)-6-methyl-pyrimidin-4-yl]-1-tetrahydropyran-2-yl-indazol-5-ol

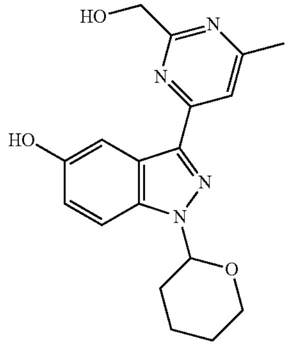 [SMILES: Cc1cc(-c2nn(C3CCCCO3)c3ccc(O)cc23)nc(CO)n1]

To a solution of [4-[5-[tert-butyl(dimethyl)silyl]oxy-1-tetrahydropyran-2-yl-indazol-3-yl]-6-methyl-pyrimidin-2-yl]methyl acetate intermediate 200 (1.33 g, 2.5 mmol) in methanol (12 mL) and water (12 mL) at room temperature was added potassium carbonate (690 mg, 5 mmol). The reaction mixture was stirred at 50° C. for 24 h. Methanol was evaporated under reduced pressure. The resulting precipitate was filtrated, washed with water and dried to afford 3-[2-(hydroxymethyl)-6-methyl-pyrimidin-4-yl]-1-tetrahydropyran-2-yl-indazol-5-ol intermediate 201 as a cream powder.

LCMS method F: $[M+H]^+$=341.2, $t_R$=1.99 min

Preparation of Intermediate 202: (13R)-4,13-dimethyl-19-(oxan-2-yl)-8,14-dioxa-5,10,19,20,23-pentaazatetracyclo[13.5.2.$1^{2,6}$.$0^{18,21}$]tricosa-1(20),2(23),3,5,15(22),16,18(21)-heptaen-9-one

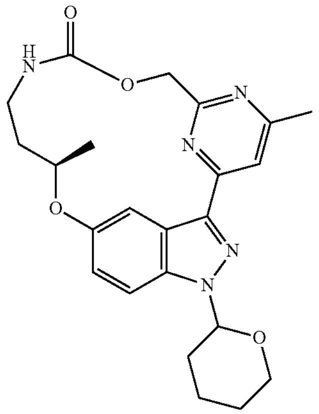 [SMILES: Cc1cc2nc(n1)COC(=O)NCC[C@@H](C)Oc1ccc3c(c1)c-2nn3C1CCCCO1]

To a mixture of 3-[2-(hydroxymethyl)-6-methyl-pyrimidin-4-yl]-1-tetrahydropyran-2-yl-indazol-5-ol intermediate 201 (361 mg, 1.06 mmol) in N,N-dimethylformamide (8 mL) at room temperature was added cesium carbonate (689 mg, 2.12 mmol). The reaction mixture was stirred for 20 min and [(1S)-3-(benzyloxycarbonylamino)-1-methyl-propyl] methanesulfonate intermediate 199 (383 mg, 1.27 mmol) in N,N-dimethylformamide (2 mL) was added. The reaction mixture was stirred at room temperature for 16 h. Additional [(1S)-3-(benzyloxycarbonylamino)-1-methyl-propyl]methanesulfonate intermediate 199 (64 mg, 0.21 mmol) in N,N-dimethylformamide (1 mL) was added. The reaction mixture was stirred at room temperature for 2 h then diluted with DMF (106 mL) and cesium carbonate (1.03 g, 3.18 mmol) was added. The reaction mixture was heated at 50° C. for 16 h. Additional cesium carbonate (344 mg, 1.06 mmol) was added and the reaction mixture was heated at 50° C. for 3 h. The reaction mixture was concentrated under reduced pressure then diluted with ethyl acetate and water. After separation, the aqueous layer was extracted with ethyl acetate. The combined organic layers were washed with brine, dried over anhydrous sodium sulfate, filtered and concentrated under reduced pressure. The residue was purified by silica gel column chromatography using cyclohexane/ethyl acetate 100/0 to 50/50 as eluent to afford (13R)-4.13-dimethyl-19-(oxan-2-yl)-8,14-dioxa-5,10,19,20,23-pentaazatetracyclo [13.5.2.$1^{2,6}$.$0^{18,21}$]tricosa-1(20),2(23),3,5,15(22),16,18(21)-heptaen-9-one intermediate 202 as a white solid.

LCMS method F: $[M+H]^+$=438.3, $t_R$=2.57 min

Preparation of Example 148: (13R)-4,13-dimethyl-8,14-dioxa-5,10,19,20,23-pentaazatetra cyclo [$13.5.2.1^{2,6}.0^{18,21}$]tricosa-1(20),2(23),3,5,15(22),16,18(21)-heptaen-9-one

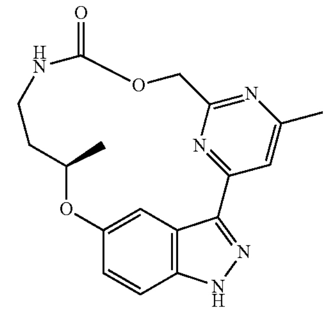 [SMILES: Cc1cc2nc(n1)COC(=O)NCC[C@@H](C)Oc1ccc3[nH]nc-2c3c1]

To a solution of (13R)-4,13-dimethyl-19-(oxan-2-yl)-8,14-dioxa-5,10,19,20,23-pentaaza tetracyclo[$13.5.2.1^{2,6}.0^{18,21}$]tricosa-1(20),2(23),3,5,15(22),16,18(21)-heptaen-9-one intermediate 202 (407 mg, 0.93 mmol) in methanol (16 mL) and water (2.6 mL) was added p-toluenesulfonic acid monohydrate (884 mg, 4.66 mmol). The reaction mixture was stirred at 65° C. for 16 h. Additional p-toluenesulfonic acid monohydrate (176 mg, 0.93 mmol) was added and the reaction mixture was heated at 65° C. for 24 h. The reaction mixture was evaporated under reduced pressure then diluted with dichloromethane and saturated aqueous solution of sodium bicarbonate. After separation, the aqueous layer was extracted with dichloromethane. The combined organic layers were washed with brine, dried over sodium sulfate, filtered and evaporated under reduced pressure. The residue was triturated in acetonitrile, filtrated, washed with acetonitrile and dried to afford (13R)-4,13-dimethyl-8,14-dioxa-5,10,19,20,23-pentaazatetracyclo[$13.5.2.1^{2,6}.0^{18,21}$]tricosa-1(20),2(23),3,5,15(22),16,18(21)-heptaen-9-one example 148 as a white powder.

LCMS method F: $[M+H]^+$=354.3, $t_R$=1.89 min

LCMS method G: $[M+H]^+$=354.3, $t_R$=1.91 min $^1$H NMR (400 MHz, d6-DMSO) δ 13.64 (1H, m), 7.94 (1H, s), 7.91 (1H, d, J=2.3 Hz), 7.86 (1H, m), 7.51 (1H, d, J=8.9 Hz), 6.99 (1H, dd, J=2.4, 9.0 Hz), 5.54 (1H, m), 4.95 (1H, m), 4.61 (1H, m), 3.52 (1H, m), 2.89 (1H, m), 2.50 (3H, s), 2.34 (1H, m), 1.39 (3H, d, J=6.1 Hz), 1.34 (1H, m) ppm.

Example 149: 8,14-dioxa-23-thia-4,10,19,20-tetraazatetracyclo[$13.5.2.1^{2,5}.0^{18,21}$]tricosa-1(20),2,4,15(22),16,18(21)-hexaen-9-one

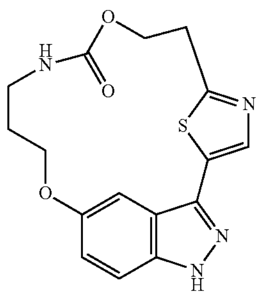 [SMILES: O=C1NCCCOc2ccc3[nH]nc(c3c2)C2=CN=C(CCO1)S2]

Example 149 is prepared according to the synthesis route described in general Scheme L.

Preparation of Intermediate 203: 2-(5-bromothiazol-2-yl)ethyl N-(3-hydroxypropyl) carbamate

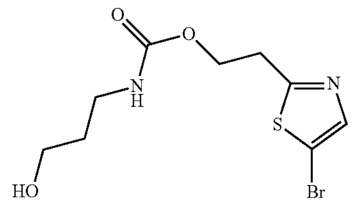 [SMILES: O=C(NCCCO)OCCc1ncc(Br)s1]

To a solution of 4-nitrophenyl chloroformate (266 mg, 1.32 mmol) and pyridine (0.194 mL, 2.40 mmol) in dichloromethane (5 mL) at room temperature was added dropwise 2-(5-bromothiazol-2-yl)ethanol (250 mg, 1.20 mmol) in dichloromethane (3 mL). The reaction mixture was stirred at room temperature for 1 h then a mixture of 3-aminopropan-1-ol (99 mg, 1.32 mmol) and DIPEA (0.418 mL, 2.40 mmol) in dichloromethane (2 mL) were added. The reaction mixture was stirred at room temperature for 2 h. The residue was diluted with 0.5 N aqueous sodium hydroxide solution and extracted with dichloromethane. The combined organic layers were washed once again with 0.5 N aqueous sodium hydroxide solution, dried over anhydrous sodium sulfate, and concentrated under reduced pressure. The residue was purified by silica gel column chromatography using dichloromethane/ethyl acetate 100/00 to 30/70 as eluent to afford 2-(5-bromothiazol-2-yl)ethyl N-(3-hydroxypropyl)carbamate intermediate 203 as a yellow oil.

LCMS method F: $[M+H]^+$=309-311, $t_R$=1.71 min

Preparation of Intermediate 204: 2-[5-[5-[tert-butyl (dimethyl)silyl]oxy-1-tetrahydro pyran-2-yl-indazol-3-yl]thiazol-2-yl]ethyl N-(3-hydroxypropyl)carbamate

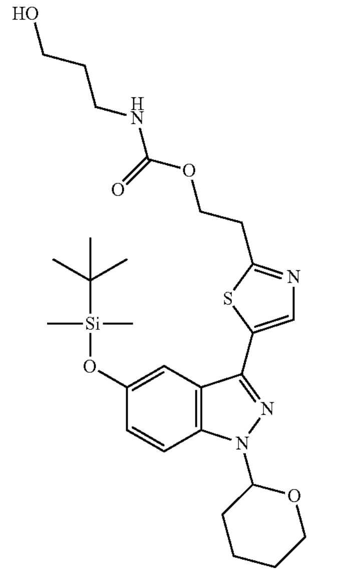 [SMILES: CC(C)(C)[Si](C)(C)Oc1ccc2c(c1)c(-c1cnc(CCOC(=O)NCCCO)s1)nn2C1CCCCO1]

To a solution of tert-butyl-dimethyl-[1-tetrahydropyran-2-yl-3-(4,4,5,5-tetramethyl-1,3,2-dioxaborolan-2-yl)indazol-5-yl]oxy-silane (409 mg, 0.89 mmol) in 1,4-dioxane (2 mL) and water (0.2 mL) at room temperature was added 2-(5-bromothiazol-2-yl)ethyl N-(3-hydroxypropyl)carbamate intermediate 203 (230 mg, 0.74 mmol), potassium phosphate tribasic (474 mg, 2.23 mmol), XPhos (35 mg, 0.07 mmol) and tetrakis(triphenylphosphine)palladium(0) (43 mg, 0.04 mmol). The reaction mixture was stirred under microwave irradiations at 90° C. for 1.5 h. The reaction mixture was diluted with saturated sodium chloride solution and extracted with ethyl acetate. The combined organic layers were dried over anhydrous sodium sulfate and concentrated under reduced pressure. The residue was purified by silica gel column chromatography using cyclohexane/ethyl acetate 100/0 to 0/100 as eluent to afford 2-[5-[5-[tert-butyl(dimethyl)silyl]oxy-1-tetrahydropyran-2-yl-indazol-3-yl]thiazol-2-yl]ethyl N-(3-hydroxypropyl)carbamate intermediate 204—as a colorless oil.

LCMS method F: $[M+H]^+$=561.3, $t_R$=3.23 min

Preparation of Intermediate 205: 3-[2-[5-[5-[tert-butyl(dimethyl)silyl]oxy-1-tetrahydro pyran-2-yl-indazol-3-yl]thiazol-2-yl]ethoxycarbonylamino]propyl methanesulfonate

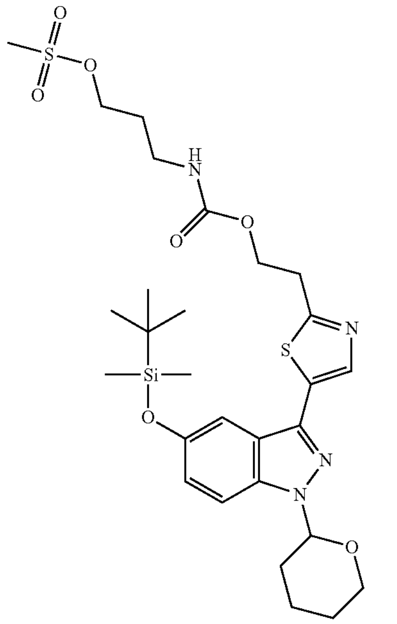 [SMILES: CC(C)(C)[Si](C)(C)Oc1ccc2c(c1)c(-c1cnc(CCOC(=O)NCCCOS(C)(=O)=O)s1)nn2C1CCCCO1]

To a solution of 2-[5-[5-[tert-butyl(dimethyl)silyl]oxy-1-tetrahydropyran-2-yl-indazol-3-yl]thiazol-2-yl]ethyl N-(3-hydroxypropyl)carbamate intermediate 204 (345 m g, 0.62 mmol) and triethylamine (0.172 mL, 1.23 mmol) in dichloromethane (5 mL) at 0° C. was added methanesulfonyl chloride (0.062 mL, 0.80 mmol) in dichloromethane (1 mL). The reaction mixture was stirred at room temperature for 2 h. The reaction mixture was diluted with saturated aqueous sodium chloride solution and extracted with dichloromethane. The combined organic layers were dried over anhydrous sodium sulfate and concentrated under reduced pressure to afford 3-[2-[5-[5-[tert-butyl(dimethyl)silyl]oxy-1-tetrahydropyran-2-yl-indazol-3-yl]thiazol-2-yl]ethoxycarbonylamino]propylmethanesulfonate intermediate 205 as a yellow oil which was used in the next step without further purification.

LCMS method F: $[M+H]^+$=639.3, $t_R$=3.37 min

Preparation of Intermediate 206: 19-(oxan-2-yl)-8,14-dioxa-23-thia-4,10,19,20-tetraaza tetracyclo [13.5.2.1$^{2}$,5s 0$^{18,21}$]tricosa-1(20),2,4,15(22),16,18(21)-hexaen-9-one

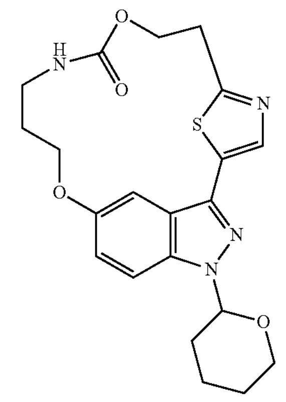 [SMILES: O=C1NCCCOc2ccc3c(c2)c(nn3C2CCCCO2)C2=CN=C(CCO1)S2]

To a suspension of cesium carbonate (601 mg, 1.85 mmol) in anhydrous N,N-dimethylformamide (155 mL) at 85° C. was added dropwise 3-[2-[5-[5-[tert-butyl(dimethyl)silyl]oxy-1-tetrahydropyran-2-yl-indazol-3-yl]thiazol-2-yl]ethoxycarbonyl amino]propylmethanesulfonate intermediate 205 (393 mg, 0.62 mmol) in N,N-dimethylformamide (155 mL). The reaction mixture was stirred at 85° C. for 2 h. The solvent was evaporated under reduced pressure, diluted with saturated sodium chloride solution and extracted with ethyl acetate. The combined organic layers were dried over anhydrous sodium sulfate and concentrated under reduced pressure. The residue was purified by silica gel column chromatography using cyclohexane/(ethyl acetate/ethanol 3/1) 100/0 to 60/40 as eluent to afford 19-(oxan-2-yl)-8,14-dioxa-23-thia-4,10,19,20-tetraazatetracyclo[13.5.2.1$^{2,5}$.0$^{18,21}$]tricosa-1(20),2,4,15(22),16,18(21)-hexaen-9-one intermediate 206 as a white solid.

LCMS method F: $[M+H]^+$=429.4, $t_R$=2.27 min

Preparation of Example 149: 8,14-dioxa-23-thia-4,10,19,20-tetraazatetracyclo[13.5.2.1$^{2,5}$.0$^{18,21}$]tricosa-1(20),2,4,15(22),16,18(21)-hexaen-9-one

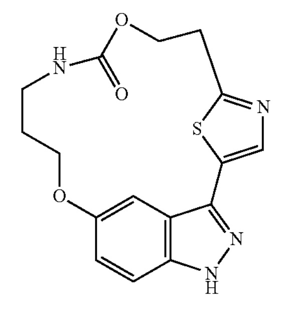 [SMILES: O=C1NCCCOc2ccc3[nH]nc(c3c2)C2=CN=C(CCO1)S2]

To a solution of 19-(oxan-2-yl)-8,14-dioxa-23-thia-4,10,19,20-tetraazatetracyclo[13.5.2.$1^{2,5}$.$0^{18,21}$]tricosa-1(20),2,4,15(22),16,18(21)-hexaen-9-one intermediate 206 (19 mg, 0.04 mmol) in methanol (14 mL) and water (2 mL) was added p-toluenesulfonic acid monohydrate (42 mg, 0.22 mmol) and the reaction mixture was stirred at 70° C. for 24 h. The solvent was evaporated under reduced pressure and the residue was quenched by slow addition of saturated aqueous sodium hydrogen carbonate solution. The residue was diluted with ethyl acetate. The phases were separated and the aqueous phase was extracted with ethyl acetate. The combined organic layers were washed with brine, dried over anhydrous sodium sulfate, filtered and evaporated under reduced pressure. The residue was triturated in acetonitrile, filtered and dried to afford 8,14-dioxa-23-thia-4,10,19,20-tetraazatetracyclo[13.5.2.$1^{2,5}$.$0^{18,21}$]tricosa-1(20),2,4,15(22),16, 18(21)-hexaen-9-one example 149 as a white solid.

LCMS method F: $[M+H]^+$=345.3, $t_R$=1.70 min

LCMS method G: $[M+H]^+$=345.3, $t_R$=1.71 min $^1$H NMR (400 MHz, d6-DMSO) δ 13.23-13.23 (1H, m), 8.00-8.00 (2H, m), 7.51-7.48 (1H, m), 7.42 (1H, d, J=2.3 Hz), 7.00 (1H, dd, J=2.3, 8.9 Hz), 4.41 (2H, t, J=5.2 Hz), 4.34-4.29 (2H, m), 3.41-3.35 (2H, m), 3.14-3.11 (2H, m), 1.91-1.84 (2H, m) ppm.

Example 150: (7S,13R)-7,13-dimethyl-8,14-dioxa-10,19,20,23-tetraazatetracyclo[13.5.2.$1^{2,6}$.$0^{18,21}$]tricosa-1(20),2(23),3,5,15(22),16,18(21)-heptaen-9-one

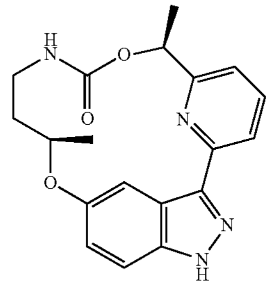 [SMILES: C[C@@H]1CCNC(=O)O[C@@H](C)c2cccc(n2)-c2n[nH]c3ccc(cc23)O1]

Example 150 is prepared according to the synthesis route described in general Scheme K.

Preparation of Intermediate 207: 1-(6-bromo-2-pyridyl)ethanol

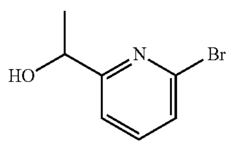

To a solution of 1-(6-bromo-2-pyridyl)ethanone (6.0 g, 30.0 mmol) in dry methanol (80 mL) at 0° C. was added solution sodium borohydride (2.30 mL, 89.9 mmol) in small portions. The reaction mixture was warmed up to room temperature and was stirred for 16 h. The reaction mixture was quenched with water then carefully by the addition of 1M aqueous hydrochloric acid solution. The reaction mixture was extracted with ethyl acetate. The organic phase was washed with brine, dried over anhydrous magnesium, filtered and evaporated to afford 1-(6-bromo-2-pyridyl)ethanol intermediate 207 as a colorless oil.

$^1$H NMR (500 MHz, d6-DMSO) δ 7.74 (t, 1H), 7.53 (d, 1H), 7.49 (d, 1H), 5.5 (d), 4.67 (m, 1H), 1.34 (d, 3H) ppm.

Preparation of Intermediate 208: 1-{6-[5-{[tert-butyl(dimethyl)silyl]oxy}-1-(oxan-2-yl)-1H-indazol-3-yl]pyridin-2-yl}ethan-1-ol

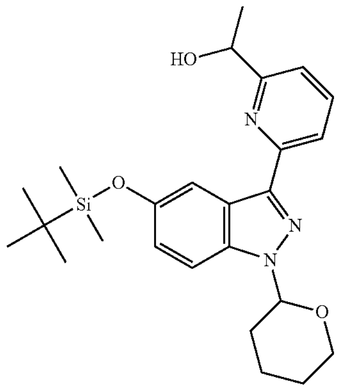 [SMILES: CC(O)c1cccc(-c2nn(C3CCCCO3)c3ccc(O[Si](C)(C)C(C)(C)C)cc23)n1]

5-{[tert-butyl(dimethyl)silyl]oxy}-1-(oxan-2-yl)-3-(4,4,5,5-tetramethyl-1,3,2-dioxaborolan-2-yl)-1H-indazole (2.4 g, 5.2 mmol), 1-(6-bromo-2-pyridyl)ethanol intermediate 207 (1.0 g, 4.9 mmol) and potassium phosphate monohydrate (2.3 g, 9.9 mmol) in a mixture of 1,4-dioxane (50 mL) and water (5 mL) was purged with nitrogen then palladium triphenylphosphane (290 mg, 0.25 mmol) was added. The reaction mixture was heated at 100° C. for 1 h. After cooling to room temperature, the reaction mixture was diluted with ethyl acetate and water. The aqueous layer was extracted with ethyl acetate. The combined organic layers were washed with brine, dried over magnesium sulfate, filtered and concentrated under reduced pressure. The residue was purified by silica gel column chromatography using heptane/ethyl acetate 20/80 to 30/70 to afford 1-{6-[5-{[tert-butyl(dimethyl)silyl]oxy}-1-(oxan-2-yl)-1H-indazol-3-yl]pyridin-2-yl}ethan-1-ol intermediate 208 as a colorless oil.

$^1$H NMR (500 MHz, d6-DMSO) δ δ (m, 2H), 8.11 (d, 1H), 7.97 (d, 1H), 7.87 (t, 1H), 7.67 (d, 1H), 7.48 (d, 1H), 7.04 (dd, 1H), 5.88 (d, 1H), 5.48 (d, 1H), 4.85 (m, 1H), 3.91/3.76 (d+m, 2H), 2.47/2.02 (m+m, 2H), 2.07/1.77 (m+m, 2H), 1.5 (d, 3H), 0.99 (s, 9H), 0.23 (s, 6H) ppm.

Preparation of Intermediate 209: benzyl[(3R)-3-({3-[6-(1-hydroxyethyl)pyridin-2-yl]-1-(oxan-2-yl)-1H-indazol-5-yl}oxy)butyl]carbamate

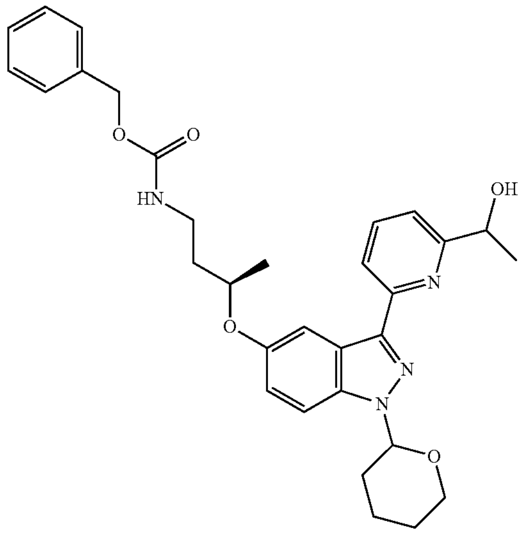 [SMILES: CC(O)c1cccc(-c2nn(C3CCCCO3)c3ccc(O[C@H](C)CCNC(=O)OCc4ccccc4)cc23)n1]

To a solution of 1-{6-[5-{[tert-butyl(dimethyl)silyl]oxy}-1-(oxan-2-yl)-1H-indazol-3-yl]pyridin-2-yl}ethan-1-ol intermediate 208 (1.84 g, 4.06 mmol) in acetonitrile (81.1 mL) was added [(1S)-3-(benzyloxycarbonylamino)-1-methyl-propyl]methanesulfonate intermediate 199 (1.47 g, 4.87 mmol) in acetonitrile (18.4 mL) and cesium carbonate (3.970 g, 12.2 mmol) at RT. The reaction mixture heated to 50° C. and stirred for 22 h. The reaction mixture was filtered and the solvent was evaporated under reduced pressure. The residue was partitioned between ethyl acetate and water. After separation, the aqueous phase washed with ethyl acetate. The combined organic phases were washed with brine, dried over anhydrous magnesium sulfate. The solvent was evaporated under reduced pressure and heptane/ethyl acetate (80/20) was added to the crude product. The precipitate was filtered off to afford benzyl[(3R)-3-({3-[6-(1-hydroxyethyl)pyridin-2-yl]-1-(oxan-2-yl)-1H-indazol-5-yl}oxy)butyl]carbamate intermediate 209 as an off-white solid.

$^1$H NMR (500 MHz, d6-DMSO) δ 8.12 (d, 1H), 7.96 (d, 1H), 7.88 (t, 1H), 7.68 (d, 1H), 7.49 (d, 1H), 7.1 (dd, 1H), 5.89 (d, 1H), 5.46 (d, 1H), 4.99/4.98 (s/s, 2H), 4.88 (m, 1H), 4.49 (m, 1H), 3.91/3.76 (d+m, 2H), 3.18 (m, 2H), 1.87/1.79 (m+m, 2H), 1.53 (d, 3H), 1.32/1.31 (d/d, 3H) ppm.

Preparation of Intermediate 210: (7S,13R)-7,13-dimethyl-19-(oxan-2-yl)-8,14-dioxa-10,19,20,23-tetraazatetracyclo[13.5.2.1$^{2,6}$.0$^{18,21}$]tricosa-1(20),2(23),3,5,15(22),16,18(21)-heptaen-9-one

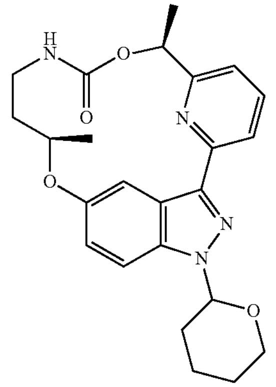 [SMILES: C[C@@H]1CCNC(=O)O[C@@H](C)c2cccc(n2)-c2nn(C3CCCCO3)c3ccc(cc23)O1]

To benzyl[(3R)-3-({3-[6-(1-hydroxyethyl)pyridin-2-yl]-1-(oxan-2-yl)-1H-indazol-5-yl}oxy)butyl]carbamate intermediate 209 (500 mg, 0.918 mmol) in acetonitrile (45 mL) was added potassium hydroxide (258 mg, 4.59 mmol). The reaction mixture was stirred at room temperature for 3 h. The reaction mixture was filtered then ethyl acetate and water were added to the filtrate. After separation, the organic phase was washed with brine, dried over anhydrous magnesium sulfate, filtered and evaporated under reduced pressure. The residue was purified by silica gel column chromatography using heptane/ethyl acetate 90/10 to 70/30 as eluent. The two diastereomers were separated. First eluted (7R,13R)-7,13-dimethyl-19-(oxan-2-yl)-8,14-dioxa-10,19,20,23-tetraazatetracyclo[13.5.2.1$^{2,6}$.0$^{18,21}$]tricosa-1(20),2(23),3,5,15(22), 16,18(21)-heptaen-9-one as a white solid. Second eluted the (7S,13R)-7,13-dimethyl-19-(oxan-2-yl)-8,14-dioxa-10,19,20,23-tetraazatetracyclo[13.5.2.1$^{2,6}$.0$^{18,21}$]tricosa-1(20),2(23), 3,5,15(22),16,18(21)-heptaen-9-one intermediate 210 as a white solid.

$^1$H NMR (500 MHz, d6-DMSO) δ (m, 6H), 8.02 (d, 1H), 7.87 (t, 1H), 7.81/7.8 (d/d, 1H), 7.76/7.74 (t/t, 1H), 7.66 (d, 1H), 7.35 (d, 1H), 7.02 (dd, 1H), 5.88 (m, 1H), 5.87 (m, 1H), 4.55 (m, 1H), 3.9/3.76 (m+m, 2H), 3.54/2.82 (m+m, 2H), 2.27/1.36 (m+m, 2H), 1.61 (d, 3H), 1.35 (d, 3H) ppm.

Preparation of Example 150: (7S,13R)-7,13-dimethyl-8,14-dioxa-10,19,20,23-tetraaza tetracyclo [13.5.2.1$^{2,6}$.0$^{18,21}$]tricosa-1(20),2(23),3,5,15(22),16,18(21)-heptaen-9-one

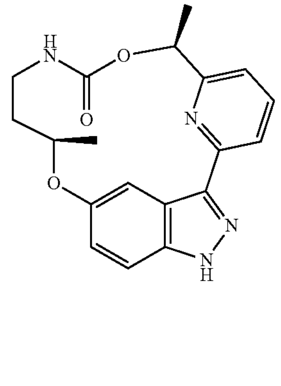 [SMILES: C[C@@H]1CCNC(=O)O[C@@H](C)c2cccc(n2)-c2n[nH]c3ccc(cc23)O1]

(7S,13R)-7,13-dimethyl-19-(oxan-2-yl)-8,14-dioxa-10,19,20,23-tetraazatetracyclo[$13.5.2.1^{2,6}.0^{18,21}$]tricosa-1(20),2(23),3,5,15(22),16,18(21)-heptaen-9-one intermediate 210 (200 mg, 0.46 mmol) and p-toluenesulfonic acid monohydrate (0.407 mL, 2.291 mmol) were added to methanol (33 mL) and water (4.5 mL). The reaction mixture was stirred at 65-C for 16 h. Methanol was removed partially by evaporation under reduced pressure and saturated aqueous sodium bicarbonate solution was added. The aqueous phase was washed with ethyl acetate. the organic phase was washed with brine, dried over anhydrous magnesium sulfate, filtered and concentrated under reduced pressure. The residue was purified by silica gel column chromatography using heptane/ethyl acetate 70/30 to 40/60 to afford (7S,13R)-7,13-dimethyl-8,14-dioxa-10,19,20,23-tetraazatetracyclo[$13.5.2.1^{2,6}.0^{18,21}$]tricosa-1(20),2(23),3,5,15(22),16, 18(21)-heptaen-9-one example 150 as a white solid.

$^1$H NMR (500 MHz, d6-DMSO) δ 13.21 (s, 1H), 8.03 (d, 1H), 7.84 (t, 1H), 7.8 (d, 1H), 7.74 (dd, 1H), 7.45 (d, 1H), 7.31 (d, 1H), 6.95 (dd, 1H), 5.87 (q, 1H), 4.54 (m, 1H), 3.54/2.82 (m+m, 2H), 2.28/1.35 (m+m, 2H), 1.61 (d, 3H), 1.34 (d, 3H) ppm.

LCMS method F: $[M+H]^+$=353.3, $t_R$=2.04 min

LCMS method G: $[M+H]^+$=353.2, $t_R$=2.10 min

Example 151: (13R)-13-methyl-9-oxo-8,14-dioxa-5,10,19,20-tetraazatetracyclo[$13.5.2.1^{2,5}.0^{18,21}$]tricosa-1(20),2(23),3,15(22),16,18(21)-hexaene-4-carbonitrile

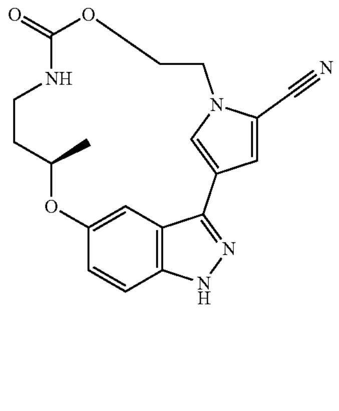 [SMILES: C[C@@H]1CCNC(=O)OCCn2cc(cc2C#N)-c2n[nH]c3ccc(cc23)O1]

Example 151 is prepared according to the synthesis route described in general Scheme O.

Preparation of Intermediate 211: 4-[5-[tert-butyl(dimethyl)silyl]oxy-1-tetrahydropyran-2-yl-indazol-3-yl]-1-(2-hydroxyethyl)pyrrole-2-carbonitrile

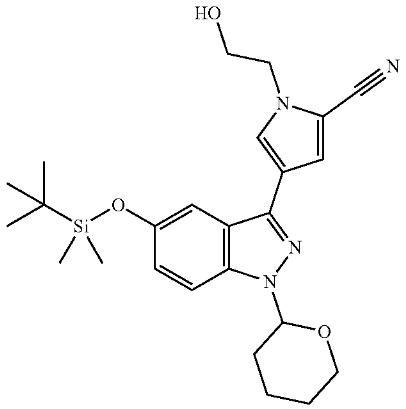 [SMILES: CC(C)(C)[Si](C)(C)Oc1ccc2c(c1)c(-c1cc(C#N)n(CCO)c1)nn2C1CCCCO1]

To a solution of tert-butyl-dimethyl-[1-tetrahydropyran-2-yl-3-(4,4,5,5-tetramethyl-1,3,2-dioxaborolan-2-yl)indazol-5-yl]oxy-silane (936 mg, 2.045 mmol), 4-bromo-1-(2-hydroxyethyl)pyrrole-2-carbonitrile (350 mg, 1.635 mmol) and potassium phosphate tribasic (1.04 g, 4.905 mmol) in 1,4-dioxane (3.5 mL) and water (250 μL) were added tetrakis(triphenylphosphine)palladium(0) (94 mg, 0.0817 mmol) and 2-dicyclohexylphosphino-2',4',6'-triisopropylbiphenyl (78 mg, 0.163 mmol). The reaction mixture was heated at 100° C. for 1 h. The reaction mixture was filtered through a Celite pad and washed with ethyl acetate. The filtrate was diluted with water and extracted with ethyl acetate. The organic layer was washed with water and brine, dried over anhydrous magnesium sulfate, filtered and concentrated under reduced pressure. The residue was purified by silica gel column chromatography using cyclohexane/ethyl acetate 100/0 to 50/50 as eluent to afford 4-[5-[tert-butyl(dimethyl)silyl]oxy-1-tetrahydropyran-2-yl-indazol-3-yl]-1-(2-hydroxyethyl) pyrrole-2-carbonitrile intermediate 211 as a yellow oil.

LCMS method F: $[M+H]^+$=467.3, $t_R$=3.37 min

Preparation of Intermediate 212: (13R)-13-methyl-19-(oxan-2-yl)-9-oxo-8,14-dioxa-5,10,19,20-tetraazatetracyclo[$13.5.2.1^{2,5}.0^{18,21}$]tricosa-1(20),2(23),3,15(22),16,18(21)-hexaene-4-carbonitrile

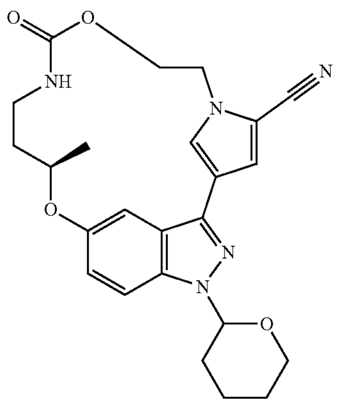 [SMILES: C[C@@H]1CCNC(=O)OCCn2cc(cc2C#N)-c2nn(C3CCCCO3)c3ccc(cc23)O1]

To a suspension of 4-[5-[tert-butyl(dimethyl)silyl]oxy-1-tetrahydropyran-2-yl-indazol-3-yl]-1-(2-hydroxyethyl)pyrrole-2-carbonitrile intermediate 211 (230 mg, 0.493 mmol) and cesium carbonate (480 mg, 1.48 mmol) in acetonitrile (60 mL) wad added [(1S)-3-(benzyloxycarbonylamino)-1-methyl-propyl]methanesulfonate (193 mg, 0.642 mmol). The reaction mixture was heated at 50° C. 4 h. Additional cesium carbonate (481 mg, 1.48 mmol) and acetonitrile (200 mL) were added. The reaction mixture was stirred at 80° C. for 16 h. The reaction mixture was concentrated under reduced pressure. The residue was dissolved between water and ethyl acetate. After separation, the aqueous phase was extracted with ethyl acetate. The organic phase was dried over anhydrous sodium sulfate, filtered and evaporated under reduced pressure. The residue was purified by silica gel column chromatography using cyclohexane/ethyl acetate 100/0 to 70/30 as eluent to afford (13R)-13-methyl-19-(oxan-2-yl)-9-oxo-8,14-dioxa-5,10,19,20-tetraazatetracyclo[13.5.2.1$^{2,5}$.0$^{18,21}$]tricosa-1(20),2(23),3,15(22), 16,18(21)-hexaene-4-carbonitrile intermediate 212 as a white powder.

LCMS method F: $[M+H]^+$=366.3, $t_R$=2.10 min

Preparation of Example 151: (13R)-13-methyl-9-oxo-8,14-dioxa-5,10,19,20-tetraaza tetracyclo [13.5.2.1$^{2,5}$.0$^{18,21}$]tricosa-1(20),2(23),3,15(22),16,18(21)-hexaene-4-carbonitrile

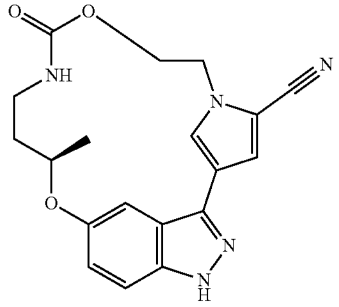 [SMILES: C[C@@H]1CCNC(=O)OCCn2cc(cc2C#N)-c2n[nH]c3ccc(cc23)O1]

To a solution of (13R)-13-methyl-19-(oxan-2-yl)-9-oxo-8,14-dioxa-5,10,19,20-tetraazatetra cyclo[13.5.2.1$^{2,5}$.0$^{18,21}$] tricosa-1(20),2(23),3,15(22),16,18(21)-hexaene-4-carbonitrile intermediate 212 (100 mg, 0.22 mmol) in methanol (10 mL) and water (1.5 mL) was added p-toluenesulfonic acid monohydrate (212 mg, 1.11 mmol). The reaction mixture was stirred at 65° C. for 2 h. The solvent was evaporated under reduced pressure. The residue was neutralized by slow addition of saturated aqueous sodium hydrogen carbonate solution and was diluted with ethyl acetate. After separation, the aqueous phase was extracted with ethyl acetate. The combined organic layer was washed with a saturated aqueous sodium bicarbonate solution, water and brine, dried over anhydrous sodium sulfate, filtered and evaporated under reduced pressure. The residue was purified by silica gel column chromatography using cyclohexane/ethyl acetate 100/0 to 50/50 as eluent. The oily product was crystallized in dichloromethane to afford (13R)-13-methyl-9-oxo-8,14-dioxa-5,10,19,20-tetraazatetracyclo[13.5.2.1$^{2,5}$.0$^{18,21}$]tricosa-1(20),2(23),3,15(22),16,18(21)-hexaene-4-carbonitrile example 151 as a yellow powder.

LCMS method F: $[M+H]^+$=no mass observed, $t_R$=2.03 min

LCMS method G: $[M+H]^+$=366.2, $t_R$=1.96 min $^1$H NMR (400 MHz, d6-DMSO) δ 12.85 (1H, s), 7.84 (1H, dd, J=4.3, 7.7 Hz), 7.54 (1H, d, J=1.7 Hz), 7.44-7.40 (1H, m), 7.28-7.27 (1H, m), 7.09 (1H, d, J=2.3 Hz), 6.93 (1H, dd, J=2.1, 8.9 Hz), 4.68-4.59 (2H, m), 4.46-4.37 (2H, m), 4.18-4.12 (1H, m), 3.49-3.48 (1H, m), 2.96-2.88 (1H, m), 2.13 (1H, t, J=14.0 Hz), 1.38-1.35 (4H, m) ppm.

Example 152: 12,12-difluoro-8,14-dioxa-10,19,20-triazatetracyclo[13.5.2.1$^{2,6}$.0$^{18,21}$]tricosa-1(20),2(23),3,5,15(22),16,18(21)-heptaen-9-one

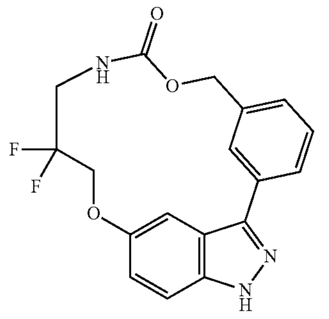 [SMILES: O=C1NCC(F)(F)COc2ccc3[nH]nc(c3c2)-c2cccc(c2)CO1]

Example 152 is prepared according to the synthesis route described in general Scheme C.

Preparation of Intermediate 213: benzyl N-(2,2-difluoro-3-hydroxy-propyl)carbamate

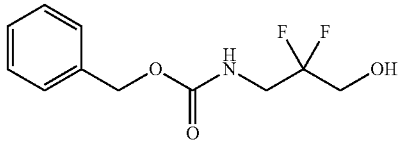 [SMILES: O=C(NCC(F)(F)CO)OCc1ccccc1]

To a solution of 3-amino-2,2-difluoropropan-1-ol (3 g, 27.005 mmol) in a mixture of 40.5 mL of THF and 40.5 mL of water was added sodium hydrogenocarbonate (4.991 g, 59.411 mmol). The suspension was cooled to 0° C. and benzyl chloroformate (8.376 mL, 59.411 mmol) was added dropwise and the reaction mixture was stirred at room temperature for 16 h. The product was diluted with EtOAc, an aqueous saturated solution of $NaHCO_3$ was added and the mixture was extracted with EtOAc (×4). The combined organic layers were dried over MgSO4, filtered and the solvents evaporated under reduced pressure. The product was purified by flash chromatography on silica gel, using as eluents heptane/EtOAc (from 100:0 to 75:25). The desired fractions were combined and concentrated under vacuum to afford benzyl (2,2-difluoro-3-hydroxypropyl)carbamate intermediate 213 as a white solid.

LCMS method B: $[M+H]^+$=246.0, $t_R$=0.526 min

Preparation of Intermediate 214: benzyl N-[2,2-difluoro-3-(3-iodo-1-tetrahydropyran-2-yl-indazol-5-yl)oxy-propyl]carbamate

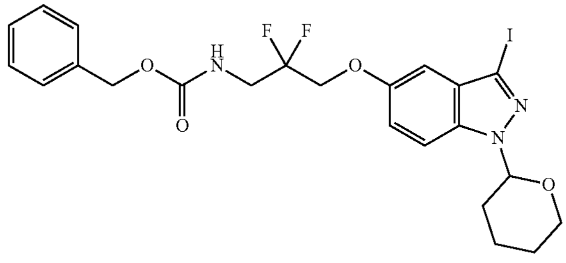 [SMILES: O=C(NCC(F)(F)COc1ccc2c(c1)c(I)nn2C1CCCCO1)OCc1ccccc1]

A solution of benzyl (2,2-difluoro-3-hydroxypropyl)carbamate intermediate 213 (2 g, 8.156 mmol) in dry THF (49 mL, 6 mL/mmol) were added 3-iodo-1-(tetrahydro-2H-pyran-2-yl)-1H-indazol-5-ol (3.368 g, 9.787 mmol) and triphenylphosphine (3.209 g, 12.234 mmol) and the mixture was stirred for 5 minutes. DIAD (2.409 mL, 12.234 mmol) was added dropwise and the reaction mixture was stirred at 90° C. for 1.5 h. The mixture was contracted under reduced pressure and the crude product was purified by flash chromatography on silica gel, using as eluents heptane/EtOAc (from 100:0 to 80:20) to afford a mixture of 3-iodo-1-(tetrahydro-2H-pyran-2-yl)-1H-indazol-5-ol and benzyl (2,2-difluoro-3-((3-iodo-1-(tetrahydro-2H-pyran-2-yl)-1H-indazol-5-yl)oxy)propyl)carbamate. The mixture was purified by flash chromatography on silica gel, using as eluents DCM/EtOAc (from 100:0 to 98:2) to afford benzyl (2,2-difluoro-3-((3-iodo-1-(tetrahydro-2H-pyran-2-yl)-1H-indazol-5-yl)oxy) propyl)carbamate intermediate 214 as a white solid.

LCMS method E: $[M+H]^+=572.0$, $t_R=4.275$ min

Preparation of Intermediate 215: N-[2,2-difluoro-3-[3-[3-(hydroxymethyl)phenyl]-1-tetrahydro pyran-2-yl-indazol-5-yl]oxy-propyl]carbamate

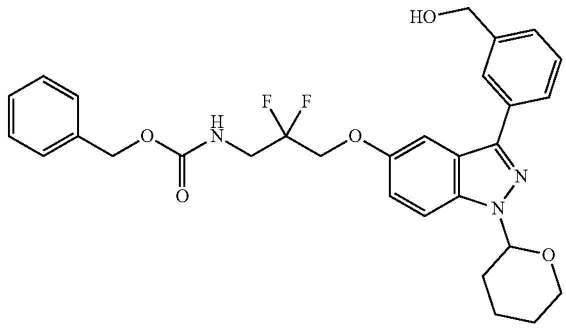 [SMILES: O=C(NCC(F)(F)COc1ccc2c(c1)c(-c1cccc(CO)c1)nn2C1CCCCO1)OCc1ccccc1]

To a solution of benzyl N-[2,2-difluoro-3-(3-iodo-1-tetrahydropyran-2-yl-indazol-5-yl)oxy-propyl]carbamate intermediate 214 (250 mg, 0.44 mmol), [3-(hydroxymethyl) phenyl]boronic acid (79 mg, 0.52 mmol) and potassium phosphate tribasic (280 mg, 1.32 mmol) in 1,4-dioxane (3.2 mL) and water (1.6 mL), were added tetrakis(triphenylphosphine)palladium(0) (25 mg, 0.022 mmol) and 2-dicyclohexylphosphino-2',4',6'-triisopropylbiphenyl (21 mg, 0.044 mmol). The reaction mixture was heated at 100° C. for 2 h. The reaction mixture was filtered through a Celite pad and washed with ethyl acetate. The filtrate was diluted with water and extracted with ethyl acetate. The organic layer was washed with water, brine, dried over anhydrous magnesium sulfate, filtered and concentrated under reduced pressure. The residue was purified by silica gel column chromatography using cyclohexane/ethyl acetate 99/1 to 40/60 as a eluent to afford benzyl N-[2,2-difluoro-3-[3-[3-(hydroxymethyl)phenyl]-1-tetrahydropyran-2-yl-indazol-5-yl]oxy-propyl]carbamate intermediate 215 as a colorless oil.

LCMS method F: $[M+H]^+=552.3$, $t_R=2.90$ min

Preparation of Intermediate 216: 12,12-difluoro-19-(oxan-2-yl)-8,14-dioxa-10,19,20-triaza tetracyclo [13.5.2.1$^{2,6}$.0$^{18,21}$]tricosa-1(20),2(23),3,5,15(22),16,18(21)-heptaen-9-one

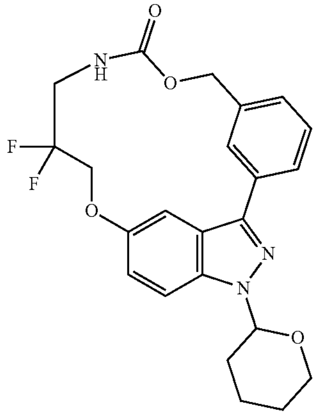 [SMILES: O=C1NCC(F)(F)COc2ccc3c(c2)c(nn3C2CCCCO2)-c2cccc(c2)CO1]

To a solution of benzyl N-[2,2-difluoro-3-[3-[3-(hydroxymethyl)phenyl]-1-tetrahydropyran-2-yl-indazol-5-yl]oxy-propyl]carbamate intermediate 215 (243 mg, 0.44 mmol) in dry acetonitrile (28 mL) at room temperature was added potassium hydroxide (0.123 g, 2.20 mmol) in one portion. The reaction mixture was stirred at room temperature for 8 h. The reaction mixture was filtered then washed with ethyl acetate and the filtrate was evaporated under reduced pressure. The residue was purified by silica gel column chromatography using cyclohexane/(ethyl acetate/ethanol (3-1)) 100/0 to 80/20 as eluent to afford 12,12-difluoro-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one intermediate 216 as a white solid.

LCMS method F: $[M+H]^+=444.3$, $t_R=2.78$ min

Preparation of Example 152: 12,12-difluoro-8,14-dioxa-10,19,20-triazatetracyclo[13.5.2.1$^{2,6}$.0$^{18,21}$]tricosa-1(20),2(23),3,5,15(22),16,18(21)-heptaen-9-one

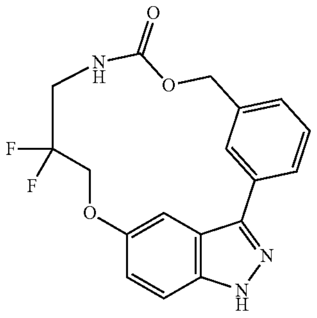 [SMILES: O=C1NCC(F)(F)COc2ccc3[nH]nc(c3c2)-c2cccc(c2)CO1]

To a solution of 12,12-difluoro-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one intermediate 216 (65 mg, 0.15 mmol) in dichloromethane (4 mL) was added trifluoroacetic acid (230 μL, 3.0 mmol). The reaction mixture was heated at 50° C. for 2 h. The reaction mixture was evaporated under reduced pressure and the residue was dissolved in ethyl acetate and saturated aqueous sodium bicarbonate solution. After separation, the aqueous layer was extracted with ethyl acetate. The organic layers were washed with water then brine, dried over sodium sulfate, filtered and evaporated under reduced pressure. The residue was purified by silica gel column chromatography using dichloromethane/ethanol 100/0 to 95/5 as eluent. The resulting product was triturated in dichloromethane, filtered and dried to afford 12,12-difluoro-8,14-dioxa-10,19,20-triazatetracyclo[13.5.2.1$^{2,6}$.0$^{18,21}$]tricosa-1(20),2(23),3,5,15(22),16,18(21)-heptaen-9-one example 152 as a white solid.

LCMS method F: $[M+H]^+$=360.3, $t_R$=2.09 min

LCMS method G: $[M+H]^+$=360.2, $t_R$=2.10 min $^1$H NMR (400 MHz, d6-DMSO, 80° C.) δ 12.93 (1H, s), 8.00-7.99 (1H, m), 7.90-7.88 (2H, m), 7.51-7.45 (3H, m), 7.31-7.28 (1H, m), 7.13-7.07 (1H, m), 5.39-5.31 (2H, m), 4.71 (2H, t, J=16.9 Hz), 3.71-3.52 (2H, m) ppm.

Example 153: (13R)-17-fluoro-13-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one

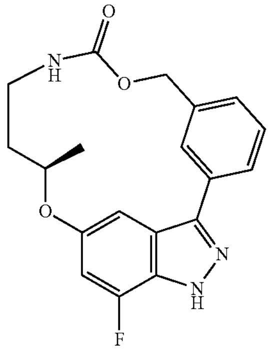 [SMILES: C[C@@H]1CCNC(=O)OCc2cccc(c2)-c2n[nH]c3c(F)cc(cc23)O1]

Example 153 is prepared according to the synthesis route described in general Scheme C.

Preparation of Intermediate 217: tert-butyl-[(7-fluoro-1H-indazol-5-yl)oxy]-dimethyl-silane

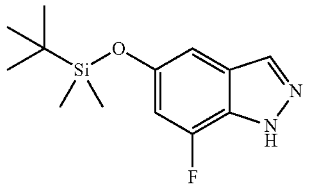 [SMILES: CC(C)(C)[Si](C)(C)Oc1cc(F)c2[nH]ncc2c1]

To a stirred solution of 7-fluoro-1H-indazol-5-ol (4.858 g, 31.933 mmol) in DCM (100 mL) was added imidazole (2.609 g, 38.32 mmol) followed by tert-butyldimethylchlorosilane (5.295 g, 35.126 mmol). The reaction mixture was stirred at room temperature for 16 h. The mixture was filtered over a pad of celite and was washed with dichloromethane. The filtrate was concentrated under vacuum to afford tert-butyl-[(7-fluoro-1H-indazol-5-yl)oxy]-dimethyl-silane intermediate 217. The product was used in the next step without further purification.

LCMS method B: $[M+H]^+$=267.0, $t_R$=1.153 min

Preparation of Intermediate 218: tert-butyl-[(7-fluoro-3-iodo-1H-indazol-5-yl)oxy]-dimethyl-silane

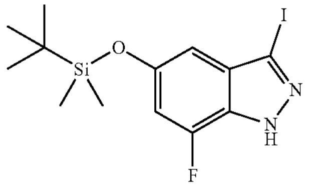 [SMILES: CC(C)(C)[Si](C)(C)Oc1cc(F)c2[nH]nc(I)c2c1]

1-iodopyrrolidine-2,5-dione (7.601 g, 33.785 mmole) in DMF (30 mL) was added to a solution of tert-butyl-[(7-fluoro-1H-indazol-5-yl)oxy]-dimethyl-silane intermediate 217 (6 g, 22.523 mmol) in DMF (15 mL). The reaction mixture was stirred at room temperature for 1 h. A solution of 10% sodium thiosulfate (300 ml) was added at 0° C. and the mixture was extracted with EtOAc (4×200 ml). The combined organic layers were dried over MgSO4, filtered and the solvent was removed under reduced pressure. The product was purified by column chromatography on silica gel using as eluent heptane/EtOAc (90:10) to afford tert-butyl-[(7-fluoro-3-iodo-1H-indazol-5-yl)oxy]-dimethyl-silane intermediate 218 as a sticky transparent gum.

LCMS method B: $[M+H]^+$=392.9, $t_R$=1.316 min

Preparation of Intermediate 219: tert-butyl-(7-fluoro-3-iodo-1-tetrahydropyran-2-yl-indazol-5-yl)oxy-dimethyl-silane

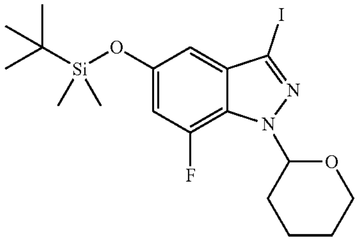 [SMILES: CC(C)(C)[Si](C)(C)Oc1cc(F)c2c(c1)c(I)nn2C1CCCCO1]

To a solution of tert-butyl-[(7-fluoro-3-iodo-1H-indazol-5-yl)oxy]-dimethyl-silane intermediate 218 (5.340 g, 13.612 mmol) in 54 ml of DCM were added 4-methylbenzenesulfonic acid monohydrate (0.518 g, 2.722 mmol) and 3,4-dihydro-2H-pyran (3.734 ml, 40.836 mmol) and the reaction mixture was stirred at room temperature for 16 hours. The reaction mixture was diluted with DCM and washed with a saturated aqueous NaHCO3 solution (3×500 ml) and brine (500 ml). The organic phase was dried over MgSO4, filtered and evaporated under reduced pressure. The crude product was purified by flash column chromatography on silica gel using a gradient of n-heptane/EtOAc (100:0 to 90:10) as eluents. The desired fractions were combined and the solvent was removed under reduced pressure to afford tert-butyl-(7-fluoro-3-iodo-1-tetrahydropyran-2-yl-indazol-5-yl)oxy-dimethyl-silane intermediate 219 as a colourless oil.

LCMS method B: $[M-84+H]^+$=392.9, $t_R$=1.577 min

Preparation of Intermediate 220: 7-fluoro-3-iodo-1-tetrahydropyran-2-yl-indazol-5-ol

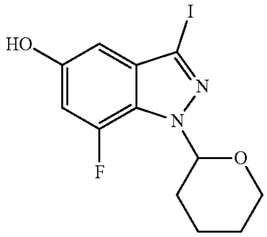 [SMILES: Oc1cc(F)c2c(c1)c(I)nn2C1CCCCO1]

Tert-butyl-(7-fluoro-3-iodo-1-tetrahydropyran-2-yl-indazol-5-yl)oxy-dimethyl-silane intermediate 219 (5.390 g, 11.314 mmol) was dissolved in 35 ml of THF. The mixture was cooled to 0° C. and TBAF 1 M in THE (14.708 ml, 14.708 mmol) was added. The reaction mixture was stirred at RT for 2 h. The reaction mixture was cooled to 0° C., diluted with EtOAc and the mixture was washed with a saturated aqueous solution of $NaHCO_3$(×3). The organic layer was dried over MgSO4, filtered and the solvent was removed under reduced pressure to obtain a solid that was triturated with DCM to obtain 7-fluoro-3-iodo-1-tetrahydropyran-2-yl-indazol-5-ol intermediate 220 as a white solid.

LCMS method C: $[M+H]^+$=363.0, $t_R$=4.563 min

Preparation of Intermediate 221: Benzyl N-[(3R)-3-(7-fluoro-3-iodo-1-tetrahydropyran-2-yl-indazol-5-yl)oxybutyl]carbamate

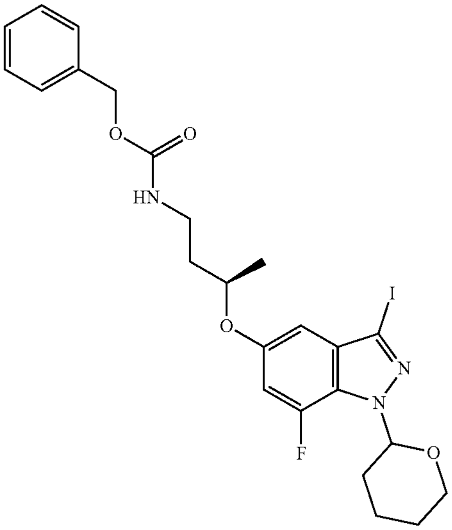 [SMILES: C[C@H](CCNC(=O)OCc1ccccc1)Oc1cc(F)c2c(c1)c(I)nn2C1CCCCO1]

To a solution of 7-fluoro-3-iodo-1-tetrahydropyran-2-yl-indazol-5-ol intermediate 220 (700 mg, 1.93 mmol) in N,N-dimethylformamide (8 mL) at room temperature was added cesium carbonate (942 mg, 2.90 mmol). The reaction mixture was stirred at room temperature for 30 min and a solution of [(1S)-3-(benzyloxycarbonylamino)-1-methyl-propyl]methanesulfonate (638 mg, 2.12 mmol) in N,N-dimethylformamide (2 mL) was added dropwise. The reaction mixture was stirred at room temperature for 5 h. The reaction mixture was filtered, washed with ethyl acetate and concentrated under reduced pressure. The residue was purified by silica gel column chromatography using cyclohexane/ethyl acetate 100/0 to 80/20 as eluent to afford benzyl N-[(3R)-3-(7-fluoro-3-iodo-1-tetrahydropyran-2-yl-indazol-5-yl)oxybutyl]carbamate intermediate 221 as a colorless oil.

LCMS method F: $[M+H]^+$=568.2, $t_R$=3.30 min

Preparation of Intermediate 222: Benzyl N-[(3R)-3-[7-fluoro-3-[3-(hydroxymethyl)phenyl]-1-tetrahydropyran-2-yl-indazol-5-yl]oxybutyl]carbamate

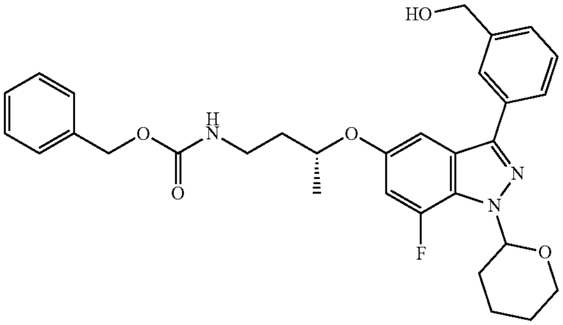 [SMILES: C[C@H](CCNC(=O)OCc1ccccc1)Oc1cc(F)c2c(c1)c(-c1cccc(CO)c1)nn2C1CCCCO1]

To a solution of benzyl N-[(3R)-3-(7-fluoro-3-iodo-1-tetrahydropyran-2-yl-indazol-5-yl)oxybutyl]carbamate intermediate 221 (755 mg, 1.33 mmol), [3-(hydroxymethyl) phenyl]boronic acid (241 mg, 1.60 mmol) and potassium phosphate tribasic (848 mg, 4.00 mmol) in 1,4-dioxane (12 mL) and water (2 mL), were added tetrakis(triphenylphosphine)palladium(0) (76 mg, 0.066 mmol) and 2-dicyclohexylphosphino-2',4',6'-triisopropylbiphenyl (62 mg, 0.13 mmol). The reaction mixture was stirred at 100° C. for 2 h. The reaction mixture was filtered through a Celite pad and washed with ethyl acetate. The filtrate was diluted with water and extracted with ethyl acetate. The organic layer was washed with water, brine, dried over anhydrous magnesium sulfate, filtered and concentrated under reduced pressure. The residue was purified by silica gel column chromatography using cyclohexane/ethyl acetate using 99/1 to 40/60 as eluent to afford benzyl N-[(3R)-3-[7-fluoro-3-[3-(hydroxymethyl)phenyl]-1-tetrahydropyran-2-yl-indazol-5-yl] oxybutyl]carbamate intermediate 222 as a yellow solid.

LCMS method F: $[M+H]^+$=548.4, $t_R$=3.09 min

Preparation of Intermediate 223: (13R)-17-fluoro-13-methyl-19-(oxan-2-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one

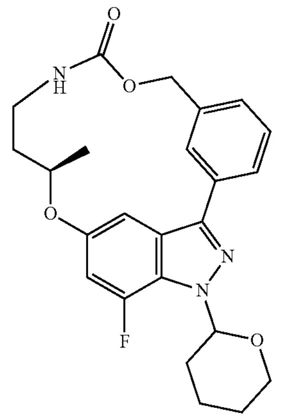 [SMILES: C[C@@H]1CCNC(=O)OCc2cccc(c2)-c2nn(C3CCCCO3)c3c(F)cc(cc23)O1]

A solution of benzyl N-[(3R)-3-[7-fluoro-3-[3-(hydroxymethyl)phenyl]-1-tetrahydropyran-2-yl-indazol-5-yl] oxybutyl]carbamate intermediate 222 (550 mg, 1.00 mmol) and cesium carbonate (1.95 g, 6.00 mmol) in dry acetonitrile (150 mL) was stirred at 85° C. for 16 h. The reaction mixture was filtered, washed with ethyl acetate and evaporated under reduced pressure. The residue was purified by silica gel column chromatography using cyclohexane/(ethyl acetate/ethanol 3/1) 100/0 to 80/20 as eluent to afford (13R)-17-fluoro-13-methyl-19-(oxan-2-yl)-8,14-dioxa-10,19,20-triazatetracyclo[13.5.2.$1^{2,6}$.$0^{18,21}$]tricosa-1(20),2(23),3,5,15 (22), 16,18(21)-heptaen-9-one intermediate 223 as a white solid.

LCMS method F: $[M+H]^+$=440.3, $t_R$=3.08 min

Preparation of Example 153: (13R)-17-fluoro-13-methyl-8,14-dioxa-10,19,20-triazatetra cyclo [13.5.2.$1^{2,6}$.$0^{18,21}$]tricosa-1(20),2(23),3,5,15(22),16,18(21)-heptaen-9-one

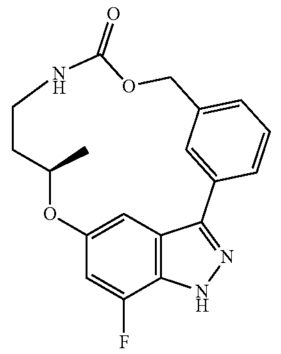 [SMILES: C[C@@H]1CCNC(=O)OCc2cccc(c2)-c2n[nH]c3c(F)cc(cc23)O1]

To a solution of (13R)-17-fluoro-13-methyl-19-(oxan-2-yl)-8,14-dioxa-10,19,20-triazatetracyclo[13.5.2.$1^{2,6}$.$0^{18,21}$] tricosa-1(20),2(23),3,5,15(22),16,18(21)-heptaen-9-one intermediate 223 (346 mg, 0.79 mmol) in dichloromethane (19 mL) was added trifluoroacetic acid (1.20 mL, 15.8 mmol). The reaction mixture was heated at 50° C. for 16 h. The reaction mixture was evaporated under reduced pressure. The residue was dissolved in ethyl acetate and saturated aqueous solution of sodium bicarbonate was added. After separation, the aqueous layer was extracted with ethyl acetate. The combined organic layers were washed with water, brine, dried over anhydrous sodium sulfate, filtered and evaporated under reduced pressure. The residue was purified by silica gel column chromatography using dichloromethane/methanol 100/0 to 95/5 as eluent. The resulting product was triturated in dichloromethane, filtered and dried to afford (13R)-17-fluoro-13-methyl-8,14-dioxa-10,19,20-triazatetracyclo[13.5.2.$1^{2,6}$.$0^{18,21}$]tricosa-1(20),2(23),3,5,15 (22),16,18(21)-heptaen-9-one example 153 as a white solid.

LCMS method F: $[M+H]^+$=356.2, $t_R$=2.41 min

LCMS method G: $[M+H]^+$=356.2, $t_R$=2.33 min $^1$H NMR (400 MHz, d6-DMSO) δ 13.70 (1H, s), 7.93-7.81 (3H, m), 7.51-7.46 (1H, m), 7.33-7.29 (1H, m), 7.08 (1H, s), 6.88 (1H, dd, J=1.3, 12.1 Hz), 5.77-5.73 (1H, m), 4.84-4.80 (1H, m), 4.62-4.54 (1H, m), 3.58-3.53 (1H, m), 2.93-2.85 (1H, m), 2.44-2.37 (1H, m), 1.41-1.38 (4H, m) ppm.

Example 154: (7S,13R)-7,13-dimethyl-8,14-dioxa-4,10,19,20,23-pentaazatetracyclo[13.5.2.$1^{2,6}$.$0^{18,21}$] tricosa-1(20),2(23),3,5,15(22),16,18(21)-heptaen-9-one

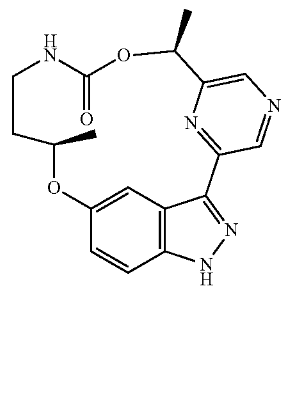 [SMILES: C[C@@H]1CCNC(=O)O[C@@H](C)c2cncc(n2)-c2n[nH]c3ccc(cc23)O1]

Example 154 is prepared according to the synthesis route described below.

Preparation of Intermediate 224: 1-(6-chloropyrazin-2-yl)ethanol

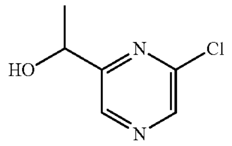

To a solution of 1-(6-chloropyrazin-2-yl)ethanone (1.00 g, 6.39 mmol) in methanol (15 mL) at 0° C. was added sodium borohydride (725 mg, 19.2 mmol) in small portions. The reaction mixture was stirred at 0° C. for 3 h. Water was added to reaction mixture then 1M aqueous hydrochloric acid solution. The reaction mixture was extracted with ethyl acetate. The organic phase was washed with brine, dried over anhydrous magnesium sulfate, filtered and evaporated under reduced pressure to afford 1-(6-chloropyrazin-2-yl) ethanol intermediate 224 as a colorless oil.

$^1$H NMR (500 MHz, d6-DMSO) δ 8.74 (s, 1H), 8.69 (s, 1H), 5.73 (d, 1H), 4.79 (m, 1H), 1.4 (d, 3H) ppm.

Preparation of Intermediate 225: 1-[6-[5-[tert-butyl (dimethyl)silyl]oxy-1-tetrahydropyran-2-yl-indazol-3-yl]pyrazin-2-yl]ethanol

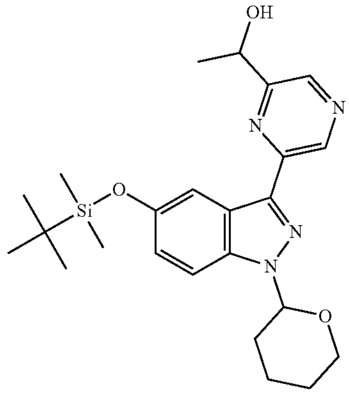 [SMILES: CC(O)c1cncc(-c2nn(C3CCCCO3)c3ccc(O[Si](C)(C)C(C)(C)C)cc23)n1]

1-(6-chloropyrazin-2-yl)ethanol intermediate 224 (970 mg, 6.12 mmol) in 1,4-dioxane (60 mL) was warmed to 60° C. and all the insoluble solid was filtered out. To the filtrate water (6 mL), tert-butyl-dimethyl-[1-tetrahydropyran-2-yl-3-(4,4,5,5-tetramethyl-1,3,2-dioxaborolan-2-yl) indazol-5-yl]oxy-silane (3.08 g, 6.73 mmol), potassium carbonate (1.69 g, 12.2 mmol) and finally palladium, triphenylphosphane (212 mg, 0.183 mmol) were added. The reaction mixture was purged with nitrogen for 10 min, then it was refluxed under nitrogen for 40 min. The reaction mixture was cooled to room temperature, diluted with ethyl acetate, washed with water, then the aqueous layer was extracted with ethyl acetate. The combined organic layer was washed with brine, dried over anhydrous magnesium sulfate, filtered and concentrated under reduced pressure. The residue was purified by silica gel column chromatography using heptane/ethyl acetate 80/20 to 50/50 as eluent to afford 1-[6-[5-[tert-butyl(dimethyl)silyl]oxy-1-tetrahydropyran-2-yl-indazol-3-yl]pyrazin-2-yl]ethanol intermediate 225 as a brown oil.

$^1$H NMR (500 MHz, d6-DMSO) δ 9.19 (s, 1H), 8.7 (s, 1H), 7.98 (d, 1H), 7.74 (d, 1H), 7.09 (dd, 1H), 5.94 (dd, 1H), 5.7 (d, 1H), 4.94 (qn, 1H), 3.93/3.78 (dt+td, 2H), 2.48/2.05 (m+dd, 2H), 2.09/1.79 (m+m, 2H), 1.62 (qn, 2H), 1.55 (d, 3H), 0.99 (s, 9H), 0.24/0.23 (s/s, 6H) ppm.

Preparation of Intermediate 226: 3-[6-(1-hydroxyethyl)pyrazin-2-yl]-1-tetrahydropyran-2-yl-indazol-5-olate(tetrabutylammonium salt)

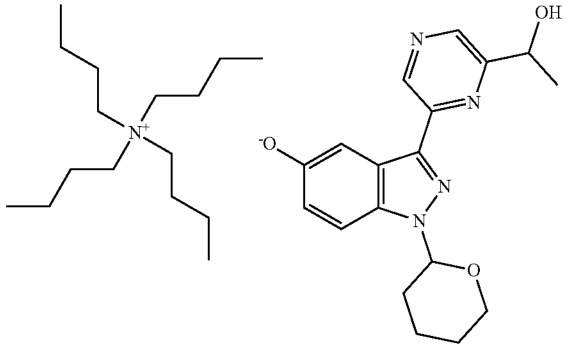

To a solution of 1-[6-[5-[tert-Butyl(dimethyl)silyl]oxy-1-tetrahydropyran-2-yl-indazol-3-yl]pyrazin-2-yl]ethanol intermediate 225 (2.61 g, 5.74 mmol) in tetrahydrofuran (15 mL) at room temperature was added 1M tetrabutylammonium fluoride solution in THF (6.3 ML, 6.32 mmol) dropwise. The reaction mixture was stirred for 1 h. The reaction mixture was stirred at 0° C. for 10 min and the solid was filtered out then washed with THE (10 mL) and with diethyl ether to afford 3-[6-(1-hydroxyethyl)pyrazin-2-yl]-1-tetrahydropyran-2-yl-indazol-5-olate tetrabutyl ammonium intermediate 226 as an off-white solid. The base acid ratio is ca. 1:2.

$^1$H NMR (500 MHz, d6-DMSO) δ 9.1 (s, 1H), 8.59 (s, 1H), 7.52 (brs., 1H), 7.39 (d, 1H), 6.9 (dd, 1H), 5.78 (dd, 1H), 4.9 (q, 1H), 3.91/3.73 (brd+td, 2H), 2.53-1.53 (m, 6H), 1.51 (d, 3H) ppm.

Preparation of Intermediate 227. Benzyl N-[(3R)-3-[3-[6-(1-hydroxyethyl)pyrazin-2-yl]-1-tetrahydropyran-2-yl-indazol-5-yl]oxybutyl]carbamate

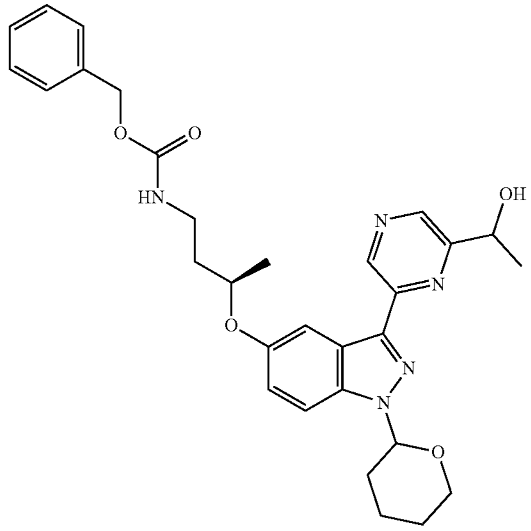 [SMILES: CC(O)c1cncc(-c2nn(C3CCCCO3)c3ccc(O[C@H](C)CCNC(=O)OCc4ccccc4)cc23)n1]

To a suspension of 3-[6-(1-hydroxyethyl)pyrazin-2-yl]-1-tetrahydropyran-2-yl-indazol-5-olate tetrabutylammonium intermediate 226 (2.24 g, 3.96 mmol) in N,N-dimethylformamide (20 mL) at 45° C. was added cesium carbonate (5.21 g, 16.0 mmol). The reaction mixture was stirred for 3 min, then a solution of [(1S)-3-(benzyloxycarbonylamino)-1-methyl-propyl]methane sulfonate (1.51 g, 5.00 mmol) in N,N-dimethylformamide (5 mL) was added. The reaction mixture was stirred at 45° C. for 3 h. The warm solution was filtered and the filtrate was diluted with ethyl acetate then washed with brine. The organic phase was dried over anhydrous sodium sulfate, filtered and evaporated under reduced pressure. The solid was suspended in diethyl ether then filtered and dried to afford benzyl N-[(3R)-3-[3-[6-(1-hydroxyethyl)pyrazin-2-yl]-1-tetrahydropyran-2-yl-indazol-5-yl]oxybutyl]carbamate as a mixture of diastereomers intermediate 227 as a beige solid.

$^1$H NMR (500 MHz, d6-DMSO) δ 9.19 (s, 1H), 8.7 (s, 1H), 7.98 (d, 1H), 7.74 (d, 1H), 7.41-7.19 (m, 6H), 7.15 (dd, 1H), 5.94 (dd, 1H), 5.68 (d, 1H), 4.98 (s, 2H), 4.97 (m, 1H), 4.51 (m, 1H), 3.92/3.78 (brd+m, 2H), 3.18 (m, 2H), 2.48/2.04 (m+m, 2H), 2.08/1.78 (m+m, 2H), 1.87/1.79 (m+m, 2H), 1.62 (m, 2H), 1.57 (d, 3H), 1.31 (d, 3H) ppm.

Preparation of Intermediate 228: (7S,13R)-7,13-dimethyl-19-(oxan-2-yl)-8,14-dioxa-4,10,19,20,23-pentaazatetracyclo[13.5.2.1$^{2,6}$.0$^{18,21}$]tricosa-1(20),2(23),3,5,15(22),16,18(21)-heptaen-9-one

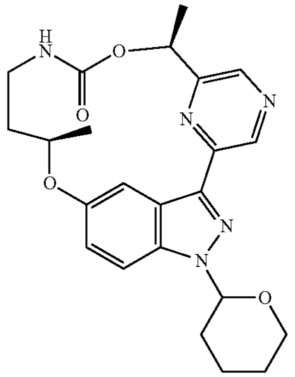 [SMILES: C[C@@H]1CCNC(=O)O[C@@H](C)c2cncc(n2)-c2nn(C3CCCCO3)c3ccc(cc23)O1]

To a solution of benzyl N-[(3R)-3-[3-[6-(1-hydroxyethyl)pyrazin-2-yl]-1-tetrahydropyran-2-yl-indazol-5-yl]oxy-butyl]carbamate intermediate 227 (1.80 g, 3.30 mmol) in dry N,N-dimethyl formamide (50 mL) was added potassium hydroxide (555 mg, 9.90 mmol) at 30° C. in one portion. The reaction mixture was stirred at 30° C. for 60 min. The solid was filtered out and washed with ethyl acetate. The filtrate was diluted with ethyl acetate, washed with brine, dried over anhydrous magnesium sulfate, filtered and evaporated under reduced pressure. The residue was purified and separated as diastereomers by silica gel column chromatography using heptane/ethyl acetate 50/50 to 0/100 as eluent to afford (7S,13R)-7,13-dimethyl-19-(oxan-2-yl)-8,14-dioxa-4,10,19,20,23-pentaazatetracyclo[13.5.2.1$^{2,6}$.0$^{18,21}$]tricosa-1(20),2(23),3, 5, 15(22).16.18(21)-heptaen-9-one intermediate 228 as a white solid.

$^1$H NMR (500 MHz, d6-DMSO) δ 9.23 (d, 1H), 8.66 (d, 1H), 7.87/7.85 (t/t, 1H), 7.78/7.77 (d/d, 1H), 7.72/7.71 (d/d, 1H), 7.05 (dd, 1H), 5.94 (q, 1H), 5.93 (dd, 1H), 4.56 (m, 1H), 3.91/3.77 (dq+td, 2H), 3.53/2.83 (m+m, 2H), 2.48/2.05 (m+m, 2H), 2.3/1.33 (td+td, 2H), 2.09/1.8 (m+m, 2H), 1.68 (d, 3H), 1.62 (m, 2H), 1.37 (d, 3H) ppm.

Preparation of Example 154: (7S,13R)-7,13-dimethyl-8,14-dioxa-4,10,19,20,23-pentaaza tetracyclo [13.5.2.1$^{2,6}$.0$^{18,21}$]tricosa-1(20),2(23),3,5,15(22),16,18(21)-heptaen-9-one

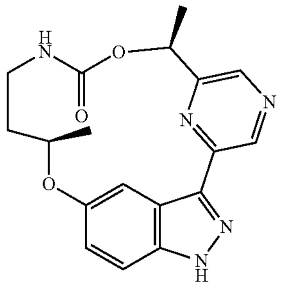 [SMILES: C[C@@H]1CCNC(=O)O[C@@H](C)c2cncc(n2)-c2n[nH]c3ccc(cc23)O1]

To a suspension of (7S,13R)-7,13-dimethyl-19-(oxan-2-yl)-8,14-dioxa-4,10,19,20,23-pentaaza tetracyclo [13.5.2.1$^{2,6}$.0$^{18,21}$]tricosa-1(20),2(23),3,5,15(22),16,18(21)-heptaen-9-one intermediate 228 (460 mg, 1.1 mmol) in a mixture of methanol (77 mL) and water (11 mL) was added p-toluenesulfonic acid monohydrate (0.93 mL, 5.3 mmol). The reaction mixture was stirred at 65° C. for 16 h. The reaction mixture was cooled to room temperature and saturated aqueous sodium bicarbonate solution was added. Methanol was evaporated under reduced pressure. The reaction mixture was extracted with ethyl acetate. The combined organic phases were washed with brine, dried over anhydrous magnesium sulfate, filtered and concentrated under reduced pressure. The residue was purified by silica gel column chromatography using dichloromethane/ethyl acetate 90/10 to 0/100 as eluent to afford (7S,13R)-7,13-dimethyl-8,14-dioxa-4,10,19,20,23-pentaazatetracyclo [13.5.2.1$^{2,6}$.0$^{18,21}$]tricosa-1(20),2(23),3,5,15(22), 16,18 (21)-heptaen-9-one example 154 as a white solid.

LCMS method F: [M+H]$^+$=354.2, $t_R$=2.03 min

LCMS method G: [M+H]$^+$=354.3, $t_R$=1.89 min $^1$H NMR (500 MHz, d6-DMSO) δ 13.48 (s, 1H), 9.24 (s, 1H), 8.62 (s, 1H), 7.85 (dd, 1H), 7.77 (d, 1H), 7.51 (d, 1H), 6.99 (dd, 1H), 5.94 (q, 1H), 4.56 (m, 1H), 3.53/2.83 (dq+td, 2H), 2.32/1.33 (t+td, 2H), 1.68 (d, 3H), 1.37 (d, 3H) ppm.

Example 155: (7R,13R)-7,13-dimethyl-8,14-dioxa-4,10,19,20,23-pentaazatetracyclo[13.5. 2.1$^{2,6}$.0$^{18,21}$] tricosa-1(20),2(23),3,5,15(22),16,18(21)-heptaen-9-one

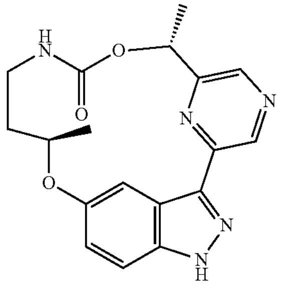 [SMILES: C[C@@H]1CCNC(=O)O[C@H](C)c2cncc(n2)-c2n[nH]c3ccc(cc23)O1]

Example 155 is prepared according to the synthesis route described in general Scheme K.

Preparation of Intermediate 229: (7R,13R)-7,13-dimethyl-19-(oxan-2-yl)-8,14-dioxa-4,10,19,20,23-pentaazatetracyclo$[13.5.2.1^{2,5}.0^{18,21}]$tricosa-1(20),2(23),3,5,15(22),16,18(21)-heptaen-9-one

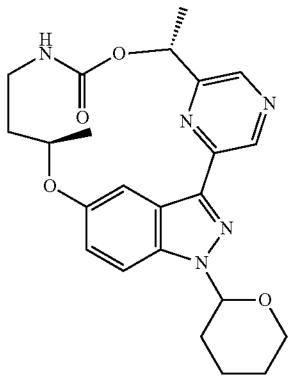 [SMILES: C[C@@H]1CCNC(=O)O[C@H](C)c2cncc(n2)-c2nn(C3CCCCO3)c3ccc(cc23)O1]

To a solution of benzyl N-[(3R)-3-[3-[6-(I-hydroxyethyl)pyrazin-2-yl]-1-tetrahydropyran-2-yl-indazol-5-yl]oxy-butyl]carbamate intermediate 227 (1.80 g, 3.30 mmol) in dry N,N-dimethyl formamide (50 mL) was added potassium hydroxide (555 mg, 9.90 mmol) at 30° C. in one portion. The reaction mixture was stirred at 30° C. for 60 min. The solid was filtered out and washed with ethyl acetate. The filtrate was diluted with ethyl acetate, washed with brine, dried over anhydrous magnesium sulfate, filtered and evaporated under reduced pressure. The residue was purified and separated as diastereomers by silica gel column chromatography using heptane/ethyl acetate 50/50 to 0/100 as eluent to afford (7R,13R)-7,13-dimethyl-19-(oxan-2-yl)-8,14-dioxa-4,10,19,20,23-pentaazatetracyclo$[13.5.2.1^{2,6}.0^{18,21}]$tricosa-1(20),2(23),3, 5, 15(22),16,18(21)-heptaen-9-one intermediate 229 as a white solid.

$^1$H NMR (500 MHz, d6-DMSO) δ 9.28/9.1 (s/s, 1H), 8.65 (s, 1H), 8.13/7.91 (d/d, 1H), 7.72/7.69 (d/d, 1H), 7.56/7.18 (t/t, 1H), 7.06/7.04 (dd/dd, 1H), 6.14/5.78 (q/q, 1H), 5.93 (dd, 1H), 4.89 (m, 1H), 3.93/3.78 (dq+td, 2H), 3.24/2.98 (dq+dt, 2H), 2.46/2.03 (td+dq, 2H), 2.07/1.78 (m+m, 2H), 1.75/1.6 (m+m, 2H), 1.75 (d, 3H), 1.61 (m, 2H), 1.5/1.4 (d/d, 3H) ppm.

Preparation of Example 155: (7R,13R)-7,13-dimethyl-8,14-dioxa-4,10,19,20,23-pentaaza tetracyclo$[13.5.2.1^{2,6}.0^{18,21}]$tricosa-1(20),2(23),3,5,15(22),16,18(21)-heptaen-9-one

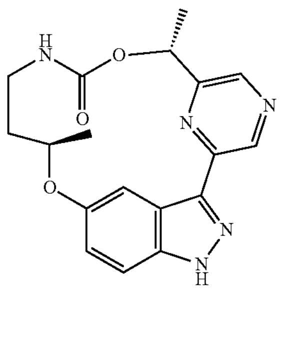 [SMILES: C[C@@H]1CCNC(=O)O[C@H](C)c2cncc(n2)-c2n[nH]c3ccc(cc23)O1]

To a suspension of (7R,13R)-7,13-dimethyl-19-(oxan-2-yl)-8,14-dioxa-4,10,19,20,23-pentaazatetracyclo$[13.5.2.1^{2,6}.0^{18,21}]$tricosa-1(20),2(23),3,5,15(22),16,18(21)-heptaen-9-one intermediate 229 (86 mg, 0.20 mmol) in a mixture of methanol (14 mL) and water (2.0 mL) was added p-toluenesulfonic acid monohydrate (190 mg, 0.98 mmol) and the reaction mixture was stirred at 65° C. for 48 h. The reaction mixture was cooled to room temperature and saturated aqueous sodium bicarbonate solution and water were added. Methanol was evaporated meanwhile solid was precipitated. The solid was filtered and dried under reduced pressure. The residue was purified by silica gel column chromatography to afford (7R,13R)-7,13-dimethyl-8,14-dioxa-4,10,19,20,23-pentaazatetracyclo$[13.5.2.1^{2,6}.0^{18,21}]$tricosa-1(20),2(23),3,5,15(22), 16,18(21)-heptaen-9-one example 155 as a white solid.

LCMS method F: $[M+H]^+$=354.2, $t_R$=2.14 min

LCMS method G: $[M+H]^+$=354.3, $t_R$=2.03 min $^1$H NMR (500 MHz, d6-DMSO) δ 13.47 (s, 1H), 9.29/9.11 (s/s, 1H), 8.61 (s, 1H), 8.15/7.9 (d/d, 1H), 7.55/7.17 (dd/dd, 1H), 7.52/7.48 (d/d, 1H), 7/6.98 (dd/dd, 1H), 6.13/5.78 (q/q, 1H), 4.89/4.34 (m/m, 1H), 3.69/3.24/2.98/2.98 (dq+dq/dq+dq, 2H), 2.76/1.77/1.59/1.42 (dd+td/dd+td, 2H), 1.75/1.51 (d/d, 3H), 1.38/1.37 (d/d, 3H) ppm.

Example 156: (13S)-13-methyl-8,14-dioxa-4,10,19,20,23-pentaazatetracyclo$[13.5.2.1^{2,6}.0^{18,21}]$tricosa-1(20),2(23),3,5,15(22),16,18(21)-heptaen-9-one

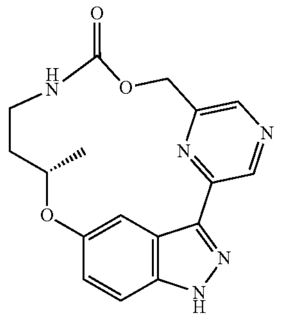 [SMILES: C[C@H]1CCNC(=O)OCc2cncc(n2)-c2n[nH]c3ccc(cc23)O1]

Example 156 is prepared according to the synthesis route described in general Scheme K.

Preparation of Intermediate 230: [6-[5-[tert-butyl(dimethyl)silyl]oxy-1-tetrahydropyran-2-yl-indazol-3-yl]pyrazin-2-yl]methanol

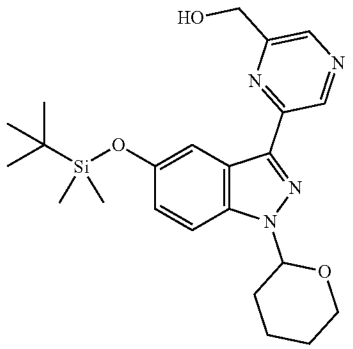 [SMILES: CC(C)(C)[Si](C)(C)Oc1ccc2c(c1)c(-c1cncc(CO)n1)nn2C1CCCCO1]

To a solution of (6-chloropyrazin-2-yl)methanol (200 mg, 1.66 mmol) in 1,4-dioxane (10.8 mL) and water (1.2 mL) was added at room temperature tert-butyl-dimethyl-[1-tetrahydropyran-2-yl-3-(4,4,5,5-tetramethyl-1,3,2-dioxaborolan-2-yl)indazol-5-yl]oxy-silane (760 mg, 1.66 mmol) and potassium carbonate (380 mg, 2.76 mmol). The reaction mixture was purged with nitrogen and tetrakis(triphenylphosphine)palladium(0) (161 mg, 0.14 mmol) was added. The reaction mixture was stirred at 80° C. for 16 h. The reaction mixture was filtered through a Celite pad and washed with ethyl acetate. The filtrate was diluted with water and extracted with ethyl acetate. The organic layer was washed with water, brine, dried over anhydrous magnesium sulfate, filtered and concentrated under reduced pressure. The residue was purified by silica gel column chromatography using cyclohexane/ethyl acetate 99/1 to 70/30 as eluent to afford [6-[5-[tert-butyl(dimethyl)silyl]oxy-1-tetrahydropyran-2-yl-indazol-3-yl]pyrazin-2-yl]methanol intermediate 230 as a yellow solid.

LCMS method F: $[M+H]^+$=441.3, $t_R$=3.36 min

Preparation of Intermediate 231: 3-[6-(hydroxymethyl)pyrazin-2-yl]-1-tetrahydropyran-2-yl-indazol-5-ol

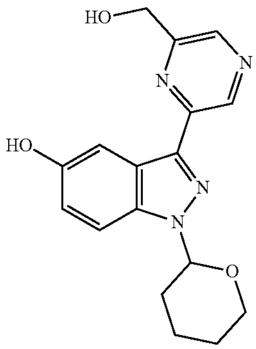 [SMILES: OCc1cncc(-c2nn(C3CCCCO3)c3ccc(O)cc23)n1]

To a solution of [6-[5-[tert-butyl(dimethyl)silyl]oxy-1-tetrahydropyran-2-yl-indazol-3-yl]pyrazin-2-yl]methanol intermediate 230 (594 g, 1.35 mmol) in THE (10 mL) was added dropwise at room temperature 1.0 M tetrabutylammonium fluoride solution in THE (1.48 mL, 1.48 mmol). The reaction mixture was stirred at room temperature for 16 h. The reaction mixture was poured into ice water and stirred for 20 min. The aqueous layer was extracted with ethyl acetate then combined organic layers were washed with brine, dried over anhydrous magnesium sulfate, filtered and concentrated under reduced pressure to give 3-[6-(hydroxymethyl)pyrazin-2-yl]-1-tetrahydropyran-2-yl-indazol-5-ol intermediate 231 as a yellow solid which was used in the next step without further purification.

LCMS method F: $[M+H]^+$=327.3, $t_R$=2.01 min

Preparation of Intermediate 232: benzyl N-[(3S)-3-[3-[6-(hydroxymethyl)pyrazin-2-yl]-1-tetrahydropyran-2-yl-indazol-5-yl]oxybutyl]carbamate

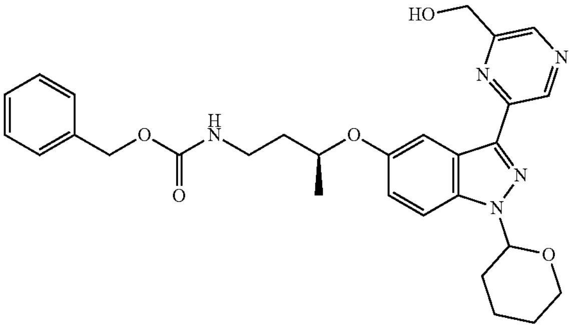 [SMILES: C[C@@H](CCNC(=O)OCc1ccccc1)Oc1ccc2c(c1)c(-c1cncc(CO)n1)nn2C1CCCCO1]

[(1R)-3-(benzyloxycarbonylamino)-1-methyl-propyl] methanesulfonate was prepared according to the same synthesis procedures as intermediate 199 starting from (2R)-4-aminobutan-2-ol.

To a mixture of 3-[6-(hydroxymethyl)pyrazin-2-yl]-1-tetrahydropyran-2-yl-indazol-5-ol intermediate 231 (0.414 g, 1.27 mmol) in N,N-dimethylformamide (12 mL) was added cesium carbonate (825 mg, 2.54 mmol). The reaction mixture was stirred for 20 min. Then, [(1R)-3-(benzyloxycarbonylamino)-1-methyl-propyl]methanesulfonate (421 mg, 1.40 mmol) was added. The reaction mixture was stirred at room temperature for 16 h. Additional [(1R)-3-(benzyloxycarbonylamino)-1-methyl-propyl]methanesulfonate was added (57 mg, 0.19 mmol) and the reaction mixture was stirred at room temperature for 2 h. The reaction mixture was concentrated under reduced pressure then diluted with water and extracted with ethyl acetate.

The combined organic layer was washed with brine, dried over anhydrous sodium sulfate, filtered and evaporated under reduced pressure. The residue was purified by silica gel column chromatography using dichloromethane/methanol 100/0 to 95/5 as eluent to afford benzyl N-[(3S)-3-[3-[6-(hydroxymethyl)pyrazin-2-yl]-1-tetrahydropyran-2-yl-indazol-5-yl]oxybutyl]carbamate intermediate 232 as a yellow solid.

LCMS method F: $[M+H]^+$=532.3, $t_R$=2.79 min

Preparation of Intermediate 233: (13S)-13-methyl-19-(oxan-2-yl)-8,14-dioxa-4,10,19,20,23-pentaazatetracyclo[13.5.2.1$^{2,6}$.0$^{18,21}$]tricosa-1(20),2(23),3,5,15(22),16,18(21)-heptaen-9-one

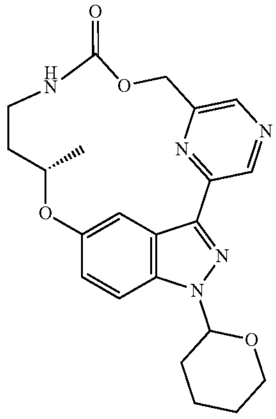 [SMILES: C[C@H]1CCNC(=O)OCc2cncc(n2)-c2nn(C3CCCCO3)c3ccc(cc23)O1]

To a solution of benzyl N-[(3S)-3-[3-[6-(hydroxymethyl)pyrazin-2-yl]-1-tetrahydropyran-2-yl-indazol-5-yl]oxy-butyl]carbamate intermediate 232 (562 mg, 1.06 mmol) in dry acetonitrile (53 mL) at room temperature was added potassium hydroxide (297 mg, 5.30 mmol) in one portion. The reaction mixture was stirred at room temperature for 4 h. The reaction mixture was filtered and rinsed with acetonitrile and the filtrate was evaporated under reduced pressure. The residue was purified by silica gel column chromatography using dichloromethane/methanol 100/0 to 95/5 as eluent to afford (13S)-13-methyl-19-(oxan-2-yl)-8,14-dioxa-4,10,19,20,23-pentaazatetra cyclo[13.5.2.1$^{2,6}$.0$^{18,21}$]tricosa-1(20),2(23),3,5,15(22),16,18(21)-heptaen-9-one intermediate 233 as a yellow foam.

LCMS method F: $[M+H]^+$=424.3, $t_R$=2.54 min

Preparation of Example 156: (13S)-13-methyl-8,14-dioxa-4,10,19,20,23-pentaazatetra cyclo[13.5.2.1$^{2,6}$.0$^{18,21}$]tricosa-1(20),2(23),3,5,15(22),16,18(21)-heptaen-9-one

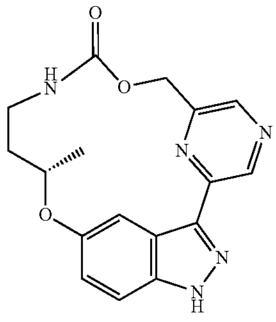 [SMILES: C[C@H]1CCNC(=O)OCc2cncc(n2)-c2n[nH]c3ccc(cc23)O1]

To a solution of (13S)-13-methyl-19-(oxan-2-yl)-8,14-dioxa-4,10,19,20,23-pentaazatetracyclo[13.5.2.1$^{2,6}$.0$^{18,21}$]tricosa-1(20),2(23),3,5,15(22),16,18(21)-heptaen-9-one intermediate 233 (183 mg, 0.43 mmol) in methanol (7.4 mL) and water (1.2 mL) was added p-toluenesulfonic acid monohydrate (409 mg, 2.15 mmol) and the reaction mixture was stirred at 65° C. for 16 h. The reaction mixture was diluted with dichloromethane and saturated aqueous solution of sodium bicarbonate. After separation, the aqueous layer was extracted with dichloromethane. The combined organic layers were washed brine, dried over anhydrous magnesium sulfate, filtered and evaporated under reduced pressure. The residue was crystallized in dichloromethane, filtered, and dried to afford (13S)-13-methyl-8,14-dioxa-4,10,19,20,23-pentaazatetra cyclo[13.5.2.1$^{2,6}$.0$^{18,21}$]tricosa-1(20),2(23),3,5,15(22),16,18(21)-heptaen-9-one example 156 as a cream powder.

LCMS method F: $[M+H]^+$=340.2, $t_R$=1.86 min

LCMS method G: $[M+H]^+$=340.3, $t_R$=1.81 min $^1$H NMR (400 MHz, d6-DMSO) δ 13.49-13.48 (1H, m), 9.27 (1H, s), 8.52 (1H, s), 7.86-7.81 (2H, m), 7.51 (1H, d, J=8.8 Hz), 6.99 (1H, dd, J=2.4, 9.0 Hz), 5.69 (1H, d, J=15.6 Hz), 5.18-5.14 (1H, m), 4.62-4.58 (1H, m), 3.52-3.46 (1H, m), 2.95-2.87 (1H, m), 2.35-2.28 (1H, m), 1.40-1.37 (4H, m) ppm.

Example 157: (13R)-13-methyl-8,14-dioxa-10,19,20,22-tetraazatetracyclo[13.5.2.1$^{2,6}$.0$^{18,21}$]tricosa-1(20),2(23),3,5,15,17,21-heptaen-9-one

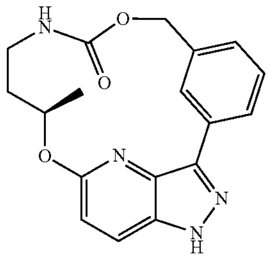 [SMILES: C[C@@H]1CCNC(=O)OCc2cccc(c2)-c2n[nH]c3ccc(nc23)O1]

Example 157 is prepared according to the synthesis route described in general Scheme C.

Preparation of Intermediate 234: 5-methoxy-1H-pyrazolo[4,3-b]pyridine

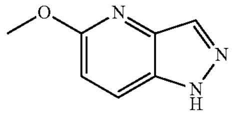

To a solution of 6-methoxy-2-methyl-pyridin-3-amine (4.0 g, 28.95 mmol) in acetic acid (40 mL) at 0° C. was added dropwise a solution of sodium nitrate (2.99 g, 43.42 mmol) in water (8 mL). The reaction mixture was stirred at room temperature for 1 h. A saturated aqueous sodium bicarbonate solution was added and the reaction mixture was extracted with ethyl acetate. The combined organic layers were dried over anhydrous magnesium sulfate, filtered and the solvent was removed under reduced pressure. The residue was purified by silica gel column chromatography using cyclohexane/ethyl acetate 100/0 to 80/20 as eluent to afford 5-methoxy-1H-pyrazolo[4,3-b]pyridine intermediate 234 as a brown solid.

LCMS method F: $[M+H]^+$=150.2, $t_R$=1.33 min

Preparation of Intermediate 235: 3-iodo-5-methoxy-1H-pyrazolo[4,3-b]pyridine

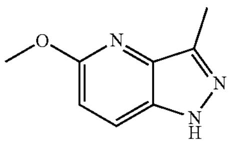

To a solution of 5-methoxy-1H-pyrazolo[4,3-b]pyridine intermediate 234 (1.88 g, 12.6 mmol) in acetonitrile (20 mL) was added N-iodosuccinimide (3.40 g, 15.12 mmol). The reaction mixture was heated under microwave irradiations at 120° C. for 20 min. The reaction mixture was diluted with a saturated solution of sodium thiosulfate and ethyl acetate was added. After separation, the aqueous layer was extracted with ethyl acetate. The combined organic layers were dried over anhydrous magnesium sulfate, filtered and the solvent was removed under reduced pressure. The residue was purified by silica gel column chromatography using cyclohexane/ethyl acetate 100/0 to 70/30 as eluent to afford 3-iodo-5-methoxy-1H-pyrazolo[4,3-b]pyridine intermediate 235 as an orange solid.

LCMS method F: $[M+H]^+$=276.0, $t_R$=2.08 min

Preparation of Intermediate 236: 3-iodo-5-methoxy-1-tetrahydropyran-2-yl-pyrazolo[4,3-b]pyridine

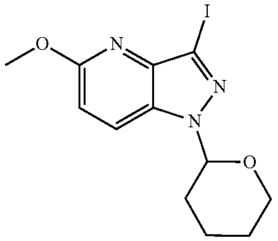 [SMILES: COc1ccc2c(n1)c(I)nn2C1CCCCO1]

To a solution of 3-iodo-5-methoxy-1H-pyrazolo[4,3-b]pyridine intermediate 235 (700 mg, 2.54 mmol) in dichloromethane (4.6 mL) was added 4-methylbenzenesulfonic acid monohydrate (242 mg, 1.27 mmol) and 3,4-dihydro-2H-pyran (0.46 mL, 5.08 mmol). The reaction mixture was stirred at room temperature for 2 h. The reaction mixture was diluted with dichloromethane and a saturated aqueous sodium bicarbonate solution was added. After separation, the aqueous layer was extracted with dichloromethane. The combined organic layers were dried over anhydrous magnesium sulfate, filtered and the solvent was evaporated under reduced pressure to afford 3-iodo-5-methoxy-1-tetrahydropyran-2-yl-pyrazolo[4,3-b]pyridine intermediate 236 as an orange oil.

LCMS method F: $[M+H]^+$=360.1, $t_R$=2.82 min

Preparation of Intermediate 237: 3-iodo-1-tetrahydropyran-2-yl-pyrazolo[4,3-b]pyridin-5-ol

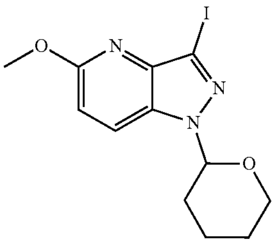 [SMILES: COc1ccc2c(n1)c(I)nn2C1CCCCO1]

To a solution of 3-iodo-5-methoxy-1-tetrahydropyran-2-yl-pyrazolo[4,3-b]pyridine intermediate 236 (912 mg, 2.54 mmol) in acetonitrile (5 mL) was added sodium iodide (1.14 g, 7.62 mmol) and trimethylchlorosilane (0.97 mL, 7.62 mmol). The reaction mixture was stirred at 80° C. for 1.5 h. The reaction mixture was diluted with water and ethyl acetate. After separation, the aqueous layer was extracted with ethyl acetate. The combined organic layers were dried over anhydrous magnesium sulfate, filtered and the solvent was removed under reduced pressure. The residue was purified by silica gel column chromatography using cyclohexane/(ethyl acetate/ethanol (3:1)) 100/0 to 30/70 as eluent. The resulting product was triturated in acetonitrile, filtered and dried to afford 3-iodo-1-tetrahydropyran-2-yl-pyrazolo[4,3-b]pyridin-5-ol intermediate 237 as a pale yellow solid.

LCMS method F: $[M+H]^+$=346.1, $t_R$=1.74 min

Preparation of Intermediate 238: benzyl N-[(3R)-3-(3-iodo-1-tetrahydropyran-2-yl-pyrazolo[4,3-b]pyridin-5-yl)oxybutyl]carbamate

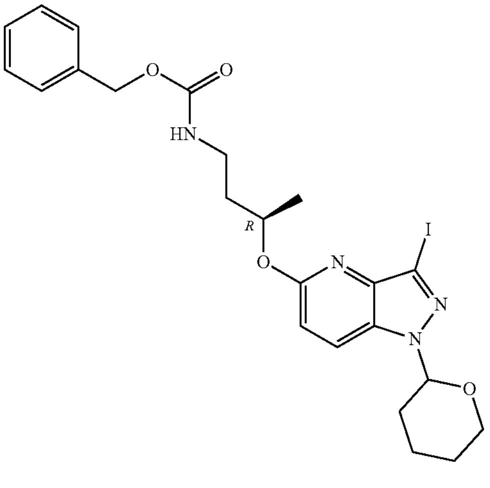

To a solution of 3-iodo-1-tetrahydropyran-2-yl-pyrazolo[4,3-b]pyridin-5-ol intermediate 237 (140 mg, 0.41 mmol) in acetonitrile (3.5 mL) was added cesium carbonate (240 mg, 0.81 mmol) and [(1S)-3-(benzyloxycarbonylamino)-1-methyl-propyl]methanesulfonate intermediate 199 (159 mg, 0.53 mmol). The reaction mixture was stirred at 75° C. for 1 h. The reaction mixture was cooled to room temperature and diluted with ethyl acetate. After separation, the aqueous layer was extracted with ethyl acetate and the combined organic layers were dried over anhydrous magnesium sulfate, filtered and concentrated under reduced pressure to afford benzyl N-[(3R)-3-(3-iodo-1-tetrahydropyran-2-yl-pyrazolo[4,3-b]pyridin-5-yl)oxybutyl]carbamate intermediate 238 (as a beige solid.

LCMS method F: $[M+H]^+$=551.2, $t_R$=3.17 min Preparation of Intermediate 239: Benzyl N-[(3R)-3-[3-[3-(hydroxymethyl)phenyl]-1-tetrahydropyran-2-yl-pyrazolo[4,3-b]pyridin-5-yl]oxybutyl]carbamate

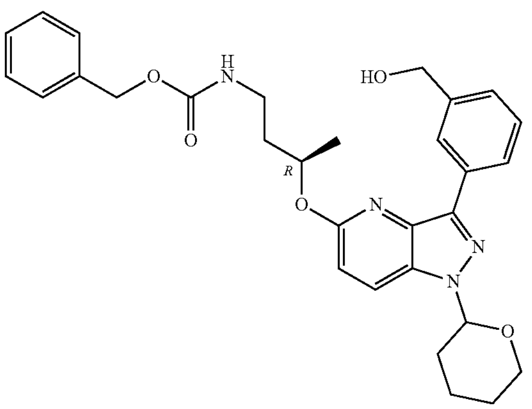

To a suspension of benzyl N-[(3R)-3-(3-iodo-1-tetrahydropyran-2-yl-pyrazolo[4,3-b]pyridin-5-yl)oxybutyl]carbamate intermediate 238 (210 mg, 0.38 mmol) in 1,4-dioxane (2.2 mL) and water (0.11 mL) was added [3-(hydroxymethyl)phenyl]boronic acid (69 mg, 0.46 mmol) and potassium phosphate tribasic (242 mg, 1.14 mmol). The reaction mixture was degassed with argon for 10 min and tetrakis(triphenylphosphine)palladium(0) (22 mg, 0.02 mmol) and Xphos (18 mg, 0.04 mmol) were added. The mixture was stirred at 105° C. for 7 h. The reaction mixture was cooled to room temperature and diluted with water and ethyl acetate. After separation, the aqueous layer was extracted with ethyl acetate. The organic layers were washed with brine, dried over anhydrous sodium sulfate, filtered and evaporated under reduced pressure. The residue was purified by silica gel column chromatography using cyclohexane/ethyl acetate 100/0 to 60/40 as eluent to afford benzyl N-[(3R)-3-[3-[3-(hydroxymethyl)phenyl]-1-tetrahydropyran-2-yl-pyrazolo[4,3-b]pyridin-5-yl]oxybutyl]carbamate intermediate 239 as a colorless oil.

LCMS method F: $[M+H]^+$=531.4, $t_R$=3.00 min

Preparation of Intermediate 240: (13R)-13-methyl-19-(oxan-2-yl)-8,14-dioxa-10,19,20,22-tetraazatetracyclo[13.5.2.1$^{2,6}$.0$^{18,21}$]tricosa-1(20),2(23),3,5,15,17,21-heptaen-9-one

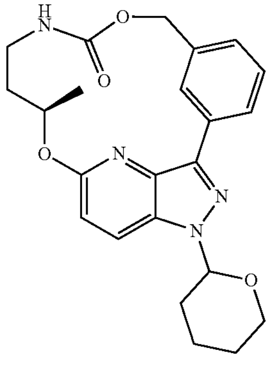 [SMILES: C[C@@H]1CCNC(=O)OCc2cccc(c2)-c2nn(C3CCCCO3)c3ccc(nc23)O1]

To a solution of benzyl N-[(3R)-3-[3-[3-(hydroxymethyl)phenyl]-1-tetrahydropyran-2-yl-pyrazolo[4,3-b]pyridin-5-yl]oxybutyl]carbamate intermediate 239 (156 mg, 0.29 mmol) in dry acetonitrile (40 mL) was added cesium carbonate (574 mg, 1.76 mmol). The resulting mixture was stirred at 90° C. for 2 h. The suspension was filtered and the salts were washed with acetonitrile. The filtrate was evaporated under reduced pressure. The residue was purified by silica gel column chromatography using dichloromethane/methanol 100/0 to 95/5 as eluent to afford (13R)-13-methyl-19-(oxan-2-yl)-8,14-dioxa-10,19,20,22-tetraazatetracyclo[13.5.2.1$^{2,6}$.0$^{18,21}$]tricosa-1(20),2(23),3,5,15,17,21-heptaen-9-one intermediate 240 as a colorless oil.

LCMS method F: $[M+H]^+$=423.4, $t_R$=2.88 min

Preparation of Example 157: (13R)-13-methyl-8,14-dioxa-10,19,20,22-tetraazatetracyclo[13.5.2.1$^{2,6}$.0$^{18,21}$]tricosa-1(20),2(23),3,5,15,17,21-heptaen-9-one

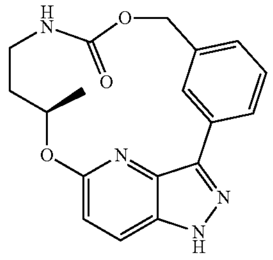 [SMILES: C[C@@H]1CCNC(=O)OCc2cccc(c2)-c2n[nH]c3ccc(nc23)O1]

To a solution of (13R)-13-methyl-19-(oxan-2-yl)-8,14-dioxa-10,19,20,22-tetraazatetracyclo[13.5.2.1$^{2,6}$.0$^{18,21}$]tricosa-1(20),2(23),3,5,15,17,21-heptaen-9-one intermediate 240 (124 mg, 0.29 mmol) in methanol (5.5 mL) and water (0.8 mL) was added p-toluenesulfonic acid (280 mg, 1.47 mmol). The reaction mixture was stirred at 65° C. for 2 h. The reaction mixture was cooled to room temperature and the reaction was carefully quenched with a saturated aqueous sodium bicarbonate solution then ethyl acetate was added. After separation, the aqueous layer was extracted with ethyl acetate and the organic layers were washed with brine, dried over anhydrous sodium sulfate, filtered and evaporated under reduced pressure. The residue was purified by silica gel column chromatography using dichloromethane/methanol 100/0 to 96/4 as eluent to afford (13R)-13-methyl-8,14-dioxa-10,19,20,22-tetraazatetracyclo[13.5.2.1$^{2,6}$.0$^{18,21}$]tricosa-1(20),2(23),3,5,15,17,21-heptaen-9-one example 157 as a white solid.

LCMS method F: $[M+H]^+$=339.3, $t_R$=2.17 min

LCMS method G: $[M+H]^+$=339.3, $t_R$=2.15 min $^1$H NMR (400 MHz, d6-DMSO) δ 13.25 (1H, brs), 8.58 (1H, s), 8.04-7.93 (2H, m), 7.71 (1H, t, J=6.3 Hz), 7.42 (1H, t, J=7.7 Hz), 7.22-7.18 (1H, m), 6.81 (1H, d, J=9.1 Hz), 5.61-5.53 (1H, m), 5.51-5.44 (1H, m), 5.10-5.03 (1H, m), 3.43-3.36 (1H, m), 3.02-2.94 (1H, m), 2.45-2.36 (1H, m), 1.39 (3H, d, J=6.2 Hz), 1.38-1.34 (1H, m) ppm.

Example 158: (12R)-4,12-dimethyl-7,13-dioxa-4,9,18,19,22-pentaazatetracyclo[12.5.2.1$^{2,5}$.0$^{17,20}$]docosa-1(19),2,5(22),14(21),15,17(20)-hexaen-8-one

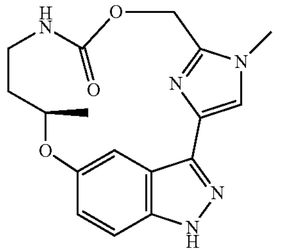 [SMILES: C[C@@H]1CCNC(=O)OCc2nc(cn2C)-c2n[nH]c3ccc(cc23)O1]

Example 158 is prepared according to the synthesis route described in general Scheme K.

Preparation of Intermediate 241: (4-bromo-1-methyl-imidazol-2-yl)methanol

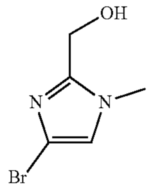

To a suspension of methyl 4-bromo-1-methyl-imidazole-2-carboxylate (3.0 g, 13.76 mmol) in methanol (30 mL) at 0° C. was added portion wise sodium borohydride (1.14 g, 30.27 mmol). The reaction mixture was stirred at 0° C. for 2 h. Additional sodium borohydride (1.14 g, 30.27 mmol) was added and the reaction mixture was stirred at room temperature for 3 h. The reaction mixture was quenched by addition of water and methanol then evaporated under reduced pressure. The aqueous phase was extracted with ethyl acetate. The organic phases were washed with brine, dried over anhydrous sodium sulfate, filtered and evaporated under reduced pressure to afford (4-bromo-1-methyl-imidazol-2-yl)methanol intermediate 241 as a white solid.

LCMS method H: $[M+H]^+$=191-193, $t_R$=0.93 min

Preparation of Intermediate 242: [4-[5-[tert-butyl(dimethyl)silyl]oxy-1-tetrahydropyran-2-yl-indazol-3-yl]-1-methyl-imidazol-2-yl]methanol

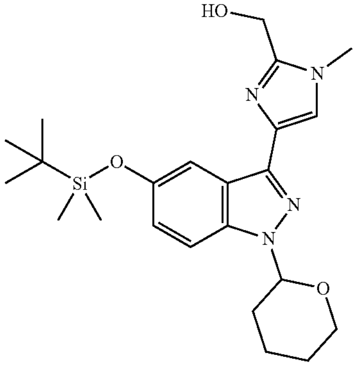 [SMILES: Cn1cc(-c2nn(C3CCCCO3)c3ccc(O[Si](C)(C)C(C)(C)C)cc23)nc1CO]

To a solution of tert-butyl-dimethyl-[1-tetrahydropyran-2-yl-3-(4,4,5,5-tetramethyl-1,3,2-dioxaborolan-2-yl)indazol-5-yl]oxy-silane (753 mg, 1.64 mmol), (4-bromo-1-methyl-imidazol-2-yl)methanol intermediate 241 (250 mg, 1.31 mmol) and potassium phosphate tribasic (833 mg, 3.93 mmol) in 1,4-dioxane (3 mL) and water (150 μL) were added tetrakis (triphenylphosphine) palladium(0) (76 mg, 0.065 mmol) and 2-dicyclohexylphosphino-2',4',6'-triisopropylbiphenyl (62 mg, 0.131 mmol). The reaction mixture was heated at 100° C. for 1 h. The solvent was evaporated under reduced pressure and the residue was portioned between water and ethyl acetate. The aqueous layer was extracted with ethyl acetate. The organic layer was dried over anhydrous sodium sulfate, filtered and evaporated under reduced pressure. The residue was purified by silica gel column chromatography using cyclohexane/ethyl acetate 100/0 to 50/50 then dichloromethane/methanol 90/10 to afford [4-[5-[tert-butyl(dimethyl)silyl]oxy-1-tetrahydropyran-2-yl-indazol-3-yl]-1-methyl-imidazol-2-yl]methanol intermediate 242 as a yellow oil.

LCMS method F: $[M+H]^+$=443.3, $t_R$=2.33 min

Preparation of Intermediate 243: benzyl N-[(3R)-3-[3-[2-(hydroxymethyl)-1-methyl-imidazol-4-yl]-1-tetrahydropyran-2-yl-indazol-S-yl]oxybutyl]carbamate

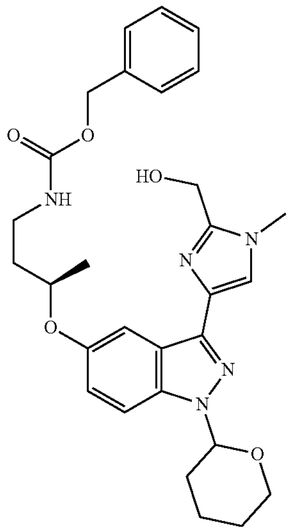 [SMILES: C[C@H](CCNC(=O)OCc1ccccc1)Oc1ccc2c(c1)c(-c1cn(C)c(CO)n1)nn2C1CCCCO1]

To a suspension of [4-[5-[tert-butyl(dimethyl)silyl]oxy-1-tetrahydropyran-2-yl-indazol-3-yl]-1-methyl-imidazol-2-yl] methanol intermediate 242 (100 mg, 0.226 mmol) and cesium carbonate (220 mg, 0.678 mmol) in acetonitrile (30 mL) wad added [(1S)-3-(benzyloxycarbonylamino)-1-methyl-propyl]methanesulfonate (88 mg, 0.294 mmol). The reaction mixture was stirred at 50° C. for 16 h. Additional cesium carbonate (220 mg, 0.678 mmol) was added and the mixture was stirred at 60° C. for 16 h. The solvent was evaporated under reduced pressure. The residue was portioned between water and ethyl acetate. After separation, the aqueous layer was extracted with ethyl acetate. The organic phase was dried over anhydrous sodium sulfate, filtered and the solvent was evaporated under reduced pressure. The residue was purified by silica gel column chromatography using cyclohexane/ethyl acetate 100/0 to 70/30 as eluent to afford benzyl N-[(3R)-3-[3-[2-(hydroxymethyl)-1-methyl-imidazol-4-yl]-1-tetrahydropyran-2-yl-indazol-5-yl]oxy-butyl]carbamate intermediate 243 as a yellow oil.

LCMS method F: $[M+H]^+=534.4$, $t_R=2.08$ min

Preparation of Intermediate 244: (12R)-4,12-dimethyl-18-(oxan-2-yl)-7,13-dioxa-4,9,18,19,22-pentaazatetracyclo[12.5.2.1$^{2,5}$.0$^{17,20}$]docosa-1(19),2,5(22),14(21),15,17(20)-hexaen-8-one

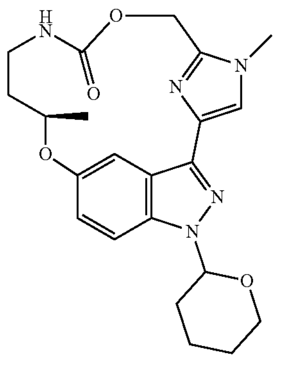 [SMILES: C[C@@H]1CCNC(=O)OCc2nc(cn2C)-c2nn(C3CCCCO3)c3ccc(cc23)O1]

To a solution of benzyl N-[(3R)-3-[3-[2-(hydroxymethyl)-1-methyl-imidazol-4-yl]-1-tetrahydropyran-2-yl-indazol-5-yl]oxybutyl]carbamate intermediate 243 (200 mg, 0.375 mmol) in acetonitrile (20 mL) was added potassium hydroxide (105 mg, 1.87 mmol). The reaction mixture was stirred at room temperature for 16 h. The solvent was evaporated under reduced pressure and the residue was dissolved in ethyl acetate and washed with water. The organic layer was dried over anhydrous sodium sulfate, filtered and evaporated under reduced pressure. The residue was purified by silica gel column chromatography using dichloromethane/methanol 100/0 to 90/10 as eluent to (12R)-4,12-dimethyl-18-(oxan-2-yl)-7,13-dioxa-4,9,18,19,22-pentaazatetracyclo[12.5.2.1$^{2,5}$.0$^{17,20}$]docosa-1(19),2,5(22),14(21),15, 17(20)-hexaen-8-one intermediate 244 as a yellow oil.

LCMS method F: $[M+H]^+=426.3$, $t_R=2.16$ min

Preparation of Example 158: (12R)-4,12-dimethyl-7,13-dioxa-4,9,18,19,22-pentaazatetra cyclo [12.5.2.1$^{2,5}$.0$^{17,20]docosa-}$1(19),2,5(22),14(21),15,17(20)-hexaen-8-one

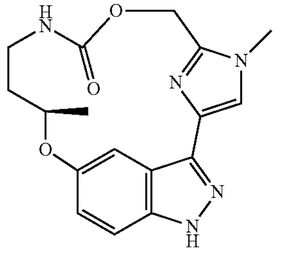 [SMILES: C[C@@H]1CCNC(=O)OCc2nc(cn2C)-c2n[nH]c3ccc(cc23)O1]

To a solution of (12R)-4,12-dimethyl-18-(oxan-2-yl)-7,13-dioxa-4,9,18,19,22-pentaaza tetracyclo[12.5.2.1$^{2,5}$.0$^{17,}$ $_{20}$]docosa-1(19),2,5(22),14(21),15,17(20)-hexaen-8-one intermediate 244 (56 mg, 0.13 mmol) in methanol (5 mL) and water (0.5 mL) was added p-toluenesulfonic acid monohydrate (125 mg, 0.66 mmol). The reaction mixture was stirred at 65° C. for 2 h. The solvent was evaporated under reduced pressure and the residue was neutralized by slow addition of saturated aqueous sodium bicarbonate solution. The residue was diluted with ethyl acetate. After separation, the aqueous layer was extracted with ethyl acetate. The organic layer was washed with saturated aqueous sodium bicarbonate solution, water and brine, dried over anhydrous sodium sulfate, filtered and evaporated under reduced pressure. The residue was purified by preparative TLC using dichloromethane/methanol 100/0 to 95/5 as eluent to afford (12R)-4,12-dimethyl-7,13-dioxa-4,9,18,19,22-pentaazatetracyclo[12.5.2.1$^{2,5}$.0$^{17,20}$]docosa-1(19),2,5(22),14(21),15, 17(20)-hexaen-8-one example 158 as a cream powder.

LCMS method F: $[M+H]^+=342.3$, $t_R=1.67$ min

LCMS method G: $[M+H]^+=342.3$, $t_R=1.73$ min $^1$H NMR (400 MHz, d6-DMSO) δ 12.6-12.4 (1H; m), 8.32 (1H, d, J=2.3 Hz), 7.88-7.85 (1H, m), 7.42 (1H, s), 7.32-7.29 (1H, m), 6.85 (1H, dd, J=2.5, 8.9 Hz), 5.48 (1H, d, J=14.8 Hz), 5.01-4.96 (1H, m), 4.62-4.52 (1H, m), 3.63-3.62 (3H, m), 2.91-2.78 (1H, m), 2.45-2.38 (1H, m), 1.39 (3H, d, J=5.9 Hz), 1.27-1.24 (2H, m) ppm.

Example 159: (13R)-13-methyl-8,14-dioxa-4,5,10,19,20,23-hexaazatetracyclo[13.5.2.1$^{2,5}$.0$^{18,21}$]tricosa-1(20),2(23),3,15,17,21-hexaen-9-one

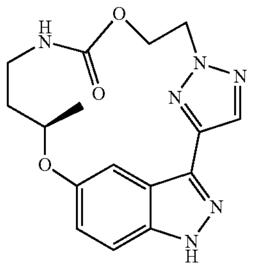 [SMILES: C[C@@H]1CCNC(=O)OCCn2ncc(n2)-c2n[nH]c3ccc(cc23)O1]

Example 159 is prepared according to the synthesis route described in general Scheme O.

Preparation of Intermediate 245: 4,5-dibromo-2-(2-tetrahydropyran-2-yloxyethyl)triazole

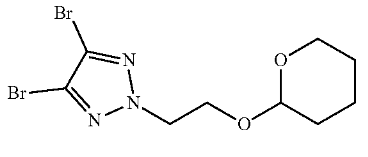 [SMILES: Brc1nn(CCOC2CCCCO2)nc1Br]

To a solution of 4,5-dibromo-2H-triazole (3.40 g, 15.0 mmol) in N,N-dimethylformamide (100 mL) cooled at −10° C. was added potassium carbonate (4.14 g, 30.0 mmol). The reaction mixture was stirred at room temperature for 15 min. 2-(2-bromoethoxy)tetrahydropyran (3.44 g, 16.50 mmol) in N,N-dimethylformamide (10 mL) was added dropwise and the reaction mixture was stirred at room temperature for 16 h. The reaction mixture was quenched by addition of water then extracted with ethyl acetate. The combined organic layers were washed with brine, dried over anhydrous magnesium sulfate, filtered and the solvent was removed under reduced pressure. The residue was purified by silica gel column chromatography using heptane/ethyl acetate 90/10 to 80/20 as eluent to afford 4,5-dibromo-2-(2-tetrahydropyran-2-yloxyethyl)triazole intermediate 245 as a colorless liquid.

LCMS method F: $[M+H]^+$=356.1, $t_R$=2.69 min

Preparation of Intermediate 246: 4-bromo-2-(2-tetrahydropyran-2-yloxyethyl)triazole

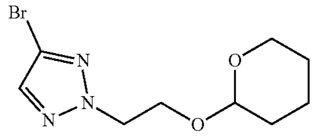 [SMILES: Brc1cnn(CCOC2CCCCO2)n1]

To a solution of 4,5-dibromo-2-(2-tetrahydropyran-2-yloxyethyl)triazole intermediate 245 (1.90 g, 5.35 mmol) in THE (50 mL) cooled at −20° C. was added dropwise a 2M of isopropylmagnesium chloride solution in THE (3.20 mL, 6.42 mmol). The reaction mixture was stirred at room temperature for 16 h then diluted with a saturated ammonium chloride solution. After separation, the aqueous layer was extracted with ethyl acetate. The combined organic layers were washed with brine, dried over anhydrous magnesium sulfate, filtered and evaporated under reduced pressure. The residue was purified by silica gel column chromatography using heptane/ethyl acetate 100/0 to 90/10 as eluent to afford 4-bromo-2-(2-tetrahydropyran-2-yloxyethyl)triazole intermediate 246 as a colorless liquid.

LCMS method F: $[M+H]^+$=276-278, $t_R$=2.34 min

Preparation of Intermediate 247: 2-(4-bromotriazol-2-yl)ethanol

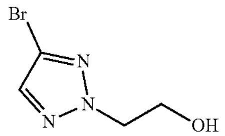

To a solution of 4-bromo-2-(2-tetrahydropyran-2-yloxyethyl)triazole intermediate 246 (2.45 g, 8.88 mmol) in THE (70 mL) cooled at 0° C. was added 4M hydrogen chloride solution in 1,4-dioxane (6.66 mL, 26.61 mmol). The reaction mixture was stirred at room temperature for 24 h. The reaction mixture was diluted with a saturated aqueous sodium bicarbonate solution. After separation, the aqueous layer was extracted with ethyl acetate. The combined organic layers were washed with brine, dried over anhydrous magnesium sulfate, filtered and evaporated under reduced pressure. The residue was purified by silica gel flash chromatography using heptane/ethyl acetate 70/30 as eluent to afford 2-(4-bromotriazol-2-yl)ethanol intermediate 247 as a colorless liquid.

LCMS method F: $[M+H]^+$=192-194, $t_R$=1.20 min

Preparation of Intermediate 248: 2-[4-[5-[tert-butyl(dimethyl)silyl]oxy-1-tetrahydropyran-2-yl-indazol-3-yl]triazol-2-yl]ethanol

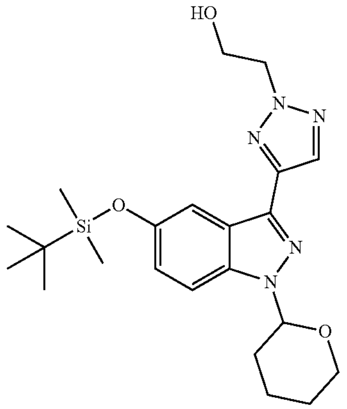 [SMILES: CC(C)(C)[Si](C)(C)Oc1ccc2c(c1)c(-c1cnn(CCO)n1)nn2C1CCCCO1]

To a solution of 2-(4-bromotriazol-2-yl)ethanol intermediate 247 (420 mg, 2.18 mmol) in 1,4-dioxane (70 mL) and water (7 mL) was added tert-butyl-dimethyl-[1-tetrahydropyran-2-yl-3-(4,4,5,5-tetramethyl-1,3,2-dioxaborolan-2-yl)indazol-5-yl]oxy-silane (1.20 g, 2.62 mmol) and potassium phosphate tribasic (1.39 g, 6.56 mmol). The solution was purged with argon and tetrakis(triphenylphosphine)palladium(0) (126 mg, 0.11 mmol) was added. The reaction mixture was stirred at 90° C. for 16 h. The solvent was evaporated under reduced pressure and the residue was diluted with water and ethyl acetate. After separation, the aqueous layer was extracted with ethyl acetate. The combined organic layers were washed with brine, dried over anhydrous magnesium sulfate, filtered and evaporated under reduced pressure. The residue was purified by silica gel flash chromatography using heptane/ethyl acetate 80/20 as eluent to afford 2-[4-[5-[tert-butyl(dimethyl)silyl]oxy-1-tetrahydropyran-2-yl-indazol-3-yl]triazol-2-yl]ethanol intermediate 248 as a pale brown oil.

LCMS method F: $[M+H]^+$=444.3, $t_R$=3.28 min

Preparation of Intermediate 249: (13R)-13-methyl-19-(oxan-2-yl)-8,14-dioxa-4,5,10,19,20,23-hexaazatetracyclo[13.5.2.$1^{2,5}$.$0^{18,21}$]tricosa-1(20),2(23),3,15,17,21-hexaen-9-one

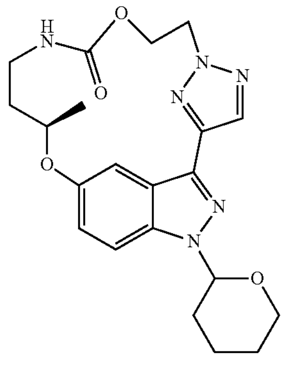 [SMILES: C[C@@H]1CCNC(=O)OCCn2ncc(n2)-c2nn(C3CCCCO3)c3ccc(cc23)O1]

To a suspension of 2-[4-[5-[tert-butyl(dimethyl)silyl]oxy-1-tetrahydropyran-2-yl-indazol-3-yl]triazol-2-yl]ethanol intermediate 248 (480 mg, 1.08 mmol) and cesium carbonate (1.05 g, 3.24 mmol) in acetonitrile (25 mL) was added a solution of [(1S)-3-(benzyloxycarbonylamino)-1-methyl-propyl]methanesulfonate (391 mg, 1.29 mmol) in acetonitrile (5 mL). The resulting mixture was stirred at 50° C. for 16 h. Additional acetonitrile (25 mL) and cesium carbonate (1.05 g, 3.24 mmol) were added. The reaction mixture was stirred at 70° C. for 3 h. The reaction mixture was filtered to remove salts and washed with acetonitrile. The filtrate was concentrated under reduced pressure. The residue was purified by silica gel column chromatography using heptane/ethyl acetate 70/30 to 60/40 as eluent to afford (13R)-13-methyl-19-(oxan-2-yl)-8,14-dioxa-4,5,10,19,20,23-hexaazatetracyclo[13.5.2.$1^{2,5}$.$0^{18,21}$]tricosa-1(20),2(23),3,15,17,21-hexaen-9-one intermediate 249 as a white solid.

LCMS method F: $[M+H]^+$=427.3, $t_R$=2.50 min

Preparation of Example 159: (13R)-13-methyl-8,14-dioxa-4,5,10,19,20,23-hexaaza tetra cyclo [13.5.2.$1^{2,5}$.$0^{18,21}$]tricosa-1(20),2(23),3,15,17,21-hexaen-9-one

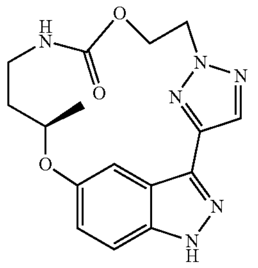 [SMILES: C[C@@H]1CCNC(=O)OCCn2ncc(n2)-c2n[nH]c3ccc(cc23)O1]

To a solution of (13R)-13-methyl-19-(oxan-2-yl)-8,14-dioxa-4,5,10,19,20,23-hexaazatetra cyclo[13.5.2.$1^{2,5}$.$0^{18,21}$] tricosa-1(20),2(23),3,15,17,21-hexaen-9-one intermediate 249 (100 mg, 0.23 mmol) in methanol (14 mL)) and water (2 mL) was added p-toluenesulfonic acid monohydrate (222 mg, 1.17 mmol). The reaction mixture was stirred at 65° C. for 16 h. The solvent was partially removed under reduced pressure and a saturated aqueous sodium bicarbonate solution was added. The aqueous layer was extracted with ethyl acetate. The combined organic layers were washed with brine, dried over anhydrous magnesium sulfate, filtered and the solvent was evaporated under reduced pressure. The residue was purified by silica gel column chromatography using dichloromethane/methanol 100/0 to 95/5 as eluent.

The resulting product was recrystallized in acetonitrile, filtered and dried to afford (13R)-13-methyl-8,14-dioxa-4,5,10,19,20,23-hexaazatetracyclo[13.5.2.$1^{2,5}$.$0^{18,21}$]tricosa-1(20),2(23),3,15,17,21-hexaen-9-one example 159 as a white solid.

LCMS method F: $[M+H]^+$=343.3, $t_R$=1.89 min

LCMS method G: $[M+H]^+$=343.3, $t_R$=1.90 min $^1$H NMR (400 MHz, d6-DMSO) δ 13.12 (1H, s), 8.12 (1H, s), 7.64 (1H, t, J=6.0 Hz), 7.53-7.44 (2H, m), 6.96 (1H, dd, J=2.0, 9.0 Hz), 4.90-4.84 (1H, m), 4.78-4.72 (2H, m), 4.62-4.56 (1H, m), 4.34-4.27 (1H, m), 3.42-3.29 (1H, m), 2.96-2.89 (1H, m), 2.13-2.06 (1H, m), 1.38-1.34 (4H, m) ppm.

Example 160: (13R)-13-methyl-8,14-dioxa-23-thia-4,10,19,20-tetraazatetracyclo[13.5.2.$1^{2,5}$.$0^{18,21}$]tricosa-1(20),2,4,15,17,21-hexaen-9-one

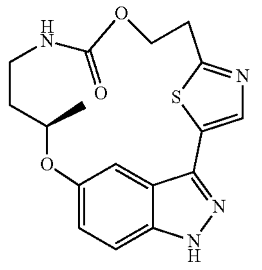 [SMILES: C[C@@H]1CCNC(=O)OCCC2=NC=C(S2)c2n[nH]c3ccc(cc23)O1]

Example 160 is prepared according to the synthesis route described in general Scheme L.

Preparation of Intermediate 250: 2-(5-bromothiazol-2-yl)ethanol

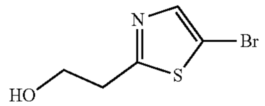

To a solution of ethyl 2-(5-bromothiazol-2-yl)acetate (1.50 g, 6.00 mmol) in THE (20 mL) cooled at 0° C. was added a solution of sodium borohydride (340 mg, 9.00 mmol) in ethanol (4 mL). The reaction mixture was stirred at room temperature for 48 h. The reaction mixture was quenched by addition of water at 0° C. and the reaction mixture was extracted with ethyl acetate. The combined organic layers were washed with brine, dried over anhydrous magnesium sulfate, filtered and the solvent was evaporated under reduced pressure. The residue was purified by silica gel column chromatography using heptane/ethyl acetate 100/0 to 50/50 as eluent to afford 2-(5-bromothiazol-2-yl) ethanol intermediate 250 as a yellow oil.

LCMS method F: $[M+H]^+$=208-210, $t_R$=1.46 min

Preparation of Intermediate 251: 2-(5-bromothiazol-2-yl)ethyl N-[(3S)-3-hydroxybutyl]carbamate

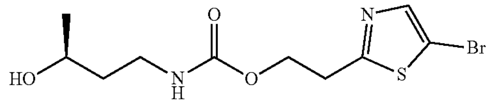 [SMILES: C[C@H](O)CCNC(=O)OCCc1ncc(Br)s1]

To a solution of 4-nitrophenyl chloroformate (480 mg, 2.38 mmol) and pyridine (0.35 mL, 4.32 mmol) in dichloromethane (5 mL) was added dropwise a solution of 2-(5-bromothiazol-2-yl)ethanol intermediate 250 (450 mg, 2.16 mmol) in dichloromethane (3 mL). The reaction mixture was stirred at room temperature for 1 h. Then a solution of (2S)-4-aminobutan-2-ol (210 mg, 2.38 mmol) and DIPEA (0.75 mL, 4.32 mmol) in dichloromethane (3 mL) was added. The reaction mixture was stirred at room temperature for 16 h. The reaction mixture was diluted with an 0.5 M aqueous sodium hydroxide solution and extracted with dichloromethane. The combined organic layers were washed again with a 0.5 M aqueous sodium hydroxide solution, dried over anhydrous magnesium sulfate, filtered and evaporated under reduced pressure. The residue was purified by silica gel column chromatography using dichloromethane/ethyl acetate 100/0 to 20/80 as eluent to afford 2-(5-bromothiazol-2-yl)ethyl N-[(3S)-3-hydroxybutyl]carbamate intermediate 251 as a yellow oil.

LCMS method F: $[M+H]^+$=325.1, $t_R$=1.75 min

Preparation of Intermediate 252: 2-[5-[5-[tert-butyl(dimethyl)silyl]oxy-1-tetrahydropyran-2-yl-indazol-3-yl]thiazol-2-yl]ethyl N-[(3S)-3-hydroxybutyl]carbamate

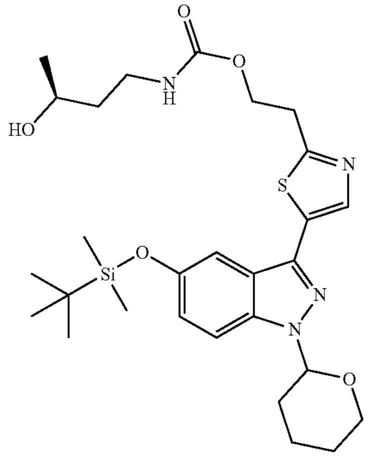 [SMILES: C[C@H](O)CCNC(=O)OCCc1ncc(-c2nn(C3CCCCO3)c3ccc(O[Si](C)(C)C(C)(C)C)cc23)s1]

To a solution of 2-(5-bromothiazol-2-yl)ethyl N-[(3S)-3-hydroxybutyl]carbamate intermediate 251 (350 mg, 1.08 mmol) in 1,4-dioxane (10 mL) and water (1 mL) was added tert-butyl-dimethyl-[1-tetrahydropyran-2-yl-3-(4,4,5,5-tetramethyl-1,3,2-dioxaborolan-2-yl)indazol-5-yl]oxy-silane (600 mg, 1.30 mmol) and potassium phosphate tribasic (690 mg, 3.25 mmol). The solution was purged with nitrogen then XPhos (52 mg, 0.11 mmol) and tetrakis(triphenylphosphine) palladium(0) (63 mg, 0.05 mmol) were added. The reaction mixture was stirred under microwave irradiations at 90° C. for 1.5 h. The reaction was diluted with brine and extracted with ethyl acetate. The combined organic layers were dried over anhydrous magnesium sulfate, filtered and the solvent was removed under reduced pressure. The residue was purified by silica gel column chromatography using heptane/ethyl acetate 100/0 to 30/70 as eluent to afford 2-[5-[5-[tert-butyl(dimethyl)silyl]oxy-1-tetrahydropyran-2-yl-indazol-3-yl]thiazol-2-yl]ethyl N-[(3S)-3-hydroxybutyl]carbamate intermediate 252 as a colorless oil.

LCMS method F: $[M+H]^+$=575.4, $t_R$=3.32 min

Preparation of Intermediate 253: [(1S)-3-[2-[5-[5-[tert-butyl(dimethyl)silyl]oxy-1-tetrahydro pyran-2-yl-indazol-3-yl]thiazol-2-yl]ethoxycarbonylamino]-1-methyl-propyl]methane sulfonate

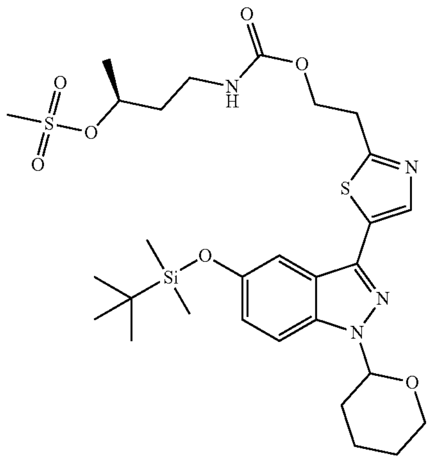 [SMILES: C[C@@H](CCNC(=O)OCCc1ncc(-c2nn(C3CCCCO3)c3ccc(O[Si](C)(C)C(C)(C)C)cc23)s1)OS(C)(=O)=O]

To a solution of 2-[5-[5-[tert-butyl(dimethyl)silyl]oxy-1-tetrahydropyran-2-yl-indazol-3-yl]thiazol-2-yl]ethyl N-[(3S)-3-hydroxybutyl]carbamate intermediate 252 (530 mg, 0.92 mmol) and triethylamine (0.26 mL, 1.84 mmol) in dichlormethane (8 mL) cooled at 0° C. was added methanesulfonyl chloride (0.09 mL, 1.20 mmol) in dichloromethane (2 mL). The reaction mixture was stirred at room temperature for 16 h. The reaction mixture was diluted with brine and extracted with dichloromethane. The combined organic layers were washed with brine, dried over anhydrous magnesium sulfate, filtered and the solvent was removed under reduced pressure to afford [(1S)-3-[2-[5-[5-[tert-butyl(dimethyl)silyl]oxy-1-tetrahydropyran-2-yl-indazol-3-yl]thiazol-2-yl]ethoxycarbonylamino]-1-methyl-propyl]methanesulfonate intermediate 253 as a yellow oil.

LCMS method F: $[M+H]^+$=653.5, $t_R$=3.45 min

Preparation of Intermediate 254: (13R)-13-methyl-19-(oxan-2-yl)-8,14-dioxa-23-thia-4,10,19,20-tetraazatetracyclo[13.5.2.$1^{2,5}$.$0^{18,21}$]tricosa-1(20),2,4,15,17,21-hexaen-9-one

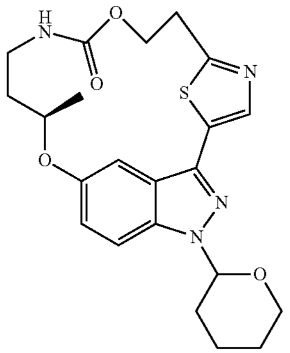 [SMILES: C[C@@H]1CCNC(=O)OCCC2=NC=C(S2)c2nn(C3CCCCO3)c3ccc(cc23)O1]

To a solution of [(1S)-3-[2-[5-[5-[tert-butyl(dimethyl)silyl]oxy-1-tetrahydropyran-2-yl-indazol-3-yl]thiazol-2-yl]ethoxycarbonylamino]-1-methyl-propyl]methanesulfonate intermediate 253 (500 mg, 0.77 mmol) in dry N,N-dimethylformamide (195 mL) at 80° C. was added dropwise over 2 h a solution of cesium carbonate (750 mg, 2.30 mmol) in dry N,N-dimethylformamide (190 mL). The reaction mixture was stirred at 80° C. for 1 h. The solvent was evaporated under reduced pressure and the residue was diluted with brine and ethyl acetate. The aqueous layer was extracted with ethyl acetate. The combined organic layers were washed with brine, dried over anhydrous magnesium sulfate, filtered and the solvent was evaporated under reduced pressure The residue was purified by silica gel column chromatography using dichloromethane/ethyl acetate 100/0 to 20/80 as eluent to afford (13R)-13-methyl-19-(oxan-2-yl)-8,14-dioxa-23-thia-4,10,19,20-tetraazatetracyclo [13.5.2.1$^{2,5}$.0$^{18,21}$]tricosa-1(20),2,4,15,17,21-hexaen-9-one intermediate 254 as a colorless oil.

LCMS method F: $[M+H]^+$=443.4, $t_R$=2.43 min

Preparation of Example 160: (13R)-13-methyl-8,14-dioxa-23-thia-4,10,19,20-tetraaza tetracyclo [13.5.2.1$^{2,5}$.0$^{18,21}$]tricosa-1(20),2,4,15,17,21-hexaen-9-one

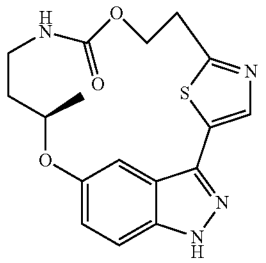 [SMILES: C[C@@H]1CCNC(=O)OCCC2=NC=C(S2)c2n[nH]c3ccc(cc23)O1]

To a solution of (13R)-13-methyl-19-(oxan-2-yl)-8,14-dioxa-23-thia-4,10,19,20-tetraazatetra cyclo[13.5.2.1$^{2,5}$.0$^{18,21}$]tricosa-1(20),2,4,15,17,21-hexaen-9-one intermediate 254 (44 mg, 0.10 mmol) in methanol (7 mL) and water (1 mL) was added p-toluenesulfonic acid monohydrate (95 mg, 0.50 mmol). The reaction mixture was stirred at 70° C. for 24 h. The solvent was partially removed under reduced pressure and a saturated aqueous sodium bicarbonate solution was added. The aqueous layer was extracted with ethyl acetate. The combined organic layers were washed with brine, dried over anhydrous magnesium sulfate, filtered and the solvent was removed under reduced pressure. The residue was triturated in diisopropylether, filtered and dried to afford (13R)-13-methyl-8,14-dioxa-23-thia-4,10,19,20-tetraazatetracyclo[13.5.2.1$^{2,5}$.0$^{18,21}$]tricosa-1(20),2,4,15,17,21-hexaen-9-one example 160 as a light yellow solid.

LCMS method F: $[M+H]^+$=359.3, $t_R$=1.87 min
LCMS method G: $[M+H]^+$=359.3, $t_R$=1.87 min $^1$H NMR (400 MHz, d6-DMSO) δ 13.22 (1H, s), 7.99 (1H, s), 7.92 (1H, dd, J=4.4, 8.2 Hz), 7.50-7.47 (1H, m), 7.39 (1H, d, J=2.5 Hz), 6.97 (1H, dd, J=2.4, 9.0 Hz), 4.71-4.61 (2H, m), 4.14-4.08 (1H, m), 3.61-3.53 (1H, m), 3.41-3.34 (2H, m), 2.93-2.86 (1H, m), 2.08-2.08 (1H, m), 1.41-1.38 (4H, m) ppm.

Example 161: (13R)-4,13-dimethyl-8,14-dioxa-4,10,19,20,23-pentaazatetracyclo[13.5.2.1$^{2,5}$.0$^{18,21}$]tricosa-1(20),2,5(23),15(22),16,18(21)-hexaen-9-one

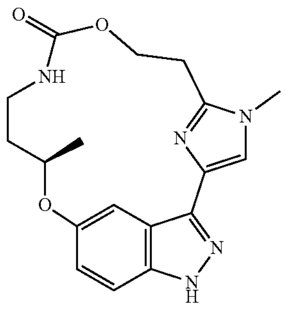 [SMILES: C[C@@H]1CCNC(=O)OCCc2nc(cn2C)-c2n[nH]c3ccc(cc23)O1]

Example 161 is prepared according to the synthesis route described in general Scheme L.

Preparation of Intermediate 255: tert-butyl-[2-(1H-imidazol-2-yl)ethoxy]-dimethyl-silane

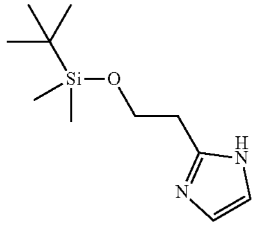

To a solution of 2-(1H-imidazol-2-yl)ethanol (1.2 g, 10.7 mmol) in N,N-dimethylformamide (11.5 mL) at room temperature was added imidazole (1.09 g, 16.05 mmol) and tert-butyldimethylsilyl chloride (1.61 g, 10.7 mmol). The reaction mixture was stirred at room temperature for 16 h. The reaction mixture was poured in water (150 mL) and extracted with ethyl acetate. The combined organic layers were washed with 10% lithium chloride aqueous solution, water and brine, dried over anhydrous sodium sulfate, filtered and concentrated under reduced pressure to yield tert-butyl-[2-(1H-imidazol-2-yl)ethoxy]-dimethyl-silane intermediate 255 as a yellow oil which was used in the next step without further purification.

LCMS method F: $[M+H]^+$=227.3, $t_R$=1.64 min

Preparation of intermediates 256A and 256B: tert-butyl-[2-(4,5-dibromo-1H-imidazol-2-yl)ethoxy]-dimethyl-silane and 2-(4-bromo-1H-imidazol-2-yl)ethoxy-tert-butyl-dimethyl-silane Intermediate 256A

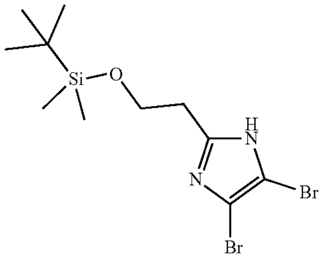

Intermediate 256B

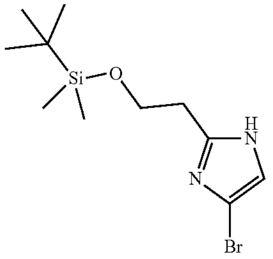

To a suspension of tert-butyl-[2-(1H-imidazol-2-yl)ethoxy]-dimethyl-silane intermediate 255 (2.379 g, 10.52 mmol) in THF (350 mL) at room temperature was added N-bromosuccinimide (1.955 g, 11.05 mmol). The reaction mixture was stirred at room temperature for 30 min. The reaction mixture was diluted with ethyl acetate, washed with water and brine, dried over anhydrous magnesium sulfate, filtered and concentrated under reduced pressure. The residue was purified by silica gel column chromatography using cyclohexane/ethyl acetate 100/0 to 95/5 as eluent, to afford two different products: tert-butyl-[2-(4,5-dibromo-1H-imidazol-2-yl)ethoxy]-dimethyl-silane intermediate 256A as a colorless oil; LCMS method F: $[M+H]^+$=383.1-385.1-387.0, $t_R$=3.00 min, and 2-(4-bromo-1H-imidazol-2-yl)ethoxy-tert-butyl-dimethyl-silane intermediate 256B as a colorless oil; LCMS method F: $[M+H]^+$=305.1-307.1, $t_R$=2.34 min Preparation of Intermediate 257: tert-butyl-[2-(4,5-dibromo-1-methyl-imidazol-2-yl)ethoxy]-dimethyl-silane

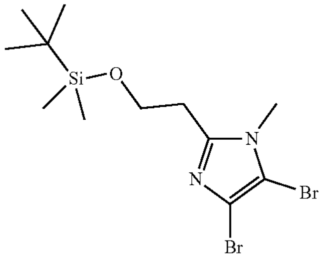 [SMILES: Cn1c(CCO[Si](C)(C)C(C)(C)C)nc(Br)c1Br]

To a suspension of tert-butyl-[2-(4,5-dibromo-1H-imidazol-2-yl)ethoxy]-dimethyl-silane intermediate 256A (600 mg, 1.56 mmol) in N,N-dimethylformamide (2.5 mL) at room temperature was added potassium carbonate (473 mg, 3.43 mmol) followed by iodomethane (0.11 mL, 1.87 mmol). The reaction mixture was stirred at room temperature for 16 h. The reaction mixture was diluted with dichloromethane, washed with water and brine, dried over anhydrous magnesium sulfate, filtered and concentrated under reduced pressure to afford tert-butyl-[2-(4,5-dibromo-1-methyl-imidazol-2-yl)ethoxy]-dimethyl-silane intermediate 257 as a yellow solid which was used without further purification.

LCMS method F: $[M+H]^+$=397.0-399.1-401.0, $t_R$=3.24 min

Preparation of Intermediate 258: 2-(4-bromo-1-methyl-imidazol-2-yl)ethoxy-tert-butyl-dimethyl silane

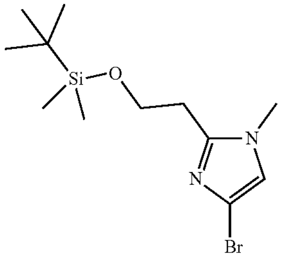 [SMILES: Cn1cc(Br)nc1CCO[Si](C)(C)C(C)(C)C]

To a degassed solution of tert-butyl-[2-(4,5-dibromo-1-methyl-imidazol-2-yl)ethoxy]-dimethyl-silane intermediate 257 (614 mg, 1.54 mmol) in dry THF (24 mL) at −78° C., was added 2.5 M n-BuLi solution in THF (0.6 mL, 1.54 mmol). The reaction mixture was stirred at −78° C. for 30 min. The reaction mixture was quenched by addition of water and warmed to room temperature. The aqueous layer was extracted with ethyl acetate. The combined organic layers were washed with brine, dried over anhydrous sodium sulfate, filtered and concentrated under reduced pressure to afford 2-(4-bromo-1-methyl-imidazol-2-yl)ethoxy-tert-butyl-dimethyl-silane intermediate 258 as a yellow oil.

LCMS method F: $[M+H]^+$=319.2-321.2, $t_R$=2.70 min

Preparation of Intermediate 259: 2-(4-bromo-1-methyl-imidazol-2-yl)ethanol

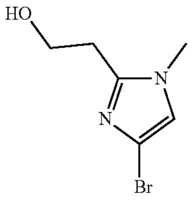

To a solution of 2-(4-bromo-1-methyl-imidazol-2-yl)ethoxy-tert-butyl-dimethyl-silane intermediate 258 (300 mg, 0.94 mmol) in THF (4 mL) at room temperature was added dropwise a solution of tetrabutylammonium fluoride 1 M in THF (1.03 mL, 1.03 mmol). The reaction mixture was stirred at room temperature for 6 h. The reaction mixture was poured into ice water and stirred for 20 min. The aqueous phase was extracted with ethyl acetate. The organic layers were washed with brine, dried over anhydrous magnesium sulfate and concentrated under reduced pressure. The residue was purified by silica gel column chromatography using dichloromethane/methanol 100/0 to 95/5 as eluent to afford 2-(4-bromo-1-methyl-imidazol-2-yl)ethanol intermediate 259 as a white solid.

$^1$H NMR (400 MHz, CDCl3) δ 6.78 (1H, s), 4.02 (2H, t, J=5.6 Hz), 3.89 (1H, br. s), 3.57 (3H, s), 2.83 (2H, t, J=5.8 Hz) ppm.

Preparation of Intermediate 260: 2-(4-bromo-1-methyl-imidazol-2-yl)ethyl-N-[(3S)-3-hydroxy butyl]carbamate

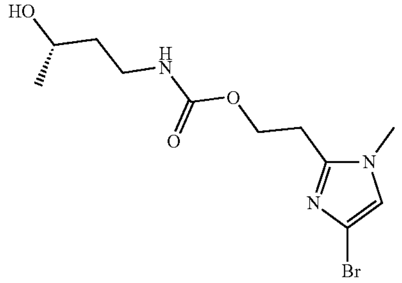 [SMILES: C[C@H](O)CCNC(=O)OCCc1nc(Br)cn1C]

To a solution of 4-nitrophenyl chloroformate (137 m g, 0.68 mmol) and pyridine (0.10 mL, 1.24 mmol) in dichloromethane (2.5 mL) at room temperature was added dropwise 2-(4-bromo-1-methyl-imidazol-2-yl)ethanol intermediate 259 (128 mg, 0.62 mmol) in dichloromethane (1.5 mL). The reaction mixture was stirred at room temperature for 1 h. A mixture of (2S)-4-aminobutan-2-ol (60 mg, 0.68 mmol) and DIPEA (0.21 mL, 1.24 mmol) in dichloromethane (1 mL) was added. The reaction mixture was stirred at room temperature for 2 h. The reaction mixture was diluted with 0.5 N aqueous sodium hydroxide solution and extracted with dichloromethane. The combined organic layers were washed with 0.5 N aqueous sodium hydroxide solution and dried over anhydrous magnesium sulfate, filtered and concentrated under reduced pressure. The residue was purified by silica gel column chromatography using dichloromethane/ethyl acetate 100/0 to 30/70 as eluent to afford 2-(4-bromo-1-methyl-imidazol-2-yl)ethyl N-[(3S)-3-hydroxybutyl]carbamate intermediate 260 as a colorless oil.

LCMS method F: $[M+H]^+$=320.1-322.1, $t_R$=1.17 min

Preparation of Intermediate 261: 2-[4-[5-[tert-butyl (dimethyl)silyl]oxy-1-tetrahydropyran-2-yl-indazol-3-yl]-1-methyl-imidazol-2-yl]ethyl-N-[(3S)-3-hydroxybutyl]carbamate

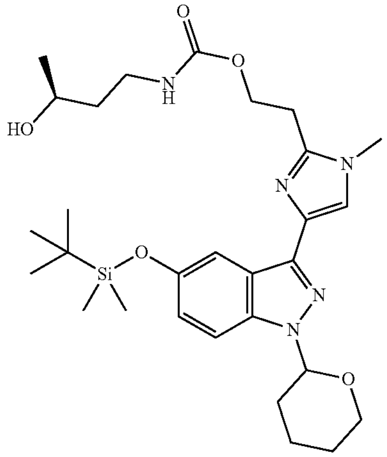 [SMILES: C[C@H](O)CCNC(=O)OCCc1nc(-c2nn(C3CCCCO3)c3ccc(O[Si](C)(C)C(C)(C)C)cc23)cn1C]

To a degassed solution of 2-(4-bromo-1-methyl-imidazol-2-yl)ethyl-N-[(3S)-3-hydroxybutyl]carbamate intermediate 260 (102 mg, 0.32 mmol), tert-butyl-dimethyl-[1-tetrahydropyran-2-yl-3-(4,4,5,5-tetramethyl-1,3,2-dioxaborolan-2-yl)indazol-5-yl]oxy-silane (175 mg, 0.38 mmol) and potassium phosphate tribasic (204 mg, 0.96 mmol) in 1,4-dioxane (2.7 mL) and water (0.1 mL), were added tetrakis(triphenylphosphine)palladium(0) (19 mg, 0.016 mmol) and 2-dicyclohexylphosphino-2',4',6'-triisopropylbiphenyl (15 mg, 0.032 mmol). The reaction mixture was heated at 125° C. for 1 h. The reaction mixture was filtered through a Celite pad and washed with ethyl acetate. The filtrate was diluted with water and extracted with ethyl acetate. The organic layer was washed with water, brine, dried over anhydrous magnesium sulfate, filtered and concentrated under reduced pressure. The residue was purified by silica gel column chromatography using dichloromethane/methanol 100/0 to 98/2 as eluent to afford 2-[4-[5-[tert-butyl(dimethyl)silyl]oxy-1-tetrahydropyran-2-yl-indazol-3-yl]-1-methyl-imidazol-2-yl] ethyl N-[(3S)-3-hydroxybutyl]carbamate intermediate 261 as a yellow oil.

LCMS method F: $[M+H]^+$=572.4, $t_R$=2.28 min

Preparation of Intermediate 262: [(1S)-3-[2-[4-[5-[tert-butyl(dimethyl)silyl]oxy-1-tetrahydro pyran-2-yl-indazol-3-yl]-1-methyl-imidazol-2-yl]ethoxycarbonylamino]-1-methyl-propyl]methanesulfonate

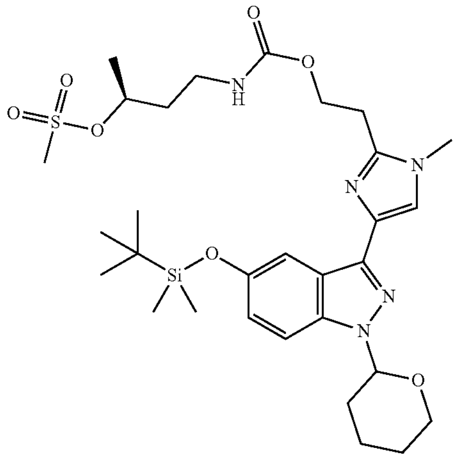 [SMILES: C[C@@H](CCNC(=O)OCCc1nc(-c2nn(C3CCCCO3)c3ccc(O[Si](C)(C)C(C)(C)C)cc23)cn1C)OS(C)(=O)=O]

To a solution of 2-[4-[5-[tert-butyl(dimethyl)silyl]oxy-1-tetrahydropyran-2-yl-indazol-3-yl]-1-methyl-imidazol-2-yl]ethyl N-[(3S)-3-hydroxybutyl]carbamate intermediate 261 (112 mg, 0.20 mmol) and triethylamine (56 μL, 0.40 mmol) in dichloromethane (2.2 mL) at 0° C. was added dropwise methanesulfonyl chloride (20 μL, 0.26 mmol). The reaction mixture was stirred at room temperature for 2 h. The reaction mixture was diluted with water and extracted with dichloromethane. The combined organics were washed with brine, dried over anhydrous magnesium sulfate, filtered and concentrated under reduced pressure to afford [(1S)-3-[2-[4-[5-[tert-butyl(dimethyl)silyl]oxy-1-tetrahydropyran-2-yl-indazol-3-yl]-1-methyl-imidazol-2-yl]ethoxycarbonylamino]-1-methyl-propyl]methanesulfonate intermediate 262 as a colorless oil.

LCMS method F: $[M+H]^+$=650.4, $t_R$=2.53 min

Preparation of Intermediate 263: (13R)-4,13-dimethyl-19-(oxan-2-yl)-8,14-dioxa-4,10,19,20,23-pentaazatetracyclo[$13.5.2.1^{2}$,5s $0^{18,21}$]tricosa-1(20),2,5(23),15(22),16,18(21)-hexaen-9-one

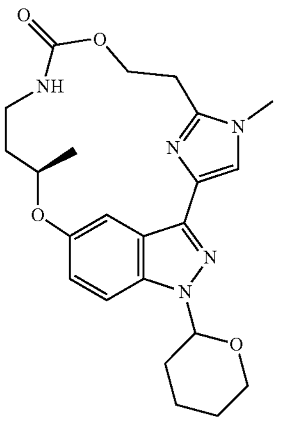 [SMILES: C[C@@H]1CCNC(=O)OCCc2nc(cn2C)-c2nn(C3CCCCO3)c3ccc(cc23)O1]

To a suspension of cesium carbonate (112 mg, 0.34 mmol) in anhydrous N,N-dimethylformamide (6 mL) at 60° C. was added dropwise [(1S)-3-[2-[4-[5-[tert-butyl(dimethyl)silyl]oxy-1-tetrahydropyran-2-yl-indazol-3-yl]-1-methyl-imidazol-2-yl]ethoxy carbonylamino]-1-methyl-propyl]methanesulfonate intermediate 262 (75 mg, 0.11 mmol) in N,N-dimethyl formamide (3 mL). The reaction mixture was stirred at 60° C. for 2 h. The reaction mixture was allowed to cool down to room temperature, then filtered over a Celite pad, washed with ethyl acetate. The filtrate was concentrated under reduced pressure. The residue was purified by silica gel column chromatography using cyclohexane/(ethyl acetate/ethanol (3/1)) 100/0 to 60/40 as eluent to afford (13R)-4,13-dimethyl-19-(oxan-2-yl)-8,14-dioxa-4,10,19,20,23-pentaazatetracyclo[$13.5.2.1^{2,5}.0^{18,21}$]tricosa-1(20),2,5(23),15(22),16,18(21)-hexaen-9-one intermediate 263 as a yellow oil.

LCMS method F: $[M+H]^+$=440.3, $t_R$=1.71 min

Preparation of Example 161: (13R)-4,13-dimethyl-8,14-dioxa-4,10,19,20,23-pentaazatetra cyclo[$13.5.2.1^{2,5}.0^{18,21}$]tricosa-1(20),2,5(23),15(22),16,18(21)-hexaen-9-one

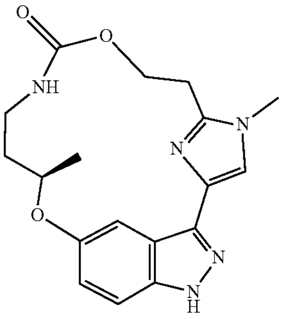 [SMILES: C[C@@H]1CCNC(=O)OCCc2nc(cn2C)-c2n[nH]c3ccc(cc23)O1]

To a solution of (13R)-4,13-dimethyl-19-(oxan-2-yl)-8,14-dioxa-4,10,19,20,23-pentaazatetra cyclo[$13.5.2.1^{2,5}.0^{18,21}$]tricosa-1(20),2,5(23),15(22),16,18(21)-hexaen-9-one intermediate 263 (38 mg, 0.086 mmol) in methanol (6 mL) and water (0.8 mL) was added p-toluenesulfonic acid monohydrate (82 mg, 0.43 mmol). The reaction mixture was stirred at 65° C. for 22 h. The reaction mixture was diluted with dichloromethane and saturated aqueous sodium bicarbonate solution. After separation, the aqueous layer was extracted with ethyl Acetate. The combined organic layer was washed with brine, dried over anhydrous sodium sulfate, filtered and evaporated under reduced pressure. The residue was purified by preparative TLC on silica gel using dichloromethane/methanol 90/10 as eluent to afford (13R)-4,13-dimethyl-8,14-dioxa-4,10,19,20,23-pentaazatetracyclo[$13.5.2.1^{2,5}.0^{18,21}$]tricosa-1(20),2,5(23),15(22),16,18(21)-hexaen-9-one example 161 as a white solid.

LCMS method F: $[M+H]^+$=356.3, $t_R$=1.27 min

LCMS method G: $[M+H]^+$=356.3, $t_R$=1.76 min $^1$H NMR (400 MHz, $CDCl_3$) δ 7.89-7.85 (1H, m), 7.34 (1H, s), 7.24 (1H, d, J=9.6 Hz), 6.96 (1H, dd, J=2.4, 9.6 Hz), 5.58 (1H, br. s), 4.77-4.67 (2H, m), 4.60-4.55 (1H, m), 3.67-3.62 (4H, m), 3.45-3.32 (2H, m), 3.04-2.94 (2H, m), 2.18-2.09 (1H, m), 1.64-1.50 (1H, m), 1.46-1.39 (3H, m) ppm.

Example 162: (13R)-13-methyl-8,14-dioxa-10,16,19,20-tetraazatetracyclo[$13.5.2.1^{2,6}.0^{18,21}$]tricosa-1(20),2(23),3,5,15(22),16,18(21)-heptaen-9-one

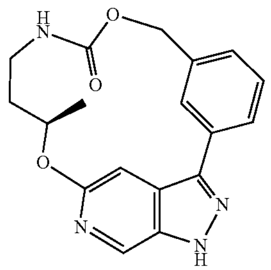 [SMILES: C[C@@H]1CCNC(=O)OCc2cccc(c2)-c2n[nH]c3cnc(cc23)O1]

Example 162 is prepared according to the synthesis route described in detail below.

Preparation of Intermediate 264: 2- [(3R)-3-[(4-methyl-5-nitro-2-pyridyl)oxy]butyl]isoindoline-1,3-dione

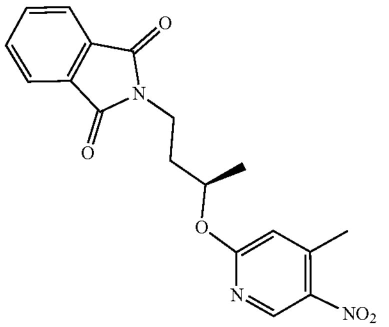 [SMILES: Cc1cc(O[C@H](C)CCN2C(=O)c3ccccc3C2=O)ncc1[N+](=O)[O-]]

A pressure vial containing a mixture of cesium carbonate (26.41 g, 83.56 mmol), $Pd_2(dba)_3$ (1.64 g, 1.791 mmol), rac-BINAP (2.23 g, 3.581 mmol), (R)-2-(3-hydroxybutyl) isoindoline-1,3-dione (18.32 g, 83.56 mmol) and 2-chloro-4-methyl-5-nitropyridine (10.3 g, 59.686 mmol) were suspended in toluene (78 mL) under nitrogen atmosphere. The reaction mixture was stirred at 110° C. for 16 h. The reaction mixture was diluted with ethyl acetate and filtered over a pad of celite. The filtrate was concentrated under reduced pressure. The residue was purified by silica gel column chromatography using heptane/ethl acetate 100/0 to 90/10 as eluent to afford 2-[(3R)-3-[(4-methyl-5-nitro-2-pyridyl)oxy] butyl]isoindoline-1,3-dione intermediate 264 as a white solid.

LCMS method B: $[M+H]^+$=356.0, $t_R$=1.020 min

Preparation of Intermediate 265: 2- [(3R)-3-[(5-amino-4-methyl-2-pyridyl)oxy]butyl]isoindoline-1,3-dione

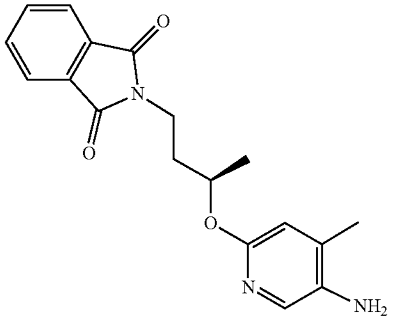 [SMILES: Cc1cc(O[C@H](C)CCN2C(=O)c3ccccc3C2=O)ncc1N]

To a solution of 2-[(3R)-3-[(4-methyl-5-nitro-2-pyridyl) oxy]butyl]isoindoline-1,3-dione intermediate 264 (14.6 g, 41.086 mmol) in ethyl acetate (240 mL) under nitrogen atmosphere was added palladium 10% wt on carbon (2.9 g). The reaction mixture was stirred under hydrogen atmosphere at RT for 20 h. The suspension was filtered over a pad of celite and washed with ethyl acetate. The solvent was removed under reduced pressure. The residue was purified by silica gel column chromatography using heptane/ethyl acetate 100/0 to 40/60 as eluent to afford 2-[(3R)-3-[(5-amino-4-methyl-2-pyridyl)oxy]butyl]isoindoline-1,3-dione intermediate 265 as a orange foam.

LCMS method E: $[M+H]^+$=3526.1, $t_R$=2.092 min

Preparation of Intermediate 266: N-[6-[(1R)-3-(1,3-dioxoisoindolin-2-yl)-1-methyl-propoxy]-4-methyl-3-pyridyl]acetamide

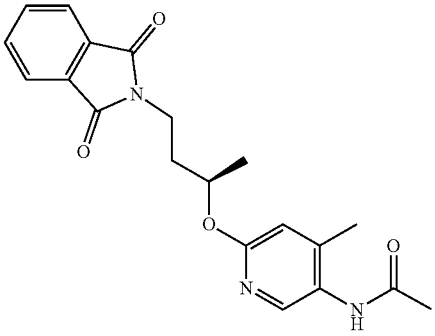 [SMILES: CC(=O)Nc1cnc(O[C@H](C)CCN2C(=O)c3ccccc3C2=O)cc1C]

To solution of 2-[(3R)-3-[(5-amino-4-methyl-2-pyridyl) oxy]butyl]isoindoline-1,3-dione intermediate 265 (5.0 g, 15.36 mmol) and triethylamine (4.26 mL, 30.37 mmol) in dichloromethane (75 mL) at 0° C. was added acetic anhydride (2.18 mL, 23.05 mmol). The reaction mixture was stirred at 0° C. for 5 min then warmed to room temperature and stirred for 1 h. The reaction mixture was filtered and rinsed with dichloromethane. The filtrate was evaporated under reduced pressure and the residue was purified by silica gel column chromatography using cyclohexane/ethyl acetate 100/0 to 50/50 as eluent to afford N-[6-[(1R)-3-(1,3-dioxoisoindolin-2-yl)-1-methyl-propoxy]-4-methyl-3-pyridyl]acetamide intermediate 266 as a white solid.

LCMS method F: $[M+H]^+$=368.2, $t_R$=2.13 min

Preparation of Intermediate 267: 2- [(3R)-3-(1-acetylpyrazolo[3,4-c]pyridin-5-yl)oxybutyl]isoindoline-1,3-dione

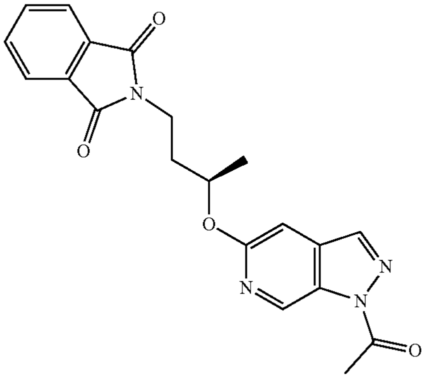 [SMILES: CC(=O)n1ncc2cc(O[C@H](C)CCN3C(=O)c4ccccc4C3=O)ncc21]

A solution of N-[6-[(1R)-3-(1,3-dioxoisoindolin-2-yl)-1-methyl-propoxy]-4-methyl-3-pyridyl]acetamide intermediate 266 (5.0 g, 13.60 mmol), acetic anhydride (5.79 mL, 61.24 mmol) and potassium acetate (2.39 g, 20.41 mmol) in toluene (70 mL) was stirred at 80° C. Isoamyl nitrite (7.33 mL, 54.437 mmol) was added and the resulting mixture was stirred at 80° C. for 16 h. The reaction mixture was cooled to room temperature and filtered. The filtrate was concentrated under reduced pressure. The residue was purified by silica gel column chromatography using cyclohexane/ethyl acetate 100/0 to 2/1 as eluent to afford 2-[(3R)-3-(1-acetylpyrazolo[3,4-c]pyridin-5-yl)oxybutyl]isoindoline-1,3-dione intermediate 267 as a yellow solid.

LCMS method F: $[M+H]^+$=379.3, $t_R$=2.63 min

Preparation of Intermediate 268: [(3R)-3-(1H-pyrazolo[3,4-c]pyridin-5-yloxy)butyl]isoindoline-1,3-dione

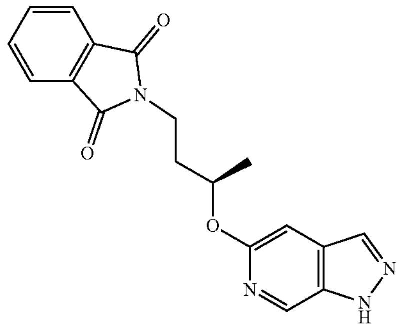 [SMILES: C[C@H](CCN1C(=O)c2ccccc2C1=O)Oc1cc2cn[nH]c2cn1]

To a solution of 2-[(3R)-3-(1-acetylpyrazolo[3,4-c]pyridin-5-yl)oxybutyl]isoindoline-1,3-dione intermediate 267 (2.75 g, 7.28 mmol) in methanol (36 mL) was added 7N ammonia solution in methanol (5.20 mL, 36.42 mmol). The reaction mixture was stirred at room temperature for 2 h. Solvents were concentrated under reduced pressure and the residue was purified by silica gel column chromatography using cyclohexane/ethyl acetate 100/0 to 50/50 as eluent to afford 2-[(3R)-3-(1H-pyrazolo[3,4-c]pyridin-5-yloxy)butyl] isoindoline-1,3-dione intermediate 268 as a pale orange solid.

LCMS method F: $[M+H]^+$=337.3, $t_R$=2.09 min

Preparation of Intermediate 269: 2- [(3R)-3-[(3-iodo-1H-pyrazolo[3,4-c]pyridin-5-yl)oxy]butyl] isoindoline-1,3-dione

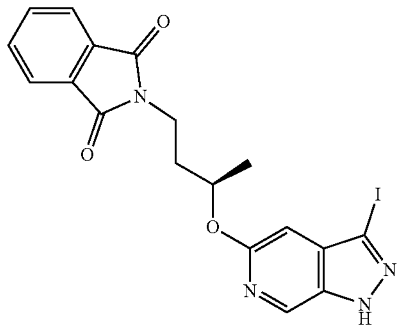 [SMILES: C[C@H](CCN1C(=O)c2ccccc2C1=O)Oc1cc2c(I)n[nH]c2cn1]

To a solution of 2-[(3R)-3-(1H-pyrazolo[3,4-c]pyridin-5-yloxy)butyl]isoindoline-1,3-dione intermediate 268 (673 mg, 2 mmol) in DMF (20 mL) was added N-iodo-succinimide (675 mg, 3 mmol). The reaction mixture was stirred at room temperature for 16 h. The reaction mixture was partitioned between ethyl acetate and water. The aqueous layer was extracted with ethyl acetate and the combined organic extracts were washed with saturated aqueous sodium chloride solution, dried over anhydrous sodium sulfate, filtered and concentrated under reduced pressure. The residue was purified by silica gel column chromatography using cyclohexane/ethyl acetate 100/0 to 50/50 as eluent to afford 2-[(3R)-3-[(3-iodo-1H-pyrazolo[3,4-c]pyridin-5-yl)oxy]butyl]isoindoline-1,3-dione intermediate 269 as a yellow solid.

LCMS method F: $[M+H]^+$=463.2, $t_R$=2.54 min

Preparation of Intermediate 270: 2- [(3R)-3-(3-iodo-1-tetrahydropyran-2-yl-pyrazolo[3,4-c]pyridin-5-yl)oxybutyl]isoindoline-1,3-dione

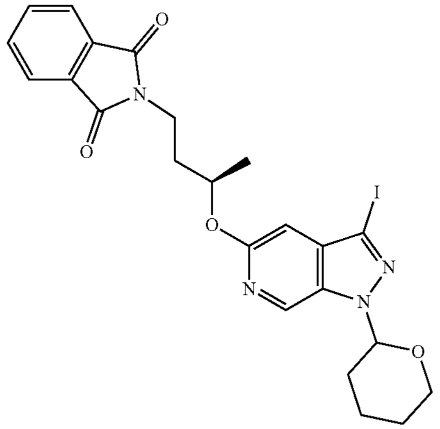 [SMILES: C[C@H](CCN1C(=O)c2ccccc2C1=O)Oc1cc2c(I)nn(C3CCCCO3)c2cn1]

To a solution of 2-[(3R)-3-[(3-iodo-1H-pyrazolo[3,4-c] pyridin-5-yl)oxy]butyl]isoindoline-1,3-dione intermediate 269 (897 mg, 1.94 mmol) and DHP (0.53 mL, 5.82 mmol) in dichloromethane (15 mL) and THE (5 mL) was added methanesulfonic acid (25 μL, 0.38 mmol). The reaction mixture was stirred at room temperature for 3 h. Saturated aqueous sodium bicarbonate solution was added. After separation, the aqueous layer was extracted with dichloromethane and the combined organic extracts were washed with saturated aqueous sodium chloride solution, dried over anhydrous sodium sulfate, filtered and concentrated under reduced pressure. The residue was purified by silica gel column chromatography using cyclohexane/ethyl acetate 100/0 to 35/65 as eluent to afford 2-[(3R)-3-(3-iodo-1-tetrahydropyran-2-yl-pyrazolo[3,4-c]pyridin-5-yl)oxybutyl] isoindoline-1,3-dione intermediate 270 as a yellow solid.

LCMS method F: $[M+H]^+$=547.2, $t_R$=3.17 min

Preparation of Intermediate 271: (3R)-3-(3-iodo-1-tetrahydropyran-2-yl-pyrazolo[3,4-c]pyridin-5-yl) oxybutan-1-amine

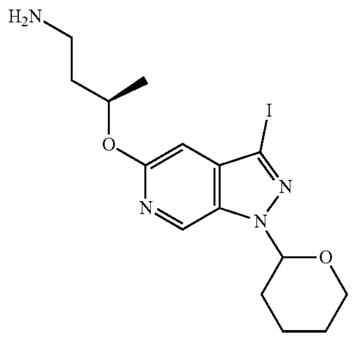 [SMILES: C[C@H](CCN)Oc1cc2c(I)nn(C3CCCCO3)c2cn1]

To a solution of 2-[(3R)-3-(3-iodo-1-tetrahydropyran-2-yl-pyrazolo[3,4-c]pyridin-5-yl)oxybutyl]isoindoline-1,3-dione intermediate 270 (800 mg, 1.464 mmol) in ethanol (15.0 mL) at 0° C. was added hydrazine monohydrate (0.22 mL, 4.392 mmol). The reaction mixture was stirred at 0° C. for 5 minutes and at room temperature for 16 h. THF (60 mL) was added and the mixture was stirred for 5 minutes, filtered and the solvent was removed under reduced pressure. The residue was diluted with THF (15 mL), filtered and the filtrate was concentrated under reduced pressure to afford crude (3R)-3-(3-iodo-1-tetrahydropyran-2-yl-pyrazolo[3,4-c]pyridin-5-yl)oxybutan-1-amine intermediate 271 as an orange solid. The product was used in the next step without further purification.

LCMS method F: $[M+H]^+$=417.2, $t_R$=1.63 min

Preparation of Intermediate 272: benzyl N-[(3R)-3-(3-iodo-1-tetrahydropyran-2-yl-pyrazolo[3,4-c]pyridin-5-yl)oxybutyl]carbamate

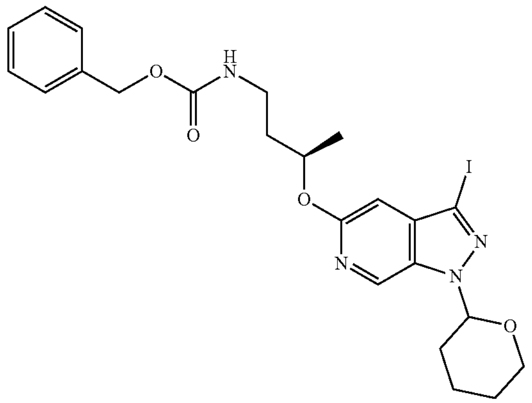 [SMILES: C[C@H](CCNC(=O)OCc1ccccc1)Oc1cc2c(I)nn(C3CCCCO3)c2cn1]

To a solution of (3R)-3-(3-iodo-1-tetrahydropyran-2-yl-pyrazolo[3,4-c]pyridin-5-yl)oxybutan-1-amine intermediate 271 (650 mg, 1.464 mmol) in dichloromethane (15 mL) at 0° C. were successively added triethylamine (0.24 mL, 1.75 mmol) and benzyl chloroformate (0.23 mL, 1.610 mmol). The reaction mixture was stirred at 0° C. for 5 min then warmed to room temperature and stirred for 16 h. The reaction mixture was diluted with water. After separation, the aqueous layer was extracted with dichloromethane and the combined organic extracts were washed with saturated aqueous sodium chloride, dried over anhydrous sodium sulfate, filtered and concentrated under reduced pressure. The residue was purified by silica gel column chromatography using cyclohexane/ethyl acetate 100:0 to 50:50 as eluent to afford benzyl N-[(3R)-3-(3-iodo-1-tetrahydropyran-2-yl-pyrazolo[3,4-c]pyridin-5-yl)oxybutyl]carbamate intermediate 272 as a transparent oil.

LCMS method F: $[M+H]^+$=551.1, $t_R$=3.17 min

Preparation of Intermediate 273: benzyl N-[(3R)-3-[3-[3-(hydroxymethyl)phenyl]-1-tetra hydropyran-2-yl-pyrazolo[3,4-c]pyridin-5-yl]oxybutyl]carbamate

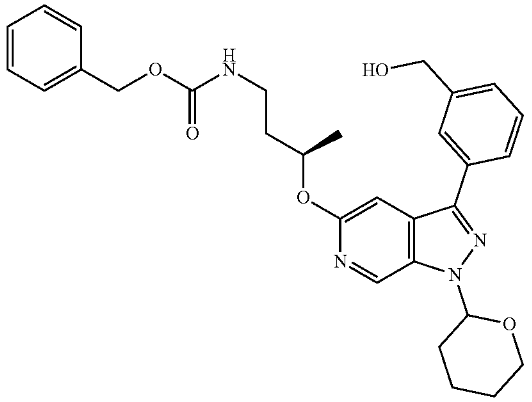 [SMILES: C[C@H](CCNC(=O)OCc1ccccc1)Oc1cc2c(-c3cccc(CO)c3)nn(C3CCCCO3)c2cn1]

To a with argon degassed solution of benzyl N-[(3R)-3-(3-iodo-1-tetrahydropyran-2-yl-pyrazolo[3,4-c]pyridin-5-yl)oxybutyl]carbamate intermediate 272 (320 mg, 0.581 mmol), 3-(hydroxy methyl)phenylboronic acid (106 mg, 0.698 mmol), potassium phosphate tribasic (370 mg, 1.744 mmol) and XPhos (28 mg, 0.058 mmol) in 1,4-dioxane (5.5 mL) and water (0.5 mL) was added tetrakis(triphenylphosphine)palladium(0) (34 mg, 0.029 mmol). The reaction mixture was heated at 100° C. for 1 h. The reaction mixture was cooled and diluted with ethyl acetate and water. After separation, the aqueous layer was extracted with ethyl acetate and the combined organic extracts were washed with saturated aqueous sodium chloride solution, dried over anhydrous sodium sulfate, filtered and concentrated under reduced pressure. The residue was purified by column chromatography using cyclohexane/ethyl acetate 100/0 to 1/1 as eluent to afford benzyl N-[(3R)-3-[3-[3-(hydroxymethyl)phenyl]-1-tetrahydropyran-2-yl-pyrazolo[3,4-c]pyridin-5-yl]oxybutyl]carbamate intermediate 273 as a pale yellow oil.

LCMS method F: $[M+H]^+$=531.3, $t_R$=2.90 min

Preparation of Intermediate 274: (13R)-13-methyl-19-(oxan-2-yl)-8,14-dioxa-10,16,19,20-tetraazatetracyclo[13.5.2.1$^{2,6}$.0$^{18,21}$]tricosa-1(20),2(23),3,5,15(22),16,18(21)-heptaen-9-one

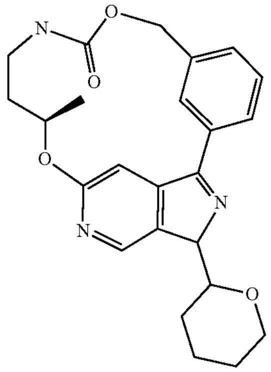

To a solution of benzyl N-[(3R)-3-[3-[3-(hydroxymethyl)phenyl]-1-tetrahydropyran-2-yl-pyrazolo[3,4-c]pyridin-5-yl]oxybutyl]carbamate intermediate 273 (180 mg, 0.339 mmol) in acetonitrile (170 mL) was added potassium hydroxide (95 mg, 1.69 mmol). The reaction mixture was heated at 50° C. for 16 h. The reaction mixture was cooled to room temperature, filtered and concentrated under reduced pressure. The residue was purified by silica gel column chromatography using cyclohexane/ethyl acetate 100/0 to 50/50 as eluent to afford (13R)-13-methyl-19-(oxan-2-yl)-8,14-dioxa-10,16,19,20-tetraazatetracyclo[13.5.2.1$^{2,6}$.0$^{18,21}$]tricosa-1(20),2(23),3,5,15(22), 16,18(21)-heptaen-9-one intermediate 274 as a yellow solid.

LCMS method F: $[M+H]^+$=423.4, $t_R$=2.49 min

Preparation of Example 162: (13R)-13-methyl-8,14-dioxa-10,16,19,20-tetraazatetracyclo[13.5.2.1$^{2,6}$.0$^{18,21}$]tricosa-1(20),2(23),3,5,15(22),16,18(21)-heptaen-9-one

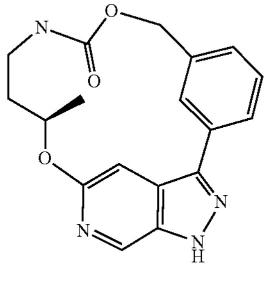

To a solution of (13R)-13-methyl-19-(oxan-2-yl)-8,14-dioxa-10,16,19,20-tetraazatetracyclo[13.5.2.1$^{2,6}$.0$^{18,21}$]tricosa-1(20),2(23),3,5,15(22),16,18(21)-heptaen-9-one intermediate 274 (84 mg, 0.199 mmol) in methanol (1.8 mL) and water (0.2 mL) was added p-toluenesulfonic acid monohydrate (189 mg, 0.994 mmol). The reaction mixture was stirred at 65° C. for 80 h. Solvents were evaporated under reduced pressure and the residue was partitioned between ethyl acetate and water. The aqueous layer was extracted with ethyl acetate and the combined organic extracts were washed with saturated aqueous sodium bicarbonate solution then with saturated aqueous sodium chloride solution, dried over anhydrous sodium sulfate, filtered and concentrated under reduced pressure. The reaction mixture was triturated with diisopropyl ether, filtered and dried to afford (13R)-13-methyl-8,14-dioxa-10,16,19,20-tetraazatetracyclo[13.5.2.1$^{2,6}$.0$^{18,21}$]tricosa-1(20),2(23),3,5,15(22),16,18(21)-heptaen-9-one example 162 as a white solid.

LCMS method F: $[M+H]^+$=339.3, $t_R$=2.45 min

LCMS method G: $[M+H]^+$=339.3, $t_R$=2.48 min $^1$H NMR (400 MHz, d6-DMSO) δ 13.64 (s, 1H), 8.76 (s, 1H), 7.97 (dd, J=4.8, 6.8 Hz, 1H), 7.88 (d, J=7.6 Hz, 1H), 7.84 (s, 1H), 7.49 (t, J=7.2 Hz, 1H), 7.31 (d, J=8.4 Hz, 1H), 7.10 (s, 1H), 5.76 (d, J=12.8 Hz, 1H), 4.84 (d, J=15.2 Hz, 1H), 4.62-4.54 (m, 1H), 3.61-3.58 (m, 1H), 2.91 (t, J=14.0 Hz, 1H), 2.36 (t, J=12.4 Hz, 1H), 1.48-1.46 (m, 1H), 1.44 (d, J=5.6 Hz, 3H) ppm.

Example 163: 14-methyl-8-oxa-10,14,19,20-tetraazatetracyclo[13.5.2.1$^{2,6}$.0$^{18,21}$]tricosa-1(20),2(23),3,5,15,17,21-heptaen-9-one

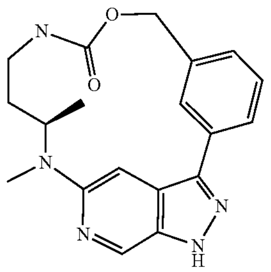

Example 163 is prepared according to the synthesis route described in detail below.

Preparation of Intermediate 275: N-(3-iodo-1-tetrahydropyran-2-yl-indazol-5-yl)-2-nitro-benzenesulfonamide

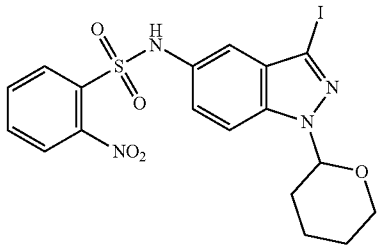 [SMILES: O=[N+]([O-])c1ccccc1S(=O)(=O)Nc1ccc2c(c1)c(I)nn2C1CCCCO1]

To a mixture of 3-iodo-1-(oxan-2-yl)-1H-indazol-5-amine (2.0 g, 5.83 mmol) in acetonitrile (100 mL) was added pyridine (943 μL, 11.66 mmol) and 2-nitrobenzenesulfonyl chloride (1.29 g, 5.83 mmol). The reaction mixture was stirred at room temperature for 16 h. The solvent was removed under reduced pressure and the residue was portioned between ethyl acetate and water. After separation, the aqueous phase was extracted with ethyl acetate. The organic phases were dried over anhydrous sodium sulfate, filtered and evaporated under reduced pressure. The residue was purified by silica gel column chromatography using cyclohexane/ethyl acetate 100/0 to 70/30 as eluent to afford N-(3-iodo-1-tetrahydropyran-2-yl-indazol-5-yl)-2-nitro-benzenesulfonamide intermediate 275 as a pink solid.

LCMS method F: $[M+H]^+$=529.1, $t_R$=2.83 min

Preparation of Intermediate 276: Benzyl N-[3-[(3-iodo-1-tetrahydropyran-2-yl-indazol-5-yl)-(2-nitrophenyl)sulfonyl-amino]propyl]carbamate

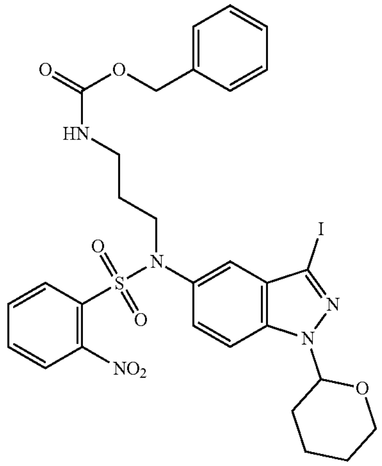 [SMILES: O=C(NCCCN(c1ccc2c(c1)c(I)nn2C1CCCCO1)S(=O)(=O)c1ccccc1[N+](=O)[O-])OCc1ccccc1]

To a mixture of N-(3-iodo-1-tetrahydropyran-2-yl-indazol-5-yl)-2-nitro-benzenesulfonamide intermediate 275 (800 mg, 1.51 mmol) in acetonitrile (200 mL) was added potassium carbonate (229 mg, 1.66 mmol) and benzyl N-(3-bromopropyl)carbamate (410 mg, 1.51 mmol). The reaction mixture was stirred at 90° C. for 16 h. Additional potassium carbonate (229 mg, 1.66 mmol) and benzyl N-(3-bromopropyl)carbamate (410 mg, 1.51 mmol) were added. The reaction mixture was stirred at 90° C. for 16 h. The solvent was removed under reduced pressure and the reaction mixture was dissolved with ethyl acetate and water. After separation, the aqueous layer was extracted with ethyl acetate. The organic layers were dried over anhydrous sodium sulfate, filtered and evaporated under reduced pressure. The residue was purified by silica gel column chromatography using cyclohexane/ethyl acetate 100/0 to 50/50 as eluent to afford benzyl N-[3-[(3-iodo-1-tetrahydropyran-2-yl-indazol-5-yl)-(2-nitrophenyl)sulfonyl-amino]propyl]carbamate intermediate 276 as a yellow oil.

LCMS method F: $[M+H]^+$=720.2, $t_R$=3.09 min

Preparation of Intermediate 277: benzyl N-[3-[(3-iodo-1-tetrahydropyran-2-yl-indazol-5-yl)amino]propyl]carbamate

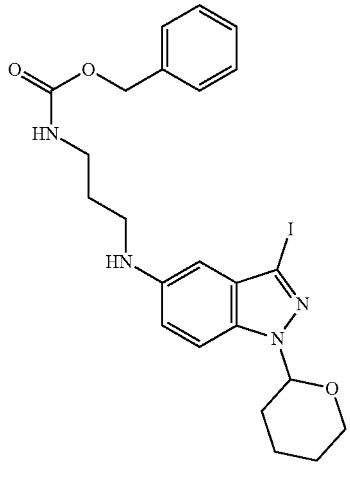 [SMILES: O=C(NCCCNc1ccc2c(c1)c(I)nn2C1CCCCO1)OCc1ccccc1]

To a suspension of benzyl N-[3-[(3-iodo-1-tetrahydropyran-2-yl-indazol-5-yl)-(2-nitrophenyl)sulfonyl-amino]propyl]carbamate intermediate 276 (810 mg, 1.15 mmol) and cesium carbonate (749 mg, 2.30 mmol) in N,N-dimethylformamide (40 mL) was added 4-methylbenzenethiol (171 mg, 1.38 mmol). The reaction mixture was stirred at room temperature for 16 h. The solvent was evaporated under reduced pressure. The reaction mixture was diluted with ethyl acetate and washed with water and brine. The organic layer was dried over anhydrous sodium sulfate, filtered and the solvent was removed under reduced pressure. The residue was purified by silica gel column chromatography using cyclohexane/ethyl acetate 100/0 to 50/50 as eluent to afford benzyl N-[3-[(3-iodo-1-tetrahydropyran-2-yl-indazol-5-yl)amino]propyl]carbamate intermediate 277 as a white solid.

LCMS method F: $[M+H]^+$=535.1, $t_R$=2.75 min

Preparation of Intermediate 278: benzyl N-[3-[(3-iodo-1-tetrahydropyran-2-yl-indazol-5-yl)-methyl-amino]propyl]carbamate

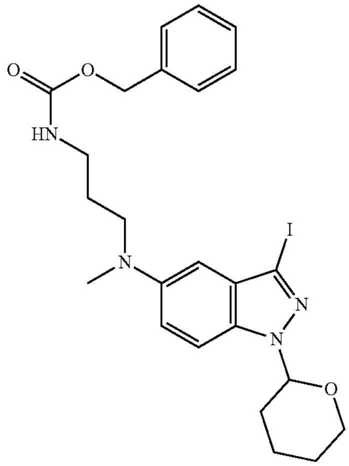 [SMILES: CN(CCCNC(=O)OCc1ccccc1)c1ccc2c(c1)c(I)nn2C1CCCCO1]

To a solution of benzyl N-[3-[(3-iodo-1-tetrahydropyran-2-yl-indazol-5-yl)amino]propyl]carbamate intermediate 277 (360 mg, 0.673 mmol) in acetonitrile (54 mL) was added formaldehyde (37% solution) (18 mL) and sodium triacetoxyborohydride (570 mg, 2.69 mmol). The reaction mixture was stirred at room temperature for 16 h. The solvent was evaporated under reduced pressure. The residue was diluted with ethyl acetate and washed with water. The organic layer was dried over anhydrous sodium sulfate, filtered and evaporated under reduced pressure. The residue was purified by silica gel column chromatography using cyclohexane/ethyl acetate 100/0 to 50/50 to afford benzyl N-[3-[(3-iodo-1-tetrahydropyran-2-yl-indazol-5-yl)-methyl-amino]propyl]carbamate intermediate 278 as a brown oil.

LCMS method F: $[M+H]^+$=549.2, $t_R$=2.73 min

Preparation of Intermediate 279: benzyl N-[3-[[3-[3-(hydroxymethyl)phenyl]-1-tetrahydro pyran-2-yl-indazol-5-yl]-methyl-amino]propyl]carbamate

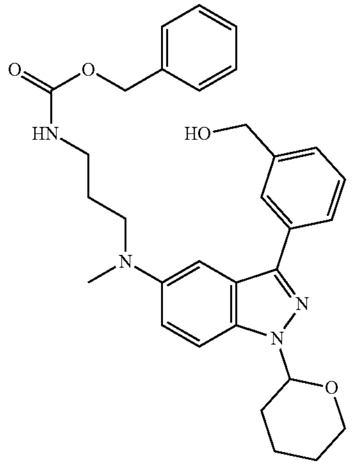 [SMILES: CN(CCCNC(=O)OCc1ccccc1)c1ccc2c(c1)c(-c1cccc(CO)c1)nn2C1CCCCO1]

To a suspension of benzyl N-[3-[(3-iodo-1-tetrahydropyran-2-yl-indazol-5-yl)-methyl-amino]propyl]carbamate intermediate 278 (150 mg, 0.273 mmol) in 1,4-dioxane (2.2 mL) and water (0.11 mL) was added [3-(hydroxymethyl)phenyl]boronic acid (50 mg, 0.327 mmol) and potassium phosphate tribasic (173 mg, 0.819 mmol). The reaction was purged with argon for 10 min and tetrakis(triphenylphosphine)palladium(0) (15 mg, 0.0136 mmol) and XPhos (13 mg, 0.0273 mmol) were added. The resulting mixture was stirred at 100° C. for 16 h. The reaction mixture was cooled to room temperature and evaporated under reduced pressure. The residue was diluted with ethyl acetate and water. After separation, the aqueous layer was extracted with ethyl acetate. The organic layers were washed with brine, dried over anhydrous sodium sulfate, filtered and evaporated under reduced pressure. The residue was purified on silica gel column chromatography using cyclohexane/ethyl acetate 100/0 to 40/60 as eluent to afford benzyl N-[3-[[3-[3-(hydroxymethyl)phenyl]-1-tetrahydropyran-2-yl-indazol-5-yl]-methyl-amino]propyl]carbamate intermediate 279 as a yellow oil.

LCMS method F: $[M+H]^+$=529.4, $t_R$=2.23 min

Preparation of Intermediate 280: 14-methyl-19-(oxan-2-yl)-8-oxa-10,14,19,20-tetraaza tetracyclo[13.5.2.1$^{2,6}$.0$^{18,21}$]tricosa-1(20),2(23),3,5,15,17,21-heptaen-9-one

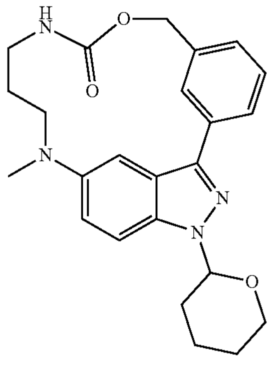 [SMILES: CN1CCCNC(=O)OCc2cccc(c2)-c2nn(C3CCCCO3)c3ccc1cc23]

To a solution of benzyl N-[3-[[3-[3-(hydroxymethyl)phenyl]-1-tetrahydropyran-2-yl-indazol-5-yl]-methyl-amino]propyl]carbamate intermediate 279 (110 mg, 0.208 mmol) in dry acetonitrile (30 mL) was added cesium carbonate (406 mg, 1.24 mmol). The reaction mixture was stirred at 90° C. for 16 h. The suspension was filtered and washed with acetonitrile. The filtrate was evaporated under reduced pressure. The residue was purified on silica gel column chromatography using cyclohexane/ethyl acetate 100/0 to 50/50 as eluent to afford 14-methyl-19-(oxan-2-yl)-8-oxa-10,14,19,20-tetraazatetracyclo[13.5.2.1$^{2,6}$.0$^{18,21}$]tricosa-1(20),2(23),3,5,15,17,21-heptaen-9-one intermediate 280 as a yellow solid.

LCMS method F: $[M+H]^+$=421.3, $t_R$=2.59 min

Preparation of Example 163: 14-methyl-8-oxa-10,14,19,20-tetraazatetracyclo[13.5.2.1$^{2,6}$.0$^{18,21}$]tricosa-1(20),2(23),3,5,15,17,21-heptaen-9-one

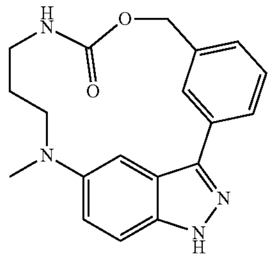 [SMILES: CN1CCCNC(=O)OCc2cccc(c2)-c2n[nH]c3ccc1cc23]

To a solution of 14-methyl-19-(oxan-2-yl)-8-oxa-10,14,19,20-tetraazatetracyclo[13.5.2.1$^{2,6}$.0$^{18,21}$]tricosa-1(20),2(23),3,5,15,17,21-heptaen-9-one intermediate 280 (40 mg, 0.095 mmol) in methanol (1.8 mL) and water (0.26 mL) was added p-toluenesulfonic acid monohydrate (90 mg, 0.475 mmol). The reaction mixture was stirred at 65° C. for 16 h. The reaction mixture was cooled to room temperature and quenched with a saturated aqueous sodium bicarbonate solution. Ethyl acetate was added. After separation, the aqueous layer was extracted with ethyl acetate and the organic layers were washed with brine, dried over anhydrous sodium sulfate, filtered and evaporated under reduced pressure. The residue was purified on silica gel column chromatography using dichloromethane/methanol 100/0 to 95/5 as eluent to afford 14-methyl-8-oxa-10,14,19,20-tetraazatetracyclo[13.5.2.1$^{2,6}$.0$^{18,21}$]tricosa-1(20),2(23),3,5,15,17,21-heptaen-9-one example 163 as a yellow solid.

LCMS method F: $[M+H]^+$=337.1, $t_R$=1.70 min

LCMS method G: $[M+H]^+$=337.3, $t_R$=2.12 min $^1$H NMR (400 MHz, $CDCl_3$) δ 9.97 (1H, bs), 8.03 (1H, s), 7.98-7.94 (1H, m), 7.48-7.36 (2H, m), 7.23-7.20 (2H, m), 7.01 (1H, dd, J=2.3, 9.1 Hz), 5.45-5.26 (3H, m), 3.49-3.27 (4H, m), 3.06-3.05 (3H, s), 2.05-1.97 (2H, m) ppm.

Example 164: (13R)-13-methyl-8,14-dioxa-4,10,19,20,22-pentaazatetracyclo[13.5.2.1$^{2,6}$.0$^{18,21}$]tricosa-1(20),2(23),3,5,15,17,21-heptaen-9-one

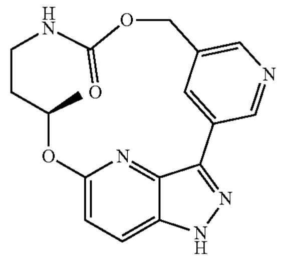 [SMILES: C[C@@H]1CCNC(=O)OCc2cncc(c2)-c2n[nH]c3ccc(nc23)O1]

Example 164 is prepared according to the synthesis route described in detail below.

Preparation of Intermediate 281: 5-chloro-3-iodo-1H-pyrazolo[4,3-b]pyridine

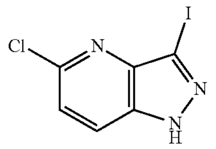 [SMILES: Clc1ccc2[nH]nc(I)c2n1]

To a solution of 5-chloro-1H-pyrazolo[4,3-b]pyridine (1.0 g, 6.51 mmol) in acetonitrile (10 mL) was added N-iodo-succinimide (1.75 g, 7.81 mmol). The reaction mixture was heated under microwave irradiations at 100° C. for 25 min. The solvent was partially evaporated under reduced pressure and the residue was diluted with water and ethyl acetate. After separation, the organic layer was washed with a saturated sodium thiosulfate solution. The aqueous layer was extracted with ethyl acetate and the combined organic layers were dried over anhydrous sodium sulfate, filtered and evaporated under reduced pressure. The residue was purified on silica gel column chromatography using cyclo-hexane/ethyl acetate 100/0 to 60/40 as eluent to afford 5-chloro-3-iodo-1H-pyrazolo[4,3-b]pyridine intermediate 281 as a yellow solid.

LCMS method F: $[M+H]^+$=279.9, $t_R$=2.00 min

Preparation of Intermediate 282: 5-chloro-3-iodo-1-tetrahydropyran-2-yl-pyrazolo[4,3-b]pyridine

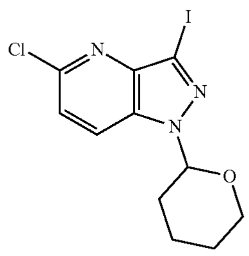 [SMILES: Clc1ccc2c(n1)c(I)nn2C1CCCCO1]

To a solution of 5-chloro-3-iodo-1H-pyrazolo[4,3-b]pyridine intermediate 281 (7.00 g, 25.05 mmol) in dichloromethane (45 mL) were added p-toluenesulfonic acid monohydrate (2.38 g, 12.53 mmol) and then 3,4-dihydro-2H-pyran (4.11 mL, 45.09 mmol). The reaction mixture was stirred at room temperature for 1 h. The reaction mixture was diluted with a saturated aqueous sodium bicarbonate solution and more dichloromethane was added. After separation, the aqueous layer was extracted with dichloromethane and the combined organic layers were dried over anhydrous sodium sulfate, filtered and evaporated under reduced pressure. The residue was purified on silica gel column chromatography using cyclohexane/ethyl acetate 100/0 to 75/25 as eluent to afford 5-chloro-3-iodo-1-tetrahydropyran-2-yl-pyrazolo[4,3-b]pyridine intermediate 282 as a pale yellow solid.

LCMS method F: $[M+H]^+$=364.0, $t_R$=2.75 min

Preparation of Intermediate 283: 3-iodo-5-methoxy-1-tetrahydropyran-2-yl-pyrazolo[4,3-b]pyridine

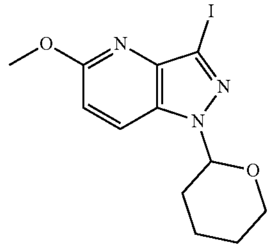 [SMILES: COc1ccc2c(n1)c(I)nn2C1CCCCO1]

To a solution of 5-chloro-3-iodo-1-tetrahydropyran-2-yl-pyrazolo[4,3-b]pyridine intermediate 282 (4.10 g, 11.28 mmol) in dry N,N-dimethylformamide (160 mL) was added sodium hydride (60% dispersion in mineral oil) (2.25 g, 56.38 mmol) and methanol (2.28 mL, 56.38 mmol). The reaction mixture was stirred at 50° C. for 2 h. The reaction mixture was cooled to room temperature and carefully quenched with water. The solvent was partially evaporated reduced pressure and water and ethyl acetate were added. After separation, the aqueous layer was extracted with ethyl acetate and the combined organic layers were dried over anhydrous sodium sulfate, filtered and evaporated under reduced pressure. The residue was purified on silica gel column chromatography using cyclohexane/ethyl acetate 100/0 to 85/15 as eluent to afford 3-iodo-5-methoxy-1-tetrahydropyran-2-yl-pyrazolo[4,3-b]pyridine intermediate 283 as a pale yellow oil.

LCMS method F: $[M+H]^+$=360.0, $t_R$=2.82 min

Preparation of Intermediate 284: 3-iodo-1-tetrahydropyran-2-yl-pyrazolo[4,3-b]pyridin-5-ol

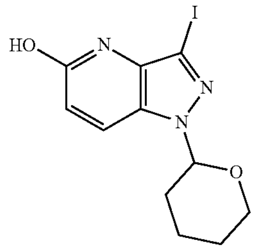 [SMILES: Oc1ccc2c(n1)c(I)nn2C1CCCCO1]

To a solution of 3-iodo-5-methoxy-1-tetrahydropyran-2-yl-pyrazolo[4,3-b]pyridine intermediate 283 (1.73 g, 4.84 mmol) in acetonitrile (18 mL) and 1,2-dichloroethane (18 mL) were added sodium iodide (2.17 g, 14.52 mmol) and then trimethylchlorosilane (1.22 mL, 9.67 mmol). The reaction mixture was stirred at 40° C. for 4 h. The reaction mixture was diluted with a saturated aqueous sodium thiosulfate solution and ethyl acetate. After separation, the aqueous layer was extracted with ethyl acetate and the combined organic layers were washed with brine, dried over anhydrous sodium sulfate, filtered and evaporated under reduced pressure. The residue was purified on silica gel column chromatography using cyclohexane/(ethyl acetate/ethanol (3/1)) 100/0 to 30/70 as eluent. The resulting solid was triturated in acetonitrile, filtered and dried to afford 3-iodo-1-tetrahydropyran-2-yl-pyrazolo[4,3-b]pyridin-5-ol intermediate 284 as a white solid.

LCMS method F: $[M+H]^+$=346.0, $t_R$=1.85 min

Preparation of Intermediate 285: benzyl N-[(3R)-3-(3-iodo-1-tetrahydropyran-2-yl-pyrazolo[4,3-b]pyridin-5-yl)oxybutyl]carbamate

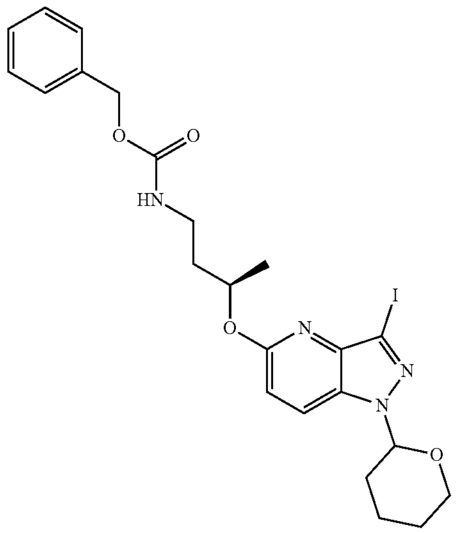 [SMILES: C[C@H](CCNC(=O)OCc1ccccc1)Oc1ccc2c(n1)c(I)nn2C1CCCCO1]

To a solution of [(1S)-3-(benzyloxycarbonylamino)-1-methyl-propyl]methanesulfonate intermediate 199 (783 mg, 2.6 mmol) in dry acetonitrile (20 mL) was added cesium carbonate (1.3 g, 4.0 mmol) and 3-iodo-1-tetrahydropyran-2-yl-pyrazolo[4,3-b]pyridin-5-ol intermediate 284 (702 mg, 2.0 mmol). The reaction mixture was stirred at reflux for 16 h. The reaction mixture was evaporated under reduced pressure and partitioned with water and ethyl acetate. After separation, the aqueous layer was extracted with ethyl acetate and the combined organic layers were washed with brine, dried over anhydrous sodium sulfate, filtered and evaporated under reduced pressure. The residue was purified by silica gel column chromatography using cyclohexane/ethyl acetate 100/0 to 40/60 as eluent to afford benzyl N-[(3R)-3-(3-iodo-1-tetrahydropyran-2-yl-pyrazolo[4,3-b]pyridin-5-yl)oxybutyl]carbamate intermediate 285 as a white solid.

LCMS method F: $[M+H]^+$=551.2, $t_R$=3.17 min

Preparation of Intermediate 286: Benzyl N-[(3R)-3-[3-[5-(hydroxymethyl)-3-pyridyl]-1-tetrahydropyran-2-yl-pyrazolo[4,3-b]pyridin-5-yl]oxybutyl]carbamate

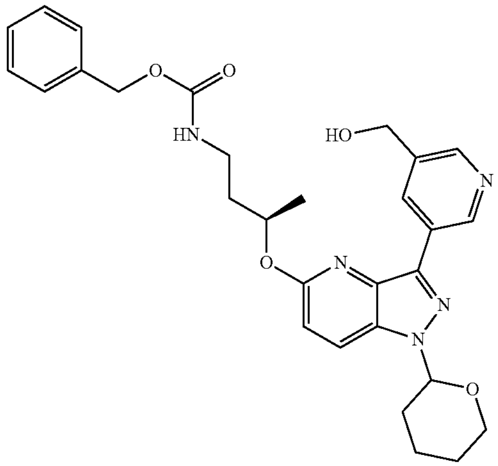 [SMILES: C[C@H](CCNC(=O)OCc1ccccc1)Oc1ccc2c(n1)c(-c1cncc(CO)c1)nn2C1CCCCO1]

To a suspension of benzyl N-[(3R)-3-(3-iodo-1-tetrahydropyran-2-yl-pyrazolo[4,3-b]pyridin-5-yl)oxybutyl]carbamate intermediate 285 (420 mg, 0.76 mmol) in 1,4-dioxane (4.0 mL) and water (0.2 mL) was added (5-(4,4,5,5-tetramethyl-1,3,2-dioxaborolan-2-yl)pyridin-3-yl)methanol (214 mg, 0.91 mmol) and potassium phosphate tribasic (484 mg, 2.28 mmol). The reaction was purged with argon for 10 min then Xphos (36 mg, 0.08 mmol) and tetrakis(triphenylphosphine)palladium(0) (44 mg, 0.04 mmol) were added. The reaction mixture was stirred at reflux for 4 h. The reaction mixture was cooled to room temperature and diluted with water and ethyl acetate. After separation, the aqueous layer was extracted with ethyl acetate and the combined organic layers were washed with brine, dried over anhydrous sodium sulfate, filtered and evaporated under reduced pressure. The residue was purified on silica gel column chromatography using cyclohexane/(ethyl acetate/ethanol (3/1)) 90/10 to 50/50 as eluent to afford benzyl N-[(3R)-3-[3-[5-(hydroxymethyl)-3-pyridyl]-1-tetrahydropyran-2-yl-pyrazolo[4,3-b]pyridin-5-yl]oxybutyl]carbamate intermediate 286 as a white foam.

LCMS method F: $[M+H]^+$=532.3, $t_R$=2.23 min

Preparation of Intermediate 287: (13R)-13-methyl-19-(oxan-2-yl)-8,14-dioxa-4,10,19,20,22-pentaaza-tetracyclo[13.5.2.$1^{2,6}$.$0^{18,21}$]tricosa-1(20),2(23),3,5,15,17,21-heptaen-9-one

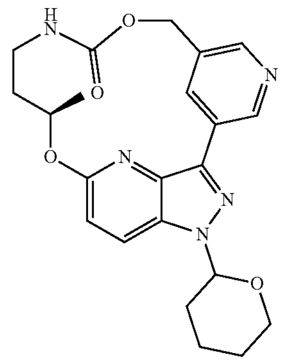 [SMILES: C[C@@H]1CCNC(=O)OCc2cncc(c2)-c2nn(C3CCCCO3)c3ccc(nc23)O1]

To a solution of benzyl N-[(3R)-3-[3-[5-(hydroxymethyl)-3-pyridyl]-1-tetrahydropyran-2-yl-pyrazolo[4,3-b]pyridin-5-yl]oxybutyl]carbamate intermediate 286 (250 mg, 0.47 mmol) in dry acetonitrile (80 mL) was added cesium carbonate (919 mg, 2.82 mmol). The reaction mixture was stirred at 90° C. for 2 h. The suspension was filtered and the salts were washed with acetonitrile. The filtrate was evaporated under reduced pressure. The residue was purified on silica gel column chromatography using dichloromethane/methanol 100/0 to 95/5 as eluent to afford (13R)-13-methyl-19-(oxan-2-yl)-8,14-dioxa-4,10,19,20,22-pentaazatetracyclo[13.5.2.$1^{2,6}$.$0^{18,21}$]tricosa-1(20),2(23),3,5,15,17,21-heptaen-9-one intermediate 287 as a colorless oil.

LCMS method F: $[M+H]^+$=424.3, $t_R$=2.17 min

Preparation of Example 164: (13R)-13-methyl-8,14-dioxa-4,10,19,20,22-pentaaza tetracyclo[13.5.2.$1^{2,6}$.$0^{18,21}$]tricosa-1(20),2(23),3,5,15,17,21-heptaen-9-one

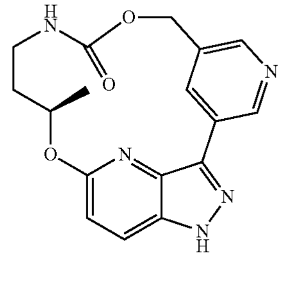 [SMILES: C[C@@H]1CCNC(=O)OCc2cncc(c2)-c2n[nH]c3ccc(nc23)O1]

To a solution of (13R)-13-methyl-19-(oxan-2-yl)-8,14-dioxa-4,10,19,20,22-pentaazatetracyclo[13.5.2.$1^{2,6}$.$0^{18,21}$]tricosa-1(20),2(23),3,5,15,17,21-heptaen-9-one intermediate 287 (200 mg, 0.47 mmol) in methanol (11 mL) and water (1.6 mL) was added p-toluenesulfonic acid monohydrate (446 mg, 2.35 mmol). The reaction mixture was stirred at 65° C. for 2 h then cooled to room temperature and carefully quenched with a saturated aqueous sodium bicarbonate solution. Ethyl acetate was added. After separation, the aqueous layer was extracted with ethyl acetate and the combined organic layers were washed with brine, dried over anhydrous sodium sulfate, filtered and evaporated under reduced pressure. The residue was purified on silica gel column chromatography using cyclohexane/(ethyl acetate-ethanol (3-1)) 80/20 to 20/80 as eluent. The resulting solid was triturated in diethyl ether, filtered then dissolved in dichloromethane/methanol and evaporated under reduced pressure to afford (13R)-13-methyl-8,14-dioxa-4,10,19,20,22-pentaazatetracyclo[13.5.2.$1^{2,6}$.$0^{18,21}$]tricosa-1(20),2(23),3,5,15,17,21-heptaen-9-one example 164 as a white solid.

LCMS method F: $[M+H]^+$=340.3, $t_R$=1.63 min

LCMS method G: $[M+H]^+$=340.3, $t_R$=1.97 min $^1$H NMR (400 MHz, d6-DMSO) δ 13.45 (1H, s), 9.19-9.18 (1H, m), 8.88 (1H, s), 8.46-8.44 (1H, m), 8.02-7.98 (1H, m), 7.87-7.82 (1H, m), 6.86-6.83 (1H, m), 5.57-5.46 (2H, m), 5.12-5.08 (1H, m), 3.46-3.40 (1H, m), 3.00-2.92 (1H, m), 2.45 (1H, d, J=14.3 Hz), 1.41-1.38 (4H, m) ppm.

Example 165: (13R)-13-methyl-8,14-dioxa-10,17,19,20-tetraazatetracyclo[13.5.2.$1^{2,6}$.$0^{18,21}$]tricosa-1(20),2(23),3,5,15(22),16,18(21)-heptaen-9-one

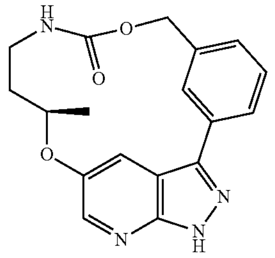 [SMILES: C[C@@H]1CCNC(=O)OCc2cccc(c2)-c2n[nH]c3ncc(cc23)O1]

Example 165 is prepared according to the synthesis route described in detail below.

Preparation of Intermediate 288: 5-bromo-1-tetrahydropyran-2-yl-pyrazolo[3,4-b]pyridine

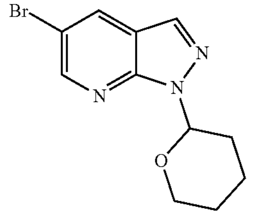 [SMILES: Brc1cnc2c(cnn2C2CCCCO2)c1]

To a solution of 5-bromo-1H-pyrazolo[3,4-b]pyridine (3.96 g, 20.0 mmol) and 3,4-dihydropyran (5.49 mL, 60.0 mmol) in dichloromethane (45 mL) and THE (15 mL) was added methanesulfonic acid (0.26 mL, 4.0 mmol). The reaction mixture was stirred at room temperature for 3 h. Saturated aqueous sodium bicarbonate solution was added. After separation, the aqueous layer was extracted with dichloromethane and the combined organic extracts were washed with brine, dried over anhydrous sodium sulfate, filtered and concentrated under reduced pressure. The residue was purified by silica gel column chromatography using cyclohexane/ethyl acetate 100/0 to 70/30 as eluent to afford 5-bromo-1-tetrahydropyran-2-yl-pyrazolo[3,4-b]pyridine intermediate 288 as a pale yellow oil.

LCMS method F: $[M+H]^+$=282.0-284.0, $t_R$=2.45 min

Preparation of Intermediate 289: 1-tetrahydropyran-2-yl-5-(4,4,5,5-tetramethyl-1,3,2-dioxaborolan-2-yl) pyrazolo[3,4-b]pyridine

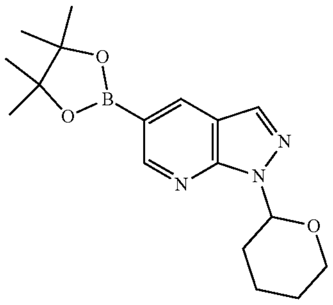 [SMILES: CC1(C)OB(c2cnc3c(cnn3C3CCCCO3)c2)OC1(C)C]

To an argon degassed mixture of 5-bromo-1-tetrahydro-pyran-2-yl-pyrazolo[3,4-b]pyridine intermediate 288 (1.25 g, 4.43 mmol), bis(pinacolato)diboron (2.81 g, 11.07 mmol), potassium acetate (1.30 g, 13.29 mmol) in DMF (20 mL) was added [1,1'-Bis(diphenylphosphino)ferrocene]dichloropalladium(II), complex with dichloromethane (91 mg, 0.111 mmol). The reaction mixture heated to 100° C. for 2 h. The solvent was concentrated under reduced pressure and the residue was partitioned between ethyl acetate and water. The aqueous layer was extracted with ethyl acetate and the combined organic extracts were washed with brine, dried over anhydrous sodium sulfate, filtered and concentrated under reduced pressure to afford 1-tetrahydropyran-2-yl-5-(4,4,5,5-tetramethyl-1,3,2-dioxaborolan-2-yl)pyrazolo[3,4-b]pyridine intermediate 289 as a brown oil which was used in the next step without further purification.

LCMS method F: $[M+H]^+$=330.3, $t_R$=2.73 min

Preparation of Intermediate 290: 1-tetrahydropyran-2-ylpyrazolo[3,4-b]pyridin-5-ol

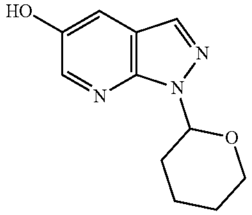 [SMILES: Oc1cnc2c(cnn2C2CCCCO2)c1]

To a solution of 1-tetrahydropyran-2-yl-5-(4,4,5,5-tetramethyl-1,3,2-dioxaborolan-2-yl) pyrazolo[3,4-b]pyridine intermediate 289 (6.0 g, 17.72 mmol) in THE (45 mL) and 1 N aqueous sodium hydroxide solution (45 mL) was added hydrogen peroxide (30% wt aqueous solution, 2.0 mL, 53.166 mmol). The reaction mixture was stirred at room temperature for 2 h. The reaction mixture was quenched with saturated aqueous sodium thiosulfate solution and diluted with ethyl acetate. After separation, the aqueous layer was extracted with ethyl acetate and the combined organic extracts were washed with brine, dried over anhydrous sodium sulfate, filtered and concentrated under reduced pressure to afford 1-tetrahydropyran-2-ylpyrazolo [3,4-b]pyridin-5-ol intermediate 290 as a brown oil.

LCMS method F: $[M+H]^+$=220.3, $t_R$=1.58 min

Preparation of Intermediate 291: tert-butyl-dimethyl-(1H-pyrazolo[3,4-b]pyridin-5-yloxy) silane

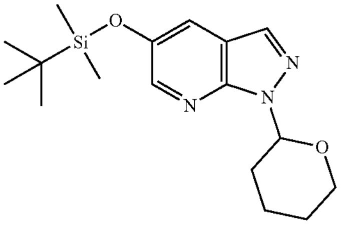 [SMILES: CC(C)(C)[Si](C)(C)Oc1cnc2c(cnn2C2CCCCO2)c1]

To a solution of 1-tetrahydropyran-2-ylpyrazolo[3,4-b] pyridin-5-ol intermediate 290 (2.37 g, 17.59 mmol) and imidazole (1.43 g, 21.11 mmol) in DMF (18 mL) at 0° C. was added tert-butyldimethylsilyl chloride (2.91 g, 19.35 mmol). The reaction mixture was stirred at 0° C. for 5 min then warmed to room temperature and stirred for 16 h. Solvents were evaporated under reduced pressure and the residue was partitioned between ethyl acetate and water. The aqueous layer was extracted with ethyl acetate and the combined organic extracts were washed with brine, dried over anhydrous sodium sulfate, filtered and concentrated under reduced pressure to afford tert-butyl-dimethyl-(1H-pyrazolo[3,4-b]pyridin-5-yloxy)silane intermediate 291 as a brown oil which was used in the next step without further purification.

LCMS method F: $[M+H]^+$=334.2, $t_R$=3.29 min

Preparation of Intermediate 292: 1H-pyrazolo[3,4-b]pyridin-5-ol

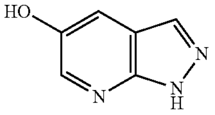

To a solution of tert-butyl-dimethyl-(1-tetrahydropyran-2-ylpyrazolo[3,4-b]pyridin-5-yl)oxy-silane intermediate 291 (4.69 g, 14.50 mmol) in methanol (60 mL) and water (12 mL) was added toluenesulfonic acid monohydrate (5.52 g, 29.01 mmol). The solution was stirred at room temperature for 2 h. Solvents were evaporated and the residue was partitioned between ethyl acetate and water. The aqueous layer was washed with ethyl acetate, collected and evaporated under reduced pressure. The residue was purified by reverse-phase column chromatography using acetonitrile/water 10/90 to 50/50 as eluent. The requisite fraction were concentrated under reduced pressure and triturated with diisopropyl ether to afford 1H-pyrazolo[3,4-b]pyridin-5-ol intermediate 292 as a beige solid.

LCMS method F: $[M+H]^+$=136.1, $t_R$=1.36 min

Preparation of Intermediate 293: tert-butyl-dimethyl-(1H-pyrazolo[3,4-b]pyridin-5-yloxy) silane

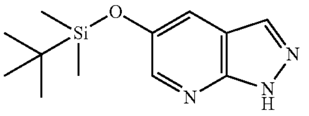 [SMILES: CC(C)(C)[Si](C)(C)Oc1cnc2[nH]ncc2c1]

To a solution of crude 1H-pyrazolo[3,4-b]pyridin-5-ol intermediate 292 (500 mg, 3.70 mmol) in DMF (16 mL) were successively added imidazole (504 mg, 7.40 mmol) and tert-butyldimethylsilyl chloride (669 mg, 4.44 mmol). The reaction mixture was stirred at room temperature for 16 h. Saturated aqueous ammonium chloride and ethyl acetate were added. After separation, the aqueous layer was extracted with ethyl acetate and the combined organic extracts were washed with brine, dried over anhydrous sodium sulfate, filtered and concentrated under reduced pressure to afford tert-butyl-dimethyl-(1H-pyrazolo[3,4-b]pyridin-5-yloxy)silane intermediate 293 as a yellow oil which was used in the next step without further purification.

LCMS method F: $[M+H]^+$=250.3, $t_R$=2.73 min

Preparation of Intermediate 294: tert-butyl-[(3-iodo-1H-pyrazolo[3,4-b]pyridin-5-yl)oxy]-dimethyl-silane

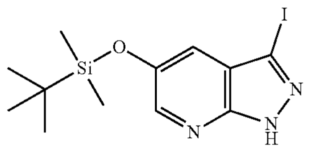 [SMILES: CC(C)(C)[Si](C)(C)Oc1cnc2[nH]nc(I)c2c1]

To a solution of tert-butyl-dimethyl-(1H-pyrazolo[3,4-b]pyridin-5-yloxy)silane intermediate 293 (3.00 g, 12.03 mmol) in DMF (60 mL) was added N-Iodosuccinimide (3.24 g, 14.43 mmol). The reaction mixture was stirred at room temperature for 16 h. Additional N-Iodosuccinimide (1.12 g, 5.0 mmol) was added and the reaction mixture was stirred for 5 h. Solvents were concentrated under reduced pressure and the residue was partitioned between ethyl acetate and saturated aqueous sodium thiosulfate solution. The aqueous layer was extracted with ethyl acetate and the combined organic extracts were washed with saturated aqueous sodium bicarbonate solution then with brine, dried over anhydrous anhydrous sodium sulfate, filtered and concentrated under reduced pressure to afford tert-butyl-[(3-iodo-1H-pyrazolo[3,4-b]pyridin-5-yl)oxy]-dimethyl-silane intermediate 294 as a yellow solid which was used in the next step without further purification.

LCMS method F: $[M+H]^+$=376.2, $t_R$=3.20 min

Preparation of Intermediate 295: tert-butyl-(3-iodo-1-tetrahydropyran-2-yl-pyrazolo[3,4-b]pyridin-5-yl)oxy-dimethyl-silane

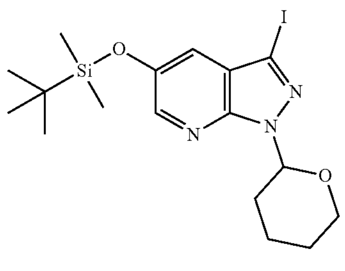 [SMILES: CC(C)(C)[Si](C)(C)Oc1cnc2c(c1)c(I)nn2C1CCCCO1]

To a solution of tert-butyl-[(3-iodo-1H-pyrazolo[3,4-b]pyridin-5-yl)oxy]-dimethyl-silane intermediate 294 (1.16 g, 3.10 mmol) and DHP (0.85 mL, 9.303 mmol) in dichloromethane (12 mL) and THE (4 mL) was added methanesulfonic acid (40 μL, 0.62 mmol). The reaction mixture was stirred at room temperature for 16 h. Saturated aqueous sodium bicarbonate solution was added. After separation, the aqueous layer was extracted with dichloromethane and the combined organic extracts were washed with brine, dried over anhydrous sodium sulfate, filtered and concentrated under reduced pressure. The residue was purified by silica gel column chromatography using cyclohexane/ethyl acetate 100/0 to 70/30 as eluent to afford tert-butyl-(3-iodo-1-tetrahydropyran-2-yl-pyrazolo[3,4-b]pyridin-5-yl)oxy-dimethyl-silane intermediate 295 as a pale yellow oil.

LCMS method F: $[M+H]^+$=460.1, $t_R$=3.67 min

Preparation of Intermediate 296: 3-iodo-1-tetrahydropyran-2-yl-pyrazolo[3,4-b]pyridin-5-ol

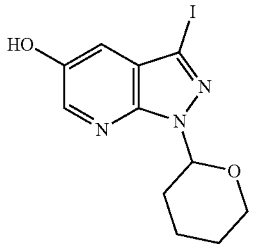 [SMILES: Oc1cnc2c(c1)c(I)nn2C1CCCCO1]

To a 0° C. solution of tert-butyl-(3-iodo-1-tetrahydropyran-2-yl-pyrazolo[3,4-b]pyridin-5-yl)oxy-dimethyl-silane intermediate 295 (630 mg, 1.371 mmol) in THE (15 mL) was added 1M TBAF solution in THE (1.64 mL, 1.64 mmol) dropwise over 5 min. The reaction mixture was stirred at 0° C. for 5 min then warmed to room temperature and stirred for 16 h. Solvents were evaporated under reduced pressure and the residue was partitioned between ethyl acetate and saturated aqueous ammonium chloride solution. The aqueous layer was extracted with ethyl acetate and the combined organic extracts were washed with brine, dried over anhydrous sodium sulfate, filtered and concentrated under reduced pressure to afford 3-iodo-1-tetrahydropyran-2-yl-pyrazolo[3,4-b]pyridin-5-ol intermediate 296 as a yellow solid which was used in the next step without further purification.

LCMS method F: $[M+H]^+$=346.1, $t_R$=2.17 min

Preparation of Intermediate 297: benzyl N-[(3R)-3-(3-iodo-1-tetrahydropyran-2-yl-pyrazolo 15 [3,4-b]pyridin-5-yl)oxybutyl]carbamate

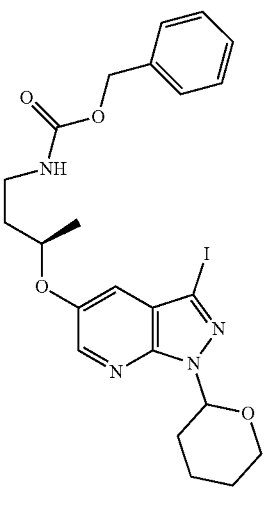 [SMILES: C[C@H](CCNC(=O)OCc1ccccc1)Oc1cnc2c(c1)c(I)nn2C1CCCCO1]

To a solution of 3-iodo-1-tetrahydropyran-2-yl-pyrazolo[3,4-b]pyridin-5-ol intermediate 296 (270 mg, 0.781 mmol) in DMF (4 mL) was added cesium carbonate (382 mg, 1.17 mmol). The reaction mixture was stirred at room temperature for 30 min, then a solution of [(1S)-3-(benzyloxycarbonylamino)-1-methyl-propyl]methanesulfonate intermediate 199 (259 mg, 0.859 mmol) in DMF (4 mL) was added dropwise over 2 min. The reaction mixture was stirred at room temperature for 72 h. The reaction mixture was filtered. Ethyl acetate and water were added. After separation, the aqueous layer was extracted with ethyl acetate and the combined organic extracts were washed with brine, dried over anhydrous sodium sulfate, filtered and concentrated under reduced pressure to afford benzyl N-[(3R)-3-(3-iodo-1-tetrahydropyran-2-yl-pyrazolo[3,4-b]pyridin-5-yl)oxybutyl]carbamate intermediate 297 as a yellow oil which was used in the next step without further purification.

LCMS method F: $[M+H]^+$=551.2, $t_R$=3.06 min

Preparation of Intermediate 298: benzyl N-[(3R)-3-[3-[3-(hydroxymethyl)phenyl]-1-tetra hydropyran-2-yl-pyrazolo[3,4-b]pyridin-5-yl]oxybutyl]carbamate

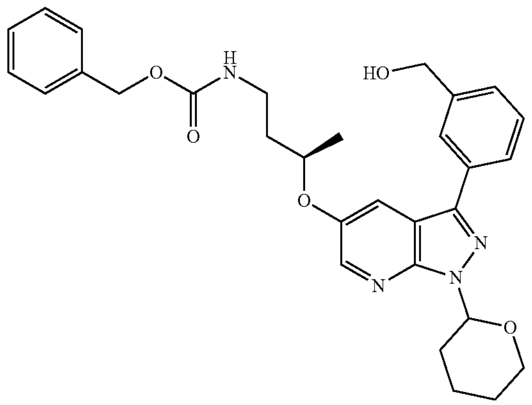 [SMILES: C[C@H](CCNC(=O)OCc1ccccc1)Oc1cnc2c(c1)c(-c1cccc(CO)c1)nn2C1CCCCO1]

To an argon degassed solution of benzyl N-[(3R)-3-(3-iodo-1-tetrahydropyran-2-yl-pyrazolo[3,4-b]pyridin-5-yl)oxybutyl]carbamate intermediate 297 (260 mg, 0.472 mmol), [3-(hydroxy methyl)phenyl]boronic acid (79 mg, 0.52 mmol), potassium phosphate tribasic (301 mg, 1.41 mmol) and XPhos (22 mg, 0.047 mmol) in dioxane (4.75 mL) and water (0.25 mL) was added tetrakis(triphenylphosphine)-palladium(0) (28 mg, 0.024 mmol). The reaction mixture was stirred at 90° C. for 1 h. The reaction mixture was cooled to room temperature and ethyl acetate and water were added. After separation, the aqueous layer was extracted with ethyl acetate and the combined organic extracts were washed with brine, dried over anhydrous sodium sulfate, filtered and concentrated under reduced pressure. The residue was purified by silica gel column chromatography using cyclohexane/ethyl acetate 100/0 to 60/40 as eluent to afford benzyl N-[(3R)-3-[3-[3-(hydroxymethyl)phenyl]-1-tetrahydropyran-2-yl-pyrazolo[3,4-b]pyridin-5-yl]oxybutyl]carbamate intermediate 298 as a pale yellow solid.

LCMS method F: $[M+H]^+$=531.4, $t_R$=2.82 min

Preparation of Intermediate 299: (13R)-13-methyl-19-(oxan-2-yl)-8,14-dioxa-10,17,19,20-tetraazatetracyclo[$13.5.2.1^{2,6}.0^{18,21}$]tricosa-1(20),2(23),3,5,15(22),16,18(21)-heptaen-9-one

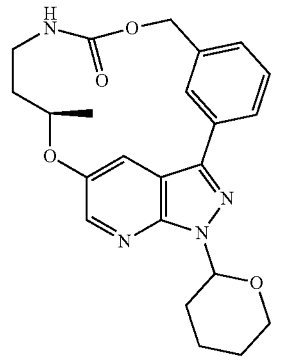 [SMILES: C[C@@H]1CCNC(=O)OCc2cccc(c2)-c2nn(C3CCCCO3)c3ncc(cc23)O1]

To a solution of benzyl N-[(3R)-3-[3-[3-(hydroxymethyl)phenyl]-1-tetrahydropyran-2-yl-pyrazolo[3,4-b]pyridin-5-yl]oxybutyl]carbamate intermediate 298 (300 mg, 0.565 mmol) in acetonitrile (300 mL) was added potassium hydroxide (159 mg, 2.82 mmol). The reaction mixture was stirred at room temperature for 2 h. The reaction mixture was filtered and solvents were concentrated under reduced pressure. The residue was partitioned between ethyl acetate and water. after separation, the aqueous layer was extracted with ethyl acetate and the combined organic extracts were washed with brine, dried over anhydrous sodium sulfate, filtered and concentrated under reduced pressure. The residue was purified by silica gel column chromatography using dichloromethane/methanol 100/0 to 95/5 as eluent to afford (13R)-13-methyl-19-(oxan-2-yl)-8,14-dioxa-10,17,19,20-tetraazatetracyclo[$13.5.2.1^{2,6}.0^{18,21}$]tricosa-1(20),2(23),3,5,15(22),16,18(21)-heptaen-9-one intermediate 299 as a pale yellow foam.

LCMS method F: $[M+H]^+$=423.2, $t_R$=2.73 min

Preparation of Example 165: (13R)-13-methyl-8,14-dioxa-10,17,19,20-tetraazatetracyclo[$13.5.2.1^{2,6}.0^{18,21}$]tricosa-1(20),2(23),3,5,15(22),16,18(21)-heptaen-9-one

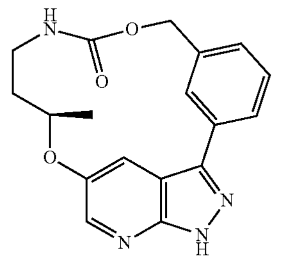 [SMILES: C[C@@H]1CCNC(=O)OCc2cccc(c2)-c2n[nH]c3ncc(cc23)O1]

To a solution of (13R)-13-methyl-19-(oxan-2-yl)-8,14-dioxa-10,17,19,20-tetraazatetracyclo[$13.5.2.1^{2,6}.0^{18,21}$]tricosa-1(20),2(23),3,5,15(22),16,18(21)-heptaen-9-one intermediate 299 (160 mg, 0.378 mmol) in methanol (3 mL) and water (1 mL) was added p-toluenesulfonic acid monohydrate (360 mg, 1.89 mmol). The reaction mixture at 50° C. for 16 h. Solvents were concentrated under reduced pressure and the residue was partitioned between ethyl acetate and saturated aqueous sodium bicarbonate solution. After separation, the aqueous layer was extracted with ethyl acetate and the combined organic extracts were washed with brine, dried over anhydrous sodium sulfate, filtered and concentrated under reduced pressure. The residue was purified by silica gel column chromatography using dichloromethane/methanol 100/0 to 90/10 as eluent. The requisite fractions were concentrated under reduced pressure and triturated in pentane/diethyl ether (10/1) solution to afford (13R)-13-methyl-8,14-dioxa-10,17,19,20-tetraazatetracyclo[13.5.2.$1^{2,6}$.$0^{18,21}$]tricosa-1(20),2(23),3,5,15(22),16,18(21)-heptaen-9-one example 165 as a white solid.

LCMS method F: $[M+H]^+$=339.3, $t_R$=2.76 min

LCMS method G: $[M+H]^+$=339.3, $t_R$=2.75 min $^1$H NMR (400 MHz, d6-DMSO) δ 13.73 (s, 1H), 8.27 (d, J=2.9 Hz, 1H), 7.97 (dd, J=4.9, 7.2 Hz, 1H), 7.87 (d, J=7.9 Hz, 1H), 7.81 (s, 1H), 7.69 (d, J=2.7 Hz, 1H), 7.50 (t, J=7.7 Hz, 1H), 7.31 (d, J=8.0 Hz, 1H), 5.79-5.74 (m, 1H), 4.83 (d, J=13.5 Hz, 1H), 4.58 (dd, J=5.9, 10.5 Hz, 1H), 3.60-3.56 (m, 1H), 2.91 (t, J=13.6 Hz, 1H), 2.33 (t, J=12.7 Hz, 1H), 1.45 (d, J=6.2 Hz, 3H), 1.42-1.39 (m, 1H) ppm.

Example 166: 8,14-dioxa-4,5,10,19,20,23-hexaazatetracyclo[13.5.2.$1^{2,5}$.$0^{18,21}$]tricosa-1(20),2(23),3,15(22),16,18(21)-hexaen-9-one

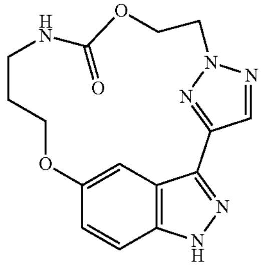 [SMILES: O=C1NCCCOc2ccc3[nH]nc(c3c2)-c2cnn(n2)CCO1]

Example 166 is prepared according to the synthesis route described in general scheme K.

Preparation of Intermediate 300: benzyl N-[3-[3-[2-(2-hydroxyethyl)triazol-4-yl]-1-tetrahydropyran-2-yl-indazol-5-yl]oxypropyl]carbamate

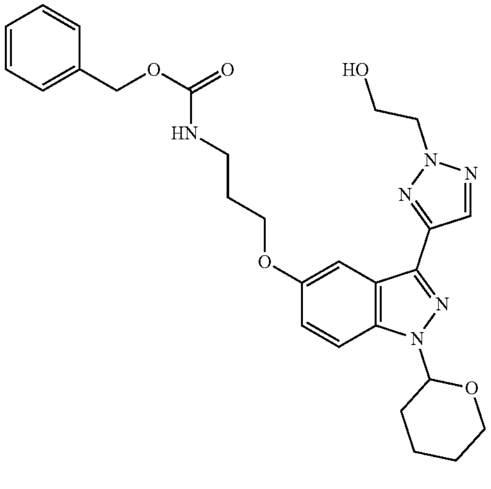 [SMILES: O=C(NCCCOc1ccc2c(c1)c(-c1cnn(CCO)n1)nn2C1CCCCO1)OCc1ccccc1]

To a stirred mixture of 2-[4-[5-[tert-butyl(dimethyl)silyl]oxy-1-tetrahydropyran-2-yl-indazol-3-yl]triazol-2-yl]ethanol intermediate 248 (443 mg, 1 mmol), and cesium carbonate (977 mg, 3.24 mmol) in acetonitrile (20 mL) was added a solution of benzyl N-(3-bromopropyl)carbamate (272 mg, 1.1 mmol) in acetonitrile (2 mL). The reaction mixture was stirred at 50° C. for 16 hours. The salts were removed by filtration, rinsed with acetonitrile and the filtrate was concentrated under reduced pressure. The residue was purified by silica gel column chromatography using cyclohexane/ethyl acetate 50/50 to 20/80 as eluent to afford benzyl N-[3-[3-[2-(2-hydroxyethyl)triazol-4-yl]-1-tetrahydropyran-2-yl-indazol-5-yl]oxy propyl]carbamate intermediate 300 as a white solid.

LCMS method F: $[M+H]^+$=521.3, $t_R$=2.64 min

Preparation of Intermediate 301: 19-(oxan-2-yl)-8,14-dioxa-4,5,10,19,20,23-hexaazatetra cyclo[13.5.2.$1^{2,5}$.$0^{18,21}$]tricosa-1(20),2(23),3,15(22),16,18(21)-hexaen-9-one

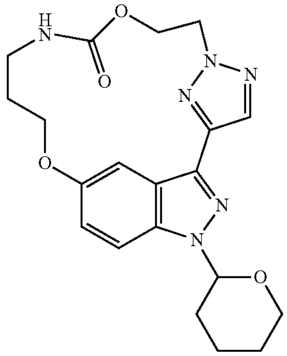 [SMILES: O=C1NCCCOc2ccc3c(c2)c(nn3C2CCCCO2)-c2cnn(n2)CCO1]

To a solution of benzyl N-[3-[3-[2-(2-hydroxyethyl)triazol-4-yl]-1-tetrahydropyran-2-yl-indazol-5-yl]oxypropyl]carbamate intermediate 300 (230 mg, 0.44 mmol, 1 eq) in acetonitrile (50 mL) was added cesium carbonate (860 mg, 2.65 mmol). The suspension was stirred at reflux for 48 h. The suspension was filtered and the salts were rinsed with acetonitrile. The filtrate was evaporated under reduced pressure and the residue was purified by silica gel column chromatography using cyclohexane/ethyl acetate 50/50 to 30/70 to afford 19-(oxan-2-yl)-8,14-dioxa-4,5,10,19,20,23-hexaazatetracyclo[13.5.2.$1^{2,5}$.$0^{18,21}$]tricosa-1(20),2(23),3,15(22),16, 18(21)-hexaen-9-one intermediate 301 as a white solid.

LCMS method F: $[M+H]^+$=413.2, $t_R$=2.33 min

Preparation of Example 166: 8,14-dioxa-4,5,10,19,20,23-hexaazatetracyclo[13.5.2.1$^{2,5}$.0$^{18,21}$]tricosa-1(20),2(23),3,15(22),16,18(21)-hexaen-9-one

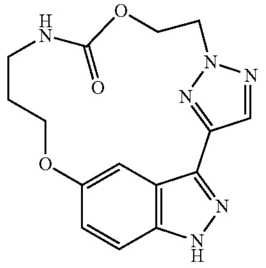 [SMILES: O=C1NCCCOc2ccc3[nH]nc(c3c2)-c2cnn(n2)CCO1]

To a suspension of 19-(oxan-2-yl)-8,14-dioxa-4,5,10,19,20,23-hexaazatetracyclo[13.5.2.1$^{25}$.0$^{18,21}$]tricosa-1(20),2(23),3,15(22),16,18(21)-hexaen-9-one intermediate 301 (50 mg, 0.12 mmol) in methanol (7 mL) and water (1 mL) was added para-toluenesulfonic acid monohydrate (115 mg, 0.6 mmol). The reaction mixture was heated at 65° C. for 6 h. Methanol was partially removed under reduced pressure and a saturated aqueous $NaHCO_3$ was added until pH basic. The aqueous phase was extracted with ethyl acetate. The organic layer was washed with brine, dried over anhydrous sodium sulfate, filtered and evaporated under reduced pressure. The residue was purified by silica gel column chromatography using dichloromethane/methanol 100/0 to 95/5 as eluent. The solid was triturated with diethyl ether, filtered and dried to give 8,14-dioxa-4,5,10,19,20,23-hexaazatetracyclo[13.5.2.1$^{2,5}$.0$^{18,21}$]tricosa-1(20),2(23),3,15(22),16,18(21)-hexaen-9-one example 166 as a white solid.

LCMS method F: $[M+H]^+$=329.2, $t_R$=1.72 min

LCMS method G: $[M+H]^+$=329.2, $t_R$=1.75 min $^1H$ NMR (400 MHz, d6-DMSO) δ 13.15 (1H, s), 8.13 (1H, s), 7.69 (1H, t, J=6.1 Hz), 7.53-7.45 (2H, m), 6.98 (1H, dd, J=2.3, 8.9 Hz), 4.84-4.79 (2H, m), 4.53 (2H, dd, J=2.9, 5.2 Hz), 4.31-4.24 (2H, m), 3.09-3.06 (2H, m), 1.91-1.85 (2H, m) ppm.

Example 167: 12,12-difluoro-8,14-dioxa-4,5,10,19,20,23-hexaazatetracyclo[13.5.2.1$^{2,5}$.0$^{18,21}$]tricosa-1(20),2(23),3,15(22),16,18(21)-hexaen-9-one

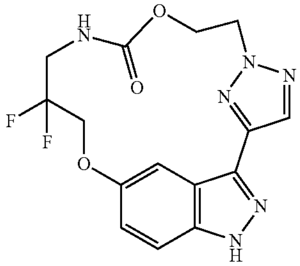 [SMILES: O=C1NCC(F)(F)COc2ccc3[nH]nc(c3c2)-c2cnn(n2)CCO1]

Example 167 is prepared according to the synthesis route described in general scheme K.

Preparation of Intermediate 302: [3-(benzyloxycarbonylamino)-2,2-difluoro-propyl]trifluoromethanesulfonate

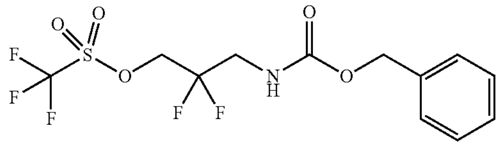 [SMILES: O=C(NCC(F)(F)COS(=O)(=O)C(F)(F)F)OCc1ccccc1]

To a solution of benzyl N-(2,2-difluoro-3-hydroxy-propyl)carbamate intermediate 213 (2.63 g, 10.725 mmol) and triethylamine (2.97 mL, 21.45 mmol) in dichloromethane (100 mL) at 0° C. under argon atmosphere was added dropwise over a period of 5 min $Tf_2O$ (2.65 mL, 16.088 mmol). The reaction mixture was stirred at 0° C. for 5 min and at room temperature for 16 h. A saturated aqueous $NaHCO_3$ solution was added and layers were separated. The aqueous layer was extracted with dichloromethane and the combined organic layers were washed with brine, dried over anhydrous sodium sulfate, filtered and the solvent was removed under reduced pressure to afford crude [3-(benzyloxycarbonylamino)-2,2-difluoro-propyl]trifluoromethane sulfonate intermediate 302 as a brown oil. The product was used in the next step without further purification.

$^1H$ NMR (400 MHz, d6 DMSO) δ 7.38-7.32 (m, 5H), 5.14-5.06 (m, 3H), 3.64 (dt, J=6.5, 14.5 Hz, 2H), 3.14-3.07 (m, 1H). [1 labile proton was not visible in this solvent]

Preparation of Intermediate 303: benzyl N-[2,2-difluoro-3-[3-[2-(2-hydroxyethyl)triazol-4-yl]-1-tetrahydropyran-2-yl-indazol-5-yl]oxy-propyl]carbamate

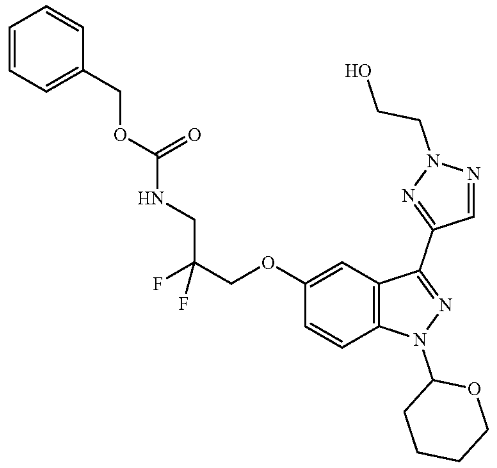 [SMILES: O=C(NCC(F)(F)COc1ccc2c(c1)c(-c1cnn(CCO)n1)nn2C1CCCCO1)OCc1ccccc1]

To a mixture of 3-[2-(2-hydroxyethyl)triazol-4-yl]-1-tetrahydropyran-2-yl-indazol-5-ol (210 mg, 0.638 mmol) and [[3-(benzyloxycarbonylamino)-2,2-difluoro-propyl]trifluoromethane sulfonate intermediate 302 (361 mg, 0.957 mmol) in dry acetonitrile (20 mL) under argon atmosphere was added cesium carbonate (249 mg, 0.766 mmol). The reaction mixture was stirred at 70° C. for 16 h. Additional [[3-(benzyloxycarbonylamino)-2,2-difluoro-propyl]trifluoro methanesulfonate intermediate 302 (361 mg, 0.957 mmol)

was added. The reaction mixture was stirred 4 h at 70° C. Additional [[3-(benzyloxycarbonylamino)-2,2-difluoro-propyl]trifluoro methanesulfonate intermediate 302 (361 mg, 0.957 mmol) was added. The reaction mixture was stirred overnight at 70° C. The solvent was removed under reduced pressure, ethyl acetate and water were added, the layers were separated and the aqueous layer was extracted with ethyl acetate. The combined organic layers were dried over anhydrous sodium sulfate, filtered and evaporated under reduced pressure. The residue was purified by silica gel column chromatographychromatography using cyclohexane/ethyl acetate 100/0 to 50/50 to afford benzyl N-[2,2-difluoro-3-[3-[2-(2-hydroxyethyl)triazol-4-yl]-1-tetrahydro pyran-2-yl-indazol-5-yl]oxy-propyl]carbamate intermediate 303 as a yellow oil.

LCMS method F: $[M+H]^+$=557.4, $t_R$=2.66 min

Preparation of Intermediate 304: 12,12-difluoro-19-(oxan-2-yl)-8,14-dioxa-4,5,10,19,20,23-hexaazatetracyclo[13.5.2.1$^{2,5}$. 0$^{18,21}$]tricosa-1(20),2(23),3,15(22),16,18(21)-hexaen-9-one

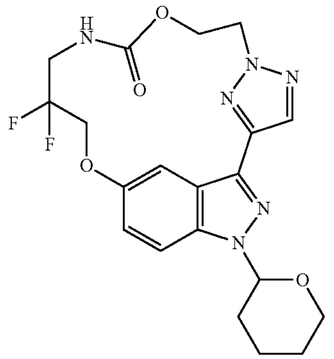 [SMILES: O=C1NCC(F)(F)COc2ccc3c(c2)c(nn3C2CCCCO2)-c2cnn(n2)CCO1]

A stirred solution of benzyl N-[2,2-difluoro-3-[3-[2-(2-hydroxyethyl)triazol-4-yl]-1-tetrahydro pyran-2-yl-indazol-5-yl]oxy-propyl]carbamate intermediate 303 (240 mg, 0.431 mmol) and cesium carbonate (844 mg, 2.59 mmol) in acetonitrile (42 mL) was heated at reflux temperature for 24 h. The reaction mixture was filtered and the salts were rinsed with acetonitrile. The filtrate was then evaporated under reduced pressure. The residue was purified by silica gel column chromatography using cyclohexane/ethyl acetate 70/30/ to 50/50 as eluent to afford 12,12-difluoro-19-(oxan-2-yl)-8,14-dioxa-4,5,10,19,20,23-exaazatetracyclo [13.5.2.1$^{2,5}$.0$^{18,21}$]tricosa-1(20), 2(23),3,15(22),16,18(21)-hexaen-9-one intermediate 304 as a cream solid.

LCMS method F: $[M+H]^+$=449.1, $t_R$=2.45 min

Preparation of Example 167; 12,12-difluoro-8,14-dioxa-4,5,10,19,20,23-hexaazatetra cyclo [13.5.2.1$^{2,5}$.0$^{18,21}$]tricosa-1(20),2(23),3,15(22),16,18 (21)-hexaen-9-one

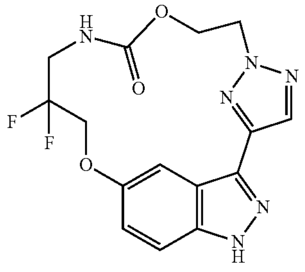 [SMILES: O=C1NCC(F)(F)COc2ccc3[nH]nc(c3c2)-c2cnn(n2)CCO1]

To a suspension of 12,12-difluoro-19-(oxan-2-yl)-8,14-dioxa-4,5,10,19,20,23-hexaazatetra cyclo[13.5.2.1$^{2,5}$.0$^{18,21}$] tricosa-1(20),2(23),3,15(22),16,18(21)-hexaen-9-one intermediate 304 (85 mg, 0.19 mmol in methanol (12 mL) and water (1.7 mL) was added para-toluenesulfonic acid monohydrate (180 mg, 0.948 mmol). The reaction mixture was heated at 65° C. for 16 h. Methanol was partially removed under reduced pressure and a saturated aqueous $NaHCO_3$ solution of was added until pH basic. The aqueous phase was extracted with EtOAc and the organic extract was washed with brine, dried over anhydrous sodium sulfate, filtered and evaporated under reduced pressure. The residue was triturated in dichloromethane and filtered. The solid obtained was recrystallized from acetonitrile to give 12,12-difluoro-8,14-dioxa-4,5,10,19,20,23-hexaazatetracyclo[13.5.2.1$^{2,5}$. 0$^{18,21}$]tricosa-1(20),2(23),3,15(22),16,18(21)-hexaen-9-one example 167 as a white solid.

LCMS method F: $[M+H]^+$=365.1, $t_R$=1.89 min

LCMS method G: $[M+H]^+$=365.2, $t_R$=1.87 min $^1$H NMR (400 MHz, d6-DMSO) δ 13.37 (1H, s), 8.16-8.15 (2H, m), 7.62 (1H, s), 7.51-7.46 (1H, m), 7.13-7.08 (1H, m), 4.84 (2H, t, J=4.4 Hz), 4.68-4.59 (4H, m), 3.59-3.52 (2H, m).

Example 168: (12R)-12-fluoro-8,14-dioxa-10,19,20-triazatetracyclo[13.5.2.1$^{2,6}$.0$^{8 21}$1]tricosa-1(20),2(23), 3,5,15(22),16,18(21)-heptaen-9-one

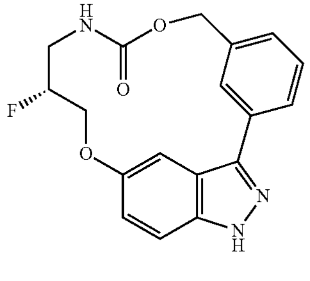 [SMILES: O=C1NC[C@@H](F)COc2ccc3[nH]nc(c3c2)-c2cccc(c2)CO1]

Example 168 is prepared according to the synthesis route described in general scheme E.

Preparation of Intermediate 305: methyl (2S)-2-(dibenzylamino)-3-hydroxy-propanoate

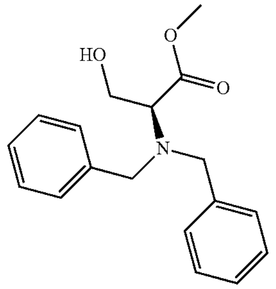 [SMILES: COC(=O)[C@H](CO)N(Cc1ccccc1)Cc1ccccc1]

To a solution of L-serine methyl ester hydrochloride (2 g, 12.9 mmol) in acetonitrile (30 mL) was added at room temperature potassium carbonate (3.56 g, 25.8 mmol) and benzyl bromide (3.1 mL, 25.8 mmol). The reaction mixture was stirred at room temperature for 3.5 h. The reaction mixture was filtered and concentrated under reduced pressure. The crude product was purified by silica gel column chromatography using cyclohexane/ethyl acetate 100/0 to 80/20 as eluent to afford methyl (2S)-2-(dibenzylamino)-3-hydroxy-propanoate intermediate 305 as a colorless oil.

LCMS method F: $[M+H]^+$=300.2, $t_R$=2.64 min

Preparation of Intermediate 306: methyl (2R)-3-(dibenzylamino)-2-fluoro-propanoate

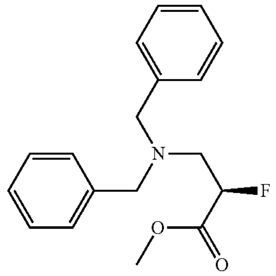 [SMILES: COC(=O)[C@H](F)CN(Cc1ccccc1)Cc1ccccc1]

To a solution of DAST (1 mL, 7.91 mmol) in dry THE (15 mL) was slowly added, at room temperature a solution of methyl (2S)-2-(dibenzylamino)-3-hydroxy-propanoate intermediate RECTIFIED SHEET (RULE 91) ISA/EP 305 (2.15 g, 7.19 mmol) in dry THE (15 mL). The reaction mixture was stirred at room temperature for 30 min. Ice water and ethyl acetate were added. The organic layer was washed 5% aqueous $NaHCO_3$ solution then brine, dried over anhydrous sodium sulfate, filtered and concentrated to afford methyl (2R)-3-(dibenzylamino)-2-fluoro-propanoate intermediate 306 as a yellow viscous oil. The product was used in the next step without further purification.

LCMS method F: $[M+H]^+$=302.3, $t_R$=2.81 min

Preparation of Intermediate 307: (2R)-3-(dibenzylamino)-2-fluoro-propan-1-ol

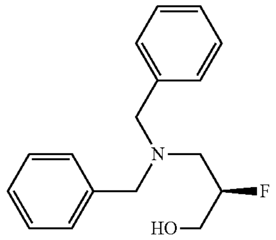 [SMILES: OC[C@H](F)CN(Cc1ccccc1)Cc1ccccc1]

To a degassed solution of lithium borohydride (302 mg, 7.97 mmol) in dry THE (10 mL) at −10° C. was added dropwise a solution of methyl (2R)-3-(dibenzylamino)-2-fluoro-propanoate intermediate 306 (2 g, 6.64 mmol) in dry THE (10 mL). The mixture was allowed to warm to room temperature and stirred overnight. The reaction mixture was cooled to 0° C. and quenched with a saturated aqueous solution of ammonium chloride. The mixture was extracted with ethyl acetate. The combined organic layers were dried over anhydrous sodium sulfate, filtered and concentrated under reduced pressure. The crude product was dissolved in 2 M hydrochloric acid (9 mL, until pH=2) and the aqueous layer was washed with diethyl ether. The aqueous layer was basified to approximately pH=10 with a saturated aqueous solution of $NaHCO_3$ and extracted with EtOAc. The combined organic layers were washed with brine, dried over anhydrous sodium sulfate, filtered and evaporated. The crude was dissolved in ethanol and filtered, then the filtrate was concentrated to afford (2R)-3-(dibenzylamino)-2-fluoro-propan-1-ol intermediate 307 as a white viscous oil.

LCMS method F: $[M+H]^+$=274.3, $t_R$=1.32 min

Preparation of Intermediate 308: (2R)-3-amino-2-fluoro-propan-1-ol

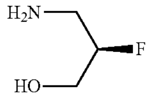

To a solution of (2R)-3-(dibenzylamino)-2-fluoro-propan-1-ol intermediate 307 (1.55 g, 5.68 mmol) in ethanol (20 mL) was added at room temperature palladium hydroxide 10 wt. % loading (155 mg). The reaction mixture was stirred under hydrogen atmosphere at room temperature for 2 days. The reaction mixture was filtered and the filtrate was concentrated under reduced pressure to give (2R)-3-amino-2-fluoro-propan-1-ol intermediate 308 as a yellow liquid. The product was used in the next step without further purification.

$^1H$ NMR (400 MHz, $CDCl_3$) δ 4.62-4.5 (1H, m), 3.9 (1H, m), 3.84 (1H, m), 3.1 (1H, m), 3.04 (1H, m), 2.0 (3H, br).

Preparation of Intermediate 309: benzyl N-[(2R)-2-fluoro-3-hydroxy-propyl]carbamate

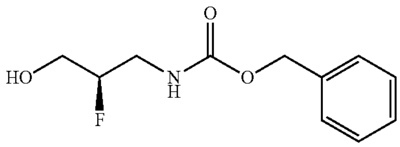 [SMILES: O=C(NC[C@@H](F)CO)OCc1ccccc1]

To a solution of (2R)-3-amino-2-fluoro-propan-1-ol intermediate 308 (541 mg, 5.68 mmol) in a mixture of THE (9 mL) and water (9 mL) was added sodium hydrogenocarbonate (525 mg, 6.25 mmol). The suspension was cooled to 0° C. and benzyl chloroformate (0.89 mL, 6.25 mmol) was added dropwise and the reaction mixture was stirred at room temperature overnight. The reaction mixture was diluted with water and extracted with ethyl acetate. The combined organic layers were washed with brine, dried over anhydrous sodium sulfate, filtered and evaporated under reduced pressure. The crude product was purified by silica gel column chromatography using cyclohexane/EtOAc 100/0 to 60/40 as eluent to afford benzyl N-[(2R)-2-fluoro-3-hydroxy-propyl]carbamate intermediate 309 as a white solid.

LCMS method F: $[M+Na]^+$=250.1, $t_R$=1.79 min

Preparation of Intermediate 310: [(2R)-3-(benzyloxycarbonylamino)-2-fluoro-propyl]methanesulfonate

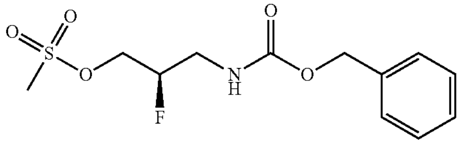 [SMILES: CS(=O)(=O)OC[C@H](F)CNC(=O)OCc1ccccc1]

To a solution of benzyl N-[(2R)-2-fluoro-3-hydroxy-propyl]carbamate intermediate 309 (726 mg, 3.2 mmol) in dicholoromethane (13 mL) was added triethylamine (0.89 mL, 6.4 mmol). At 0° C. was added methanesulfonyl chloride (0.32 mL, 4.16 mmol). The reaction mixture was stirred at room temperature for 1.5 h. The reaction mixture was quenched by addition of ammonium chloride solution and the mixture was extracted with dichloromethane. The organic layer was washed with a saturated aqueous $NaHCO_3$ solution and brine, dried over anhydrous sodium sulfate, filtered and concentrated under reduced pressure to give [(2R)-3-(benzyloxycarbonylamino)-2-fluoro-propyl]methanesulfonate intermediate 310 as an orange oil. The product was used in the next step without further purification.

LCMS method F: $[M+H]^+$=306.1, $t_R$=2.15 min

Preparation of Intermediate 311: benzyl N-[(2R)-2-fluoro-3-[3-[3-(hydroxymethyl)phenyl]-1-tetrahydropyran-2-yl-indazol-5-yl]oxy-propyl]carbamate

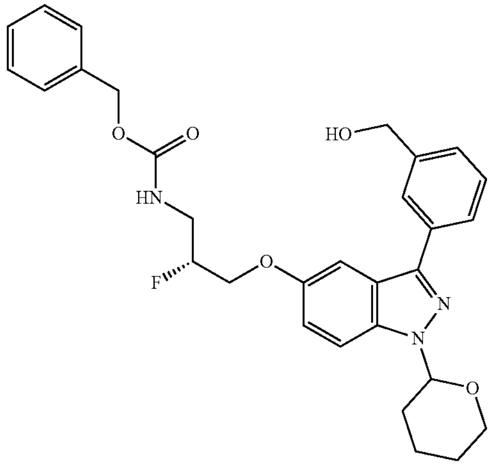 [SMILES: O=C(NC[C@@H](F)COc1ccc2c(c1)c(-c1cccc(CO)c1)nn2C1CCCCO1)OCc1ccccc1]

To a mixture of 3-[3-(hydroxymethyl)phenyl]-1-tetrahydropyran-2-yl-indazol-5-ol (518 mg, 1.60 mmol) in DMF (18 mL) was added cesium carbonate (1.04 g, 3.20 mmol). The reaction mixture was stirred for 20 min. [(2R)-3-(benzyloxycarbonylamino)-2-fluoro-propyl]methane sulfonate intermediate 310 (1.032 g, 3.2 mmol) in DMF (6 mL) was added. The reaction mixture was stirred at room temperature for 4 days. The reaction mixture was filtered and rinsed with ethyl acetate. The filtrate was diluted with water and extracted with ethyl acetate. The combined organic layers were washed with brine, dried over anhydrous sodium sulfate, filtered and concentrated. The crude was purified by silica gel column chromatography using cyclohexane/ethyl acetate 100/0 to 60/40 as eluent to afford benzyl N-[(2R)-2-fluoro-3-[3-[3-(hydroxymethyl)phenyl]-1-tetrahydropyran-2-yl-indazol-5-yl]oxy-propyl]carbamate intermediate 311 as a white oil which crystallized at room temperature.

LCMS method F: $[M+H]^+$=534.2, $t_R$=2.83 min

Preparation of Intermediate 312: (12R)-12-fluoro-19-(oxan-2-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one

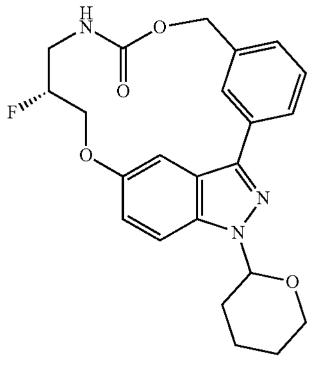 [SMILES: O=C1NC[C@@H](F)COc2ccc3c(c2)c(nn3C2CCCCO2)-c2cccc(c2)CO1]

To a solution of benzyl N-[(2R)-2-fluoro-3-[3-[3-(hydroxymethyl)phenyl]-1-tetrahydropyran-2-yl-indazol-5-yl]oxy-propyl]carbamate intermediate 311 (167 mg, 0.31 mmol) in dry acetonitrile (16 mL) was added at room temperature finely powdered potassium hydroxide (87 mg, 1.55 mmol) in one portion. The reaction mixture was stirred at room temperature overnight. The reaction mixture was filtered, rinsed with acetonitrile and evaporated under reduced pressure. The residue was purified by silica gel column chromatography using cyclohexane/ethyl acetate 100/0 to 70/30 as eluent to afford (12R)-12-fluoro-19-(oxan-2-yl)-8,14-dioxa-10,19,20-triazatetracyclo[13.5.2.$1^{2,6}$.$0^{18,21}$]tricosa-1(20),2(23),3,5,15(22), 16,18(21)-heptaen-9-one intermediate 312 as a white solid.

LCMS method F: $[M+H]^+=426.4$, $t_R=2.76$ min

Preparation of Example 168; (12R)-12-fluoro-8,14-dioxa-10,19,20-triazatetracyclo[13.5.2. $1^{2,6}$.$0^{18,21}$]tricosa-1(20),2(23),3,5,15(22),16,18(21)-heptaen-9-one

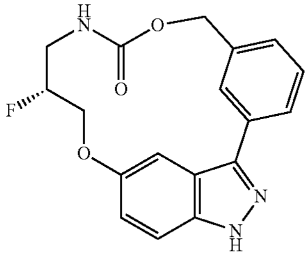 [SMILES: O=C1NC[C@@H](F)COc2ccc3[nH]nc(c3c2)-c2cccc(c2)CO1]

To a solution of (12R)-12-fluoro-19-(oxan-2-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one intermediate 312 (116 mg, 0.27 mmol) in methanol (4.6 mL) and water (0.8 mL) was added p-toluenesulfonic acid monohydrate (259 mg, 1.36 mmol). The reaction mixture was stirred at 65° C. overnight. The reaction mixture was diluted with dichloromethane and a saturated aqueous $NaHCO_3$ solution. The aqueous layer was extracted with dichloromethane. The combined organic layers were washed with brine, dried over sodium sulfate, filtered and evaporated under reduced pressure. The residue was purified by silica gel column chromatography using cyclohexane/ethyl acetate 100/0 to 60/40 as eluent. The cream solid was triturated with diethyl ether, filtered and dried to afford (12R)-12-fluoro-8,14-dioxa-10,19,20-triazatetracyclo[13.5.2.$1^{2,6}$.$0^{18,21}$]tricosa-1(20),2(23),3,5,15(22),16,18(21)-heptaen-9-one example 168 as a white powder.

LCMS method F: $[M+H]^+=342.2$, $t_R=2.08$ min

LCMS method G: $[M+H]^+=342.3$, $t_R=2.07$ min $^1$H NMR (400 MHz, d6-DMSO) δ 13.21 (1H, s), 8.05 (1H, t, J=5.7 Hz), 7.86 (1H, d, J=7.9 Hz), 7.77 (1H, s), 7.56 (1H, d, J=8.5 Hz), 7.49 (1H, t, J=7.5 Hz), 7.31 (1H, m), 7.15 (1H, m), 7.08 (1H, dd, J=9.2, 2.2 Hz), 5.80 (1H, m), 5.16 (1H, m), 4.85 (1H, m), 4.61 (1H, m), 4.35 (1H, m, 3.61 (1H, m), 3.11 (1H, m) ppm.

Example 169: (12S)-12-fluoro-8,14-dioxa-10,19,20-triazatetracyclo[13.5.2.$1^{2,6}$.$0^{18,21}$]tricosa-1(20),2(23),3,5,15(22),16,18(21)-heptaen-9-one

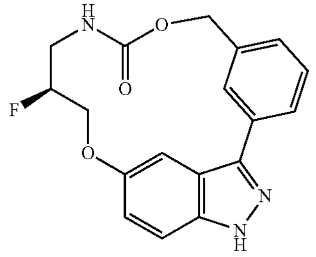 [SMILES: O=C1NC[C@H](F)COc2ccc3[nH]nc(c3c2)-c2cccc(c2)CO1]

Example 169 is prepared according to the synthesis route described in general scheme E and according to the same methods described for example 168.

Preparation of Intermediate 313: (12S)-12-fluoro-19-(oxan-2-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one

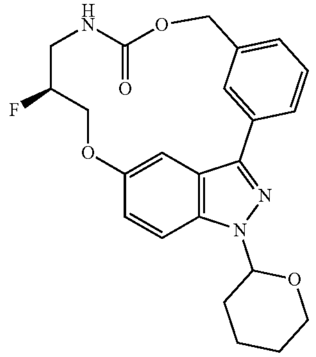 [SMILES: O=C1NC[C@H](F)COc2ccc3c(c2)c(nn3C2CCCCO2)-c2cccc(c2)CO1]

To a solution of benzyl N-[(2S)-2-fluoro-3-[3-[3-(hydroxymethyl)phenyl]-1-tetrahydropyran-2-yl-indazol-5-yl]oxy-propyl]carbamate (0.265 g, 0.50 mmol) in dry acetonitrile (32 mL) was added at room temperature finely powdered potassium hydroxide (140 mg, 2.50 mmol) in one portion. The reaction mixture was stirred at room temperature for 16 h. The reaction mixture was filtered and rinsed with acetonitrile. The filtrate was evaporated under reduced pressure. The residue was purified by silica gel column chromatography using cyclohexane/ethyl acetate 90/10 to 50/50 as eluent to afford (12S)-12-fluoro-19-(oxan-2-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one intermediate 313 as a white solid.

LCMS method F: $[M+H]^+=426.2$, $t_R=2.78$ min

Preparation of Example 169: (12S)-12-fluoro-8,14-dioxa-10,19,20-triazatetracyclo[13.5.2.1$^{2,6}$.0$^{18,21}$]tricosa-1(20),2(23),3,5,15(22),16,18(21)-heptaen-9-one

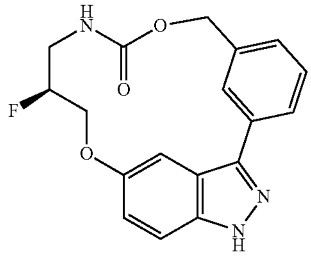 [SMILES: O=C1NC[C@H](F)COc2ccc3[nH]nc(c3c2)-c2cccc(c2)CO1]

To a solution of (12S)-12-fluoro-19-(oxan-2-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one intermediate 313 (115 mg, 0.27 mmol) in methanol (4.6 mL) and water (0.8 mL) was added p-toluenesulfonic acid monohydrate (259 mg, 1.36 mmol). The reaction mixture was stirred at 65° C. overnight. The reaction mixture was diluted with dichloromethane and a saturated aqueous $NaHCO_3$ solution. The aqueous layer was extracted with dichloromethane. The combined organic layers were washed with brine, dried over sodium sulfate, filtered and evaporated under reduced pressure. The residue was purified by silica gel column chromatography using cyclohexane/ethyl acetate 100/0 to 60/40 as eluent. The white solid was triturated with diethyl ether, filtered and dried to afford (12S)-12-fluoro-8,14-dioxa-10,19,20-triazatetracyclo[13.5.2.1$^{2,6}$.0$^{18,21}$]tricosa-1(20),2(23),3,5,15(22),16,18(21)-heptaen-9-one example 169 as a white powder.

LCMS method F: $[M+H]^+$=342.2, $t_R$=2.08 min

LCMS method G: $[M+H]^+$=342.2, $t_R$=2.07 min $^1$H NMR (400 MHz, d6-DMSO) δ 13.21 (1H, s), 8.05 (1H, t, J=5.7 Hz), 7.86 (1H, d, J=7.9 Hz), 7.77 (1H, s), 7.55 (1H, d, J=8.5 Hz), 7.49 (1H, t, J=7.5 Hz), 7.31 (1H, m), 7.15 (1H, m), 7.08 (1H, dd, J=9.2, 2.2 Hz), 5.80 (1H, m), 5.16 (1H, m), 4.85 (1H, m), 4.61 (1H, m), 4.35 (1H, m), 3.61 (1H, m), 3.11 (1H, m) ppm.

Example 170: 12,12-Difluoro-8,14-dioxa-4,10,19,20,23-pentaazatetracyclo[13.5.2.1$^{2,6}$.0$^{18,21}$]tricosa-1(20),2(23),3,5,15(22),16,18(21)-heptaen-9-one

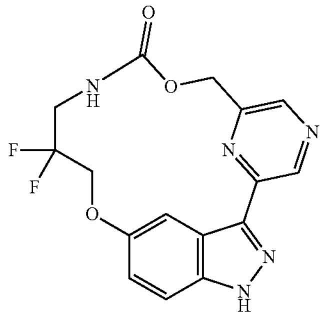 [SMILES: O=C1NCC(F)(F)COc2ccc3[nH]nc(c3c2)-c2cncc(n2)CO1]

Example 170 is prepared according to the synthesis route described in general Scheme K.

Preparation of Intermediate 314: benzyl N-[2,2-difluoro-3-[3-[6-(hydroxymethyl)pyrazin-2-yl]-1-tetrahydropyran-2-yl-indazol-5-yl]oxy-propyl]carbamate

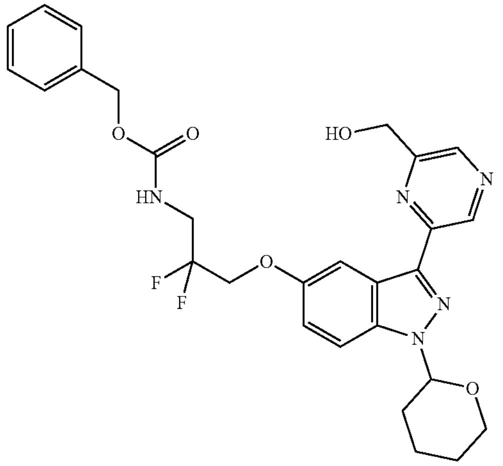 [SMILES: O=C(NCC(F)(F)COc1ccc2c(c1)c(-c1cncc(CO)n1)nn2C1CCCCO1)OCc1ccccc1]

To a mixture of 3-[6-(hydroxymethyl)pyrazin-2-yl]-1-tetrahydropyran-2-yl-indazol-5-ol (125 mg, 0.38 mmol) and [3-(benzyloxycarbonylamino)-2,2-difluoro-propyl]trifluoromethane sulfonate (158 mg, 0.42 mmol) in acetonitrile (4 mL) was added potassium carbonate (157 mg, 1.14 mmol). The reaction mixture was stirred at 75° C. for 2 h. The reaction mixture was filtered and rinsed with ethyl acetate. The filtrate was concentrated under reduced pressure. The residue was purified by silica gel column chromatography using cyclohexane/ethyl acetate 99/1 to 50/50 as eluent to afford benzyl N-[2,2-difluoro-3-[3-[6-(hydroxymethyl)pyrazin-2-yl]-1-tetrahydropyran-2-yl-indazol-5-yl]oxy-propyl]carbamate 314 as a yellow solid.

LCMS method F: $[M+H]^+$=554.2, $t_R$=2.75 min

Preparation of Intermediate 315: 12,12-difluoro-19-(oxan-2-yl)-8,14-dioxa-4,10,19,20,23-pentaazatetracyclo[13.5.2.1$^{2,6}$.0$^{18,21}$]tricosa-1(20),2(23),3,5,15(22),16,18(21)-heptaen-9-one

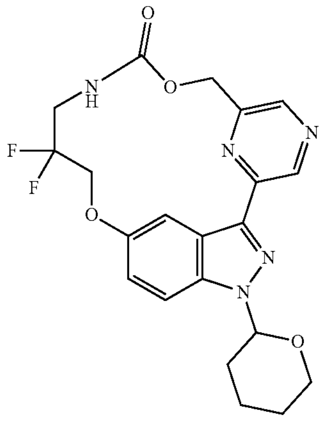 [SMILES: O=C1NCC(F)(F)COc2ccc3c(c2)c(nn3C2CCCCO2)-c2cncc(n2)CO1]

To a stirred solution of benzyl N-[2,2-difluoro-3-[3-[6-(hydroxymethyl)pyrazin-2-yl]-1-tetra hydropyran-2-yl-indazol-5-yl]oxy-propyl]carbamate 314 (57 mg, 0.11 mmol) in acetonitrile (12 mL) was added cesium carbonate (208 mg, 0.64 mmol) and the reaction mixture was stirred at reflux for 24 h. The reaction mixture was filtered and rinsed with acetonitrile. The filtrate was evaporated under reduced pressure. The residue was purified by silica gel column chromatography using cyclohexane/ethyl acetate 70/30 to 50/50 as eluent to afford 12,12-difluoro-19-(oxan-2-yl)-8,14-dioxa-4,10,19,20,23-pentaazatetracyclo[13.5.2.1$^{2,6}$.0$^{18,21}$]tricosa-1(20),2(23),3,5,15(22),16,18(21)-heptaen-9-one 315 as a white solid.

LCMS method F: $[M+H]^+$=446.1, $t_R$=2.50 min

Preparation of Example 170: 12,12-difluoro-8,14-dioxa-4,10,19,20,23-pentaazatetracyclo[13.5.2.1$^{2,6}$.0$^{18,21}$]tricosa-1(20),2(23),3,5,15(22),16,18(21)-heptaen-9-one

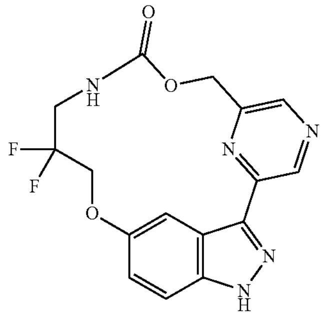 [SMILES: O=C1NCC(F)(F)COc2ccc3[nH]nc(c3c2)-c2cncc(n2)CO1]

To a solution of 12,12-difluoro-19-(oxan-2-yl)-8,14-dioxa-4,10,19,20,23-pentaazatetracyclo[13.5.2.1$^{2,6}$.0$^{18,21}$]tricosa-1(20),2(23),3,5,15(22),16,18(21)-heptaen-9-one 315 (13 mg, 0.029 mmol) in methanol (0.55 mL) and water (85 μL) was added p-toluenesulfonic acid monohydrate (28 mg, 0.145 mmol). The reaction mixture was stirred at 65° C. overnight. Additional p-toluenesulfonic acid monohydrate (28 mg, 0.145 mmol), methanol (0.55 mL) and water (85 μL) were added and the reaction mixture was stirred at 65° C. for 24 h. The reaction mixture was diluted with dichloromethane and saturated aqueous $NaHCO_3$ solution. After separation, the aqueous layer was extracted with dichloromethane. The combined organic layer was washed brine, dried over anhydrous sodium sulfate, filtered and evaporated under reduced pressure. The residue was purified by silica gel column chromatography using cyclohexane/ethyl acetate 100/0 to 60/40 as eluent. The resulting solid was triturated with dichloromethane, filtered and dried to afford 12,12-difluoro-8,14-dioxa-4,10,19,20,23-pentaazatetracyclo[13.5.2.1$^{2,6}$.0$^{18,21}$]tricosa-1(20),2(23),3,5,15(22),16,18(21)-heptaen-9-one example 170 as a white powder.

LCMS method F: $[M+H]^+$=362.2, $t_R$=1.88 min

LCMS method G: $[M+H]^+$=362.2, $t_R$=1.85 min $^1$H NMR (400 MHz, DMSO): 13.57 (1H, s), 9.29 (1H, s), 8.57 (1H, s), 8.19 (1H, t, J=6.6 Hz), 8.00 (1H, d, J=1.1 Hz), 7.55 (1H, d, J=8.9 Hz), 7.14 (1H, dd, J=2.6, 9.0 Hz), 4.73 (2H, m), 3.61 (2H, m), 3.51 (2H, s) ppm.

Example 171: (12S)-12-Fluoro-8,14-dioxa-4,10,19,20,23-pentaazatetracyclo[13.5.2.1$^{2,6}$.0$^{18,21}$]tricosa-1(20),2(23),3,5,15,17,21-heptaen-9-one

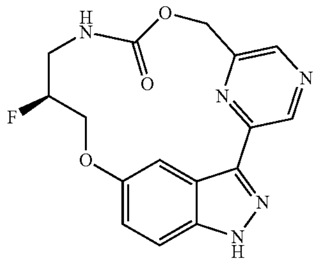 [SMILES: O=C1NC[C@H](F)COc2ccc3[nH]nc(c3c2)-c2cncc(n2)CO1]

Example 171 is prepared according to the synthesis route described in general Scheme K.

Preparation of Intermediate 316: (12S)-12-fluoro-19-(oxan-2-yl)-8,14-dioxa-4,10,19,20,23-pentaazatetracyclo[13.5.2.1$^{2,6}$.0$^{18,21}$]tricosa-1(20),2(23),3,5,15,17,21-heptaen-9-one

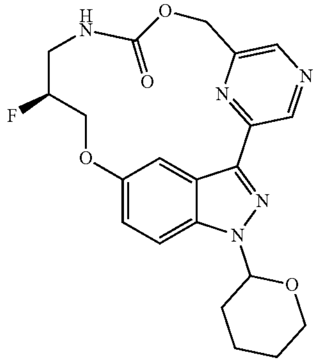 [SMILES: O=C1NC[C@H](F)COc2ccc3c(c2)c(nn3C2CCCCO2)-c2cncc(n2)CO1]

To a mixture of 3-[6-(hydroxymethyl)pyrazin-2-yl]-1-tetrahydropyran-2-yl-indazol-5-ol (195 mg, 0.597 mmol) and benzyl [(2S)-3-(benzyloxycarbonylamino)-2-fluoro-propyl]methane sulfonate (260 mg, 0.66 mmol) in acetonitrile (10 mL) was added potassium carbonate (247 mg, 1.79 mmol). The reaction mixture was stirred at 75° C. for 2 h then overnight. Additional cesium carbonate (583 mg, 1.79 mmol) was added and the reaction was stirred at reflux for 3 h. Solvent was evaporated under reduced pressure and the residue was partitioned between ethyl acetate and water. The organic layer dried over anhydrous sodium sulfate, filtered and evaporated under reduced pressure. The residue was purified by silica gel column chromatography using dichloromethane/methanol 100/0 to 95/5 as eluent to afford (12S)-12-fluoro-19-(oxan-2-yl)-8,14-dioxa-4,10,19,20,23-pentaazatetracyclo[13.5.2.1$^{2,6}$.0$^{18,21}$]tricosa-1(20),2(23),3,5,15,17,21-heptaen-9-one 316 as a white solid.

LCMS method J: $[M+H]^+$=428.4, $t_R$=3.58 min

Preparation of Example 171: (12S)-12-fluoro-8,14-dioxa-4,10,19,20,23-pentaazatetracyclo[13.5.2.$1^{2,6}$.$0^{18,21}$]tricosa-1(20),2(23),3,5,15,17,21-heptaen-9-one

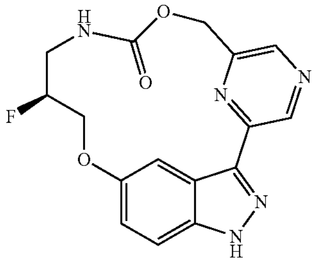 [SMILES: O=C1NC[C@H](F)COc2ccc3[nH]nc(c3c2)-c2cncc(n2)CO1]

To a solution of afford (12S)-12-fluoro-19-(oxan-2-yl)-8,14-dioxa-4,10,19,20,23-pentaazatetra cyclo[13.5.2.$1^{2,6}$.$0^{18,21}$]tricosa-1(20),2(23),3,5,15,17,21-heptaen-9-one 316 (30 mg, 0.07 mmol) in methanol (3 mL) and water (1 mL) was added p-toluenesulfonic acid monohydrate (67 mg, 0.35 mmol) and the reaction mixture was stirred at 75° C. overnight. Additional p-toluenesulfonic acid monohydrate (67 mg, 0.35 mmol) was added and the reaction mixture was stirred at 75° C. for 6 h then at 60° C. 72 h. The reaction mixture was diluted with ethyl acetate and saturated aqueous $NaHCO_3$ solution. After separation, the aqueous layer was extracted with ethyl acetate. The combined organic layers were washed with brine, dried over anhydrous sodium sulfate, filtered and evaporated under reduced pressure. The residue was purified by $NH_2$ silica gel column chromatography using dichloromethane/methanol 100/0 to 95/5 as eluent. The resulting solid was successively triturated with hot methanol then hot water, filtered and dried to afford (12S)-12-fluoro-8,14-dioxa-4,10,19,20,23-pentaazatetracyclo[13.5.2.$1^{2,6}$.$0^{18,21}$]tricosa-1(20), 2(23),3,5,15,17,21-heptaen-9-one example 171 as a cream powder.

LCMS method F: $[M+H]^+$=344.2, $t_R$=1.87 min

LCMS method G: $[M+H]^+$=344.2, $t_R$=1.88 min $^1H$ NMR (400 MHz, DMSO) 13.59 (1H, s), 9.30-9.29 (1H, m), 8.56-8.54 (1H, m), 8.04-8.00 (1H, m), 7.73-7.71 (1H, m), 7.61-7.58 (1H, m), 7.11 (1H, dd, J=2.4, 9.0 Hz), 5.78-4.92 (3H, m), 4.74-4.58 (1H, m), 4.41-4.28 (1H, m), 3.56-3.47 (1H, m), 3.14 (1H, s) ppm.

Example 172: (12R)-12-Fluoro-8,14-dioxa-4,10,19,20,23-pentaazatetracyclo[13.5.2.$1^{2,6}$.$0^{18,21}$]tricosa-1(20),2(23),3,5,15,17,21-heptaen-9-one

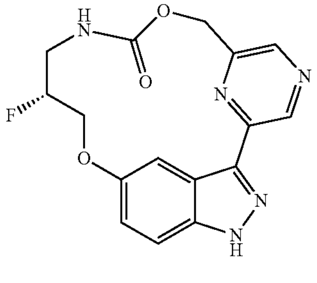 [SMILES: O=C1NC[C@@H](F)COc2ccc3[nH]nc(c3c2)-c2cncc(n2)CO1]

Example 172 is prepared according to the synthesis route described in general Scheme K.

Preparation of Intermediate 317: benzyl N-[(2R)-2-fluoro-3-({3-[6-(hydroxymethyl)pyrazin-2-yl]-1-(oxan-2-yl)-1H-indazol-5-yl}oxy)propyl]carbamate

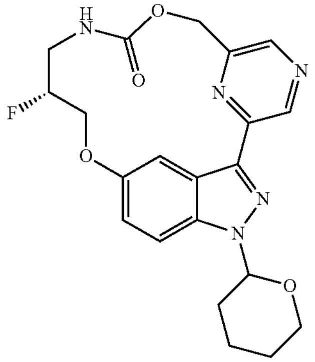 [SMILES: O=C1NC[C@@H](F)COc2ccc3c(c2)c(nn3C2CCCCO2)-c2cncc(n2)CO1]

To a solution of 3-[6-(hydroxymethyl)pyrazin-2-yl]-1-tetrahydropyran-2-yl-indazol-5-01 (400 mg, 1.23 mmol) and [(2R)-3-(benzyloxycarbonylamino)-2-fluoro-propyl]methanesulfonate (460 mg, 1.36 mmol) in acetonitrile (20 mL) was added cesium carbonate (1.2 g, 3.69 mmol). The reaction mixture was stirred at reflux for 4 h. Solvent was evaporated under reduced pressure. The residue was partitioned between ethyl acetate and water. The organic layer was dried over anhydrous sodium sulfate, filtered and evaporated under reduced pressure. The residue was purified by silica gel column chromatography using dichloromethane/methanol 100/0 to 95/5 as eluent to afford (12R)-12-fluoro-19-(oxan-2-yl)-8,14-dioxa-4,10,19,20,23-pentaazatetracyclo[13.5.2.$1^{2,6}$.$0^{18,21}$]tricosa-1(20),2(23),3,5,15,17,21-heptaen-9-one 317 as a light yellow solid.

LCMS method F. $[M+H]^+$=428.4.2, $t_R$=2.48 min

Preparation of Example 172: (12R)-12-fluoro-8,14-dioxa-4,10,19,20,23-pentaazatetracyclo[13.5.2.$1^{2,6}$.$0^{18,21}$]tricosa-1(20),2(23),3,5,15,17,21-heptaen-9-one

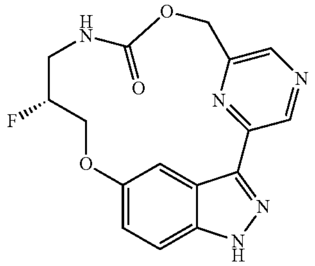 [SMILES: O=C1NC[C@@H](F)COc2ccc3[nH]nc(c3c2)-c2cncc(n2)CO1]

To a solution of (12R)-12-fluoro-19-(oxan-2-yl)-8,14-dioxa-4,10,19,20,23-pentaazatetracyclo[13.5.2.$1^{2,6}$.$0^{18,21}$]tricosa-1(20),2(23),3,5,15,17,21-heptaen-9-one 317 (291 mg, 0.681 mmol) in methanol (25 mL) and water (8 mL) was added p-toluenesulfonic acid monohydrate (647 mg, 3.4 mmol). The reaction mixture was stirred at 60° C. for 72 h. Additional p-toluenesulfonic acid monohydrate (647 mg, 3.4 mmol) was added and the mixture was stirred at 75° C. for 2 h.

The solvents were evaporated under reduced pressure and the residue was diluted with ethyl acetate and saturated aqueous $NaHCO_3$ solution. After separation, the aqueous layer was extracted with ethyl acetate. The combined organic layers were washed with brine, dried over anhydrous sodium sulfate, filtered and evaporated under reduced pressure. The residue was purified by $NH_2$ silica gel column chromatography using dichloromethane/methanol 100/0 to 95/5 as eluent. The resulting solid was triturated with hot water, filtered an dried to afford (12R)-12-fluoro-8,14-dioxa-4,10,19,20,23-pentaazatetracyclo[13.5.2.$1^{2,6}$.$0^{18,21}$]tricosa-1(20), 2(23),3,5,15,17,21-heptaen-9-one example 172 as a cream solid.

LCMS method F: $[M+H]^+$=344.3, $t_R$=1.80 min

LCMS method G: $[M+H]^+$=344.2, $t_R$=1.80 min $^1$H NMR (400 MHz, DMSO) 13.59 (1H, s), 9.30 (1H, s), 8.56-8.54 (1H, m), 8.02 (1H, t, J=5.0 Hz), 7.73-7.71 (1H, m), 7.62-7.58 (1H, m), 7.11 (1H, dd, J=2.4, 9.0 Hz), 5.78-4.92 (3H, m), 4.73-4.58 (1H, m), 4.40-4.28 (1H, m), 3.52-3.48 (1H, m), 3.14 (1H, s) ppm.

Example 173: (12S)-12-fluoro-8,14-dioxa-4,5,10,19,20,23-hexaazatetracyclo[13.5.2.$1^{2,5}$.$0^{18,21}$]tricosa-1(20),2(23),3,15,17,21-hexaen-9-one

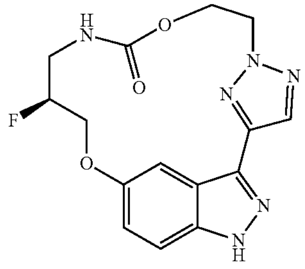 [SMILES: O=C1NC[C@H](F)COc2ccc3[nH]nc(c3c2)-c2cnn(n2)CCO1]

Example 173 is prepared according to the synthesis route described in general Scheme 0.

Preparation of Intermediate 318: (12S)-12-fluoro-19-(oxan-2-yl)-8,14-dioxa-4,5,10,19,20,23-hexaazatetracyclo[13.5.2.$1^{2,5}$.$0^{18,21}$]tricosa-1(20),2(23),3,15,17,21-hexaen-9-one

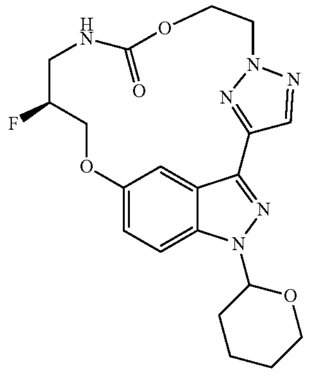 [SMILES: O=C1NC[C@H](F)COc2ccc3c(c2)c(nn3C2CCCCO2)-c2cnn(n2)CCO1]

To a mixture of 3-[2-(2-hydroxyethyl)triazol-4-yl]-1-tetrahydropyran-2-yl-indazol-5-ol (250 mg, 0.759 mmol) and [(2S)-3-(benzyloxycarbonylamino)-2-fluoro-propyl]methanesulfonate (348 mg, 1.14 mmol) in acetonitrile (50 mL) was added cesium carbonate (743 mg, 2.28 mmol). The reaction mixture was stirred at reflux for 6 h. The solvents were evaporated under reduced pressure. The residue was partitioned between ethyl acetate and water. The organic layer was dried over anhydrous sodium sulfate, filtered and evaporated under reduced pressure. The resulting solid was triturated with methanol, filtered and dried to afford (12S)-12-fluoro-19-(oxan-2-yl)-8,14-dioxa-4,5,10,19,20,23-hexaazatetracyclo[13.5.2.$1^{2,5}$.$0^{18,21}$]tricosa-1(20), 2(23),3,15,17,21-hexaen-9-one 318 as a white solid.

LCMS method F: $[M+H]^+$=431.4, $t_R$=2.46 min

Preparation of Example 173: (12S)-12-fluoro-8,14-dioxa-4,5,10,19,20,23-hexaazatetra cyclo[13.5.2.$1^{2,5}$.$0^{18,21}$]tricosa-1(20),2(23),3,15,17,21-hexaen-9-one

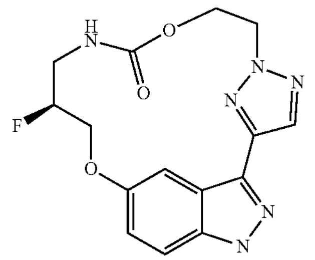 [SMILES: O=C1NC[C@H](F)COc2ccc3[nH]nc(c3c2)-c2cnn(n2)CCO1]

To a solution of (12S)-12-fluoro-19-(oxan-2-yl)-8,14-dioxa-4,5,10,19,20,23-hexaazatetracyclo[13.5.2.$1^{2,5}$.$0^{18,21}$]tricosa-1(20),2(23),3,15,17,21-hexaen-9-one 318 (130 mg, 0.302 mmol) in methanol (12 mL) and water (4 mL) was added p-toluenesulfonic acid monohydrate (287 mg, 1.51 mmol). The reaction mixture was stirred at 75° C. for 8 h. Methanol was evaporated under reduced pressure. The resulting solid was triturated with saturated aqueous $NaHCO_3$ solution and filtered then washed with water and dried to afford (12S)-12-fluoro-8,14-dioxa-4,5,10,19,20,23-hexaazatetracyclo[13.5.2.$1^{2,5}$.$0^{18,21}$]tricosa-1(20),2(23),3,15,17,21-hexaen-9-one example 173 as a white solid.

LCMS method F: $[M+H]^+$=347.3, $t_R$=1.82 min

LCMS method G: $[M+H]^+$=347.3, $t_R$=1.75 min $^1$H NMR (400 MHz, DMSO) 13.24 (1H, s), 8.16 (1H, s), 7.88-7.84 (1H, m), 7.55-7.51 (1H, m), 7.39 (1H, d, J=2.1 Hz), 7.08 (1H, dd, J=2.4, 9.0 Hz), 4.94-4.43 (6H, m), 4.35-4.24 (1H, m), 3.47-3.42 (1H, m), 3.20-3.11 (1H, m) ppm.

Example 174: (12R)-12-fluoro-8,14-dioxa-4,5,10,19,20,23-hexaazatetracyclo[13.5.2.$1^{2,5}$.$0^{18,21}$]tricosa-1(20),2(23),3,15,17,21-hexaen-9-one

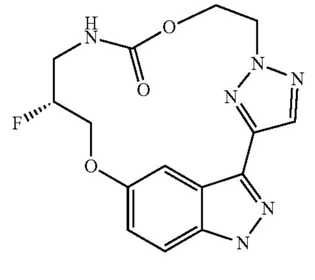 [SMILES: O=C1NC[C@@H](F)COc2ccc3[nH]nc(c3c2)-c2cnn(n2)CCO1]

Example 174 is prepared according to the synthesis route described in general Scheme O.

Preparation of Intermediate 319: (12R)-12-fluoro-19-(oxan-2-yl)-8,14-dioxa-4,5,10,19,20,23-hexaaza-tetracyclo[13.5.2.1$^{2,5}$.0$^{18,21}$]tricosa-1(20),2(23),3,15,17,21-hexaen-9-one

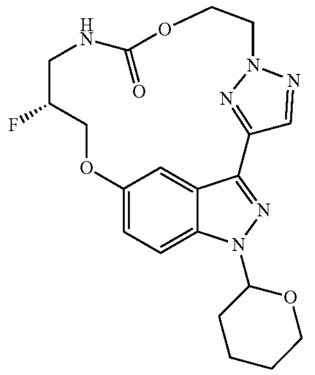 [SMILES: O=C1NC[C@@H](F)COc2ccc3c(c2)c(nn3C2CCCCO2)-c2cnn(n2)CCO1]

To a solution of 3-[2-(2-hydroxyethyl)triazol-4-yl]-1-tetrahydropyran-2-yl-indazol-5-ol (345 mg, 1.05 mmol) and [(2R)-3-(benzyloxycarbonylamino)-2-fluoro-propyl]methanesulfonate (530 mg, 0.482 mmol) in acetonitrile (70 mL) was added cesium carbonate (1.03 g, 3.15 mmol).

The reaction mixture was stirred at reflux for 8 h. Solvent was removed under reduced pressure. The residue was triturated with methanol, filtered, rinsed with methanol and dried to afford (12R)-12-fluoro-19-(oxan-2-yl)-8,14-dioxa-4,5,10,19,20,23-hexaazatetracyclo[13.5.2.1$^{2,5}$.0$^{18,21}$]tricosa-1(20),2(23),3,15,17,21-hexaen-9-one 319 as a white solid.

LCMS method F: $[M+H]^+$=431.4, $t_R$=2.44 min

Preparation of Example 174: (12R)-12-fluoro-8,14-dioxa-4,5,10,19,20,23-hexaazatetra cyclo [13.5.2.1$^{2,5}$.0$^{18,21}$]tricosa-1(20),2(23),3,15,17,21-hexaen-9-one

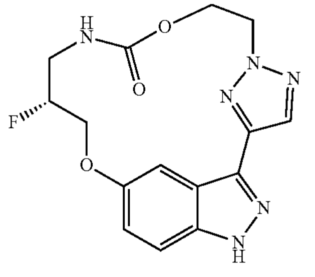 [SMILES: O=C1NC[C@@H](F)COc2ccc3[nH]nc(c3c2)-c2cnn(n2)CCO1]

To a solution of (12R)-12-fluoro-19-(oxan-2-yl)-8,14-dioxa-4,5,10,19,20,23-hexaazatetracyclo[13.5.2.1$^{2,5}$.0$^{18,21}$] tricosa-1(20),2(23),3,15,17,21-hexaen-9-one 319 (230 mg, 0.534 mmol) in methanol (24 mL) and water (8 mL) was added p-toluenesulfonic acid monohydrate (508 mg, 2.67 mmol). The reaction mixture was stirred at 65° C. overnight. The solvents were evaporated under reduced pressure. The resulting solid was triturated with saturated aqueous $NaHCO_3$ solution. After filtration the solid was washed with water and dried to afford (12R)-12-fluoro-8,14-dioxa-4,5,10,19,20,23-hexaazatetracyclo[13.5.2.1$^{2,5}$.0$^{18,21}$]tricosa-1(20),2(23),3,15,17,21-hexaen-9-one example 174 as a cream solid.

LCMS method F: $[M+H]^+$=347.2, $t_R$=1.82 min

LCMS method G: $[M+H]^+$=347.3, $t_R$=1.75 min $^1$H NMR (400 MHz, DMSO) 13.24 (1H, s), 8.16 (1H, s), 7.89-7.83 (1H, m), 7.57-7.46 (1H, m), 7.40-7.37 (1H, m), 7.15-7.05 (1H, m), 4.93-4.85 (1H, m), 4.81-4.57 (4H, m), 4.49-4.43 (1H, m), 4.36-4.23 (1H, m), 3.50-3.41 (1H, m), 3.21-3.12 (1H, m) ppm.

Example 175: 8',14'-Dioxa-10',19',20'-triazaspiro[cyclopropane-1,13'-tetracyclo[13.5.2.1$^{2,6}$.0$^{18,21}$]tricosane]-1'(20'),2'(23'),3',5',15'(22'),16',18'(21')-heptaen-9'-one

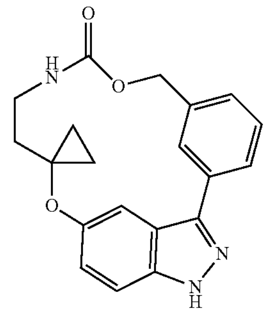 [SMILES: O=C1NCCC2(CC2)Oc2ccc3[nH]nc(c3c2)-c2cccc(c2)CO1]

Example 175 is prepared according to the synthesis route described in detail below.

Preparation of Intermediate 320: (3-iodo-1-tetrahydropyran-2-yl-indazol-5-yl)$_3$-(dibenzyl amino)propanoate

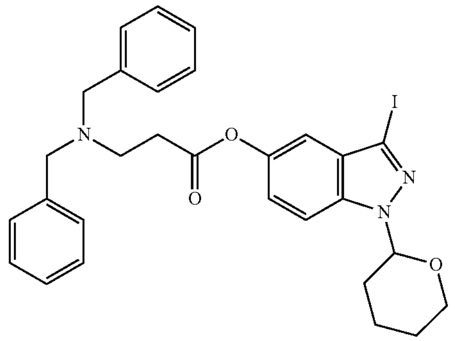 [SMILES: O=C(CCN(Cc1ccccc1)Cc1ccccc1)Oc1ccc2c(c1)c(I)nn2C1CCCCO1]

To a solution of the 3-(dibenzylamino)propanoic acid hydrochloride (864 mg, 2.83 mmol) in DMF (10 mL) was added N-ethyl-N,N-diisopropylamine (1.47 mL, 8.50 mmol). The reaction mixture was cooled to 0° C. then N-(3-dimethylaminopropyl)-N'-ethylcarbodiimide hydrochloride (1.088 g, 5.67 mmol), 1-hydroxybenzotriazole (867 mg, 5.67 mmol) and the 3-iodo-1-tetrahydropyran-2-yl-indazol-5-ol (1.46 g, 4.25 mmol) were added. The reaction mixture was stirred at RT overnight. The mixture was poured onto water then extracted with ethyl acetate. The organic layer was successively washed with a saturated aqueous $NaHCO_3$ solution, water, saturated aqueous ammonium chloride solution then brine, dried over anhydrous magnesium sulfate, filtered and concentrated under reduced pressure. The residue was purified by silica gel column chromatography using cyclohexane/ethyl acetate 99/1 to 80/20 as eluent to provide (3-iodo-1-tetrahydropyran-2-yl-indazol-5-yl)-3-(dibenzylamino) propanoate 320 as a colorless oil.

LCMS method F: $[M+H]^+$=596.1, $t_R$=2.73 min

Preparation of Intermediate 321: N,N-dibenzyl-3-(3-iodo-1-tetrahydropyran-2-yl-indazol-5-yl)oxy-but-3-en-1-amine

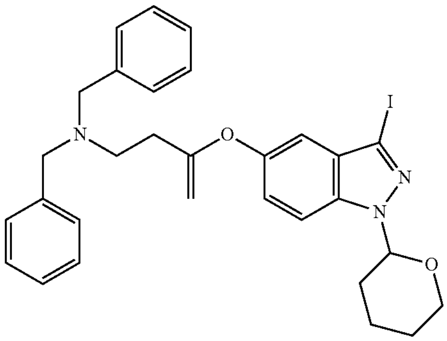 [SMILES: C=C(CCN(Cc1ccccc1)Cc1ccccc1)Oc1ccc2c(c1)c(I)nn2C1CCCCO1]

To a solution of (3-iodo-1-tetrahydropyran-2-yl-indazol-5-yl)-3-(dibenzylamino)propanoate 320 (1.541 g, 2.59 mmol) in dry THE (15 mL) at 0° C. was added dropwise Tebbe reagent (0.5 M solution in toluene) (6.22 mL, 3.11 mmol). The reaction mixture was allowed to reach RT and stirred overnight. The reaction mixture was poured into ice/water then 1M aqueous sodium hydroxide solution was added. The aqueous layer was extracted with ethyl acetate. The combined organic layers were washed with brine, dried over anhydrous magnesium sulfate, filtered and concentrated under reduced pressure. The residue was purified by silica gel column chromatography using cyclohexane/ethyl acetate 99/1 to 80/20 as eluent to afford N,N-dibenzyl-3-(3-iodo-1-tetrahydropyran-2-yl-indazol-5-yl)oxy-but-3-en-1-amine 321 as a colorless oil.

LCMS method F: $[M+H]^+$=594.1, $t_R$=2.65 min

Preparation of Intermediate 322: N,N-dibenzyl-3-[3-[3-[[tert-butyl(dimethyl)silyl]oxymethyl]phenyl]-1-tetrahydropyran-2-yl-indazol-5-yl]oxy-but-3-en-1-amine

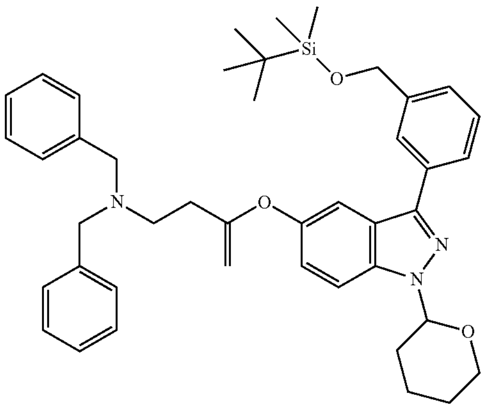 [SMILES: C=C(CCN(Cc1ccccc1)Cc1ccccc1)Oc1ccc2c(c1)c(-c1cccc(CO[Si](C)(C)C(C)(C)C)c1)nn2C1CCCCO1]

To a degassed solution of N,N-dibenzyl-3-(3-iodo-1-tetrahydropyran-2-yl-indazol-5-yl)oxy-but-3-en-1-amine 321 (642 mg, 1.08 mmol), tert-butyl-dimethyl-[[3-(4,4,5,5-tetramethyl-1,3,2-dioxaborolan-2-yl)phenyl]methoxy]silane (487 mg, 1.40 mmol) and potassium phosphate tribasic (686 mg, 3.24 mmol) in dioxane (5.35 mL) and water (1.50 mL) was added tetrakis(triphenylphosphine)palladium(0) (57 mg, 0.05 mmol) and 2-dicyclohexylphosphino-2',4',6'-triisopropylbiphenyl (52 mg, 0.11 mmol). The reaction mixture was stirred at 100° C. for 1 h. The reaction mixture was diluted with water and extracted with ethyl acetate. The organic layer was washed with water, brine, dried over anhydrous magnesium sulfate, filtered and concentrated under reduced pressure. The residue was purified by silica gel column chromatography using cyclohexane/ethyl acetate 100/0 to 85/15 as eluent to afford N,N-di benzyl-3-[3-[3-[[tert-butyl(dimethyl)silyl]oxymethyl]phenyl]-1-tetrahydropyran-2-yl-indazol-5-yl]oxy-but-3-en-1-amine 322 as a slightly yellow oil.

LCMS method J: $[M+H]^+$=688.6, $t_R$=5.42 min

Preparation of Intermediate 323: N,N-dibenzyl-2-[1-[3-[3-[[tert-butyl(dimethyl)silyl]oxy methyl]phenyl]-1-tetrahydropyran-2-yl-indazol-5-yl]oxycyclopropyl]ethanamine

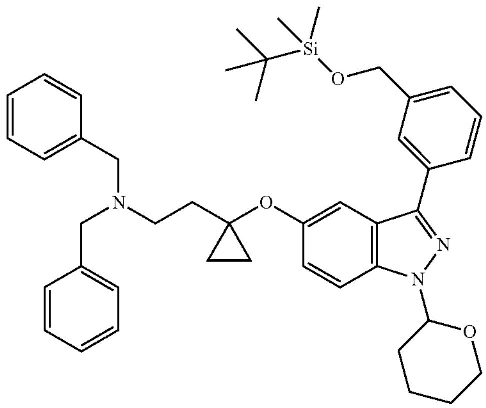 [SMILES: CC(C)(C)[Si](C)(C)OCc1cccc(-c2nn(C3CCCCO3)c3ccc(OC4(CCN(Cc5ccccc5)Cc5ccccc5)CC4)cc23)c1]

Dry DCE (20 mL) was degassed in a sealed tube then diethylzinc (1 M in heptane) (2.43 mL, 2.43 mmol) and diiodomethane (210 µL, 2.43 mmol) were added at RT. The solution was stirred at RT for 5 min. A solution of N,N-dibenzyl-3-[3-[3-[[tert-butyl(dimethyl)silyl]oxymethyl]phenyl]-1-tetrahydropyran-2-yl-indazol-5-yl]oxy-but-3-en-1-amine 322 (745 mg, 1.06 mmol) in dry DCE (20 mL) was added dropwise and the resulting mixture was stirred at RT for 16.5 h. In a separate flask, under argon, dry DCE (20 mL) was degassed then diethylzinc 1M in heptane (2.43 mL, 2.43 mmol) and diiodomethane (210 µL, 2.43 mmol) were added at RT for 5 min. The resulting suspension was added to the initial reaction mixture and allowed to stirred at RT overnight. The reaction mixture was quenched by pouring onto an aqueous solution of ammonium chloride then extracted with dichloromethane. The combined organic layers were washed with water, dried over anhydrous magnesium sulfate, filtered and concentrated under reduced pressure. The residue was purified by silica gel column chromatography using cyclohexane/ethyl acetate 100/0 to 85/15 as eluent to afford N,N-dibenzyl-2-[1-[3-[3-[[tert-butyl(dimethyl)silyl]

oxymethyl]phenyl]-1-tetrahydropyran-2-yl-indazol-5-yl]oxycyclopropyl]ethanamine 323 as a colorless oil.

LCMS method F: $[M+H]^+$=702.4, $t_R$=3.14 min

Preparation of Intermediate 324: 2-[1-[3-[3-[[tert-butyl(dimethyl)silyl]oxymethyl]phenyl]-1-tetrahydropyran-2-yl-indazol-5-yl]oxycyclopropyl]ethanamine

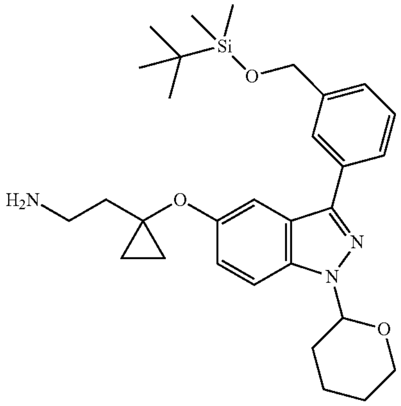 [SMILES: CC(C)(C)[Si](C)(C)OCc1cccc(-c2nn(C3CCCCO3)c3ccc(OC4(CCN)CC4)cc23)c1]

To a solution of N,N-dibenzyl-2-[1-[3-[3-[[tert-butyl(dimethyl)silyl]oxymethyl]phenyl]-1-tetrahydropyran-2-yl-indazol-5-yl]oxycyclopropyl]ethanamine 323 (210 mg, 0.30 mmol) in methanol (3 mL) and dichloromethane (3 mL) at RT was added palladium hydroxide on carbon 10 wt. % loading (5 mg). The reaction mixture was stirred under hydrogen atmosphere at RT for 2 h. The reaction mixture was filtered, rinsed with ethyl acetate and evaporated under reduced pressure to afford 2-[1-[3-[3-[[tert-butyl(dimethyl)silyl]oxymethyl]phenyl]-1-tetra hydropyran-2-yl-indazol-5-yl]oxycyclopropyl]ethanamine 324 as a white foam which was used in the next step without any further purification.

LCMS method F: $[M+H]^+$=522.5, $t_R$=2.68 min

Preparation of Intermediate 325: benzyl N-[2-[1-[3-[3-[[tert-butyl(dimethyl)silyl]oxymethyl]phenyl]-1-tetrahydropyran-2-yl-indazol-5-yl]oxycyclopropyl]ethyl]carbamate

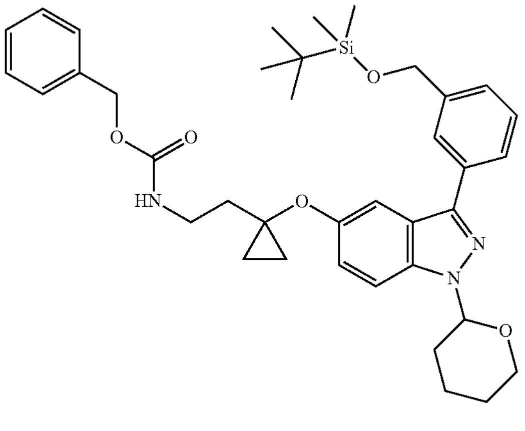 [SMILES: CC(C)(C)[Si](C)(C)OCc1cccc(-c2nn(C3CCCCO3)c3ccc(OC4(CCNC(=O)OCc5ccccc5)CC4)cc23)c1]

To a solution of 2-[1-[3-[3-[[tert-butyl(dimethyl)silyl]oxymethyl]phenyl]-1-tetrahydropyran-2-yl-indazol-5-yl]oxycyclopropyl]ethanamine 324 (156 mg, 0.30 mmol) in THF (2 mL) and water (1.5 mL) was added sodium hydrogenocarbonate (28 mg, 0.33 mmol). The suspension was cooled to 0° C. and benzyl chloroformate (50 μL, 0.33 mmol) was added dropwise. The reaction mixture was stirred at RT for 2 h. The solution was diluted with water and extracted with ethyl acetate. The combined organic layers were washed with brine, dried over anhydrous sodium sulfate, filtered and evaporated under reduced pressure. The residue was purified by silica gel column chromatography using cyclohexane/ethyl acetate 100/0 to 85/15 as eluent to afford benzyl N-[2-[1-[3-[3-[[tert-butyl(dimethyl)silyl]oxymethyl]phenyl]-1-tetrahydropyran-2-yl-indazol-5-yl]oxycyclopropyl]ethyl]carbamate 325 as a colorless oil.

LCMS method F. $[M+H]^+$=656.3, $t_R$=3.89 min

Preparation of Intermediate 326: benzyl N-[2-[1-[3-[3-(hydroxymethyl)phenyl]-1-tetrahydro pyran-2-yl-indazol-5-yl]oxycyclopropyl]ethyl]carbamate

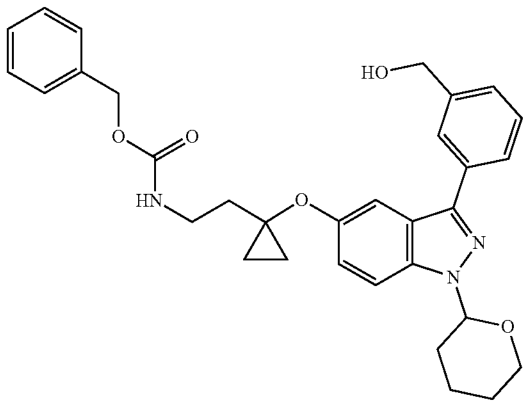 [SMILES: O=C(NCCC1(Oc2ccc3c(c2)c(-c2cccc(CO)c2)nn3C2CCCCO2)CC1)OCc1ccccc1]

To a solution of benzyl N-[2-[1-[3-[3-[[tert-butyl(dimethyl)silyl]oxymethyl]phenyl]-1-tetra hydropyran-2-yl-indazol-5-yl]oxycyclopropyl]ethyl]carbamate 325 (90 mg, 0.14 mmol) in THF (1.5 mL) at RT was added dropwise tetrabutylammonium fluoride (10 Min THF (0.15 mL, 0.15 mmol). The reaction mixture was stirred at RT overnight. The reaction mixture was poured into ice water and stirred for 20 min. The aqueous layer was extracted with ethyl acetate and the combined organic layers were washed with brine, dried over anhydrous magnesium sulfate, filtered and concentrated under reduced pressure to afford benzyl N-[2-[1-[3-[3-(hydroxymethyl)phenyl]-1-tetrahydropyran-2-yl-indazol-5-yl]oxycyclopropyl]ethyl]carbamate 326 as a colorless oil which was used in the next step without further purification.

LCMS method J: $[M+H]^+$=542.4, $t_R$=4.57 min

Preparation of Intermediate 327: 19'-(oxan-2-yl)-8',14'-dioxa-10',19',20'-triazaspiro[cyclo propane-1,13'-tetracyclo[13.5.2.1$^{2,6}$.0$^{18,21}$]tricosane]-1'(20'),2'(23'),3,5,15'(22'),16,18'(21)-heptaen-9'-one

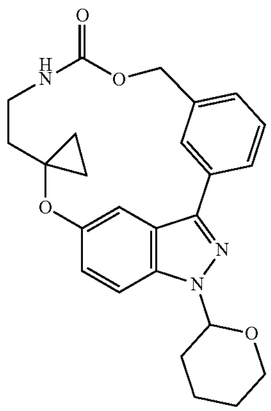 [SMILES: O=C1NCCC2(CC2)Oc2ccc3c(c2)c(nn3C2CCCCO2)-c2cccc(c2)CO1]

To a solution of benzyl N-[2-[1-[3-[3-(hydroxymethyl) phenyl]-1-tetrahydropyran-2-yl-indazol-5-yl]oxycyclopropyl]ethyl]carbamate 326 (65 mg, 0.12 mmol) in dry acetonitrile (10 mL) was added at RT potassium hydroxide (33 mg, 0.60 mmol) in one portion. The reaction mixture was stirred at RT for 16 h. The reaction mixture was filtered then rinsed with ethyl acetate and evaporated under reduced pressure. The residue was purified by silica gel column chromatography using dichloromethane/ethyl acetate 100/0 to 80/20 as eluent to afford 19'-(oxan-2-yl)-8',14'-dioxa-10',19',20'-triazaspiro[cyclopropane-1,13'-tetracyclo[13.5.2.1$^{2,6}$.0$^{18,21}$] tricosane]-1'(20'),2'(23'),3',5',15'(22'),16',18'(21')-heptaen-9'-one 327 as a white solid.

LCMS method J: $[M+H]^+$=434.4, $t_R$=4.43 min

Preparation of Example 175: 8',14'-dioxa-10',19',20'-triazaspiro[cyclopropane-1,13'-tetra cyclo [13.5.2.1$^{2,6}$.0$^{18,21}$]tricosane]-1'(20'),2'(23'),3',5',15'(22'),16',18'(21')-heptaen-9'-one

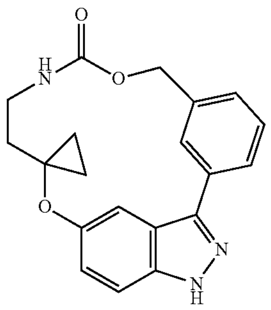 [SMILES: O=C1NCCC2(CC2)Oc2ccc3[nH]nc(c3c2)-c2cccc(c2)CO1]

To a solution of 19'-(oxan-2-yl)-8',14'-dioxa-10',19',20'-triazaspiro[cyclopropane-1,13'-tetra cyclo[13.5.2.1$^{2,6}$.0$^{18,21}$]tricosane]-1'(20'),2'(23'),3',5',15'(22'),16',18'(21')-heptaen-9'-one 327 (41 mg, 0.095 mmol) in methanol (2 mL) and water (0.3 mL) was added p-toluenesulfonic acid monohydrate (90 mg, 0.47 mmol). The reaction mixture was stirred at 65° C. overnight. The reaction mixture was diluted with dichloromethane and saturated aqueous $NaHCO_3$ solution. After separation, the aqueous layer was extracted with dichloromethane. The combined organic layers were washed brine, dried over anhydrous magnesium sulfate, filtered and evaporated under reduced pressure. The residue was purified by preparative TLC using dichloromethane/methanol 95/5 as eluent to afford 8',14'-dioxa-10',19',20'-triazaspiro[cyclopropane-1,13'-tetra cyclo[13.5.2.1$^{2,6}$.0$^{18,21}$]tricosane]-1'(20'),2'(23'),3',5',15'(22'),16',18'(21')-heptaen-9'-one example 175 as a white solid.

LCMS method F: $[M+H]^+$=350.1, $t_R$=2.30 min

LCMS method G: $[M+H]^+$=350.2, $t_R$=2.18 min $^1$H NMR (400 MHz, DMSO-d6, 80° C.): 12.85 (1H, s), 7.95 (1H, s), 7.86 (1H, d, J=7.6 Hz), 7.51 (1H, d, J=2.0 Hz), 7.49-7.40 (3H, m), 7.30-7.27 (1H, m), 6.90 (1H, dd, J=2.3, 9.1 Hz), 5.27 (2H, s), 3.01-2.95 (2H, m), 2.58-2.52 (2H, m), 1.13-1.11 (2H, m), 0.79-0.75 (2H, m) ppm.

Table 1 provides the example number, the IUPAC name and the general scheme according to which the compounds have been made.

TABLE 1

| Example number | IUPAC Name | General scheme |
|---|---|---|
| Example 1 | 8,14-dioxa-4,10,19,20-tetraazatetracyclo[13.5.2.1$^{2,6}$.0$^{18,21}$]tricosa-1(20),2,4,6(23),15,17,21-heptaen-9-one | Scheme A |
| Example 2 | 10-methyl-8,14-dioxa-4,10,19,20-tetraazatetracyclo[13.5.2.1$^{2,6}$.0$^{18,21}$]tricosa-1(20),2,4,6(23),15,17,21-heptaen-9-one | Scheme A |
| Example 3 | 4-fluoro-8,14-dioxa-10,19,20-triazatetracyclo[13.5.2.1$^{2,6}$.0$^{18,21}$]tricosa-1(20),2,4,6(23),15,17,21-heptaen-9-one | Scheme A |
| Example 4 | 8,14-dioxa-10,19,20,23-tetraazatetracyclo[13.5.2.1$^{2,6}$.0$^{18,21}$]tricosa-1(20),2,4,6(23),15,17,21-heptaen-9-one | Scheme B |
| Example 5 | 8,14-dioxa-10,19,20-triazatetracyclo[13.5.2.1$^{2,6}$.0$^{18,21}$]tricosa-1(20),2,4,6(23),15,17,21-heptaen-9-one | Scheme A |
| Example 6 | 10-(propan-2-yl)-8,14-dioxa-4,10,19,20-tetraazatetracyclo[13.5.2.1$^{2,6}$.0$^{18,21}$]tricosa-1(20),2,4,6(23),15,17,21-heptaen-9-one | Scheme A |

TABLE 1-continued

| Example number | IUPAC Name | General scheme |
|---|---|---|
| Example 7 | 8,14-dioxa-5,10,19,20-tetraazatetracyclo[13.5.2.1$^{2,6}$.0$^{18,21}$]tricosa-1(20),2,4,6(23),15,17,21-heptaen-9-one | Scheme B |
| Example 8 | 4-methoxy-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 9 | 4-bromo-8,14-dioxa-10,19,20-triazatetracyclo[13.5.2.1$^{2,6}$.0$^{18,21}$]tricosa-1(20),2,4,6(23),15,17,21-heptaen-9-one | Scheme D |
| Example 10 | 5-fluoro-8,14-dioxa-10,19,20-triazatetracyclo[13.5.2.1$^{2,6}$.0$^{18,21}$]tricosa-1(20),2,4,6(23),15,17,21-heptaen-9-one | Scheme E |
| Example 11 | 5-methyl-8,14-dioxa-10,19,20-triazatetracyclo[13.5.2.1$^{2,6}$.0$^{18,21}$]tricosa-1(20),2,4,6(23),15,17,21-heptaen-9-one | Scheme F |
| Example 12 | 4-(pyrrolidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 13 | 4-[4-(propan-2-yl)piperazin-1-yl]-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 14 | 4-{2-oxa-6-azaspiro[3.4]octan-6-yl}-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 15 | 4-[4-(oxetan-3-yl)piperazin-1-yl]-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 16 | 4-(morpholin-4-yl)-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 17 | 4-[(2R,6S)-2,6-dimethylmorpholin-4-yl]-8,14-dioxa-10,19,20-triazatetracyclo[13.5.2.1$^{2,6}$.0$^{18,21}$] tricosa-1(20),2,4,6(23),15,17,21-heptaen-9-one | Scheme C |
| Example 18 | 4-methyl-8,14-dioxa-10,19,20-triazatetracyclo[13.5.2.1$^{2,6}$.0$^{18,21}$]tricosa-1(20),2,4,6(23),15,17,21-heptaen-9-one | Scheme F |
| Example 19 | 5-methoxy-8,14-dioxa-10,19,20-triazatetracyclo[13.5.2.1$^{2,6}$.0$^{18,21}$]tricosa-1(20),2,4,6(23),15,17,21-heptaen-9-one | Scheme F |
| Example 20 | 4-(4,4-difluoropiperidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 21 | 4-(3,3-difluoropyrrolidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 22 | 7-methyl-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 23 | 4-[4-(2-methoxyethyl)piperidin-1-yl]-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 24 | 9,14-dioxa-11,19,20-triazatetracyclo[13.5.2.1$^{2,6}$.0$^{18,21}$]tricosa-1(20),2,4,6(23),15,17,21-heptaen-10-one | Scheme C |
| Example 25 | 4-[(3R)-3-hydroxypyrrolidin-1-yl]-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 26 | 4-[(2-methoxyethyl)(methyl)amino]-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 27 | 4-chloro-8,14-dioxa-10,19,20-triazatetracyclo[13.5.2.1$^{2,6}$.0$^{18,21}$]tricosa-1(20),2,4,6(23),15,17,21-heptaen-9-one | Scheme F |
| Example 28 | 4-fluoro-5-methyl-8,14-dioxa-10,19,20-triazatetracyclo[13.5.2.1$^{2,6}$.0$^{18,21}$]tricosa-1(20),2,4,6(23),15,17,21-heptaen-9-one | Scheme G |
| Example 29 | 4,5-difluoro-8,14-dioxa-10,19,20-triazatetracyclo[13.5.2.1$^{2,6}$.0$^{18,21}$]tricosa-1(20),2,4,6(23),15,17,21-heptaen-9-one | Scheme F |
| Example 30 | 5-bromo-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 31 | 4-(4-methylpiperazin-1-yl)-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 32 | 4-(3-methoxyazetidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one | Scheme C |

TABLE 1-continued

| Example number | IUPAC Name | General scheme |
|---|---|---|
| Example 33 | 1-{9-oxo-8,14-dioxa-10,19,20-triazatetra cyclo[13.5.2.1$^{2,6}$.0$^{18,21}$]tricosa-1(20),2,4,6(23), 15,17,21-heptaen-4-yl}piperidine-4-carbonitrile | Scheme C |
| Example 34 | 4-[4-(pyrrolidin-1-yl)piperidin-1-yl]-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 35 | 4-(azetidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 36 | 4-(piperidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one | Scheme A |
| Example 37 | 4-(2,5-dihydrofuran-3-yl)-8,14-dioxa-10,19,20-triazatetracyclo[13.5.2.1$^{2,6}$.0$^{18,21}$]tricosa-1(20),2,4,6(23),15,17,21-heptaen-9-one | Scheme A |
| Example 38 | 4-[4-(morpholin-4-yl)piperidin-1-yl]-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 39 | 4-(1-methyl-1,2,3,6-tetrahydropyridin-4-yl)-8,14-dioxa-10,19,20-triazatetracyclo[13.5.2.1$^{2,6}$.0$^{18,21}$] tricosa-1(20),2,4,6(23),15,17,21-heptaen-9-one | Scheme A |
| Example 40 | 4-[(2S,5S)-2,5-dimethylmorpholin-4-yl]-8,14-dioxa-10,19,20-triazatetracyclo[13.5.2.1$^{2,6}$.0$^{18,21}$] tricosa-1(20),2,4,6(23),15,17,21-heptaen-9-one | Scheme C |
| Example 41 | 4-[(morpholin-4-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 42 | 4-[(pyrrolidin-1-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 43 | 4-[(pyrrolidin-1-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 44 | 4-[(4-methylpiperazin-1-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 45 | 5-(morpholin-4-yl)-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 46 | 4-[4-(2-methoxyethyl)piperazin-1-yl]-8,14-dioxa-10,19,20-triazatetracyclo[13.5.2.1$^{2,6}$.0$^{18,21}$]tricosa-1(20),2,4,6(23),15,17,21-heptaen-9-one | Scheme A |
| Example 47 | 4-(diethylamino)-8,14-dioxa-10,19,20-triazatetracyclo[13.5.2.1$^{2,6}$.0$^{18,21}$]tricosa-1(20),2,4,6(23),15,17,21-heptaen-9-one | Scheme A |
| Example 48 | 4-cyclopropyl-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 49 | 5-(4-methylpiperazin-1-yl)-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 50 | 13-methyl-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 51 | 8,14-dioxa-4,5,10,19,20-pentaazatetracyclo[13.5.2.1$^{2,5}$.0$^{18,21}$]tricosa-1(20),2(23),3,15(22),16,18(21)-hexaen-9-one | Scheme C |
| Example 52 | 4-[methyl(oxetan-3-yl)amino]-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 53 | 4-[(dimethylamino)methyl]-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 54 | 4,10-dimethyl-8,14-dioxa-10,19,20-triazatetracyclo[13.5.2.1$^{2,6}$.0$^{18,21}$]tricosa-1(20),2,4,6(23),15,17,21-heptaen-9-one | Scheme F |
| Example 55 | 4-(propan-2-yloxy)-8,14-dioxa-10,19,20-triazatetracyclo[13.5.2.1$^{2,6}$.0$^{18,21}$]tricosa-1(20),2,4,6(23),15,17,21-heptaen-9-one | Scheme F |
| Example 56 | 4-fluoro-7-methyl-8,14-dioxa-10,19,20-triazatetracyclo[13.5.2.1$^{2,6}$.0$^{18,21}$]tricosa-1(20),2,4,6(23),15,17,21-heptaen-9-one | Scheme A |
| Example 57 | 4-[1-(oxetan-3-yl)-1,2,3,6-tetrahydropyridin-4-yl]-8,14-dioxa-10,19,20-triazatetracyclo[13.5.2.1$^{2,6}$.0$^{18,21}$]tricosa-1(20),2,4,6(23),15,17,21-heptaen-9-one | Scheme C |

TABLE 1-continued

| Example number | IUPAC Name | General scheme |
|---|---|---|
| Example 58 | 4-(3-methylpiperidin-1-yl)-8,14-dioxa-10,19,20-triazatetracyclo[13.5.2.$1^{2,6}$.$0^{18,21}$]tricosa-1(20),2,4,6(23),15,17,21-heptaen-9-one | Scheme C |
| Example 59 | 4-[(3S)-3-hydroxypyrrolidin-1-yl]-8,14-dioxa-10,19,20-triazatetracyclo[13.5.2.$1^{2,6}$.$0^{18,21}$]tricosa-1(20),2,4,6(23),15,17,21-heptaen-9-one | Scheme C |
| Example 60 | 4-fluoro-8,14-dioxa-10,19,20-triazapentacyclo[13.5.2.$1^{2,6}$.$1^{7,10}$.$0^{18,21}$]tetracosa-1(20),2(24),3,5,15(22),16,18(21)-heptaen-9-one | Synthesis described in details |
| Example 61 | 4-(oxolan-3-yl)-8,14-dioxa-10,19,20-triazatetracyclo[13.5.2.$1^{2,6}$.$0^{18,21}$]tricosa-1(20),2,4,6(23),15,17,21-heptaen-9-one | Scheme A |
| Example 62 | (13S)-13-methyl-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme C |
| Example 63 | (13R)-13-methyl-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme C |
| Example 64 | 4-(1-methyl-1H-pyrazol-3-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme C |
| Example 65 | (7S)-7-methyl-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme C |
| Example 66 | 4-[2-(morpholin-4-yl)ethoxy]-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme F |
| Example 67 | 4-(2-methoxyethyl)-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme A |
| Example 68 | (7R)-7-methyl-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme C |
| Example 69 | 5-cyclopropyl-8,14-dioxa-10,19,20-triazatetracyclo[13.5.2.$1^{2,6}$.$0^{18,21}$]tricosa-1(20),2,4,6(23),15,17,21-heptaen-9-one | Scheme C |
| Example 70 | 4-(2-methoxyethoxy)-8,14-dioxa-10,19,20-triazatetracyclo[13.5.2.$1^{2,6}$.$0^{18,21}$]tricosa-1(20),2,4,6(23),15,17,21-heptaen-9-one | Scheme F |
| Example 71 | 4-fluoro-13-methyl-8,14-dioxa-10,19,20-triazatetracyclo[13.5.2.$1^{2,6}$.$0^{18,21}$]tricosa-1(20),2,4,6(23),15,17,21-heptaen-9-one | Scheme C |
| Example 72 | 11-methyl-8,14-dioxa-10,19,20-triazatetracyclo[13.5.2.$1^{2,6}$.$0^{18,21}$]tricosa-1(20),2,4,6(23),15,17,21-heptaen-9-one | Scheme C |
| Example 73 | 4-(3-oxomorpholin-4-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme C |
| Example 74 | 4-(2-oxopyrrolidin-1-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme C |
| Example 75 | 5-(2-oxopyrrolidin-1-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme C |
| Example 76 | 4-(2-methylpyrrolidin-1-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme C |
| Example 77 | 2-{9-oxo-8,14-dioxa-10,19,20-triazatetracyclo[13.5.2.12.6.018,21]tricosa-1(20),2(23),3,5,15(22),16,18(21)-heptaen-4-yl}acetonitrile | Scheme C |
| Example 78 | (11R) or (11S)-11-methyl-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme C |
| Example 79 | (11R) or (11S)-11-methyl-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme C |
| Example 80 | 4-ethynyl-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme C |
| Example 81 | 4-(piperazin-1-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme A |
| Example 82 | 4-(1,2,3,6-tetrahydropyridin-4-yl)-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme A |
| Example 83 | 11-(methoxymethyl)-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme C |

TABLE 1-continued

| Example number | IUPAC Name | General scheme |
|---|---|---|
| Example 84 | 8,14-dioxa-5,10,19,20,23-pentaazatetracyclo[13.5.2.$1^{2,5}$.$0^{18,21}$]tricosa-1(20),2(23),3,15(22),16,18(21)-hexaen-9-one | Scheme K |
| Example 85 | 11-methyl-8,14-dioxa-4,5,10,19,20-pentaazatetracyclo[13.5.2.$1^{2,5}$.$0^{18,21}$]tricosa-1(20),2(23),3,15(22),16,18(21)-hexaen-9-one | Scheme C |
| Example 86 | 12-methyl-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme E |
| Example 87 | 11-ethyl-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme E |
| Example 88 | 4-fluoro-5,7-dimethyl-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme A |
| Example 89 | 4-fluoro-5-methoxy-7-methyl-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme A |
| Example 90 | 5-fluoro-4,7-dimethyl-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme A |
| Example 91 | 8,14-dioxa-10,19,20-triazapentacyclo[13.5.2.$1^{2,6}$.$1^{7,10}$.$0^{18,21}$]tetracosa-1(20),2(24),3,5,15(22),16,18(21)-heptaen-9-one | Synthesis described in details |
| Example 92 | 13-methyl-8,14-dioxa-10,19,20,23-tetraazatetracyclo[13.5.2.$1^{2,6}$.$0^{18,21}$]tricosa-1(20),2(23),3,5,15(22),16,18(21)-heptaen-9-one | Scheme B |
| Example 93 | 12-methyl-8,14-dioxa-4,5,10,19,20-pentaazatetracyclo[13.5.2.$1^{2,5}$.$0^{18,21}$]tricosa-1(20),2(23),3,15(22),16,18(21)-hexaen-9-one | Scheme C |
| Example 94 | 7-methyl-8,14-dioxa-4,5,10,19,20-pentaazatetracyclo[13.5.2.$1^{2,5}$.$0^{18,21}$]tricosa-1(20),2(23),3,15(22),16,18(21)-hexaen-9-one | Scheme C |
| Example 95 | 5-fluoro-4-methoxy-7-methyl-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme A |
| Example 96 | (7R,13R)-7,13-dimethyl-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme C |
| Example 97 | (13R)-13-methyl-8,14-dioxa-4,5,10,19,20-pentaazatetracyclo[13.5.2.$1^{2,5}$.$0^{18,21}$]tricosa-1(20),2(23),3,15,17,21-hexaen-9-one | Scheme C |
| Example 98 | 8,15-dioxa-4,10,20,21-tetraazapentacyclo[14.5.2.$1^{2,6}$.$1^{10,13}$.$0^{19,22}$]pentacosa-1(21),2(25),3,5,16(23),17,19(22)-heptaen-9-one | Scheme N |
| Example 99 | 8,14-dioxa-5,10,19,20-tetraazatetracyclo[13.5.2.$1^{2,5}$.$0^{18,21}$]tricosa-1(20),2(23),3,15(22),16,18(21)-hexaen-9-one | Scheme J |
| Example 100 | (13R) or (13S)-4-fluoro-13-methyl-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme C |
| Example 101 | (13R) or (13S)-4-fluoro-13-methyl-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme C |
| Example 102 | (13R)-13-methyl-8,14-dioxa-4,10,19,20-tetraazatetracyclo[13.5.2.$1^{2,6}$.$0^{18,21}$]tricosa-1(20),2(23),3,5,15(22),16,18(21)-heptaen-9-one | Scheme C |
| Example 103 | 6-cyclopropyl-8,14-dioxa-4,5,10,19,20-pentaazatetracyclo[13.5.2.$1^{2,5}$.$0^{18,21}$]tricosa-1(20),2(23),3,15(22),16,18(21)-hexaen-9-one | Scheme B |
| Example 104 | 7-ethyl-8,14-dioxa-10,19,20-triazatetracyclo[13.5.2.$1^{2,6}$.$0^{18,21}$]tricosa-1(20),2,4,6(23),15,17,21-heptaen-9-one | Scheme G |
| Example 105 | (13R)-13-methyl-8,14-dioxa-5,10,19,20,23-pentaazatetracyclo[13.5.2.$1^{2,6}$.$0^{18,21}$]tricosa-1(20),2,4,6(23),15,17,21-heptaen-9-one | Scheme B |
| Example 106 | (7R,13R)-4-fluoro-7,13-dimethyl-8,14-dioxa-10,19,20-triazatetracyclo[13.5.2.$1^{2,6}$.$0^{18,21}$]tricosa-1(20),2,4,6(23),15,17,21-heptaen-9-one | Scheme C |
| Example 107 | 7-methyl-8,14-dioxa-4,10,19,20-tetraazatetracyclo[13.5.2.$1^{2,6}$.$0^{18,21}$]tricosa-1(20),2,4,6(23),15,17,21-heptaen-9-one | Scheme H |
| Example 108 | (7R)- or (7S)-4-fluoro-7-methyl-8,14-dioxa-10,19,20-triazatetracyclo[13.5.2.$1^{2,6}$.$0^{18,21}$]tricosa-1(20),2,4,6(23),15,17,21-heptaen-9-one | Scheme A |
| Example 109 | (7R)- or (7S)-4-fluoro-7-methyl-8,14-dioxa-10,19,20-triazatetracyclo[13.5.2.$1^{2,6}$.$0^{18,21}$]tricosa-1(20),2,4,6(23),15,17,21-heptaen-9-one | Scheme A |

TABLE 1-continued

| Example number | IUPAC Name | General scheme |
|---|---|---|
| Example 110 | 6-methyl-8,14-dioxa-4,5,10,19,20-pentaazatetracyclo[13.5.2.1$^{2,5}$.0$^{18,21}$]tricosa-1(20),2(23),3,15,17,21-hexaen-9-one | Scheme B |
| Example 111 | 7-methyl-8,14-dioxa-10,19,20,23-tetraazatetracyclo[13.5.2.1$^{2,6}$.0$^{18,21}$]tricosa-1(20),2,4,6(23),15,17,21-heptaen-9-one | Scheme H |
| Example 112 | 6-(propan-2-yl)-8,14-dioxa-4,5,10,19,20-pentaazatetracyclo[13.5.2.1$^{2,5}$.0$^{18,21}$]tricosa-1(20),2(23),3,15(22),16,18(21)-hexaen-9-one | Scheme B |
| Example 113 | (13R)-7,13-dimethyl-8,14-dioxa-4,5,10,19,20-pentaazatetracyclo[13.5.2.1$^{2,5}$.0$^{18,21}$]tricosa-1(20),2(23),3,15(22),16,18(21)-hexaen-9-one | Scheme C |
| Example 114 | (13R)-13-methyl-8,14-dioxa-10,19,20,23-tetraazatetracyclo[13.5.2.1$^{2,6}$.0$^{18,21}$]tricosa-1(20),2,4,6(23),15,17,21-heptaen-9-one | Scheme K |
| Example 115 | (7R)- or (7S)-7-ethyl-8,14-dioxa-10,19,20-triazatetracyclo[13.5.2.1$^{2,6}$.0$^{18,21}$]tricosa-1(20),2,4,6(23),15,17,21-heptaen-9-one | Scheme G |
| Example 116 | (7R)- or (7S)-7-ethyl-8,14-dioxa-10,19,20-triazatetracyclo[13.5.2.1$^{2,6}$.0$^{18,21}$]tricosa-1(20),2,4,6(23),15,17,21-heptaen-9-one | Scheme G |
| Example 117 | (13R)-13-methyl-8,14-dioxa-5,10,19,20-tetraazatetracyclo[13.5.2.1$^{2,6}$.0$^{18,21}$]tricosa-1(20),2,4,6(23),15,17,21-heptaen-9-one | Scheme K |
| Example 118 | 6-(oxan-4-yl)-8,14-dioxa-4,5,10,19,20-pentaazatetracyclo[13.5.2.1$^{2,5}$.0$^{18,21}$]tricosa-1(20),2(23),3,15,17,21-hexaen-9-one | Scheme B |
| Example 119 | 4-ethyl-8,14-dioxa-5,10,19,20,23-pentaazatetracyclo[13.5.2.1$^{2,5}$.0$^{18,21}$]tricosa-1(20),2(23),15,17,21-pentaen-9-one | Scheme B |
| Example 120 | (13R)-23-fluoro-13-methyl-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 121 | 9,14-dioxa-4,5,11,19,20-pentaazatetracyclo[13.5.2.1$^{2,5}$.0$^{18,21}$]tricosa-1(20),2(23),3,15,17,21-hexaen-10-one | Scheme A |
| Example 122 | 4-ethyl-8,14-dioxa-5,10,19,20,23-pentaazatetracyclo[13.5.2.1$^{2,5}$.0$^{18,21}$]tricosa-1(20),2(23),3,15,17,21-hexaen-9-one | Scheme B |
| Example 123 | 3,9,15-trioxa-4,11,20,21-tetraazatetracyclo[14.5.2.1$^{2,5}$.0$^{19,22}$]tetracosa-1(21),2(24),4,16,18,22-hexaen-10-one | Scheme M |
| Example 124 | (13R)-16-fluoro-13-methyl-8,14-dioxa-4,10,19,20-tetraazatetracyclo[13.5.2.1$^{2,6}$.0$^{18,21}$]tricosa-1(20),2,4,6(23),15,17,21-heptaen-9-one | Scheme C |
| Example 125 | (13R)-4-chloro-13-methyl-8,14-dioxa-10,19,20,23-tetraazatetracyclo[13.5.2.1$^{2,6}$.0$^{18,21}$]tricosa-1(20),2(23),3,5,15(22),16,18(21)-heptaen-9-one | Scheme K |
| Example 126 | 8,14-dioxa-2,4,10,19,20-pentaazatetracyclo[13.5.2.1$^{2,5}$.0$^{18,21}$]tricosa-1(20),3,5(23),15(22),16,18(21)-hexaen-9-one | Scheme A |
| Example 127 | (13R)-4-methoxy-13-methyl-8,14-dioxa-10,19,20,23-tetraazatetracyclo[13.5.2.1$^{2,6}$.0$^{18,21}$]tricosa-1(20),2,4,6(23),15,17,21-heptaen-9-one | Scheme K |
| Example 128 | (13R)-13-methyl-9-oxo-8,14-dioxa-10,19,20-triazatetracyclo[13.5.2.1$^{2,6}$.0$^{18,21}$]tricosa-1(20),2,4,6(23),15,17,21-heptaene-5-carbonitrile | Scheme B |
| Example 129 | (13R)-13-methyl-4-(pyrrolidin-1-yl)-8,14-dioxa-5,10,19,20,23-pentaazatetracyclo[13.5.2.1$^{2,6}$.0$^{18,21}$]tricosa-1(20),2,4,6(23),15,17,21-heptaen-9-one | Synthesis described in details |
| Example 130 | (7R,13R)- or (7S,13R)-7,13-dimethyl-8,14-dioxa-5,10,19,20,23-pentaazatetracyclo[13.5.2.1$^{2,6}$.0$^{18,21}$]tricosa-1(20),2,4,6(23),15,17,21-heptaen-9-one | Synthesis described in details |
| Example 131 | (7R,13R)- or (7S,13R)-7,13-dimethyl-8,14-dioxa-5,10,19,20,23-pentaazatetracyclo[13.5.2.1$^{2,6}$.0$^{18,21}$]tricosa-1(20),2,4,6(23),15,17,21-heptaen-9-one | Scheme K |
| Example 132 | (13R)-16-fluoro-13-methyl-8,14-dioxa-10,19,20-triazatetracyclo[13.5.2.1$^{2,6}$.0$^{18,21}$]tricosa-1(20),2,4,6(23),15,17,21-heptaen-9-one | Scheme C |
| Example 133 | (13R)-13-methyl-8,14-dioxa-4,10,19,20,23-pentaazatetracyclo[13.5.2.1$^{2,6}$.0$^{18,21}$]tricosa-1(20),2,4,6(23),15,17,21-heptaen-9-one | Scheme K |
| Example 134 | 8,14-dioxa-4-thia-10,19,20,23-tetraazatetracyclo[13.5.2.1$^{2,5}$.0$^{18,21}$]tricosa-1(20),2,5(23),15,17,21-hexaen-9-one | Scheme L |
| Example 135 | 8,14-dioxa-3-thia-10,19,20,23-tetraazatetracyclo[13.5.2.1$^{2,5}$.0$^{18,21}$]tricosa-1(20),2(23),4,15,17,21-hexaen-9-one | Scheme L |

TABLE 1-continued

| Example number | IUPAC Name | General scheme |
|---|---|---|
| Example 136 | (7R,13R)-7,13-dimethyl-8,14-dioxa-10,19,20,23-tetraazatetracyclo[13.5.2.1$^{2,6}$.0$^{18,21}$]tricosa-1(20),2,4,6(23),15,17,21-heptaen-9-one | Scheme K |
| Example 137 | (13R)-4-[(3R)-3-methoxypyrrolidin-1-yl]-13-methyl-8,14-dioxa-5,10,19,20,23-pentaazatetracyclo[13.5.2.1$^{2,6}$.0$^{18,21}$]tricosa-1(20),2,4,6(23),15,17,21-heptaen-9-one | Scheme K |
| Example 138 | (13R)-16-chloro-13-methyl-8,14-dioxa-10,19,20-triazatetracyclo[13.5.2.1$^{2,6}$.0$^{18,21}$]tricosa-1(20),2,4,6(23),15,17,21-heptaen-9-one | Scheme K |
| Example 139 | (13R)-13,16-dimethyl-8,14-dioxa-10,19,20-triazatetracyclo[13.5.2.1$^{2,6}$.0$^{18,21}$]tricosa-1(20),2,4,6(23),15,17,21-heptaen-9-one | Scheme K |
| Example 140 | (13R)-13-methyl-8,14-dioxa-3,10,19,20,23-pentaazatetracyclo[13.5.2.1$^{2,6}$.0$^{18,21}$]tricosa-1(20),2,4,6(23),15,17,21-heptaen-9-one | Scheme B |
| Example 141 | 8-oxa-10,14,19,20-tetraazatetracyclo [13.5.2.1$^{2,6}$.0$^{18,21}$]tricosa-1(20),2(23),3,5,15(22),16,18(21)-heptaen-9-one | Scheme I |
| Example 142 | 8-oxa-10,19,20-triazatetracyclo [13.5.2.1$^{2,6}$.0$^{18,21}$]tricosa-1(20),2(23),3,5,15(22),16,18(21)-heptaen-9-one | Synthesis described in details |
| Example 143 | (13R)-5-methoxy-13-methyl-8,14-dioxa-4,10,19,20-tetraazatetracyclo[13.5.2.1$^{2,6}$.0$^{18,21}$] tricosa-1(20),2,4,6(23),15,17,21-heptaen-9-one | Scheme O |
| Example 144 | (13R)-13-methyl-8,14-dioxa-4,10,19,20-tetraazatetracyclo[13.5.2.1$^{2,6}$.0$^{18,21}$]tricosa-1(20),2,6(23),15,17,21-hexaene-5,9-dione | Demethylation of example 143 |
| Example 145 | 4-methyl-8,14-dioxa-3,4,10,19,20-pentaazatetracyclo[13.5.2.1$^{2,5}$.0$^{18,21}$]tricosa-1(20),2,5(23),15(22),16,18(21)-hexaen-9-one | Scheme L |
| Example 146 | (13R)-16-fluoro-13-methyl-8,14-dioxa-10,19,20,23-tetraazatetracyclo[13.5.2.1$^{2,6}$.0$^{18,21}$] tricosa-1(20),2,4,6(23),15,17,21-heptaen-9-one | Scheme O |
| Example 147 | 7,13-dioxa-4-thia-9,18,19,22-tetraazatetracyclo[12.5.2.1$^{2,5}$.0$^{17,20}$]docosa-1(19),2,5(22),14(21),15,17(20)-hexaen-8-one | Scheme L |
| Example 148 | (13R)-4,13-dimethyl-8,14-dioxa-5,10,19,20,23-pentaazatetracyclo[13.5.2.1$^{2,6}$.0$^{18,21}$]tricosa-1(20),2(23),3,5,15(22),16,18(21)-heptaen-9-one | Scheme O |
| Example 149 | 8,14-dioxa-23-thia-4,10,19,20-tetraazatetracyclo[13.5.2.1$^{2,5}$.0$^{18,21}$]tricosa-1(20),2,4,15(22),16,18(21)-hexaen-9-one | Scheme L |
| Example 150 | (7S,13R)-7,13-dimethyl-8,14-dioxa-10,19,20,23-tetraazatetracyclo[13.5.2.1$^{2,6}$.0$^{18,21}$]tricosa-1(20),2(23),3,5,15(22),16,18(21)-heptaen-9-one | Scheme K |
| Example 151 | (13R)-13-methyl-9-oxo-8,14-dioxa-5,10,19,20-tetraazatetracyclo[13.5.2.1$^{2,5}$.0$^{18,21}$]tricosa-1(20), 2(23),3,15(22),16,18(21)-hexaene-4-carbonitrile | Scheme O |
| Example 152 | 12,12-difluoro-8,14-dioxa-10,19,20-triazatetracyclo[13.5.2.1$^{2,6}$.0$^{18,21}$]tricosa-1(20),2(23),3,5,15(22),16,18(21)-heptaen-9-one | Scheme C |
| Example 153 | (13R)-17-fluoro-13-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one | Scheme C |
| Example 154 | (7S,13R)-7,13-dimethyl-8,14-dioxa-4,10,19, 20,23-pentaazatetracyclo[13.5.2.1$^{2,6}$.0$^{18,21}$]tricosa-1(20),2(23),3,5,15(22),16,18(21)-heptaen-9-one | Synthesis described in details |
| Example 155 | (7R,13R)-7,13-dimethyl-8,14-dioxa-4,10,19,20, 23-pentaazatetracyclo[13.5.2.1$^{2,6}$.0$^{18,21}$]tricosa-1(20),2(23),3,5,15(22),16,18(21)-heptaen-9-one | Scheme K |
| Example 156 | (13S)-13-methyl-8,14-dioxa-4,10,19,20,23-pentaazatetracyclo[13.5.2.1$^{2,6}$.0$^{18,21}$]tricosa-1(20),2(23),3,5,15(22),16,18(21)-heptaen-9-one | Scheme K |
| Example 157 | (13R)-13-methyl-8,14-dioxa-10,19,20,22-tetraazatetracyclo[13.5.2.1$^{2,6}$.0$^{18,21}$]tricosa-1(20),2(23),3,5,15,17,21-heptaen-9-one | Scheme C |
| Example 158 | (12R)-4,12-dimethyl-7,13-dioxa-4,9,18,19,22-pentaazatetracyclo[12.5.2.1$^{2,5}$.0$^{17,20}$]docosa-1(19),2,5(22),14(21),15,17(20)-hexaen-8-one | Scheme K |
| Example 159 | (13R)-13-methyl-8,14-dioxa-4,5,10,19,20,23-hexaazatetracyclo[13.5.2.1$^{2,5}$.0$^{18,21}$]tricosa-1(20),2(23),3,15,17,21-hexaen-9-one | Scheme O |
| Example 160 | (13R)-13-methyl-8,14-dioxa-23-thia-4,10,19,20-tetraazatetracyclo[13.5.2.1$^{2,5}$.0$^{18,21}$]tricosa-1(20),2,4,15,17,21-hexaen-9-one | Scheme L |

TABLE 1-continued

| Example number | IUPAC Name | General scheme |
|---|---|---|
| Example 161 | (13R)-4,13-dimethyl-8,14-dioxa-4,10,19,20,23-pentaazatetracyclo[13.5.2.$1^{2,5}$.$0^{18,21}$]tricosa-1(20),2,5(23),15(22),16,18(21)-hexaen-9-one | Scheme L |
| Example 162 | (13R)-13-methyl-8,14-dioxa-10,16,19,20-tetraazatetracyclo[13.5.2.$1^{2,6}$.$0^{18,21}$]tricosa-1(20),2(23),3,5,15(22),16,18(21)-heptaen-9-one | Synthesis described in details |
| Example 163 | 14-methyl-8-oxa-10,14,19,20-tetraazatetracyclo[13.5.2.$1^{2,6}$.$0^{18,21}$]tricosa-1(20),2(23),3,5,15,17,21-heptaen-9-one | Synthesis described in details |
| Example 164 | (13R)-13-methyl-8,14-dioxa-4,10,19,20,22-pentaazatetracyclo[13.5.2.$1^{2,6}$.$0^{18,21}$]tricosa-1(20),2(23),3,5,15,17,21-heptaen-9-one | Synthesis described in details |
| Example 165 | (13R)-13-methyl-8,14-dioxa-10,17,19,20-tetraazatetracyclo[13.5.2.$1^{2,6}$.$0^{18,21}$]tricosa-1(20),2(23),3,5,15(22),16,18(21)-heptaen-9-one | Synthesis described in details |
| Example 166 | 8,14-dioxa-4,5,10,19,20,23-hexaazatetracyclo [13.5.2.$1^{2,5}$.$0^{18,21}$]tricosa-1(20),2(23),3,15(22),16,18(21)-hexaen-9-one | Scheme K |
| Example 167 | 12,12-difluoro-8,14-dioxa-4,5,10,19,20,23-hexaazatetracyclo[13.5.2.$1^{2,5}$.$0^{18,21}$]tricosa-1(20),2(23),3,15(22),16,18(21)-hexaen-9-one | Scheme K |
| Example 168 | (12R)-12-fluoro-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme E |
| Example 169 | (12S)-12-fluoro-8,14-dioxa-10,19,20-triazatetracyclo[13.5.2.$1^{2,6}$.$0^{18,21}$]tricosa-1(20),2(23),3,5,15(22),16,18(21)-heptaen-9-one | Scheme E |
| Example 170 | 12,12-difluoro-8,14-dioxa-4,10,19,20,23-pentaazatetracyclo [13.5.2.$1^{2,6}$.$0^{18,21}$]tricosa-1(20),2(23),3,5,15(22),16,18(21)-heptaen-9-one | Scheme K |
| Example 171 | (12S)-12-fluoro-8,14-dioxa-4,10,19,20,23-pentaazatetracyclo [13.5.2.$1^{2,6}$.$0^{18,21}$]tricosa-1(20),2(23),3,5,15,17,21-heptaen-9-one | Scheme K |
| Example 172 | (12R)-12-fluoro-8,14-dioxa-4,10,19,20,23-pentaazatetracyclo [13.5.2.$1^{2,6}$.$0^{18,21}$]tricosa-1(20),2(23),3,5,15,17,21-heptaen-9-one | Scheme K |
| Example 173 | (12S)-12-fluoro-8,14-dioxa-4,5,10,19,20,23-hexaazatetracyclo[13.5.2.$1^{2,5}$.$0^{18,21}$]tricosa-1(20),2(23),3,15,17,21-hexaen-9-one | Scheme O |
| Example 174 | (12R)-12-fluoro-8,14-dioxa-4,5,10,19,20,23-hexaazatetracyclo[13.5.2.$1^{2,5}$.$0^{18,21}$]tricosa-1(20),2(23),3,15,17,21-hexaen-9-one | Scheme O |
| Example 175 | 8',14'-dioxa-10',19',20'-triazaspiro[cyclopropane-1,13'-tetracyclo[13.5.2.$1^{2,6}$.$0^{18,21}$]tricosane]-1'(20'),2'(23'),3',5',15'(22'),16',18'(21')-heptaen-9'-one | Synthesis described in details |

Pharmacological Study

Example A: LRRK2 Kinase Activity Assay

Protocol

LRRK2 Kinase reactions were carried out in 384-well white polystyrene plates in a final volume of 6 µl using ADP-Glo™ Kinase Assay kit (Promega Corp.). Compound and substrates (LRRKtide peptide and ATP) in assay buffer were first dispensed in wells. Kinase reaction was then started by the addition of human recombinant LRRK2 protein. After 1 h-incubation at 37° C., the enzymatic reaction was stopped by the addition of 6 µl of ADP-Glo Reagent-1 and an additional 40-minutes incubation at 23° C. (residual ATP depletion). A final 30-minutes incubation after 12 µL reagent-2 addition (ADP to ATP conversion and luciferin/luciferase reaction) was performed before luminescent signal acquisition (EnVision™ multimode plate reader-PerkinElmer, Inc.). Data from 10 individual concentrations of tested compounds (N=2) were fitted (XLfit™—ID Business Solutions Ltd) to deliver $IC_{50}$s (compound concentration leading to 50% inhibition of reference enzymatic activity).

Compounds

The compounds are dissolved to 5 mM in DMSO. When needed, solutions are sonicated in a bath sonicator.

Table 2 provides the $IC_{50}$ values of the compounds according to the invention, obtained using the above-mentioned kinase assay. Activities are represented as +++, ++ and +, having the following meanings:

+++ means $IC_{50}$<10 nM

++ means 10 nM≤$IC_{50}$<100 nM

+ means 100 nM≤$IC_{50}$<1 µM.

TABLE 2

| Example number | $IC_{50}$ LRRK2 wt ADP-Glo |
|---|---|
| Example 1 | +++ |
| Example 2 | ++ |
| Example 3 | +++ |
| Example 4 | +++ |
| Example 5 | +++ |
| Example 6 | ++ |
| Example 7 | +++ |
| Example 8 | +++ |
| Example 9 | +++ |
| Example 10 | +++ |
| Example 11 | +++ |
| Example 12 | +++ |
| Example 13 | +++ |
| Example 14 | +++ |
| Example 15 | +++ |

TABLE 2-continued

| Example number | $IC_{50}$ LRRK2 wt ADP-Glo |
|---|---|
| Example 16 | +++ |
| Example 17 | +++ |
| Example 18 | +++ |
| Example 19 | +++ |
| Example 20 | +++ |
| Example 21 | +++ |
| Example 22 | +++ |
| Example 23 | +++ |
| Example 24 | ++ |
| Example 25 | +++ |
| Example 26 | +++ |
| Example 27 | +++ |
| Example 28 | +++ |
| Example 29 | +++ |
| Example 30 | +++ |
| Example 31 | +++ |
| Example 32 | +++ |
| Example 33 | +++ |
| Example 34 | +++ |
| Example 35 | +++ |
| Example 36 | +++ |
| Example 37 | +++ |
| Example 38 | +++ |
| Example 39 | +++ |
| Example 40 | +++ |
| Example 41 | +++ |
| Example 42 | +++ |
| Example 43 | ++ |
| Example 44 | +++ |
| Example 45 | +++ |
| Example 46 | +++ |
| Example 47 | +++ |
| Example 48 | +++ |
| Example 49 | ++ |
| Example 50 | +++ |
| Example 51 | +++ |
| Example 52 | +++ |
| Example 53 | ++ |
| Example 54 | +++ |
| Example 55 | +++ |
| Example 56 | +++ |
| Example 57 | +++ |
| Example 58 | +++ |
| Example 59 | +++ |
| Example 60 | +++ |
| Example 61 | +++ |
| Example 62 | +++ |
| Example 63 | +++ |
| Example 64 | +++ |
| Example 65 | ++ |
| Example 66 | +++ |
| Example 67 | +++ |
| Example 68 | +++ |
| Example 69 | +++ |
| Example 70 | +++ |
| Example 71 | +++ |
| Example 72 | +++ |
| Example 73 | +++ |
| Example 74 | +++ |
| Example 75 | +++ |
| Example 76 | +++ |
| Example 77 | +++ |
| Example 78 | +++ |
| Example 79 | +++ |
| Example 80 | +++ |
| Example 81 | +++ |
| Example 82 | +++ |
| Example 83 | +++ |
| Example 84 | ++ |
| Example 85 | ++ |
| Example 86 | +++ |
| Example 87 | +++ |
| Example 88 | ++ |
| Example 89 | + |
| Example 90 | +++ |
| Example 91 | +++ |
| Example 92 | +++ |

TABLE 2-continued

| Example number | $IC_{50}$ LRRK2 wt ADP-Glo |
|---|---|
| Example 93 | +++ |
| Example 94 | +++ |
| Example 95 | +++ |
| Example 96 | +++ |
| Example 97 | +++ |
| Example 98 | +++ |
| Example 99 | +++ |
| Example 100 | +++ |
| Example 101 | +++ |
| Example 102 | +++ |
| Example 103 | +++ |
| Example 104 | ++ |
| Example 105 | +++ |
| Example 106 | +++ |
| Example 107 | +++ |
| Example 108 | ++ |
| Example 109 | +++ |
| Example 110 | +++ |
| Example 111 | ++ |
| Example 112 | ++ |
| Example 113 | +++ |
| Example 114 | +++ |
| Example 115 | + |
| Example 116 | +++ |
| Example 117 | +++ |
| Example 118 | + |
| Example 119 | ++ |
| Example 120 | + |
| Example 121 | + |
| Example 122 | +++ |
| Example 123 | +++ |
| Example 124 | +++ |
| Example 125 | +++ |
| Example 126 | ++ |
| Example 127 | +++ |
| Example 128 | +++ |
| Example 129 | +++ |
| Example 130 | ++ |
| Example 131 | +++ |
| Example 132 | +++ |
| Example 133 | +++ |
| Example 134 | +++ |
| Example 135 | +++ |
| Example 136 | +++ |
| Example 137 | +++ |
| Example 138 | +++ |
| Example 139 | +++ |
| Example 140 | ++ |
| Example 141 | + |
| Example 142 | +++ |
| Example 143 | +++ |
| Example 144 | +++ |
| Example 145 | + |
| Example 146 | +++ |
| Example 147 | +++ |
| Example 148 | +++ |
| Example 149 | +++ |
| Example 150 | ++ |
| Example 151 | +++ |
| Example 152 | +++ |
| Example 153 | +++ |
| Example 154 | ++ |
| Example 155 | +++ |
| Example 156 | +++ |
| Example 157 | +++ |
| Example 158 | ++ |
| Example 159 | +++ |
| Example 160 | +++ |
| Example 161 | ++ |
| Example 162 | +++ |
| Example 163 | +++ |
| Example 164 | +++ |
| Example 165 | +++ |
| Example 166 | +++ |
| Example 167 | +++ |
| Example 168 | +++ |
| Example 169 | +++ |

TABLE 2-continued

| Example number | $IC_{50}$ LRRK2 wt ADP-Glo |
|---|---|
| Example 170 | +++ |
| Example 171 | +++ |
| Example 172 | +++ |
| Example 173 | +++ |
| Example 174 | +++ |
| Example 175 | +++ |

Example B: Pharmaceutical Composition: Tablets

| | |
|---|---|
| 1000 tablets containing a dose of 5 mg of a compound selected from Examples 1 to 175 . . . | 5 g |
| Wheat starch . . . | 20 g |
| Maize starch . . . | 20 g |
| Lactose . . . | 30 g |
| Magnesium stearate . . . | 2 g |
| Silica . . . | 1 g |
| Hydroxypropylcellulose . . . | 2 g |

The invention claimed is:

1. A compound of formula (I):

(I)

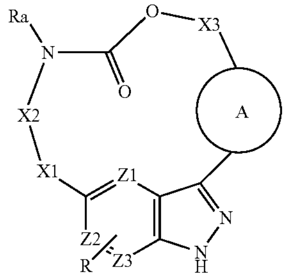

wherein:

R represents a hydrogen atom, a halogen atom or an alkyl group,

Z1, Z2, Z3, each independently represent a carbon or a nitrogen atom, wherein the 6-membered cycle containing Z1, Z2 and Z3 can have 0, 1 or 2 nitrogen atoms;

—X1- is absent or represents —O—, —S—, or —N(R'a)-, wherein R'a represents a hydrogen atom or an alkyl group;

—X2- represents an alkanediyl group optionally substituted by one or more substituents, which may be identical or different, selected from a halogen atom, polyhalogenoalkyl group, alkoxy group, hydroxy group, amino group, alkylamino group, dialkylamino group and cyano group, wherein the carbon atom in the alpha position of —N(Ra), and the carbon atom in alpha position of —X1- when —X1- represents —O—, —S—, or —N(R'a)-, cannot be substituted with an oxygen or a nitrogen heteroatom;

—X3- represents an alkanediyl group optionally substituted by one or more substituents, which may be identical or different, selected from a halogen atom, polyhalogenoalkyl group, alkoxy group, hydroxy group, amino group, alkylamino group, dialkylamino group, cyano group, cycloalkyl group and heterocycloalkyl group, wherein the carbon atom in alpha position of —O—, and the carbon atom in alpha position of A1 when A1 represents a nitrogen atom, cannot be substituted with an oxygen or a nitrogen heteroatom;

Ra represents a hydrogen atom or an alkyl group, wherein, when Ra represents an alkyl group, one carbon atom of Ra can be linked to a carbon atom of —X2-, or to a carbon atom of —X3- to form a cyclic moiety having 5 or 6 ring-members;

A represents an aromatic or partially hydrogenated cyclic group of the formula (a):

(a)

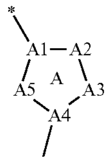

wherein

A1 and A4 each independently represent a carbon atom or a nitrogen atom,

A2, A3 and A5 each independently represents a carbon atom, an oxygen atom, a sulfur atom or a nitrogen atom, wherein A1, A2, A3, A4 and A5 cannot simultaneously represent a heteroatom, or an aromatic or partially hydrogenated cyclic group of the formula (b):

(b)

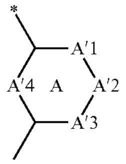

wherein A'1, A'2, A'3 and A'4 each independently represent a carbon atom or a nitrogen atom, wherein * means that the bond is linked to X3, and wherein the aromatic or partially hydrogenated cyclic group A may be optionally substituted with one or more substituents, which may be identical or different, selected from a halogen atom, alkyl group, alkoxy group, hydroxy group, oxo group, alkoxyalkyl group, alkoxyalkoxy group, polyhalogenoalkyl group, polyhalogenoalkoxy group, heterocycloalkyl group, heterocycloalkylalkyl group, (alkoxyalkyl)(alkyl)amino group, amino group, alkylamino group, dialkylamino group, cycloalkyl group, (heterocycloalkyl)(alkyl)amino group, dialkylaminoalkyl group, heterocycloalkylalkoxy group, cyano group and cyanoalkyl group, wherein the heterocycloalkyl and cycloalkyl group may be optionally substituted by one or more substituents selected from alkyl group, halogen atoms, polyhalogenoalkyl group, polyhalogenoalkoxy group, alkoxy group, alkoxyalkyl group, hydroxy group, cyano group and oxo group;

its enantiomers, diastereoisomers, tautomers, racemic, hydrates, solvates, N-oxide, isotopes, deuterated derivatives and addition salts thereof with a pharmaceutically acceptable acid or base.

2. The compound according to claim 1, wherein R represents a hydrogen atom.

3. The compound according to claim 1, wherein R represents a halogen atom.

4. The compound according to claim 1, wherein Z1, Z2 and Z3 each represent a carbon atom.

5. The compound according to claim 1, wherein one of Z1 or Z2 represents a nitrogen atom and Z3 represents a carbon atom.

6. The compound according to claim 1, wherein —X1- represents —O—.

7. The compound according to claim 1, wherein —X2- represents a linear or branched alkanediyl group having 2, 3, 4 or 5 carbon atoms.

8. The compound according to claim 1, wherein —X2- represents $-(CH_2)_3-$, $-CH(CH_3)-(CH_2)_2-$, $-CH_2-CHF-CH_2-$, $-CH_2-CF_2-CH_2-$, or $-(CH_2)_2-CH(CH_3)-$.

9. The compound according to claim 1, wherein Ra is a hydrogen atom.

10. The compound according to claim 1, wherein —X3- represents a linear or branched alkanediyl group having 1, 2, 3, 4 or 5 carbon atoms.

11. The compound according to claim 10, wherein —X3- represents $-(CH_2)_2-$, $-CH_2-$ or $-CH(CH_3)-$.

12. The compound according to claim 1, wherein A represents a group of formula (b):

(b)

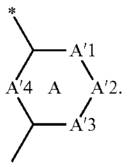

13. The compound according to claim 12, wherein A represents

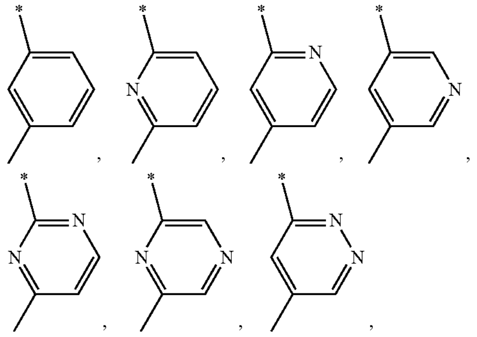

which groups may be substituted or unsubstituted.

14. The compound according to claim 12, wherein A represents a phenyl group.

15. The compound according to claim 12, wherein A represents a pyridinyl group.

16. The compound according to claim 12, wherein A represents a pyrazinyl group.

17. The compound according to claim 11, wherein A represents a group of formula (a):

(a)

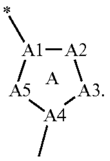

18. The compound according to claim 17, wherein A represents

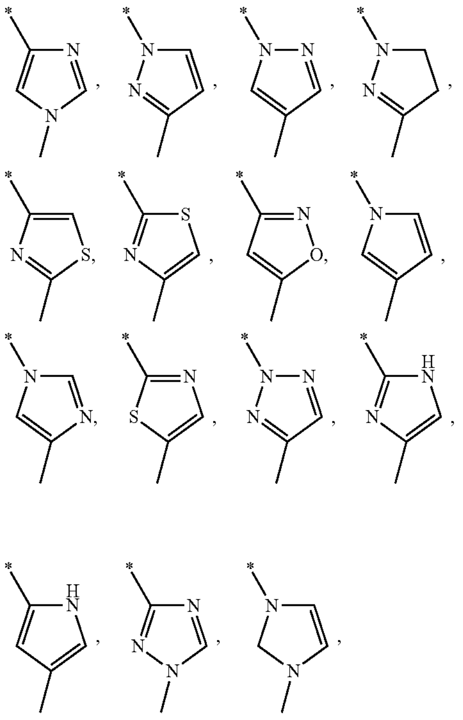

which groups may be substituted or unsubstituted.

19. The compound according to claim 17, wherein A represents a triazolyl group.

20. The compound according to claim 17, wherein A represents a pyrazolyl group.

21. The compound according to claim 13, wherein A is unsubstituted.

22. The compound according to claim 13, wherein A is substituted with one or more groups chosen from halogen atoms, cyano group, cyanoalkyl group, oxo group, alkoxy group, alkyl group, cycloalkyl group and heterocycloalkyl group.

23. The compound according to claim 18, wherein A is unsubstituted.

24. The compound according to claim 18, wherein A is substituted with one or more groups chosen from halogen atoms, cyano group, cyanoalkyl group, oxo group, alkoxy group, alkyl group, cycloalkyl group and heterocycloalkyl group.

25. The compound according to claim 1, which is compound of formula (I-a):

(I-a)

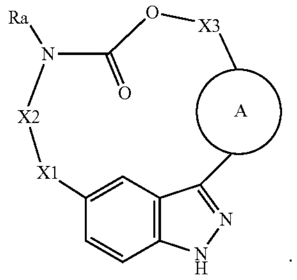

26. The compound according to claim 25, which is compound of formula (I-b):

(I-b)

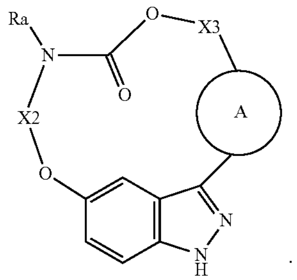

27. The compound according to claim 25, which is compound of formula (I-c) or (I-c'):

(I-c)

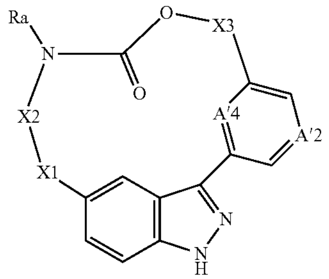

(I-c')

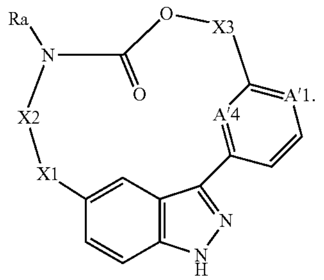

28. The compound according to claim 25, which is compound of formula (I-d) or (I-d'):

(I-d)

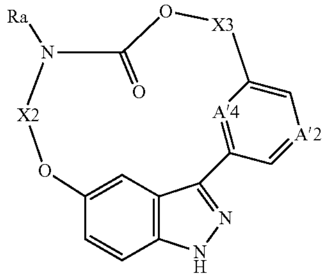

(I-d')

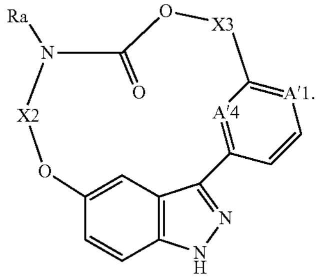

29. The compound according to claim 25, which is compound of formula (I-e):

(I-e)

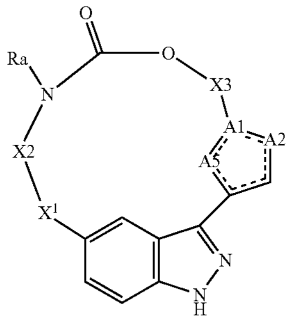

30. The compound according to claim 25, which is compound of formula (I-f):

(I-f)

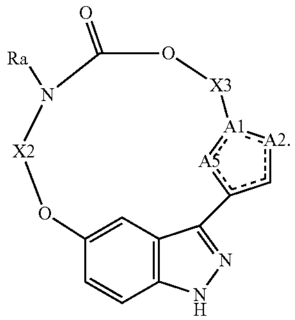

31. The compound according to claim 25, wherein the —X1-X2-N(Ra)—C(O)O—X3- chain represents —O—$(CH_2)_3$—NHC(O)O—$CH_2$—, —O—$CH(CH_3)$—$(CH_2)_2$—NHC(O)O—$CH_2$—,

—O—$CH_2$—CHF—$CH_2$—NHC(O)O—$CH_2$—,

—O—$CH_2$—$CF_2$—$CH_2$—NHC(O)O—$CH_2$—,

—O—$CH(CH_3)$—$(CH_2)_2$—NHC(O)O—$(CH_2)_2$— or —O—$CH(CH_3)$—$(CH_2)_2$—NH—C(O)O—$CH(CH_3)$—.

32. The compound according to claim 1 which is selected from the group consisting of:

8,14-dioxa-4,10,19,20-tetraazatetracyclo[13.5.2.1$^{2,6}$.0$^{18,21}$]tricosa-1(20),2,4,6(23),15,17,21-heptaen-9-one;

10-methyl-8,14-dioxa-4,10,19,20-tetraazatetracyclo[13.5.2.1$^{2,6}$.0$^{18,21}$]tricosa-1(20),2,4, 6(23),15,17,21-heptaen-9-one;

4-fluoro-8,14-dioxa-10,19,20-triazatetracyclo[13.5.2.1$^{2,6}$.0$^{18,21}$]tricosa-1(20),2,4,6(23), 15,17,21-heptaen-9-one;

8,14-dioxa-10,19,20,23-tetraazatetracyclo[13.5.2.1$^{2,6}$.0$^{18,21}$]tricosa-1(20),2,4,6(23), 15,17,21-heptaen-9-one;

8,14-dioxa-10,19,20-triazatetracyclo[13.5.2.1$^{2,6}$.0$^{18,21}$]tricosa-1(20),2,4,6(23),15,17,21-heptaen-9-one;

10-(propan-2-yl)-8,14-dioxa-4,10,19,20-tetraazatetracyclo[13.5.2.1$^{2,6}$.0$^{18,21}$]tricosa-1(20),2,4,6(23),15,17,21-heptaen-9-one;

8,14-dioxa-5,10,19,20-tetraazatetracyclo[13.5.2.1$^{2,6}$.0$^{18,21}$]tricosa-1(20),2,4,6(23), 15,17,21-heptaen-9-one;

4-methoxy-8,14-dioxa-10,19,20-triazatetracyclo[13.5.2.1$^{2,6}$.0$^{18,21}$]tricosa-1(20),2,4, 6(23),15,17,21-heptaen-9-one;

4-bromo-8,14-dioxa-10,19,20-triazatetracyclo[13.5.2.1$^{2,6}$.0$^{18,21}$]tricosa-1(20),2,4,6(23), 15,17,21-heptaen-9-one;

5-fluoro-8,14-dioxa-10,19,20-triazatetracyclo[13.5.2.1$^{2,6}$.0$^{18,21}$]tricosa-1(20),2,4,6(23), 15,17,21-heptaen-9-one;

5-methyl-8,14-dioxa-10,19,20-triazatetracyclo[13.5.2.1$^{2,6}$.0$^{18,21}$]tricosa-1(20),2,4,6(23), 15,17,21-heptaen-9-one;

4-(pyrrolidin-1-yl)-8,14-dioxa-10,19,20-triazatetracyclo[13.5.2.1$^{2,6}$.0$^{18,21}$]tricosa-1(20), 2,4,6(23),15,17,21-heptaen-9-one;

4-[4-(propan-2-yl)piperazin-1-yl]-8,14-dioxa-10,19,20-triazatetracyclo [13.5.2.1$^{2,6}$.0$^{18,21}$]tricosa-1(20),2,4,6(23),15,17,21-heptaen-9-one;

4-{2-oxa-6-azaspiro[3.4]octan-6-yl}-8,14-dioxa-10,19,20-triazatetracyclo [13.5.2.1$^{2,6}$.0$^{18,21}$]tricosa-1(20),2,4,6(23),15,17,21-heptaen-9-one;

4-[4-(oxetan-3-yl)piperazin-1-yl]-8,14-dioxa-10,19,20-triazatetracyclo [13.5.2.1$^{2,6}$.0$^{18,21}$]tricosa-1(20),2,4,6(23),15,17,21-heptaen-9-one;

4-(morpholin-4-yl)-8,14-dioxa-10,19,20-triazatetracyclo[13.5.2.1$^{2,6}$.0$^{18,21}$]tricosa-1(20), 2,4,6(23),15,17,21-heptaen-9-one;

4-[(2R,6S)-2,6-dimethylmorpholin-4-yl]-8,14-dioxa-10,19,20-triazatetracyclo [13.5.2.1$^{2,6}$.0$^{18,21}$]tricosa-1(20),2,4,6(23),15,17,21-heptaen-9-one;

4-methyl-8,14-dioxa-10,19,20-triazatetracyclo[13.5.2.1$^{2,6}$.0$^{18,21}$]tricosa-1(20),2,4,6(23), 15,17,21-heptaen-9-one;

5-methoxy-8,14-dioxa-10,19,20-triazatetracyclo[13.5.2.1$^{2,6}$.0$^{18,21}$]tricosa-1(20),2,4, 6(23),15,17,21-heptaen-9-one;

4-(4,4-difluoropiperidin-1-yl)-8,14-dioxa-10,19,20-triazatetracyclo[13.5.2.1$^{2,6}$.0$^{18,21}$]tricosa-1(20),2,4,6(23), 15,17,21-heptaen-9-one;

4-(3,3-difluoropyrrolidin-1-yl)-8,14-dioxa-10,19,20-triazatetracyclo [13.5.2.1$^{2,6}$.0$^{18,21}$]tricosa-1(20),2,4,6(23),15,17,21-heptaen-9-one;

7-methyl-8,14-dioxa-10,19,20-triazatetracyclo[13.5.2.1$^{2,6}$.0$^{18,21}$]tricosa-1(20),2,4,6(23),15,17,21-heptaen-9-one;

4-[4-(2-methoxyethyl)piperidin-1-yl]-8,14-dioxa-10,19,20-triazatetracyclo [13.5.2.1$^{2,6}$.0$^{18,21}$]tricosa-1(20),2,4,6(23),15,17,21-heptaen-9-one;

9,14-dioxa-11,19,20-triazatetracyclo[13.5.2.1$^{2,6}$.0$^{18,21}$]tricosa-1(20),2,4,6(23),15,17,21-heptaen-10-one;

4-[(3R)-3-hydroxypyrrolidin-1-yl]-8,14-dioxa-10,19,20-triazatetracyclo [13.5.2.1$^{2,6}$.0$^{18,21}$]tricosa-1(20),2,4,6(23),15,17,21-heptaen-9-one;

4-[(2-methoxyethyl)(methyl)amino]-8,14-dioxa-10,19,20-triazatetracyclo [13.5.2.1$^{2,6}$.0$^{18,21}$]tricosa-1(20),2,4,6(23),15,17,21-heptaen-9-one;

4-chloro-8,14-dioxa-10,19,20-triazatetracyclo[13.5.2.1$^{2,6}$.0$^{18,21}$]tricosa-1(20),2,4,6(23), 15,17,21-heptaen-9-one;

4-fluoro-5-methyl-8,14-dioxa-10,19,20-triazatetracyclo[13.5.2.1$^{2,6}$.0$^{18,21}$]tricosa-1(20),2,4,6(23),15,17,21-heptaen-9-one;

4,5-difluoro-8,14-dioxa-10,19,20-triazatetracyclo[13.5.2.1$^{2,6}$.0$^{18,21}$]tricosa-1(20),2,4, 6(23),15,17,21-heptaen-9-one;

5-bromo-8,14-dioxa-10,19,20-triazatetracyclo[13.5.2.1$^{2,6}$.0$^{18,21}$]tricosa-1(20),2,4,6(23),15,17,21-heptaen-9-one;

4-(4-methylpiperazin-1-yl)-8,14-dioxa-10,19,20-triazatetracyclo[13.5.2.1$^{2,6}$.0$^{18,21}$]tricosa-1(20),2,4,6(23),15,17,21-heptaen-9-one;

4-(3-methoxyazetidin-1-yl)-8,14-dioxa-10,19,20-triazatetracyclo[13.5.2.1$^{2,6}$.0$^{18,21}$]tricosa-1(20),2, 4,6(23),15,17,21-heptaen-9-one;

1-{9-oxo-8,14-dioxa-10,19,20-triazatetracyclo[13.5.2.1$^{2,6}$.0$^{18}$,21]tricosa-1(20),2,4,6(23), 15,17,21-heptaen-4-yl}piperidine-4-carbonitrile;

4-[4-(pyrrolidin-1-yl)piperidin-1-yl]-8,14-dioxa-10,19,20-triazatetracyclo [13.5.2.1$^{2,6}$.0$^{18,21}$]tricosa-1(20),2,4,6(23),15,17,21-heptaen-9-one;

4-(azetidin-1-yl)-8,14-dioxa-10,19,20-triazatetracyclo[13.5.2.1$^{2,6}$.0$^{18,21}$]tricosa-1(20),2, 4,6(23),15,17,21-heptaen-9-one;

4-(piperidin-1-yl)-8,14-dioxa-10,19,20-triazatetracyclo[13.5.2.1$^{2,6}$.0$^{18,21}$]tricosa-1(20),2, 4,6(23),15,17,21-heptaen-9-one;

4-(2,5-dihydrofuran-3-yl)-8,14-dioxa-10,19,20-triazatetracyclo[13.5.2.1$^{2,6}$.0$^{18,21}$]tricosa-1(20),2,4,6(23),15,17,21-heptaen-9-one;

4-[4-(morpholin-4-yl)piperidin-1-yl]-8,14-dioxa-10,19,20-triazatetracyclo [13.5.2.1$^{2,6}$.0$^{18,21}$]tricosa-1(20),2,4,6(23),15,17,21-heptaen-9-one;

4-(1-methyl-1,2,3,6-tetrahydropyridin-4-yl)-8,14-dioxa-10,19,20-triazatetracyclo [13.5.2.1$^{2,6}$.0$^{18,21}$]tricosa-1(20),2,4,6(23),15,17,21-heptaen-9-one;

4-[(2S,5S)-2,5-dimethylmorpholin-4-yl]-8,14-dioxa-10,19,20-triazatetracyclo [13.5.2.1$^{2,6}$.0$^{18,21}$]tricosa-1(20),2,4,6(23),15,17,21-heptaen-9-one;

4-[(morpholin-4-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one;

4-[(pyrrolidin-1-yl)methyl]-8,14-dioxa-10,19,20-triazatetracyclo[13.5.2.1$^{2,6}$.0$^{18,21}$]tricosa-1(20),2,4,6(23),15,17,21-heptaen-9-one;

4-[(4-methylpiperazin-1-yl)methyl]-8,14-dioxa-10,19,20-triazatetracyclo [13.5.2.1$^{2,6}$.0$^{18,21}$]tricosa-1(20),2,4,6(23),15,17,21-heptaen-9-one;

5-(morpholin-4-yl)-8,14-dioxa-10,19,20-triazatetracyclo[13.5.2.1$^{2,6}$.0$^{18,21}$]tricosa-1(20),2,4,6(23),15,17,21-heptaen-9-one;

4-[4-(2-methoxyethyl)piperazin-1-yl]-8,14-dioxa-10,19,20-triazatetracyclo [13.5.2.1$^{2,6}$.0$^{18,21}$]tricosa-1(20),2,4,6(23),15,17,21-heptaen-9-one;

4-(diethylamino)-8,14-dioxa-10,19,20-triazatetracyclo [13.5.2.1$^{2,6}$.0$^{18,21}$]tricosa-1(20),2, 4,6(23),15,17,21-heptaen-9-one;

4-cyclopropyl-8,14-dioxa-10,19,20-triazatetracyclo [13.5.2.1$^{2,6}$.0$^{18,21}$]tricosa-1(20),2, 4,6(23),15,17,21-heptaen-9-one;

5-(4-methylpiperazin-1-yl)-8,14-dioxa-10,19,20-triazatetracyclo[13.5.2.1$^{2,6}$.0$^{18,21}$]tricosa-1(20),2,4,6(23),15,17,21-heptaen-9-one;

13-methyl-8,14-dioxa-10,19,20-triazatetracyclo [13.5.2.1$^{2,6}$.0$^{18,21}$]tricosa-1(20),2,4,6(23), 15,17,21-heptaen-9-one;

8,14-dioxa-4,5,10,19,20-pentaazatetracyclo[13.5.2.1$^{2,5}$.0$^{18,21}$]tricosa-1(20),2(23),3, 15(22),16,18(21)-hexaen-9-one;

4-[methyl(oxetan-3-yl)amino]-8,14-dioxa-10,19,20-triazatetracyclo[13.5.2.1$^{2,6}$.0$^{18,21}$]tricosa-1(20),2,4,6(23),15,17,21-heptaen-9-one;

4-[(dimethylamino)methyl]-8,14-dioxa-10,19,20-triazatetracyclo[13.5.2.1$^{2,6}$.0$^{18,21}$]tricosa-1(20),2,4,6(23),15,17,21-heptaen-9-one;

4,10-dimethyl-8,14-dioxa-10,19,20-triazatetracyclo [13.5.2.1$^{2,6}$.0$^{18,21}$]tricosa-1(20),2,4, 6(23),15,17,21-heptaen-9-one;

4-(propan-2-yloxy)-8,14-dioxa-10,19,20-triazatetracyclo [13.5.2.1$^{2,6}$.0$^{18,21}$]tricosa-1(20),2,4,6(23),15,17,21-heptaen-9-one;

4-fluoro-7-methyl-8,14-dioxa-10,19,20-triazatetracyclo [13.5.2.1$^{2,6}$.0$^{18,21}$]tricosa-1(20),2,4,6(23),15,17,21-heptaen-9-one;

4-[1-(oxetan-3-yl)-1,2,3,6-tetrahydropyridin-4-yl]-8,14-dioxa-10,19,20-triazatetracyclo[13.5.2.1$^{2,6}$.0$^{18,21}$]tricosa-1(20),2,4,6(23),15,17,21-heptaen-9-one;

4-(3-methylpiperidin-1-yl)-8,14-dioxa-10,19,20-triazatetracyclo[13.5.2.1$^{2,6}$.0$^{18,21}$]tricosa-1(20),2,4,6(23),15,17,21-heptaen-9-one;

4-[(3S)-3-hydroxypyrrolidin-1-yl]-8,14-dioxa-10,19,20-triazatetracyclo [13.5.2.1$^{2,6}$.0$^{18,21}$]tricosa-1(20),2,4,6 (23),15,17,21-heptaen-9-one;

4-fluoro-8,14-dioxa-10,19,20-triazapentacyclo [13.5.2.1$^{2,6}$.1$^{7,10}$.0$^{18,21}$]tetracosa-1(20), 2(24),3,5,15 (22),16,18(21)-heptaen-9-one;

4-(oxolan-3-yl)-8,14-dioxa-10,19,20-triazatetracyclo [13.5.2.1$^{2,6}$.018,21]tricosa-1(20), 2,4,6(23),15,17,21-heptaen-9-one;

(13S)-13-methyl-8,14-dioxa-10,19,20-triazatetracyclo [13.5.2.1$^{2,6}$.0$^{18,21}$]tricosa-1(20), 2(23),3,5,15(22),16,18(21)-heptaen-9-one;

(13R)-13-methyl-8,14-dioxa-10,19,20-triazatetracyclo [13.5.2.1$^{2,6}$.0$^{18,21}$]tricosa-1(20), 2(23),3,5,15(22),16,18(21)-heptaen-9-one;

4-(1-methyl-1H-pyrazol-3-yl)-8,14-dioxa-10,19,20-triazatetracyclo [13.5.2.1$^{2,6}$.0$^{18,21}$]tricosa-1(20),2(23),3,5,15(22),16,18(21)-heptaen-9-one;

(7S)-7-methyl-8,14-dioxa-10,19,20-triazatetracyclo [13.5.2.1$^{2,6}$.0$^{18,21}$]tricosa-1(20), 2(23),3,5,15(22),16,18(21)-heptaen-9-one;

4-[2-(morpholin-4-yl)ethoxy]-8,14-dioxa-10,19,20-triazatetracyclo[13.5.2.1$^{2,6}$.0$^{18,21}$]tricosa-1(20),2(23),3,5,15(22),16,18(21)-heptaen-9-one;

4-(2-methoxyethyl)-8,14-dioxa-10,19,20-triazatetracyclo [13.5.2.1$^{2,6}$.0$^{18,21}$]tricosa-1(20), 2(23), 3,5,15(22),16,18(21)-heptaen-9-one;

(7R)-7-methyl-8,14-dioxa-10,19,20-triazatetracyclo [13.5.2.1$^{2,6}$.0$^{18,21}$]tricosa-1(20), 2(23),3,5,15(22),16,18(21)-heptaen-9-one;

5-cyclopropyl-8,14-dioxa-10,19,20-triazatetracyclo [13.5.2.1$^{2,6}$.0$^{18,21}$]tricosa-1(20),2,4,6(23),15,17,21-heptaen-9-one;

4-(2-methoxyethoxy)-8,14-dioxa-10,19,20-triazatetracyclo[13.5.2.1$^{2,6}$.0$^{18,21}$]tricosa-1(20),2,4,6(23),15,17,21-heptaen-9-one;

4-fluoro-13-methyl-8,14-dioxa-10,19,20-triazatetracyclo [13.5.2.1$^{2,6}$.0$^{18,21}$]tricosa-1(20), 2,4,6(23),15,17,21-heptaen-9-one;

11-methyl-8,14-dioxa-10,19,20-triazatetracyclo [13.5.2.1$^{2,6}$.0$^{18}$,21]tricosa-1(20),2,4,6(23), 15,17,21-heptaen-9-one;

4-(3-oxomorpholin-4-yl)-8,14-dioxa-10,19,20-triazatetracyclo[13.5.2.1$^{2,6}$.0$^{18,21}$]tricosa-1(20),2(23),3,5,15 (22),16,18(21)-heptaen-9-one;

4-(2-oxopyrrolidin-1-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one;

5-(2-oxopyrrolidin-1-yl)-8,14-dioxa-10,19,20-triazatetracyclo[13.5.2.1$^{2,6}$.0$^{18,21}$]tricosa-1(20),2(23),3,5,15(22),16,18(21)-heptaen-9-one;

4-(2-methylpyrrolidin-1-yl)-8,14-dioxa-10,19,20-triazatetracyclo[13.5.2.1$^{2,6}$.0$^{18}$,21]tricosa-1(20),2(23),3,5,15 (22),16,18(21)-heptaen-9-one;

2-{9-oxo-8,14-dioxa-10,19,20-triazatetracyclo [13.5.2.1$^{2,6}$.0$^{18,21}$]tricosa-1(20),2(23), 3,5,15(22),16,18(21)-heptaen-4-yl}acetonitrile;

(11R)-11-methyl-8,14-dioxa-10,19,20-triazatetracyclo [13.5.2.1$^{2,6}$.0$^{18,21}$]tricosa-1(20), 2(23),3,5,15(22),16,18(21)-heptaen-9-one;

(11S)-11-methyl-8,14-dioxa-10,19,20-triazatetracyclo [13.5.2.1$^{2,6}$.0$^{18,21}$]tricosa-1(20), 2(23),3,5,15(22),16,18(21)-heptaen-9-one;

4-ethynyl-8,14-dioxa-10,19,20-triazatetracyclo [13.5.2.1$^{2,6}$.0$^{18,21}$]tricosa-1(20),2(23),3,5,15(22),16,18 (21)-heptaen-9-one;

4-(piperazin-1-yl)-8,14-dioxa-10,19,20-triazatetracyclo [13.5.2.1$^{2,6}$.0$^{18,21}$]tricosa-1(20), 2(23),3,5,15(22),16,18(21)-heptaen-9-one;

4-(1,2,3,6-tetrahydropyridin-4-yl)-8,14-dioxa-10,19,20-triazatetracyclo [13.5.2.1$^{2,6}$.0$^{18,21}$]tricosa-1(20),2(23),3,5,15(22),16,18(21)-heptaen-9-one;

11-(methoxymethyl)-8,14-dioxa-10,19,20-triazatetracyclo[13.5.2.1$^{2,6}$.0$^{18,21}$]tricosa-1(20),2(23),3,5,15(22),16,18(21)-heptaen-9-one;

8,14-dioxa-5,10,19,20,23-pentaazatetracyclo [13.5.2.1$^{2,5}$.0$^{18,21}$]tricosa-1(20),2(23),3, 15(22),16,18 (21)-hexaen-9-one;

11-methyl-8,14-dioxa-4,5,10,19,20-pentaazatetracyclo [13.5.2.1$^{2,5}$.0$^{18,21}$]tricosa-1(20), 2(23),3,15(22),16,18 (21)-hexaen-9-one;

12-methyl-8,14-dioxa-10,19,20-triazatetracyclo [13.5.2.1$^{2,6}$.0$^{18,21}$]tricosa-1(20),2(23),3,5, 15(22),16,18(21)-heptaen-9-one;

11-ethyl-8,14-dioxa-10,19,20-triazatetracyclo [13.5.2.1$^{2,6}$.0$^{18,21}$]tricosa-1(20),2(23),3,5, 15(22),16,18(21)-heptaen-9-one;

4-fluoro-5,7-dimethyl-8,14-dioxa-10,19,20-triazatetracyclo[13.5.2.1$^{2,6}$.0$^{18,21}$]tricosa-1(20),2(23), 3,5,15(22),16,18(21)-heptaen-9-one;

4-fluoro-5-methoxy-7-methyl-8,14-dioxa-10,19,20-triazatetracyclo [13.5.2.1$^{2,6}$.0$^{18,21}$]tricosa-1(20),2(23),3,5,15(22),16,18(21)-heptaen-9-one;

5-fluoro-4,7-dimethyl-8,14-dioxa-10,19,20-triazatetracyclo[13.5.2.1$^{2,6}$.0$^{18,21}$]tricosa-1(20),2(23),3,5,15(22),16,18(21)-heptaen-9-one;

8,14-dioxa-10,19,20-triazapentacyclo[13.5.2.1$^{2,6}$.1$^{7,10}$.0$^{18,21}$]tetracosa-1(20),2(24),3,5, 15(22),16,18(21)-heptaen-9-one;

13-methyl-8,14-dioxa-10,19,20,23-tetraazatetracyclo[13.5.2.1$^{2,6}$.0$^{18,21}$]tricosa-1(20), 2(23),3,5,15(22),16,18(21)-heptaen-9-one;

12-methyl-8,14-dioxa-4,5,10,19,20-pentaazatetracyclo[13.5.2.1$^{2,5}$.0$^{18,21}$]tricosa-1(20), 2(23),3,15(22),16,18(21)-hexaen-9-one;

7-methyl-8,14-dioxa-4,5,10,19,20-pentaazatetracyclo[13.5.2.1$^{2,5}$.0$^{18,21}$]tricosa-1(20), 2(23),3,15(22),16,18(21)-hexaen-9-one;

5-fluoro-4-methoxy-7-methyl-8,14-dioxa-10,19,20-triazatetracyclo [13.5.2.1$^{2,6}$.0$^{18,21}$]tricosa-1(20),2(23),3,5,15(22),16,18(21)-heptaen-9-one;

(7R,13R)-7,13-dimethyl-8,14-dioxa-10,19,20-triazatetracyclo[13.5.2.1$^{2,6}$.0$^{18,21}$]tricosa-1(20),2(23),3,5,15(22),16,18(21)-heptaen-9-one;

(13R)-13-methyl-8,14-dioxa-4,5,10,19,20-pentaazatetracyclo[13.5.2. 1$^{2,5}$.0$^{18,21}$]tricosa-1(20),2(23),3,15,17,21-hexaen-9-one;

8,15-dioxa-4,10,20,21-tetraazapentacyclo[14.5.2.1$^{2,6}$.1$^{10,13}$.0$^{19,22}$]pentacosa-1(21),2(25), 3,5,16(23),17,19(22)-heptaen-9-one;

8,14-dioxa-5,10,19,20-tetraazatetracyclo[13.5.2.1$^{2,5}$.0$^{18,21}$]tricosa-1(20),2(23),3,15(22),16,18(21)-hexaen-9-one;

(13S)-4-fluoro-13-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one;

(13R)-4-fluoro-13-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one;

(13R)-13-methyl-8,14-dioxa-4,10,19,20-tetraazatetracyclo[13.5.2.1$^{2,6}$.0$^{18,21}$]tricosa-1(20),2(23),3,5,15(22),16,18(21)-heptaen-9-one;

6-cyclopropyl-8,14-dioxa-4,5,10,19,20-pentaazatetracyclo[13.5.2.1$^{2,6}$.0$^{18,21}$]tricosa-1(20), 2(23),3,15(22),16,18(21)-hexaen-9-one;

7-ethyl-8,14-dioxa-10,19,20-triazatetracyclo[13.5.2.1$^{2,6}$.0$^{18,21}$]tricosa-1(20),2,4,6(23),15,17,21-heptaen-9-one;

(13R)-13-ethyl-8,14-dioxa-5,10,19,20,23-pentaazatetracyclo[13.5.2.1$^{2,6}$.0$^{18,21}$]tricosa-1(20),2,4,6(23), 15,17,21-heptaen-9-one;

(7R,13R)-4-fluoro-7,13-dimethyl-8,14-dioxa-10,19,20-triazatetracyclo [13.5.2.1$^{2,6}$.0$^{18,21}$]tricosa-1(20),2,4,6(23),15,17,21-heptaen-9-one;

7-methyl-8,14-dioxa-4,10,19,20-tetraazatetracyclo[13.5.2.1$^{2,6}$.0$^{18,21}$]tricosa-1(20),2,4, 6(23),15,17,21-heptaen-9-one;

(7R)-4-fluoro-7-methyl-8,14-dioxa-10,19,20-triazatetracyclo[13.5.2.1$^{2,6}$.0$^{18,21}$]tricosa-1(20),2,4,6(23),15,17,21-heptaen-9-one;

(7S)-4-fluoro-7-methyl-8,14-dioxa-10,19,20-triazatetracyclo[13.5.2.1$^{2,6}$.0$^{18,21}$]tricosa-1(20),2,4,6(23),15,17,21-heptaen-9-one;

6-methyl-8,14-dioxa-4,5,10,19,20-pentaazatetracyclo[13.5.2.1$^{2,5}$.0$^{18,21}$]tricosa-1(20), 2(23),3,15,17,21-hexaen-9-one;

7-methyl-8,14-dioxa-10,19,20,23-tetraazatetracyclo[13.5.2.1$^{2,6}$.0$^{18,21}$]tricosa-1(20),2,4, 6(23),15,17,21-heptaen-9-one;

6-(propan-2-yl)-8,14-dioxa-4,5,10,19,20-pentaazatetracyclo[13.5.2.1$^{2,5}$.0$^{18,21}$]tricosa-1(20),2(23),3,15(22),16,18(21)-hexaen-9-one;

(13R)-7,13-dimethyl-8,14-dioxa-4,5,10,19,20-pentaazatetracyclo[13.5.2.1$^{2,5}$.0$^{18,21}$]tricosa-1(20),2(23),3,15(22),16,18(21)-hexaen-9-one;

(13R)-13-methyl-8,14-dioxa-10,19,20,23-tetraazatetracyclo[13.5.2.1$^{2,6}$.0$^{18,21}$]tricosa-1(20),2,4,6(23),15,17,21-heptaen-9-one;

(7R)-7-ethyl-8,14-dioxa-10,19,20-triazatetracyclo[13.5.2.1$^{2,6}$.0$^{18,21}$]tricosa-1(20),2,4, 6(23),15, 17,21-heptaen-9-one;

(7S)-7-ethyl-8,14-dioxa-10,19,20-triazatetracyclo[13.5.2.1$^{2,6}$.0$^{18,21}$]tricosa-1(20),2,4, 6(23),15,17,21-heptaen-9-one;

(13R)-13-methyl-8,14-dioxa-5,10,19,20-tetraazatetracyclo[13.5.2.1$^{2,6}$.0$^{18,21}$]tricosa-1(20),2,4,6(23),15,17,21-heptaen-9-one;

6-(oxan-4-yl)-8,14-dioxa-4,5,10,19,20-pentaazatetracyclo[13.5.2.1$^{2,5}$.0$^{18,21}$]tricosa-1(20),2(23),3,15,17,21-hexaen-9-one;

4-ethyl-8,14-dioxa-5,10,19,20,23-pentaazatetracyclo[13.5.2.1$^{2,5}$.0$^{18,21}$]tricosa-1(20), 2(23),15,17,21-pentaen-9-one;

(13R)-23-fluoro-13-methyl-8,14-dioxa-10,19,20-triazatetracyclo[13.5.2.1$^{2,6}$.0$^{18,21}$]tricosa-1(20),2,4,6(23),15,17,21-heptaen-9-one;

9,14-dioxa-4,5,11,19,20-pentaazatetracyclo[13.5.2.1$^{2,5}$.0$^{18,21}$]tricosa-1(20),2(23), 3,15,17,21-hexaen-10-one;

4-ethyl-8,14-dioxa-5,10,19,20,23-pentaazatetracyclo[13.5.2.1$^{2,5}$.0$^{18,21}$]tricosa-1(20), 2(23),3,15,17,21-hexaen-9-one;

3,9,15-trioxa-4,11,20,21-tetraazatetracyclo[14.5.2.1$^{2,5}$.0$^{19,22}$]tetracosa-1(21),2(24), 4,16,18,22-hexaen-10-one;

(13R)-16-fluoro-13-methyl-8,14-dioxa-4,10,19,20-tetraazatetracyclo [13.5.2.1$^{2,6}$.0$^{18,21}$]tricosa-1(20),2,4,6(23),15,17,21-heptaen-9-one;

(13R)-4-chloro-13-methyl-8,14-dioxa-10,19,20,23-tetraazatetracyclo [13.5.2.1$^{2,6}$.0$^{18,21}$]tricosa-1(20),2(23),3,5,15(22),16,18(21)-heptaen-9-one;

8,14-dioxa-2,4,10,19,20-pentaazatetracyclo[13.5.2.1$^{2,5}$.0$^{18,21}$]tricosa-1(20),3,5(23), 15(22),16,18(21)-hexaen-9-one;

(13R)-4-methoxy-13-methyl-8,14-dioxa-10,19,20,23-tetraazatetracyclo [13.5.2.1$^{2,6}$.0$^{18,21}$]tricosa-1(20),2,4,6(23),15,17,21-heptaen-9-one;

(13R)-13-methyl-9-oxo-8,14-dioxa-10,19,20-triazatetracyclo[13.5.2.1$^{2,6}$.0$^{18,21}$]tricosa-1(20),2,4,6(23),15,17,21-heptaene-5-carbonitrile;

(13R)-13-methyl-4-(pyrrolidin-1-yl)-8,14-dioxa-5,10,19,20,23-pentaazatetracyclo [13.5.2.1$^{2,6}$.0$^{18,21}$]tricosa-1(20),2,4,6(23),15,17,21-heptaen-9-one;

(7S,13R)-7,13-dimethyl-8,14-dioxa-5,10,19,20,23-pentaazatetracyclo [13.5.2.1$^{2,6}$.0$^{18,21}$]tricosa-1(20),2,4,6(23),15,17,21-heptaen-9-one;

(7R,13R)-7,13-dimethyl-8,14-dioxa-5,10,19,20,23-pentaazatetracyclo[13.5.2.1$^{2,6}$.0$^{18,21}$]tricosa-1(20),2,4,6(23),15,17,21-heptaen-9-one;

(13R)-16-fluoro-13-methyl-8,14-dioxa-10,19,20-triazatetracyclo[13.5.2.1$^{2,6}$.0$^{18,21}$]tricosa-1(20),2,4,6(23),15,17,21-heptaen-9-one;

(13R)-13-methyl-8,14-dioxa-4,10,19,20,23-pentaazatetracyclo[13.5.2.1$^{2,6}$.0$^{18,21}$]tricosa-1(20),2,4,6(23),15,17,21-heptaen-9-one;

8,14-dioxa-4-thia-10,19,20,23-tetraazatetracyclo [13.5.2.1$^{2,5}$.0$^{18,21}$]tricosa-1(20),2,5(23), 15,17,21-hexaen-9-one;

8,14-dioxa-3-thia-10,19,20,23-tetraazatetracyclo [13.5.2.1$^{2,5}$.0$^{18,21}$]tricosa-1(20),2(23),4,15,17,21-hexaen-9-one;

(7R,13R)-7,13-dimethyl-8,14-dioxa-10,19,20,23-tetraazatetracyclo[13.5.2.1$^{2,6}$.0$^{18,21}$]tricosa-1(20),2,4,6(23),15,17,21-heptaen-9-one;

(13R)-4-[(3R)-3-methoxypyrrolidin-1-yl]-13-methyl-8,14-dioxa-5,10,19,20,23-pentaazatetracyclo [13.5.2.1$^{2,6}$.0$^{18,21}$]tricosa-1(20),2,4,6(23),15,17,21-heptaen-9-one;

(13R)-16-chloro-13-methyl-8,14-dioxa-10,19,20-triazatetracyclo[13.5.2.1$^{2,6}$.0$^{18}$,21]tricosa-1(20),2, 4,6(23), 15,17,21-heptaen-9-one;

(13R)-13,16-dimethyl-8,14-dioxa-10,19,20-triazatetracyclo[13.5.2.1$^{2,6}$.0$^{18,21}$]tricosa-1(20),2,4, 6(23),15,17,21-heptaen-9-one;

(13R)-13-methyl-8,14-dioxa-3,10,19,20,23-pentaazatetracyclo[13.5.2.1$^{2,6}$.0$^{18}$,21]tricosa-1(20),2,4,6(23),15,17,21-heptaen-9-one;

8-oxa-10,14,19,20-tetraazatetracyclo[13.5.2.1$^{2,6}$.0$^{18,21}$] tricosa-1(20),2(23),3,5, 15(22),16,18(21)-heptaen-9-one hydrochloride;

8-oxa-10,19,20-triazatetracyclo[13.5.2.1$^{2,6}$.0$^{18,21}$]tricosa-1(20),2(23),3,5,15(22),16, 18(21)-heptaen-9-one;

(13R)-5-methoxy-13-methyl-8,14-dioxa-4,10,19,20-tetraazatetracyclo [13.5.2.1$^{2,6}$.0$^{18,21}$]tricosa-1(20),2,4,6(23),15,17,21-heptaen-9-one;

(13R)-13-methyl-8,14-dioxa-4,10,19,20-tetraazatetracyclo[13.5.2.1$^{2,6}$.0$^{18,21}$]tricosa-1(20),2, 6(23),15,17,21-hexaene-5,9-dione;

4-methyl-8,14-dioxa-3,4,10,19,20-pentaazatetracyclo [13.5.2.1$^{2,5}$.0$^{18,21}$]tricosa-1(20),2, 5(23),15(22),16,18(21)-hexaen-9-one;

(13R)-16-fluoro-13-methyl-8,14-dioxa-10,19,20,23-tetraazatetracyclo [13.5.2.1$^{2,6}$.0$^{18,21}$]tricosa-1(20),2,4,6(23),15,17,21-heptaen-9-one;

7,13-dioxa-4-thia-9,18,19,22-tetraazatetracyclo [12.5.2.1$^{2,5}$.0$^{17,20}$]docosa-1(19),2,5(22),14(21),15,17(20)-hexaen-8-one;

(13R)-4,13-dimethyl-8,14-dioxa-5,10,19,20,23-pentaazatetracyclo[13.5.2.1$^{2,6}$.0$^{18,21}$]tricosa-1(20),2(23),3,5,15(22),16,18(21)-heptaen-9-one;

8,14-dioxa-23-thia-4,10,19,20-tetraazatetracyclo [13.5.2.1$^{2,5}$.0$^{18,21}$]tricosa-1(20),2,4,15(22), 16,18(21)-hexaen-9-one;

(7S,13R)-7,13-dimethyl-8,14-dioxa-10,19,20,23-tetraazatetracyclo [13.5.2.1$^{2,6}$.0$^{18,21}$]tricosa-1(20),2(23),3,5,15(22),16,18(21)-heptaen-9-one;

(13R)-13-methyl-9-oxo-8,14-dioxa-5,10,19,20-tetraazatetracyclo[13.5.2.1$^{2,6}$.0$^{18,21}$]tricosa-1(20), 2(23),3,15(22),16,18(21)-hexaene-4-carbonitrile;

12,12-difluoro-8,14-dioxa-10,19,20-triazatetracyclo [13.5.2.1$^{2,6}$.0$^{18,21}$]tricosa-1(20),2(23), 3,5,15(22),16,18(21)-heptaen-9-one;

(13R)-17-fluoro-13-methyl-8,14-dioxa-10,19,20-triazatetracyclo[13.5.2.1$^{2,6}$.0$^{18,21}$]tricosa-1(20),2(23),3,5,15(22),16,18(21)-heptaen-9-one;

(7S,13R)-7,13-dimethyl-8,14-dioxa-4,10,19,20,23-pentaazatetracyclo [13.5.2.1$^{2,6}$.0$^{18,21}$]tricosa-1(20),2(23),3,5,15(22),16,18(21)-heptaen-9-one;

(7R,13R)-7,13-dimethyl-8,14-dioxa-4,10,19,20,23-pentaazatetracyclo [13.5.2.1$^{2,6}$.0$^{18,21}$]tricosa-1(20),2(23),3,5,15(22),16,18(21)-heptaen-9-one;

(13S)-13-methyl-8,14-dioxa-4,10,19,20,23-pentaazatetracyclo[13.5.2.1$^{2,6}$.0$^{18,21}$]tricosa-1(20),2(23),3,5,15(22),16,18(21)-heptaen-9-one;

(13R)-13-methyl-8,14-dioxa-10,19,20,22-tetraazatetracyclo[13.5.2.1$^{2,6}$.0$^{18,21}$]tricosa-1(20), 2(23),3,5,15,17,21-heptaen-9-one;

(12R)-4,12-dimethyl-7,13-dioxa-4,9,18,19,22-pentaazatetracyclo[12.5.2.1$^{2,5}$.0$^{17,20}$]docosa-1(19),2,5(22),14(21),15,17(20)-hexaen-8-one;

(13R)-13-methyl-8,14-dioxa-4,5,10,19,20,23-hexaazatetracyclo[13.5.2.1$^{2,5}$.0$^{18,21}$]tricosa-1(20),2(23),3,15,17,21-hexaen-9-one;

(13R)-13-methyl-8,14-dioxa-23-thia-4,10,19,20-tetraazatetracyclo[13.5.2.1$^{2,5}$.0$^{18,21}$]tricosa-1(20),2,4,15,17,21-hexaen-9-one;

(13R)-4,13-dimethyl-8,14-dioxa-4,10,19,20,23-pentaazatetracyclo[13.5.2.1$^{2,5}$.0$^{18,21}$]tricosa-1(20),2,5(23),15(22),16,18(21)-hexaen-9-one;

(13R)-13-methyl-8,14-dioxa-10,16,19,20-tetraazatetracyclo[13.5.2.1$^{2,6}$.0$^{18,21}$]tricosa-1(20),2(23),3,5,15(22),16,18(21)-heptaen-9-one;

14-methyl-8-oxa-10,14,19,20-tetraazatetracyclo [13.5.2.1$^{2,6}$.0$^{18,21}$]tricosa-1(20),2(23),3,5, 15,17,21-heptaen-9-one;

(13R)-13-methyl-8,14-dioxa-4,10,19,20,22-pentaazatetracyclo[13.5.2.1$^{2,6}$.0$^{18,21}$]tricosa-1(20),2(23),3,5,15,17,21-heptaen-9-one;

(13R)-13-methyl-8,14-dioxa-10,17,19,20-tetraazatetracyclo[13.5.2.1$^{2,6}$.0$^{18,21}$]tricosa-1(20),2(23),3,5,15(22),16,18(21)-heptaen-9-one;

8,14-dioxa-4,5,10,19,20,23-hexaazatetracyclo [13.5.2.1$^{2,5}$.0$^{18,21}$]tricosa-1(20),2(23),3, 15(22),16,18(21)-hexaen-9-one;

12,12-difluoro-8,14-dioxa-4,5,10,19,20,23-hexaazatetracyclo[13.5.2.1$^{2,5}$.0$^{18,21}$]tricosa-1(20),2(23),3,15(22),16,18(21)-hexaen-9-one;

(12R)-12-fluoro-8,14-dioxa-10,19,20-triazatetracyclo [13.5.2.1$^{2,6}$.0$^{18,21}$]tricosa-1(20),2(23), 3,5,15(22),16,18(21)-heptaen-9-one;

(12S)-12-fluoro-8,14-dioxa-10,19,20-triazatetracyclo [13.5.2.1$^{2,6}$.0$^{18,21}$]tricosa-1(20),2(23), 3,5,15(22),16,18(21)-heptaen-9-one;

12,12-difluoro-8,14-dioxa-4,10,19,20,23-pentaazatetracyclo[13.5.2.1$^{2,6}$.0$^{18,21}$]tricosa-1(20),2(23),3,5,15(22),16,18(21)-heptaen-9-one;

(12S)-12-fluoro-8,14-dioxa-4,10,19,20,23-pentaazatetracyclo[13.5.2.1$^{2,6}$.0$^{18,21}$]tricosa-1(20),2(23),3,5,15,17,21-heptaen-9-one;

(12R)-12-fluoro-8,14-dioxa-4,10,19,20,23-pentaazatetracyclo[13.5.2.1$^{2,6}$.0$^{18}$,21]tricosa-1(20),2(23),3,5,15,17,21-heptaen-9-one;

(12S)-12-fluoro-8,14-dioxa-4,5,10,19,20,23-hexaazatetracyclo[13.5.2.1$^{2,5}$.0$^{18,21}$]tricosa-1(20),2(23),3,15,17,21-hexaen-9-one;

(12R)-12-fluoro-8,14-dioxa-4,5,10,19,20,23-hexaazatetracyclo[13.5.2.1$^{2,5}$.0$^{18,21}$]tricosa-1(20),2(23),3,15,17,21-hexaen-9-one; and 8',14'-dioxa-10',19',20'-triazaspiro[cyclopropane-1,13'-tetracyclo[13.5.2.1$^{2,6}$.0$^{18,21}$]tricosane]-1'(20'),2'(23'),3',5',15'(22'),16',18'(21')-heptaen-9'-one.

33. A pharmaceutical composition comprising the compound according to claim 1, or an addition salt thereof with a pharmaceutically acceptable acid or base, in combination with one or more pharmaceutically acceptable excipients.

34. A method of inhibiting LRRK2 kinase activity in a subject in need thereof, comprising administration of an effective amount of the compound according to claim 1, alone or in combination with one or more pharmaceutically acceptable excipients.

35. The method according to claim 34, wherein the subject in need is one diagnosed with a neurological disease selected from Parkinson's disease, Alzheimer's disease, amyotrophic lateral sclerosis (ALS), dementia, diabetic neuropathy, age related memory dysfunction, argyrophilic grain disease, Pick's disease, epilepsy, tauopathies, multiple system atrophy, frontotemporal dementia, inherited frontotemporal dementia, ischemic stroke, traumatic brain injury, and multiple sclerosis.

36. The method according to claim 34, wherein the subject in need is one diagnosed with a neurological disease selected from Parkinson's disease and Alzheimer's disease.

37. The method according to claim 34, wherein the subject in need is one diagnosed with an endosomal-lysosomal disorder selected from Niemann-Pick Type A, B or C disease and Gaucher's disease.

38. The method according to claim 34, wherein the subject in need is one diagnosed with an inflammatory disease, wherein the inflammatory disease is ankylosing spondylitis.

39. The method according to claim 34, wherein the subject in need is one diagnosed with an autoimmune disease selected from Crohn's disease, rheumatoid arthritis, ulcerative colitis, lupus, obesity, and leprosy.

40. The method according to claim 34, wherein the subject in need is one diagnosed with a cancer selected from thyroid cancer, renal cancer, breast cancer, hormone-related cancer, adeno- and squamous lung cancer, non-small-cell lung cancer, colon cancer, prostate cancers, skin cancers, leukemias and lymphomas.

41. The method according to claim 34, wherein the subject in need is one diagnosed with a cardiovascular disease, wherein the cardiovasclular disease is stroke.

42. The method according to claim 34, wherein the subject in need is one diagnosed with a bacterial or viral infection selected from leprosy, tuberculosis, SARS-CoV, MERS-CoV and SARS-CoV-2, HIV, West Nile virus and chikungunya virus.

43. The method of claim 35, wherein the tauopathies are selected from progressive supranuclear palsy and corticobasal degeneration.

44. The method of claim 34, wherein the subject in need is one diagnosed with a pulmonary disease selected from chronic obstructive pulmonary disease and idiopathic pulmonary fibrosis.

45. The method of claim 34, wherein the subject in need is one diagnosed with Parkinson's disease.

46. A method of treating Parkinson's disease in a subject in need thereof, comprising administration of an effective amount of the compound according to claim 1, alone or in combination with one or more pharmaceutically acceptable excipients.

* * * * *